United States Patent
Zhang et al.

(10) Patent No.: US 10,781,444 B2
(45) Date of Patent: Sep. 22, 2020

(54) FUNCTIONAL GENOMICS USING CRISPR-CAS SYSTEMS, COMPOSITIONS, METHODS, SCREENS AND APPLICATIONS THEREOF

(71) Applicants: THE BROAD INSTITUTE, INC., Cambridge, MA (US); MASSACHUSETTS INSTITUTE OF TECHNOLOGY, Cambridge, MA (US)

(72) Inventors: Feng Zhang, Cambridge, MA (US); Ophir Shalem, Albany, CA (US); Neville Espi Sanjana, Cambridge, MA (US); John Doench, Boston, MA (US); David Root, Brookline, MA (US); Ella Nicole Biewener Hartenian, Brookline, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 14/973,062

(22) Filed: Dec. 17, 2015

(65) Prior Publication Data

US 2016/0272965 A1     Sep. 22, 2016

Related U.S. Application Data

(63) Continuation of application No. PCT/US2014/041806, filed on Jun. 10, 2014, and a continuation of application No. PCT/US2013/074800, filed on Dec. 12, 2013.

(60) Provisional application No. 61/836,123, filed on Jun. 17, 2013, provisional application No. 61/960,777, filed on Sep. 25, 2013, provisional application No. 61/995,636, filed on Apr. 15, 2014.

(51) Int. Cl.
*C12N 15/10* (2006.01)
*C12N 15/63* (2006.01)
*C12N 9/22* (2006.01)
*C12N 15/90* (2006.01)

(52) U.S. Cl.
CPC .......... *C12N 15/1093* (2013.01); *C12N 9/22* (2013.01); *C12N 15/102* (2013.01); *C12N 15/1082* (2013.01); *C12N 15/63* (2013.01); *C12N 15/907* (2013.01); *C12N 2310/20* (2017.05)

(58) Field of Classification Search
None
See application file for complete search history.

(56) References Cited

U.S. PATENT DOCUMENTS

| | | |
|---|---|---|
| 5,622,856 A | 4/1997 | Natsoulis |
| 6,251,677 B1 | 6/2001 | Wilson et al. |
| 7,601,492 B2 | 10/2009 | Fu et al. |
| 7,691,995 B2 | 4/2010 | Zamore et al. |
| 8,697,359 B1 * | 4/2014 | Zhang ............ C12N 15/85 424/94.1 |
| 8,771,945 B1 | 7/2014 | Zhang |
| 8,865,406 B2 | 10/2014 | Zhang et al. |
| 8,871,445 B2 | 10/2014 | Cong et al. |
| 8,889,418 B2 | 11/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 9,549,901 B2 | 1/2017 | Shi et al. |
| 9,597,357 B2 | 3/2017 | Gregory et al. |
| 9,623,071 B2 | 4/2017 | Guo et al. |
| 9,834,791 B2 | 12/2017 | Zhang et al. |
| 10,301,651 B2 | 5/2019 | Doudna et al. |
| 2003/0186238 A1 | 10/2003 | Allawi et al. |
| 2004/0111221 A1 | 10/2004 | Beattie |
| 2005/0196851 A1 | 9/2005 | Uckun |
| 2006/0178297 A1 | 8/2006 | Troy et al. |
| 2006/0234247 A1 | 10/2006 | Puttaraju et al. |
| 2007/0016012 A1 | 1/2007 | Hartlep |
| 2007/0244031 A1 | 10/2007 | Lu et al. |
| 2010/0055798 A1 | 3/2010 | Battersby |
| 2010/0076057 A1 | 3/2010 | Sontheimer et al. |
| 2010/0081707 A1 | 4/2010 | Ali et al. |
| 2010/0093617 A1 | 4/2010 | Barrangou et al. |
| 2010/0233084 A1 | 9/2010 | Narasimhaswamy et al. |
| 2011/0016540 A1 | 1/2011 | Weinstein |
| 2011/0059502 A1 | 3/2011 | Chalasani |
| 2011/0189776 A1 | 8/2011 | Terns et al. |
| 2011/0223638 A1 | 9/2011 | Wiedenheft et al. |
| 2011/0239315 A1 | 9/2011 | Bonas et al. |

(Continued)

FOREIGN PATENT DOCUMENTS

| | | |
|---|---|---|
| CN | 101228176 | 7/2008 |
| CN | 103388006 | 11/2013 |

(Continued)

OTHER PUBLICATIONS

Request for Ex Parte Reexamination of U.S. Pat. No. 8,771,945 filed Feb. 16, 2016.

(Continued)

*Primary Examiner* — Nancy J Leith
(74) *Attorney, Agent, or Firm* — Foley & Lardner LLP; Sunit Talapatra

(57) ABSTRACT

The present invention generally relates to libraries, compositions, methods, applications, kits and screens used in functional genomics that focus on gene function in a cell and that may use vector systems and other aspects related to Clustered Regularly Interspaced Short Palindromic Repeats (CRISPR)-Cas systems and components thereof. Provided are vectors and vector systems, some of which encode one or more components of a CRISPR complex, as well as methods for the design and use of such vectors. Also provided are methods of directing CRISPR complex formation in eukaryotic cells and methods for utilizing the CRISPR-Cas system.

15 Claims, 105 Drawing Sheets

Specification includes a Sequence Listing.

(56) References Cited

U.S. PATENT DOCUMENTS

| | | |
|---|---|---|
| 2012/0029891 A1 | 2/2012 | Behlke et al. |
| 2013/0096182 A1 | 4/2013 | Chatterjee et al. |
| 2013/0130248 A1 | 5/2013 | Haurwitz et al. |
| 2013/0315831 A1 | 11/2013 | Shi et al. |
| 2014/0068797 A1 | 3/2014 | Doudna et al. |
| 2014/0294771 A1 | 10/2014 | Schaffer et al. |
| 2014/0295557 A1 | 10/2014 | Joung et al. |
| 2014/0315985 A1 | 10/2014 | May et al. |
| 2014/0342456 A1 | 11/2014 | Mali et al. |
| 2014/0356956 A1 | 12/2014 | Church et al. |
| 2014/0357530 A1 | 12/2014 | Zhang et al. |
| 2015/0045546 A1 | 2/2015 | Siksnys et al. |
| 2015/0071899 A1 | 3/2015 | Liu et al. |
| 2015/0071903 A1 | 3/2015 | Liu et al. |
| 2015/0071906 A1 | 3/2015 | Liu et al. |
| 2015/0232881 A1 | 8/2015 | Glucksmann et al. |
| 2015/0247150 A1 | 9/2015 | Zhang et al. |
| 2015/0291965 A1 | 10/2015 | Zhang et al. |
| 2015/0322457 A1 | 11/2015 | Kim et al. |
| 2015/0353905 A1 | 12/2015 | Weiss et al. |
| 2016/0017366 A1 | 1/2016 | Chen et al. |
| 2016/0024510 A1 | 1/2016 | Bikard et al. |
| 2016/0024524 A1 | 1/2016 | Joung et al. |
| 2016/0130609 A1 | 5/2016 | Doudna et al. |
| 2016/0237456 A1 | 8/2016 | Church et al. |
| 2016/0251648 A1* | 9/2016 | Wang ............... C12N 15/1082 506/10 |
| 2016/0281072 A1 | 9/2016 | Zhang |
| 2016/0298135 A1 | 10/2016 | Chen et al. |
| 2016/0298137 A1 | 10/2016 | Chen et al. |
| 2016/0324938 A1 | 11/2016 | Bikard et al. |
| 2016/0340662 A1 | 11/2016 | Zhang et al. |
| 2017/0175144 A1 | 6/2017 | Zhang et al. |
| 2018/0127783 A1 | 5/2018 | Zhang et al. |
| 2018/0230495 A1 | 8/2018 | Doudna et al. |
| 2019/0010471 A1 | 1/2019 | Zhang et al. |

FOREIGN PATENT DOCUMENTS

| | | |
|---|---|---|
| CN | 103668472 | 3/2014 |
| CN | 104854241 A | 8/2015 |
| EP | 2591770 | 5/2013 |
| EP | 2 784 162 | 1/2014 |
| EP | 2764103 | 8/2014 |
| EP | 2771468 | 9/2014 |
| EP | 2 828 386 A1 | 1/2015 |
| FR | 2872170 A1 | 12/2005 |
| JP | 2004-519245 A | 7/2004 |
| JP | 2004-537285 A | 12/2004 |
| JP | 2005-509409 A | 4/2005 |
| JP | 2006-513694 A | 4/2006 |
| JP | 2006-518996 A | 8/2006 |
| JP | 2007-501626 A | 2/2007 |
| JP | 2009-502170 A | 1/2009 |
| JP | 2009-536827 A | 10/2009 |
| JP | 2010-522547 A | 7/2010 |
| JP | 2012-508235 | 4/2012 |
| JP | 2012-510812 A | 5/2012 |
| JP | 2012-511332 A | 5/2012 |
| JP | 2012-529287 A | 11/2012 |
| JP | 2013-500045 A | 1/2013 |
| JP | 2013-518602 A | 5/2013 |
| JP | 2013-544077 A | 12/2013 |
| JP | 2014-526279 A | 10/2014 |
| JP | 2015-523856 A | 8/2015 |
| JP | 2016-500003 A | 1/2016 |
| JP | 2016-500262 | 1/2016 |
| JP | 2016-501532 A | 1/2016 |
| JP | 2016-025710 | 2/2016 |
| JP | 2016-502840 A | 2/2016 |
| JP | 2016-504026 A | 2/2016 |
| JP | 2016-093196 | 5/2016 |
| JP | 2016-516169 A | 6/2016 |
| JP | 2016-517954 A | 6/2016 |
| JP | 2016-131404 A | 7/2016 |
| JP | 2016-520317 A | 7/2016 |
| JP | 2016-521554 A | 7/2016 |
| JP | 2016-521975 A | 7/2016 |
| JP | 2016-523082 A | 8/2016 |
| JP | 2016-182140 A | 10/2016 |
| JP | 2017-501151 A | 1/2017 |
| JP | 2017-501699 | 1/2017 |
| JP | 6395765 | 9/2018 |
| RU | 2009136452 A | 4/2011 |
| WO | WO-02/074968 A1 | 9/2002 |
| WO | WO-02/080851 A2 | 10/2002 |
| WO | WO-03/014318 A2 | 2/2003 |
| WO | WO-03/104414 A2 | 12/2003 |
| WO | 2004029219 | 4/2004 |
| WO | WO-2004/029219 A2 | 4/2004 |
| WO | WO-2004/046321 A2 | 6/2004 |
| WO | WO-2004/062618 A2 | 7/2004 |
| WO | WO-2005/014791 | 2/2005 |
| WO | WO-2005/049642 A2 | 6/2005 |
| WO | WO-2007/014275 A2 | 2/2007 |
| WO | WO-2007/134161 A2 | 11/2007 |
| WO | WO-2008/093152 A1 | 8/2008 |
| WO | 2008108989 | 9/2008 |
| WO | WO-2008/116860 A2 | 10/2008 |
| WO | 2010054108 | 5/2010 |
| WO | WO-2010/065123 A1 | 6/2010 |
| WO | WO-2010/068816 A1 | 6/2010 |
| WO | WO-2010/075424 A2 | 7/2010 |
| WO | WO-2010/079430 A1 | 7/2010 |
| WO | WO-2010/143917 | 12/2010 |
| WO | WO-2011/011767 A1 | 1/2011 |
| WO | WO-2011/016840 A2 | 2/2011 |
| WO | 2011076873 | 6/2011 |
| WO | WO-2011/064736 A1 | 6/2011 |
| WO | WO-2011/076873 A1 | 6/2011 |
| WO | WO-2011/100058 | 8/2011 |
| WO | 2011146121 | 11/2011 |
| WO | WO-2012/012738 A1 | 1/2012 |
| WO | WO-2012/031205 | 3/2012 |
| WO | WO-2012/051343 A1 | 4/2012 |
| WO | WO-2012/149470 A1 | 11/2012 |
| WO | 2012164565 | 12/2012 |
| WO | WO-2013/044008 A2 | 3/2013 |
| WO | WO-2013/052681 | 4/2013 |
| WO | WO-2013/155572 | 4/2013 |
| WO | WO-2013/071440 A1 | 5/2013 |
| WO | WO-2013/078400 A1 | 5/2013 |
| WO | 2013082519 | 6/2013 |
| WO | 2013098244 | 7/2013 |
| WO | 2013130824 | 9/2013 |
| WO | 2013141680 | 9/2013 |
| WO | 2013142578 | 9/2013 |
| WO | WO 2013/176772 A1 | 11/2013 |
| WO | WO-2014/165349 A1 | 3/2014 |
| WO | 2014065596 | 5/2014 |
| WO | 2014089290 | 6/2014 |
| WO | 2014093479 | 6/2014 |
| WO | 2014093622 | 6/2014 |
| WO | 2014093661 | 6/2014 |
| WO | 2014093712 | 6/2014 |
| WO | 2014099744 | 6/2014 |
| WO | 2014099750 | 6/2014 |
| WO | WO-2014/093595 | 6/2014 |
| WO | WO-2014/093635 A1 | 6/2014 |
| WO | WO-2014/093655 | 6/2014 |
| WO | WO-2014/093694 | 6/2014 |
| WO | WO-2014/093701 A1 | 6/2014 |
| WO | WO-2014/093709 | 6/2014 |
| WO | WO-2014/093718 | 6/2014 |
| WO | WO-2015/031775 | 8/2014 |
| WO | WO-2014/144761 | 9/2014 |
| WO | WO-2014/186585 A2 | 11/2014 |
| WO | 2014204729 | 12/2014 |
| WO | WO-2014/191518 A1 | 12/2014 |
| WO | WO-2014/197568 A2 | 12/2014 |
| WO | WO-2014/197748 | 12/2014 |
| WO | WO-2014/204724 | 12/2014 |
| WO | WO-2014/204725 | 12/2014 |

(56) References Cited

FOREIGN PATENT DOCUMENTS

| | | | |
|---|---|---|---|
| WO | WO-2014/204726 | 12/2014 | |
| WO | WO-2014/204727 A1 | 12/2014 | |
| WO | WO-2014/204728 | 12/2014 | |
| WO | WO-2015/006747 A2 | 1/2015 | |
| WO | WO-2015/035136 A2 | 3/2015 | |
| WO | WO-2015/048577 | 4/2015 | |
| WO | WO 2015/065964 * | 5/2015 | ......... C12N 15/1082 |
| WO | WO-2015/070083 A1 | 5/2015 | |
| WO | WO-2015/071474 | 5/2015 | |
| WO | WO-2015/089351 A1 | 6/2015 | |
| WO | WO-2015/089364 | 6/2015 | |
| WO | WO-2015/089419 | 6/2015 | |
| WO | WO-2015/089427 A1 | 6/2015 | |
| WO | WO-2015/113063 A1 | 7/2015 | |
| WO | WO-2016/022866 A1 | 2/2016 | |
| WO | WO-2016/141224 A1 | 9/2016 | |

OTHER PUBLICATIONS

EP Communication pursuant to Article 94(3) dated Feb. 7, 2017, which issued during prosecution of European Application No. 14736205.7.
Janssen, et al., "Mouse Models of K-ras-Initiated Carcinogenesis" Biochimicia et Biophysica Acta, 2005, 1756:145-154.
Jinek, et al., "RNA-programmed genome editing in human cells;" 2013, eLife 2013:e00471, DOI:10.7554/eLife.00471.
Kanasty, et al. "Delivery materials for siRNA therapeutics" Nature Materials, 2013, 12:967-977.
Karvelis, et al. "crRNA and tracrRNA guide Cas9-mediated DNA interference in *Streptococcus thermophiles* " RNA Biology, 2013, 10(5):841-851.
Karvelis, et al. "Supplemental Material to: crRNA and tracrRNA guide Cas9-mediated DNA interference in *Streptococcus thermophiles*" Landes Bioscience, 2013, 10(5), http://dx.doi.org/10.4161/rna.24203.
Kim, et al. "Crystal structure of Cas1 from Archaeoglobus fulgidus and characterization of its nucleolytic activity" Biochemical and Biophysical Research Communications, 2013, 441:720-725.
Konermann, et al, "Genome-scale transcriptional activation by an engineered CRISPR-Cas9 complex" Nature, 2015, 517:583-588.
Koornneef, et al. "Apoliprotein B Knockdown by AAV-Delivered shRNA Lowers Plasma Cholesterol in Mice" Molecular Therapy, Apr. 2011, 19( 4)731-740.
Lambowitz, et al. "Group II Introns: Mobile Ribozymes that Invade DNA" Cold Spring Harb Perspect Biol., 2011, 3:a003616.
Larson, et al. "CRISPR interference (CRISPRi) for sequence-specific control of gene expression" Nature Protocols, 2013, 8(11):2180-2196.
Lewis, et al. "The c-myc and PyMT oncogenes induce different tumor types in a somatic mouse model for pancreatic cancer" Genes & Development, 2003, 17:3127-3138.
Li, et al. "In vivo genome editing restores hemostasis in a mouse model of hemophilia" Nature, 2011, 475 (7355):217-221 doi: 10.1038/nature10177.
Li, et al. "Multiplex and homologous recombination-mediated genome editing in *Arabidopsis* and Nicotaina benthamiana using guide RNA and Cas9" Nature Biotechnology, 2013, 31(9):688-691.
Lombardo, et al., "Gene editing in human stem cells using zinc finger nucleases and integrase-defective lentiviral vector delivery" Nature Biotechnology, 2007, 25(11):1298-1306.
Luo, et al., "Highly parallel identification of essential genes in cancer cells", Proceeding of the National Academy of Sciences, 2008, 105(51);20380-20385.
Ma, et al. "A Guide RNA Sequence Design Platform for the CRISPR/Cas9 System for Model Organism Genomes", BioMed Research International, 2014, 2013:270805-4. http://dx.doi.org/10.1155/2014/270805.
Maeder, et al. "CRISPR RNA-guided activation of endogenous human genes" Nature Methods, 2013, 10(10):977-979. doi.10.1038/nmeth.2556.

Makarova, et al, "Evolution and classification of the CRISPR-CAS Systems" Nature Reviews Microbiology, 2011, 9(6):467-477.
Makarova et al. "Unification of Cas protein families and a simple scenario for the origin and evolution of CRISPR-Cas systms" Biology Direct, 2011, 6:38. http:///www.biology-direct.com/content/6/1/38.
Mali, et al. "Supplementary Materials for-RNA-Guided Human Genome Engineering Via Cas9" Science, 2013, 339:823-826.
Mali, et al. "RNA-Guided Human Genome engineering Via Cas9" Science, 2013, DOI: 10.1126/SCIENCE.1232033.
Mali, et al. "CAS9 transcriptional activators for target specificity screening and paired nickases for cooperative genome engineering" nature biotechnology, 2013, 31(9):833-840.
Mali, et al. "Supplementary Information: Use of adjacent sgRNA:Cas9 complexes for transcriptional activation and genome engineering" Nature Biotechnoly, doi:10.1037/nbt.2675, 2013.
Malina, et al. "Repurposing CRISPR/Cas9 for in situ functional assays" Genes & Development, 2013, 27:2602-2614.
Marraffini, et al. "Self vs. non-self discrimination during CRISPR RNa-directed immunity" Nature, 2010, 463 (7280):568-571.
Mastroianni, et al. "Group II Intron-Based Gene Targeting Reactions in Eukaryotes" Plos One, 2008, 3(9):e3121. Doi:10.1371/journal.pone.0003121.
Meshorer, et al. "Chromatin in pluripotent embryonic stem cells and differentiation" Nature Reviews Molecular Cell Biology, 2006, 7:540-546.
Miller, et al. "A TALE nuclease architecture for efficient genome editing" Nature Biotechnology, 2011, 29(2):143-150.
Minton, "How can biochemical reactions within cells differ from those in test tubes?" Journal of Cell Science, 2006, 119:2863-2869.
Mojica, et al. "Short motif sequences determine the targets of the prokaryotic CRISPR defence system", Microbiology, 2009, 155:733-740.
Morgan, et al. "Inducible Expression and Cytogenetic Effects of the EcoRI Restriction Endonuclease in Chinese Hamster Ovary Cells" Molecular and Cellular Biology, 1988, 8(10):4204-4211.
Mukhopadyay, "On the Same Wavelength," ASBMBTODAY, Aug. 2014, http://www.asbmb.org/asbmbtoday/201408/Features/Doudna/.
Nakamura, et al. "Codon usage tabulated from international DNA sequence databases: status for the year 2000" Nucleic Acids Research, 2000, 28(1): 292.
Nomura, et al., "Low-density lipoprotein receptor gene therapy using helper-dependent adenovirus produces long-term protection against atherosclerosis in a mouse model of familial hypercholesterolemia" Gene Therapy, 2004, 11:1540-1548.
Nishimasu et al. "Crystal Structure of *Staphylococcus aureus* Cas9," Cell 162, 1113-1126, Aug. 27, 2015.
Nishimasu, et al. Crystal Structure of Cas9 in Complex with Guide RNA and Target DNA, Cell, 2014, 156:935-949.
Oost, "New Tool for Genome Surgery" Science, Feb. 15, 2013, 399:768-770.
Panyam, et al. "Biodegradable nanoparticles for drug and gene delivery to cells and tissue" Advanced Drug Delivery Reviews, 2003, 55:329-347.
Patterson, et al. "Codon optimization of bacterial luciferase (lux) for expression in mammalian cells" J. Ind. Microbio. Biotechnology, 2005, 32:115-123.
Pinera, et al. "RNA-guided gene activation by CRISPR-Cas9-based transcription factors" Nature Methods, 2013, 10(10):973-978.
Platt, et al. "CRISPR-Cas9 Knockin Mice for Genome Editing and Cancer Modeling" Cell, 2014, 159(2):440-455.
Porteus, et al. "Gene targeting using zinc finger nucleases" Nature Biotechnology, 2005, 23(8):967-973.
Pougach, et al. "Transcription, Processing and Function of CRISPR Cassettes in *Escherichia coli*" Mol. Microbiol, 2010, 77(6):1367-1379.
Qi, et al. "Repurposing CRISPR as an RNA-Guided Platform for Sequence-Specific Control of Gene Expression" Cell, 2013, 152(5):1173-1183.
Ran, et al, "In vivo genome editing using *Staphylococcus aureus* Cas9," Nature, 2015, doi:10.1038/nature14299.

(56) References Cited

OTHER PUBLICATIONS

Ran et al. "Double Nicking by RNA-Guided CRISPR Cas9 for Enhanced Genome Editing Specificity," Cell 154, 1-10, Sep. 12, 2013.
Ran, et al. "Genome engineering using the CRISPR-Cas9 system" Nature Protocols, 2013, 8(11):2281-2308.
Rand, et al. "Argonaute2 Cleaves the Anti-Guide Strand of siRNA during RISC Activation" Cell, 2005, 123:621-629.
Raymond, et al. "High-Efficiency FLP and φC31 Site-Specific Recombination in Mammalian Cells" PLoS One, 2007, 2(1):e162. Doi. 10.1371/journal.pone.0000162.
Rebar, et al. "Induction of angiogenesis in a mouse model using engineered transcription factors" Nature Medicine, Dec. 2002, 8(12):1427-1432.
International Search Report dated Jan. 2, 2015, which issued during prosecution of International Application No. PCT/US2014/041806.
Wang, et al. "One-Step Generation of Mice Carrying Mutations in Multiple Genes by CRISPR/Cas-Mediated Genome Engineering" Cell 153(4):910-918, May 2013.
Woong, et al. "Efficient genome editing in zebrafish using a CRISPR-CAS system" Nature BioTechnology, 31(3):227-229, Jan. 2013.
Cong et al. "Multiplex Genome Engineering Using CRISPR/Cas Systems" Science 339(6121):819-823, Feb. 2013.
Cong et al. "Supplementary Material for: Multiplex Genome Engineering Using CRISPR/Cas Systems" Science 339(6121):819-823, Jan. 2013.
Jinek, et al. "A Programmable Dual-RNA-Guided DNA Endonuclease in Adaptive Bacterial Immunity" Science 337 (6096):816-821, Aug. 2012.
Jinek, et al. "Supplementary Materials for: A Programmable Dual-RNA-Guided DNA Endonuclease in Adaptive Bacterial Immunity" Science 337(6096):816-821, Aug. 2012.
Chylinski et al. "The tracrRNA and Cas9 families of type II CRISPR-Cas immunity systems", RNA Biology, 10(5):726-737, May 2013.
G. Gasiunas et al. "Cas9-crRNA ribonucleoprotein complex mediates specific DNA cleavage for adaptive immunity in bacteria" Proceedings of the National Academy of Sciences, 109(39:E2579-E2586), Sep. 2012.
Wiedenheft et al. "RNA-guided genetic silencing systems in bacteria and archaea", Nature 482(7385):331-338, Feb. 2012.
Elitza Deltcheva et al. "CRISPR RNA maturation by trans-encoded small RNA and host factor RNase III", -Nature 471(7340):602-607, Mar. 31, 2011.
Terns et al. "CRISPR-based adaptive immune systems", Current Opinion in Microbiology, 14(3):321-327, Jun. 2011.
Gaj, et al. "ZFN, TALEN, and CRISPR/Cas-based methods for genome engineering" Trends in Biotechnology 31(7):397-405, Jul. 2013.
Gilbert, et al. "CRISPR-Mediated Modular RNA-Guided Regulation of Transcription in Eukaryotes" Cell 154(2):442-451, Jul. 2013.
Hsu, et al. "Development and Applications of CRISPR-Cas9 for Genome Engineering", Cell 157(6):1262-1278, Jun. 2014.
Jiang Wenyan et al. "RNA-guided editing of bacterial genomes using CRISPR-Cas systems", Nature Biotechnology, 31(3):233-239, Mar. 2013.
U.S. Appl. No. 61/734,256, filed Dec. 6, 2012, Fuqiang Chen.
U.S. Appl. No. 61/758,624, filed Jan. 1, 2013, Fuqiang Chen.
U.S. Appl. No. 61/761,046, filed Feb. 5, 2013, Scott Knight.
U.S. Appl. No. 61/761,422, filed Mar. 15, 2013, Scott Knight.
U.S. Appl. No. 61/735,876, filed Dec. 11, 2012, Blake A. Wiedenheft.
U.S. Appl. No. 61/799,531, filed Mar. 15, 2013, Blake A. Wiedenheft.
U.S. Appl. No. 61/738,355, filed Dec. 17, 2012, George M. Church.
U.S. Appl. No. 61/799,169, filed Mar. 13, 2012, Prashant Mali.
U.S. Appl. No. 61/133,373, filed Mar. 20, 2012, Virginijus Siksnys.
U.S. Appl. No. 61/625,420, filed Apr. 17, 2012, Virginijus Siksnys.
U.S. Appl. No. 61/652,086, filed May 25, 2012, Martin Jinek.
U.S. Appl. No. 61/716,256, filed Oct. 19, 2012, Martin Jinek.
U.S. Appl. No. 61/736,527, filed Dec. 12, 2012, F. Zhang.
U.S. Appl. No. 61/757,640, filed Jan. 28, 2013, Jinek.
U.S. Appl. No. 61/794,422, filed Mar. 15, 2013, Knight.
Andreas, et al. "Enhanced efficiency through nuclear localization signal fusion on phage C31-integrase: activity comparison with Cre and FLPe recombinase in mammalian cells" Nucleic Acids Research, 2002, 30(11):2299-2306.
Asuri, et al. "Directed Evolution of Adeno-Associated Virus for Enhanced Gene Delivery and Gene Targeting in Human Pluripotent Stem Cells" Molecular Therapy, Feb. 2012, 30(2):329-338.
Al-Attar, et al., "Clustered regularly interspaced short palindromic repeats (CRISPRs): the hallmark of an ingenious antiviral defense mechanism in prokaryotes" Biol Chem., 2011, 392(4):277-289.
Baker, "Gene editing at CRISPR Speed" Nature Biotechnology, 2014, 32(4):309-312.
Banaszewska, et al. "Proprotein Convertase Subtilisin/Kexin Type 9: A New Target Molecule for Gene Therapy" Cellular & Molecular Biology Letters, Feb. 2012, 17(2):228-239.
Barrangou, "RNA-mediated programmable DNA cleavage" Nature Biotechnology, Sep. 2012, 30(9):836-388.
Bergemann, et al. "Excision of specific DNA-sequences from integrated retroviral vectors via site-specific recombination" Nucleic Acids Res., 1995, 23(21):4451-4456.
Bikard, et al. "CRISPR Interference Can Prevent Natural Transformation and Virulence Acquisition During In Vivo Bacterial Infection" Cell Host & Microbe, Aug. 2012, vol. 12:177-186.
Boch, et al. "Breaking the Code of DNA Binding Specificity of TAL-Type III Effecors" Science, 2009, 326:1509-1512.
Boch, et al. "Xanthomonas AvrBs3 Family-Type III Effectors: Discovery and Function" Annu. Rev. Phytopathol, 2010, Vo. 48:419-436.
Bogdanove, et al. "TAL Effectors:Customizable Proteins for DNA Targeting" Science, 2011, 333:1843-1846.
Briner, et al. "Guide RNA Functional Modules Direct Cas9 Activity and Orthogonality" Molecular Cell, Oct. 2014, 56:333-339.
Carroll, "A CRISPR Approach to Gene Targeting" Molecular Therapy, 2012, 20(9): 1658-1660.
Cermak, et al. Efficient design and assembly of custom TALEN and other TAL Effector-Based Constructs for DNA Targeting, Nucleic Acids Research (2011) vol. 39, No. 12, e82, p. 1-11.
Chen, et al. "Dynamic Imaging of Genomic Loci in Living Human Cells by an Optimized CRISPR/Cas System" Cell, Dec. 2013, vol. 155:1479-1491.
Jieliang Chen, et al. "An Efficient Antiviral Strategy for Targeting Hepatitis B Virus Genome Using Transcription Activator-Like Effector Nucleases" Molecular Therapy, 2014, 22(2):303-311.
Sidi Chen, et al., "Genome-wide CRISPR Screen in a Mouse Model of Tumor Growth and Metastasis," Cell, 2015, 160:1-15, http://dx.doi.org/10.1016/j.cell.2015.02.038.
Cho, et al. "Generation of Transgenic Mice" Curr Protoc Cell Biol., 2011, 19.11.doi:10.1002/0471143030. cb1911s42.
Choulika, et al., "Transfer of Single Gene-Containing Long Terminal Repeats into the Genome of Mammalian Cells by a Retroviral Vector Carrying the cre Gene and the loxP site" Journal of Virology, 1996, 70(3):1792-1798.
Christian, et al. "Targeting DNA Double-Strand Breaks With TAL Effector Nucleases" Genetics, Oct. 2010, vol. 186:757-761.
Christian, et al. "Supporting Information-Targeting DNA Double-Strand Breaks With TAL Effector Nucleases" Genetics, 2010, DOI:10.1534/110.120717:1SI-8SI.
Gong, et al. "Comprehensive interrogation of natural TALE DNA-binding modules and transcriptional repressor domains" Nature Communications, 2012, 3:968, DOI:10/2038/ncomms1962.
Connor, "Scientific split—the human genome breakthrough dividing former colleagues," Science, The Independent, Apr. 25, 2014, http://www.independent.co.uk/news/science/scientific-split-the-human-genome-breakthrough-dividing-former-colleagues-9300456.html.
Dahlman, et al. "In vivo endothelial siRNA delivery using polymeric nanoparticles with low molecular weight" Nat. Nanotechnol., 2014, 9(8)648-655. doi:10.1038/nnano.2014.84.
Datensenko, et al. "Molecular memory of prior infections activates the CRISPR/Cas adaptive bacterial immunity system" Nature Communications, Jul. 10, 2012, 3:935, DOI:10.1038/ncomms1937.

(56) References Cited

OTHER PUBLICATIONS

Dingwall, et al. "Abstract: A Polypeptide Domain That Specifies Migration of Nucleoplasmin into The Nucleus" Cell, 1982, 30(2):449-58.
Deltcheva, et al. "Supplementary Information: CRISPR RNA Maturation by Trans-Encoded Small RNA and Host Factor RNase III" www.Nature.com/doi:10.1038/nature09886:1-35, 2011.
Drittanti, et al. "High throughput production, screening and anyalysis of adeno-associated viral vectors" Gene Therapy, 2000, 7:924-929.
Ebina, et al. "Harnessing the CRISPR/Cas9 system to disrupt latent HIV-1 provirus" Scientific Reports, 2013, 2:2510, doi:10.1038/srep02510.
Ellis, et al. Macromolecular Crowding: Obvious But Underappreciated, TRENDS in Biochemical Sciences, Oct. 2001, 26(10):597-604.
Ellis, et al. "Zinc-finger nuclease-mediated gene correction using single AAV vector transduction and enhanced by Food and Drug Administration-Approved Drugs" Gene Therapy, 2013, vol. 20:35-42.
Enyeart, et al., "Biotechnological applications of mobile group II introns and their reverse transcriptases: gene targeting, RNA-seq, and non-coding RNA analysis" Mobile DNA, 2014, 5:2, http://www.mobilednajournal.com/contents5/1/2.
Gabriel, et al. "An unbiased genome-wide analysis of zinc-finger nuclease specificity" Nature Biotechnology, Aug. 2011, 29(9):816-823.
Garneau, et al. "The CRISPR-Cas bacterial immune systems cleaves bacteriophage and plasmid DNA" Nature, Nov. 2010, 468:67-71.
Goldfarb, et al. "Synthetic peptides as nuclear localization signals" Nature, Aug. 1986, 322(14):641-644.
Grens, Enzyme Improves CRISPR A smaller Cas9 protein enables in vivo genome engineering via viral vectors, The Scientist, Apr. 1, 2015.
Gustafsson, et al. "Codon Bias and heterologous protein expression" TRENDS in Biotechnology, Jul. 2004, 22(7):346-353.
Haft, et al. "Protein Families and Multiple CRISPR/Cas Subtypes Exist in Prokaryotic Genomes" PLoS Computational Biology, 2005, 1(6):0474-483.
Haft, et al. "A Guild of 45 CRISPR-Associated (Cas) Protein Families and Multiple CRISPR/Cas Subtypes Exist in Prokaryotic Genomes" PLoS Computational Biology, 2005, 1(6):0474-0483.
Hale, et al. "Essential Features and Rational Design of CRISPR RNAs that Function With the Cas RAMP Module complex to Cleave RNAs" Molecular Cell, 2012, 45(3):292-302.
Hale, et al. "RNA-Guided RNA Cleavage by a CRISPR RNA-Cas Protein Complex" Cell, 2009, 139:945-956.
Hale, et al. "Prokaryotic siliencing (psi) RNAs in Pyrococcus furiosus", RNA, 2008, 14:2572-2579.
Handel, et al. "Versatile and Efficient Genome Editing in Human Cells by Combining Zinc-Finger Nucleases With Adeno-Associated Viral-Vectors" Human Gene Therapy, Mar. 2012, 23:321-329.
Hibbitt, et al. "RNAi-mediated knockdown of HMG CoA reductase enhances gene expression from physiologically regulated low-density lipoprotein receptor therapeutic vectors in vivo" Gene Therapy, 2012, 19:463-467.
Hou, et al., "Efficient genome engineering in human pluripotent stem cells using Cas9 from Neisseria meningitides," PNAS, 2013, 110(39):15644-15649.
Horvath et al. "RNA-guidded genome editing ala carte" Cell Research, 2013, 23:733-734, doi:10.1038/cr.2013.39.
Hsu et al., "DNA targeting specificity of RNA-guided Cas9 nucleases," Nature Biotechnology, 2013, 31(9):827-834.
Hsu et al., "Supplementary Information-DNA targeting specificity of RNA-guided Cas9 nucleases," Nature Biotechnology, 2013, doi:10.1038/nbt.2647.
Hwang Woong, et al. "Efficient genome editing in zebrafish using a CRISPR-Cas System" Nature Biotechnology, Mar. 2013, 31(3):227-229.

Hwang Woong, et al. "Efficient In Vivo Genome Editing Usng RNA-Guided Nucleases" Nat. Biotechnol., 2013, 31(3):227.229. doi. 1.1038/mbt.2501.
Reiss, et al. "RecA protein stimulates homologous recombination in plants" Proc. Natl. Acad. Sci. USA, 1996, 93:3094-3098.
Sanders, et al. "Use of a macromolecular crowding agent to dissect interactions and define functions in transcriptional activation by a DNA-tracking protein: Bacteriophage T4 gene 45 protein and late transcription" PNAS, 1994, 9:7703-7707.
Sapranauskas, et al. "The Streptococcus thermophilus CRISPR-Cas system provides immunity in Escherichia coli" Nucleic Acids Research, 2011, 39(21): 9275-9282.
Sauer, "Functional Expression of the cre-lox Site-Specific Recombination System in the Yeast Saccharomyces cerevisiae" Mol. Cell. Biol., 1987, 7(6):2087-2096.
Sauer, et al. "Site-specific DNA recombination in mammalian cells by the Cre recombinase of bacteriophage P1" Proc. Natl. Acad. Sci. U.S.A., 1988, 85:5166-5170.
Schiffer, et al. "Predictors of Hepatitis B Cure Using Gene Therapy to Deliver DNA Cleavage Enzymes: A Mathematical Modeling Approach" PLOS Computational Biology,, 2013, 9(7):e1003131. www.ploscompbiol.org.
Scholze, et al. "TAL effector-DNA specificity" Virulence, 2010, 1(5):428-432, DOI:10.4161/viru.1.5.12863.
Schramm et al. "Recruitment of RNA polymerase III to its target promoters" Genes & Development, 2002, 16:2593-2620.
Seung Woo Cho, et al., "Targeted genome engineering in human cells with the Cas9 RNA-guided endonuclease" Nature Biotechnology, Mar. 2013, 31(3):230-232.
Seung Woo Cho, et al. "Supplementary Information: Targeted genome engineering in human cells with RNA-guided endonuclease" Nature Biotechnology, Mar. 2013, 31(3):1-10.
Seung Woo Cho, et al. "Analysis off-target effects of CRISPR/Cas-derived RNA-guided endonucleases and nickases" Genome Research, Nov. 2014, 24:132-141.
Shalem et al., "Genome-Scale CRISPR-Cas9 Knockout Screening in Human Cells", Science, 2014, 343;84-87. DOI:10.1126/science.1247005.
Shen, et al. "Efficient genome modification by CRISPR-Cas9 mickase with minimal off-target effects" 2014, Nature Methods, 11(4):399-404.
Shen, et al. "Generation of gene-modified mice via Cas9/RNA-mediated gene targeting" Cell Research, 2013, 23:720-723.
Sims, et al., "High-throughput RNA interference screening using pooled shRNA libraries and next generation sequencing", Genome Biology 12(10):R104, Oct. 2011.
Sontheimer, "Project 7: Establishing RNA-Directed DNA Targeting in Eukaryotic Cells" Physical Sciences—Onc., Nov. 16, 2011-Dec. 31, 2012, htt://groups.molbiosci.northwestern.edu/sontheimer/Sontheimer_cv.php) Molecular Biosciences.
Sosa, et a. "Animal transgenesis: an overiew" Brain Struct Funct, 2010, 214:91-109.
Stolfi, et al, "Tissue-specific genome editing in Ciona embryos by CRISPR/Cas9," Development, 2014, 141:4115-4120 doi:10.1242/dev.114488.
Swiech et al., "In vivo interrogation of gene function in the mammalian brain using CRISPR-Cas9," Nature Biotechnology, 2015, doi:10.1038/nbt.3055.
Tolia, et al. "Slicer and the Argonautes" Nature Chemical Biology, 2007, 3(1):36-43.
Trevino, et al. "Genome Editing Using Cas9 Nickases" Methods in Enxymology, 2014, 546:161-174.
Urnov, et al. "Highly efficient endogenous human gene correction using designed zinc-finger nucleases" Nature, 2005, 435:646-651.
Wu, et al. "Genome-wide binding of the CRISPR endonuclease Cas9 in mammalian cells" Nature Biotechnology, 2014, doi:10.1038/nbt.2889.
Xiao, et al. "Chromosomal deletions and inversions mediated by TALENs and CRIPPR/Cas in zebrafish" Nucleic Acids Research, 2013, 41(14):E141. doi:10.1093/nar/gkt464.
Xiao, et al. Production of High-Titer Recombinant Adeno-Associated Virus Vectors in the Absence of Helper Adenovirus, 1998.

(56) References Cited

OTHER PUBLICATIONS

Zetsche et al. "A split-Cas9 architecture for inducible genome editing and transcription modulation," Nature biotechnology, 2015, 33(2): 139-142.

Zhang, X. D., et al., "cSSMD: assessing collective activity for addressing off-target effects in genome-scale RNA interference screens", Bioinformatics (Oxford), 27(20);2775-2781, Oct. 2011.

Zhang, et al. "Efficient construction of sequence-specific TAL effectors for modulating mammalian transcription" nature biotechnology, 2011, 29(2):149-154.

Zhu, et al. "Crystal structure of Cmr2 suggests a nucleotide cyclase-related enzyme in type III CRISPR-Cas sytems" FEBS Letters, 2012, 939-945. Doi:10.1016/j.febslet2012.02.036.

Geißler, et al. "Trancscriptional Activators of Human Genes with Programmable DNA-Specificity" PLos One, 2011, 6(5):e19509. Doi:10.1371/hournal.pone.0019509.

"Crispr genome engineering" XP055167591, Oct. 5, 2013, https://web.archive.org/web/2013100500 [retrieved on Feb. 5, 2015].

"Fixes, extra genomes, and improvements to the CRISPR Design Tool" Google Groups, XP055167583, Oct. 21, 2013, URL:https://groups.google.com/forum/#!topic/crispr/g9Q8U1tNSis [retrieved on Feb. 5, 2015].

"The CRISPR Revolution," Catalyst Magazine, College of Chemistry, University of California, Berkeley, http://catalyst.berkeley.edu/slideshow/the-crispr-revolution/[19/12/2014 12:40:53] (Jul. 9, 2014).

Abudayyeh, et al., "C2c2 is a single-component programmable RNA-guided RNA-targeting CRISPR effector," Science, vol. 10, dated 2016.

Addgene Materials May 2015.

Addgene Materials Oct. 2014 including Addgene News 2013.

Alberts, et al., Molecular Biology of The Cell, fourth edition, 2002, 671-676.

*Arbitron, Inc.* v. *Kiefl*, No. 09-CV-04013 PAC, 2010 WL 3239414, at *1 (S.D.N.Y. Aug. 13, 2010).

Au, et al. "Characterization of a baculovirus nuclear localization signal domain in the late express factor 3 protein", Virology, 2009, 385:209-217.

Ausubel, et al. "Compendium of Methods from Current Protocols in Molecular Biology", Short Protocols in Molecular Biology, Fourth Edition, 1999, 9: 9-3-9-4.

Autofluorescence MIT Flow Cytometry Core Facility (2018), 6 pages.

Baena-Lopez, L., et al., "Accelerated homologous recombination and subsequent genome modification in *Drosophila*," Development, vol. 140, No. 23, pp. 4818-4825, dated Dec. 2013, 18 pages, including Supplementary Material.

Baiker, et al. "The Immediate-Early 63 Protein of Varicella-Zoster Virus: Analysis of Functional Domains Required for Replication In Vitro and for T-Cell and Skin Tropism in the SCIDhu Model In Vivo", Journal of Virology, 2004, 78(3):1181-1194.

Balboa et al., "Conditionally Stabilized dCas9 Activator for Controlling Gene Expression in Human Cell Reprogramming and Differentiation. (plus Supplemental Information)", Stem Cell Reports, vol. 5, No. 3, Sep. 8, 2015, pp. 448-459 16PP.

Barrangou and Van Der Oost (Eds.), "CRISPR-Cas Systems," Springer Heidelberg (2013; written in 2012 before the publication of Cong et al.).

Barrangou, R. et al.: "CRISPR provides acquired resistance against viruses in prokaryotes," Science, vol. 315, pp. 1709-1712, dated Mar. 23, 2007, 5 pages.

Bassett, et al. "Highly Efficient Targeted Mutagenesis of *Drosophila* with the CRISPR/Cas9 System" Cell Reports, 2013, 4:220-228.

Bassett, et al., "A Genome-Wide CRISPR Library for High-Throughput Genetic Screening in *Drosophila* Cells," Journal of Genetics and Genomics, vol. 42, pp. 301-309, dated 2015.

Bauer, et al., "An Erythroid Enhancer of BCL11A Subject to Genetic Variation Determines Fetal Hemoglobin Level," Science, vol. 342, pp. 253-257, dated 2013.

Beerli, et al. "Positive and negative regulation of endogenous genes by designed transcription factors:" PNAS, 2000, 97(4):1495-1500.

Beerli, et al. "Toward controlling gene expression at will: Specific regulation of the erbB-2/HER-2 promoter by using polydactyl zinc finger proteins constructed from modular building blocks", Proc. Natl. Acad. Sci., 1998, 95:14628-14633.

Beerli, R., et al., "Engineering polydactyl zinc-finger transcription factors," Nature Biotechnology, vol. 20, pp. 135-141, dated Feb. 2002, 7 pages.

Bennett et al., "Stable transgene expression in rod photoreceptors after recombinant adeno-associated virus-mediated gene transfer to monkey retina", Proc. Natl. Acad. Sci., USA, vol. 96, Aug. 1999, pp. 9920-9925.

Berns, K., et al. "A Large-Scale RNAi Screen in Human Cells Identifies New Components of the p53 Pathway," Nature 2004, vol. 428, pp. 431-437, dated Mar. 25, 2004, 7 pages.

Bhaya, D., et al., "CRISPR-Cas Systems in Bacteria and Archaea: Versatile Small RNAs for Adaptive Defense and Regulation," Annual Review of Genetics, vol. 45, No. 1, pp. 273-297, dated Dec. 15, 2011, 27 pages.

Bikard, et al. Supplementary Information for: "CRISPR Interference Can Prevent Natural Transformation and Virulence Acquisition During In Vivo Bacterial Infection," Cell Host & Microbe, vol. 12, No. 2, pp. 177-186, dated Aug. 16, 2012, 10 pages.

Birch, et al. "Plant Transformation: Problems and Strategies for Practical Application", Annu. Rev. Plant Physiol. Plant Mol. Biol., 1997, 48:297-326.

Bloom et al., "Inactivation of hepatitis B virus replication in cultured cells and in vivo with engineered transcription activator-like effector nucleases", Molecular Therapy, Aug. 20, 2013, vol. 21, No. 10, pp. 1889-1897.

Bobis-Wozowicz, S., et al., "Targeted genome editing in pluripotent stem cells using zinc-finger nucleases," Methods, vol. 53, pp. 339-346, dated 2011, 8 pages.

Boden, et al. "Efficient Gene Transfer of HIV-1-Specific Short Hairpin RNA into Human Lymphocytic Cells Using Recombinant Adeno-associated Virus Vectors", Molecular Therapy, 2004, 9(3):396-402.

Bohm, "The computer program LUDI: A new method for the de novo design of enzyme inhibitors", Journal of Computer-Aided Molecular Design, 1992, vol. 6, pp. 61-78.

Bouard, et al. "Themed Section: Vector Design and Drug Delivery Review, Viral vectors: from virology to transgene expression", British Journal of Pharmacology, 2009, 157:153-165.

Boutros et al.: "Genome-wide RNAi analysis of growth and viability in *Drosophila* cells," Science, American Association for the Advancement of Science, vol. 303, No. 5659, pp. 832-835, dated Feb. 6, 2004, 4 pages.

Branden, C., and Tooze, J., "Prediction, Engineering, and Design of Protein Structures," Introduction to Protein Structure, Chapter 16, p. 247, Garland Publishing, Inc., New York, dated 1991, 3 pages.

Brouns, S, "A Swiss Army Knife of Immunity," Science, vol. 337, No. 6096, pp. 808-809, dated Aug. 17, 2012, 3 pages.

Brouns, S., et al., "Small CRISPR RNAs Guide Antiviral Defense in Prokaryotes," Science, vol. 321, pp. 960-964, dated Aug. 15, 2008, 6 pages.

Campeau, et al. "A Versatile Viral System for Expression and Depletion of Proteins in Mammalian Cells", PLoS One, 2009, 4(8):e6529.

Canver, et al., "BCL11A enhancer dissection by Cas9-mediated in situ saturating mutagenesis," Nature, vol. 527, pp. 192-197, including Supplementary Material, dated 2015.

Carr, et al., "Genome engineering", Nature Biotechnology, 2009, 27(12):1151-1162.

Carroll, "Genome Engineering With Zing-Finger Nucleases", Genetics, 2011, 188:773.782.

Carroll, "Progress and prospects: Zinc-finger nucleases as gene therapy agents", Gene Therapy, 2008, 15:1463-1468.

Chan, et al. "Characterization of the Kinetochore Binding Domain of CENP-E Reveals Interactions with the Kinetochore Proteins CENP-F and hBuBR1", The Journal of Cell Biology, 1998, 143:49-63.

(56) References Cited

OTHER PUBLICATIONS

Chan, Wai-Ting, et al. "Toxin-Antitoxin Genes of the Gram-Positive Pathogen *Streptococcus pneumoniae*: So Few and Yet So Many", Microbiology and Molecular Biology Reviews, 2012, 76(4):773-791.

Chang, N., et al. "Genome editing with RNA-guided Cas9 nuclease in Zebrafish embryos", Cell Research, vol. 23, pp. 465-472, dated Mar. 26, 2013, 8 pages.

Chen, Fuqiang et al. "High-frequency genome editing using ssDNA oligonucleotides with zinc-finger nucleases". Nature Methods, 2011, 8(9):753-755, including Supplemental Online Methods.

Chinnasamy, D., et al., "Multicistronic lentiviral vectors containing the FMCV 2A Cleavage factor demonstrate robust expression of encoded genes at limiting MOI," Virology Journal, vol. 3, No. 4, dated Mar. 15, 2006, 16 pages.

Chiu et al, "Engineered GFP as a vital reporter in plants", Current Biology, (1996), 6(3):325-330.

Chou, JY, and Mansfield, BC, "Recombinant AAV-directed gene therapy for type I glycogen storage diseases," Expert Opinion on Biological Therapy, vol. 11, No. 8, pp. 1011-1024, dated Apr. 20, 2011, 21 pages.

Chylinski, et al. "Classification and evolution of type II CRISPR-Cas systems", Nucleic Acids Research, 2014, 42(10):6091-6105,doi:10.1093InarIgku241.

Clark, K., et al., "A Tale of Two Nucleases: Gene Targeting for the Masses?" Zebrafish, vol. 8, No. 3, pp. 147-149, dated 2011, 3 pages.

Cockrell, "Berkeley's Wikipedian-in-residence is a first," NewsCenter, Feb. 25, 2014.

Community Corner, "CRISPR technology for gene therapy," Nature Medicine, vol. 20, No. 5, pp. 476-477, dated May 2014, 3 pages.

Cong, et al., Oct. 5, 2012 Manuscript including Supplementary Materials, "CRISPR-Assisted Mammalian Genome Engineering," published as "Multiplex Genome Engineering Using CRISPR-Cas Systems," Science, vol. 339, pp. 819-823, dated Feb. 15, 2013, 36 pages.

Cong, L., et al., "In Vivo Genome Engineering With AAV Vector Carrying CRISPR-Cas9 System," Molecular Therapy, vol. 22, Supplement 1, p. S214, dated May 23, 2014, 1 page.

Cong, L., et al., Supplementary Material for: "Multiplex Genome Engineering Using CRISPR-Cas Systems," Science Express, dated Jul. 5, 2012.

Costantino, et al., "Enhanced levels of alpha Red-mediated recombinants in mismatch repair mutants", PNAS, 100(26):15748-15753, 2003.

Cotropia, et al., "Copying in Patent Law," N.C.L. Rev., Stanford Public Law Working Paper No. 1270160 (2009), 87:1421.

Cummings et al., "Fourteen and counting: unraveling trinucleotide repeat diseases", Human Molecular Genetics, 2000, vol. 9, No. 6, pp. 909-916.

Daboussi, F., et al., "Chromosomal context and epigenetic mechanisms control the efficacy of genome editing by rare-cutting designer endonucleases," Nucleic Acids Research, vol. 40, No. 13, pp. 6367-6379, dated Jul. 13, 2012, 13 pages.

Dai, et al. "Genes:Structures and Regulation: The Transcription Factors GATA4 and dHAND Physically Interact to Synergistically Activate Cardiac Gene Expression through a p300-dependent Mechanism", J. Biol. Chem., 2002, 277:24390-24398.

Daley, J., and Wilson, T., "Rejoining of DNA Double-Strand Breaks as a Function of Overhang Length," Molecular and Cellular Biology, vol. 25, No. 3, pp. 896-906, dated Feb. 2005, 11 pages.

Damian, M., and Porteus, M., "A Crisper Look at Genome Editing: RNA-guided Genome Modification," Molecular Therapy, vol. 21, No. 4, pp. 720-722, dated Apr. 2013, 3 pages.

Database GenBank, "*Staphlococcus aureus* subsp.*aureus* ORFX gene and pseudo SCCmec-SCC-SCCCRISPR element, strain M06/0171," Accession No. HE980450, http://www.ncbi.nlm.nih.gov/nuccore/HE980450, dated Aug. 18, 2016, 22 pages.

Database GenBank: "CRISPR-associated protein, Csn1 family, *Staphylococcus pseudintermedius* ED99," Accession No. ADX75954, http://www.uniprot.org/uniprot/G1UFN3.txt?version=3, dated Nov. 21, 2011, 1 page.

Database UniProt: "CRISPR-associated endonuclease Cas9: *Staphylococcus aureus*," UniProtKB, J7RUA5 (CAS9_STAAU), XP002738511M, https://www.uniprot.org/uniprot/J7RUA5#, dated Oct. 31, 2012, 7 pages.

Database UniProtKB/TrEMBL [online], Accession No. Q0P897, "The genome sequence of the foodborne pathogen Campylobacter jejuni reveals hypervariable sequences," Subname: Full=Putative CRISPR-associated protein, Oct. 3, 2012 uploaded, [retrieved on Nov. 22, 2017], URL, http://www.uniprot.org/uniprot/Q0P897.txt?version=28.

Database UniProtKB/TrEMBL, Accession No. D0W2Z9, http://www.uniprot.org/uniprot/D0W2Z9.txt?version=4, dated Oct. 3, 2012, 1 page.

Database UniProtKB/TrEMBL, Accession No. G1UFN3, http://www.uniprot.org/uniprot/G1UFN3.txt?version=3, dated Oct. 3, 2012, 1 page.

Database UniProtKB/TrEMBL, Accession No. J3TRJ9, http://www.uniprot.org/uniprot/J3TRJ9.txt?version=2, dated Oct. 31, 2012, 1 page.

Database UniProtKB/TrEMBL, Accession No. Q0P897, http://www.uniprot.org/uniprot/Q0P897.txt?version=28, dated Oct. 3, 2012, 1 page.

Database UniProtKB/TrEMBL, Accession No. Q6NK13, http://www.uniprot.org/uniprot/Q6NKI3.txt?version=43, dated Jun. 13, 2012, 1 page.

Database UniProtKB/TrEMBL, Accession No. Q73QW6, http://www.uniprot.org/uniprot/Q73QW6.txt?version=4, dated Nov. 28, 2012, 2 pages.

Database WPI, Week 201437 Thomson Scientific, London, GB; AN 2014-J79552, XP-002737563, 2 pages.

Declaration of Feng Zhang for U.S. Appl. No. 14/054,414 dated Jan. 30, 2014, 10 pages.

Declaration of Paul Simons dated Dec. 22, 2015.

Dicarlo, et al. "Genome engineering in *Saccharomyces cerevisiae* using CRISPTR-Cas systems", Nucleic Acids Research, 2013, 41(7):4336-4343, doi:10.1093/nar/gkt135.

Dingwall, et al. "The Nucleoplasmin Nuclear Location Sequence Is Larger and More Complex than That of SV-40 Large T Antigen", The Journal of Cell Biology, 1988, 107:841-849.

Do, et al. "Identification of multiple nuclear localization signals in murine Elf3, an ETS transcription factor" FEBS Letters, 2006, 580:1865-1871.

Doench, et al., "Rational design of highly active sgRNAs tor CRISPR-cas9-mediated gene inactivation," Nature Biotechnology, vol. 32, No. 12, pp. 1262-1267, including Supplementary Material, dated 2014.

Dominguez, et al., "Beyond editing: repurposing CRISPR-Cas 9 for precision genome regulation and interrogation" Nat Rev Mol Cell Biol., 2016, 17(1):5-15, doi:10.1038/nrm.2015.2.

Dong, et al. "The crystal structure of Cpf1 in complex with CRISPR RNA," Nature, vol. 532, pp. 523-525, including Research Letter, dated 2016.

Dworetzky, S., et al., "The Effects of Variations in the Number and Sequence of Targeting Signals on Nuclear Uptake," The Journal of Cell Biology, vol. 107, pp. 1279-1287, dated Oct. 1988, 9 pages.

Ellis, Hilary, et al. "High efficiency mutagenesis, repair, and engineering of chromosomal DNA using single-stranded oligonucleotids" PNAS, 2001, 98(12):6742-6746.

Espinoza, et al., "Characterization of the structure, function, and mechanism of B2 RNA, an ncRNA repressor of RNA polymerase II transcription", RNA, 2007, 13(4):583-596.

Excerpt from Declaration of Feng Zhang, dated Sep. 9, 2015.

Federal Circuit decision in *Dow Chemical Co.* v. *Nova Chemicals Corp.*, Appeal Nos. 2014-1431, 2014-1462 (Fed. Cir. Aug. 28, 2015) (*Dow* v. *Nova*), 25 pages.

Feldgarden et al., "*Staphylococcus aureus* M0408 acrHk-supercont1.1, whole genome shotgun sequence", NCBI Reference Sequence: NK_KB821326.1, Direct Submission, Dec. 10, 2012, pp. 1-4.

(56) References Cited

OTHER PUBLICATIONS

Fieck, et al. "Modifications of the *E. coli* Lac repressor for expression in eukaryotic cells: effects of nuclear signal sequences on protein activity and nuclear accumulation", Nucleic Acids Research, 1992, 20(7):1785-1791.

Fischer-Fantuzzi, L., and Vesco, C., "Cell-dependent efficiency of reiterated nuclear signals in a mutant simian virus 40 oncoprotein targeted to the nucleus," Molecular and Cellular Biology, vol. 8, No. 12, pp. 5495-5503, dated 1988, 10 pages.

Fleming, J., et al.: "Adeno-Associated Virus and Lentivirus Vectors Mediate Efficient and Sustained Transduction of Cultured Mouse and Human Dorsal Root Ganglia Sensory Neurons," Human Gene Therapy, vol. 12, pp. 77-86, dated Jan. 1, 2001, 10 pages.

Foecking, et al. "Powerful and versatile enhance-promoter unit for mammalian expression vectors", Gene, 1986, 101-105.

Fonfara et al., "Phylogeny of Cas9 determines functional exchangeability of dual-RNA and Cas9 among orthologous type II CRISPR-Cas systems", Nucleic Acids Research, 2014, vol. 42, No. 4, pp. 2577-2590.

Freitas, et al. "Mechanisms and Signals for the Nuclear Import of Proteins", Current Genomics, 2009, 10:550-557.

Fu et al, "Targeted genome editing in human cells using CRISPR/Cas nucleases and truncated guide RNAsc", Jan. 1, 2014, The Use of CRISPR/Cas9 ZFNs and Talens in Generating Site-Specific Genome Alterations; Methods in Enzymology; ISSN 1557-7988, vol. 546, Elsevier, NL, pp. 21-45.

Fu, et al. "High-frequency off-target mutagenesis induced by CRISPR-Cas nucleases in human cells", Nature Biotechnology, 2013, 31(9):822-826.

Gaj, T., et al., Targeted gene knockout by direct delivery of zinc-finger nuclease proteins. Nature Methods, vol. 9, No. 8, pp. 805-807, dated Aug. 2012, 5 pages.

Gao, et al. "Engineered Cpf1 Enzymes with Altered PAM Specificities", BioRxiv Preprint, XP-002769442, 2016, doi:http://dx.doi.org/10.1101/091611, 1-13, including Figure Legends.

Gao, et al. "Engineered Cpf1 variants with altered PAM specificities", Nature Biotechnology, 2017, 1-4, doi:10.1038/nbt.3900, advanced online publication including Supplementary Information.

Garcia-Bustos, et al. "Nuclear protein localization", Biochimica et Biophysica Acta, 1991, 1071:83-101.

Gardlik, R., et al., "Vectors and delivery systems in gene therapy," Medical Science Monitor, vol. 11, No. 4, pp. RA110-RA121, dated Apr. 1, 2005, 12 pages.

Garg, et al. "Engineering synthetic TAL effectors with orthogonal target sites", Nucleic Acids Research, 2012, 40(15):7584-7595, doi:10.1093/nar/gks404.

Garriga-Canut, M., et al., "Synthetic zinc finger repressors reduce mutant huntingtin expression in the brain of R6/2 mice," Proceedings of the National Academy of Sciences, vol. 109, No. 45, pp. E3136-E3145, dated Nov. 6, 2012, 10 pages.

Geisinger et al., "In vivo blunt-end cloning through CRISPR /CAS9-facilitated non-homologous end-joining", Nucleic Acid Research Advance Access, Jan. 13, 2016, pp. 1-15.

Gomaa, et al. "Programmable removal of bacterial strains by use of genome-targeting CRISPR-Cas systems", MBio., 2014, 5(1):e00928-13.

Goncalves, M., et al., "Concerted nicking of donor and chromosomal acceptor DNA promotes homology-directed gene targeting in Human Cells," Nucleic Acids Research, vol. 40, No. 8, pp. 3443-3455, dated Dec. 20, 2011, 13 pages.

Gratz, et al. "Genome Engineering of *Drosophila* with the CRISPR RNA-Guided Cas9 Nuclease", Genetics, 2013, 194:1029-1035.

Greenspan, et al. "Two Nuclear Location Signals in the Influenza Virus NS1 Nonstructural Protein", Journal of Virology, 1988, 62(8):3020-3026.

Grieger, J., and Samulski, R., "Packaging Capacity of Adeno-Associated Virus Serotypes: Impact of Larger Genomes on Infectivity and Postentry Steps," Journal of Virology, vol. 79, No. 15, pp. 9933-9944, dated Aug. 2005, 12 pages.

Grissa, I., et al., "CRISPRFinder: a web tool to identify clustered regularly interspaced short palindromic repeats," Nucleic Acids Research, vol. 35, pp. W52-W57, dated 2007, 6 pages.

Guan, et al. "Heritable endogenous gene regulation in plants with designed polydactyl zinc finger transcription factors", PNAS, 2002, 99(20):13296-13301.

Habib, N., Assignment to Broad Institute, dated Jun. 9, 2014, 4 pages.

Haft, D.H., "HMM Summary Page: TIGR04330", 2012, XP-002757584, http:cvi.org/cgi-bin/tigrfams/HmmReportPage.cgi?acc=TIGR04330.

Hall, B., et al., "Overview: Generation of Gene Knockout Mice," Current Protocols in Cell Biology, unit 19.12, suppl. 44, pp. 1-17, dated 2009, 17 pages.

Harrison et al., "A CRISPR view of development", Genes & Development, vol. 28, No. 17, Sep. 1, 2014, pp. 1859-1872.

Heintze, et al. "A CRISPR CASe for high-throughput silencing", Frontiers in Genetics, Oct. 2013, 4(193): DOI:10.3389/gfene.2013.00193.

Hicks, et al. "Protein Import Into the Nucleus: An Integrated View", Annu. Rev. Cell Dev. Biol., 1995, 11:155-188.

Ho, et al, "Targeting non-coding RNAs with the CRISPR/Cas9 system in human cell lines," Nucleic Acids Research, vol. 43, No. 3, p. e17, dated 2015.

Hockemeyer, et al. "Highly efficient gene targeting of expressed and silent genes in human ESCs and iPSCs using zinc finger nucleases", Nat Biotechnol., 2009, 27(9):851-857, doi:10.1038/nbt.1562.

Holkers, M., et al., "Adenoviral vector DNA for accurate genome editing with engineered nucleases," Nature Methods, vol. 11, No. 10, pp. 1051-1057, Aug. 24, 2014, 8 pages (Only Abstract Available).

Holmes, "CRISPR Genome Engineering Resources" XP055167586, Oct. 2, 2013, https://groups.google/forum/#!top1c/crispr/5BpJj_Y3yIG [retrieved on Feb. 5, 2015].

Holmes, "Understanding Scores" XP055167918, Oct. 23, 2013, https://groups.google.com/forum/#!profo_nt50txrP9Yb6e_LXccolb9hNf7gKeMLt6rgaVQ4fOsQ/crispr/fkhX7Fu3r-1/rziHxKT76pYJ [retrieved on Feb. 6, 2015].

Houdebine, L., "The methods to generate transgenic animals and to control transgene expression," Journal of Biotechnology, vol. 98, pp. 145-160, dated 2002, 16 pages.

*Huang v. California Institute of Technology*, 2004 WL 2296330 (C.D. Cal. Feb. 18, 2004).

Hung, S., et al., "AAV-Mediated CRISPR/Cas Gene Editing of Retinal Cells in Vivo," Investigative Ophthalmology & Visual Science, vol. 57, No. 7, pp. 3470-3476, dated Jun. 2016, 7 pages.

Imagawa, et al. "Two nuclear localization signals are required for nuclear translocation of nuclear factor 1-A", FEBS Letters, 2000, 484118-124.

Incontro, S., et al., "Efficient, Complete Deletion of Synaptic Proteins using CRISPR," Neuron, vol. 83, No. 5, pp. 1051-1057, dated Sep. 3, 2014, 13 pages.

Iwamoto et al., "A General Chemical Method to Regulate Protein Stability in the Mammalian Central Nervous System", Chemistry and Biology, Current Biology, London, GB, vol. 17, No. 9, Sep. 24, 2010, pp. 981-988.

Jackson, A., et al. "Widespread siRNA "off-target" transcript silencing mediated by seed region sequence complementarity," RNA 2006, vol. 12, No. 7, dated Mar. 16, 2006, 10 pages.

Jao, et al. Proceeding of the National Academy of Sciences, 2013, www.pnas.org/cgi/doi/10.1073/pnas.1308335110.

Jiang, W., et al., "RNA-guided editing of bacterial genomes using CRISPR-Cas systems," Nature Biotechnology, vol. 31, No. 3, pp. 233-239, dated Mar. 2013, 30 pages, including Supplementary Materials.

Jinek, M., et al, "A programmable Dual-RNA-Guided DNA Endonuclease in adaptive bacterial immunity," Science, vol. 337, n. 6096, pp. 816-821, dated Aug. 17, 2012, 7 pages.

Jinek, M., et al., Figures and figure supplements for: "RNA-programmed genome editing in human cells," eLIFE, vol. 2, No. e00471, dated Jan. 29, 2013, 5 pages.

(56) References Cited

OTHER PUBLICATIONS

Joseph, T., and Osman, R., "Thermodynamic basis of selectivity in guide-target-mismatched RNA interference," Proteins, vol. 80, No. 5, pp. 1283-1298, dated May 2012, 26 pages.
Joshi, et al., "Evolution of I-SceI homing endonucleases with increased DNA recognition site specificity", Journal of Molecular Biology, 2011, 405(1):185-200; ePub: Oct. 26, 2010.
Joung, et al. "TALENs: a widely applicable technology for targeted genome editing", Nat Ref. Mol. Cell Biol., 2013, 14(1):49-55. doi:10.1038/nrm3586.
Kalderon, et al. "A Short Amino Acid Sequence Able to Specify Nuclear Location", Cell, 1984, 39:499-509.
Kiani, et al. "CAS9 gRNA engineering for genome editing, activation and repression", Nature Methods, Advanced Online Publication, 2015, DOI:10.1038/NMETH.3580.
Kim, E., et al., "Precision genome engineering with programmable DNA-nicking enzymes," Genome Research, vol. 22, pp. 1327-1333, dated 2012, 8 pages.
Kim, S., et al., "CRISPER RNAs trigger innate immune responses in human cells," Genome Research, pp. 1-7, dated Feb. 22, 2018, 8 pages.
Kinnevery, P., et al., "Emergence of Sequence Type 779 Methicillin-Resistant *Staphylococcus aureus* Harboring a Novel Pseudo Staphylococcal Cassette Chromosome mec (SCCmec)-SCC-SCC CRISPR Composite Element in Irish Hospitals," Antimicrobial Agents and Chemotherapy, vol. 57, No. 1, pp. 524-531, dated Jan. 2013, 8 pages.
Kleinstiver et al., "High-fidelity CRISP-Cas9 nucleases with no detectable genome-wide off-target effects", Nature, vol. 529, No. 7587, Jan. 28, 2016, pp. 490-495.
Kleinstiver, et al. "Engineered CRISPR-Cas9 nucleases with altered PAM specificities," Nature, vol. 523, pp. 481-485, including Research Letter, dated 2015.
Kondo, et al. "Highly Improved Gene Targeting by Germline-Specific Cas9 Expression in *Drosphila*", Genetics, 2013, 195:715-721.
Kosugi, et al. "Six Classes of Nuclear Localization Signals Specific to Different Binding Grooves of Importin a . . . " The Journal of Biological Chemistry, 2009, 284(1):478-485.
Kowalski, Thomas J., PowerPoint Presentation, "interview Sep. 9, 2015."
Krauer, et al. "Identification of the nuclear localization signals within the Epstein-Barr virus EBNA-6 protein", Journal of General Virology, 2004, 85:165-172.
Kuhlman, et al. "A place for everything$201 D Chromosomal intergration of large constructs", Bioengineered Bugs, Jul./Aug. 2010, 1(4)296-299.
Kuhlman, et al. "Site-specific chromosomal integration of large synthetic constructs", Nucleic Acids Research, 2010, 38(6):1-10, doi:10.1093/nar/gkp1193.
Kumar, M., et al., "Systematic Determination of the Packaging Limit of Lentiviral Vectors," Human Gene Therapy, vol. 12, pp. 1893-1905, dated Oct. 10, 2001, 21 pages.
Kuwayama, H., "Enhancement of Homologous Recombination Efficiency by Homologous Oligonucleotides," Cell Interaction Sivakumar Gowder, IntechOpen, DOI: 10.5772/47779, dated Oct. 10, 2012, 12 pages.
Lanford, et al. "Induction of Nuclear Transport with a Synthetic Peptide Homologous to the SV40 T Antigen Transport Signal", Cell, 1986, 46:575-582.
Lange, et al. "Classical Nuclear Localization Signals: Definition, Function, and Interaction with Importin$2026" J. Biol. Chem., 2007, 282(8):5101-5105.
Lebherz, C., et al., "Gene therapy with novel adeno-associated virus vectors substantially diminished atherosclerosis in a murine model of familial hypercholesterolemia," The Journal of Gene Medicine, vol. 6, pp. 663-672, dated Mar. 2, 2004, 10 pages.

Lee, C., et al., "Correction of the F508 Mutation in the Cystic Fibrosis Transmembrane Conductance Regulator Gene by Zinc-Finger Nuclease Homology-Directed Repair," Bioresearch Open Access, vol. 1, No. 3, pp. 99-108, dated 2012, 12 pages.
Leenay, et al. "Identifying and Visualizing Functional PAM Diversity across CRISPR-Cas Systems", Molecular Cell, 2016, 62:137-147.
Lemay, et al. "Folding of the Adenine Riboswitch", Chemistry & Biology, 2006, 13:857-868.
Levitt, J., et al., "Intrinsic fluorescence and redox changes associated with apoptosis of primary human epithelial cells," Journal of Biomedical Optics, vol. 11, No. 6, pp. 064012 1-10, dated Nov./Dec. 2006, 10 pages.
Lewin, et al. "Nuclear localization sequences target proteins to the nucleus" Cells, 2006, 5:224.
Li et al., "Coevolution of CRISPR-Cas system with bacteria and phages", Hereditas, vol. 33, No. 3, Mar. 31, 2011, pp. 213-218.
Li, P., et al., "Biallelic knockout of alpha-1,3 galactosyltransferase gene in porcine liver-derived cells using zing finger nucleases," Journal of Surgical Research, vol. 181, No. 1, pp. E39-E45, dated Jul. 3, 2012, 7 pages.
Li, Ting, et al. "Modularly assembled designer TAL effector nucleases for targeted gene knockout and gene replacement in eukaryotes" Nucleic Acids Research, 2011, 39(14):6315-6325.
Liu, et al. "Epstein-Darr Virus DNase Contains Two Nuclear Localization signals Which Are Different in Sensitivity to the Hydrophobic Regions" Virology, 1998, 247:62-73.
Los, et al. "Halotag Technology: Cell Imaging and Protein Analysis" Cell Notes, 2006, 14:10-14.
Luo, Ming, et al. "Multiple Nuclear Localization Sequences Allow Modulation of 5-Lipoxygenase Nuclear Import" Traffic, 2004, 5:847-854.
Lyssenko, et al. "Cognate putative nuclear localization signal effects strong nuclear localization of a GFP reporter and facilitates gene expression studies in Caenorhabditis elegans" BioTechniques, 2007, 43:596-600.
Ma, M., et al., "A Guide RNA Sequence Design Platform for the CRISPR/Cas9 System for Model Organism Genomes," Hindawi, vol. 2013, art. 270805, BioMed Research International, dated Sep. 13, 2013, 5 pages.
Maczuga, P., et al., "Embedding siRNA sequences targeting Apolipoprotein B100 in shRNA and miRNA scaffolds results in differential processing and in vivo efficacy," Molecular Therapy, vol. 21, No. 1, pp. 217-227, dated Jan. 2013, 11 pages.
Maeder, M., and Gersbach, C., "Genome-editing Technologies for Gene and Cell Therapy," Molecular Therapy, vol. 24, No. 3, pp. 430-446, dated Mar. 2016, 17 pages.
Maeder, M., et al., "Robust, synergistic regulation of human gene expression using TALE activators," Nature Methods, vol. 10, No. 3, pp. 243-245, dated Mar. 2013, 9 pages.
Mahfouz, et al. "Targeted transcriptional repression using a chimeric TALE-SRDX repressor protein" Plant Mol Biol, 2012, 78:311-321.
Mahfouz, M., et al., "De novo-engineered transcription activator-like effector (TALE) hybrid nuclease with novel DNA binding specificity creates double-strand breaks," Proceedings of the National Academy of Science, vol. 108, No. 6, pp. 2623-2628, dated Feb. 8, 2011, 6 pages.
Makarova, et al. "An updated evolutionary classification of CRISPR-Cas systems" Nature Reviews—Microbiology, 2015, 13:722-736.
Mali et al., "CAS9 transcriptional activators for target specificity screening and paired nickases for cooperative genome engineering", Nature Biotechnology, Sep. 2013, vol. 31, No. 9, pp. 833-837.
Mali, et al, Supplementary Information for "Use of adjacent sgRNA: Cas9 complexes for transcriptional activation and genome engineering," Nature Biotechnology, doi:10.1037/nbt.2675, 2013.
Mali, P., et al., Supplementary Materials for: "CAS9 transcriptional activators for target specificity screening and paired nickases for cooperative genome engineering," Nature Biotechnology, vol. 31, No. 9, pp. 833-838, dated Aug. 1, 2013, 36 pages.
Manjunath, N., et al., "Newer Gene Editing Technologies toward HIV Gene Therapy," Viruses, vol. 5, No. 11, pp. 2748-2766, dated Nov. 14, 2013, 19 pages.

(56) References Cited

OTHER PUBLICATIONS

*Manning v. Paradis*, 296 F.3d 1098 (Fed. Cir. 2012).
Marraffini, L., "CRISPR-Cas Immunity against Phages: Its Effects on the Evolution and Survival of Bacterial Pathogens," PLOS, Pathogens, dated Dec. 12, 2013, 6 pages.
Marraffini, L., Assignment to Rockefeller University, dated Dec. 12, 2013, 3 pages.
*Maxwell v. The Stanley Works*, 2006 WL 1967012, *5 (M.D. Tenn. Jul. 11, 2006).
Mincer, J., and Simon, S., "Simulations of nuclear pore transport yield mechanistic insights and quantitative predictions," Proceedings of the National Academy of Science, vol. 108, No. 31, pp. E351-E358, dated Aug. 2, 2011, 8 pages.
Mojica, F. J., et al., Supplementary Material for: "Short motif sequences determine the targets of the prokaryotic CRISPR defence system," Microbiology, vol. 155, No. 3, pp. 733-740, dated Mar. 1, 2009, 8 pages.
Morbitzer, et al. "Assembly of custom TALE-type DNA binding domains by modular cloning" 2011, 39(13):5790-5799.
Morbitzer, et al. "Regulation of selected genome loci using de novo-engineered transcription activator-like effector (TALE)-type transcription factors" PNAS, 2010, 108(50):21617-21622.
Morin, et al. "Nuclear Localization of the Adenovirus DNA-Binding Protein: Requirement for Two Signals and Complementation during Viral Infection" Molecular and Cellular Biology, 1989, 9(10):4372-4380.
Morris et al., "Distributed automated docking of flexible ligands to proteins: Parallel applications of AutoDock 2.4*", Journal of Computer-Aided Molecular Design, 1996, vol. 10, pp. 293-304.
Moscou, et al. "A Simple Cipher Governs DNA Regognition by TAL Effectors" Science, 2009, 326:1501.
Mussolino, et al. "TALE nucleases: tailored genome engineering made easy" Current Opinion in Biotechnology, 2012, 23(5):644-650.
Muther, N., et al.: "Viral Hybrid Vectors for Somatic Integration—Are They the Better Solution?" Viruses, vol. 1, pp. 1295-1324, dated Dec. 15, 2009, 30 pages.
Nagarajan, et al. "A Hierarchy of Nuclear Localization Signals Governs the Import of the Regulatory Factor X Complex Subunits and MHC Class II Expression" The Journal of Immunology, 2004, 173:410.419.
Nakai, et al. "PSORT: a program for detecting sorting signals in proteins and predicting their subcellular localization" Trends in Biochem Sciences, 1999 24:34-35.
Noguchi, et al. "PDX-1 Protein Containing Its Own Antennapedia-Like Protein Transduction Domain Can Transduce Pancreatic Duct and Islet Cells" Diabetes, 2003, 52:1732-1737.
Notice of Opposition filed Aug. 11, 2017 by Schlich against EP Patent No. 2840140.
Notice of Opposition filed Aug. 14, 2017 by Grund against EP Patent No. 2840140.
Notice of Opposition filed Aug. 16, 2017 by Mathys & Squire LLP against EP Patent No. 2840140.
Notice of Opposition filed by Aug. 16, 2017 by Vossius against EP Patent No. 2840140.
O'Hare, et al. "Transformation of mouse fibroblasts to methotrexate resistance by a recombinant plasmid expressing a prokaryotic dihydrofolate reductase" Proc. Natl. Acad. Sci., 1981, 78(3):1527-1531.
Opposition Against Appl. Serial No. EP13818570.7 submitted by Schlich dated Oct. 26, 2015, 8 pages.
Opposition Against EP Appl. Ser. No. 2771468-B1 dated Oct. 26, 2015.
Ozawa, K., "Gene therapy using AAV," Uirusu, vol. 57, No. 1, pp. 47-55, dated Nov. 27, 2007, 13 pages (with English Abstract; No English Translation).
Pandika, et al., www.ozy.com/rising-stars-and-provocateurs/jennifer-doudna-crispr-code-killer/4690; 2014 (Jul. 1, 2014).
Park, et al. "Regulation of Ribosomal S6 Kinase 2 by Mammalian Target of Rapamycin", The Journal of Biological Chemistry, 2002, 277(35):31423-31429.
Pattanayak, et al., "High-throughput profiling of off-target DNA cleavage reveals RNA-programmed Cas9 nuclease specificity," Nature Biotechnology, vol. 31, No. 9, pp. 839-843, dated 2013, including Supplementary Materials.
Perez-Pinera, et al. "Advances in Targeted Genome Editiong" Curr Opin Chem Biol., 2012, 16(3-4):268.277, doi:10.1016/j.cbpa.2012.06.007.
Phillips, A., "The challenge of gene therapy and DNA delivery," The Journal of Pharmacy and Pharmacology, vol. 53, pp. 1169-1174, dated 2001, 6 pages.
Planey, et al. "Mechanisms of Signal Transduction: Inhibition of Glucocorticoid-induced Apoptosis in 697 Pre-B Lymphocytes by the Mineralocorticoid Receptor N-terminal Domain", J. Biol. Chem., 2002, 277:42188-42196.
Porteus, M., and Balitmore, D., "Chimeric Nucleases Stimulate Gene Targeting in Human Cells," Science, vol. 300, p. 763, dated May 2, 2003, 2 pages.
Posfai, et al. "Markerless gene replacement in *Escherichia coli* stimulated by a double-strand break in the chromosome" Nucleic Acids Resarch, 1999, 27(22):4409-4415.
Pougach, K.S., et al.: "CRISPR Adaptive Immunity Systems of Prokaryotes," Molecular Biology, vol. 46, No. 2, Apr. 2012, pp. 195-203, 1 page (English Abstract).
PowerPoint slide entitled "Development and Applications of CRISPR-Cas9 for Genome Editing" dated Sep. 9, 2015.
Pride, D., et al., "Analysis of Streptococcal CRISPRs from Human Saliva Reveals Substantial Sequence Diversity Within and Between Subjects Over Time," Genome Research, vol. 21, No. 1, pp. 126-136, dated Jan. 2011, 11 pages.
Primo, et al. "Lentiviral vectors for cutaneous RNA managing" Experimental Dermatology, 2012, 21:162-170.
Qi, J., et al., "microRNAs regulate human embryonic stem cell division," Cell Cycle, vol. 8, No. 22, pp. 3729-3741, dated Nov. 15, 2009, 13 pages.
Radecke, S., et al., "Zinc-finger Nuclease-induced Gene Repair With Oligodeoxynucleotides: Wanted and Unwanted Target Locus Modifications," Molecular Therapy, vol. 18, No. 4, pp. 743-753, dated Apr. 2010, 11 pages.
Radulovich, et al. "Modified gateway system for double shRNA expression and Cre/lox based gene expression" BMC Biotechnology, 2011, 11(24):1-9.
Ran et al., "Double Nicking by RNA-guided CRISPR Cas9 for enhanced genome editing specificity", Cell, Sep. 2013, vol. 154, pp. 1380-1389.
Redeclaration—37 C.F.R. 41.203(c); filed Mar. 17, 2016.
Rho, M., et al., "Diverse CRISPRs Evolving in Human Microbiomes," PLOS Genetics, vol. 8, No. 6, pp. e1002441, dated Jun. 2012, 12 pages.
Rhun, A., and Charpentier, E., "Small RNAs in streptococci," RNA Biology, vol. 9, No. 4, pp. 414-426, dated Apr. 2012, 13 pages.
Roberts, et al. "Nuclear location signal-mediated protein transport" Biochimica et Biophysica Acta, 1989, 1008:263-280.
Roberts, et al. "The Effect of Protein Content on Nuclear Location Signal Function" Cell, 1987, 50:465-475.
Rockefeller University and Broad Institute of MIT and Harvard announce update to CRISPR-Cas9 portfolio filed by Broad, Press Release dated Jan. 15, 2018, retrieved from: https://www.broadinstitute.org/news/rockefeller-university-and-broad-institute-mit-and-harvard-announce-update-crispr-cas9, 3 pages.
Rodrigues, et al. "Red Fluorescent Protein (DsRed) as a Reporter in *Saccharomyces cerevisiae*" Journal of Bacteriology, 2001, 183(12):3791-3794.
Rodriguez et al., "AAV-CRISPR: A New Therapeutic Approach to Nucleotide Repeat Diseases", Molecular Therapy, vol. 22, Supplement 1, Abstract 247, May 2014, p. S94.
Rolling, "Recombinant AAV-mediated gene transfer to the retina: gene therapy perspectives", Gene Therapy, Vo. 11, 2004, pp. S26-S32.
*Rubin v. The General Hospital Corp.*, 2011-1439 (Fed. Cir. Mar. 28, 2013).

(56) References Cited

OTHER PUBLICATIONS

Sadowski, M., and Jones, D., "The sequence-structure relationship and protein function prediction," Current Opinion in Structural Biology, vol. 19, pp. 357-362, dated May 4, 2009, 6 pages.
Sambrook, et al., Molecular Cloning, A Laboratory Manual on the Web, 2001, Chapter 16.
Sander, et al., "CRISPR-Cas systems for editing, regulating and targeting genomes," Nature Biotechnology, vol. 32, pp. 347-355, dated 2014.
Sanders, UC Berkeley Jan. 7, 2013 Press Release, available at http://newscenter.berkeley.edu/2013/01/07/cheap-and-easy-technique-to-snip-dna-could-revolutionize-gene-therapy/.
Sanjana, et al., "Improved vectors and genome-wide libraries for CRISPR screening," HHS Public Access Author Manuscript, 2014, 11(8):2145-2148.
Sanjana, N., et al., "A Transcription Activator-Like Effector (TALE) Toolbox for Genome Engineering," Nature Protocols, vol. 7, No. 1, pp. 171-192, dated Jan. 1, 2012, 39 pages.
Sato, et al. "Generation of Adeno-Associated Virus Vector Enabling Functional Expression of Oxytocin Receptor and Fluorescence Marker Genes Using the Human elF4G Internal Ribosome Entry Site Elemet" Biosci. Biotechno. Biochem, 2009, 73(9):2145-2148.
Schunder, et al. "First indication for a functional CRISPR/Cas system in Francisella tularensis" International Journal of Medical Microbiology, 2013, 303:1438-4221.
Sebastiani, et al., "BCL11A enhancer haplotypes and fetal hemoglobin in sickle cell anemia," Blood Cells, vol. 54, No. 3, pp. 1079-9796, dated 2015.
Sebo, et al. "A simplified and efficient germline-specific CRISPR/Cas9 system for *Drosophila* genomic engineering" Fly, 2014, 8(1):52-57.
Seffernick, J., et al., "Melamine Deaminase and Atrazine Chlorohydrolase: 98 Percent Identical but Functionally Different," Journal of Bacteriology, vol. 183, No. 8, pp. 2405-2410, dated Apr. 2001, 6 pages.
Senis, E., et al., "CRISPR/Cas9-mediated genome engineering: An adeno-associated viral (AAV) vector toolbox," Biotechnology Journal, vol. 9, No. 11, Sp. Iss. SI, pp. 1402-1412, dated Sep. 4, 2014, 2 pages (Only Abstract Available).
Senturk et al., "A rapid and tunable method to temporally control cas9 expression enables the identification of essential genes and the interrogation of functional gene interactions in vitro and in vivo", Jul. 28, 2015, pp. 1-27, XP002756303, doi:10.1101/023366, Retrieved from the Internet: URL:http://biorxiv.org/content/early/2015/07/28/023366 [retrieved on Apr. 11, 2016).
Shalem, et al., "High-throughput functional genomics using CRISP-Cas9," Nature Reviews Genetics, vol. 16, No. 5, pp. 1471-0056, dated 2015.
Sharan, et al. "Recombineering: A Homologous Recombination-Based Method of Genetic Engineering" Nat. Protoc., 2009, 4(2):206-223, doi:10.1038/nprot.2008.227.
Shengdar Tsai et al., "Dimeric CRISPR RNS-guided FokI nucleases for highly specific genome editing", Nature Biotechnology, vol. 32, No. 6, Apr. 25, 2014, pp. 569-576.
Shieh, et al. "Nuclear Targeting of the Maize R. Protein Requires Two Nuclear Localization Sequences" Plant Physiol, 1993, 101:353-361.
Siegl, et al. "I-SceI endonuclease: a new tool for DNA repair studies and genetic manipulations in streptomycetes" Appl Microbiol Bitotechnol, 2010, 87:1525-1532.
Singer, et al. "Applications of Lentiviral Vectors for ShRNA Delivery and Transgenesis" Curr Gene Ther., 2008, 8(6):483-488.
Slaymaker et al., Rationally engineered Cas9 nucleases with improved specificity, Science, American Association for the Advancement of Science, US, vol. 351, No. 6268, Jan. 1, 2016, pp. 84-88.
Stoller, J. and Aboussouan, L., "Alpha1-antitrypsin deficiency," The Lancet, Seminar, vol. 365, No. 9478, pp. 2225-2236, dated Jun. 25, 2005, 12 pages.

Stratikopoulos, E., et al., "The hormonal action of IGF1 in postnatal mouse growth," Proceedings of the National Academy of Sciences, vol. 105, No. 49, pp. 19378-19383, dated Dec. 9, 2008, 6 pages.
Straub, C., et al., "CRISPR/Cas9-Mediated Gene Knock-Down in Post-Mitotic Neurons," PLOS One, vol. 9, No. 8, art. E105584, pp. 1-5, dated Aug. 2014, 6 pages.
Sung, et al. "An rpsL Cassette, Janus, for Gene Replacement through Negative Selectionin *Streptococcus pneumoniae*" Applied and Environmental Microbiology, 2001, 67(11):5190-5196.
Sung, M., et al., "The importance of valency in enhancing the import and cell routing potential of protein transduction domain-containing molecules," Biochimica et Biophysica Aeta, vol. 1758, pp. 355-363, dated 2006, 9 pages.
Sung, Young Hoon, et al. "Mouse genetics: Catalogue and scissors" BMB Reports, 2012, 45(12):686-692.
Suzuki, K., et al., "In vivo genome editing via CRISPR/Cas9 mediated homology-independent targeted integration," Nature, vol. 540, art. 7631, pp. 144-149, dated Dec. 1, 2016, 44 pages.
Swarthout, J., et al., "Zinc Finger Nucleases: A new era for transgenic animals," Annals of Neurosciences, vol. 18, No. 1, pp. 25-28, dated Jan. 2011, 4 pages.
Tang, T., et al., "A mouse knockout library for secreted and transmembrane proteins," Nature Biotechnology, vol. 28, No. 7, pp. 749-755, dated Jul. 2010, 9 pages.
*The Broad Inst. v. The Regents of University of UCA*—Decision on Motions for Patent Interference No. 106,048 filed Feb. 15, 2017.
Third Party Observations Concerning App. No. GB1420270.9 dated Jun. 30, 2015.
Third Party Observations Concerning Appl. No. EP2800811, dated Jul. 24, 2015.
Third Party Observations Concerning Appl. No. EP2800811, dated Sep. 4, 2015.
Third Party Observations Concerning Appl. No. GB1420270.9 dated Jun. 30, 2015.
Third Party Observations Concerning Appl. No. GB1420270.9, dated Jul. 13, 2015.
Third Party Observations in Accordance with Article 115 EPC, Appl. No. EP13624232.6, Pub. No. EP2764103A, Mar. 25, 2015.
Third Party Observations submitted by Broad Institute Inc. Concerning Appl. Serial No. EP13793997.1 dated Jul. 24, 2015, 108 pages.
Third Party Observations submitted by Broad Institute Inc. Concerning Appl. Serial No. EP13793997.1 dated Sep. 4, 2015, 25 pages.
Third Party Observations submitted by Regents of the University of California et al. Concerning App. No. GB1420270.9 dated Jul. 13, 2015, 18 pages.
Third Party-Observations, Appl. No. 1382432.6, Pub. No. EP2764103, Feb. 16, 2015.
Tinland, et al. "The T-DNA-linked VirD2 protein contains two distinct functional nuclear localization signals" Proc. Natl. Acad. Sci, 1992, 89:7442-7446.
Tiscornia, et al. "Development of Lentiviral Vectors Expressing siRNA" Gene Transfer-Delivery and Expression of DNA and RNA—A Laboratory Manual, 2007, Chapter 3:23-34.
Trafton, A., "CRISPR-carrying nanoparticles edit the genome," MIT News, dated Nov. 13, 2017, 3 pages.
Tulpan, D., et al., "Free energy estimation of short DNA duplex hybridizations," BMC Bioinformatics, vol. 11, pp. 105-127, dated 2012, 22 pages.
Type V CRISPR-associated protein Cpf1 [*Acidaminococcus* sp. Bv3L6], 2017, NCBI Reference Sequence: WP_02173622.1, Non-redundant Protein Sequence.
*Ultra-Precision Mfg. Ltd. v. Ford Motor Co.*, 2004 WL 3507671, *7, *11-12 (E.D. Mich. Mar. 30, 2004).
Urnov, F., et al., "Genome editing with engineered zinc finger nucleases," Nature Reviews, Genetics, vol. 11, pp. 637-646, dated Sep. 2010, 11 pages.
Urrutia, et al. "KRAB-containing zing finger repressor proteins" Genome Biology, 2003, 4(10):231-231.8.
Van Den Ackerveken, et al. "Recognition of the Bacterial Avirulence Protein AvrBs3 Occurs inside the Host Plant Cell" Cell, 1996, 87:1307-1316.

(56) References Cited

OTHER PUBLICATIONS

Van Der Oost, "New tool for genome surgery", Science, Feb. 2013, vol. 339, pp. 768-770.
Van Nierop, G., et al., "Stimulation of homology-directed gene targeting at an endogenous human locus by a nicking endonuclease," Nucleic Acids Research, vol. 37, No. 17, pp. 5725-5736, dated Aug. 3, 2009, 12 pages.
Vestergaard et al., "CRISPR adaptive immune systems of Archaea", RNA Biology, 2014, vol. 11, No. 2, pp. 156-167.
Villion, et al. "The double-edged sword of CRISPR/Cas systems" Cell Research, 2013, 23:15-17.
Wang, et al. "Genetic Screens in Human Cells Using the CRISPR-Cas9 System", Science, 2014, 343:80-84.
Welch, et al. "Designing Genes for Successful Protein Expression" Methods in Enzymology, 2011, 498:43-66, DOI: 10.1016/B978-0-12-385120-8.00003-6.
Wienert, B., et al., "In vitro transcribed guide RNAs trigger an innate immune response via the RIG-I pathway," BioRxiv Preprint, dated Mar. 3, 2018, 28 pages.
Witkowski, A., et al., "Conversion of a Beta-Ketoacyl Synthase to a Malonyl Decarboxylase by Replacement of the Active-Site Cysteine with Glutamine," Biochemistry, vol. 38, pp. 11643-11650, dated Aug. 18, 1999, 8 pages.
Wittmann et al., "Engineered riboswitches: Expanding researchers' toolbox with synthetic RNA regulators", FEBS Letters, vol. 586, No. 15, Feb. 28, 2012, pp. 2076-2083.
Wolff, et al. "Nuclear security breached" Nature Biotechnology, 2001, 19:1118-1120.
Wu, Y., et al., "Correction of a Genetic Disease in Mouse via Use of CRISPR-Cas9," Cell Stem Cell, vol. 13, No. 6, pp. 659-662, dated Dec. 5, 2013, 4 pages.
Wu, Z., et al., "Effect of Genome Size on AAV Vector Packaging," The American Society of Gene & Cell Therapy, vol. 18, No. 1, pp. 80-86, dated Jan. 2010, 7 pages.
Xie, et al. "RNA-Guided Genome Editing in Plants Using a CRISPR-Cas System" Molecular Plant, 2013, 6(6):1975-1983.
Yaghmai, et al. "Optimized Regulation of Gene Expression Using Artificial Transcription Factors", Molecular Therapy, 2002, 5(6):685-694.
Yamano, et al. "Crystal Structure of Cpf1 in Complex with Guide RNA and Target DNA" Cell, 2016, 165:949-962.
Yanfang Fu et al., "Improving CRISPR-Cas nuclease specificity using truncated guide RNAs" (with Supplement Table), Nature Biotechnology, vol. 32, No. 3, Jan. 26, 2014, pp. 279-284.
Yang, H., et al., "One-Step Generation of Mice Carrying Reporter and Conditional Alleles by CRISPR/Cas-Mediated Genome Engineering," Cell, vol. 154, No. 6, pp. 1370-1379, dated Sep. 12, 2013, 14 pages.
Yi, et al. "Current Advances in Retroviral Gene Therapy" Current Gene Therapy, 2011, 11:218:228.
Yin, H., et al., "Structure-guided chemical modification of guide RNA enables potent non-viral in vivo genome editing," Nature Biotechnology, vol. 35, pp. 1179-1187, dated Nov. 13, 2017, 22 pages.
Yu, et al. "An efficient recombination system for chromosome engineering in *Escherichia coli*" PNAS, 2000, 97(11):5978-5983.
Yu, W., et al., "Nrl knockdown by aav-delivered CRISPR/Cas9 prevents retinal degeneration in mice," Nature Communications, vol. 8, art. 14716, dated Mar. 14, 2017, 15 pages.
Yu, Zhongshen, et al. "Highly Efficient Genome Modifications Mediated by CRISPR/Cas9 in *Drosophila*" Genetics, 2013, 195:289-291.
Yusuke Miyazaki et al., Destabilizing Domains Derived from the Human Estrogen Receptor:, Journal of the American Chemical Society, vol. 134, No. 9, Mar. 7, 2012, pp. 3942-3945.
Zetsche et al., "Cpf1 is a single RNA-guided endonuclease of a class 2 CRISPR-Cas system", Cell, Oct. 2015, vol. 163, No. 3, pp. 759-771.
Zhang, et al. "Optogenetic interrogation of neural circuits: technology for probing mammalian brain structures" Nat Protoc., 2010, 5(3):439-456, doi:10.1038/nprot.2009.226.
Zhang, et al., "Optimized CRISPR Design", MIT, XP055167487, Oct. 23, 2013, URL:http//crispr.mit.edu/about[retrieved on Feb. 5, 2015].
Zhang, F., PowerPoint Presentation: "Development and Applications of CRISPR-Cas9 for Genome Editing," Broad Institute/MIT, dated Sep. 9, 2015, 50 pages.
Zhang, L., et al., "Efficient Expression of CFTR Function with Adeno-Associated Virus Vectors that Carry Shortened CFTR Genes," Proceedings of the National Academy of Science USA, vol. 95, pp. 10158-10163, dated Aug. 1998, 6 pages.
Zhou, et al., "High-throughput screening of a CRISPR/Cas9 library for functional genomics in human cells," Nature, vol. 509, pp. 487-491, dated 2014.
Zolkiewska, et al. "ADAM Proteases:Ligand Processing and Modulation of the Notch Pathway" Cell Mol Life Sci, 2008, 65(13):2056-2068.
A. Amsterdam et al., "Identification of 315 genes essential for early zebrafish development," proc Natl Acad Sci U.S.A., vol. 101(35), pp. 12792-12797 (Aug. 31, 2004).
A. Fire et al., "Potent and specific genetic interference by double-stranded RNA in Caenorhabditis elegans," Nature, vol. 391 (6669), pp. 806-811 (Feb. 19, 1998).
A. Subramanian et al., "Gene set enrichment analysis: a knowledge-based approach for interpreting genome-wide expression profiles," Proc Natl Acad Sci U.S.A., vol. 102, p. 15545 (Oct. 25, 2005).
A.C. Spradling et al., "The Berkeley *Drosophila* Genome Project Gene Disruption Project: Single P-Element Insertions Mutating 25% of Vital *Drosophila* Genes," Genetics, vol. 153, pp. 135-177 (1999).
A.H. Tong et al., "Global mapping of the yeast genetic interaction network," Science, vol. 303, p. 808 (Feb. 6, 2004).
A.L. Lin and D.H Gutmann, "Advances in the treatment of neurofibromatosis-associated tumours," Nature reviews. Clinical oncology, (Aug. 13, 2013).
A.P. Blanchard and L. Hood, "Sequence to array: probing the genome's secrets," Nat Biotechnol, vol. 14, p. 1649 (Dec. 1996).
Addgene, "gRNA_Cloning Vector", retrieved on Jan. 30, 2019, <https://www/addgenen.org/41824/>, 2 pages.
Allen, et al., "Liposomal drug delivery systems: From concept to clinical applications" Advanced Drug Delivery Reviews 65, Oct. 1, 2012, pp. 36-48.
B. Langmead et al., "Ultrafast and memory-efficient alignment of short DNA sequences to the human genome," Genome biology, vol. 10, p. R25 (2009).
B.Langmead and S.L. Salzberg, "Fast gapped-read alignment with Bowtie 2," Nat Meth, vol. 9, pp. 357-359 (2012).
B.Scappini et al., "Changes associated with the development of resistance to imatinib (STI571) in two leukemia cell lines expressing p210 Bcr/Abl protein," Cancer, vol. 100, p. 1459 (2004).
B.Sonnichsen et al., "Full-genome RNAi profiling of early embryogenesis in Caenorhabditis elegans," Nature, vol. 434, pp. 462-469 (2005).
Bae, T. and Schneewind, O. "Allelic replacement in *Staphylococcus aureus* with inducible counter-selection," Plasmid, vol. 55, pp. 58-63 (2006).
Botta, S. et al, "Transcriptional Repression with Zinc-Finger and Tale Protein Scaffold", Molecular Therapy, May 2013, vol., Supplement 1, p. S208, Abstract No. 539.
Brummelkamp TR et al., "A system for stable expression of short interfering RNAs in mammalian cells," Science, vol. 296 (5567), pp. 550-553 (Apr. 19, 2002, Epub Mar. 21, 2002).
C. Cayrol et al., "The THAP-zinc finger protein THAP1 regulates endothelial cell proliferation through modulation of pRB/E2F cell-cycle target genes," Blood, vol. 109, pp. 584-594 (2007).
C. Trapnell et al., "Differential gene and transcript expression analysis of RNA-seq experiments with TopHat and Cufflinks," Nature protocols, vol. 7, p. 562 (Mar. 2012).
C. Trapnell et al., "TopHat: discovering splice junctions with RNA-Seq.," Bioinformatics, vol. 25, p. 1105 (May 1, 2009).

(56) References Cited

OTHER PUBLICATIONS

C.J, Echeverri et al., "Minimizing the risk of reporting false positives in large-scale RNAi screens," Nature methods, vol. 3, p. 777 (Oct. 2006).
C.M Johannessen et al., "COT drives resistance to RAF inhibition through MAP kinase pathway reactivation," Nature, vol. 468, p. 968 (Dec. 16, 2010).
C.M. Johnston et al., "Large-scale population study of human cell lines indicate that dosage compensation is virtually complete," PLoS Genet, vol. 4, p. e9 (2008).
Carte, J., et al., "Cas6 is an endoribonuclease that generates guide RNAs for invader defense in prokaryotes," Genes Dev., vol. 22, pp. 3489-3496 (2008).
Chadderton, N., et al., "Improved Retinal Function in a Mouse Model of Dominant Retinitis Pigmentosa Following AAV-delivered Gene Therapy", Molecular Therapy, 2009, vol. 17, pp. 593-599.
Cho, Minseon, et al., "Quantitative selection and parallel characterization of aptamers," PNAS, Nov. 12, 2013, vol. 110, No. 46, pp. 18460-18465 (6 pages).
D.J.Burgess et al., "Topoisomerase levels determine chemotherapy response in vitro and in vivo," Proceedings of the National Academy of Sciences, vol. 105, p. 9053 (Jul. 1, 2008).
Dean, "Recent Advances in Drug Design Methods: Where Will They Lead?", BioEssays, vol. 16, No. 9, Sep. 1994, pp. 683-687.
Deveau, H. et al., "Phage response to CRISPR-encoded resistance in *Streptococcus thermophilus*. J. Bacteriol.," vol. 190, pp. 1390-1400 (2008).
Deveau, H., et al., "CRISPR/Cas system and its role in phage-bacteria interactions," Annu. Rev. Microbiol, vol. 64, pp. 475-493 (2010).
E.S. Lander, "Initial impact of the sequencing of the human genome," Nature, vol. 470, p. 187 (Feb. 10, 2011).
Edgar, R. and Qimron, U., "The *Escherichia coli* CRISPR system protects from λ lysogenization, lysogens, and prophage induction," J. Bacteriol., vol. 192, pp. 6291-6294 (2010).
Fischer, S. et al., "An archaeal immune system can detect multiple Protospacer Adjacent Motifs (PAMs) to target invader DNA," J. Biol. Chem., vol. 287, pp. 33351-33363 (2012).
Flannery, J. G., "Ribozyme-Mediated Gene Therapy for Autosomal Dominant Retinal Degeneration", Retinal Degenerative Diseases and Experimental Therapy, 1999, pp. 277-291.
G. Giaever et al., "Functional profiling of the *Saccharomyces cerevisiae* genome," Nature, vol. 418, p. 387 (2002).
G. Guo et al., "Mismatch repair genes identified using genetic screens in Blm-deficient embryonic stem cells," Nature, vol. 429, p. 891 (2004).
Gaj, T., et al., "Targeted Gene knockout by direct delivery of zinc-finger nuclease proteins," Nature Methods, vol. 9, No. 8, pp. 805-809, dated Aug. 2012, 5 pages.
Gao, et al., "A Sustained, Cytoplasmic Transgene Expression System delivered by Cationic Liposomes", Biochemical and Biophysical Research Communications, vol. 200, No. 3, May 16, 1994, pp. 1201-1206.
Gibson, D.G. et al., "Enzymatic assembly of DNA molecules up to several hundred kilobases," Nat methods, vol. 6, pp. 343-345 (2009).
Goncalves, Manuel A. F. V., et al. "Concerted Nicking of Donor and Chromosomal Acceptor DNA Promotes Homology-directed gene targeting in human cells," Nucleic Acids Research, vol. 40, No. 8, pp. 3443-3455, dated Dec. 20, 2011, 13 pages.
Greenwald, D L, et al., "Engineered Zinc Finger Nuclease-Mediated Homologous Recombination of the Human Rhodopsin Gene", Investigative Ophthalmology & Visual Science, Dec. 2010, vol. 51, No. 12, pp. 6374-6380.
Gudbergsdottir, S. et al., "Dynamic properties of the Sulfolobus CRISPR/Cas and CRISPR/Cmr systems when challenged with vector-borne viral and plasmid genes and protospacers," Mol. Microbiol., vol. 79, pp. 35-49 (2011).
H. Davies et al., "Mutations of the BRAF gene in human cancer," Nature, vol. 417, p. 949 (Jun. 27, 2002).

H.W Cheung et al., "Systematic investigation of genetic vulnerabilities across cancer cell lines reveals lineage-specific dependencies in ovarian cancer," Proceedings of the National Academy of Sciences, vol. 108, p. 12372 (Jul. 26, 2011).
Hatoum-Aslan, A., et al., "Mature clustered, regularly interspaced, short palindromic repeats RNA (crRNA) length is measured by a ruler mechanism anchored at the precursor processing site," Proc. Natl. Acad. Sci. U.S.A., vol. 108, pp. 21218-21222 (2011).
Haurwitz, R.E., et al., "Sequence- and structure-specific RNA processing by a CRISPR endonuclease," Science, vol. 329, pp. 1355-1358 (2010).
Havarstein, L.S., et al., "An unmodified heptadecapeptide pheromone induces competence for genetic transformation in *Streptococcus pneumoniae*, " Proc. Natl. Acad. Sci. U.S.A., vol. 92, pp. 11140-11144 (1995).
Hemann et al., "An epi-allelic series of p53 hypomorphs created by stable RNAi produces distinct tumor phenotypes in vivo," Nat Genet., vol. 33(3), pp. 396-400 (Mar. 2003, Epub Feb. 3, 2003).
Horinouchi, S. and Weisblum, B., "Nucleotide sequence and functional map of pC194, a plasmid that specifies inducible chloramphenicol resistance," J. Bacteriol., vol. 150, pp. 815-825 (1982).
Horton, R.M., "In Vitro recombination and Mutagenesis of DNA: SOEing Together Tailor-Made Genes," Methods Mol. Biol., vol. 15, pp. 251-261 (1993).
Horvath, P. and Barrangou, R. "CRISPR/Cas, the immune system of bacteria and archaea," Science, vol. 327, pp. 167-170 (2010).
Hosaka, T. et al., "The novel mutation K87E in ribosomal protein S12 enhances protein synthesis activity during the late growth phase in *Escherichia coli*." Mol. Genet. Genomics, vol. 271, pp. 317-324 (2004).
Hoskins, J. et al., "Genome of the bacterium *Streptococcus pneumoniae* strain R6," J.Bacteriol., vol. 183, pp. 5709-5717 (2001).
Husmann, L.K.,et al., "Expression of the Arp protein, a member of the M protein family, is not sufficient to inhibit phagocytosis of *Streptococcus pyogenes*," Infection and immunity, vol. 63, pp. 345-348(1995).
Ishino Y. et al., "Nucleotide sequence of the iap gene, responsible for alkaline phosphatase isozyme conversion in *Escherichia coli*, and identification of the gene product," J. Bacteriol., vol. 169 (12), pp. 5429-5433 (Dec. 1987).
J. Merkin et al., "Evolutionary dynamics of gene and isoform regulation in Mammalian tissues," Science, vol. 338, p. 1593 (Dec. 21, 2012).
J.E. Carette et al., "Haploid genetic screens in human cells identify host factors used by pathogens," Science, vol. 326, p. 1231 (Nov. 27, 2009).
J.F. Rual et al., "Toward Improving Caenorhabditis elegans Phenome Mapping with an ORFeome-Based RNAi Library," Genome Research, vol. 14, pp. 2162-2168 (2004).
J.M. Engreitz et al., "The Xist lncRNA exploits three-dimensional genome architecture to spread across the X chromosome," Science, vol. 341(6147) (Aug. 16, 2013).
Jansen R. et al., "Identification of genes that are associated with DNA repeats in prokaryotes," Molecular Microbiology, vol. 43(6), pp. 1565-1575 (2002).
JL. Mummery-Widmer et al., "Genome-wide analysis of Notch signalling in *Drosophila* by transgenic RNAi," Nature, vol. 458, pp. 987-992 (2009).
K. Yoshimoto et al., "Complex DNA repair pathways as possible therapeutic targets to overcome temozolomide resistance in glioblastoma," Front Oncol., vol. 2, p. 186 (Dec. 5, 2012).
K.T Flaherty et al., "Inhibition of mutated, activated BRAF in metastatic melanoma," The New England journal of medicine, vol. 363, p. 809 (Aug. 26, 2010).
Kim et al., "High Cleavage Efficiency of a 2A Peptide Derived from Porcine Teschovirus-1 in Human Cell Lines, Zebrafish and Mice," PLoS One, 6(4):el 8556, (2011).
Koike-Yusa, H., et al., "Genome-wide recessive genetic screening in mammalian cells with a lentiviral CRISPR-guide RNA library," Nat Biotechnol (2013). doi:10.1038/nbt.2800.
Koo et al., "Measuring and Reducing Off-Target Activities of Programmable Nucleases Including CRISPR-Cas9", Molecules and Cells, vol. 38, No. 6, May 19, 2015, pp. 475-481.

(56) References Cited

OTHER PUBLICATIONS

Laganiere et al., "An Engineered Zinc Finger Protein Activator of the Endogenous Glial Cell Line-Derived Neurotrophic Factor Gene Provides Functional Neuroprotection in a Rat Model of Parkinson's Disease", The Journal of Neuroscience (J. Neurosci.), Dec. 8, 2010, vol. 30, Issue 49, pp. 16469-16474.
M. Booker et al., "False negative rates in *Drosophila* cell-based RNAi screens: a case study," BMC Genomics, vol. 12, p. 50 (2011).
M. Costanzo et al., "The genetic landscape of a cell," Science, vol. 327, p. 425 (Jan. 22, 2010).
Marraffini, L.A., et al., "O. Sortases and the art of anchoring proteins to the envelopes of gram-positive bacteria," Microbiol. Mol. Biol. Rev., vol. 70, pp. 192-221 (2006).
Martin, M., "Cutadapt removes adapter sequences from high-throughput sequencing reads," EMBnet.journal, vol. 17, pp. 10-12 (2011).
Moffat J et al., "A lentiviral RNAi library for human and mouse genes applied to an arrayed viral high-content screen," Cell, vol. 124(6), pp. 1283-1298 (Mar. 24, 2006).
Mojica F. J. M et al., "Biological significance of a family of regularly spaced repeats in the genomes of Archaea, Bacteria and mitochondria," Molecular Microbiology, vol. 36(1), pp. 244-246 (2000).
Motamedi, M.R., et al., "Double-strand-break repair recombination in *Escherichia coli*: physical evidence for a DNA replication mechanism in vivo," Genes Dev., vol. 13, pp. 2889-2903 (1999).
Musunuru, "Abstract 18593: Use of a CRISPR/Cas System for Cardiovascular Disease Modeling and Therapeutic Applications", Circulation, vol. 128, No. 22, Suppl. 1, Nov. 26, 2013, 4 pages (Meeting info: American Heart Association, 2013 Scientific Sessions and Resuscitation Science Symposium, Dallas, TX, US, Nov. 16-20, 2013).
Paddison PJ et al., "A resource for large-scale RNA-interference-based screens in mammals," Nature, vol. 428(6981), pp. 427-431 (Mar. 25, 2004).
Podbielski, A., et al., "R. Novel series of plasmid vectors for gene inactivation and expression analysis in group A streptococci (GAS)," Gene, vol. 177, pp. 137-147 (1996).
R. Rad et al., "PiggyBac transposon mutagenesis: a tool for cancer gene discovery in mice," Science, vol. 330, p. 1104 (Nov. 19, 2010).
R.D Kolodner and G.T. Marsischky, "Eukaryotic DNA mismatch repair," Current Opinion in Genetics and Development, vol. 9, p. 89 (1999).
R.Renella et al., "Codanin-1 mutations in congenital dyserthropoietic anemia type 1 affect HP1α localization in erythroblasts," Blood, vol. 117, pp. 6928-6938 (2011).
Response to Third Party Observations in EP No. 13824232.6 filed Oct. 2, 2014, with Redlined and Clean Amended Claims.
S. Huang et al., "MED12 Controls the Response to Multiple Cancer Drugs through Regulation of TGF-β; Receptor Signaling," Cell, vol. 151, p. 937 (Nov. 21, 2012).
S. Konermann et al., "Optical control of mammalian endogenous transcription and epigenetic states," Nature, vol. 500, p. 472 (Aug. 22, 2013).
S.H. Chen et al., "A Knockout Mouse Approach Reveals that TCTP Functions as an Essential Factor for Cell Proliferation and Survival in a Tissue- or Cell Type-specific Manner," Molecular Biology of the Cell, vol. 18, pp. 2525-2532 (2007).
S.R. Whittaker et al., "A Genome-Scale RNA Interference Screen Implicates NF1 Loss in Resistance to RAF Inhibition," Cancer Discovery, vol. 3, p. 350 (Apr. 7, 2013).
S.S. Liu et al., "Identification and characterization of a novel gene, c1orf109, encoding a CK2 substrate that is involved in cancer cell proliferation," Journal of Biomedical Science, vol. 19, p. 49 (2012).
S.Xue and M. Barna, "Specialized ribosomes: a new frontier in gene regulation and organismal biology," Nat Rev Mol Cell Biol, vol. 13, p. 355 (2012).
Sarra, G., et al., "Gene replacement therapy in the retinal degeneration slow (rds) mouse: the effect on retinal degeneration following partial transduction of the retina", Human Molecular Genetics, 2001, vol. 10, pp. 2353-2361.
Semenova, E. et al., "Interference by clustered regularly interspaced short palindromic repeat (CRISPR) RNA is governed by a seed sequence," Proc. Natl. Acad. Sci. U.S.A. (2011).
Stewart SA et al., "Lentivirus-delivered stable gene silencing by RNAi in primary cells," RNA, vol. 9(4), pp. 493-501 (Apr. 2003).
Chevalier et al., "Homing endonuclease: structural and functional insight into the catalysts of intron/intein mobility," Oxford University Press., vol. 29, pp. 3757-3774 (2001).
Swarthout, John T., et al. "Zin Finger Nucleases: A new Era for Transgenic Animals," Animals of Neurosciences, vol. 18, No. 1 pp. 25-28, dated Jan. 2011, 4 pages.
Swiech et al., "CRISPR-Mediated Genome Editing in the Mammalian Brain", Molecular Therapy, vol. 22, 749, May 2014, p. S289.
Symington et al., "Double-Strand Break End Resection and Repair Pathway Choice", Annual Review of Genetics 2011, vol. 45, Sep. 12, 2011, pp. 247-271.
T. Horii et al., "Generation of an ICF Syndrome Model by Efficient Genome Editing of Human Induced Pluripotent Stem Cells Using the CRISPR System," International Journal of Molecular Sciences, vol. 14, p. 19774 (2013).
T.J. Cradick et al., "CRISPR/Cas9 systems targeting β-globin and CCR5 genes have substantial off-target activity," Nucleic Acids research (Aug. 11, 2013).
T.Yan et al., "DNA mismatch repair (MMR) mediates 6-thioguanine genetoxicity by introducing single-strand breaks to signal a G2-M arrest in MMR-proficient RKO cells," Clinical Cancer Research, vol. 9, p. 2327 (Jun. 1, 2003, 2003).
Takara Bio USA, Inc., "Lenti-X™ Tet-On © 3G CRISPR/Cas9 System User Manual", 2016, pp. 1-35.
Third Party Observation for Application No. EP20130824232 filed Sep. 22, 2014.
Third Party Observation in Application No. PCT/US2013/074819 dated Apr. 10, 2015.
Third Party Observation Under Article 115 EPC in Application No. 13818570.7 dated Oct. 1, 2014.
Third-Party Observation for Application No. EP20130824232 Aug. 9, 2014.
V.N. Ngo et al., "A loss-of-function RNA interference screen for molecular targets in cancer," Nature, vol. 441, p. 106 (Apr. 29, 2006).
Van Der Oost, J., et al., "CRISPR-based adaptive and heritable immunity in prokaryotes," Trends. Biochem. Sci., vol. 34, pp. 401-407 (2009).
Venken et al., "P[acman]: A BAC Transgenic Platform for Targeted Insertion of Large DNA Fragments in *D. melanogaster*", Science, vol. 314, No. 5806, Nov. 30, 2006, pp. 1747-1751.
W.G. Kaelin, "Use and Abuse of RNAi to Study Mammalian Gene Function," Science, vol. 337, p. 421 (Jul. 26, 2012).
Wang, H.H. et al., "Genome-scale promoter engineering by coselection MAGE," Nat methods, vol. 9, pp. 591-593 (2012).
Weber et al., "TALENs Targeting HBV: Designer Endonuclease Therapies for Viral Infections", Molecular Therapy, vol. 21, No. 10, Oct. 2013, pp. 1819-1821.
Wiedenheft, B. et al., "RNA-guided complex from a bacterial immune system enhances target recognition through seed sequence interactions.," Proc. Natl. Acad. Sci. U.S.A. (2011).
X.Liu et al., "STAGA recruits Mediator to the MYC oncoprotein to stimulate transcription and cell proliferation," Molecular and cellular biology, vol. 28, p. 108 (Jan. 2008).
Xu, Zhi-Li et al., "Regulated gene expression from adenovirus vectors: a systematic comparison of various inducible systems," Gene, 2003, vol. 309, pp. 145-151 (7 pages).
Yang et al., "HIV-1 TAT-mediated protein transduction and subcellular localization using novel expression vectors," FEBS Letters 532:36-44, (2002).
Zahner, D. and Hakenbeck, R. "The *Streptococcus pneumoniae* beta-galactosidase is a surface protein," J. Bacteriol., vol. 182, pp. 5919-5921 (2000).

(56) References Cited

OTHER PUBLICATIONS

Zeng Y et al., "Both natural and designed micro RNAs can inhibit the expression of cognate mRNAs when expressed in human cells," Mol Cell., vol. 9(6), pp. 1327-1333 (Jun. 2002).

Zhang, "Processing-Independent CRISPR RNAs Limit Natural Transformation in Neisseria meningitidis", Molecular Cell, vol. 50, May 23, 2013. pp. 488-503.

Zuris, et al., "Cationic lipid-mediated delivery of proteins enables efficient protein-based genome editing in vitro and in vivo" Nature Biotechnology, 2014, Advanced Online publication, doi:10.1038/nbt.3081.

Zuris, et al., Supplementary Information—"Cationic lipid-mediated delivery proteins enables efficient protein-based genome editing in vitro and in vivo" Nature Biotechnology, 2014, Advanced Online publication, doi:10.1038/nbt.3081.

\* cited by examiner

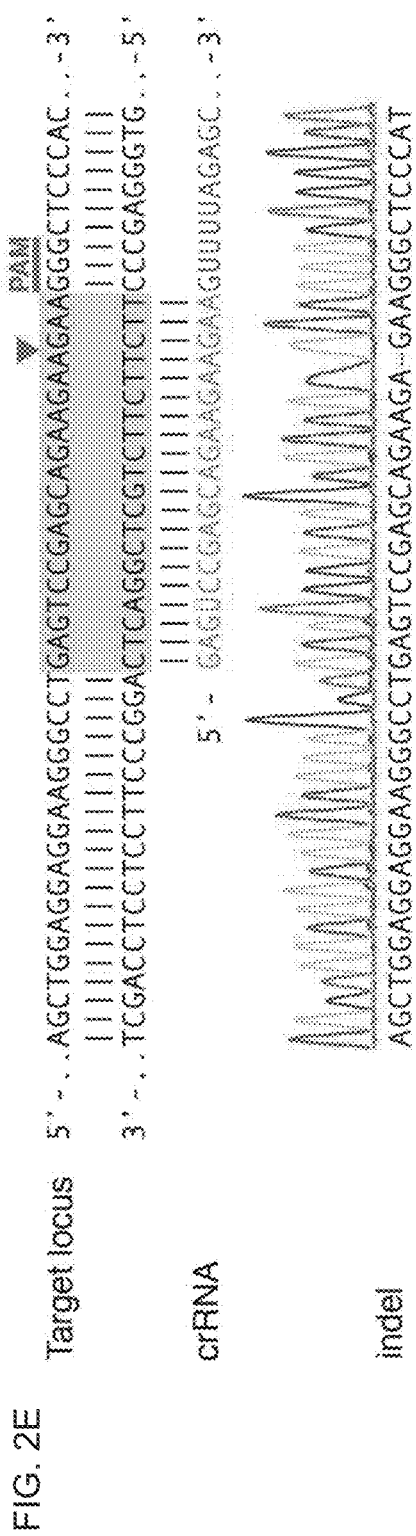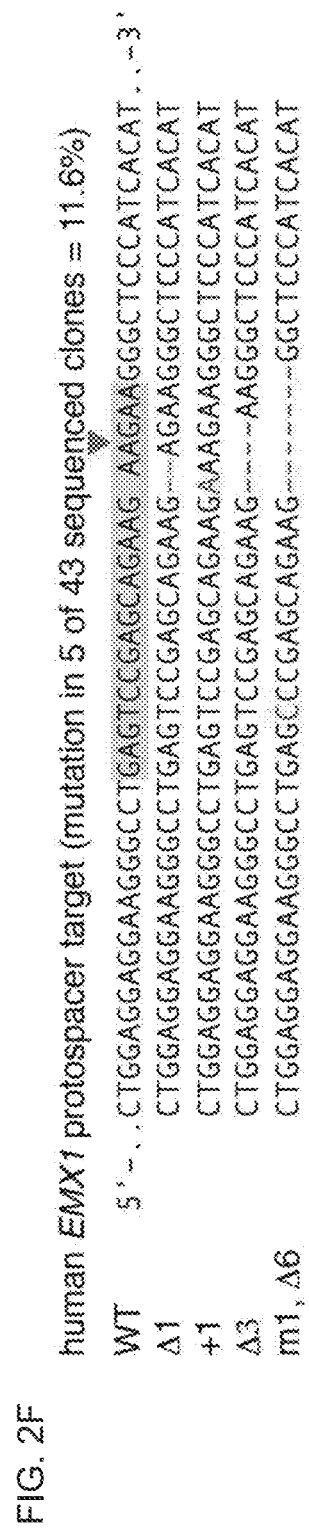

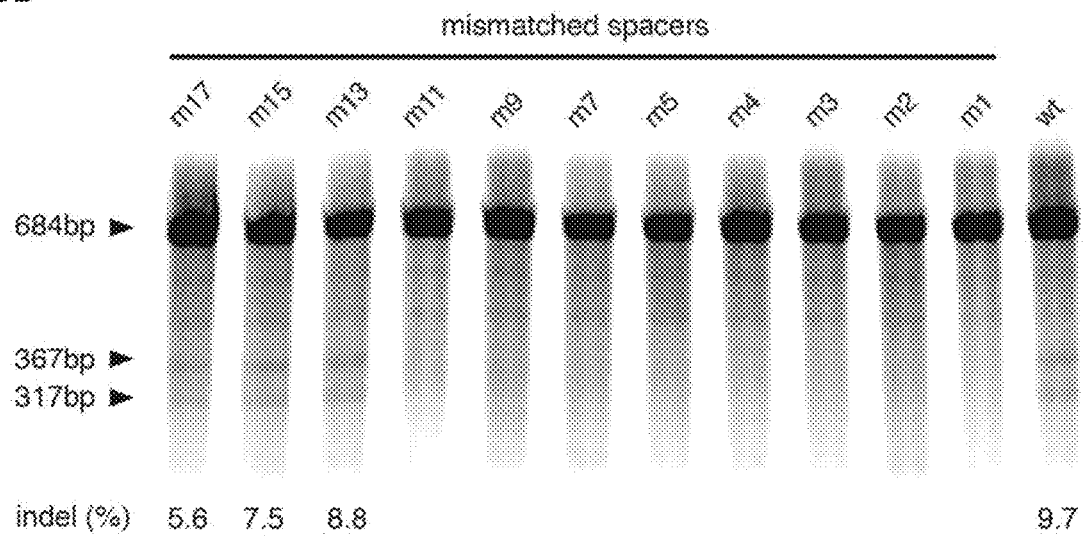

| Cas9 | target species | gene | protospacer ID | protospacer sequence (5' to 3') | PAM | strand | cell line tested | % indel (pre-crRNA + tracrRNA) | % indel (chimeric RNA) |
|---|---|---|---|---|---|---|---|---|---|
| S. pyogenes SF370 type II CRISPR | Homo sapiens | EMX1 | 1 | GGAAGGGCCTGAGTCCGAGCAGAAGAAGAA | GGG | + | 293FT | 20 ± 1.8 | 6.7 ± 0.62 |
| | | EMX1 | 2 | CATTGGAGGTGACATCGATGTCCTCCCCAT | TGG | − | 293FT | 2.1 ± 0.31 | N.D. |
| | | EMX1 | 3 | GGACATCGATGTCACCTCCAATGACTAGGG | TGG | + | 293FT | 14 ± 1.1 | N.D. |
| | | EMX1 | 4 | CATCGATGTCCTCCCCATTGGCCTGCTTCG | TGG | − | 293FT | 11 ± 1.7 | N.D. |
| | | EMX1 | 5 | TTCGTGGCAATGCGCCACCGGTTGATGTGA | TGG | − | 293FT | 4.9 ± 0.46 | 2.1 ± 0.51 |
| | | EMX1 | 6 | TCGTGGCAATGCGCCACCGGTTGATGTGAT | GGG | − | 293FT | 4.0 ± 0.88 | 0.41 ± 0.25 |
| | | EMX1 | 7 | TCCAGCTTCTGCCGTTTGTACTTTGTCCTC | CGG | − | 293FT | 1.5 ± 0.12 | N.D. |
| | | EMX1 | 8 | GGAGGACAAGGCGCAGATGAGGAAACTCAAG | AGG | − | 293FT | 7.8 ± 0.83 | 2.3 ± 1.2 |
| | | PVALB | 9 | AGGGGCCCAGATTGGGTGTTCAGGGCAGAG | AGG | + | 293FT | 21 ± 2.6 | 6.5 ± 0.32 |
| | | PVALB | 10 | ATCAGGAGGGTGGCAGAGGGCCGAGAT | TGG | + | 293FT | N.D. | N.D. |
| | | PVALB | 11 | GGTGGGCGAGAGGGGCCGAGATTGGTGTTC | AGG | + | 293FT | N.D. | N.D. |
| | Mus musculus | Th | 12 | CAAGCACTCAGTGCCATTAGCTAAATGCAT | AGG | − | Neuro2A | 27 ± 4.3 | 4.1 ± 2.2 |
| | | Th | 13 | AATGCATAGGTACCACCACAGTGCCAG | GGG | − | Neuro2A | 4.8 ± 1.2 | N.D. |
| | | Th | 14 | ACACACATGGGAAAGCCTCTGGCACAGAA | AGG | + | Neuro2A | 11.3 ± 1.3 | N.D. |
| S. thermophilus LMD-9 CRISPR1 | Homo sapiens | EMX1 | 15 | GGAAGGAGGTAGTATACAGAAACACAGAA | GTAGAAT | − | 293FT | 14 ± 0.89 | N.T. |
| | | EMX1 | 16 | AGAATGTAAGAAGAGTCACAGAAACTTAGCA | CTAGAAA | − | 293FT | 7.8 ± 0.77 | N.T. |

FIG. 5

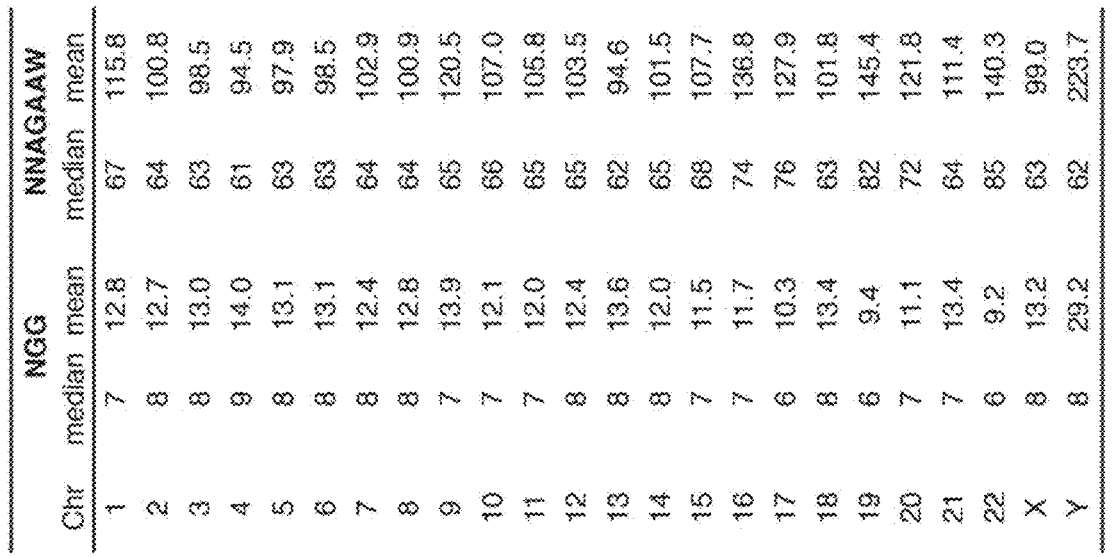
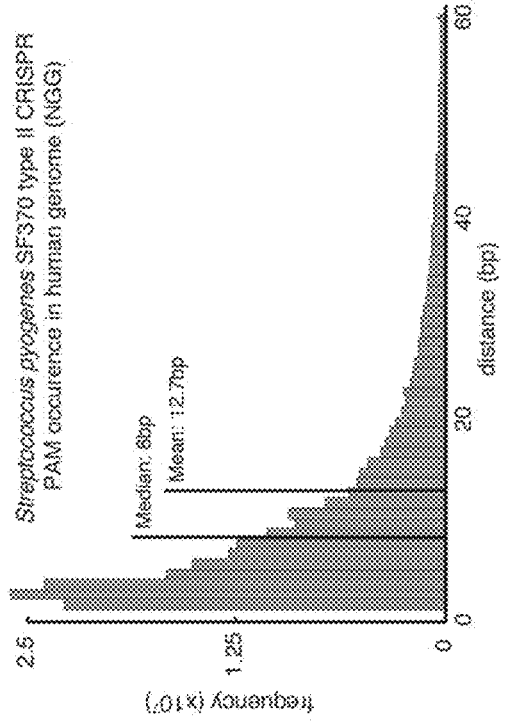
FIG. 9A
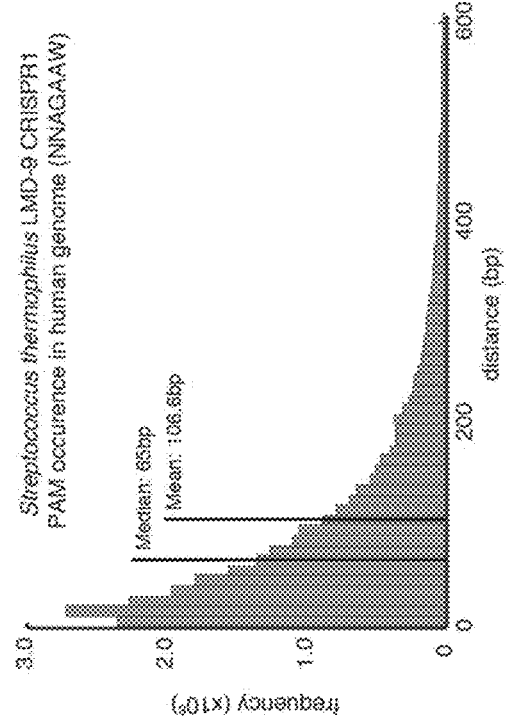
FIG. 9B
FIG. 9C

| Primer name | Assay | Genomic Target | Primer sequence |
|---|---|---|---|
| Sp-EMX1-F | SURVEYOR assay, sequencing | EMX1 | AAAACCACCCTTCTCTCTGGC |
| Sp-EMX1-R | SURVEYOR assay, sequencing | EMX1 | GGAGATTGGAGACACGGAGAG |
| Sp-PVALB-F | SURVEYOR assay, sequencing | PVALB | CTGGAAAGCCAATGCCTGAC |
| Sp-PVALB-R | SURVEYOR assay, sequencing | PVALB | GGCAGCAAACTCCTTGTCCT |
| Sp-Th-F | SURVEYOR assay, sequencing | Th | GTGCTTTGCAGAGGCCTACC |
| Sp-Th-R | SURVEYOR assay, sequencing | Th | CCTGGAGCGCATGCAGTAGT |
| St-EMX1-F | SURVEYOR assay, sequencing | EMX1 | ACCTTCTGTGTTTCCACCATTC |
| St-EMX1-R | SURVEYOR assay, sequencing | EMX1 | TTGGGGAGTGCACAGACTTC |
| Sp-EMX1-RFLP-F | RFLP, sequencing | EMX1 | GGCTCCCTGGGTTCAAAGTA |
| Sp-EMX1-RFLP-R | RFLP, sequencing | EMX1 | AGAGGGGTCTGGATGTCGTAA |
| Pb_EMX1_sp1 | Northern Blot Probe | Not applicable | TAGCTCTAAAACTTCTTCTTCTGCTCGGAC |
| Pb_tracrRNA | Northern Blot Probe | Not applicable | CTAGCCTTATTTTAACTTGCTATGCTGTTT |

FIG. 15

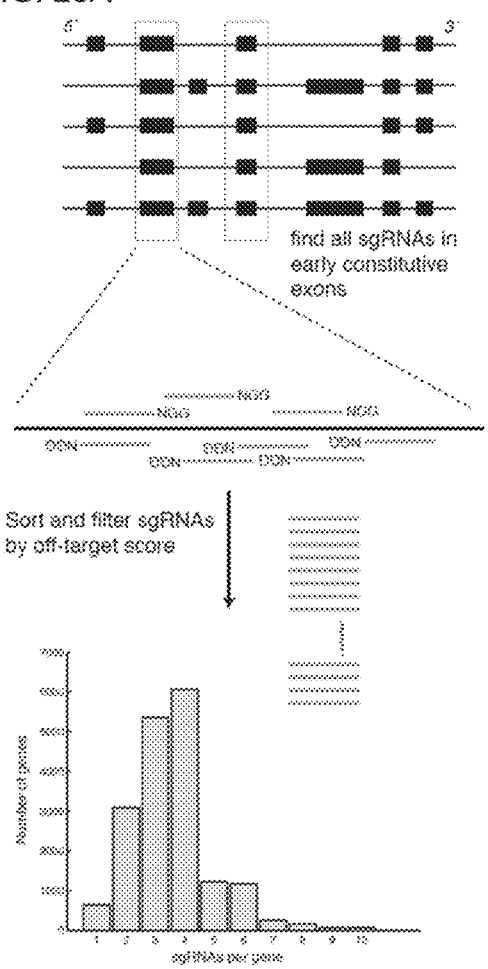
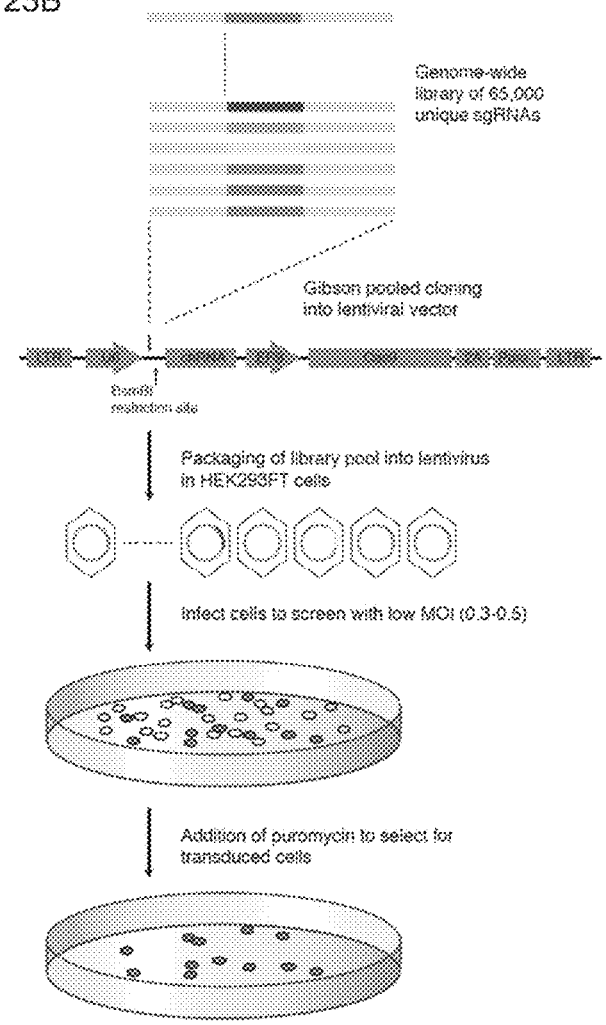
FIG. 23A
FIG. 23B

FIG. 23D  NGS indel data on EGFP cells

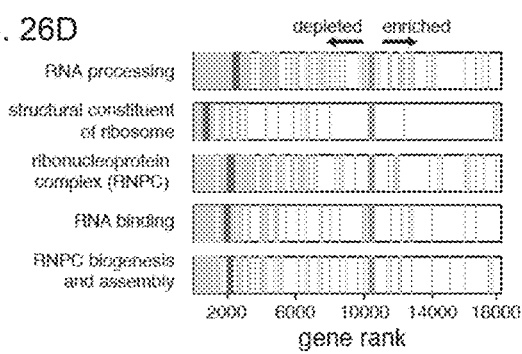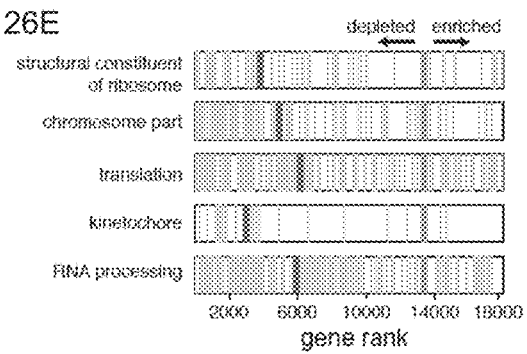

```
                    EGFP gRNA 1                              EGFP gRNA 2            EGFP gRNA 3
ATGGTGAGCAAGGGCGAGGAGCTGTTCACCGGGGTGGTGCCCATCCTGGTCGAGCTGGACGGCGACGTAAACGGCCACAAGTTCAGCGTGTCCGGCGAGG
||||||||||||||||||||||||||||||||||||||||||||||||||||||||||||||||||||||||||||||||||||||||||||||||||
TACCACTCGTTCCCGCTCCTCGACAAGTGGCCCCACCACGGGTAGGACCAGCTCGACCTGCCGCTGCATTTGCCGGTGTTCAAGTCGCACAGGCCGCTCC

GCGAGGGCGATGCCACCTACGGCAAGCTGACCCTGAAGTTCATCTGCACCACCGGCAAGCTGCCCGTGCCCTGGCCCACCCTCGTGACCACCCTGACCTA
||||||||||||||||||||||||||||||||||||||||||||||||||||||||||||||||||||||||||||||||||||||||||||||||||
CGCTCCCGCTACGGTGGATGCCGTTCGACTGGGACTTCAAGTAGACGTGGTGGCCGTTCGACGGGCACGGGACCGGGTGGGAGCACTGGTGGGACTGGAT

EGFP gRNA 4
CGGCGTGCAGTGCTTCAGCCGCTACCCCGACCACATGAAGCAGCACGACTTCTTCAAGTCCGCCATGCCCGAAGGCTACGTCCAGGAGCGCACCATCTTC
||||||||||||||||||||||||||||||||||||||||||||||||||||||||||||||||||||||||||||||||||||||||||||||||||
GCCGCACGTCACGAAGTCGGCGATGGGGCTGGTGTACTTCGTCGTGCTGAAGAAGTTCAGGCGGTACGGGCTTCCGATGCAGGTCCTCGCGTGGTAGAAG

EGFP gRNA 4 (cont.)                          EGFP gRNA 5            EGFP gRNA 6
TTCAAGGACGACGGCAACTACAAGACCCGCGCCGAGGTGAAGTTCGAGGGCGACACCCTGGTGAACCGCATCGAGCTGAAGGGCATCGACTTCAAGGAGG
||||||||||||||||||||||||||||||||||||||||||||||||||||||||||||||||||||||||||||||||||||||||||||||||||
AAGTTCCTGCTGCCGTTGATGTTCTGGGCGCGGCTCCACTTCAAGCTCCCGCTGTGGGACCACTTGGCGTAGCTCGACTTCCCGTAGCTGAAGTTCCTCC ACGGCAACATCCTGGGGCACAAGCTGGAGTACAACTACAACAGCCACAACGTCTATATCATGGCCGACAAGCAGAAGAACGGCATCAAGGTGAACTTCAA
||||||||||||||||||||||||||||||||||||||||||||||||||||||||||||||||||||||||||||||||||||||||||||||||||
TGCCGTTGTAGGACCCCGTGTTCGACCTCATGTTGATGTTGTCGGTGTTGCAGATATAGTACCGGCTGTTCGTCTTCTTGCCGTAGTTCCACTTGAAGTT GATCCGCCACAACATCGAGGACGGCAGCGTGCAGCTCGCCGACCACTACCAGCAGAACACCCCCATCGGCGACGGCCCCGTGCTGCTGCCCGACAACCAC
||||||||||||||||||||||||||||||||||||||||||||||||||||||||||||||||||||||||||||||||||||||||||||||||||
CTAGGCGGTGTTGTAGCTCCTGCCGTCGCACGTCGAGCGGCTGGTGATGGTCGTCTTGTGGGGGTAGCCGCTGCCGGGGCACGACGACGGGCTGTTGGTG TACCTGAGCACCCAGTCCGCCCTGAGCAAAGACCCCAACGAGAAGCGCGATCACATGGTCCTGCTGGAGTTCGTGACCGCCGCCGGGATCACTCTCGGCA
||||||||||||||||||||||||||||||||||||||||||||||||||||||||||||||||||||||||||||||||||||||||||||||||||
ATGGACTCGTGGGTCAGGCGGGACTCGTTTCTGGGGTTGCTCTTCGCGCTAGTGTACCAGGACGACCTCAAGCACTGGCGGCGGCCCTAGTGAGAGCCGT

TGGACGAGCTGTACAAGTAA
||||||||||||||||||||
ACCTGCTCGACATGTTCATT
```

FIG. 29

| A375 | | HUES62 | |
|---|---|---|---|
| gene_name | mean depletion | gene_name | mean depletion |
| RPS19 | -2.882652431 | RPS19 | -3.183585341 |
| TCOF1 | -2.808435977 | SUMO1 | -2.958691468 |
| NIP7 | -2.577017439 | IGFN1 | -2.816486619 |
| CARS2 | -2.524564219 | AGAP5 | -2.781890338 |
| RPL7 | -2.510763424 | VOPP1 | -2.764536999 |
| ARL17A | -2.452404991 | JAKMIP1 | -2.722075866 |
| RPS18 | -2.360007937 | HIST2H2AC | -2.609990396 |
| RPS11 | -2.331818955 | SPHAR | -2.582311984 |
| RPL32 | -2.27812036 | LCE3E | -2.525929706 |
| DENR | -2.257042611 | PDRG1 | -2.499694407 |
| RPL6 | -2.23869209 | RRP1B | -2.361922343 |
| ADSL | -2.237218508 | PFDN4 | -2.321026472 |
| DNM2 | -2.213359485 | OVGP1 | -2.294064989 |
| ACTL6A | -2.197447807 | CCDC58 | -2.290819552 |
| PPAN | -2.178384698 | HIST1H2BJ | -2.288803994 |
| NT5C1B-RDH | -2.175777594 | CCDC73 | -2.279966592 |
| ENO1 | -2.17247027 | ZSCAN18 | -2.277760787 |
| DOLK | -2.140854234 | DENR | -2.253261386 |
| ASH2L | -2.137162022 | CHKA | -2.231856136 |
| SNRPF | -2.129389793 | FAM185A | -2.226396662 |
| RPL26 | -2.125670091 | OCM | -2.225306785 |
| GABPA | -2.106954316 | KBTBD11 | -2.2083224 |
| VOPP1 | -2.088272162 | RPL32 | -2.198484015 |
| RSL1D1 | -2.077068149 | RBMXL2 | -2.193406936 |
| RRAGA | -2.075755103 | LRRC37A3 | -2.188978264 |
| URB1 | -2.061968502 | SNRPG | -2.180311606 |
| MRP63 | -2.058260881 | POLR2J | -2.179863073 |
| NAA30 | -2.056104946 | EID1 | -2.177256367 |
| KPNB1 | -2.045863711 | HMGN4 | -2.152073487 |
| RPL39 | -2.042789125 | FJX1 | -2.144074596 |
| EIF2B5 | -2.018537107 | MRPS18C | -2.143839164 |
| XRN1 | -2.007802712 | UTP18 | -2.13822949 |
| LSM2 | -2.006908746 | GCSH | -2.123373465 |
| MASP2 | -1.996597431 | HIST1H2AG | -2.10248405 |
| DEFB131 | -1.981628571 | MT1E | -2.102441783 |
| LSM7 | -1.977614338 | RPL30 | -2.087694615 |
| NHP2L1 | -1.977025309 | TMEM52 | -2.078628045 |
| RPS15A | -1.964623412 | XPA | -2.075701399 |
| EEF1A1 | -1.940570892 | ARHGEF19 | -2.074475526 |
| RBX1 | -1.931878232 | RAMP2 | -2.071163793 |
| PTPMT1 | -1.931127795 | MTA3 | -2.060680607 |
| CCDC146 | -1.930330138 | POLRMT | -2.058734986 |
| COBRA1 | -1.924683023 | ZNF524 | -2.051959832 |
| VPS25 | -1.919175993 | RSL24D1 | -2.047403722 |
| RPL8 | -1.915827854 | EXOSC1 | -2.036942474 |
| POLR2I | -1.914363716 | BATF | -2.035568177 |
| NHP2 | -1.908840701 | KRTAP11-1 | -2.033591989 |
| OR5M3 | -1.903054531 | FCF1 | -2.03040005 |
| SDAD1 | -1.898279431 | NEUROG1 | -2.024122047 |
| DNAJA3 | -1.895932148 | NSRP1 | -2.016177389 |
| IMP4 | -1.886050088 | XYLT1 | -2.013363239 |
| MOAP1 | -1.882851477 | CNIH4 | -2.010919939 |
| NUTF2 | -1.873263167 | RPS7 | -2.005077402 |
| PTPN23 | -1.869411288 | PLAC9 | -1.99787552 |
| RPL14 | -1.854061225 | DCPS | -1.993526745 |
| RP11-110H1. | -1.838203216 | HMGN1 | -1.985137369 |
| TPT1 | -1.834186561 | HIST1H2BM | -1.966034904 |
| COPS3 | -1.830313031 | RPS11 | -1.958203408 |
| HARS | -1.808567224 | TP53TG5 | -1.952603327 |
| ATP6V0C | -1.806752366 | KRT82 | -1.951720459 |
| CCNH | -1.802427683 | MRP63 | -1.950917553 |
| RPL7A | -1.801850968 | OR51V1 | -1.950395101 |
| COL25A1 | -1.789186395 | RPL7A | -1.945684794 |
| EEF2 | -1.773430832 | MTMR1 | -1.942316422 |
| EEFSEC | -1.773082367 | TMEM144 | -1.940658066 |
| LGALS8 | -1.772564445 | ACSM1 | -1.938959493 |
| SFPQ | -1.771314781 | RRN3 | -1.933600629 |
| EIF2S3 | -1.769731164 | IPO4 | -1.932523341 |
| COPB1 | -1.762259717 | HNRNPU | -1.929921878 |
| RBMX2 | -1.758857017 | GTF3C1 | -1.924067851 |
| POLR3H | -1.753585716 | RPL6 | -1.923613883 |
| RPL10 | -1.75174146 | CCDC90B | -1.916359703 |
| TMLHE | -1.750717975 | C15orf42 | -1.912360544 |
| TUBG1 | -1.749877928 | CITED4 | -1.912125059 |
| ANKRD30A | -1.74932094 | CXCR3 | -1.910371663 |
| KCNJ16 | -1.74542423 | ICOS | -1.907257673 |
| ZNF207 | -1.743830295 | AKR1A1 | -1.904032674 |
| PTRH2 | -1.735681069 | WDR83OS | -1.902920977 |
| CAPZB | -1.733659665 | RMI1 | -1.900641673 |

FIG. 45A

| | | | |
|---|---|---|---|
| HNRNPU | -1.732106008 | RFC5 | -1.894008779 |
| YEATS2 | -1.72409334 | OR5AR1 | -1.888994891 |
| RPL37 | -1.72397052 | FAM96B | -1.88827946 |
| RPF1 | -1.722952482 | PCDH81 | -1.887315952 |
| SUMO2 | -1.722198581 | RPL8 | -1.862649576 |
| ACACA | -1.719950822 | TTLL4 | -1.862595159 |
| CAPZA1 | -1.719035764 | ELOVL2 | -1.858705763 |
| FARSB | -1.707506458 | JAG2 | -1.853386152 |
| CTDP1 | -1.705884315 | RBMX2 | -1.842871507 |
| SS18L2 | -1.70390379 | POLR3K | -1.8372641 |
| CENPI | -1.703824885 | ZBTB39 | -1.834577541 |
| PRPF38B | -1.703372866 | PKD1 | -1.834139042 |
| SF3B1 | -1.702731503 | MFSD2A | -1.833483748 |
| MAPK1 | -1.69651763 | RAE1 | -1.833119559 |
| MOCS3 | -1.686665595 | RIMBP3B | -1.832150575 |
| POP7 | -1.685420318 | PKN3 | -1.831875987 |
| UTP18 | -1.684192052 | YY1 | -1.830589818 |
| ME3 | -1.683035372 | CWC25 | -1.829810575 |
| PSMC2 | -1.681322654 | ARSE | -1.823179326 |
| TBC1D2B | -1.680850452 | NBR1 | -1.823032991 |
| MRPL17 | -1.678664073 | PRNP | -1.815793705 |
| PIGW | -1.676457135 | NUDC | -1.81045846 |
| RPL30 | -1.674678234 | KDM4E | -1.810122958 |
| GFM1 | -1.672030725 | RBX1 | -1.800761527 |
| APPL1 | -1.667691292 | TSPYL2 | -1.800195078 |
| PRAMEF18 | -1.661579353 | RALGDS | -1.798929091 |
| THOC2 | -1.659978325 | C14orf80 | -1.796756631 |
| DCP5 | -1.65488046 | APBA3 | -1.791344673 |
| RPS21 | -1.649662797 | ENO1 | -1.79011033 |
| POLR2L | -1.647400059 | SMG1 | -1.784878697 |
| DPPA3 | -1.643632209 | C9orf169 | -1.778113126 |
| PRAMEF11 | -1.640377216 | ZNRD1 | -1.774181477 |
| TBCC | -1.637735404 | KCNJ16 | -1.769711082 |
| MRPS12 | -1.637593143 | POLR2I | -1.769423783 |
| EFTUD2 | -1.63609533 | UBA52 | -1.768260354 |
| BEX1 | -1.634269725 | NOC4L | -1.764945455 |
| NOL6 | -1.63270992 | HORMAD2 | -1.764870613 |
| HNRNPK | -1.631201515 | OR9Q2 | -1.760481348 |
| SNRNP70 | -1.630423532 | HPN | -1.75865726 |
| RPL4 | -1.628309405 | KRT24 | -1.758465732 |
| H3F3B | -1.621875698 | FOXH1 | -1.757242912 |
| MATR3 | -1.620666917 | GDF9 | -1.756109302 |
| RPL38 | -1.618433284 | CEP290 | -1.753803294 |
| PGD | -1.617906932 | ADRA2C | -1.753773058 |
| DAP3 | -1.616024661 | TULP1 | -1.749849627 |
| TSR1 | -1.612896573 | LTBR | -1.749021049 |
| SMC1A | -1.607195432 | ZCCHC12 | -1.746744432 |
| RPL9 | -1.60619161 | RPAIN | -1.73474472 |
| RPS12 | -1.603986362 | B3GALT4 | -1.733297288 |
| SNRNP200 | -1.597597784 | ATP1A2 | -1.728486738 |
| ZNRD1 | -1.595667827 | PCDHB16 | -1.728250573 |
| TFAM | -1.592538964 | CDAN1 | -1.724068055 |
| TLN1 | -1.592240013 | PIP5K1C | -1.723834562 |
| CHST7 | -1.591104236 | MPP4 | -1.722234521 |
| RFK | -1.589972652 | SPOCD1 | -1.721697697 |
| VARS | -1.589849258 | H3F3B | -1.721342781 |
| WT1 | -1.588292311 | RPS21 | -1.717399432 |
| PDAP1 | -1.588174658 | BEX1 | -1.716075951 |
| WARS2 | -1.586972934 | DDX41 | -1.716023943 |
| OCM | -1.586564929 | ATP12A | -1.714599078 |
| TEX14 | -1.582436009 | PLEKHA6 | -1.71359395 |
| OR7C2 | -1.580970812 | SIGLEC5 | -1.711535603 |
| SNAP23 | -1.579522004 | GPR115 | -1.711244409 |
| FURIN | -1.579107358 | PGBD4 | -1.709127717 |
| C19orf25 | -1.576034681 | ABCC3 | -1.709096583 |
| GNB2L1 | -1.57535027 | C1QTNF4 | -1.704914364 |
| PCF11 | -1.573868556 | SUZ12 | -1.702460494 |
| C6orf226 | -1.573804931 | IRS1 | -1.701590078 |
| DHX15 | -1.570412486 | POLR1A | -1.7013335 |
| NUP88 | -1.567264532 | TMEM183A | -1.700220613 |
| EIF2S1 | -1.563321294 | OR52B4 | -1.699496045 |
| PET117 | -1.562889941 | SLC13A2 | -1.699062296 |
| PPP2CA | -1.562824258 | TUBGCP3 | -1.695027009 |
| CMPK1 | -1.557510591 | GGT7 | -1.690668273 |
| RAE1 | -1.553916339 | OR1D2 | -1.689507147 |
| CIRH1A | -1.55196902 | TUBG2 | -1.686771713 |
| DDX42 | -1.548957925 | FOXB1 | -1.686159699 |
| POLR3A | -1.54531119 | COX4I2 | -1.685145656 |
| RPS5 | -1.544242565 | CFHR5 | -1.684484434 |
| RUVBL2 | -1.54307586 | COX7B2 | -1.683824823 |
| KHDRBS1 | -1.540530485 | ZMYND8 | -1.679931871 |
| UBQLN3 | -1.539875621 | ANKLE2 | -1.67977325 |
| SART3 | -1.538803977 | ZBTB32 | -1.677758798 |
| CTU2 | -1.532672693 | MEX3A | -1.67283445 |
| EXOSC9 | -1.53240283 | IRF2BPL | -1.66817721 |

FIG. 45B

| Gene | Value | Gene | Value |
|---|---|---|---|
| EIF3D | -1.531272229 | XPO1 | -1.665911185 |
| FOSL1 | -1.525912762 | SERPINB3 | -1.665420952 |
| SKIV2L2 | -1.524792166 | SPC24 | -1.664003074 |
| NSL1 | -1.523902984 | ZNF835 | -1.663591136 |
| PKD2L2 | -1.522030203 | HSP90AB1 | -1.65845304 |
| COX17 | -1.521428227 | C1orf52 | -1.657906239 |
| RAB3GAP1 | -1.518439462 | EXOSC8 | -1.657418649 |
| SBDS | -1.518313565 | PPP1R7 | -1.654337881 |
| HSD17B10 | -1.516651173 | ANAPC7 | -1.654087519 |
| RPL34 | -1.514777041 | PDP2 | -1.652883515 |
| MRPL41 | -1.514148656 | LRRC6 | -1.649462528 |
| KIF23 | -1.511701917 | PCDHGC5 | -1.641146446 |
| BRIP1 | -1.510169164 | ECH1 | -1.637984733 |
| PSMA3 | -1.50978052 | BIRC6 | -1.635174985 |
| MYO18A | -1.506084393 | CHMP4C | -1.631396522 |
| OR5K3 | -1.501361245 | URB1 | -1.628023834 |
| PCNA | -1.500086419 | PPP4C | -1.626848674 |
| COX4I1 | -1.495514571 | LRRC3 | -1.624158807 |
| CCDC23 | -1.491525997 | FAM207A | -1.623564041 |
| SLC26A7 | -1.491379231 | TSSK1B | -1.623386054 |
| GJA3 | -1.490625294 | SNRNP35 | -1.622193825 |
| PMF1 | -1.489084741 | ENTPD7 | -1.621420381 |
| ZNF259 | -1.488562555 | ZNF559 | -1.619457887 |
| ARHGAP11A | -1.487361831 | PLEKHA3 | -1.619359014 |
| INTS8 | -1.485702565 | PSMB11 | -1.619357614 |
| COX5B | -1.483628484 | C12orf57 | -1.6192204 |
| BCL2L2-PABP | -1.479334824 | BCL9L | -1.616431663 |
| ATP6AP2 | -1.476781098 | COL6A2 | -1.616189888 |
| FNTB | -1.473951658 | PHLDA2 | -1.616178629 |
| MTA3 | -1.473861711 | ERAS | -1.613501381 |
| TDRD10 | -1.473540335 | GAS8 | -1.611441409 |
| TSG101 | -1.472472944 | ANAPC1 | -1.609927961 |
| HSP90B1 | -1.472220581 | PHIP | -1.606091841 |
| KIF2A | -1.471850262 | TMEM234 | -1.605376698 |
| MED14 | -1.469852205 | RPL13A | -1.603258551 |
| ANKRD49 | -1.469829543 | USP44 | -1.601487248 |
| PSMB4 | -1.468797099 | HNRNPA0 | -1.601341264 |
| COX5A | -1.467673157 | COX6B1 | -1.598937125 |
| PCBP1 | -1.465993867 | KRTCAP2 | -1.597973049 |
| FCF1 | -1.465773243 | CASKIN1 | -1.597967074 |
| TINF2 | -1.465625197 | IFNB1 | -1.588890032 |
| LAMTOR3 | -1.461323319 | MED21 | -1.588539266 |
| RPL11 | -1.459385197 | SDSL | -1.588435672 |
| MDM2 | -1.457827281 | RPS6 | -1.587775088 |
| CTNNBL1 | -1.45731148 | DDX42 | -1.587535926 |
| RPL15 | -1.457245851 | LIN7C | -1.587142859 |
| SOX10 | -1.457045107 | UBXN4 | -1.587070505 |
| TUBGCP3 | -1.455922895 | DSN1 | -1.582628585 |
| KDSR | -1.45079145 | NTAN1 | -1.581097107 |
| HSPA8 | -1.44920478 | CDC26 | -1.580081851 |
| MAD2L1 | -1.448620304 | PIGM | -1.578178236 |
| ZFHX3 | -1.447869343 | CHD6 | -1.577282235 |
| DYNLL1 | -1.446908968 | CHORDC1 | -1.574916503 |
| C17orf81 | -1.444492658 | UVRAG | -1.573957952 |
| NGDN | -1.444452376 | ZNF580 | -1.572557983 |
| CENPC1 | -1.444330973 | OR4D10 | -1.570303265 |
| POLR3K | -1.444320245 | COG6 | -1.569988804 |
| KRI1 | -1.443946118 | FBXO41 | -1.567074156 |
| DNAJB1 | -1.443734639 | C1orf150 | -1.566762543 |
| SLC35C2 | -1.442854155 | MMP23B | -1.56595931 |
| SAE1 | -1.437585047 | FFAR3 | -1.562720247 |
| NR1I3 | -1.437194199 | PIGW | -1.562033012 |
| NKAP | -1.436957722 | ZRSR2 | -1.560314358 |
| TBCA | -1.436566244 | ARMC7 | -1.56023241 |
| CABIN1 | -1.434611745 | EIF6 | -1.558951618 |
| HJURP | -1.433849464 | ANKRD49 | -1.55887604 |
| TRMT112 | -1.433490187 | PIK3CA | -1.558845668 |
| ZNF529 | -1.432525336 | DEFB131 | -1.55797361 |
| RPS27A | -1.432347982 | CLDN4 | -1.550420395 |
| ARMC7 | -1.429603057 | C5orf62 | -1.548815903 |
| AGAP6 | -1.429039924 | C7 | -1.548712647 |
| POLR1B | -1.428651863 | COPB1 | -1.548302258 |
| FAM96B | -1.427271021 | STX18 | -1.547594206 |
| PMVK | -1.42708923 | MASP2 | -1.545823489 |
| CSNK2B | -1.426586006 | RP11-528L24.3 | -1.545098873 |
| KPNA4 | -1.426305655 | PEX16 | -1.544210673 |
| RPL13 | -1.425968515 | TMCC3 | -1.542308989 |
| RPL35A | -1.425528555 | FTSJD1 | -1.54122008 |
| CUL1 | -1.425420937 | PDF | -1.540774209 |
| SUPT6H | -1.424775226 | TSR1 | -1.537975442 |
| RPS3 | -1.424672812 | WWC2 | -1.535385295 |
| RRP1 | -1.424495031 | EIF4E1B | -1.535041313 |
| SF1 | -1.422731301 | PCDHB7 | -1.534750337 |
| IL9 | -1.422056509 | ASNS | -1.533747699 |
| BUB1 | -1.421531126 | GNG7 | -1.533427432 |

FIG. 45C

| Gene | Value | Gene | Value |
|---|---|---|---|
| YY1 | -1.419062109 | RBM48 | -1.531893314 |
| SMARCA5 | -1.416042074 | HIST2H2BE | -1.530781789 |
| PSMD12 | -1.415969492 | CGB1 | -1.530628903 |
| RANBP1 | -1.415302054 | S100A11 | -1.529786068 |
| PSMB1 | -1.415056441 | EIF5 | -1.52717872 |
| WDR74 | -1.414139191 | DGCR8 | -1.52706625 |
| RPL13A | -1.413479285 | ZNF226 | -1.526829346 |
| BUD31 | -1.413072743 | PI4K2A | -1.523505S73 |
| CDC45 | -1.412488904 | LRRK1 | -1.520636889 |
| PPA1 | -1.410634008 | SGTA | -1.519321666 |
| RPS14 | -1.410592726 | TOMM22 | -1.518878323 |
| NOC4L | -1.409986802 | POTED | -1.517539425 |
| CCDC59 | -1.409761529 | PSME3 | -1.514880312 |
| EXOSC8 | -1.409548516 | ZBTB8OS | -1.514406895 |
| POLR2E | -1.408878942 | LCN8 | -1.513494042 |
| DGCR8 | -1.406358064 | CDC42BPB | -1.512815457 |
| TOR1AIP1 | -1.406117404 | PA2G4 | -1.511632954 |
| EXOSC5 | -1.405249481 | PLEKHH1 | -1.510365559 |
| CSTF3 | -1.403919466 | POP7 | -1.50968476 |
| USP1 | -1.403815672 | TFAM | -1.509576181 |
| ANAPC7 | -1.401430164 | ATP6V0C | -1.508572478 |
| MDN1 | -1.401349647 | C6orf226 | -1.507967003 |
| GAPDH | -1.400273726 | MEIS1 | -1.506671145 |
| ST13 | -1.398019204 | PRDM14 | -1.505804106 |
| CCDC73 | -1.394548173 | QRFP | -1.504909604 |
| TERF2 | -1.394231255 | BRAT1 | -1.504170191 |
| NOL12 | -1.391253457 | WDR76 | -1.502637608 |
| DBR1 | -1.390682155 | VWDE | -1.499084118 |
| RBBP5 | -1.390436818 | KLHL34 | -1.497309165 |
| CASC5 | -1.390361403 | ALLC | -1.497016423 |
| ARL2 | -1.390023083 | CAPZA1 | -1.496931761 |
| ISCA2 | -1.38933325 | CTU1 | -1.496320563 |
| MTHFD1 | -1.386699362 | C1orf106 | -1.494150836 |
| RFC5 | -1.383251013 | C8orf87 | -1.491902933 |
| PRKRIR | -1.382824438 | KRT13 | -1.49155935 |
| UBC | -1.382750556 | CLUL1 | -1.491275178 |
| CHTF8 | -1.38225867 | PSMB3 | -1.490755153 |
| MORF4L1 | -1.381829505 | OR4D9 | -1.489301628 |
| CAD | -1.379757313 | ZNF286B | -1.488105536 |
| HDAC3 | -1.37833297 | KIF7 | -1.486770611 |
| DDX56 | -1.377476726 | LIPA | -1.486482578 |
| PPP1R8 | -1.375613344 | DDN | -1.485213685 |
| PSMB3 | -1.374687561 | RSL1D1 | -1.48495182 |
| VCP | -1.374559966 | SNAPC4 | -1.481726315 |
| RAB1B | -1.373544935 | TWF1 | -1.478742287 |
| KRT18 | -1.372653828 | SKIDA1 | -1.477895018 |
| EIF3H | -1.372395627 | DSCAM | -1.477613686 |
| MRPS21 | -1.371688338 | CEND1 | -1.476763069 |
| SPATA5 | -1.371546126 | USP43 | -1.47642241 |
| SF3B5 | -1.369704708 | PHPT1 | -1.475208586 |
| DHX36 | -1.368521429 | IGSF23 | -1.473471073 |
| CTDSPL | -1.368281653 | CTSZ | -1.473223599 |
| C15orf63 | -1.368169783 | HYI | -1.471848137 |
| MND1 | -1.367148567 | UCN | -1.471798831 |
| CHEK1 | -1.365498493 | JUNB | -1.471440183 |
| PSMB2 | -1.364829623 | GRB2 | -1.471324217 |
| HSCB | -1.36414551 | TAF1C | -1.469335239 |
| PFN1 | -1.363847136 | PFDN6 | -1.4692714 |
| GTPBP4 | -1.363346727 | EID2B | -1.468609431 |
| TRAPPC4 | -1.363085076 | GSTZ1 | -1.468284552 |
| TSEN54 | -1.362994692 | PPYR1 | -1.467815553 |
| RAPGEF6 | -1.362698559 | W8P1L | -1.467487002 |
| CDCA8 | -1.361945902 | ATR | -1.46714143 |
| ATP2A2 | -1.359896755 | CAPZB | -1.466475244 |
| PSMA6 | -1.359123109 | EBF2 | -1.465721319 |
| COX6B1 | -1.358954106 | RFC4 | -1.465537537 |
| CDK11A | -1.358922606 | SBDS | -1.465522817 |
| SNRPD3 | -1.358794551 | GCNT4 | -1.465420968 |
| ZBTB8OS | -1.357703857 | USF2 | -1.464916149 |
| MRTO4 | -1.356742848 | ANKRD39 | -1.462602755 |
| AP3B1 | -1.355796412 | ZNF207 | -1.461823849 |
| INTS6 | -1.35449457 | SLC43A1 | -1.461538671 |
| EIF6 | -1.35358833 | NOL3 | -1.46141808 |
| RPLP0 | -1.353376057 | MARCH11 | -1.461169146 |
| CDAN1 | -1.351102352 | SMPD2 | -1.460881076 |
| ZFAND1 | -1.350180008 | C11orf86 | -1.460075591 |
| RSL24D1 | -1.349719816 | MTRNR2L5 | -1.459134583 |
| SRSF10 | -1.349670653 | ZRANB2 | -1.458627153 |
| CINP | -1.349546146 | OR5K3 | -1.458559144 |
| PES1 | -1.348241514 | HOXA5 | -1.458453821 |
| EIF1AD | -1.347681684 | ARL17A | -1.457715258 |
| SKP1 | -1.347077683 | PPP2CA | -1.455987502 |
| CLEC10A | -1.346590066 | TBL3 | -1.455849732 |
| POLR2D | -1.344792099 | RNF20 | -1.455503496 |
| EIF1 | -1.344559124 | TBCA | -1.455477108 |

FIG. 45D

| | | | |
|---|---|---|---|
| WDR83 | -1.344216107 | RP11-865813.1 | -1.455277909 |
| SOD1 | -1.340312573 | PCBP1 | -1.454318626 |
| SRSF3 | -1.340212883 | KDSR | -1.453151002 |
| TAF3 | -1.340156516 | BCAS2 | -1.451342376 |
| SNRPC | -1.338898127 | XIAP | -1.450998896 |
| HMGCS1 | -1.338505207 | TPM1 | -1.449883189 |
| HSPD1 | -1.33600512 | GPAM | -1.449815505 |
| PPA2 | -1.335089026 | GARS | -1.449537798 |
| PFDN6 | -1.334945087 | ALPK3 | -1.448868238 |
| NDUFB10 | -1.332788339 | TFPT | -1.447926352 |
| IRS2 | -1.332719121 | RNF112 | -1.447803365 |
| MED21 | -1.330290534 | TCTEX1D2 | -1.446558259 |
| CRCP | -1.329915908 | SLC27A5 | -1.446399836 |
| SCO2 | -1.329754225 | VPS13C | -1.445038424 |
| LYRM4 | -1.328951694 | IBSP | -1.443552161 |
| NDUF89 | -1.32771624 | NBPF3 | -1.443366804 |
| WDR55 | -1.327002318 | KRTAP4-6 | -1.4424052 |
| PSMD6 | -1.325359209 | OR9I1 | -1.44221679 |
| C10orf55 | -1.324464755 | CMTM3 | -1.437804933 |
| SNAPC2 | -1.323520448 | AGR2 | -1.436764518 |
| TRAIP | -1.322210841 | HSD17B10 | -1.436364916 |
| FBL | -1.319362758 | MSI2 | -1.436233319 |
| SRSF11 | -1.319216433 | DCAF12 | -1.435991517 |
| DIMT1 | -1.317151465 | DNAJC11 | -1.435812507 |
| MKI67IP | -1.315985385 | NIP7 | -1.434745113 |
| NOP16 | -1.312616718 | MKL1 | -1.434161817 |
| CWC25 | -1.31108751 | PATE2 | -1.434142561 |
| FSCN1 | -1.310209463 | RTEL1 | -1.432960631 |
| UBE2M | -1.309779639 | F10 | -1.432954392 |
| SRP54 | -1.30952802 | KCND2 | -1.432764699 |
| RPA3 | -1.309065263 | PRR23C | -1.432736286 |
| C11orf75 | -1.308307405 | EXOSC7 | -1.431428179 |
| AMD1 | -1.307680016 | RIF1 | -1.429355634 |
| PTK2 | -1.307634623 | KRT28 | -1.426931464 |
| PRRG4 | -1.304157843 | GPR124 | -1.426512806 |
| SFXN4 | -1.303922126 | DLL3 | -1.422088402 |
| DHX8 | -1.302999971 | C10orf131 | -1.421588642 |
| SMC2 | -1.302938995 | ATF5 | -1.420593385 |
| ACY1 | -1.302662808 | KRTAP19-4 | -1.420517301 |
| GPN3 | -1.298923505 | PRODH | -1.41981364 |
| SOCS3 | -1.298536471 | C21orf59 | -1.419547323 |
| NTN4 | -1.296514333 | LCE3D | -1.418646134 |
| UTP14A | -1.296499694 | CRH | -1.418237482 |
| CHORDC1 | -1.295389856 | BCL2L1 | -1.418154714 |
| RBM48 | -1.294610249 | TOX4 | -1.416333246 |
| MRPS27 | -1.291129159 | FAM98B | -1.416148755 |
| DDX41 | -1.290973169 | MYC | -1.415587444 |
| MARS2 | -1.2900804 | PSIP1 | -1.414341502 |
| PSME3 | -1.289452298 | NRF1 | -1.414197906 |
| CENPE | -1.288374691 | EEF1A1 | -1.414055367 |
| VPS54 | -1.288113709 | OR4F5 | -1.41217241 |
| C1orf21 | -1.287670003 | MPLKIP | -1.412154342 |
| AURKA | -1.287485326 | LRRN1 | -1.412104794 |
| NCL | -1.286720673 | CASC4 | -1.411972135 |
| RNGTT | -1.286293458 | NUTF2 | -1.410112582 |
| RPS20 | -1.285376604 | TC2N | -1.409869276 |
| PRIM1 | -1.285117926 | C19orf60 | -1.409097495 |
| CERS1 | -1.28449224 | DESI1 | -1.408796498 |
| SRRM1 | -1.283215691 | AHSA2 | -1.408275819 |
| RPS9 | -1.281865487 | BCHE | -1.408238246 |
| POLR3B | -1.280777839 | CHIC1 | -1.408053615 |
| MPLKIP | -1.280705404 | CUBN | -1.406323811 |
| UFD1L | -1.278303239 | C1orf159 | -1.40503451 |
| ATP6AP1 | -1.277872404 | OSBPL7 | -1.404804585 |
| ZMYND8 | -1.273803762 | FGF11 | -1.403468367 |
| CCDC7 | -1.273509948 | FAM70B | -1.403401331 |
| ABHD11 | -1.273190504 | EIF2C2 | -1.402259615 |
| CCNA2 | -1.272760173 | C9orf152 | -1.401137235 |
| GABPB1 | -1.269810752 | KRTAP4-2 | -1.400786406 |
| HIVEP3 | -1.269565848 | NT5DC1 | -1.400673886 |
| BRD2 | -1.267679421 | RPS27A | -1.399937957 |
| DCTN4 | -1.26703886 | C19orf52 | -1.399507166 |
| BUB3 | -1.26667183 | NAA30 | -1.399482582 |
| CDS2 | -1.266463258 | SLN | -1.39886606 |
| UGGT2 | -1.26644049 | CEACAM19 | -1.398622812 |
| AC021066.1 | -1.262823058 | ZDHHC22 | -1.398296295 |
| ROMO1 | -1.262617798 | CDCA5 | -1.398148249 |
| DPY30 | -1.262071007 | KIF5A | -1.39306444 |
| ALG2 | -1.262064248 | USP12 | -1.393017011 |
| C21orf91 | -1.260758473 | C17orf85 | -1.392817653 |
| RPAIN | -1.259313103 | RNF186 | -1.392626488 |
| PSMG3 | -1.257309475 | GLS2 | -1.391718029 |
| METTL14 | -1.256067935 | ADM2 | -1.391549928 |
| NLE1 | -1.255704259 | GLRA1 | -1.39120265 |
| PLDN | -1.254998982 | RFC3 | -1.391106035 |

FIG. 45E

| Gene | Value | Gene | Value |
|---|---|---|---|
| EIF2S2 | -1.253613636 | HIST1H1B | -1.390959146 |
| SNAPC4 | -1.252507915 | EIF2S2 | -1.389038266 |
| PSMC3 | -1.252237063 | LSM2 | -1.388382414 |
| FCGR1A | -1.250801945 | UBASH3A | -1.388123983 |
| C10orf111 | -1.250410155 | GINS1 | -1.386895008 |
| ELMOD3 | -1.249168045 | PCDH18 | -1.386154855 |
| PFDN4 | -1.248643001 | CLN6 | -1.385735235 |
| EIF3A | -1.247652565 | NSUN5 | -1.384773039 |
| GPN1 | -1.246678919 | C5orf55 | -1.384724887 |
| MRPL53 | -1.246345719 | MYLPF | -1.384722044 |
| VMP1 | -1.245973445 | SGCA | -1.384606557 |
| C5orf62 | -1.245529521 | CIRH1A | -1.383945728 |
| ENTHD1 | -1.245322091 | ACTR6 | -1.38346989 |
| C7orf23 | -1.245093698 | FNBP4 | -1.383464816 |
| ANAPC4 | -1.243819302 | SAFB | -1.382666602 |
| C20orf111 | -1.242250028 | ZXDC | -1.381995699 |
| FAM118B | -1.240759583 | HAUS1 | -1.381551871 |
| ZNF662 | -1.24014827 | POM121 | -1.381439568 |
| ASXL3 | -1.24012825 | C3orf71 | -1.381187345 |
| COPB2 | -1.240117622 | NAALAD2 | -1.380921778 |
| REV3L | -1.239474867 | LGALS3BP | -1.379993411 |
| EMC7 | -1.237474252 | SMURF2 | -1.378588024 |
| PGP | -1.237066107 | FGF17 | -1.378469131 |
| ACTR6 | -1.237008101 | DLG5 | -1.378430761 |
| CNPY2 | -1.236908843 | SAE1 | -1.377958941 |
| CCDC8 | -1.236367735 | EVX1 | -1.377129469 |
| DDX43 | -1.236336025 | VPS13D | -1.376473958 |
| NUP93 | -1.235748149 | CST5 | -1.376150445 |
| MCM3AP | -1.235507764 | UTP14A | -1.374721263 |
| POLE2 | -1.235250832 | DUOX1 | -1.373580298 |
| PHTF2 | -1.234956081 | MOCS3 | -1.373232039 |
| SERAC1 | -1.234566406 | CRYGC | -1.371555233 |
| SOD2 | -1.234331381 | MED1 | -1.370418999 |
| SERPINH1 | -1.23380727 | HIGD2A | -1.370369165 |
| RFC3 | -1.233260688 | C1D | -1.370106538 |
| PLK1 | -1.233203838 | OR51F1 | -1.369826586 |
| CD36 | -1.232948853 | WDR38 | -1.369345635 |
| POLR1A | -1.232242665 | VTN | -1.368899379 |
| RABGGTB | -1.230581642 | MRPL24 | -1.368804619 |
| GEMIN5 | -1.230490006 | KDELR2 | -1.368235204 |
| COG1 | -1.229778648 | COX6B2 | -1.367659662 |
| RPL24 | -1.228478564 | C15orf26 | -1.367240793 |
| YBEY | -1.227685906 | CCDC74A | -1.366619756 |
| SLC25A26 | -1.223487939 | CALML6 | -1.366577799 |
| PKM | -1.223253054 | TXLNG | -1.365995186 |
| AP2M1 | -1.222511508 | PRPF38B | -1.365813346 |
| DDX1 | -1.222329678 | FAM171B | -1.364097696 |
| NOD1 | -1.222163777 | OR2V1 | -1.361959507 |
| ZW10 | -1.220811588 | KIAA0586 | -1.361875388 |
| NAA50 | -1.219337957 | CCNA2 | -1.3611912 |
| CEP152 | -1.217191245 | GPR158 | -1.360513184 |
| ATAD1 | -1.21710062 | SLCO1B7 | -1.360342489 |
| CDK9 | -1.216810421 | RANBP1 | -1.359068915 |
| TRMT6 | -1.214842285 | PIGS | -1.359026633 |
| EIF4E | -1.214767047 | ARL4D | -1.358847203 |
| YPEL1 | -1.214622995 | TSSK6 | -1.358756483 |
| HEATR1 | -1.212823082 | PARM1 | -1.358529964 |
| TXNRD3NB | -1.212362854 | COMMD3 | -1.358148481 |
| TRIAP1 | -1.211850501 | TMEM97 | -1.357995121 |
| TOR1B | -1.211612357 | CTU2 | -1.35618708 |
| OR5AR1 | -1.211248944 | SPAG17 | -1.355854461 |
| VPS36 | -1.210217087 | RRH | -1.355793945 |
| PIK3C3 | -1.209547893 | DUSP27 | -1.355709242 |
| MAX | -1.208188717 | CDC45 | -1.355669646 |
| INO80E | -1.208066348 | GLIPR2 | -1.355630221 |
| STX18 | -1.207721724 | PPP1R36 | -1.354665552 |
| SNRPG | -1.205566222 | PCDHB3 | -1.35424942 |
| CXorf36 | -1.204906269 | DVL2 | -1.353664249 |
| ARPC4 | -1.203668806 | SMEK2 | -1.353253501 |
| MIOS | -1.203407099 | CATSPERB | -1.352848215 |
| FMO5 | -1.203239408 | YME1L1 | -1.352625477 |
| RPA1 | -1.202357297 | BSX | -1.351907715 |
| RBMX | -1.202132754 | OR7C1 | -1.351017588 |
| VAC14 | -1.200270595 | CTTNBP2NL | -1.350201785 |
| COASY | -1.199434983 | PSMC2 | -1.34990278 |
| TPR | -1.199227411 | CEP250 | -1.349774107 |
| IGBP1 | -1.194961933 | CD70 | -1.349522814 |
| DIS3 | -1.193716642 | NKAIN1 | -1.349086317 |
| CRKL | -1.193291148 | TRIM61 | -1.34874964 |
| IL36G | -1.192801712 | BRI3 | -1.348477965 |
| CUL2 | -1.192688233 | BTF3L4 | -1.346826486 |
| POLRMT | -1.192245098 | SART3 | -1.345977605 |
| GCSH | -1.191032683 | LSS | -1.345250492 |
| PDRG1 | -1.190777209 | NDUFA7 | -1.344087552 |
| NRF1 | -1.190661017 | FOXC2 | -1.343846067 |

FIG. 45F

| Gene | Value | Gene | Value |
|---|---|---|---|
| EIF5 | -1.190554147 | PPP2R3C | -1.342320823 |
| LIPT1 | -1.189385756 | EIF3H | -1.341234842 |
| DTYMK | -1.189362568 | GRPEL1 | -1.340914975 |
| C11orf10 | -1.187078268 | TTC30A | -1.340200386 |
| RPS8 | -1.185370569 | ZFYVE20 | -1.339636254 |
| AP2B1 | -1.183349851 | TRIAP1 | -1.339070801 |
| ELAC2 | -1.183255107 | CFHR4 | -1.339041868 |
| USP24 | -1.18298842 | RTLPL1 | -1.338786857 |
| TRAPPC11 | -1.182986448 | NEK7 | -1.338619307 |
| LAS1L | -1.182768104 | YIPF3 | -1.338477848 |
| ORC6 | -1.182407257 | H1FNT | -1.338271675 |
| ATP6V0D1 | -1.181753715 | RPL37A | -1.338252799 |
| PSMB6 | -1.180012028 | GPR125 | -1.33796122 |
| CENPW | -1.178819363 | CYP39A1 | -1.335737633 |
| RAN | -1.178639669 | HIST1H2A8 | -1.335236803 |
| ARGLU1 | -1.177706953 | CCDC28B | -1.333231002 |
| ZWINT | -1.177622511 | HIST1H2AA | -1.331941737 |
| CD2 | -1.17577558 | CEACAM5 | -1.331889985 |
| RPAP3 | -1.174222309 | TCHHL1 | -1.331605136 |
| PPP1R37 | -1.169861545 | DOK1 | -1.331588865 |
| BCAS2 | -1.169813503 | RPL10 | -1.330485089 |
| NR2C2AP | -1.169190743 | DUSP12 | -1.330474476 |
| GINS3 | -1.168900802 | PSMA6 | -1.329932606 |
| CTU1 | -1.168672797 | FOXF2 | -1.329367582 |
| PFDN2 | -1.168490662 | TPT1 | -1.32921217 |
| CCT6B | -1.166890337 | FAM75A1 | -1.327873728 |
| DCLRE1B | -1.165112882 | MYPN | -1.326591013 |
| THAP1 | -1.164708443 | C12orf76 | -1.325023563 |
| EPHB6 | -1.164094347 | DHH | -1.324505465 |
| C12orf50 | -1.163923228 | ACTL6A | -1.324089056 |
| SRM | -1.162425297 | PITPNA | -1.323550188 |
| CCT6A | -1.161600828 | SNRPF | -1.322855177 |
| CNIH4 | -1.161143723 | CCR7 | -1.322225566 |
| VCL | -1.160033322 | PADI4 | -1.322023506 |
| TIPRL | -1.159975204 | RBPMS | -1.321787351 |
| EXOSC1 | -1.159391695 | SLC38A5 | -1.321627333 |
| GINS2 | -1.159330215 | ASH2L | -1.321380735 |
| POLR2G | -1.159291555 | C11orf87 | -1.320546465 |
| SMU1 | -1.158961843 | USP3 | -1.319967007 |
| TAF1C | -1.158389693 | ZNF259 | -1.319516798 |
| ATP10B | -1.155904663 | ZBTB34 | -1.319356965 |
| EIF5A | -1.155231855 | PDE6C | -1.318981816 |
| PSMD14 | -1.15495698 | C15orf63 | -1.318881749 |
| TARS | -1.154929744 | SUSD3 | -1.318679868 |
| SIAE | -1.154924856 | TUBG1 | -1.318445333 |
| CIAO1 | -1.152202616 | CPSF4L | -1.317067473 |
| VPS4A | -1.151884009 | RBM28 | -1.316596094 |
| RBBP6 | -1.151745314 | EEF2 | -1.315436524 |
| DHX9 | -1.151186658 | OR7D4 | -1.31497022 |
| POLD3 | -1.150523831 | SRCAP | -1.313693399 |
| UQCC | -1.150131829 | RPL36 | -1.313347615 |
| RRP9 | -1.148982525 | OR6B1 | -1.311657279 |
| MRC1 | -1.148911799 | UBQLN4 | -1.310950948 |
| MAP3K2 | -1.148652316 | 39880 | -1.310145651 |
| RQCD1 | -1.148569283 | SH3TC1 | -1.309541761 |
| SF3A2 | -1.148353051 | TTC36 | -1.308622776 |
| TMED3 | -1.147828583 | C11orf35 | -1.307697103 |
| PRPF4 | -1.147629016 | DNAJC17 | -1.307558425 |
| CTDSP2 | -1.14696236 | WDR91 | -1.307428734 |
| KHSRP | -1.14691668 | RGS9 | -1.307422463 |
| RPL36 | -1.146558928 | C12orf75 | -1.307402341 |
| EXOSC10 | -1.146338594 | C6orf89 | -1.307252925 |
| MRPS18C | -1.146127592 | AGTR2 | -1.306679621 |
| NFS1 | -1.142463597 | ATP2B3 | -1.306345401 |
| SGSM3 | -1.140855098 | SNRNP200 | -1.306334581 |
| MRPL36 | -1.14048396 | FKBPL | -1.306307148 |
| RPL19 | -1.140146421 | KCNJ15 | -1.306238033 |
| C1orf228 | -1.139447078 | PRKCH | -1.306146129 |
| CCT8 | -1.137811964 | EID2 | -1.305751897 |
| ACO2 | -1.137710016 | UBL4B | -1.304917945 |
| MFAP3 | -1.13741397 | KDM1A | -1.304656676 |
| FERMT2 | -1.136351485 | BHLHA9 | -1.304141607 |
| S100G | -1.136310018 | MEF2BNB | -1.303573291 |
| FXN | -1.135711566 | PPFIA4 | -1.303480594 |
| NME5 | -1.13560789 | SLC4A1 | -1.303428597 |
| KLF1 | -1.135604126 | CNPY2 | -1.302819574 |
| EIF3B | -1.135426481 | GPR85 | -1.302577615 |
| SLC35D1 | -1.135048079 | C17orf81 | -1.301560659 |
| TSEN34 | -1.133407996 | TIMM22 | -1.300694924 |
| FAM185A | -1.133299596 | LMOD3 | -1.299696123 |
| YARS2 | -1.132928814 | TDO2 | -1.298072075 |
| VN1R2 | -1.132829488 | SRSF7 | -1.297876366 |
| SETDB1 | -1.132566535 | H2BFM | -1.297338338 |
| ARIH1 | -1.131807267 | PPP2R5D | -1.29660803 |
| VPS13D | -1.129654371 | RNF168 | -1.295142446 |

FIG. 45G

| | | | |
|---|---|---|---|
| ANAPC1 | -1.127929837 | WDR88 | -1.295032877 |
| C16orf72 | -1.126828866 | DSC3 | -1.295010072 |
| WWTR1 | -1.126787364 | GJA9 | -1.293636712 |
| CEBPZ | -1.126574933 | TCFL5 | -1.293523283 |
| TCEB2 | -1.124750634 | C3orf25 | -1.293387208 |
| NDUFA2 | -1.124713541 | CCL13 | -1.29259661 |
| STX5 | -1.124386769 | BEGAIN | -1.292257661 |
| RPL5 | -1.123550445 | DUSP21 | -1.291745466 |
| U2AF1L4 | -1.12303907 | TBX5 | -1.291047766 |
| FARSA | -1.122975506 | GTPBP4 | -1.290879142 |
| MAT2A | -1.12249972 | FBXW4 | -1.290656771 |
| CCDC101 | -1.12247241 | TRAF3IP3 | -1.289221532 |
| NBR1 | -1.122159404 | LAIR2 | -1.289006794 |
| S100PBP | -1.120559064 | CCDC17 | -1.288946689 |
| PSMD2 | -1.120410134 | NSUN6 | -1.288379213 |
| CIT | -1.12012829 | HSD17B7 | -1.287990136 |
| TUBGCP4 | -1.119913794 | SIGLEC15 | -1.286365988 |
| POLG2 | -1.119353373 | YPEL1 | -1.285892981 |
| MASTL | -1.119162982 | C12orf71 | -1.284890782 |
| PSMC5 | -1.116680643 | RPS18 | -1.284861476 |
| TRA2B | -1.116641119 | PAQR3 | -1.284117989 |
| FUS | -1.115787787 | PRPF6 | -1.283508664 |
| LMLN | -1.115653475 | HSPA8 | -1.283421376 |
| XRCC4 | -1.115385414 | PLS1 | -1.283356689 |
| XPO1 | -1.115279503 | FXYD7 | -1.283150611 |
| KRTCAP2 | -1.113876033 | OR10A7 | -1.283133705 |
| C19orf69 | -1.113102098 | IDI1 | -1.282895812 |
| RRP1B | -1.112248171 | PRRC2A | -1.28242491 |
| SLC25A3 | -1.111489522 | NDNL2 | -1.281118975 |
| TCP1 | -1.111045616 | SYNGR2 | -1.280972586 |
| TNFSF12-TNF | -1.110535589 | ADO | -1.280890515 |
| PHF5A | -1.110430938 | C7orf50 | -1.280705584 |
| ACTR2 | -1.110401685 | NKD2 | -1.280529982 |
| PRMT5 | -1.110228976 | RBFOX3 | -1.280326165 |
| NUDCD3 | -1.110181528 | AIDA | -1.280056233 |
| SPTLC1 | -1.109882016 | RPS5 | -1.279801141 |
| SLC6A20 | -1.10960873 | MMS22L | -1.279507467 |
| NSA2 | -1.108398885 | THUMPD2 | -1.278957779 |
| EIF1AX | -1.107846414 | RBM39 | -1.278334778 |
| CFHR4 | -1.107841871 | CLCF1 | -1.278317998 |
| ATG5 | -1.106912764 | BLOC1S3 | -1.278020097 |
| SRCAP | -1.106872561 | C14orf102 | -1.277830268 |
| HAUS1 | -1.10619977 | SHC2 | -1.277777602 |
| N6AMT1 | -1.105902466 | PIEZO1 | -1.277394418 |
| ATR | -1.105837161 | FBXO22 | -1.277239442 |
| AHSA2 | -1.105334266 | SCTR | -1.276928082 |
| EIF3E | -1.104727511 | POLR1B | -1.274172151 |
| SPHAR | -1.104417387 | IMPDH1 | -1.271891241 |
| UBLCP1 | -1.104115654 | TRAF3IP1 | -1.271830307 |
| MRPL13 | -1.103021585 | RBM12B | -1.271554476 |
| RPLP2 | -1.102899636 | BUD31 | -1.271033674 |
| SLC39A7 | -1.102517103 | FANCM | -1.270720506 |
| TRIM59 | -1.101629427 | TGFBI | -1.270325791 |
| UQCRFS1 | -1.101448558 | FAHD2B | -1.270249913 |
| DR1 | -1.101431414 | DNAJC4 | -1.270196078 |
| CKAP2 | -1.100557384 | EIF1 | -1.269589844 |
| TAF5 | -1.100398036 | SLC11A1 | -1.268889719 |
| SRSF1 | -1.100306853 | CHD4 | -1.268686586 |
| FBXW11 | -1.100215742 | RPS9 | -1.268593949 |
| VPS28 | -1.099537324 | SPATA6 | -1.268105502 |
| PGM5 | -1.099134342 | PI4K2B | -1.267829829 |
| F11 | -1.099064319 | TCF3 | -1.267404331 |
| NUPL1 | -1.09900294 | MMGT1 | -1.266883109 |
| PMPCB | -1.098865487 | LILRA3 | -1.266264471 |
| UFM1 | -1.098637778 | OR5C1 | -1.265249631 |
| PHB2 | -1.098532471 | RBBP4 | -1.264947428 |
| HMGCR | -1.09752676 | ISM1 | -1.264866462 |
| SMG1 | -1.097265312 | KPNB1 | -1.264830663 |
| ZNF687 | -1.09657735 | SSTR1 | -1.26426376 |
| DCTN5 | -1.096499524 | TGM7 | -1.264152913 |
| PPP2R1A | -1.096393988 | C9orf16 | -1.261885101 |
| KIAA0586 | -1.095557469 | PAPPA | -1.261561488 |
| CCT4 | -1.094423341 | PNPLA6 | -1.261024012 |
| EMC6 | -1.092820255 | CLDN25 | -1.260772739 |
| RPP21 | -1.092777508 | CCDC135 | -1.260731285 |
| IPO11 | -1.092724416 | ELAC2 | -1.260434805 |
| NFYB | -1.091286106 | RPL37 | -1.260333546 |
| EIF4ENIF1 | -1.089089412 | MUSK | -1.259642432 |
| C9orf114 | -1.08779364 | NANOGNB | -1.259692167 |
| LSM11 | -1.086214526 | SLC6A12 | -1.259572819 |
| VRK1 | -1.085903324 | ATP5I | -1.257875017 |
| TBC1D8B | -1.085879458 | OR5I1 | -1.257011177 |
| MNAT1 | -1.085864628 | TMEM108 | -1.256942661 |
| NDNL2 | -1.085694726 | GUSB | -1.256846011 |
| BBX | -1.084538793 | KIAA0907 | -1.256773131 |

FIG. 45H

| | | | |
|---|---|---|---|
| SEC61B | -1.084477868 | CALML3 | -1.256468225 |
| OR5H14 | -1.083994931 | CXorf69 | -1.256375774 |
| ACTL6B | -1.083909903 | SLC6A7 | -1.255921349 |
| RCL1 | -1.08390836 | RSPH6A | -1.25582562 |
| CSF3R | -1.083676018 | UBR5 | -1.254988844 |
| NOP14 | -1.083433165 | FLT3LG | -1.254392482 |
| RPL18 | -1.082684121 | TOR1B | -1.252985237 |
| MMS22L | -1.081960406 | PCF11 | -1.252952564 |
| UBA52 | -1.081345178 | TAZ | -1.252841935 |
| SMG7 | -1.08026779 | GPR6 | -1.252350231 |
| C10orf2 | -1.079750514 | METTL24 | -1.252115773 |
| INTS4 | -1.078930568 | IRF2BP1 | -1.250916795 |
| FAM193B | -1.078919565 | PTPRCAP | -1.250840383 |
| PRMT1 | -1.078538807 | HOXC12 | -1.250203552 |
| DNM1L | -1.078189135 | NCL | -1.249314414 |
| POTEG | -1.077913378 | HS3ST4 | -1.249259524 |
| RPE | -1.077516895 | PPAN | -1.249103141 |
| ALG11 | -1.076921234 | PAF1 | -1.249100724 |
| NCOA6 | -1.076214389 | IL17F | -1.249081312 |
| HNRNPC | -1.075667291 | RAB1B | -1.24893481 |
| DEF8 | -1.07564974 | C14orf182 | -1.248906915 |
| POLR2F | -1.075425174 | ABCA2 | -1.247666282 |
| EXOC7 | -1.075263175 | SGSH | -1.246684444 |
| TLCD1 | -1.075185546 | ARID5B | -1.246500494 |
| PPP2R3C | -1.074589668 | GABPA | -1.245979186 |
| CCDC80 | -1.073109498 | FAM110C | -1.245498786 |
| HYOU1 | -1.072267629 | HDAC3 | -1.245107157 |
| PXDN | -1.072229736 | SLFNL1 | -1.244651245 |
| PRPF19 | -1.071373607 | NUF2 | -1.244465095 |
| TXN2 | -1.071195412 | MCM10 | -1.243457887 |
| NUBP2 | -1.070243769 | SKP1 | -1.24308702 |
| MPDU1 | -1.069829362 | OR11G2 | -1.243033762 |
| LIMS1 | -1.068624485 | FCGR1A | -1.242907399 |
| TDGF1 | -1.068623975 | SLC52A3 | -1.241971506 |
| ABCB7 | -1.068075668 | ARL11 | -1.24181862 |
| RAB5A | -1.06710304 | ENDOG | -1.241603576 |
| GTF2A2 | -1.066927423 | ZMIZ1 | -1.240752857 |
| PRPF6 | -1.066762079 | CCDC64B | -1.240671479 |
| ECD | -1.066306395 | CXCR6 | -1.240561222 |
| LSG1 | -1.066166811 | PKD2L1 | -1.23962038 |
| RCC1 | -1.065960233 | ADAM23 | -1.239416475 |
| ATP5I | -1.065074601 | LCA5L | -1.239150196 |
| SERPINE2 | -1.061809596 | POLR3H | -1.238997098 |
| EIF5B | -1.061589138 | RPIA | -1.238667289 |
| PMM2 | -1.061509898 | EGR1 | -1.238577588 |
| HCFC1 | -1.060512155 | UBA3 | -1.237905617 |
| PPP1R10 | -1.059547758 | CHERP | -1.237857017 |
| BAI3 | -1.059330662 | RNF24 | -1.237140122 |
| SNRNP48 | -1.059000499 | PDCL3 | -1.237007234 |
| PABPN1 | -1.058415348 | UFD1L | -1.236799288 |
| GFM2 | -1.057955433 | RAN | -1.236747906 |
| EPS15L1 | -1.057193106 | ADORA1 | -1.236481798 |
| RPS4X | -1.057139324 | CELA1 | -1.236286873 |
| BARD1 | -1.05653207 | C7orf23 | -1.236025047 |
| GS1-211B7.1 | -1.055638252 | RBBP5 | -1.235719984 |
| RANBP3L | -1.055603566 | HOXD9 | -1.235074569 |
| C19orf43 | -1.055590894 | NPFF | -1.234690934 |
| PSMA4 | -1.054967252 | CUL1 | -1.234042029 |
| CDC16 | -1.054451543 | C2orf84 | -1.233967522 |
| SFSWAP | -1.054306701 | TRIM4 | -1.233856391 |
| RER1 | -1.053547878 | ZKSCAN2 | -1.233848704 |
| BOD1L1 | -1.053227865 | CEBPZ | -1.233787188 |
| FPGT | -1.052739242 | TRAF4 | -1.233764083 |
| G6PD | -1.052583161 | PRPF38A | -1.233432633 |
| MBD6 | -1.051540404 | RP4-725G10.1 | -1.233421201 |
| TIRAP | -1.051294407 | MCL1 | -1.2331853 |
| FLI1 | -1.050933914 | C11orf52 | -1.230877202 |
| KIF11 | -1.050846083 | SHROOM1 | -1.230429373 |
| GINS1 | -1.050225728 | KDM5A | -1.230174275 |
| ATP5B | -1.049973223 | AKR1C2 | -1.228724497 |
| GNL2 | -1.049765519 | PLEKHG4 | -1.228060686 |
| MRPL12 | -1.049447717 | POLR3B | -1.227057585 |
| CHMP3 | -1.049124508 | PIGY | -1.227016347 |
| PWP2 | -1.049006238 | PYGO2 | -1.226863313 |
| PPP4C | -1.048409595 | TWSG1 | -1.226773792 |
| ZNF513 | -1.047739956 | C1orf158 | -1.226411543 |
| AKIRIN2 | -1.046196936 | ABHD15 | -1.226344221 |
| C15orf42 | -1.046178886 | PLLP | -1.225999885 |
| ZFC3H1 | -1.045841485 | PDCD7 | -1.225947903 |
| CHKA | -1.045766653 | HIGD1A | -1.225303705 |
| MAPK10 | -1.045274203 | VN1R2 | -1.224415174 |
| LAMA2 | -1.044167976 | OR1L3 | -1.223408953 |
| UTP3 | -1.042571135 | C3orf33 | -1.223260954 |
| MED11 | -1.04114091 | ANO1 | -1.223137022 |
| RPRD1B | -1.040728493 | RBMX | -1.222987895 |

FIG. 45I

| | | | |
|---|---|---|---|
| AWAT1 | -1.040684879 | DZIP1 | -1.222901383 |
| RBM39 | -1.04067574 | DOCK5 | -1.222322295 |
| MCMBP | -1.040424041 | KCTD10 | -1.221109248 |
| ZNHIT6 | -1.039714905 | UBL7 | -1.220450127 |
| CENPH | -1.039411904 | KCTD3 | -1.219907579 |
| HAUS5 | -1.039171405 | PMF1 | -1.219794741 |
| KIAA1731 | -1.039098244 | PYGL | -1.21943985 |
| RABGEF1 | -1.038855914 | TRIP13 | -1.219009527 |
| ENOPH1 | -1.038800689 | ALKBH3 | -1.218969454 |
| FANCM | -1.038460637 | GSTA1 | -1.218703181 |
| FPGS | -1.038400291 | JMJD8 | -1.218210725 |
| EFCAB4A | -1.038199677 | PNMA1 | -1.217902567 |
| DNAJC17 | -1.038010644 | PAX4 | -1.217814145 |
| ASB11 | -1.036929888 | PTAR1 | -1.217028717 |
| ORC3 | -1.03682261 | PMM1 | -1.216559665 |
| MTOR | -1.035784209 | GINS2 | -1.216551298 |
| HAUS3 | -1.03550743 | ALDH3B2 | -1.216469875 |
| CHMP2A | -1.034698839 | TULP3 | -1.216324414 |
| SPICE1 | -1.03438403 | ARL3 | -1.216315431 |
| COPS6 | -1.034307376 | GCGR | -1.215878806 |
| ZNHIT2 | -1.033205846 | HAUS5 | -1.215854539 |
| SNRNP25 | -1.03234706 | RPS15A | -1.21583725 |
| RPS13 | -1.032046119 | PDAP1 | -1.215830382 |
| M6PR | -1.031904362 | ATP5B | -1.215816343 |
| GUF1 | -1.031816394 | RABEP2 | -1.214264623 |
| C3orf67 | -1.030683122 | P2RX1 | -1.213876172 |
| PPP1R12A | -1.02965238 | RDBP | -1.213758401 |
| RPL28 | -1.029185679 | FKBP1A | -1.213560915 |
| C21orf59 | -1.028385996 | HIST1H2AD | -1.213480645 |
| RAB6C | -1.02779821 | RAD18 | -1.213377205 |
| WARS | -1.027713458 | GTF3C2 | -1.213167613 |
| TDO2 | -1.027643685 | SLC43A3 | -1.213037935 |
| CNKSR2 | -1.027506652 | NAA40 | -1.212609012 |
| TUBB | -1.027459775 | SNRNP70 | -1.212520924 |
| CISD2 | -1.026484231 | DEFB1 | -1.212123838 |
| SKA1 | -1.026374844 | AP3M1 | -1.211835974 |
| IL32 | -1.025804163 | ACAN | -1.211816439 |
| PARP14 | -1.023925458 | C2orf66 | -1.210920926 |
| BRAT1 | -1.023290534 | GRPR | -1.210663229 |
| OR2A5 | -1.023199598 | AURKA | -1.210453093 |
| ATP6V0B | -1.023178105 | KTI12 | -1.210192529 |
| HINFP | -1.022734346 | MAPK1 | -1.209830295 |
| KCTD15 | -1.021975211 | OR2V2 | -1.209764782 |
| NDUFB2 | -1.021247536 | C16orf48 | -1.209577881 |
| PBRM1 | -1.021207796 | ARL2 | -1.209176992 |
| ANXA10 | -1.020889365 | PRR14 | -1.208238549 |
| NOP10 | -1.020826147 | ZC3H15 | -1.20763772 |
| TMEM106B | -1.020700587 | RBBP9 | -1.207494145 |
| NOP58 | -1.019570934 | JRKL | -1.207250525 |
| TMX2 | -1.018594261 | TLE4 | -1.206517106 |
| PSMD8 | -1.01767613 | DUS3L | -1.206353618 |
| EIF2B1 | -1.017493236 | ZBTB5 | -1.205970284 |
| PTPDC1 | -1.014494149 | MRPS17 | -1.205828906 |
| MMD2 | -1.014114046 | MYPOP | -1.205188753 |
| HEATR7B2 | -1.013780521 | ADRB3 | -1.205153273 |
| STXBP3 | -1.013247945 | POU6F1 | -1.205067176 |
| TOMM22 | -1.012558371 | ASPDH | -1.204316403 |
| CEP192 | -1.012469221 | U2AF1 | -1.203610591 |
| HAUS7 | -1.011401537 | GMEB2 | -1.203026471 |
| OVGP1 | -1.01054944 | MGST1 | -1.202845243 |
| SCD | -1.009733678 | ALG2 | -1.202776548 |
| MRPS16 | -1.009396417 | SMURF1 | -1.202329155 |
| RFT1 | -1.009339903 | TTC16 | -1.20179783 |
| SEPHS2 | -1.008627614 | RHOD | -1.201014791 |
| LRMP | -1.008251055 | MFAP1 | -1.200742731 |
| TSPAN33 | -1.007460428 | SFSWAP | -1.200478122 |
| MED26 | -1.00731284 | MAX | -1.200087952 |
| NCAPG | -1.006836369 | NHP2L1 | -1.199623442 |
| PPCDC | -1.006405797 | PRDX1 | -1.199068532 |
| CSTL1 | -1.005623976 | SAYSD1 | -1.1987253 |
| RRP8 | -1.005554672 | MGEA5 | -1.198453769 |
| HNRPDL | -1.005407422 | OR8H1 | -1.198218642 |
| TOR1AIP2 | -1.004804503 | ABR | -1.19759339 |
| SMC5 | -1.00450648 | MCM3AP | -1.197466411 |
| LRRC55 | -1.004111456 | FBXL17 | -1.196987742 |
| C19orf52 | -1.004058784 | RPS2 | -1.19681493 |
| PARN | -1.00373213 | RP4-811H24.6 | -1.196547503 |
| ARPC3 | -1.002802732 | RPL27A | -1.196479726 |
| DDB1 | -1.001257599 | ZBTB17 | -1.196076621 |
| WDR33 | -1.000650574 | HELZ | -1.196045885 |
| LCE1A | -1.000021373 | IL10RA | -1.195419237 |
| U2AF1 | -1.00001316 | SRRM2 | -1.195138055 |
| HSDL2 | -0.99953368 | RPP21 | -1.194847512 |
| CCNYL1 | -0.999129699 | ARID5A | -1.194303294 |
| ZNHIT1 | -0.999059485 | TRMT6 | -1.193704371 |

FIG. 45J

| | | | |
|---|---|---|---|
| ORC5 | -0.999022729 | GLYR1 | -1.193375028 |
| TAF7 | -0.998960964 | TSR2 | -1.193336722 |
| HORMAD2 | -0.998922287 | RELL1 | -1.192137068 |
| BFSP1 | -0.997408668 | ISG20 | -1.19202823 |
| STT3A | -0.996413479 | BRWD3 | -1.191959771 |
| NDOR1 | -0.996169109 | HSPD1 | -1.191481897 |
| RRP15 | -0.995951965 | WDR55 | -1.19100909 |
| HM13 | -0.99565163 | CGNL1 | -1.190965918 |
| MCM6 | -0.99521859 | TMEM99 | -1.190704403 |
| CCDC99 | -0.992692391 | LSM11 | -1.190349618 |
| CHPF2 | -0.992254578 | GATA2 | -1.190148311 |
| GLRA1 | -0.992025418 | KRT34 | -1.189748177 |
| TTC37 | -0.991617863 | RGS9BP | -1.188853876 |
| FAM98B | -0.991481224 | KCTD11 | -1.188848339 |
| NAA38 | -0.991438467 | FARSA | -1.188748461 |
| DHDDS | -0.988691739 | PES1 | -1.188565898 |
| GTPBP2 | -0.988589701 | KRTAP19-8 | -1.188438649 |
| CLEC2L | -0.987481869 | PGP | -1.188016303 |
| ATMIN | -0.98739107 | SSH1 | -1.18739853 |
| MTRNR2L3 | -0.986897737 | KRT75 | -1.187200015 |
| PEA15 | -0.985880842 | HIST3H2A | -1.186323206 |
| NDC80 | -0.98584922 | PPM1D | -1.186030197 |
| POLR2A | -0.985787997 | COX7A2 | -1.18513762 |
| DDX39B | -0.985042674 | RADIL | -1.185009391 |
| RNF224 | -0.984658566 | ABHD12B | -1.184327384 |
| METTL23 | -0.984522151 | SLC7A6 | -1.183846881 |
| C11orf58 | -0.983361828 | ZFHX3 | -1.183840398 |
| GABPB2 | -0.982871152 | ELP3 | -1.183438845 |
| MCF2L | -0.982605638 | KIF20A | -1.182917249 |
| ERAL1 | -0.981807872 | C16orf54 | -1.181264225 |
| HUWE1 | -0.981603706 | PACSIN3 | -1.181015708 |
| HECTD3 | -0.981147627 | DYNLL1 | -1.180939788 |
| SCAP | -0.981101285 | USP40 | -1.180477424 |
| IMP3 | -0.98032947 | SORCS2 | -1.179876485 |
| IFRD1 | -0.980315771 | KRT6B | -1.179807981 |
| CSNK1D | -0.980279306 | ACTA2 | -1.179634896 |
| CHCHD1 | -0.979858879 | GNMT | -1.178859953 |
| ZNF596 | -0.979802333 | SCUBE1 | -1.178794037 |
| GKAP1 | -0.978385757 | DPM2 | -1.178333695 |
| DDX21 | -0.978364079 | ASB14 | -1.178204751 |
| MYC | -0.976957246 | C17orf28 | -1.177601279 |
| LRR1 | -0.976572281 | C19orf69 | -1.177499613 |
| GART | -0.975986622 | ADIPOR1 | -1.17704494 |
| RTTN | -0.975004871 | DEFB4A | -1.177042772 |
| SLC7A1 | -0.974823835 | RPA3 | -1.17610571 |
| PDCD7 | -0.974538454 | C22orf15 | -1.175284917 |
| MRPS35 | -0.974029897 | SALL4 | -1.17474053 |
| KRT71 | -0.973981095 | USP1 | -1.174349639 |
| PSIP1 | -0.973643021 | TRIM68 | -1.173558611 |
| ZMYND11 | -0.973034439 | RFXAP | -1.172835458 |
| TFB2M | -0.972935954 | ZNF513 | -1.172789767 |
| RPL29 | -0.971958171 | C12orf39 | -1.172351943 |
| OSGEP | -0.971890991 | DDX23 | -1.17190298 |
| AGPS | -0.971461161 | COQ3 | -1.17111272 |
| WDR18 | -0.970454648 | SUPT6H | -1.17109365 |
| SUGP1 | -0.970082497 | CHCHD6 | -1.170420985 |
| KDM4B | -0.969836749 | CTNNBL1 | -1.169866122 |
| CCDC86 | -0.969745821 | TMEM14C | -1.169789864 |
| GTF2H5 | -0.969218429 | DIABLO | -1.169779046 |
| CAPN9 | -0.968995126 | SLC2A12 | -1.169624174 |
| DCTN6 | -0.968546036 | ACTL6B | -1.169372636 |
| RNASEH2C | -0.968090028 | SHD | -1.168908091 |
| HIST2H3D | -0.967550433 | VPS26B | -1.16833126 |
| RPL27 | -0.967489478 | GGTLC1 | -1.168228071 |
| ZNF407 | -0.96713655 | EVL | -1.168155498 |
| GINS4 | -0.966658728 | RNF133 | -1.16814253 |
| ACSM4 | -0.966503553 | FAM63B | -1.167835578 |
| SLC7A4 | -0.966347303 | ATAD3B | -1.167526301 |
| ZBBX | -0.966340595 | MFSD5 | -1.166900503 |
| OR52E2 | -0.965484195 | FAM209B | -1.166659981 |
| C15orf41 | -0.965187476 | SOX3 | -1.1660714 |
| GJC1 | -0.964735678 | FAM183A | -1.165952272 |
| SLC25A5 | -0.964460262 | RGS10 | -1.165285654 |
| HNRNPCL1 | -0.962960756 | CCDC125 | -1.165112361 |
| HNRNPA2B1 | -0.961640683 | TMEM230 | -1.164754052 |
| HELZ | -0.961255936 | TM6SF2 | -1.164689242 |
| HNRNPD | -0.961148313 | PHC3 | -1.164345153 |
| SNX22 | -0.960965128 | ALG8 | -1.1636855 |
| ANKLE2 | -0.960584879 | RPL38 | -1.163530585 |
| WDR24 | -0.960325608 | SMC5 | -1.162725855 |
| ATP6V1H | -0.960046498 | TECRL | -1.162608446 |
| RPS6 | -0.959802418 | INSM2 | -1.162511608 |
| ARPC2 | -0.959198251 | ANKFN1 | -1.162254029 |
| MRPL27 | -0.958820312 | HIST3H3 | -1.161849667 |
| COA5 | -0.95865868 | MEGF10 | -1.161822231 |

FIG. 45K

| | | | |
|---|---|---|---|
| OR13C5 | -0.958613032 | ALG10 | -1.160699223 |
| PADI4 | -0.957924378 | DKKL1 | -1.160593167 |
| PRPF38A | -0.95763203 | MPV17L | -1.160523288 |
| C8orf82 | -0.957027162 | SS18L2 | -1.160401447 |
| TOP2A | -0.956991206 | TMEM120B | -1.160003583 |
| USP39 | -0.954340951 | TMEM109 | -1.159426773 |
| WDR70 | -0.952987464 | OR52H1 | -1.159077488 |
| BRCA2 | -0.952182964 | PLA2G2E | -1.158794855 |
| MCM2 | -0.951805581 | ANKMY2 | -1.158296055 |
| IER5 | -0.951797441 | FOXD4L1 | -1.158115705 |
| AHSA1 | -0.951408637 | SH2D3A | -1.157904008 |
| GEMIN7 | -0.951372303 | CRTAP | -1.157674178 |
| EED | -0.950724816 | MARCKS | -1.15760582 |
| SMAD4 | -0.950573159 | DDX46 | -1.157570195 |
| MESDC2 | -0.950053433 | RPL13 | -1.157504332 |
| SLC22A25 | -0.949922009 | FAM216B | -1.157183413 |
| NSMCE1 | -0.949292453 | PPP4R2 | -1.157119162 |
| BAP1 | -0.948836345 | TSPAN16 | -1.157094764 |
| TMEM237 | -0.948441404 | UTP6 | -1.156869212 |
| NEU3 | -0.948069192 | PI3 | -1.156510368 |
| TEN1 | -0.94697411 | BRSK1 | -1.155649364 |
| SYS1 | -0.946634416 | TNNC2 | -1.15556236 |
| TMED10 | -0.946277895 | CCDC19 | -1.155391718 |
| KLF4 | -0.946216742 | FLYWCH2 | -1.155383306 |
| S100A10 | -0.94576215 | PTCH1 | -1.155025182 |
| C11orf57 | -0.945597045 | SHISA7 | -1.154703726 |
| FAM204A | -0.945399507 | KDM4C | -1.154270933 |
| UBL5 | -0.945324581 | ARHGAP36 | -1.15423169 |
| METTL16 | -0.945208816 | YDJC | -1.154229712 |
| GTF3C1 | -0.945069331 | SPTLC1 | -1.154192067 |
| ASNS | -0.944760908 | HMHB1 | -1.153717498 |
| PKMYT1 | -0.94465765 | TNNT3 | -1.153541832 |
| MRPL44 | -0.943978471 | TTC27 | -1.15316121 |
| NUP35 | -0.943646315 | IL6R | -1.153125602 |
| PPYR1 | -0.943328666 | SYVN1 | -1.152995283 |
| SMG5 | -0.942586637 | CTNNBIP1 | -1.152695365 |
| RNF217 | -0.941885759 | CRLF3 | -1.152200608 |
| CPSF4 | -0.941442272 | SYCE2 | -1.152198016 |
| AKAP10 | -0.940566385 | KIF12 | -1.152077246 |
| WEE1 | -0.939097678 | GEMIN4 | -1.151734538 |
| C3orf77 | -0.937721113 | USP54 | -1.151450973 |
| LGALS9C | -0.937476407 | RNPEP | -1.151140802 |
| SUZ12 | -0.937098269 | CATSPER1 | -1.151075373 |
| PSMA7 | -0.936080385 | LYSMD4 | -1.150886339 |
| ALDOA | -0.935866715 | PLOD1 | -1.150877531 |
| PAK1IP1 | -0.935775537 | SHROOM2 | -1.150659978 |
| SYMPK | -0.935542469 | C2orf69 | -1.150544498 |
| GNL3L | -0.935536653 | SYCN | -1.150379088 |
| TXNDC9 | -0.935104271 | PABPN1 | -1.150224404 |
| UBE3D | -0.935012347 | TARS | -1.149025971 |
| GLYCTK | -0.93464153 | NUPL1 | -1.148997097 |
| SLC3A2 | -0.934296036 | MAN2B2 | -1.148385262 |
| TAF7L | -0.933546227 | CRYAA | -1.148277098 |
| SMS | -0.933386778 | NDST2 | -1.147847842 |
| SAFB | -0.933374052 | MRPL36 | -1.14754419 |
| RP11-466G1 | -0.932142451 | OAS2 | -1.147355516 |
| MLKL | -0.931947868 | KRT20 | -1.147237746 |
| C18orf21 | -0.931878495 | RAX | -1.146544905 |
| CENPA | -0.931850229 | MED22 | -1.14647268 |
| SMARCB1 | -0.931804265 | PCDHB8 | -1.146301319 |
| RIOK1 | -0.931217515 | EXOSC5 | -1.146019271 |
| POP5 | -0.930830015 | MTHFD2 | -1.145860082 |
| SCAF11 | -0.930571845 | TMPRSS11BNL | -1.145855673 |
| SLC44A2 | -0.930391388 | THBD | -1.145684107 |
| GRWD1 | -0.930200191 | TCOF1 | -1.145635716 |
| DMAP1 | -0.929531228 | LCP2 | -1.14563327 |
| VRTN | -0.929439281 | DDX5 | -1.145354266 |
| NARFL | -0.929338565 | CFI | -1.145305361 |
| RNF135 | -0.928162601 | SERAC1 | -1.145252469 |
| SPC24 | -0.928075601 | KCTD8 | -1.145044577 |
| FAM63B | -0.927739551 | HCFC1 | -1.143604518 |

FIG. 45L

*LentiCRISPR* (pXPR_001 available through Addgene) *plasmid map & annotation key*

 BsmBI TypeIIs sites for cloning in 20bp sgRNA guide sequence after removing 1.8kb spacer sequence
 +85 chRNA sequence for sgRNA
 EFS promoter sequence
 Human codon-optimized SpCas9 coding sequence
 P2A bicistronic linker/self-cleaving peptide
 Puromycin resistance coding sequence Online plasmid map is available at the website bit.ly/pLentiCRISPR

```
>lentiCRISPR  (pXPR_001)
TTAATGTAGTCTTATGCAATACTCTTGTAGTCTTGCAACATGGTAACGATGAGTTAGCAACATGCCTTACAAGGAGAG
AAAAAGCACCGTGCATGCCGATTGGTGGAAGTAAGGTGGTACGATCGTGCCTTATTAGGAAGGCAACAGACGGGTCTG
ACATGGATTGGACGAACCACTGAATTGCCGCATTGCAGAGATATTGTATTTAAGTGCCTAGCTCGATACATAAACGGG
TCTCTCTGGTTAGACCAGATCTGAGCCTGGGAGCTCTCTGGCTAACTAGGGAACCCACTGCTTAAGCCTCAATAAAGC
TTGCCTTGAGTGCTTCAAGTAGTGTGTGCCCGTCTGTTGTGTGACTCTGGTAACTAGAGATCCCTCAGACCCTTTTAG
TCAGTGTGGAAAATCTCTAGCAGTGGCGCCCGAACAGGGACTTGAAAGCGAAAGGGAAACCAGAGGAGCTCTCTCGAC
GCAGGACTCGGCTTGCTGAAGCGCGCACGGCAAGAGGCGAGGGGCGGCGACTGGTGAGTACGCCAAAAATTTTGACTA
GCGGAGGCTAGAAGGAGAGAGATGGGTGCGAGAGCGTCAGTATTAAGCGGGGGAGAATTAGATCGCGATGGGAAAAAA
TTCGGTTAAGGCCAGGGGGAAAGAAAAAATATAAATTAAAACATATAGTATGGGCAAGCAGGGAGCTAGAACGATTCG
CAGTTAATCCTGGCCTGTTAGAAACATCAGAAGGCTGTAGACAAATACTGGGACAGCTACAACCATCCCTTCAGACAG
GATCAGAAGAACTTAGATCATTATATAATACAGTAGCAACCCTCTATTGTGTGCATCAAAGGATAGAGATAAAAGACA
CCAAGGAAGCTTTAGACAAGATAGAGGAAGAGCAAAACAAAAGTAAGACCACCGCACAGCAAGCGGCCGCTGATCTTC
AGACCTGGAGGAGGAGATATGAGGGACAATTGGAGAAGTGAATTATATAAATATAAAGTAGTAAAAATTGAACCATTA
GGAGTAGCACCCACCAAGGCAAAGAGAAGAGTGGTGCAGAGAGAAAAAAGAGCAGTGGGAATAGGAGCTTTGTTCCTT
GGGTTCTTGGGAGCAGCAGGAAGCACTATGGGCGCAGCGTCAATGACGCTGACGGTACAGGCCAGACAATTATTGTCT
GGTATAGTGCAGCAGCAGAACAATTTGCTGAGGGCTATTGAGGCGCAACAGCATCTGTTGCAACTCACAGTCTGGGGC
ATCAAGCAGCTCCAGGCAAGAATCCTGGCTGTGGAAAGATACCTAAAGGATCAACAGCTCCTGGGGATTTGGGGTTGC
TCTGGAAAACTCATTTGCACCACTGCTGTGCCTTGGAATGCTAGTTGGAGTAATAAATCTCTGGAACAGATTTGGAAT
CACACGACCTGGATGGAGTGGGACAGAGAAATTAACAATTACACAAGCTTAATACACTCCTTAATTGAAGAATCGCAA
AACCAGCAAGAAAAGAATGAACAAGAATTATTGGAATTAGATAAATGGGCAAGTTTGTGGAATTGGTTTAACATAACA
AATTGGCTGTGGTATATAAAATTATTCATAATGATAGTAGGAGGCTTGGTAGGTTTAAGAATAGTTTTTGCTGTACTT
TCTATAGTGAATAGAGTTAGGCAGGGATATTCACCATTATCGTTTCAGACCCACCTCCCAACCCCGAGGGGACCCAGA
GAGGGCCTATTTCCCATGATTCCTTCATATTTGCATATACGATACAAGGCTGTTAGAGAGATAATTAGAATTAATTTG
ACTGTAAACACAAAGATATTAGTACAAAATACGTGACGTAGAAAGTAATAATTTCTTGGGTAGTTTGCAGTTTTAAAA
TTATGTTTTAAAATGGACTATCATATGCTTACCGTAACTTGAAAGTATTTCGATTTCTTGGCTTTATATATCTTGTGG
AAAGGACGAAACACCG[...]GTTGTAAATGAGCACACAAAATACACATGCTAAAATATTATATTCTATGACCTTTA
TAAAATCAACCAAAATCTTCTTTTTAATAACTTTAGTATCAATAATTAGAATTTTTATGTTCCTTTTTGCAAACTTTT
AATAAAAATGAGCAAAATAAAAAAACGCTAGTTTTAGTAACTCGCGTTGTTTTCTTCACCTTTAATAATAGCTACTCC
ACCACTTGTTCCTAAGCGGTCAGCTCCTGCTTCAATCATTTTTTGAGCATCTTCAAATGTTCTAACTCCACCAGCTGC
```

FIG. 46A

```
TTTAACTAAAGCATTGTCTTTAACAACTGACTTCATTAGTTTAACATCTTCAAATGTTGCACCTGATTTTGAAAATCC
TGTTGATGTTTTAACAAATTCTAATCCAGCTTCAACAGCTATTTCACAAGCTTTCATGATTTCTTCTTTTGTTAATAA
ACAATTTTCCATAATACATTTAACAACATGTGATCCAGCTGCTTTTTTTACAGCTTTCATGTCTTCTAAAACTAATTC
ATAATTTTTGTCTTTTAATGCACCAATATTTAATACCATATCAATTTCTGTTGCACCATCTTTAATTGCTTCAGAAAC
TTCGAATGCTTTTGTAGCTGTTGTGCATGCACCTAGAGGAAAACCTACAACATTTGTTATTCCTACATTTGTGCCTTT
TAATAATTCTTTACAATAGCTTGTTCAATATGAATTAACACAAACTGTTGCAAAATCAAATTCAATTGCTTCATCACA
TAATTGTTTAATTTCAGCTTTCGTAGCATCTTGTTTTAATAATGTGTGATCTATATATTTGTTTAGTTTCATTTTTTC
TCCTATATATTCATTTTTAATTTTAATTCTTTAATAATTTCGTCTACTTTAAGTTTAGCGTTTTGAACAGATTCAGCAACACCTATAAAATAAATTT
TTAGTTTAGGTTCAGTTCCACTTGGGCGAACAGCAAATCATGACTTATCTTCTAAATAAAATTTTAGTAAGTCTTGTCCTGGCATATT
ATACATTCCATCGATGTAGTCTTCAACATTAACAACTTTAAGTCCAGCAATTTGAGTTAAGGGTGTTGCTCTCAATGA
TTTCATTAATGGTTCAATTTTTAATTTCTTTTCTTCTGGTTTAAAATTCAAGTTTAAAGTGAAAGTGTAATATGCACC
CATTTCTTTAAATAAATCTTCTAAATAGTCTACTAATGTTTTATTTTGTTTTTTATAAAATCAAGCAGCCTCTGCTAT
TAATATAGAAGCTTGTATTCCATCTTTATCTCTAGCTGAGTCATCAATTACATATCCATAACTTTCTTCATAAGCAAA
AACAAAATTTAATCCGTTATCTTCTTCTTTAGCAATTTCTCTACCCATTCATTTAAATCCAGTTAAAGTTTTTACAAT
ATTAACTCCATATTTTTCATGAGCGATTCTATCACCCAAATCACTTGTTACAAAACTTGAATATAGAGCCGGATTTTT
TGGAATGCTATTTAAGCGTTTTAGATTTGATAATTTTCAATCAATTAAAATTGGTCCTGTTTGATTTCCATCTAATCT
TACAAAATGACCATCATGTTTTATTGCCATTCCAAATCTGTCAGCATCTGGGTCATTCATAATAATAATATCTGCATC
ATGTTTAATACCATATTCAAGCGGTATTTTTCATGCAGGATCAAATTCTGGATTTGGATTTACAACATTTTTAAATGT
TTCATCTTCAAATGCATGCTCTTCAACCTCAATAACGTTATATCCTGATTCACGTAATATTTTTGGGGTAAATTTAGT
TCCTGTTCCATTAACTGCGCTAAAAATAATTTTTAAATCTTTTTTAGCTTCTTGCTCTTTTTTGTACGTCTCTGTTTT
AGAGCTAGAAATAGCAAGTTAAAATAAGGCTAGTCCGTTATCAACTTGAAAAAGTGGCACCGAGTCGGTGCTTTTTTG
AATTCTAGATCTTGAGACAAATGGCAGTATTCATCCACAATTTTAAAAGAAAAGGGGGGATTGGGGGGTACAGTGCAG
GGGAAAGAATAGTAGACATAATAGCAACAGACATACAAACTAAAGAATTACAAAAACAAATTACAAAAATTCAAAATT
TTCGGGTTTATTACAGGGACAGCAGAGATCCACTTTGGCGCCGGCTCGAGTGGCTCCGGTGCCCGTCAGTGGGCAGAG
CGCACATCGCCCACAGTCCCCGAGAAGTTGGGGGGAGGGGTCGGCAATTGAACCGGTGCCTAGAGAAGGTGGCGCGGG
GTAAACTGGGAAAGTGATGTCGTGTACTGGCTCCGCCTTTTTCCCGAGGGTGGGGGAGAACCGTATATAAGTGCAGTA
GTCGCCGTGAACGTTCTTTTTCGCAACGGGTTTGCCGCCAGAACACAGGTGTCGTGACGCGGGATCCGCCACCATGGA
TTACAAAGACGATGACGATAAGATGGCCCCAAAGAAGAAGCGGAAGGTCGGTATCCACGGAGTCCCAGCAGCCGACAA
GAAGTACAGCATCGGCCTGGACATCGGCACCAACTCTGTGGGCTGGGCCGTGATCACCGACGAGTACAAGGTGCCCAG
CAAGAAATTCAAGGTGCTGGGCAACACCGACCGGCACAGCATCAAGAAGAACCTGATCGGAGCCCTGCTGTTCGACAG
CGGCGAAACAGCCGAGGCCACCCGGCTGAAGAGAACCGCCAGAAGAAGATACACCAGACGGAAGAACCGGATCTGCTA
TCTGCAAGAGATCTTCAGCAACGAGATGGCCAAGGTGGACGACAGCTTCTTCCACAGACTGGAAGAGTCCTTCCTGGT
GGAAGAGGATAAGAAGCACGAGCGGCACCCCATCTTCGGCAACATCGTGGACGAGGTGGCCTACCACGAGAAGTACCC
CACCATCTACCACCTGAGAAAGAAACTGGTGGACAGCACCGACAAGGCCGACCTGCGGCTGATCTATCTGGCCCTGGC
CCACATGATCAAGTTCCGGGGCCACTTCCTGATCGAGGGCGACCTGAACCCCGACAACAGCGACGTGGACAAGCTGTT
CATCCAGCTGGTGCAGACCTACAACCAGCTGTTCGAGGAAAACCCCATCAACGCCAGCGGCGTGGACGCCAAGGCCAT
CCTGTCTGCCAGACTGAGCAAGAGCAGACGGCTGGAAAATCTGATCGCCCAGCTGCCCGGCGAGAAGAAGAATGGCCT
GTTCGGCAACCTGATTGCCCTGAGCCTGGGCCTGACCCCCAACTTCAAGAGCAACTTCGACCTGGCCGAGGATGCCAA
ACTGCAGCTGAGCAAGGACACCTACGACGACGACCTGGACAACCTGCTGGCCCAGATCGGCGACCAGTACGCCGACCT
GTTTCTGGCCGCCAAGAACCTGTCCGACGCCATCCTGCTGAGCGACATCCTGAGAGTGAACACCGAGATCACCAAGGC
CCCCCTGAGCGCCTCTATGATCAAGAGATACGACGAGCACCACCAGGACCTGACCCTGCTGAAAGCTCTCGTGCGGCA
```

FIG. 46B

```
GCAGCTGCCTGAGAAGTACAAAGAGATTTTCTTCGACCAGAGCAAGAACGGCTACGCCGGCTACATTGACGGCGGAGC
CAGCCAGGAAGAGTTCTACAAGTTCATCAAGCCCATCCTGGAAAAGATGGACGGCACCGAGGAACTGCTCGTGAAGCT
GAACAGAGAGGACCTGCTGCGGAAGCAGCGGACCTTCGACAACGGCAGCATCCCCCACCAGATCCACCTGGGAGAGCT
GCACGCCATTCTGCGGCGGCAGGAAGATTTTTACCCATTCCTGAAGGACAACCGGGAAAAGATCGAGAAGATCCTGAC
CTTCCGCATCCCCTACTACGTGGGCCCTCTGGCCAGGGGAAACAGCAGATTCGCCTGGATGACCAGAAAGAGCGAGGA
AACCATCACCCCCTGGAACTTCGAGGAAGTGGTGGACAAGGGCGCTTCCGCCCAGAGCTTCATCGAGCGGATGACCAA
CTTCGATAAGAACCTGCCCAACGAGAAGGTGCTGCCCAAGCACAGCCTGCTGTACGAGTACTTCACCGTGTATAACGA
GCTGACCAAAGTGAAATACGTGACCGAGGGAATGAGAAAGCCCGCCTTCCTGAGCGGCGAGCAGAAAAAGGCCATCGT
GGACCTGCTGTTCAAGACCAACCGGAAAGTGACCGTGAAGCAGCTGAAAGAGGACTACTTCAAGAAAATCGAGTGCTT
CGACTCCGTGGAAATCTCCGGCGTGGAAGATCGGTTCAACGCCTCCCTGGGCACATACCACGATCTGCTGAAAATTAT
CAAGGACAAGGACTTCCTGGACAATGAGGAAAACGAGGACATTCTGGAAGATATCGTGCTGACCCTGACACTGTTTGA
GGACAGAGAGATGATCGAGGAACGGCTGAAAACCTATGCCCACCTGTTCGACGACAAAGTGATGAAGCAGCTGAAGCG
GCGGAGATACACCGGCTGGGGCAGGCTGAGCCGGAAGCTGATCAACGGCATCCGGGACAAGCAGTCCGGCAAGACAAT
CCTGGATTTCCTGAAGTCCGACGGCTTCGCCAACAGAAACTTCATGCAGCTGATCCACGACGACAGCCTGACCTTTAA
AGAGGACATCCAGAAAGCCCAGGTGTCCGGCCAGGGCGATAGCCTGCACGAGCACATTGCCAATCTGGCCGGCAGCCC
CGCCATTAAGAAGGGCATCCTGCAGACAGTGAAGGTGGTGGACGAGCTCGTGAAAGTGATGGGCCGGCACAAGCCCGA
GAACATCGTGATCGAAATGGCCAGAGAGAACCAGACCACCCAGAAGGGACAGAAGAACAGCCGCGAGAGAATGAAGCG
GATCGAAGAGGGCATCAAAGAGCTGGGCAGCCAGATCCTGAAAGAACACCCCGTGGAAAACACCCAGCTGCAGAACGA
GAAGCTGTACCTGTACTACCTGCAGAATGGGCGGGATATGTACGTGGACCAGGAACTGGACATCAACCGGCTGTCCGA
CTACGATGTGGACCATATCGTGCCTCAGAGCTTTCTGAAGGACGACTCCATCGACAACAAGGTGCTGACCAGAAGCGA
CAAGAACCGGGGCAAGAGCGACAACGTGCCCTCCGAAGAGGTCGTGAAGAAGATGAAGAACTACTGGCGGCAGCTGCT
GAACGCCAAGCTGATTACCCAGAGAAAGTTCGACAATCTGACCAAGGCCGAGAGAGGCGGCCTGAGCGAACTGGATAA
GGCCGGCTTCATCAAGAGACAGCTGGTGGAAACCCGGCAGATCACAAAGCACGTGGCACAGATCCTGGACTCCCGGAT
GAACACTAAGTACGACGAGAATGACAAGCTGATCCGGGAAGTGAAAGTGATCACCCTGAAGTCCAAGCTGGTGTCCGA
TTTCCGGAAGGATTTCCAGTTTTACAAAGTGCGCGAGATCAACAACTACCACCACGCCCACGACGCCTACCTGAACGC
CGTCGTGGGAACCGCCCTGATCAAAAAGTACCCTAAGCTGGAAAGCGAGTTCGTGTACGGCGACTACAAGGTGTACGA
CGTGCGGAAGATGATCGCCAAGAGCGAGCAGGAAATCGGCAAGGCTACCGCCAAGTACTTCTTCTACAGCAACATCAT
GAACTTTTTCAAGACCGAGATTACCCTGGCCAACGGCGAGATCCGGAAGCGGCCTCTGATCGAGACAAACGGCGAAAC
CGGGGAGATCGTGTGGGATAAGGGCCGGGATTTTGCCACCGTGCGGAAAGTGCTGAGCATGCCCCAAGTGAATATCGT
GAAAAAGACCGAGGTGCAGACAGGCGGCTTCAGCAAAGAGTCTATCCTGCCCAAGAGGAACAGCGATAAGCTGATCGC
CAGAAAGAAGGACTGGGACCCTAAGAAGTACGGCGGCTTCGACAGCCCCACCGTGGCCTATTCTGTGCTGGTGGTGGC
CAAAGTGGAAAAGGGCAAGTCCAAGAAACTGAAGAGTGTGAAAGAGCTGCTGGGGATCACCATCATGGAAAGAAGCAG
CTTCGAGAAGAATCCCATCGACTTTCTGGAAGCCAAGGGCTACAAAGAAGTGAAAAAGGACCTGATCATCAAGCTGCC
TAAGTACTCCCTGTTCGAGCTGGAAAACGGCCGGAAGAGAATGCTGGCCTCTGCCGGCGAACTGCAGAAGGGAAACGA
ACTGGCCCTGCCCTCCAAATATGTGAACTTCCTGTACCTGGCCAGCCACTATGAGAAGCTGAAGGGCTCCCCCGAGGA
TAATGAGCAGAAACAGCTGTTTGTGGAACAGCACAAGCACTACCTGGACGAGATCATCGAGCAGATCAGCGAGTTCTC
CAAGAGAGTGATCCTGGCCGACGCTAATCTGGACAAAGTGCTGTCCGCCTACAACAAGCACCGGGATAAGCCCATCAG
AGAGCAGGCCGAGAATATCATCCACCTGTTTACCCTGACCAATCTGGGAGCCCCTGCCGCCTTCAAGTACTTTGACAC
CACCATCGACCGGAAGAGGTACACCAGCACCAAAGAGGTGCTGGACGCCACCCTGATCCACCAGAGCATCACCGGCCT
GTACGAGACACGGATCGACCTGTCTCAGCTGGGAGGCGACAAGCGTCCTGCTGCTACTAAGAAAGCTGGTCAAGCTAA
GAAAAAGAAAGCTAGCGGCACCGGCGCCACCAACTTTAGCCTGCTGAAGCAGGCCGGCGACGTGGAGGAGAACCCCGG
```

FIG. 46C

GGGGATGACCGAGTACAAGCCCACGGTGCGCCTCGCCACCCGCGACGACGTGCCCAGGGCCGTACGCACCCTCGCCGC
CGCGTTCGCCGACTACCCCGCCACGCGCCACACCGTCGATCCGGACCGCCACATCGAGCGGGTCACCGAGCTGCAAGA
ACTCTTCCTCACGCGCGTCGGGCTCGACATCGGCAAGGTGTGGGTCGCGGACGACGGCGCGGCCGTGGCGGTCTGGAC
CACGCCGGAGAGCGTCGAAGCGGGGGCGGTGTTCGCCGAGATCGGCCCGCGCATGGCCGAGTTGAGCGGTTCCCGGCT
GGCCGCGCAGCAACAGATGGAAGGCCTCCTGGCGCCGCACCGGCCCAAGGAGCCCGCGTGGTTCCTGGCCACCGTCGG
AGTCTCGCCCGACCACCAGGGCAAGGGTCTGGGCAGCGCCGTCGTGCTCCCCGGGAGTGGAGGCGGCCGAGCGCGCGG
GGTGCCCGCCTTCCTGGAGACCTCCGCGCCCCGCAACCTCCCCTTCTACGAGCGGCTCGGCTTCACCGTCACCGCCGA
CGTCGAGGTGCCCGAAGGACCGCGCACCTGGTGCATGACCCGCAAGCCCGGTGCCTGAACGCGTTAAGTCGACAATCA
ACCTCTGGATTACAAAATTTGTGAAAGATTGACTGGTATTCTTAACTATGTTGCTCCTTTTACGCTATGTGGATACGC
TGCTTTAATGCCTTTGTATCATGCTATTGCTTCCCGTATGGCTTTCATTTTCTCCTCCTTGTATAAATCCTGGTTGCT
GTCTCTTTATGAGGAGTTGTGGCCCGTTGTCAGGCAACGTGGCGTGGTGTGCACTGTGTTTGCTGACGCAACCCCCAC
TGGTTGGGGCATTGCCACCACCTGTCAGCTCCTTTCCGGGACTTTCGCTTTCCCCCTCCCTATTGCCACGGCGGAACT
CATCGCCGCCTGCCTTGCCCGCTGCTGGACAGGGGCTCGGCTGTTGGGCACTGACAATTCCGTGGTGTTGTCGGGGAA
ATCATCGTCCTTTCCTTGGCTGCTCGCCTGTGTTGCCACCTGGATTCTGCGCGGGACGTCCTTCTGCTACGTCCCTTC
GGCCCTCAATCCAGCGGACCTTCCTTCCCGCGGCCTGCTGCCGGCTCTGCGGCCTCTTCCGCGTCTTCGCCTTCGCCC
TCAGACGAGTCGGATCTCCCTTTGGGCCGCCTCCCCGCGTCGACTTTAAGACCAATGACTTACAAGGCAGCTGTAGAT
CTTAGCCACTTTTTAAAAGAAAAGGGGGGACTGGAAGGGCTAATTCACTCCCAACGAAGACAAGATCTGCTTTTTGCT
TGTACTGGGTCTCTCTGGTTAGACCAGATCTGAGCCTGGGAGCTCTCTGGCTAACTAGGGAACCCACTGCTTAAGCCT
CAATAAAGCTTGCCTTGAGTGCTTCAAGTAGTGTGTGCCCGTCTGTTGTGTGACTCTGGTAACTAGAGATCCCTCAGA
CCCTTTTAGTCAGTGTGGAAAATCTCTAGCAGTACGTATAGTAGTTCATGTCATCTTATTATTCAGTATTTATAACTT
GCAAAGAAATGAATATCAGAGAGTGAGAGGAACTTGTTTATTGCAGCTTATAATGGTTACAAATAAAGCAATAGCATC
ACAAATTTCACAAATAAAGCATTTTTTCACTGCATTCTAGTTGTGGTTTGTCCAAACTCATCAATGTATCTTATCAT
GTCTGGCTCTAGCTATCCCGCCCCTAACTCCGCCCATCCCGCCCCTAACTCCGCCCAGTTCCGCCCATTCTCCGCCCC
ATGGCTGACTAATTTTTTTTATTTATGCAGAGGCCGAGGCCGCCTCGGCCTCTGAGCTATTCCAGAAGTAGTGAGGAG
GCTTTTTTGGAGGCCTAGGGACGTACCCAATTCGCCCTATAGTGAGTCGTATTACGCGCGCTCACTGGCCGTCGTTTT
ACAACGTCGTGACTGGGAAAACCCTGGCGTTACCCAACTTAATCGCCTTGCAGCACATCCCCCTTTCGCCAGCTGGCG
TAATAGCGAAGAGGCCCGCACCGATCGCCCTTCCCAACAGTTGCGCAGCCTGAATGGCGAATGGGACGCGCCCTGTAG
CGGCGCATTAAGCGCGGCGGGTGTGGTGGTTACGCGCAGCGTGACCGCTACACTTGCCAGCGCCCTAGCGCCCGCTCC
TTTCGCTTTCTTCCCTTCCTTTCTCGCCACGTTCGCCGGCTTTCCCCGTCAAGCTCTAAATCGGGGGCTCCCTTTAGG
GTTCCGATTTAGTGCTTTACGGCACCTCGACCCCAAAAAACTTGATTAGGGTGATGGTTCACGTAGTGGGCCATCGCC
CTGATAGACGGTTTTTCGCCCTTTGACGTTGGAGTCCACGTTCTTTAATAGTGGACTCTTGTTCCAAACTGGAACAAC
ACTCAACCCTATCTCGGTCTATTCTTTTGATTTATAAGGGATTTTGCCGATTTCGGCCTATTGGTTAAAAAATGAGCT
GATTTAACAAAAATTTAACGCGAATTTTAACAAAATATTAACGCTTACAATTTAGGTGGCACTTTTCGGGGAAATGTG
CGCGGAACCCCTATTTGTTTATTTTTCTAAATACATTCAAATATGTATCCGCTCATGAGACAATAACCCTGATAAATG
CTTCAATAATATTGAAAAAGGAAGAGTATGAGTATTCAACATTTCCGTGTCGCCCTTATTCCCTTTTTTGCGGCATTT
TGCCTTCCTGTTTTTGCTCACCCAGAAACGCTGGTGAAAGTAAAAGATGCTGAAGATCAGTTGGGTGCACGAGTGGGT
TACATCGAACTGGATCTCAACAGCGGTAAGATCCTTGAGAGTTTTCGCCCCGAAGAACGTTTTCCAATGATGAGCACT
TTTAAAGTTCTGCTATGTGGCGCGGTATTATCCCGTATTGACGCCGGGCAAGAGCAACTCGGTCGCCGCATACACTAT
TCTCAGAATGACTTGGTTGAGTACTCACCAGTCACAGAAAAGCATCTTACGGATGGCATGACAGTAAGAGAATTATGC
AGTGCTGCCATAACCATGAGTGATAACACTGCGGCCAACTTACTTCTGACAACGATCGGAGGACCGAAGGAGCTAACC
GCTTTTTTGCACAACATGGGGGATCATGTAACTCGCCTTGATCGTTGGGAACCGGAGCTGAATGAAGCCATACCAAAC

FIG. 46D

```
GACGAGCGTGACACCACGATGCCTGTAGCAATGGCAACAACGTTGCGCAAACTATTAACTGGCGAACTACTTACTCTA
GCTTCCCGGCAACAATTAATAGACTGGATGGAGGCGGATAAAGTTGCAGGACCACTTCTGCGCTCGGCCCTTCCGGCT
GGCTGGTTTATTGCTGATAAATCTGGAGCCGGTGAGCGTGGGTCTCGCGGTATCATTGCAGCACTGGGGCCAGATGGT
AAGCCCTCCCGTATCGTAGTTATCTACACGACGGGGAGTCAGGCAACTATGGATGAACGAAATAGACAGATCGCTGAG
ATAGGTGCCTCACTGATTAAGCATTGGTAACTGTCAGACCAAGTTTACTCATATATACTTTAGATTGATTTAAAACTT
CATTTTTAATTTAAAAGGATCTAGGTGAAGATCCTTTTTGATAATCTCATGACCAAAATCCCTTAACGTGAGTTTTCG
TTCCACTGAGCGTCAGACCCCGTAGAAAAGATCAAAGGATCTTCTTGAGATCCTTTTTTTCTGCGCGTAATCTGCTGC
TTGCAAACAAAAAAACCACCGCTACCAGCGGTGGTTTGTTTGCCGGATCAAGAGCTACCAACTCTTTTTCCGAAGGTA
ACTGGCTTCAGCAGAGCGCAGATACCAAATACTGTTCTTCTAGTGTAGCCGTAGTTAGGCCACCACTTCAAGAACTCT
GTAGCACCGCCTACATACCTCGCTCTGCTAATCCTGTTACCAGTGGCTGCTGCCAGTGGCGATAAGTCGTGTCTTACC
GGGTTGGACTCAAGACGATAGTTACCGGATAAGGCGCAGCGGTCGGGCTGAACGGGGGGTTCGTGCACACAGCCCAGC
TTGGAGCGAACGACCTACACCGAACTGAGATACCTACAGCGTGAGCTATGAGAAAGCGCCACGCTTCCCGAAGGGAGA
AAGGCGGACAGGTATCCGGTAAGCGGCAGGGTCGGAACAGGAGAGCGCACGAGGGAGCTTCCAGGGGGAAACGCCTGG
TATCTTTATAGTCCTGTCGGGTTTCGCCACCTCTGACTTGAGCGTCGATTTTTGTGATGCTCGTCAGGGGGGCGGAGC
CTATGGAAAAACGCCAGCAACGCGGCCTTTTTACGGTTCCTGGCCTTTTGCTGGCCTTTTGCTCACATGTTCTTTCCT
GCGTTATCCCCTGATTCTGTGGATAACCGTATTACCGCCTTTGAGTGAGCTGATACCGCTCGCCGCAGCCGAACGACC
GAGCGCAGCGAGTCAGTGAGCGAGGAAGCGGAAGAGCGCCCAATACGCAAACCGCCTCTCCCCGCGCGTTGGCCGATT
CATTAATGCAGCTGGCACGACAGGTTTCCCGACTGGAAAGCGGGCAGTGAGCGCAACGCAATTAATGTGAGTTAGCTC
ACTCATTAGGCACCCCAGGCTTTACACTTTATGCTTCCGGCTCGTATGTTGTGTGGAATTGTGAGCGGATAACAATTT
CACACAGGAAACAGCTATGACCATGATTACGCCAAGCGCGCAATTAACCCTCACTAAAGGGAACAAAAGCTGGAGCTG
CAAGC
```

FIG. 46E

LentiCRISPR v2

| | |
|---|---|
| ▓▓ | BsmBI TypeIIs sites for cloning in 20bp sgRNA guide sequence after removing 1.8kb spacer sequence |
| Green | +85 chRNA sequence for sgRNA |
| Gray | EFS promoter sequence |
| Yellow | Human codon-optimized SpCas9 coding sequence |
| *Italics* | FLAG peptide tag |
| ▓▓ | P2A bicistronic linker/self-cleaving peptide |
| Blue | Puromycin resistance coding sequence |

```
GTCGACGGATCGGGAGATCTCCCGATCCCCTATGGTGCACTCTCAGTACAATCTGCTCTGATGCCGCATAGTTAAGCCAGTATCTGCTCCCTG
CTTGTGTGTTGGAGGTCGCTGAGTAGTGCGCGAGCAAAATTTAAGCTACAACAAGGCAAGGCTTGACCGACAATTGCATGAAGAATCTGCTTA
GGGTTAGGCGTTTTGCGCTGCTTCGCGATGTACGGGCCAGATATACGCGTTGACATTGATTATTGACTAGTTATTAATAGTAATCAATTACGG
GGTCATTAGTTCATAGCCCATATATGGAGTTCCGCGTTACATAACTTACGGTAAATGGCCCGCCTGGCTGACCGCCCAACGACCCCCGCCCAT
TGACGTCAATAATGACGTATGTTCCCATAGTAACGCCAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACGGTAAATGGCCCGCCTGGCATTATGCCCAGTACATGA
CCTTATGGGACTTTCCTACTTGGCAGTACATCTACGTATTAGTCATCGCTATTACCATGGTGATGCGGTTTTGGCAGTACATCAATGGGCGTG
GATAGCGGTTTGACTCACGGGGATTTCCAAGTCTCCACCCCATTGACGTCAATGGGAGTTTGTTTTGGCACCAAAATCAACGGGACTTTCCAA
AATGTCGTAACAACTCCGCCCCATTGACGCAAATGGGCGGTAGGCGTGTACGGTGGGAGGTCTATATAAGCAGCGCGTTTTGCCTGTACTGGG
TCTCTCTGGTTAGACCAGATCTGAGCCTGGGAGCTCTCTGGCTAACTAGGGAACCCACTGCTTAAGCCTCAATAAAGCTTGCCTTGAGTGCTT
CAAGTAGTGTGTGCCCGTCTGTTGTGTGACTCTGGTAACTAGAGATCCCTCAGACCCTTTTAGTCAGTGTGGAAAATCTCTAGCAGTGGCGCC
CGAACAGGGACTTGAAAGCGAAAGGGAAACCAGAGGAGCTCTCTCGACGCAGGACTCGGCTTGCTGAAGCGCGCACGGCAAGAGGCGAGGGGC
GGCGACTGGTGAGTACGCCAAAAATTTTGACTAGCGGAGGCTAGAAGGAGAGAGATGGGTGCGAGAGCGTCAGTATTAAGCGGGGGAGAATTA
GATCGCGATGGGAAAAAATTCGGTTAAGGCCAGGGGGAAAGAAAAAATATAAATTAAAACATATAGTATGGGCAAGCAGGGAGCTAGAACGAT
TCGCAGTTAATCCTGGCCTGTTAGAAACATCAGAAGGCTGTAGACAAATACTGGGACAGCTACAACCATCCCTTCAGACAGGATCAGAAGAAC
TTAGATCATTATATAATACAGTAGCAACCCTCTATTGTGTGCATCAAAGGATAGAGATAAAAGACACCAAGGAAGCTTTAGACAAGATAGAGG
AAGAGCAAAACAAAAGTAAGACCACCGCACAGCAAGCGGCCGCTGATCTTCAGACCTGGAGGAGGAGATATGAGGGACAATTGGAGAAGTGAA
TTATATAAATATAAAGTAGTAAAAATTGAACCATTAGGAGTAGCACCCACCAAGGCAAAGAGAAGAGTGGTGCAGAGAGAAAAAAGAGCAGTG
GGAATAGGAGCTTTGTTCCTTGGGTTCTTGGGAGCAGCAGGAAGCACTATGGGCGCAGCGTCAATGACGCTGACGGTACAGGCCAGACAATTA
TTGTCTGGTATAGTGCAGCAGCAGAACAATTTGCTGAGGGCTATTGAGGCGCAACAGCATCTGTTGCAACTCACAGTCTGGGGCATCAAGCAG
CTCCAGGCAAGAATCCTGGCTGTGGAAAGATACCTAAAGGATCAACAGCTCCTGGGGATTTGGGGTTGCTCTGGAAAACTCATTTGCACCACT
GCTGTGCCTTGGAATGCTAGTTGGAGTAATAAATCTCTGGAACAGATTTGGAATCACACGACCTGGATGGAGTGGGACAGAGAAATTAACAAT
TACACAAGCTTAATACACTCCTTAATTGAAGAATCGCAAAACCAGCAAGAAAAGAATGAACAAGAATTATTGGAATTAGATAAATGGGCAAGT
TTGTGGAATTGGTTTAACATAACAAATTGGCTGTGGTATATAAAATTATTCATAATGATAGTAGGAGGCTTGGTAGGTTTAAGAATAGTTTTT
GCTGTACTTTCTATAGTGAATAGAGTTAGGCAGGGATATTCACCATTATCGTTTCAGACCCACCTCCCAACCCCGAGGGGACCCGACAGGCCC
GAAGGAATAGAAGAAGAAGGTGGAGAGAGAGACAGAGACAGATCCATTCGATTAGTGAACGGATCGGCACTGCGTGCGCCAATTCTGCAGACA
AATGGCAGTATTCATCCACAATTTTAAAAGAAAAGGGGGGATTGGGGGGTACAGTGCAGGGGAAAGAATAGTAGACATAATAGCAACAGACAT
ACAAACTAAAGAATTACAAAAACAAATTACAAAAATTCAAAATTTTCGGGTTTATTACAGGGACAGCAGAGATCCAGTTTGGTTAATTAAGGT
ACCGAGGGCCTATTTCCCATGATTCCTTCATATTTGCATATACGATACAAGGCTGTTAGAGAGATAATTAGAATTAATTTGACTGTAAACACA
AAGATATTAGTACAAAATACGTGACGTAGAAAGTAATAATTTCTTGGGTAGTTTGCAGTTTTAAAATTATGTTTTAAAATGGACTATCATATG
CTTACCGTAACTTGAAAGTATTTCGATTTCTTGGCTTTATATATCTTGTGGAAAGGACGAAACACCG▓▓▓▓▓GTTGTAAATGAGCACACAAA
ATACACATGCTAAAATATTATATTCTATGACCTTTATAAAATCAACCAAAATCTTCTTTTTAATAACTTTAGTATCAATAATTAGAATTTTTA
TGTTCCTTTTTGCAAACTTTTAATAAAAATGAGCAAAATAAAAAAACGCTAGTTTTAGTAACTCGCGTTGTTTTCTTCACCTTTAATAATAGC
TACTCCACCACTTGTTCCTAAGCGGTCAGCTCCTGCTTCAATCATTTTTTGAGCATCTTCAAATGTTCTAACTCCACCAGCTGCTTTAACTAA
AGCATTGTCTTTAACAACTGACTTCATTAGTTTAACATCTTCAAATGTTGCACCTGATTTTGAAAATCCTGTTGATGTTTTAACAAATTCTAA
TCCAGCTTCAACAGCTATTTCACAAGCTTTCATGATTTCTTCTTTTGTTAATAAACAATTTTCCATAATACATTTAACAACATGTGATCCAGC
TGCTTTTTTTACAGCTTTCATGTCTTCTAAAACTAATTCATAATTTTTGTCTTTAATGCACCAATATTTAATACCATATCAATTTCTGTTGC
ACCATCTTTAATTGCTTCAGAAAACTTCGAATGCTTTTGTAGCTGTTGTGCATGCACCTAGAGGAAAACCTACAACATTTGTTATTCCTACATT
```

FIG. 49A

```
TGTGCCTTTTAATAATTCTTTACAATAGCTTGTTCAATATGAATTAACACAAACTGTTGCAAAATCAAATTCAATTGCTTCATCACATAATTG
TTTAATTTCAGCTTTCGTAGCATCTTGTTTTAATAATGTGTGATCTATATATTTGTTTAGTTTCATTTTTTCTCCTATATATTCATTTTTAAT
TTTAATTCTTTAATAATTTCGTCTACTTTAACTTTAGCGTTTTGAACAGATTCACCAACACCTATAAAATAAATTTTTAGTTTAGGTTCAGTT
CCACTTGGGCGAACAGCAAATCATGACTTATCTTCTAAATAAAATTTTAGTAAGTCTTGTCCTGGCATATTATACATTCCATCGATGTAGTCT
TCAACATTAACAACTTTAAGTCCAGCAATTTGAGTTAAGGGTGTTGCTCTCAATGATTTCATTAATGGTTCAATTTTTAATTTCTTTTCTTCT
GGTTTAAAATTCAAGTTTAAAGTGAAAGTGTAATATGCACCCATTTCTTTAAATAAATCTTCTAAATAGTCTACTAATGTTTTATTTTGTTTT
TTATAAAATCAAGCAGCCTCTGCTATTAATATAGAAGCTTGTATTCCATCTTTATCTCTAGCTGAGTCATCAATTACATATCCATAACTTTCT
TCATAAGCAAAAACAAAATTTAATCCGTTATCTTCTTCTTTAGCAATTTCTCTACCCATTCATTTAAATCCAGTTAAAGTTTTACAATATTA
ACTCCATATTTTTCATGAGCGATTCTATCACCCAAATCACTTGTTACAAAACTTGAATATAGAGCCGGATTTTTTGGAATGCTATTTAAGCGT
TTTAGATTTGATAATTTTCAATCAATTAAAATTGGTCCTGTTTGATTTCCATCTAATCTTACAAAATGACCATCATGTTTTATTGCCATTCCA
AATCTGTCAGCATCTGGGTCATTCATAATAATAATATCTGCATCATGTTTAATACCATATTCAAGCGGTATTTTTCATGCAGGATCAAATTCT
GGATTTGGATTTACAACATTTTTAAATGTTTCATCTTCAAATGCATGCTCTTCAACCTCAATAACGTTATATCCTGATTCACGTAATATTTTT
GGGGTAAATTTAGTTCCTGTTCCATTAACTGCGCTAAAAATAATTTTTAAATCTTTTTTAGCTTCTTGCTCTTTTTTGTA
```

FIG. 49B

```
AACCGCCCTGATCAAAAAGTACCCTAAGCTGGAAAGCGAGTTCGTGTACGGCGACTACAAGGTGTACGACGTGCGGAAGATGATCGCCAAGAG
CGAGCAGGAAATCGGCAAGGCTACCGCCAAGTACTTCTTCTACAGCAACATCATGAACTTTTTCAAGACCGAGATTACCCTGGCCAACGGCGA
GATCCGGAAGCGGCCTCTGATCGAGACAAACGGCGAAACCGGGGAGATCGTGTGGGATAAGGGCCGGGATTTTGCCACCGTGCGGAAAGTGCT
GAGCATGCCCCAAGTGAATATCGTGAAAAAGACCGAGGTGCAGACAGGCGGCTTCAGCAAAGAGTCTATCCTGCCCAAGAGGAACAGCGATAA
GCTGATCGCCAGAAAGAAGGACTGGGACCCTAAGAAGTACGGCGGCTTCGACAGCCCCACCGTGGCCTATTCTGTGCTGGTGGTGGCCAAAGT
GGAAAAGGGCAAGTCCAAGAAACTGAAGAGTGTGAAAGAGCTGCTGGGGATCACCATCATGGAAAGAAGCAGCTTCGAGAAGAATCCCATCGA
CTTTCTGGAAGCCAAGGGCTACAAAGAAGTGAAAAAGGACCTGATCATCAAGCTGCCTAAGTACTCCCTGTTCGAGCTGGAAAACGGCCGGAA
GAGAATGCTGGCCTCTGCCGGCGAACTGCAGAAGGGAAACGAACTGGCCCTGCCCTCCAAATATGTGAACTTCCTGTACCTGGCCAGCCACTA
TGAGAAGCTGAAGGGCTCCCCCGAGGATAATGAGCAGAAACAGCTGTTTGTGGAACAGCACAAGCACTACCTGGACGAGATCATCGAGCAGAT
CAGCGAGTTCTCCAAGAGAGTGATCCTGGCCGACGCTAATCTGGACAAAGTGCTGTCCGCCTACAACAAGCACCGGGATAAGCCCATCAGAGA
GCAGGCCGAGAATATCATCCACCTGTTTACCCTGACCAATCTGGGAGCCCCTGCCGCCTTCAAGTACTTTGACACCACCATCGACCGGAAGAG
GTACACCAGCACCAAAGAGGTGCTGGACGCCACCCTGATCCACCAGAGCATCACCGGCCTGTACGAGACACGGATCGACCTGTCTCAGCTGGG
AGGCGACAAGCGACCTGCCGCCACAAAGAAGGCTGGACAGGCTAAGAAGAAGAAA*GATTACAAAGACGATGACGATAAG*...
...ACCGAGTACAAGCCCACGGTGCGCCTCGCCACCCGCGACGA
CGTCCCCAGGGCCGTACGCACCCTCGCCGCCGCGTTCGCCGACTACCCCGCCACGCGCCACACCGTCGATCGGGACGCCACATCGAGCGGGT
CACCGAGCTGCAAGAACTCTTCCTCACGCGCGTCGGGCTCGACATCGGCAAGGTGTGGGTCGCGGACGACGGCGCCGCGGTGGCGGTCTGGAC
CACGCCGGAGAGCGTCGAAGCGGGGCGGTGTTCGCCGAGATCGGCCCGCGCATGGCCGAGTTGAGCGGTTCCGGGCTGGCCGCGCAGCAACA
GATGGAAGGCCTCCTGGCCGCGCACCGGCCCAAGGAGCCCGCGTGGTTCCTGGCCACCGTCGGAGTCTCGCCGACCACCAGGGCAAGGGTCT
GGGCAGCGCCGTCGTGCTCCCCGGAGTGGAGGCGGCCGAGCGCGCCGGGGTGCCCGCCTTCCTGGAGACCTCGCGCCCCGCAACCCTCCCCTT
CTACGAGCGGCTCGGCTTCACCGTCACCGCCGACGTCGAGGTGCCCGAAGGACCGCGCACCCTGGTGCATGACCCGGAAGCCCGGTGCCTGAAC
GCGTTAAGTCGACAATCAACCTCTGGATTACAAAATTTGTGAAAGATTGACTGGTATTCTTAACTATGTTGCTCCTTTTACGCTATGTGGATA
CGCTGCTTTAATGCCTTTGTATCATGCTATTGCTTCCCGTATGGCTTTCATTTTCTCCTCCTTGTATAAATCCTGGTTGCTGTGTCTCTTTATGA
GGAGTTGTGGCCCGTTGTCAGGCAACGTGGCGTGGTGTGCACTGTGTTTGCTGACGCAACCCCCACTGGTTGGGGCATTGCCACCACCTGTCA
GCTCCTTTCCGGGACTTTCGCTTTCCCCCTCCCTATTGCCACGGCGGAACTCATCGCCGCCTGCCTTGCCCGCTGCTGGACAGGGGCTCGGCT
GTTGGGCACTGACAATTCCGTGGTGTTGTCGGGGAAATCATCGTCCTTTCCTTGGCTGCTCGCCTGTGTTGCCACCTGGATTCTGCGCGGGAC
GTCCTTCTGCTACGTCCCTTCGGCCCTCAATCCAGCGGACCTTCCTTCCCGCGGCCTGCTGCCGGCTCTGCGGCCTCTTCCGCGTCTTCGCCT
TCGCCCTCAGACGAGTCGGATCTCCCTTTGGGCCGCCTCCCCGCGTCGACTTTAAGACCAATGACTTACAAGGCAGCTGTAGATCTTAGCCAC
TTTTTAAAAGAAAAGGGGGGACTGGAAGGGCTAATTCACTCCCAACGAAGACAAGATCTGCTTTTTGCTTGTACTGGGTCTCTCTGGTTAGAC
CAGATCTGAGCCTGGGAGCTCTCTGGCTAACTAGGGAACCCACTGCTTAAGCCTCAATAAAGCTTGCCTTGAGTGCTTCAAGTAGTGTGTGCC
CGTCTGTTGTGTGACTCTGGTAACTAGAGATCCCTCAGACCCTTTTAGTCAGTGTGGAAAATCTCTAGCAGGGCCCGTTTAAACCCGCTGATC
AGCCTCGACTGTGCCTTCTAGTTGCCAGCCATCTGTTGTTTGCCCCTCCCCCGTGCCTTCCTTGACCCTGGAAGGTGCCACTCCCACTGTCCT
TTCCTAATAAAATGAGGAAATTGCATCGCATTGTCTGAGTAGGTGTCATTCTATTCTGGGGGGTGGGGTGGGGCAGGACAGCAAGGGGGAGGA
TTGGGAAGACAATAGCAGGCATGCTGGGGATGCGGTGGGCTCTATGGCTTCTGAGGCGGAAAGAACCAGCTGGGGCTCTAGGGGGTATCCCCA
CGCGCCCTGTAGCGGCGCATTAAGCGCGGCGGGTGTGGTGGTTACGCGCAGCGTGACCGCTACACTTGCCAGCGCCCTAGCGCCCGCTCCTTT
CGCTTTCTTCCCTTCCTTTCTCGCCACGTTCGCCGGCTTTCCCCGTCAAGCTCTAAATCGGGGGCTCCCTTTAGGGTTCCGATTTAGTGCTTT
ACGGCACCTCGACCCCAAAAAACTTGATTAGGGTGATGGTTCACGTAGTGGGCCATCGCCCTGATAGACGGTTTTTCGCCCTTTGACGTTGGA
GTCCACGTTCTTTAATAGTGGACTCTTGTTCCAAACTGGAACAACACTCAACCCTATCTCGGTCTATTCTTTTGATTTATAAGGGATTTTGCC
GATTTCGGCCTATTGGTTAAAAAATGAGCTGATTTAACAAAAATTTAACGCGAATTAATTCTGTGGAATGTGTGTCAGTTAGGGTGTGGAAAG
TCCCCAGGCTCCCCAGCAGGCAGAAGTATGCAAAGCATGCATCTCAATTAGTCAGCAACCAGGTGTGGAAAGTCCCCAGGCTCCCCAGCAGGC
AGAAGTATGCAAAGCATGCATCTCAATTAGTCAGCAACCATAGTCCCGCCCCTAACTCCGCCCATCCCGCCCCTAACTCCGCCCAGTTCCGCC
CATTCTCCGCCCCATGGCTGACTAATTTTTTTTATTTATGCAGAGGCCGAGGCCGCCTCTGCCTCTGAGCTATTCCAGAAGTAGTGAGGAGGC
TTTTTTGGAGGCCTAGGCTTTTGCAAAAAGCTCCCGGGAGCTTGTATATCCATTTTCGGATCTGATCAGCACGTGTTGACAATTAATCATCGG
CATAGTATATCGGCATAGTATAATACGACAAGGTGAGGAACTAAACCATGGCCAAGTTGACCAGTGCCGTTCCGGTGCTCACCGCGCGCGACG
TCGCCGGAGCGGTCGAGTTCTGGACCGACCGGCTCGGGTTCTCCCGGGACTTCGTGGAGGACGACTTCGCCGGTGTGGTCCGGGACGACGTGA
CCCTGTTCATCAGCGCGGTCCAGGACCAGGTGGTGCCGGACAACACCCTGGCCTGGGTGTGGGTGCGCGGCCTGGACGAGCTGTACGCCGAGT
GGTCGGAGGTCGTGTCCACGAACTTCCGGGACGCCTCCGGGCCGGCCATGACCGAGATCGGCGAGCAGCCGTGGGGGCGGGAGTTCGCCCTGC
GCGACCCGGCCGGCAACTGCGTGCACTTCGTGGCCGAGGAGCAGGACTGACACGTGCTACGAGATTTCGATTCCACCGCCGCCTTCTATGAAA
GGTTGGGCTTCGGAATCGTTTTCCGGGACGCCGGCTGGATGATCCTCCAGCGCGGGGATCTCATGCTGGAGTTCTTCGCCCACCCCAACTTGT
TTATTGCAGCTTATAATGGTTACAAATAAAGCAATAGCATCACAAATTTCACAAATAAAGCATTTTTTTCACTGCATTCTAGTTGTGGTTTGT
```

```
CCAAACTCATCAATGTATCTTATCATGTCTGTATACCGTCGACCTCTAGCTAGAGCTTGGCGTAATCATGGTCATAGCTGTTTCCTGTGTGAA
ATTGTTATCCGCTCACAATTCCACACAACATACGAGCCGGAAGCATAAAGTGTAAAGCCTGGGGTGCCTAATGAGTGAGCTAACTCACATTAA
TTGCGTTGCGCTCACTGCCCGCTTTCCAGTCGGGAAACCTGTCGTGCCAGCTGCATTAATGAATCGGCCAACGCGCGGGGAGAGGCGGTTTGC
GTATTGGGCGCTCTTCCGCTTCCTCGCTCACTGACTCGCTGCGCTCGGTCGTTCGGCTGCGGCGAGCGGTATCAGCTCACTCAAAGGCGGTAA
TACGGTTATCCACAGAATCAGGGGATAACGCAGGAAAGAACATGTGAGCAAAAGGCCAGCAAAAGGCCAGGAACCGTAAAAAGGCCGCGTTGC
TGGCGTTTTTCCATAGGCTCCGCCCCCCTGACGAGCATCACAAAAATCGACGCTCAAGTCAGAGGTGGCGAAACCCGACAGGACTATAAAGAT
ACCAGGCGTTTCCCCCTGGAAGCTCCCTCGTGCGCTCTCCTGTTCCGACCCTGCCGCTTACCGGATACCTGTCCGCCTTTCTCCCTTCGGGAA
GCGTGGCGCTTTCTCATAGCTCACGCTGTAGGTATCTCAGTTCGGTGTAGGTCGTTCGCTCCAAGCTGGGCTGTGTGCACGAACCCCCCGTTC
AGCCCGACCGCTGCGCCTTATCCGGTAACTATCGTCTTGAGTCCAACCCGGTAAGACACGACTTATCGCCACTGGCAGCAGCCACTGGTAACA
GGATTAGCAGAGCGAGGTATGTAGGCGGTGCTACAGAGTTCTTGAAGTGGTGGCCTAACTACGGCTACACTAGAAGAACAGTATTTGGTATCT
GCGCTCTGCTGAAGCCAGTTACCTTCGGAAAAAGAGTTGGTAGCTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTGATCTTTTCTACGGGGTCTGACGCTCAGTGGAACGAAAACTCAC
GTTAAGGGATTTTGGTCATGAGATTATCAAAAAGGATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAGCGATCTGTCTATTTCGTTCATCCATAGTTGCCTGAC
TCCCCGTCGTGTAGATAACTACGATACGGGAGGGCTTACCATCTGGCCCCAGTGCTGCAATGATACCGCGAGACCCACGCTCACCGGCTCCAG
ATTTATCAGCAATAAACCAGCCAGCCGGAAGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTACAGGCATCGTGGTGTCACGCTCGTCGTTTGGTA
TGGCTTCATTCAGCTCCGGTTCCCAACGATCAAGGCGAGTTACATGATCCCCCATGTTGTGCAAAAAAGCGGTTAGCTCCTTCGGTCCTCCGA
TCGTTGTCAGAAGTAAGTTGGCCGCAGTGTTATCACTCATGGTTATGGCAGCACTGCATAATTCTCTTACTGTCATGCCATCCGTAAGATGCT
TTTCTGTGACTGGTGAGTACTCAACCAAGTCATTCTGAGAATAGTGTATGCGGCGACCGAGTTGCTCTTGCCCGGCGTCAATACGGGATAATA
CCGCGCCACATAGCAGAACTTTAAAAGTGCTCATCATTGGAAAACGTTCTTCGGGGCGAAAACTCTCAAGGATCTTACCGCTGTTGAGATCCA
GTTCGATGTAACCCACTCGTGCACCCAACTGATCTTCAGCATCTTTTACTTTCACCAGCGTTTCTGGGTGAGCAAAAACAGGAAGGCAAAATG
CCGCAAAAAAGGGAATAAGGGCGACACGGAAATGTTGAATACTCATACTCTTCCTTTTTCAATATTATTGAAGCATTTATCAGGGTTATTGTC
TCATGAGCGGATACATATTTGAATGTATTTAGAAAAATAAACAAATAGGGGTTCCGCGCACATTTCCCCGAAAAGTGCCACCTGAC
```

FIG. 49D

*lentiCas9-Blast*
Gray        EFS promoter sequence
Yellow      Human codon-optimized SpCas9 coding sequence
*Italics*   FLAG peptide tag
▓▓▓▓        P2A bicistronic linker/self-cleaving peptide
Blue        Blast resistance coding sequence

```
GTCGACGGATCGGGAGATCTCCCGATCCCCTATGGTGCACTCTCAGTACAATCTGCTCTGATGCCGCATAGTTAAGCCAGTATCTGCTCCCTG
CTTGTGTGTTGGAGGTCGCTGAGTAGTGCGCGAGCAAAATTTAAGCTACAACAAGGCAAGGCTTGACCGACAATTGCATGAAGAATCTGCTTA
GGGTTAGGCGTTTTGCGCTGCTTCGCGATGTACGGGCCAGATATACGCGTTGACATTGATTATTGACTAGTTATTAATAGTAATCAATTACGG
GGTCATTAGTTCATAGCCCATATATGGAGTTCCGCGTTACATAACTTACGGTAAATGGCCCGCCTGGCTGACCGCCCAACGACCCCCGCCCAT
TGACGTCAATAATGACGTATGTTCCCATAGTAACGCCAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACGGTAAATGGCCCGCCTGGCATTATGCCCAGTACATGA
CCTTATGGGACTTTCCTACTTGGCAGTACATCTACGTATTAGTCATCGCTATTACCATGGTGATGCGGTTTTGGCAGTACATCAATGGGCGTG
GATAGCGGTTTGACTCACGGGGATTTCCAAGTCTCCACCCCATTGACGTCAATGGGAGTTTGTTTTGGCACCAAAATCAACGGGACTTTCCAA
AATGTCGTAACAACTCCGCCCCATTGACGCAAATGGGCGGTAGGCGTGTACGGTGGGAGGTCTATATAAGCAGCGCGTTTGCCTGTACTGGG
TCTCTCTGGTTAGACCAGATCTGAGCCTGGGAGCTCTCTGGCTAACTAGGGAACCCACTGCTTAAGCCTCAATAAAGCTTGCCTTGAGTGCTT
CAAGTAGTGTGTGCCCGTCTGTTGTGTGACTCTGGTAACTAGAGATCCCTCAGACCCTTTTAGTCAGTGTGGAAAATCTCTAGCAGTGGCGCC
CGAACAGGGACTTGAAAGCGAAAGGGAAACCAGAGGAGCTCTCTCGACGCAGGACTCGGCTTGCTGAAGCGCGCACGGCAAGAGGCGAGGGGC
GGCGACTGGTGAGTACGCCAAAAATTTTGACTAGCGGAGGCTAGAAGGAGAGAGATGGGTGCGAGAGCGTCAGTATTAAGCGGGGGAGAATTA
GATCGCGATGGGAAAAAATTCGGTTAAGGCCAGGGGGAAAGAAAAAATATAAATTAAAACATATAGTATGGGCAAGCAGGGAGCTAGAACGAT
TCGCAGTTAATCCTGGCCTGTTAGAAACATCAGAAGGCTGTAGACAAATACTGGGACAGCTACAACCATCCCTTCAGACAGGATCAGAAGAAC
TTAGATCATTATATAATACAGTAGCAACCCTCTATTGTGTGCATCAAAGGATAGAGATAAAAGACACCAAGGAAGCTTTAGACAAGATAGAGG
AAGAGCAAAACAAAAGTAAGACCACCGCACAGCAAGCGGCCGCTGATCTTCAGACCTGGAGGAGGAGATATGAGGGACAATTGGAGAAGTGAA
TTATATAAATATAAAGTAGTAAAAATTGAACCATTAGGAGTAGCACCCACCAAGGCAAAGAGAAGAGTGGTGCAGAGAGAAAAAAGAGCAGTG
GGAATAGGAGCTTTGTTCCTTGGGTTCTTGGGAGCAGCAGGAAGCACTATGGGCGCAGCGTCAATGACGCTGACGGTACAGGCCAGACAATTA
TTGTCTGGTATAGTGCAGCAGCAGAACAATTTGCTGAGGGCTATTGAGGCGCAACAGCATCTGTTGCAACTCACAGTCTGGGGCATCAAGCAG
CTCCAGGCAAGAATCCTGGCTGTGGAAAGATACCTAAAGGATCAACAGCTCCTGGGGATTTGGGGTTGCTCTGGAAAACTCATTTGCACCACT
GCTGTGCCTTGGAATGCTAGTTGGAGTAATAAATCTCTGGAACAGATTTGGAATCACACGACCTGGATGGAGTGGGACAGAGAAATTAACAAT
TACACAAGCTTAATACACTCCTTAATTGAAGAATCGCAAAACCAGCAAGAAAAGAATGAACAAGAATTATTGGAATTAGATAAATGGGCAAGT
TTGTGGAATTGGTTTAACATAACAAATTGGCTGTGGTATATAAAATTATTCATAATGATAGTAGGAGGCTTGGTAGGTTTAAGAATAGTTTTT
GCTGTACTTTCTATAGTGAATAGAGTTAGGCAGGGATATTCACCATTATCGTTTCAGACCCACCTCCCAACCCCGAGGGGACCCGACAGGCCC
GAAGGAATAGAAGAAGAAGGTGGAGAGAGAGACAGAGACAGATCCATTCGATTAGTGAACGGATCGGCACTGCGTGCGCCAATTCTGCAGACA
AATGGCAGTATTCATCCACAATTTTAAAAGAAAAGGGGGGATTGGGGGGTACAGTGCAGGGGAAAGAATAGTAGACATAATAGCAACAGACAT
ACAAACTAAAGAATTACAAAAACAAATTACAAAAATTCAAAATTTTCGGGTTTATTACAGGGACAGCAGAGATCCAGTTTGGTTAATTAAGCT
AGCTAGGTCTTGAAAGGAGTGGGAATTGGCTCCGGTGCCCGTCAGTGGGCAGAGCGCACATCGCCCACAGTCCCCGAGAAGTTGGGGGGAGGG
GTCGGCAATTGATCCGGTGCCTAGAGAAGGTGGCGCGGGGTAAACTGGGAAAGTGATGTCGTGTACTGGCTCCGCCTTTTTCCCGAGGGTGGG
GGAGAACCGTATATAAGTGCAGTAGTCGCCGTGAACGTTCTTTTTCGCAACGGGTTTGCCGCCAGAACACAGGACCGGTTCTAGAGCGCTGCC
ACCATGGACAAGAAGTACAGCATCGGCCTGGACATCGGCACCAACTCTGTGGGCTGGGCCGTGATCACCGACGAGTACAAGGTGCCCAGCAAG
AAATTCAAGGTGCTGGGCAACACCGACCGGCACAGCATCAAGAAGAACCTGATCGGAGCCCTGCTGTTCGACAGCGGCGAAACAGCCGAGGCC
ACCCGGCTGAAGAGAACCGCCAGAAGAAGATACACCAGACGGAAGAACCGGATCTGCTATCTGCAAGAGATCTTCAGCAACGAGATGGCCAAG
GTGGACGACAGCTTCTTCCACAGACTGGAAGAGTCCTTCCTGGTGGAAGAGGATAAGAAGCACGAGCGGCACCCCATCTTCGGCAACATCGTG
GACGAGGTGGCCTACCACGAGAAGTACCCCACCATCTACCACCTGAGAAAGAAACTGGTGGACAGCACCGACAAGGCCGACCTGCGGCTGATC
TATCTGGCCCTGGCCCACATGATCAAGTTCCGGGGCCACTTCCTGATCGAGGGCGACCTGAACCCCGACAACAGCGACGTGGACAAGCTGTTC
ATCCAGCTGGTGCAGACCTACAACCAGCTGTTCGAGGAAAACCCCATCAACGCCAGCGGCGTGGACGCCAAGGCCATCCTGTCTGCCAGACTG
AGCAAGAGCAGACGGCTGGAAAATCTGATCGCCCAGCTGCCCGGCGAGAAGAAGAATGGCCTGTTCGGAAACCTGATTGCCCTGAGCCTGGGC
CTGACCCCCAACTTCAAGAGCAACTTCGACCTGGCCGAGGATGCCAAACTGCAGCTGAGCAAGGACACCTACGACGACGACCTGGACAACCTG
CTGGCCCAGATCGGCGACCAGTACGCCGACCTGTTTCTGGCCGCCAAGAACCTGTCCGACGCCATCCTGCTGAGCGACATCCTGAGAGTGAAC
```

FIG. 50A

```
ACCGAGATCACCAAGGCCCCCCTGAGCGCCTCTATGATCAAGAGATACGACGAGCACCACCAGGACCTGACCCTGCTGAAAGCTCTCGTGCGG
CAGCAGCTGCCTGAGAAGTACAAAGAGATTTTCTTCGACCAGAGCAAGAACGGCTACGCCGGCTACATTGACGGCGGAGCCAGCCAGGAAGAG
TTCTACAAGTTCATCAAGCCCATCCTGGAAAAGATGGACGGCACCGAGGAACTGCTCGTGAAGCTGAACAGAGAGGACCTGCTGCGGAAGCAG
CGGACCTTCGACAACGGCAGCATCCCCCACCAGATCCACCTGGGAGAGCTGCACGCCATTCTGCGGCGGCAGGAAGATTTTTACCCATTCCTG
AAGGACAACCGGGAAAAGATCGAGAAGATCCTGACCTTCCGCATCCCCTACTACGTGGGCCCTCTGGCCAGGGGAAACAGCAGATTCGCCTGG
ATGACCAGAAAGAGCGAGGAAACCATCACCCCCTGGAACTTCGAGGAAGTGGTGGACAAGGGCGCTTCCGCCCAGAGCTTCATCGAGCGGATG
ACCAACTTCGATAAGAACCTGCCCAACGAGAAGGTGCTGCCCAAGCACAGCCTGCTGTACGAGTACTTCACCGTGTATAACGAGCTGACCAAA
GTGAAATACGTGACCGAGGGAATGAGAAAGCCCGCCTTCCTGAGCGGCGAGCAGAAAAAGGCCATCGTGGACCTGCTGTTCAAGACCAACCGG
AAAGTGACCGTGAAGCAGCTGAAAGAGGACTACTTCAAGAAAATCGAGTGCTTCGACTCCGTGGAAATCTCCGGCGTGGAAGATCGGTTCAAC
GCCTCCCTGGGCACATACCACGATCTGCTGAAAATTATCAAGGACAAGGACTTCCTGGACAATGAGGAAAACGAGGACATTCTGGAAGATATC
GTGCTGACCCTGACACTGTTTGAGGACAGAGAGATGATCGAGGAACGGCTGAAAACCTATGCCCACCTGTTCGACGACAAAGTGATGAAGCAG
CTGAAGCGGCGGAGATACACCGGCTGGGGCAGGCTGAGCCGGAAGCTGATCAACGGCATCCGGGACAAGCAGTCCGGCAAGACAATCCTGGAT
TTCCTGAAGTCCGACGGCTTCGCCAACAGAAACTTCATGCAGCTGATCCACGACGACAGCCTGACCTTTAAAGAGGACATCCAGAAAGCCCAG
GTGTCCGGCCAGGGCGATAGCCTGCACGAGCACATTGCCAATCTGGCCGGCAGCCCCGCCATTAAGAAGGGCATCCTGCAGACAGTGAAGGTG
GTGGACGAGCTCGTGAAAGTGATGGGCCGGCACAAGCCCGAGAACATCGTGATCGAAATGGCCAGAGAGAACCAGACCACCCAGAAGGGACAG
AAGAACAGCCGCGAGAGAATGAAGCGGATCGAAGAGGGCATCAAAGAGCTGGGCAGCCAGATCCTGAAAGAACACCCCGTGGAAAACACCCAG
CTGCAGAACGAGAAGCTGTACCTGTACTACCTGCAGAATGGGCGGGATATGTACGTGGACCAGGAACTGGACATCAACCGGCTGTCCGACTAC
GATGTGGACCATATCGTGCCTCAGAGCTTTCTGAAGGACGACTCCATCGACAACAAGGTGCTGACCAGAAGCGACAAGAACCGGGGCAAGAGC
GACAACGTGCCCTCCGAAGAGGTCGTGAAGAAGATGAAGAACTACTGGCGGCAGCTGCTGAACGCCAAGCTGATTACCCAGAGAAAGTTCGAC
AATCTGACCAAGGCCGAGAGAGGCGGCCTGAGCGAACTGGATAAGGCCGGCTTCATCAAGAGACAGCTGGTGGAAACCCGGCAGATCACAAAG
CACGTGGCACAGATCCTGGACTCCCGGATGAACACTAAGTACGACGAGAATGACAAGCTGATCCGGGAAGTGAAAGTGATCACCCTGAAGTCC
AAGCTGGTGTCCGATTTCCGGAAGGATTTCCAGTTTTACAAAGTGCGCGAGATCAACAACTACCACCACGCCCACGACGCCTACCTGAACGCC
GTCGTGGGAACCGCCCTGATCAAAAAGTACCCTAAGCTGGAAAGCGAGTTCGTGTACGGCGACTACAAGGTGTACGACGTGCGGAAGATGATC
GCCAAGAGCGAGCAGGAAATCGGCAAGGCTACCGCCAAGTACTTCTTCTACAGCAACATCATGAACTTTTTCAAGACCGAGATTACCCTGGCC
AACGGCGAGATCCGGAAGCGGCCTCTGATCGAGACAAACGGCGAAACCGGGGAGATCGTGTGGGATAAGGGCCGGGATTTTGCCACCGTGCGC
AAAGTGCTGAGCATGCCCCAAGTGAATATCGTGAAAAAGACCGAGGTGCAGACAGGCGGCTTCAGCAAAGAGTCTATCCTGCCCAAGAGGAAC
AGCGATAAGCTGATCGCCAGAAAGAAGGACTGGGACCCTAAGAAGTACGGCGGCTTCGACAGCCCCACCGTGGCCTATTCTGTGCTGGTGGTG
GCCAAAGTGGAAAAGGGCAAGTCCAAGAAACTGAAGAGTGTGAAAGAGCTGCTGGGGATCACCATCATGGAAAGAAGCAGCTTCGAGAAGAAT
CCCATCGACTTTCTGGAAGCCAAGGGCTACAAAGAAGTGAAAAAGGACCTGATCATCAAGCTGCCTAAGTACTCCCTGTTCGAGCTGGAAAAC
GGCCGGAAGAGAATGCTGGCCTCTGCCGGCGAACTGCAGAAGGGAAACGAACTGGCCCTGCCCTCCAAATATGTGAACTTCCTGTACCTGGCC
AGCCACTATGAGAAGCTGAAGGGCTCCCCCGAGGATAATGAGCAGAAACAGCTGTTTGTGGAACAGCACAAGCACTACCTGGACGAGATCATC
GAGCAGATCAGCGAGTTCTCCAAGAGAGTGATCCTGGCCGACGCTAATCTGGACAAAGTGCTGTCCGCCTACAACAAGCACCGGGATAAGCCC
ATCAGAGAGCAGGCCGAGAATATCATCCACCTGTTTACCCTGACCAATCTGGGAGCCCCTGCCGCCTTCAAGTACTTTGACACCACCATCGAC
CGGAAGAGGTACACCAGCACCAAAGAGGTGCTGGACGCCACCCTGATCCACCAGAGCATCACCGGCCTGTACGAGACACGGATCGACCTGTCT
CAGCTGGGAGGCGACAAGCGACCTGCCGCCACAAAGAAGGCTGGACAGGCTAAGAAGAAGAAA*GATTACAAAGACGATGACGATAAG*GGTTCT
GGCAACAAACTGGTTTTGTCTGAAAACAAGCGAAATGTGAAGAGAATGTGAAGATAATGGAATGTGGAGACATGGCCAAGCCTTTGTCTCAAGAAGAATCCACC
CTCATTGAAAGAGCAACGGCTACAATCAACAGCATCCCCATCTCTGAAGACTACAGCGTCGCCAGCGCAGCTCTCTAGCGACGGCCGCATC
TTCACTGGTGTCAATGTATATCATTTTACTGGGGGACCTTGTGCAGAACTCGTGGTGCTGGGCACTGCTGCTGCTGCGGCAGCTGGCAACCTG
ACTTGTATCGTCGCGATCGGAAATGAGAACAGGGGCATCTTGAGCCCTGCGGACGGTGCCGACAGGTGCTTCTCGATCTGCATCCTGGGATC
AAAGCCATAGTGAAGGACAGTGATGGACAGCCGACGGCAGTTGGGATTCGTGAATTGCTGCCCTCTGGTTATGTGTGGGAGGGCTAAGAATTC
GATATCAAGCTTATCGATAATCAACCTCTGGATTACAAAATTTGTGAAAGATTGACTGGTATTCTTAACTATGTTGCTCCTTTTACGCTATGT
GGATACGCTGCTTTAATGCCTTTGTATCATGCTATTGCTTCCCGTATGGCTTTCATTTTCTCCTCCTTGTATAAATCCTGGTTGCTGTCTCTT
TATGAGGAGTTGTGGCCCGTTGTCAGGCAACGTGGCGTGGTGTGCACTGTGTTTGCTGACGCAACCCCCACTGGTTGGGGCATTGCCACCACC
TGTCAGCTCCTTTCCGGGACTTTCGCTTTCCCCCTCCCTATTGCCACGGCGGAACTCATCGCCGCCTGCCTTGCCCGCTGCTGGACAGGGGCT
CGGCTGTTGGGCACTGACAATTCCGTGGTGTTGTCGGGGAAATCATCGTCCTTTCCTTGGCTGCTCGCCTGTGTTGCCACCTGGATTCTGCGC
GGGACGTCCTTCTGCTACGTCCCTTCGGCCCTCAATCCAGCGGACCTTCCTTCCCGCGGCCTGCTGCCGGCTCTGCGGCCTCTTCCGCGTCTT
CGCCTTCGCCCTCAGACGAGTCGGATCTCCCTTTGGGCCGCCTCCCCGCATCGATACCGTCGACCTCGAGACCTAGAAAAACATGGAGCAATC
ACAAGTAGCAATACAGCAGCTACCAATGCTGATTGTGCCTGGCTAGAAGCACAAGAGGAGGAGGAGGTGGGTTTTCCAGTCACACCTCAGGTA
CCTTTAAGACCAATGACTTACAAGGCAGCTGTAGATCTTAGCCACTTTTTAAAAGAAAAGGGGGGACTGGAAGGGCTAATTCACTCCCAACGA
```

```
AGACAAGATATCCTTGATCTGTGGATCTACCACACACAAGGCTACTTCCCTGATTGGCAGAACTACACACCAGGGCCAGGGATCAGATATCCA
CTGACCTTTGGATGGTGCTACAAGCTAGTACCAGTTGAGCAAGAGAAGGTAGAAGAAGCCAATGAAGGAGAGAACACCCGCTTGTTACACCCT
GTGAGCCTGCATGGGATGGATGACCCGGAGAGAGAAGTATTAGAGTGGAGGTTTGACAGCCGCCTAGCATTTCATCACATGGCCCGAGAGCTG
CATCCGGACTGTACTGGGTCTCTCTGGTTAGACCAGATCTGAGCCTGGGAGCTCTCTGGCTAACTAGGGAACCCACTGCTTAAGCCTCAATAA
AGCTTGCCTTGAGTGCTTCAAGTAGTGTGTGCCCGTCTGTTGTGTGACTCTGGTAACTAGAGATCCCTCAGACCCTTTTAGTCAGTGTGGAAA
ATCTCTAGCAGGGCCCGTTTAAACCCGCTGATCAGCCTCGACTGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGAAATTGCATCGCATTGTCTGAGTAGGTGTCATTCTATTCTGGG
GGGTGGGGTGGGGCAGGACAGCAAGGGGGAGGATTGGGAAGACAATAGCAGGCATGCTGGGGATGCGGTGGGCTCTATGGCTTCTGAGGCGGA
AAGAACCAGCTGGGGCTCTAGGGGGTATCCCCACGCGCCCTGTAGCGGCGCATTAAGCGCGGCGGGTGTGGTGGTTACGCGCAGCGTGACCGC
TACACTTGCCAGCGCCCTAGCGCCCGCTCCTTTCGCTTTCTTCCCTTCCTTTCTCGCCACGTTGGCCGGCTTTCCCCGTCAAGCTCTAAATCG
GGGGCTCCCTTTAGGGTTCCGATTTAGTGCTTTACGGCACCTCGACCCCAAAAAACTTGATTAGGGTGATGGTTCACGTAGTGGGCCATCGCC
CTGATAGACGGTTTTTCGCCCTTTGACGTTGGAGTCCACGTTCTTTAATAGTGGACTCTTGTTCCAAACTGGAACAACACTCAACCCTATCTC
GGTCTATTCTTTTGATTTATAAGGGATTTTGCCGATTTCGGCCTATTGGTTAAAAAATGAGCTGATTTAACAAAAATTTAACGCGAATTAATT
CTGTGGAATGTGTGTCAGTTAGGGTGTGGAAAGTCCCCAGGCTCCCCAGCAGGCAGAAGTATGCAAAGCATGCATCTCAATTAGTCAGCAACC
AGGTGTGGAAAGTCCCCAGGCTCCCCAGCAGGCAGAAGTATGCAAAGCATGCATCTCAATTAGTCAGCAACCATAGTCCCGCCCCTAACTCCG
CCCATCCCGCCCCTAACTCCGCCCAGTTCCGCCCATTCTCCGCCCCATGGCTGACTAATTTTTTTTATTTATGCAGAGGCCGAGGCCGCCTCT
GCCTCTGAGCTATTCCAGAAGTAGTGAGGAGGCTTTTTTGGAGGCCTAGGCTTTTGCAAAAAGCTCCCGGGAGCTTGTATATCCATTTTCGGA
TCTGATCAGCACGTGTTGACAATTAATCATCGGCATAGTATATCGGCATAGTATAATACGACAAGGTGAGGAACTAAACCATGGCCAAGTTGA
CCAGTGCCGTTCCGGTGCTCACCGCGCGCGACGTCGCCGGAGCGGTCGAGTTCTGGACCGACCGGCTCGGGTTCTCCCGGGACTTCGTGGAGG
ACGACTTCGCCGGTGTGGTCCGGGACGACGTGACCCTGTTCATCAGCGCGGTCCAGGACCAGGTGGTGCCGGACAACACCCTGGCCTGGGTGT
GGGTGCGCGGCCTGGACGAGCTGTACGCCGAGTGGTCGGAGGTCGTGTCCACGAACTTCCGGGACGCCTCCGGGCCGGCCATGACCGAGATCG
GCGAGCAGCCGTGGGGGCGGGAGTTCGCCCTGCGCGACCCGGCCGGCAACTGCGTGCACTTCGTGGCCGAGGAGCAGGACTGACACGTGCTAC
GAGATTTCGATTCCACCGCCGCCTTCTATGAAAGGTTGGGCTTCGGAATCGTTTTCCGGGACGCCGGCTGGATGATCCTCCAGCGCGGGGATC
TCATGCTGGAGTTCTTCGCCCACCCCAACTTGTTTATTGCAGCTTATAATGGTTACAAATAAAGCAATAGCATCACAAATTTCACAAATAAAG
CATTTTTTTCACTGCATTCTAGTTGTGGTTTGTCCAAACTCATCAATGTATCTTATCATGTCTGTATACCGTCGACCTCTAGCTAGAGCTTGG
CGTAATCATGGTCATAGCTGTTTCCTGTGTGAAATTGTTATCCGCTCACAATTCCACACAACATACGAGCCGGAAGCATAAAGTGTAAAGCCT
GGGGTGCCTAATGAGTGAGCTAACTCACATTAATTGCGTTGCGCTCACTGCCCGCTTTCCAGTCGGGAAACCTGTCGTGCCAGCTGCATTAAT
GAATCGGCCAACGCGCGGGGAGAGGCGGTTTGCGTATTGGGCGCTCTTCCGCTTCCTCGCTCACTGACTCGCTGCGCTCGGTCGTTCGGCTGC
GGCGAGCGGTATCAGCTCACTCAAAGGCGGTAATACGGTTATCCACAGAATCAGGGGATAACGCAGGAAAGAACATGTGAGCAAAAGGCCAGC
AAAAGGCCAGGAACCGTAAAAAGGCCGCGTTGCTGGCGTTTTTCCATAGGCTCCGCCCCCCTGACGAGCATCACAAAAATCGACGCTCAAGTC
AGAGGTGGCGAAACCCGACAGGACTATAAAGATACCAGGCGTTTCCCCCTGGAAGCTCCCTCGTGCGCTCTCCTGTTCCGACCCTGCCGCTTA
CCGGATACCTGTCCGCCTTTCTCCCTTCGGGAAGCGTGGCGCTTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCAGTTACCTTCGGAAAAAGAGTTGGTAGCTCTTGATCCGGCAAAC
AAACCACCGCTGGTAGCGGTGGTTTTTTTGTTTGCAAGCAGCAGATTACGCGCAGAAAAAAAGGATCTCAAGAAGATCCTTTGATCTTTTCTA
CGGGGTCTGACGCTCAGTGGAACGAAAACTCACGTTAAGGGATTTTGGTCATGAGATTATCAAAAAGGATCTTCACCTAGATCCTTTTAAATT
AAAAATGAAGTTTTAAATCAATCTAAAGTATATATGAGTAAACTTGGTCTGACAGTTACCAATGCTTAATCAGTGAGGCACCTATCTCAGCGA
TCTGTCTATTTCGTTCATCCATAGTTGCCTGACTCCCCGTCGTGTAGATAACTACGATACGGGAGGGCTTACCATCTGGCCCCAGTGCTGCAA
TGATACCGCGAGACCCACGCTCACCGGCTCCAGATTTATCAGCAATAAACCAGCCAGCCGGAAGGGCCGAGCGCAGAAGTGGTCCTGCAACTT
TATCCGCCTCCATCCAGTCTATTAATTGTTGCCGGGAAGCTAGAGTAAGTAGTTCGCCAGTTAATAGTTTGCGCAACGTTGTTGCCATTGCTA
CAGGCATCGTGGTGTCACGCTCGTCGTTTGGTATGGCTTCATTCAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAGTTGGCCGCAGTGTTATCACTCATGGTTATGGCAGCACTGCATA
ATTCTCTTACTGTCATGCCATCCGTAAGATGCTTTTCTGTGACTGGTGAGTACTCAACCAAGTCATTCTGAGAATAGTGTATGCGGCGACCGA
GTTGCTCTTGCCCGGCGTCAATACGGGATAATACCGCGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCACCCAACTGATCTTCAGCATCTTTTACTTTCACCAGCG
TTTCTGGGTGAGCAAAAACAGGAAGGCAAAATGCCGCAAAAAAGGGAATAAGGGCGACACGGAAATGTTGAATACTCATACTCTTCCTTTTTC
AATATTATTGAAGCATTTATCAGGGTTATTGTCTCATGAGCGGATACATATTTGAATGTATTTAGAAAAATAAACAAATAGGGGTTCCGCGCA
CATTTCCCCGAAAAGTGCCACCTGAC
```

FIG. 50C

*lentiGuide-Puro*

| | |
|---|---|
| ▓▓ | BsmBI TypeIIs sites for cloning in 20bp sgRNA guide sequence after removing 1.8kb spacer sequence |
| Green | +85 chRNA sequence for sgRNA |
| Gray | EF1a promoter sequence |
| Blue | Puromycin resistance coding sequence |

```
CCCGGGTGCAAAGATGGATAAAGTTTTAAACAGAGAGGAATCTTTGCAGCTAATGGACCTTCTAGGTCTTGAAAGGAGTGGGAATTGGCTCCG
GTGCCCGTCAGTGGGCAGAGCGCACATCGCCCACAGTCCCCGAGAAGTTGGGGGAGGGGTCGGCAATTGATCCGGTGCCTAGAGAAGGTGGC
GCGGGGTAAACTGGGAAAGTGATGTCGTGTACTGGCTCCGCCTTTTTCCCGAGGGTGGGGGAGAACCGTATATAAGTGCAGTAGTCGCCGTGA
ACGTTCTTTTTCGCAACGGGTTTGCCGCCAGAACACAGGTAAGTGCCGTGTGTGGTTCCCGCGGGCCTGGCCTCTTTACGGGTTATGGCCCTT
GCGTGCCTTGAATTACTTCCACTGGCTGCAGTACGTGATTCTTGATCCCGAGCTTCGGGTTGGAAGTGGGTGGGAGAGTTCGAGGCCTTGCGC
TTAAGGAGCCCCTTCGCCTCGTGCTTGAGTTGAGGCCTGGCCTGGGCGCTGGGGCCGCCGCGTGCGAATCTGGTGGCACCTTCGCGCCTGTCT
CGCTGCTTTCGATAAGTCTCTAGCCATTTAAAATTTTTGATGACCTGCTGCGACGCTTTTTTTCTGGCAAGATAGTCTTGTAAATGCGGGCCA
AGATCTGCACACTGGTATTTCGGTTTTTGGGGCCGCGGGCGGCGACGGGGCCCGTGCGTCCCAGCGCACATGTTCGGCGAGGCGGGGCCTGCG
AGCGCGGCCACCGAGAATCGGACGGGGGTAGTCTCAAGCTGGCCGGCCTGCTCTGGTGCCTGGCCTCGCGCCGCCGTGTATCGCCCCGCCCTG
GGCGGCAAGGCTGGCCCGGTCGGCACCAGTTGCGTGAGCGGAAAGATGGCCCGCTTCCCGGCCCTGCTGCAGGGAGCTCAAAATGGAGGACGCG
GCGCTCGGGAGAGCGGGCGGGTGAGTCACCCACACAAAGGAAAAGGGCCTTTCCGTCCTCAGCCGTCGCTTCATGTGACTCCACGGAGTACCG
GGCGCCGTCCAGGCACCTCGATTAGTTCTCGAGCTTTTGGAGTACGTCGTCTTTAGGTTGGGGGGAGGGGTTTTATGCGATGGAGTTTCCCCA
CACTGAGTGGGTGGAGACTGAAGTTAGGCCAGCTTGGCACTTGATGTAATTCTCCTTGGAATTTGCCCTTTTTGAGTTTGGATCTTGGTTCAT
TCTCAAGCCTCAGACAGTGGTTCAAAGTTTTTTTCTTCCATTTCAGGTGTCGTGACGTACGGCCACCATGACCGAGTACAAGCCCACGGTGCG
CCTCGCCACCCGCGACGACGTCCCCAGGGCCGTACGCACCCTCGCCGCCGCGTTCGCCGACTACCCCGCCACGCGCCACACCGTCGATCCGGA
CCGCCACATCGAGCGGGTCACCGAGCTGCAAGAACTCTTCCTCACGCGCGTCGGGCTCGACATCGGCAAGGTGTGGGTCGCGGACGACGGCGC
CGCCGTGGCGGTCTGGACCACGCCGGAGAGCGTCGAAGCGGGGCGGTGTTCGCCGAGATCGGCCCGCGCATGGCCGAGTTGAGCGGTTCCCG
GCTGGCCGCGCAGCAACAGATGGAAGGCCTCCTGGCGCCGCACCGGCCCAAGGAGCCCGCGTGGTTCCTGGCCACCGTCGGAGTCTCGCCCGA
CCACCAGGGCAAGGGTCTGGGCAGCGCCGTCGTGCTCCCCGGAGTGGAGGCGGCCGAGCGCGCCGGGGTGCCCGCCTTCCTGGAGACCTCCGC
GCCCCGCAACCTCCCCTTCTACGAGCGGCTCGGCTTCACCGTCACCGCCGACGTCGAGGTGCCCGAAGGACCGCGCACCTGGTGCATGACCCG
CAAGCCCGGTGCCTGAACGCGTTAAGTCGACAATCAACCTCTGGATTACAAAATTTGTGAAAGATTGACTGGTATTCTTAACTATGTTGCTCC
TTTTACGCTATGTGGATACGCTGCTTTAATGCCTTTGTATCATGCTATTGCTTCCCGTATGGCTTTCATTTTCTCCTCCTTGTATAAATCCTG
GTTGCTGTCTCTTTATGAGGAGTTGTGGCCCGTTGTCAGGCAACGTGGCGTGGTGTGCACTGTGTTTGCTGACGCAACCCCCACTGGTTGGGG
CATTGCCACCACCTGTCAGCTCCTTTCCGGGACTTTCGCTTTCCCCCTCCCTATTGCCACGGCGGAACTCATCGCCGCCTGCCTTGCCCGCTG
CTGGACAGGGGCTCGGCTGTTGGGCACTGACAATTCCGTGGTGTTGTCGGGGAAATCATCGTCCTTTCCTTGGCTGCTCGCCTGTGTTGCCAC
CTGGATTCTGCGCGGGACGTCCTTCTGCTACGTCCCTTCGGCCCTCAATCCAGCGGACCTTCCTTCCCGCGGCCTGCTGCCGGCTCTGCGGCC
TCTTCCGCGTCTTCGCCTTCGCCCTCAGACGAGTCGGATCTCCCTTTGGGCCGCCTCCCCGCGTCGACTTTAAGACCAATGACTTACAAGGCA
GCTGTAGATCTTAGCCACTTTTTAAAAGAAAAGGGGGGACTGGAAGGGCTAATTCACTCCCAACGAAGACAAGATCTGCTTTTTGCTTGTACT
GGGTCTCTCTGGTTAGACCAGATCTGAGCCTGGGAGCTCTCTGGCTAACTAGGGAACCCACTGCTTAAGCCTCAATAAAGCTTGCCTTGAGTG
CTTCAAGTAGTGTGTGCCCGTCTGTTGTGTGACTCTGGTAACTAGAGATCCCTCAGACCCTTTTAGTCAGTGTGGAAAATCTCTAGCAGTACG
TATAGTAGTTCATGTCATCTTATTATTCAGTATTTATAACTTGCAAAGAAATGAATATCAGAGAGTGAGAGGAACTTGTTTATTGCAGCTTAT
AATGGTTACAAATAAAGCAATAGCATCACAAATTTCACAAATAAAGCATTTTTTTCACTGCATTCTAGTTGTGGTTTGTCCAAACTCATCAAT
GTATCTTATCATGTCTGGCTCTAGCTATCCCGCCCCTAACTCCGCCCATCCCGCCCCTAACTCCGCCCAGTTCCGCCCATTCTCCGCCCCATG
GCTGACTAATTTTTTTATTTATGCAGAGGCCGAGGCCGCCTCGGCCTCTGAGCTATTCCAGAAGTAGTGAGGAGGCTTTTTTGGAGGCCTAG
GGACGTACCCAATTCGCCCTATAGTGAGTCGTATTACGCGCGCTCACTGGCCGTCGTTTTACAACGTCGTGACTGGGAAAACCCTGGCGTTAC
CCAACTTAATCGCCTTGCAGCACATCCCCCTTTCGCCAGCTGGCGTAATAGCGAAGAGGCCCGCACCGATCGCCCTTCCCAACAGTTGCGCAG
CCTGAATGGCGAATGGGACGCGCCCTGTAGCGGCGCATTAAGCGCGGCGGGTGTGGTGGTTACGCGCAGCGTGACCGCTACACTTGCCAGCGC
CCTAGCGCCCGCTCCTTTCGCTTTCTTCCCTTCCTTTCTCGCCACGTTCGCCGGCTTTCCCCGTCAAGCTCTAAATCGGGGGCTCCCTTTAGG
GTTCCGATTTAGTGCTTTACGGCACCTCGACCCCAAAAAACTTGATTAGGGTGATGGTTCACGTAGTGGGCCATCGCCCTGATAGACGGTTTT
TCGCCCTTTGACGTTGGAGTCCACGTTCTTTAATAGTGGACTCTTGTTCCAAACTGGAACAACACTCAACCCTATCTCGGTCTATTCTTTTGA
TTTATAAGGGATTTTGCCGATTTCGGCCTATTGGTTAAAAAATGAGCTGATTTAACAAAAATTTAACGCGAATTTTAACAAAATATTAACGCT
```

FIG. 51A

```
TACAATTTAGGTGGCACTTTTCGGGGAAATGTGCGCGGAACCCCTATTTGTTTATTTTTCTAAATACATTCAAATATGTATCCGCTCATGAGA
CAATAACCCTGATAAATGCTTCAATAATATTGAAAAAGGAAGAGTATGAGTATTCAACATTTCCGTGTCGCCCTTATTCCCTTTTTTGCGGCA
TTTTGCCTTCCTGTTTTTGCTCACCCAGAAACGCTGGTGAAAGTAAAAGATGCTGAAGATCAGTTGGGTGCACGAGTGGGTTACATCGAACTG
GATCTCAACAGCGGTAAGATCCTTGAGAGTTTTCGCCCCGAAGAACGTTTTCCAATGATGAGCACTTTTAAAGTTCTGCTATGTGGCGCGGTA
TTATCCCGTATTGACGCCGGGCAAGAGCAACTCGGTCGCCGCATACACTATTCTCAGAATGACTTGGTTGAGTACTCACCAGTCACAGAAAAG
CATCTTACGGATGGCATGACAGTAAGAGAATTATGCAGTGCTGCCATAACCATGAGTGATAACACTGCGGCCAACTTACTTCTGACAACGATC
GGAGGACCGAAGGAGCTAACCGCTTTTTTGCACAACATGGGGGATCATGTAACTCGCCTTGATCGTTGGGAACCGGAGCTGAATGAAGCCATA
CCAAACGACGAGCGTGACACCACGATGCCTGTAGCAATGGCAACAACGTTGCGCAAACTATTAACTGGCGAACTACTTACTCTAGCTTCCCGG
CAACAATTAATAGACTGGATGGAGGCGGATAAAGTTGCAGGACCACTTCTGCGCTCGGCCCTTCCGGCTGGCTGGTTTATTGCTGATAAATCT
GGAGCCGGTGAGCGTGGGTCTCGCGGTATCATTGCAGCACTGGGGCCAGATGGTAAGCCCTCCCGTATCGTAGTTATCTACACGACGGGGAGT
CAGGCAACTATGGATGAACGAAATAGACAGATCGCTGAGATAGGTGCCTCACTGATTAAGCATTGGTAACTGTCAGACCAAGTTTACTCATAT
ATACTTTAGATTGATTTAAAACTTCATTTTTAATTTAAAAGGATCTAGGTGAAGATCCTTTTTGATAATCTCATGACCAAAATCCCTTAACGT
GAGTTTTCGTTCCACTGAGCGTCAGACCCCGTAGAAAAGATCAAAGGATCTTCTTGAGATCCTTTTTTTCTGCGCGTAATCTGCTGCTTGCAA
ACAAAAAAACCACCGCTACCAGCGGTGGTTTGTTTGCCGGATCAAGAGCTACCAACTCTTTTTCCGAAGGTAACTGGCTTCAGCAGAGCGCAG
ATACCAAATACTGTTCTTCTAGTGTAGCCGTAGTTAGGCCACCACTTCAAGAACTCTGTAGCACCGCCTACATACCTCGCTCTGCTAATCCTG
TTACCAGTGGCTGCTGCCAGTGGCGATAAGTCGTGTCTTACCGGGTTGGACTCAAGACGATAGTTACCGGATAAGGCGCAGCGGTCGGGCTGA
ACGGGGGGTTCGTGCACACAGCCCAGCTTGGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGAGGGAGCTTCCAGGGGGAAACGCCTGGTAT
CTTTATAGTCCTGTCGGGTTTCGCCACCTCTGACTTGAGCGTCGATTTTTGTGATGCTCGTCAGGGGGCGGAGCCTATGGAAAAACGCCAGC
AACGCGGCCTTTTTACGGTTCCTGGCCTTTTGCTGGCCTTTTGCTCACATGTTCTTTCCTGCGTTATCCCCTGATTCTGTGGATAACCGTATT
ACCGCCTTTGAGTGAGCTGATACCGCTCGCCGCAGCCGAACGACCGAGCGCAGCGAGTCAGTGAGCGAGGAAGCGGAAGAGCGCCCAATACGC
AAACCGCCTCTCCCCGCGCGTTGGCCGATTCATTAATGCAGCTGGCACGACAGGTTTCCCGACTGGAAAGCGGGCAGTGAGCGCAACGCAATT
AATGTGAGTTAGCTCACTCATTAGGCACCCCAGGCTTTACACTTTATGCTTCCGGCTCGTATGTTGTGTGGAATTGTGAGCGGATAACAATTT
CACACAGGAAACAGCTATGACCATGATTACGCCAAGCGCGCAATTAACCCTCACTAAAGGGAACAAAAGCTGGAGCTGCAAGCTTAATGTAGT
CTTATGCAATACTCTTGTAGTCTTGCAACATGGTAACGATGAGTTAGCAACATGCCTTACAAGGAGAGAAAAAGCACCGTGCATGCCGATTGG
TGGAAGTAAGGTGGTACGATCGTGCCTTATTAGGAAGGCAACAGACGGGTCTGACATGGATTGGACGAACCACTGAATTGCCGCATTGCAGAG
ATATTGTATTTAAGTGCCTAGCTCGATACATAAACGGGTCTCTCTGGTTAGACCAGATCTGAGCCTGGGAGCTCTCTGGCTAACTAGGGAACC
CACTGCTTAAGCCTCAATAAAGCTTGCCTTGAGTGCTTCAAGTAGTGTGTGCCCGTCTGTTGTGTGACTCTGGTAACTAGAGATCCCTCAGAC
CCTTTTAGTCAGTGTGGAAAATCTCTAGCAGTGGCGCCCGAACAGGGACTTGAAAGCGAAAGGGAAACCAGAGGAGCTCTCTCGACGCAGGAC
TCGGCTTGCTGAAGCGCGCACGGCAAGAGGCGAGGGGCGGCGACTGGTGAGTACGCCAAAAATTTTGACTAGCGGAGGCTAGAAGGAGAGAGA
TGGGTGCGAGAGCGTCAGTATTAAGCGGGGGAGAATTAGATCGCGATGGGAAAAAATTCGGTTAAGGCCAGGGGGAAAGAAAAAATATAAATT
AAAACATATAGTATGGGCAAGCAGGGAGCTAGAACGATTCGCAGTTAATCCTGGCCTGTTAGAAACATCAGAAGGCTGTAGACAAATACTGGG
ACAGCTACAACCATCCCTTCAGACAGGATCAGAAGAACTTAGATCATTATATAATACAGTAGCAACCCTCTATTGTGTGCATCAAAGGATAGA
GATAAAAGACACCAAGGAAGCTTTAGACAAGATAGAGGAAGAGCAAAACAAAAGTAAGACCACCGCACAGCAAGCGGCCGCTGATCTTCAGAC
CTGGAGGAGGAGATATGAGGGACAATTGGAGAAGTGAATTATATAAATATAAAGTAGTAAAAATTGAACCATTAGGAGTAGCACCCACCAAGG
CAAAGAGAAGAGTGGTGCAGAGAGAAAAAAGAGCAGTGGGAATAGGAGCTTTGTTCCTTGGGTTCTTGGGAGCAGCAGGAAGCACTATGGGCG
CAGCGTCAATGACGCTGACGGTACAGGCCAGACAATTATTGTCTGGTATAGTGCAGCAGCAGAACAATTTGCTGAGGGCTATTGAGGCGCAAC
AGCATCTGTTGCAACTCACAGTCTGGGGCATCAAGCAGCTCCAGGCAAGAATCCTGGCTGTGGAAAGATACCTAAAGGATCAACAGCTCCTGG
GGATTTGGGGTTGCTCTGGAAAACTCATTTGCACCACTGCTGTGCCTTGGAATGCTAGTTGGAGTAATAAATCTCTGGAACAGATTTGGAATC
ACACGACCTGGATGGAGTGGGACAGAGAAATTAACAATTACACAAGCTTAATACACTCCTTAATTGAAGAATCGCAAAACCAGCAAGAAAAGA
ATGAACAAGAATTATTGGAATTAGATAAATGGGCAAGTTTGTGGAATTGGTTTAACATAACAAATTGGCTGTGGTATATAAAATTATTCATAA
TGATAGTAGGAGGCTTGGTAGGTTTAAGAATAGTTTTTGCTGTACTTTCTATAGTGAATAGAGTTAGGCAGGGATATTCACCATTATCGTTTC
AGACCCACCTCCCAACCCCGAGGGGACCCAGAGAGGGCCTATTTCCCATGATTCCTTCATATTTGCATATACGATACAAGGCTGTTAGAGAGA
TAATTAGAATTAATTTGACTGTAAACACAAAGATATTAGTACAAAATACGTGACGTAGAAAGTAATAATTTCTTGGGTAGTTTGCAGTTTTAA
AATTATGTTTTAAAATGGACTATCATATGCTTACCGTAACTTGAAAGTATTTCGATTTCTTGGCTTTATATATCTTGTGGAAAGGACGAAACA
CCG░░░░░TTGTAAATGAGCACACAAAATACACATGCTAAAATATTATATTCTATGACCTTTATAAAATCAACCAAAATCTTCTTTTTAAT
AACTTTAGTATCAATAATTAGAATTTTTATGTTCCTTTTTGCAAACTTTTAATAAAAATGAGCAAAATAAAAAAACGGCTAGTTTTAGTAACTC
GCGTTGTTTTCTTCACCTTTAATAATAGCTACTCCACCACTTGTTCCTAAGCGGTCAGCTCCTGCTTCAATCATTTTTTGAGCATCTTCAAAT
GTTCTAACTCCACCAGCTGCTTTAACTAAAGCATTGTCTTTAACAACTGACTTCATTAGTTTAACATCTTCAAATGTTGCACCTGATTTTGAA
```

FIG. 51B

```
AATCCTGTTGATGTTTTAACAAATTCTAATCCAGCTTCAACAGCTATTTCACAAGCTTTCATGATTTCTTCTTTTGTTAATAAACAATTTTCC
ATAATACATTTAACAACATGTGATCCAGCTGCTTTTTTTACAGCTTTCATGTCTTCTAAAACTAATTCATAATTTTTGTCTTTTAATGCACCA
ATATTTAATACCATATCAATTTCTGTTGCACCATCTTTAATTGCTTCAGAAACTTCGAATGCTTTTGTAGCTGTTGTGCATGCACCTAGAGGA
AAACCTACAACATTTGTTATTCCTACATTTGTGCCTTTTAATAATTCTTTACAATAGCTTGTTCAATATGAATTAACACAAACTGTTGCAAAA
TCAAATTCAATTGCTTCATCACATAATTGTTTAATTTCAGCTTTCGTAGCATCTTGTTTTAATAATGTGTGATCTATATATTTGTTTAGTTTC
ATTTTTTCTCCTATATATTCATTTTTAATTTTAATTCTTTAATAATTTCGTCTACTTTAACTTTAGCGTTTTGAACAGATTCACCAACACCTA
TAAAATAAATTTTTAGTTTAGGTTCAGTTCCACTTGGGCGAACAGCAAATCATGACTTATCTTCTAAATAAAATTTTAGTAAGTCTTGTCCTG
GCATATTATACATTCCATCGATGTAGTCTTCAACATTAACAACTTTAAGTCCAGCAATTTGAGTTAAGGGTGTTGCTCTCAATGATTTCATTA
ATGGTTCAATTTTTAATTTCTTTTCTTCTGGTTTAAAATTCAAGTTTAAAGTGAAAGTGTAATATGCACCCATTTCTTTAAATAAATCTTCTA
AATAGTCTACTAATGTTTTATTTTGTTTTTTATAAAATCAAGCAGCCTCTGCTATTAATATAGAAGCTTGTATTCCATCTTTATCTCTAGCTG
AGTCATCAATTACATATCCATAACTTTCTTCATAAGCAAAACAAAATTTAATCCGTTATCTTCTTCTTAGCAATTTCTCTACCCATTCATT
TAAATCCAGTTAAAGTTTTTACAATATTAACTCCATATTTTTCATGAGCGATTCTATCACCCAAATCACTTGTTACAAAACTTGAATATAGAG
CCGGATTTTTTGGAATGCTATTTAAGCGTTTTAGATTTGATAATTTTCAATCAATTAAAATTGGTCCTGTTTGATTTCCATCTAATCTTACAA
AATGACCATCATGTTTTATTGCCATTCCAAATCTGTCAGCATCTGGGTCATTCATAATAATAATATCTGCATCATGTTTAATACCATATTCAA
GCGGTATTTTTCATGCAGGATCAAATTCTGGATTTGGATTTACAACATTTTTAAATGTTTCATCTTCAAATGCATGCTCTTCAACCTCAATAA
CGTTATATCCTGATTCACGTAATATTTTTGGGGTAAATTTAGTTCCTGTTCCATTAACTGCGCTAAAAATAATTTTTAAATCTTTTTTAGCTT
CTTGCTCTTTTTTGTANNNNTGTTTTAGAGCTAGAAATAGCAAGTTAAAATAAGGCTAGTCCGTTATCAACTTGAAAAAGTGGCACCGAGT
NNNNNTTTTTTAAGCTTGGCGTAACTAGATCTTGAGACAAATGGCAGTATTCATCCACAATTTTAAAAGAAAAGGGGGGATTGGGGGGTACA
GTGCAGGGGAAAGAATAGTAGACATAATAGCAACAGACATACAAACTAAAGAATTACAAAAACAAATTACAAAAATTCAAAATTTTCGGGTTT
ATTACAGGGACAGCAGAGATCCACTTTGGCGCCGGCTCGAGGGGG
```

FIG. 51C ns 61/960,777 and 61/995,636, namely, Deposit Nos: PTA-121339, PTA-121340, PTA-121341, PTA-121342, PTA-121343, deposited on Jun. 10, 2014, with the American Type Culture Collection on American Type Culture Collection (ATCC), 10801 University Boulevard, Manassas, Va. 20110 USA, under and pursuant to the terms of the Budapest Treaty. Upon issuance of a patent, all restrictions upon the Deposit(s) will be irrevocably removed, and the Deposit(s) is/are intended to meet the requirements of 37 CFR §§ 1.801-1.809. The Deposit(s) will be maintained in the depository for a period of 30 years, or 5 years after the last request, or for the effective, enforceable life of the patent, whichever is longer, and will be replaced if necessary during that period; and the requirements of 37 CFR §§ 1.801-1.809 are are met.

FUNCTIONAL GENOMICS USING CRISPR-CAS SYSTEMS, COMPOSITIONS, METHODS, SCREENS AND APPLICATIONS THEREOF

RELATED APPLICATIONS AND INCORPORATION BY REFERENCE

This application is a continuation-in-part of International Application No. PCT/US14/041806, filed on Jun. 10, 2014, which claims priority to U.S. provisional patent applications 61/836,123, 61/960,777 and 61/995,636, filed on Jun. 17, 2013, Sep. 25, 2013 and Apr. 15, 2014 respectively, each incorporated herein by reference. This application is also a continuation of International Application No. PCT/US13/74800, filed Dec. 12, 2013. For purposes of the United States, this application also can be a continuation-in-part of PCT/US13/74800, filed Dec. 12, 2013; and Applicants reserve as permitted under US law to claim in the United States any right or benefit to U.S. provisional application 61/802,174, filed Mar. 15, 2013 and/or 61/736,527, filed Dec. 12, 2012, which are in the lineage of PCT/US13/74800, filed Dec. 12, 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

The foregoing patent applications, from which this application claims priority, expressly refers to a lengthy table section. Copies of the Tables have been submitted in triplicate in compact disc form (i.e., "Copy 1," "Copy 2" and "Copy 3") with the USPTO on Apr. 15, 2014 in connection with the filing of U.S. provisional application 61/995,636 and are hereby incorporated herein by reference in their entirety, and may be employed in the practice of the invention. Each compact disc (CD), created Apr. 11, 2014, contains the following files:

Table 1_hKO 65K sgRNAs with off-target scores.txt, 3,883,008 bytes
Table 2A_Human GeCKOv2 controls.txt, 53,248 bytes
Table 2B_Human GeCKOv2 controls.txt, 77,824 bytes
Table 3_Human GeCKOv2 exons A.txt, 8,069,120 bytes
Table 4_Human GeCKOv2 exons B.txt, 8,081,408 bytes
Table 5_Human GeCKOv2 miRNAs.txt, 331,776 bytes
Table 6_Mouse GeCKOv2 controls.txt, 610,304 bytes
Table 7_Mouse GeCKOv2 exons A.txt, 8,650,752 bytes
Table 8_Mouse GeCKOv2 exons B.txt, 8,671,232 bytes
Table 9_Mouse GeCKOv2 miRNAs.txt, 208,896 bytes The disclosure in each of the foregoing US provisional patent applications is particularly incorporated herein by reference and particularly the disclosure of the CDs filed with 61/960,777 and 61/995,636 is particularly incorporated herein by reference in their entirety and is also included in this disclosure by way of the Biological Deposit(s) with the ATCC of plasmids/plasmid library(ies) containing nucleic acid molecules encoding selected guide sequences having the information set forth in U.S. provisional patent applications 61/960,777 and 61/995,636, namely, Deposit Nos: PTA-121339, PTA-121340, PTA-121341, PTA-121342, PTA-121343, deposited on Jun. 10, 2014, with the American Type Culture Collection on American Type Culture Collection (ATCC), 10801 University Boulevard, Manassas, Va. 20110 USA, under and pursuant to the terms of the Budapest Treaty. Upon issuance of a patent, all restrictions upon the Deposit(s) will be irrevocably removed, and the Deposit(s) is/are intended to meet the requirements of 37 CFR §§ 1.801-1.809. The Deposit(s) will be maintained in the depository for a period of 30 years, or 5 years after the last request, or for the effective, enforceable life of the patent, whichever is longer, and will be replaced if necessary during that period; and the requirements of 37 CFR §§ 1.801-1.809 are are met.

STATEMENT AS TO FEDERALLY SPONSORED RESEARCH

This invention was made with government support under Grant No. MH100706 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on May 29, 2018, is named 114203-5001_SL.txt and is 162,193 bytes in size.

FIELD OF THE INVENTION

The present invention generally relates to libraries, compositions, methods, applications, kits and screens used in functional genomics that focus on gene function in a cell and that may use vector systems and other aspects related to Clustered Regularly Interspaced Short Palindromic Repeats (CRISPR)-Cas systems and components thereof.

BACKGROUND OF THE INVENTION

Recent advances in genome sequencing techniques and analysis methods have significantly accelerated the ability to catalog and map genetic factors associated with a diverse range of biological functions and diseases. Functional genomics is a field of molecular biology that may be considered to utilize the vast wealth of data produced by genomic projects (such as genome sequencing projects) to describe gene (and protein) functions and interactions. Contrary to classical genomics, functional genomics focuses on the dynamic aspects such as gene transcription, translation, and protein—protein interactions, as opposed to the static aspects of the genomic information such as DNA sequence or structures, though these static aspects are very important and supplement one's understanding of cellular and molecular mechanisms. Functional genomics attempts to answer questions about the function of DNA at the levels of genes, RNA transcripts, and protein products. A key characteristic of functional genomics studies is a genome-wide approach to these questions, generally involving high-throughput methods rather than a more traditional "gene-by-gene" approach. Given the vast inventory of genes and genetic information it is advantageous to use genetic screens to provide information of what these genes do, what cellular pathways they are involved in and how any alteration in gene expression can result in particular biological process. Functional genomic screens attempt to characterize gene function in the context of living cells and hence are likely to generate biologically significant data. There are three key elements for a functional genomics screen: a good reagent to perturb the gene, a good tissue culture model and a good readout of cell state.

A reagent that has been used for perturbing genes in a number of functional genomics screens is RNA interference (RNAi). One can perform loss-of-function genetic screens and facilitate the identification of components of cellular signaling pathways utilizing RNAi. Gene silencing by RNAi in mammalian cells using small interfering RNAs (siRNAs) and short hairpin RNAs (shRNAs) has become a valuable genetic tool. Development of efficient and robust approaches to perform genome scale shRNA screens have been described in Luo B et al., "Highly parallel identification of essential genes in cancer cells" Proc Natl Acad Sci USA. 2008 Dec. 23; 105(51):20380-5; Paddison P J et al., "A resource for large-scale RNA-interference-based screens in mammals" Nature. 2004 Mar. 25; 428(6981):427-31; Berns K et al., "A large-scale RNAi screen in human cells identifies new components of the p53 pathway" Nature. 2004 Mar. 25; 428(6981):431-7, the contents of all of which are incorporated by reference herein in their entirety.

However there are aspects of using shRNAs for functional genomic screens that are not advantageous. For example, there may be off-target effects for the shRNAs that limit spatial control. It is also important to note that using RNAi or other current technologies in functional genomics screens as mentioned herein results in a gene knockdown and not a gene knockout. Another minor factor that may be considered is the need for the continued expression of shRNA. Hence, there remains a need for new genome engineering technologies that are affordable, easy to set up, scalable, and amenable to knockout genes for de novo loss of function and afford spatial and temporal control with minimal off-target activity in a eukaryotic genome.

SUMMARY OF THE INVENTION

There exists a pressing need for alternative and robust systems and techniques for sequence targeting in functional genomic screens and other applications thereof. This invention addresses this need and provides related advantages. The CRISPR/Cas or the CRISPR-Cas system (both terms are used interchangeably throughout this application) does not require the generation of customized proteins (as in the case of technologies involving zinc finger proteins, meganucleases or transcription activator like effectors (TALEs)) to target specific sequences but rather a single Cas enzyme can be programmed by a short RNA molecule to recognize a specific DNA target, in other words the Cas enzyme can be recruited to a specific DNA target using said short RNA molecule. This enables parallel targeting of thousands of genomic loci using oligo library synthesis. Adding the CRISPR-Cas system to the repertoire of functional genomics tools and analysis methods may significantly simplify the methodology and accelerate the ability to catalog and map genetic factors associated with a diverse range of biological functions and diseases. The CRISPR-Cas system can be used effectively for gene targeting and knockout without deleterious effects in functional genomic screens and other applications thereof.

Aspects of the invention relate to synthesizing different unique 20 bp spacer or guide RNA sequences with which different genomic locations can be targeted with double strand breaks (DSBs) and indel mutations. It is this easy programmability that makes CRISPR an attractive targeted screening system. As with pooled shRNA libraries, array oligonucleotide synthesis technologies allow for parallel synthesis of thousands of targeting sequences that can be cloned en masse into a vector, e.g. a viral vector such as an AAV vector or a lentiviral vector, and produced as virus in a pool. This allows for targeting of the Cas9 nuclease by modification of a 20 nt RNA guide sequence and genetic perturbation on the level of the genome itself.

In one aspect, the invention provides a genome wide library comprising a plurality of unique CRISPR-Cas system guide sequences that are capable of targeting a plurality of target sequences in genomic loci, wherein said targeting results in a knockout of gene function. Aspects of the invention include the guide sequences listed in Tables 1, 3, 4, 5, 7, 8 or 9.

Aspects of the invention, including libraries, methods and kits also expressly include the library and guide sequences as described in "*Genome-scale CRISPR-Cas9 knockout screening in human cells*", Shalem O, Sanjana N E, Hartenian E, Shi X, Scott D A, Mikkelsen T S, Heckl D, Ebert B L, Root D E, Doench J G, Zhang F., Science. 2014 Jan. 3; 343(6166):84-7, including all and any disclosure thereof and all and any disclosure from the corresponding Supplementary materials available from the publisher, including Supplementary materials made available online.

Aspects of the invention, including libraries, methods and kits also expressly include the libraries and guide sequences as described on the addgene website, accessible at http://www.addgene.org/CRISPR/libraries/, under "Feng Zhang Lab (targets human genes)", including the GeCKO v1 and GeCKO v2 libraries. These libraries are alternatively referred to herein as GeCKO1 and GeCKO2. Those libraries are also disclosure in each of the priority U.S. provisional patent applications 61/960,777, 61/961,980, 61/963,643 and 61/995,636, and especially the CDs filed therewith, and the Budapest Treaty Biological Deposit(s) with the ATCC in connection with this application; namely, ATCC Deposit Nos: PTA-121339, PTA-121340, PTA-121341, PTA-121342, PTA-121343.

In one aspect, the invention provides a CRISPR library for use in a method of knocking out in parallel every gene in the genome. In one aspect, the library or libraries consist of specific sgRNA sequences for gene knock-out in either the human or mouse genome. In one aspect, each species-specific library is delivered as two half-libraries (e.g., A and B). In one aspect, when used together, the A and B libraries contain 6 sgRNAs per gene (3 sgRNAs in each half library). In one aspect, each library or half library may comprise up to 4 sgRNAs per microRNA ("miRNA"). In one aspect, each species-specific library comprises sgRNA specific for each of over 1000 miRNA per genome (e.g., 1864 in human, 1175 in mouse). In one aspect, each species-specific library comprises at least one, preferably at least 3, and most preferably at least 6 sgRNA specific to each gene in the targeted genome (e.g., 19,052 in human, 20,661 in mouse).

In one aspect, the GeCKO library is packaged in a viral vector. In one aspect, the GeCKO library is packaged in a lentivirus vector. In one aspect, the packaged GeCKO library is transduced at an MOI (multiplicity of infection) of about 10, of about 5, of about 3, of about 1 or of about less than 1, about less than 0.75, about less than 0.5, about less than 0.4, about less than 0.3, about less than 0.2 or about less than 0.1. In a further embodiment the cell is transduced with a multiplicity of infection (MOI) of 0.3-0.75, preferably, the MOI has a value close to 0.4, more preferably the MOI is 0.3 or 0.4. In one aspect, the MOI is about 0.3 or 0.4, thereby creating a panel of cells comprising about 1 CRISPR-Cas system chimeric RNA (chiRNA) per cell, after appropriate selection for successfully transfected/transduced cells, thereby providing a panel of cells comprising a cellular library with parallel knock outs of every gene in the genome.

In another aspect, the invention provides for a method of knocking out in parallel every gene in the genome, the method comprising contacting a population of cells with a composition comprising a vector system comprising one or more packaged vectors comprising
a) a first regulatory element operably linked to a CRISPR-Cas system chimeric RNA (chiRNA) polynucleotide sequence that targets a DNA molecule encoding a gene product, wherein the polynucleotide sequence comprises
   (a) a guide sequence capable of hybridizing to a target sequence,
   (b) a tracr mate sequence, and
   (c) a tracr sequence, and
b) a second regulatory element operably linked to a sequence encoding a Cas protein and a selection marker, wherein components (a) and (b) are located on same or different vectors of the system,
wherein each cell is transfected with a single packaged vector,
selecting for successfully transfected cells,
wherein when transcribed, the tracr mate sequence hybridizes to the tracr sequence and the guide sequence directs sequence-specific binding of a CRISPR complex to a target sequence in the genomic loci of the DNA molecule encoding the gene product,
wherein the CRISPR complex comprises a CRISPR enzyme complexed with (1) the guide sequence that is hybridizable to the target sequence, and (2) the tracr mate sequence that is hybridized to the tracr sequence,
wherein the guide sequence is selected from the library of the invention,
wherein the guide RNAs target the genomic loci of the DNA molecule encoding the gene product and the CRISPR enzyme cleaves the genomic loci of the DNA molecule encoding the gene product and whereby each cell in the population of cells has a unique gene knocked out in parallel. In preferred embodiments, the cell is a eukaryotic cell. In further embodiments the vector is a lentivirus, a adenovirus or a AAV and/or the first regulatory element is a Pol III promoter such as a H1 promoter and a U6 promoter and/or the second regulatory element is a Pol II promoter selected from a doxycycline inducible promoter, a cell-type specific promoter and an EFS promoter, and/or the vector system comprises one vector and/or the CRISPR enzyme is Cas9.

The invention also encompasses methods of selecting individual cell knock outs that survive under a selective pressure, the method comprising
contacting a population of cells with a composition comprising a vector system comprising one or more packaged vectors comprising
a) a first regulatory element operably linked to a CRISPR-Cas system chimeric RNA (chiRNA) polynucleotide sequence that targets a DNA molecule encoding a gene product,
   wherein the polynucleotide sequence comprises
   (a) a guide sequence capable of hybridizing to a target sequence,
   (b) a tracr mate sequence, and
   (c) a tracr sequence, and
b) a second regulatory element operably linked to a Cas protein and a selection marker,
wherein components (a) and (b) are located on same or different vectors of the system,
wherein each cell is transfected with a single packaged vector,
selecting for successfully transfected cells,
wherein when transcribed, the tracr mate sequence hybridizes to the tracr sequence and the guide sequence directs sequence-specific binding of a CRISPR complex to a target sequence in the genomic loci of the DNA molecule encoding the gene product,
wherein the CRISPR complex comprises a CRISPR enzyme complexed with (1) the guide sequence that is hybridizable to the target sequence, and (2) the tracr mate sequence that is hybridized to the tracr sequence,
wherein the guide sequence is selected from the library of the invention,
wherein the guide RNAs target the genomic loci of the DNA molecule encoding the gene product and the CRISPR enzyme cleaves the genomic loci of the DNA molecule encoding the gene product, whereby each cell in the population of cells has a unique gene knocked out in parallel,
applying the selective pressure,
and selecting the cells that survive under the selective pressure.

In preferred embodiments, the selective pressure is application of a drug, FACS sorting of cell markers or aging and/or the vector is a lentivirus, a adenovirus or a AAV and/or the first regulatory element is a Pol III promoter such as a H1 promoter and a U6 promoter and/or the second regulatory element is a Pol II promoter selected from a doxycycline inducible promoter, a cell-type specific promoter and an EFS promoter, and/or the vector system comprises one vector and/or the CRISPR enzyme is Cas9.

In other aspects, the invention encompasses methods of identifying the genetic basis of one or more medical symptoms exhibited by a subject, the method comprising obtaining a biological sample from the subject and isolating a population of cells having a first phenotype from the biological sample;
   contacting the cells having the first phenotype with a composition comprising a vector system comprising one or more packaged vectors comprising
a) a first regulatory element operably linked to a CRISPR-Cas system chimeric RNA (chiRNA) polynucleotide sequence that targets a DNA molecule encoding a gene product,
   wherein the polynucleotide sequence comprises
   (a) a guide sequence capable of hybridizing to a target sequence,
   (b) a tracr mate sequence, and
   (c) a tracr sequence, and
b) a second regulatory element operably linked to a Cas protein and a selection marker, wherein components (a) and (b) are located on same or different vectors of the system,
wherein each cell is transfected with a single packaged vector,
selecting for successfully transfected cells,
wherein when transcribed, the tracr mate sequence hybridizes to the tracr sequence and the guide sequence directs sequence-specific binding of a CRISPR complex to a target sequence in the genomic loci of the DNA molecule encoding the gene product,
wherein the CRISPR complex comprises a CRISPR enzyme complexed with (1) the guide sequence that is hybridizable to the target sequence, and (2) the tracr mate sequence that is hybridized to the tracr sequence,
wherein the guide sequence is selected from the library of the invention,
wherein the guide RNAs target the genomic loci of the DNA molecule encoding the gene product and the CRISPR enzyme cleaves the genomic loci of the DNA molecule encoding the gene product, whereby each cell in the population of cells has a unique gene knocked out in parallel,
applying the selective pressure,
selecting the cells that survive under the selective pressure,
determining the genomic loci of the DNA molecule that interacts with the first phenotype and
identifying the genetic basis of the one or more medical symptoms exhibited by the subject.

In preferred embodiments, the selective pressure is application of a drug, FACS sorting of cell markers or aging and/or the vector is a lentivirus, a adenovirus or a AAV and/or the first regulatory element is a Pol III promoter such as a H1 promoter and a U6 promoter and/or the second regulatory element is a Pol II promoter selected from a doxycycline inducible promoter, a cell-type specific promoter and an EFS promoter, and/or the vector system comprises one vector and/or the CRISPR enzyme is Cas9.

The invention also comprehends kit comprising the library of the invention. In certain aspects, the kit comprises a single container comprising one or more vectors comprising the library of the invention. In other aspects, the kit comprises a single container comprising one or more plasmids comprising the library of the invention. The invention also comprehends kits comprising a panel comprising a selection of unique CRISPR-Cas system guide sequences from the library of the invention, wherein the selection is indicative of a particular physiological condition. In preferred embodiments, the targeting is of about 100 or more sequences, about 1000 or more sequences or about 20,000 or more sequences or the entire genome. In other embodiments a panel of target sequences is focused on a relevant or desirable pathway, such as an immune pathway or cell division.

In one aspect, the invention provides a genome wide library comprising a plurality of unique CRISPR-Cas system guide sequences that are capable of targeting a plurality of target sequences in genomic loci of a plurality of genes, wherein said targeting results in a knockout of gene function. In preferred embodiments of the invention the unique CRISPR-Cas system guide sequences are selected by an algorithm that predicts the efficacy of the guide sequences based on the primary nucleotide sequence of the guide sequence and/or by a heuristic that ranks the guide sequences based on off target scores. In certain embodiments of the invention, the guide sequences are capable of targeting a plurality of target sequences in genomic loci of a plurality of genes selected from the entire genome. In embodiments, the genes may represent a subset of the entire genome; for example, genes relating to a particular pathway (for example, an enzymatic pathway) or a particular disease or group of diseases or disorders may be selected. One or more of the genes may include a plurality of target sequences; that is, one gene may be targeted by a plurality of guide sequences. In certain embodiments, a knockout of gene function is not essential, and for certain applications, the invention may be practiced where said targeting results only in a knockdown of gene function. However, this is not preferred.

Aspects of the invention may include the guide sequences listed in Tables 1, 3, 4, 5, 7, 8 or 9 as provided in the compact discs created Apr. 11, 2014, as filed in connection with U.S. applications 61/960,777 and 61/995,636. In a further embodiment, the guide sequences target constitutive exons downstream of a start codon of the gene. In an advantageous embodiment, the guide sequences target either a first or a second exon of the gene. In yet another embodiment, the guide sequences target a non-transcribed strand of the genomic loci of the gene.

In another aspect, the invention provides for a method of knocking out in parallel every gene in the genome, the method comprising contacting a population of cells with a composition comprising a vector system comprising one or more packaged vectors comprising a) a first regulatory element operably linked to a CRISPR-Cas system chimeric RNA (chiRNA) polynucleotide sequence that targets a DNA molecule encoding a gene product, wherein the polynucleotide sequence comprises
(a) a guide sequence capable of hybridizing to a target sequence,
(b) a tracr mate sequence, and
(c) a tracr sequence, and
b) a second regulatory element operably linked to a Cas protein and a selection marker, wherein components (a) and (b) are located on same or different vectors of the system, wherein each cell is transduced with a single packaged vector,
selecting for successfully transduced cells,
wherein when transcribed, the tracr mate sequence hybridizes to the tracr sequence and the guide sequence directs sequence-specific binding of a CRISPR complex to a target sequence in the genomic loci of the DNA molecule encoding the gene product,
wherein the CRISPR complex comprises a CRISPR enzyme complexed with (1) the guide sequence that is hybridizable to the target sequence, and (2) the tracr mate sequence that is hybridized to the tracr sequence,
wherein the guide sequence is selected from the library of the invention,
wherein the guide sequence targets the genomic loci of the DNA molecule encoding the gene product and the CRISPR enzyme cleaves the genomic loci of the DNA molecule encoding the gene product and whereby each cell in the population of cells has a unique gene knocked out in parallel. In preferred embodiments, the cell is a eukaryotic cell. The eukaryotic cell may be a plant or animal cell; for example, algae or microalgae; vertebrate, preferably mammalian, including murine, ungulate, primate, human; insect. In further embodiments the vector is a lentivirus, an adenovirus or an AAV and/or the first regulatory element is a Pol III promoter such as a H1 promoter and a U6 promoter and/or the second regulatory element is a Pol II promoter such as an EFS promoter or a doxycycline inducible promoter or a cell-type specific promoter as further described herein, and/or the vector system comprises one vector and/or the CRISPR enzyme is Cas9. In aspects of the invention the cell is a eukaryotic cell, preferably a human cell. In a further embodiment the cell is transduced with a multiplicity of infection (MOI) of 0.3-0.75, preferably, the MOI has a value close to 0.4, more preferably the MOI is 0.3 or 0.4.

The invention also encompasses methods of selecting individual cell knock outs that survive under a selective pressure, the method comprising
contacting a population of cells with a composition comprising a vector system comprising one or more packaged vectors comprising a) a first regulatory element operably linked to a CRISPR-Cas system chimeric RNA (chiRNA) polynucleotide sequence that targets a DNA molecule encoding a gene product, wherein the polynucleotide sequence comprises
(a) a guide sequence capable of hybridizing to a target sequence,
(b) a tracr mate sequence, and
(c) a tracr sequence, and b) a second regulatory element operably linked to a Cas protein and a selection marker, wherein components (a) and (b) are located on same or different vectors of the system, wherein each cell is transduced with a single packaged vector, selecting for successfully transduced cells, wherein when transcribed, the tracr mate sequence hybridizes to the tracr sequence and the guide sequence directs sequence-specific binding of a CRISPR complex to a target sequence in the genomic loci of the DNA molecule encoding the gene product, wherein the CRISPR complex comprises a CRISPR enzyme complexed with (1) the guide sequence that is hybridizable to the target sequence, and (2) the tracr mate sequence that is hybridized to the tracr sequence, wherein the guide sequence is selected from the library of the invention, wherein the guide sequence targets the genomic loci of the DNA molecule encoding the gene product and the CRISPR enzyme cleaves the genomic loci of the DNA molecule encoding the gene product, whereby each cell in the population of cells has a unique gene knocked out in parallel, applying the selective pressure, and selecting the cells that survive under the selective pressure.

In preferred embodiments, the selective pressure is application of a drug, FACS sorting of cell markers or aging and/or the vector is a lentivirus, a adenovirus or a AAV and/or the first regulatory element is a Pol III promoter such as a H1 promoter and a U6 promoter and/or the second regulatory element is a Pol II promoter such as an EFS promoter or a doxycycline inducible promoter or a cell-type specific promoter, and/or the vector system comprises one vector and/or the CRISPR enzyme is Cas9. In a further embodiment the cell is transduced with a multiplicity of infection (MOI) of 0.3-0.75, preferably, the MOI has a value close to 0.4, more preferably the MOI is 0.3 or 0.4. In aspects of the invention the cell is a eukaryotic cell. The eukaryotic cell may be a plant or animal cell; for example, algae or microalgae; vertebrate, preferably mammalian, including murine, ungulate, primate, human; insect. Preferably the cell is a human cell. In preferred embodiments of the invention, the method further comprises extracting DNA and determining the depletion or enrichment of the guide sequences by deep sequencing.

In other aspects, the invention encompasses methods of identifying the genetic basis of one or more medical symptoms exhibited by a subject, the method comprising obtaining a biological sample from the subject and isolating a population of cells having a first phenotype from the biological sample;

contacting the cells having the first phenotype with a composition comprising a vector system comprising one or more packaged vectors comprising a) a first regulatory element operably linked to a CRISPR-Cas system chimeric RNA (chiRNA) polynucleotide sequence that targets a DNA molecule encoding a gene product, wherein the polynucleotide sequence comprises
(a) a guide sequence capable of hybridizing to a target sequence,
(b) a tracr mate sequence, and
(c) a tracr sequence, and b) a second regulatory element operably linked to a Cas protein and a selection marker, wherein components (a) and (b) are located on same or different vectors of the system, wherein each cell is transduced with a single packaged vector, selecting for successfully transduced cells, wherein when transcribed, the tracr mate sequence hybridizes to the tracr sequence and the guide sequence directs sequence-specific binding of a CRISPR complex to a target sequence in the genomic loci of the DNA molecule encoding the gene product, wherein the CRISPR complex comprises a CRISPR enzyme complexed with (1) the guide sequence that is hybridizable to the target sequence, and (2) the tracr mate sequence that is hybridized to the tracr sequence, wherein the guide sequence is selected from the library of the invention, wherein the guide sequence targets the genomic loci of the DNA molecule encoding the gene product and the CRISPR enzyme cleaves the genomic loci of the DNA molecule encoding the gene product, whereby each cell in the population of cells has a unique gene knocked out in parallel, applying a selective pressure, selecting the cells that survive under the selective pressure, determining the genomic loci of the DNA molecule that interacts with the first phenotype and identifying the genetic basis of the one or more medical symptoms exhibited by the subject.

In preferred embodiments, the selective pressure is application of a drug, FACS sorting of cell markers or aging and/or the vector is a lentivirus, an adenovirus or an AAV and/or the first regulatory element is a Pol III promoter such as a H1 promoter and a U6 promoter and/or the second regulatory element is a Pol II promoter such as an EFS promoter or a doxycycline inducible promoter or a cell-type specific promoter, and/or the vector system comprises one vector and/or the CRISPR enzyme is Cas9. In a further embodiment the cell is transduced with a multiplicity of infection (MOI) of 0.3-0.75, preferably, the MOI has a value close to 0.4, more preferably the MOI is 0.3 or 0.4. In aspects of the invention the cell is a eukaryotic cell, preferably a human cell.

In an aspect, the library of the invention is a plasmid library. The plasmid library (preferably as further cloned into a delivery vector, such as lentivector) may be selected from the group consisting of:

(A) GeCKO1—library of sgRNA plasmids each encoding selected guide sequences and cloned into vector (lentiCRISPRv2)—ATCC Deposit No. PTA-121339;
(B) GeCKO2—half library A (human) sgRNA plasmids each encoding selected guide sequences and cloned into vector—ATCC Deposit No. PTA-121340;
(C) GeCKO2—half library B (human) of sgRNA plasmids each encoding selected guide sequences and cloned into vector—ATCC Deposit No. PTA-121341;
(D) GeCKO2—half library A (mouse) sgRNA plasmids each encoding selected guide sequences and cloned into vector—ATCC Deposit No. PTA-121342; and
(E) GeCKO2—half library A (mouse) sgRNA plasmids each encoding selected guide sequences and cloned into vector—ATCC Deposit No. PTA-121343;

wherein "GeCKO" stands for Genome-scale CRISPR-Cas9 Knock Out". The various GeCKO libraries have been generated for targeting either human or mouse genomes and consist of a one vector system or a two vector system for delivery of short 20 bp sequences of the sgRNA with or without Cas9. The GeCKO1 library consists of specific sgRNA sequences for gene knock-out in either the human or mouse genome. The GeCKO2 libraries consist of specific sgRNA sequences for gene knock-out in either the human or mouse genome, wherein each species-specific library is delivered as two half-libraries (A and B). When used together, the A and B libraries contain 6 sgRNAs per gene (3 sgRNAs in each library) and may contain 4 sgRNAs per microRNA ("miRNA") for over 1000 miRNA per genome (1864 in human, 1175 in mouse). Any one or more GeCKO library may be used in any one of the methods or in any one of the kits of the present invention. The GeCKO libraries, and specifically each of (A) to (E), above, were deposited with the American Type Culture Collection (ATCC) on Jun. 10, 2014, and are further exemplified in ATCC Deposit Nos: PTA-121339, PTA-121340, PTA-121341, PTA-121342, PTA-121343, deposited on Jun. 10, 2014, as provided herein and in the compact discs created Apr. 11, 2014, as filed in connection with U.S. applications 61/960,777 and 61/995, 636, including as the information set forth in those US applications and the compact discs filed therewith is presented herein via the ATCC Deposits.

In an aspect, the vector systems in the methods of the invention comprise one or more lentiviral vector(s). In a preferred embodiment, the one or more lentiviral vectors may comprise a codon optimized nuclear localization signal (NLS), a codon optimized P2A bicistronic linker sequence and an optimally placed U6 driven guide RNA cassette. In another aspect the vector system comprises two lentiviral vectors, wherein one lentiviral vector comprises the Cas9 enzyme and the other lentiviral vector comprises the guide RNA selected from the libraries of the invention. In an embodiment of the invention, each vector has a different selection marker, e.g. a different antibiotic resistance marker. The invention also comprehends kits comprising the libraries of the invention. In certain aspects, the kit comprises a single container comprising vectors comprising the library of the invention. In other aspects, the kit comprises a single container comprising plasmids comprising the library of the invention. The invention also comprehends kits comprising a panel comprising a selection of unique CRISPR-Cas system guide sequences from the library of the invention, wherein the selection is indicative of a particular physiological condition. In preferred embodiments, the targeting is of about 100 or more sequences, about 1000 or more sequences or about 20,000 or more sequences or the entire genome. In other embodiments a panel of target sequences is focused on a relevant or desirable pathway, such as an immune pathway or cell division.

In an aspect, the invention provides a non-human eukaryotic organism; preferably a multicellular eukaryotic organism, comprising a eukaryotic host cell according to any of the described embodiments in which a candidate gene is knocked down or knocked out. Preferably the gene is knocked out. In other aspects, the invention provides a eukaryotic organism; preferably a multicellular eukaryotic organism, comprising a eukaryotic host cell which has been altered according to any of the described embodiments. The organism in some embodiments of these aspects may be an animal; for example a mammal. Also, the organism may be an arthropod such as an insect. The organism also may be a plant. Further, the organism may be a fungus. In some embodiments, the invention provides a set of non-human eukaryotic organisms, each of which comprises a eukaryotic host cell according to any of the described embodiments in which a candidate gene is knocked down or knocked out. In preferred embodiments, the set comprises a plurality of organisms, in each of which a different gene is knocked down or knocked out.

In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cas9 enzyme. In some embodiments, the Cas9 enzyme is *S. pneumoniae*, *S. pyogenes* or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In one aspect, the CRISPR enzyme comprises at least one mutation in a catalytic domain. In one aspect, the CRISPR enzyme is a nickase. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an advantageous embodiment the guide sequence is 20 nucleotides in length.

As mentioned previously, a critical aspect of the invention is gene knock-out and not knock-down (which can be done with genome-wide siRNA or shRNA libraries). Applicants have provided the first demonstration of genome-wide knockouts that are barcoded and can be easily readout with next generation sequencing. Every single gene (or a subset of desired genes, for example, those relating to a particular enzymatic pathway or the like (e.g., including but not limited to pathways involved in signaling, metabolism, gene regulation, immune response, disease resistance, drug response and/or resistance, etc.) may be knocked OUT in parallel. This allows quantification of how well each gene KO confers a survival advantage with the selective pressure of the screen. In a preferred embodiment, the invention has advantageous pharmaceutical application, e.g., the invention may be harnessed to test how robust any new drug designed to kill cells (e.g. chemotherapeutic) is to mutations that KO genes. Cancers mutate at an exceedingly fast pace and the libraries and methods of the invention may be used in functional genomic screens to predict the ability of a chemotherapy to be robust to "escape mutations". (Refer to PLX data in BRAF V600E mutant A375 cells in Example 9. Other mutations (e.g. NF1, NF2, and MED12) allow escape from the killing action of PLX.)

Aspects of the invention comprehend many types of screens and selection mechanisms can also be used with CRISPR screening. Screens for resistance to viral or bacterial pathogens may be used to identify genes that prevent infection or pathogen replication. As in drug resistance screens, survival after pathogen exposure provides strong selection. In cancer, negative selection CRISPR screens may identify "oncogene addictions" in specific cancer subtypes that can provide the foundation for molecular targeted therapies. For developmental studies, screening in human and mouse pluripotent cells may pinpoint genes required for pluripotency or for differentiation into distinct cell types. To distinguish cell types, fluorescent or cell surface marker reporters of gene expression may be used and cells may be sorted into groups based on expression level. Gene-based reporters of physiological states, such as activity-dependent transcription during repetitive neural firing or from antigen-based immune cell activation, may also be used. Any phenotype that is compatible with rapid sorting or separation may be harnessed for pooled screening. CRISPR screening may also be used as a diagnostic tool: With patient-derived iPS cells, genome-wide libraries may be used to examine multi-gene interactions (similar to synthetic lethal screens) or how different loss-of-functions mutations accumulated through aging or disease can interact with particular drug treatments.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A-2F shows an exemplary CRISPR system, a possible mechanism of action, an example adaptation for expression in eukaryotic cells, and results of tests assessing nuclear localization and CRISPR activity. FIG. 2C discloses SEQ ID NOS 79-80, respectively, in order of appearance. FIG. 2E discloses SEQ ID NOS 81-83, respectively, in order of appearance. FIG. 2F discloses SEQ ID NOS 84-88, respectively, in order of appearance.

FIG. 3A-3D shows results of an evaluation of SpCas9 specificity for an example target. FIG. 3A discloses SEQ ID NOS 89, 82 and 90-100, respectively, in order of appearance. FIG. 3C discloses SEQ ID NO: 89.

FIG. 4E discloses SEQ ID NO: 101. FIG. 4F discloses SEQ ID NOS 102-103, respectively, in order of appearance. FIG. 4G discloses SEQ ID NOS 104-108, respectively, in order of appearance.

FIG. 5 provides a table of protospacer sequences and summarizes modification efficiency results for protospacer targets designed based on exemplary S. pyogenes and S. thermophilus CRISPR systems with corresponding PAMs against loci in human and mouse genomes. Cells were transfected with Cas9 and either pre-crRNA/tracrRNA or chimeric RNA, and analyzed 72 hours after transfection. Percent indels are calculated based on Surveyor assay results from indicated cell lines (N=3 for all protospacer targets, errors are S.E.M., N.D. indicates not detectable using the Surveyor assay, and N.T. indicates not tested in this study). FIG. 5 discloses SEQ ID NOS 17, 16, 15, 109-114, 19, 18 and 115-119, respectively, in order of appearance.

FIG. 6A discloses SEQ ID NOS 120 and 121, respectively, in order of appearance.

FIG. 8A discloses SEQ ID NOS 122-124, respectively, in order of appearance. FIG. 8B discloses SEQ ID NOS 125-127, respectively, in order of appearance.

FIG. 9A-9C shows histograms of distances between adjacent S. pyogenes SF370 locus 1 PAM (NGG) (FIG. 9A) and S. thermophilus LMD9 locus 2 PAM (NNAGAAW) (FIG. 9B) in the human genome; and distances for each PAM by chromosome (Chr) (FIG. 9C).

FIG. 10B discloses SEQ ID NOS 128-129, respectively, in order of appearance. FIG. 10C discloses SEQ ID NO: 130.

FIG. 11A discloses SEQ ID NO: 131. FIG. 11B discloses SEQ ID NO: 132-134, respectively, in order of appearance.

FIG. 12A discloses SEQ ID NO: 135.

FIG. 15 provides a table of sequences for primers (SEQ ID NOS 138-147, respectively, in order of appearance) and probes (SEQ ID NOS 148-149, respectively, in order of appearance) used for Surveyor, RFLP, genomic sequencing, and Northern blot assays.

FIG. 16A discloses SEQ ID NO: 150)

FIG. 18 discloses SEQ ID NOS 151-229, respectively, in order of appearance.

FIG. 21C discloses SEQ ID NOS 230-232, 230, 233 and 232, respectively, in order of appearance. d, SURVEYOR assay for wildtype (wt) and nickase (D10A) SpCas9-mediated indels at the EMX1 target 1 locus (n=3). Arrows indicate positions of expected fragment sizes.

FIG. 22A discloses SEQ ID NOS 234-236, respectively, in order of appearance. FIG. 22B discloses SEQ ID NO: 237.

FIG. 23A-23D shows A) Design of sgRNAs for functional knock-out of all coding genes in the human genome. Early constitutive exons for genes are identified using Illumina Human BodyMap 2.0 and NCBI CCDS datasets. sgRNAs are ranked by an off-target score using a metric that includes the number of off-targets in the genome and the type of mutations (distance from PAM and clustering) to evaluate off-target cutting. The best sgRNA (lowest off-target score) in each exon are included in the library. Most genes have 3 or 4 sgRNAs targeting early exons. B) Individual sgRNAs are synthesized using array synthesis of ssDNAs and then PCR amplified as dsDNA. These dsDNAs are cloned into the lentiviral transfer plasmid after a U6 promoter; this vector also contains a EFS promoter driving Cas9 and puromycin resistance. The pooled library is packaged into lentiviral particles in HEK 293FT cells via co-transfection with pVSVg and psPAX2. To begin the screen, cells to be screened are infected at a MOI between 0.3 to 0.5 to ensure that each cell receives only 1 viral construct. In aspects of the invention, the MOI may be between 0.3 to 0.75. After 24 hours, cells are selected via puromycin so that only cells transduced with a CRISPR construct are preserved. C) Different sgRNA targeting the initial part of EGFP are cloned into the Cas9-2A-Puro lentiviral vector and packaged into virus. Distribution of EGFP fluorescence is shown for 293 Ts expressing EGFP after transduction with each EGFP-targeting sgRNA, a Cas9-only virus, or uninfected control cells. D) States NGS indel data on EGFP cells.

FIG. 26A-26E shows GeCKO library design and application for genome-scale negative selection screening. (A) Design of sgRNA library for genome-scale knockout of coding sequences in human cells (supplementary discussion). (B), (C) Cumulative frequency of sgRNAs 3 and 14 days post transduction in A375 and hES cells respectively. Shift in the 14 day curve represents the depletion in a subset of sgRNAs. (D), (E) Five most significantly depleted gene sets in A375 cells (nominal $p<10^{-5}$, FDR-corrected $q<10^{-5}$) and HUES62 cells (nominal $p<10^{-5}$, FDR-corrected $q<10^{-3}$) identified by Gene Set Enrichment Analysis (GSEA).

FIG. 29 shows design of sgRNAs to knock out EGFP. EGFP sequence (SEQ ID NO: 238) is shown with six different sgRNAs that were designed to target the coding sequence.

FIG. 42 discloses SEQ ID NOS 239-254, respectively, in order of appearance.

FIG. 43 discloses SEQ ID NOS 255-275, respectively, in order of appearance.

FIG. 44 discloses SEQ ID NOS 276-284 and 284-298, respectively, in order of appearance.

FIG. 45A-45L shows Top 1000 depleted genes for both A375 and HUES62. Mean depletion for each gene is given as the log 2 ratio of Day 14 vs. Day 3 representation (mean over sgRNAs for the gene).

FIG. 46A-46E shows the plasmid map (SEQ ID NO: 299) & annotation key for LentiCRISPR (pXPR_001 available through Addgene)

FIG. 49A-49D shows the plasmid map (SEQ ID NO: 300) & annotation key for LentiCRISPR v2 available through Addgene.

FIG. 50A-50C shows the plasmid map (SEQ ID NO: 301) & annotation key for LentiCas9-Blast available through Addgene.

FIG. 51A-51C shows the plasmid map (SEQ ID NO: 302) & annotation key for lentiGuide-Puro available through Addgene.

Figure 1:
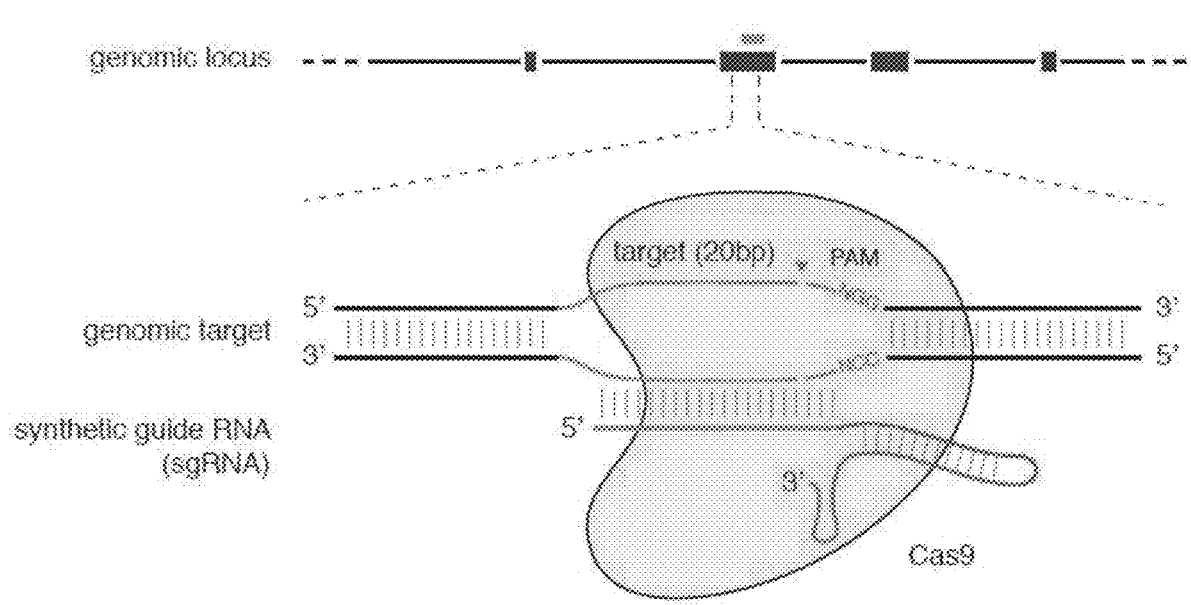
FIG. 1 shows a schematic model of the CRISPR system. The Cas9 nuclease from Streptococcus pyogenes (yellow) is targeted to genomic DNA by a synthetic guide RNA (sgRNA) consisting of a 20-nt guide sequence (blue) and a scaffold (red). The guide sequence base-pairs with the DNA target (blue), directly upstream of a requisite 5'-NGG protospacer adjacent motif (PAM; magenta), and Cas9 mediates a double-stranded break (DSB)—3 bp upstream of the PAM (red triangle).

The figures herein are for illustrative purposes only and are not necessarily drawn to scale.

DETAILED DESCRIPTION OF THE INVENTION

With respect to general information on CRISPR-Cas Systems: Reference is also made to U.S. provisional patent applications 61/736,527, 61/748,427, 61/791,409 and 61/835,931, filed on Dec. 12, 2012, Jan. 2, 2013, Mar. 15, 2013 and Jun. 17, 2013, respectively. Reference is also made to U.S. provisional applications 61/757,972 and 61/768,959, filed on Jan. 29, 2013 and Feb. 25, 2013, respectively. Reference is also made to U.S. provisional patent applications 61/835,931, 61/835,936, 61/836,127, 61/836,101, 61/836,080 and 61/835,973, each filed Jun. 17, 2013. Each of these applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference in their entirety, and may be employed in the practice of the invention. All documents (e.g., these applications and the appln cited documents) are incorporated herein by reference to the same extent as if each individual document was specifically and individually indicated to be incorporated by reference.

Also with respect to general information on CRISPR-Cas Systems, mention is made of:

*Multiplex genome engineering using CRISPR/Cas systems*. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121): 819-23 (2013);

*RNA-guided editing of bacterial genomes using CRISPR-Cas systems.* Jiang W., Bikard D., Cox D., Zhang F, Marraffini L A. Nat Biotechnol March; 31(3):233-9 (2013);

*One-Step Generation of Mice Carrying Mutations in Multiple Genes by CRISPR/Cas-Mediated Genome Engineering.* Wang H., Yang H., Shivalila C S., Dawlaty M M., Cheng A W., Zhang F., Jaenisch R. Cell May 9; 153(4):910-8 (2013);

*Optical control of mammalian endogenous transcription and epigenetic states.* Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature 12466. Epub 2013 Aug. 23;

*Double Nicking by RNA-Guided CRISPR Cas9 for Enhanced Genome Editing Specificity.* Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5. (2013);

*DNA targeting specificity of RNA-guided Cas9 nucleases.* Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

*Genome engineering using the CRISPR-Cas9 system.* Ran, F A., Hsu, P D., Wright, J., Agarwala, V., Scott, D A., Zhang, F. Nature Protocols November; 8(11):2281-308. (2013);

*Genome-Scale CRISPR-Cas9 Knockout Screening in Human Cells.* Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

*Crystal structure of cas9 in complex with guide RNA and target DNA.* Nishimasu, H., Ran, F A., Hsu, P D., Konermann, S., Shehata, S I., Dohmae, N., Ishitani, R., Zhang, F., Nureki, O. Cell February 27. (2014). 156 (5):935-49;

*Genome-wide binding of the CRISPR endonuclease Cas9 in mammalian cells.* Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. (2014) April 20. doi: 10.1038/nbt.2889, and

*Development and Applications of CRISPR-Cas9 for Genome Engineering,* Hsu et al, Cell 157, 1262-1278 (Jun. 5, 2014) (Hsu 2014), each of which is incorporated herein by reference, and discussed briefly below:

Cong et al. engineered type II CRISPR/Cas systems for use in eukaryotic cells based on both *Streptococcus thermophilus* Cas9 and also *Streptoccocus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR/Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Konermann et al. addressed the need in the art for versatile and robust technologies that enable optical and chemical modulation of DNA-binding domains based CRISPR Cas9 enzyme and also Transcriptional Activator Like Effectors As discussed in the present specification, the Cas9 nuclease from the microbial CRISPR-Cas system is targeted to specific genomic loci by a 20 nt guide sequence, which can tolerate certain mismatches to the DNA target and thereby promote undesired off-target mutagenesis. To address this, Ran et al. described an approach that combined a Cas9 nickase mutant with paired guide RNAs to introduce targeted double-strand breaks. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Hsu 2014 is a review article that discusses generally CRISPR-Cas9 history from yogurt to genome editing, including genetic screening of cells, that is in the information, data and findings of the applications in the lineage of this specification filed prior to Jun. 5, 2014. The general teachings of Hsu 2014 do not involve the specific models, animals of the instant specification.

Mention is also made of Cong et al, Supplementary Material . . . ", Science 339(6121), pp 1-25); Jinek et al, Science 337(6096), 17 Aug. 2012, pp 816-821; Gasiunas et al, PNAS 19(39), 25 Sep. 2012, pp E2579-2586; Shalem et al, Science 343(6166), pp 84-87 (2014); Haft et al, PLOS Computational Biology, Public Library of Science, vol. 1, no. 6, pp 474-83 (2005); and Wiedenheft et al, Nature 482(7385), pp 331-338 (2012), each of which, in their entirety, is hereby incorporated herein by reference, without any admission that these or any document cited herein is indeed prior art as to the instant invention.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non nucleotide components. A polynucleotide may be further modified after polymerization, such as by conjugation with a labeling component.

As used herein the term "candidate gene" refers to a cellular, viral, episomal, microbial, protozoal, fungal, animal, plant, chloroplastic, or mitochondrial gene. This term also refers to a microbial or viral gene that is part of a naturally occurring microbial or viral genome in a microbially or virally infected cell. The microbial or viral genome can be extrachromosomal or integrated into the host chromosome. This term also encompasses endogenous and exogenous genes, as well as cellular genes that are identified as ESTs. Often, the candidate genes of the invention are those for which the biological function is unknown. An assay of choice is used to determine whether or not the gene is associated with a selected phenotype upon regulation of candidate gene expression with systems of the invention. If the biological function is known, typically the candidate gene acts as a control gene, or is used to determine if one or more additional genes are associated with the same phenotype, or is used to determine if the gene participates with other genes in a particular phenotype.

A "selected phenotype" refers to any phenotype, e.g., any observable characteristic or functional effect that can be measured in an assay such as changes in cell growth, proliferation, morphology, enzyme function, signal transduction, expression patterns, downstream expression patterns, reporter gene activation, hormone release, growth factor release, neurotransmitter release, ligand binding, apoptosis, and product formation. Such assays include, e.g., transformation assays, e.g., changes in proliferation, anchorage dependence, growth factor dependence, foci formation, growth in soft agar, tumor proliferation in nude mice, and tumor vascularization in nude mice; apoptosis assays, e.g., DNA laddering and cell death, expression of genes involved in apoptosis; signal transduction assays, e.g., changes in intracellular calcium, cAMP, cGMP, IP3, changes in hormone and neurotransmittor release; receptor assays, e.g., estrogen receptor and cell growth; growth factor assays, e.g., EPO, hypoxia and erythrocyte colony forming units assays; enzyme product assays, e.g., FAD-2 induced oil desaturation; transcription assays, e.g., reporter gene assays; and protein production assays, e.g., VEGF ELISAs. A candidate gene is "associated with" a selected phenotype if modulation of gene expression of the candidate gene causes a change in the selected phenotype In aspects of the invention the terms "chimeric RNA", "chimeric guide RNA", "guide RNA", "single guide RNA" and "synthetic guide RNA" are used interchangeably and refer to the polynucleotide sequence comprising the guide sequence, the tracr sequence and the tracr mate sequence. The term "guide sequence" refers to the about 20 bp sequence within the guide RNA that specifies the target site and may be used interchangeably with the terms "guide" or "spacer". The term "tracr mate sequence" may also be used interchangeably with the term "direct repeat(s)". An exemplary CRISPR-Cas system is illustrated in FIG. 1.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refers to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Several aspects of the invention relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990), the contents of which are incorporated herein by reference. Alternatively, the recombinant expression vector can be transcribed and translated in vitro, for example the lentiviral vectors encompassed in aspects of the invention may comprise a U6 RNA pol III promoter.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-1 (Mol. Cell. Biol., Vol. 8(1), p. 466-472, 1988); SV40 enhancer; and the intron sequence between exons 2 and 3 of rabbit β-globin (Proc.

Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Some methods of the invention can include inducing expression. In some methods of the invention the organism or subject is a eukaryote (including mammal including human) or a non-human eukaryote or a non-human animal or a non-human mammal. In some methods of the invention the organism or subject is a plant. In some methods of the invention the organism or subject is a mammal or a non-human mammal. In some methods of the invention the organism or subject is algae. In some methods of the invention the viral vector is an AAV. In some methods of the invention the viral vector is a lentivirus-derived vector. In some methods of the invention the vector is an *Agrobacterium* Ti or Ri plasmid for use in plants. In some methods of the invention the CRISPR enzyme is a Cas9. In some methods of the invention the CRISPR enzyme comprises one or more mutations in one of the catalytic domains. In some methods of the invention the CRISPR enzyme is a Cas9 nickase. In some methods of the invention the expression of the guide sequence is under the control of the T7 promoter that is driven by the expression of T7 polymerase. In some methods of the invention the expression of the guide sequence is under the control of a U6 promoter.

Two ways to package Cas9 coding nucleic acid molecules, e.g., DNA, into viral vectors to mediate genome modification in vivo are preferred:

To achieve NHEJ-mediated gene knockout:
  Single virus vector:
  Vector containing two or more expression cassettes:
  Promoter-Cas9 coding nucleic acid molecule-terminator
  Promoter-gRNA1-terminator
  Promoter-gRNA2-terminator
  Promoter-gRNA(N)-terminator (up to size limit of vector)
  Double virus vector:
  Vector 1 containing one expression cassette for driving the expression of Cas9
  Promoter-Cas9 coding nucleic acid molecule-terminator
  Vector 2 containing one more expression cassettes for driving the expression of one or more guideRNAs
  Promoter-gRNA1-terminator
  Promoter-gRNA(N)-terminator (up to size limit of vector)
To mediate homology-directed repair:
  In addition to the single and double virus vector approaches described above, an additional vector is used to deliver a homology-direct repair template.

Promoters used to drive Cas9 coding nucleic acid molecule expression are matched to the cell or organism into which the vector is to be expressed. In the case of a eukaryotic organism or cell, various Pol II promoters are available. In one aspect of the invention, the choice of promoter used to drive Cas9 coding nucleic acid molecule expression can include:

AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce toxicity due to over expression of Cas9;

For ubiquitous expression, can use promoters: CMV, CAG, CBh, PGK, SV40, Ferritin heavy or light chains, etc.;

For cell-type specific expression, a variety of Pol II promoters are available. Exemplary promoters can be selected from one or more of the following nonlimiting list:
  For brain expression, can use promoters: SynapsinI for all neurons, CaMKIIalpha for excitatory neurons, GAD67 or GAD65 or VGAT for GABAergic neurons, etc.;
  For liver expression, can use Albumin promoter;
  For lung expression, can use SP-B;
  For endothelial cells, can use ICAM;
  For hematopoietic cells can use IFNbeta or CD45; and
  For Osteoblasts can use OG-2;
  Promoter used to drive guide RNA can include:
Pol III promoters such as U6 or H1;
T7 promoter that is driven by the expression of T7 polymerase;
Use of Pol II promoter and intronic cassettes to express gRNA.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid or capsid AAV1, AAV2, AAV5 or any combination thereof for targeting brain or neuronal cells; and one can select AAV4 for targeting cardiac tissue. AAV8 is useful for delivery to the liver. The above promoters and vectors are preferred individually.

Advantageous vectors include vector systems derived from lentiviruses, adenoviruses and adeno-associated viruses, and types of such vectors can also be selected for targeting particular types of cells. In aspects on the invention the vectors may include but are not limited to packaged vectors. In other aspects of the invention a population of cells or host cells may be transduced with a vector with a low multiplicity of infection (MOI). As used herein the MOI is the ratio of infectious agents (e.g. phage or virus) to infection targets (e.g. cell). For example, when referring to a group of cells inoculated with infectious virus particles, the multiplicity of infection or MOI is the ratio of the number of infectious virus particles to the number of target cells present in a defined space (e.g. a well in a plate). In embodiments of the invention the cells are transduced with an MOI of 0.3-0.75 or 0.3-0.5; in preferred embodiments, the MOI has a value close to 0.4 and in more preferred embodiments the MOI is 0.3. In aspects of the invention the vector library of the invention may be applied to a well of a plate to attain a transduction efficiency of at least 20%, 30%, 40%, 50%, 60%, 70%, or 80%. In a preferred embodiment the transduction efficiency is approximately 30% wherein it may be approximately 370-400 cells per lentiCRISPR construct. In a more preferred embodiment, it may be 400 cells per lentiCRISPR construct.

Vectors may be introduced and propagated in a prokaryote. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector. Examples of vectors for expression in yeast *Saccharomyces cerivisae* include pYepSec1 (Baldari, et al., 1987. *EMBO J.* 6: 229-234), pMFa (Kuijan and Herskowitz, 1982. *Cell* 30: 933-943), pJRY88 (Schultz et al., 1987. *Gene* 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156-2165) and the pVL series (Lucklow and Summers, 1989. *Virology* 170: 31-39).

In some embodiments, a vector is capable of driving expression of one or more sequences in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546).

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In aspects of the invention functional genomics screens allow for discovery of novel human and mammalian therapeutic applications, including the discovery of novel drugs, for, e.g., treatment of genetic diseases, cancer, fungal, protozoal, bacterial, and viral infection, ischemia, vascular disease, arthritis, immunological disorders, etc. As used herein assay systems may be used for a readout of cell state or changes in phenotype include, e.g., transformation assays, e.g., changes in proliferation, anchorage dependence, growth factor dependence, foci formation, growth in soft agar, tumor proliferation in nude mice, and tumor vascularization in nude mice; apoptosis assays, e.g., DNA laddering and cell death, expression of genes involved in apoptosis; signal transduction assays, e.g., changes in intracellular calcium, cAMP, cGMP, IP3, changes in hormone and neurotransmittor release; receptor assays, e.g., estrogen receptor and cell growth; growth factor assays, e.g., EPO, hypoxia and erythrocyte colony forming units assays; enzyme product assays, e.g., FAD-2 induced oil desaturation; transcription assays, e.g., reporter gene assays; and protein production assays, e.g., VEGF ELISAs.

Aspects of the invention relate to modulation of gene expression and modulation can be assayed by determining any parameter that is indirectly or directly affected by the expression of the target candidate gene. Such parameters include, e.g., changes in RNA or protein levels, changes in protein activity, changes in product levels, changes in downstream gene expression, changes in reporter gene transcription (luciferase, CAT, beta-galactosidase, beta-glucuronidase, GFP (see, e.g., Mistili & Spector, Nature Biotechnology 15:961-964 (1997)); changes in signal transduction, phosphorylation and dephosphorylation, receptor-ligand interactions, second messenger concentrations (e.g., cGMP, cAMP, IP3, and $Ca^{2+}$), cell growth, and neovascularization, etc., as described herein. These assays can be in vitro, in vivo, and ex vivo. Such functional effects can be measured by any means known to those skilled in the art, e.g., measurement of RNA or protein levels, measurement of RNA stability, identification of downstream or reporter gene expression, e.g., via chemiluminescence, fluorescence, calorimetric reactions, antibody binding, inducible markers, ligand binding assays; changes in intracellular second messengers such as cGMP and inositol triphosphate (IP3); changes in intracellular calcium levels; cytokine release, and the like, as described herein.

Several methods of DNA extraction and analysis are encompassed in the methods of the invention. As used herein "deep sequencing" indicates that the depth of the process is many times larger than the length of the sequence under study. Deep sequencing is encompassed in next generation sequencing methods which include but are not limited to single molecule real-time sequencing (Pacific Bio), Ion semiconductor (Ion torrent sequencing), Pyrosequencing (454), Sequencing by synthesis (Illumina), Sequencing by ligations (SOLiD sequencing) and Chain termination (Sanger sequencing).

To determine the level of gene expression modulated by the CRISPR-Cas system, cells contacted with the CRISPR-Cas system are compared to control cells, e.g., without the CRISPR-Cas system or with a non-specific CRISPR-Cas system, to examine the extent of inhibition or activation. Control samples may be assigned a relative gene expression activity value of 100%. Modulation/inhibition of gene expression is achieved when the gene expression activity value relative to the control is about 80%, preferably 50% (i.e., 0.5 times the activity of the control), more preferably 25%, more preferably 5-0%. Modulation/activation of gene expression is achieved when the gene expression activity value relative to the control is 110%, more preferably 150% (i.e., 1.5 times the activity of the control), more preferably 200-500%, more preferably 1000-2000% or more.

In general, "CRISPR system" or the "CRISPR-Cas system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing polynucleotide" or "editing sequence". In aspects of the invention, an exogenous template polynucleotide may be referred to as an editing template. In an aspect of the invention the recombination is homologous recombination.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence, it is believed that complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC 1 catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the invention, nickases may be used for genome editing via homologous recombination, For example, FIG. 21 shows genome editing via homologous recombination. FIG. 21 (a) shows the schematic of SpCas9 nickase, with D10A mutation in the RuvC 1 catalytic domain. (b) Schematic representing homologous recombination (HR) at the human EMX1 locus using either sense or antisense single stranded oligonucleotides as repair templates. (c) Sequence of region modified by HR. d, SURVEYOR assay for wildtype (wt) and nickase (D10A) SpCas9-mediated indels at the EMX1 target 1 locus (n=3). Arrows indicate positions of expected fragment sizes.

In some embodiments, a Cas9 nickase may be used in combination with one or more guide sequence(s), e.g., two guide sequences, which target respectively sense and antisense strands of the DNA duplex of the gene target. This combination allows both strands to be nicked and used to induce NHEJ. Applicants have demonstrated (data not shown) the efficacy of two nickase targets (i.e., sgRNAs targeted at the same location but to different strands of DNA) in inducing mutagenic NHEJ. A single nickase (Cas9-D10A with a single sgRNA) is unable to induce NHEJ and create indels but Applicants have shown that double nickase (Cas9-D10A and two sgRNAs targeted to different strands at the same location) can do so in human embryonic stem cells (hESCs). The efficiency is about 50% of nuclease (i.e., regular Cas9 without D10 mutation) in hESCs.

As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMM NNNXGG (SEQ ID NO: 303) where XGG (SEQ ID NO: 304) (N is A, G, T, or C; and X can be anything) has a single occurrence in the genome. A unique target sequence in a genome may include an S. pyogenes Cas9 target site of the form MMMMMMM XGG (SEQ ID NO: 305) where XGG (SEQ ID NO: 306) (N is A, G, T, or C; and X can be anything) has a single occurrence in the genome. For the S. thermophilus CRISPR1 Cas9, a unique target sequence in a genome may include a Cas9 target site of the form MMMMMMM XXAGAAW (SEQ ID NO: 1) where NNNNNNNNNNNNXXAGAAW (N is A, G, T, or C; X can be anything; and W is A or T) (SEQ ID NO: 2) has a single occurrence in the genome. A unique target sequence in a genome may include an S. thermophilus CRISPR1 Cas9 target site of the form MMMMMMM-MMNNNNNNNNNNNNXXAGAAW (SEQ ID NO: 3) where NNNNNNNNNNNNXXAGAAW (N is A, G, T, or C; X can be anything; and W is A or T) (SEQ ID NO: 4) has a single occurrence in the genome. For the S. pyogenes Cas9, a unique target sequence in a genome may include a Cas9 target site of the form MMMMM-MMNNNNNNNNNNNNXGGXG (SEQ ID NO: 307) where NNNNNNNNNNNNXGGXG (SEQ ID NO: 308) (N is A, G, T, or C; and X can be anything) has a single occurrence in the genome. A unique target sequence in a genome may include an S. pyogenes Cas9 target site of the form MMMMMMMMMNNNNNNNNNNNNXGGXG (SEQ ID NO: 309) where NNNNNNNNNNNNXGGXG (SEQ ID NO: 310) (N is A, G, T, or C; and X can be anything) has a single occurrence in the genome. In each of these sequences "M" may be A, G, T, or C, and need not be considered in identifying a sequence as unique.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and PA Carr and GM Church, 2009, Nature Biotechnology 27(12): 1151-62). Further algorithms may be found in U.S. application Ser. No. 61/836,080; incorporated herein by reference.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence.

In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. Example illustrations of optimal alignment between a tracr sequence and a tracr mate sequence are provided in FIGS. 10B and 11B. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. Preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In some embodiments, the single transcript further includes a transcription termination sequence; preferably this is a polyT sequence, for example six T nucleotides. Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNN NNNNNNNNNNNN gttttgtac tct-caagatt taGAAAtaaa tcttgcagaa gctacaaaga taaggcttca tgc-cgaaatc aacaccctgt cattttatgg cagggtgttt tcgttattta aTTTTTT (SEQ ID NO: 5); (2) NNNNNNNNNNNN NNNNNNNNNNNN gttttgtac tctcaGAAAt gcagaagcta caaagataag gcttcatgcc gaaatcaaca ccctgtcatt ttatggcagg gtgttttcgt tatttaaTTT TTT (SEQ ID NO: 6); (3) NNNNNNNNNNNN NNNNNNNNNNNN Ngttttgta ctctcaGAAA tgcagaagct acaaagata aggcttcatgccgaaat-caacaccctgtcattttatggcagggtgtTTTTTT (SEQ ID NO: 7); (4) NNNNNNNNNNNN NNNNNNNNNNNN gttttagagc taGAAAtagc aagttaaaat aaggctagtc cgttatcaac ttgaaaaagt ggcaccgagt cggtgcTTTT TT (SEQ ID NO: 8); (5) NNNNNNNNNNNN NNNNNNNNNNNN gttttagagc taGAAATAGc aagttaaaat aaggctagtccgttatcaacttgaaaaagt-gTTTTTTT (SEQ ID NO: 9); and (6) NNNNNNNNNNNN NNNNNNNNNNNN gttttagagc tagAAATAGc aagttaaaat aaggctagtc cgttatca TTTTTTTT (SEQ ID NO: 10). In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence (such as illustrated in the top portion of FIG. 11B).

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In an aspect of the invention, a reporter gene which includes but is not limited to glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP), may be introduced into a cell to encode a gene product which serves as a marker by which to measure the alteration or modification of expression of the gene product. In a further embodiment of the invention, the DNA molecule encoding the gene product may be introduced into the cell via a vector. In a preferred embodiment of the invention the gene product is luciferase. In a further embodiment of the invention the expression of the gene product is decreased.

In some aspects, the invention provides methods comprising delivering one or more polynucleotides, such as or one or more vectors as described herein, one or more transcripts thereof, and/or one or proteins transcribed therefrom, to a host or target cell. In some aspects, the invention further provides cells produced by such methods, and organisms (such as animals, plants, or fungi) comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Feigner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994). Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700), In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein to arrive at a tissue culture model. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture models are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts;

10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr −/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. In a preferred embodiment of the invention the cells that relate to aspects of the invention are HEK293FT cells. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to transfect cells from a non-human transgenic animal or transgenic plant. In some embodiments, the transgenic animal is a mammal, such as a mouse, rat, or rabbit. In certain embodiments, the organism or subject is a plant. In certain embodiments, the organism or subject or plant is algae. Cells from transgenic animals are also provided, as are transgenic plants, especially crops and algae. The cells of a transgenic animal or plant may be useful in applications outside of providing a disease model. In this regard, cells from transgenic plants, especially pulses and tubers, and animals, especially mammals such as livestock (cows, sheep, goats and pigs), but also poultry and edible insects, are preferred.

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including micro-algae), and modifying the cell or cells. Culturing may occur at any stage ex vivo. The cell or cells may even be re-introduced into the non-human animal or plant (including micro-algae).

In one aspect, the invention provides for methods of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence.

With recent advances in crop genomics, the ability to use CRISPR-Cas systems to perform efficient and cost effective gene editing and manipulation will allow the rapid selection and comparison of single and and multiplexed genetic manipulations to transform such genomes for improved production and enhanced traits. In this regard reference is made to US patents and publications: U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics:advances and applications" Nat Rev Genet. 2011 Dec. 29; 13(2):85-96 are also herein incorporated by reference in their entirety. In some methods of the invention the vector is an *Agrobacterium* Ti or Ri plasmid for use in plants.

In plants, pathogens are often host-specific. For example, *Fusarium oxysporum* f. sp. *lycopersici* causes tomato wilt but attacks only tomato, and *F. oxysporum* f. *dianthii Puccinia graminis* f. sp. *tritici* attacks only wheat. Plants have existing and induced defenses to resist most pathogens. Mutations and recombination events across plant generations lead to genetic variability that gives rise to susceptibility or reduced susceptibility or resistance, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to induce mutations. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

Screening can involve guide library synthesis, cloning of the guide RNA into a vector library to deliver the guides to cells, and the vector can include nucleic acid molecules to express Cas9 or the vector can be sequenctially or co-delivered with one or more other vectors to deliver CRISPR-Cas9 system components, e.g., a second vector that contains nucleic acid molecules to express Cas9, or the cells can be otherwise engineered to express Cas9, whereby the CRISPR-cas system forms. The vector can be any suitable vector for delivery to the desired cell. Many such vectors are herein disclosed, including as to all cells mentioned herein; for instance, as to plants various vectors useful in the practice of the invention are also discussed in the context of crop genomics. The formed CRISPR-Cas9 system can give rise to mutations, e.g., breaks, or nicks, deletions, insertions, or substitutions. As members of the library may target different positions within the DNA of the cells, a library of cells, with potentially multiple genotypes arises. Such mutations may give rise to a desired phenotype. Thus, the library or libraries of cells are screened for selection of the desired phenotype. As to plants, CRISPR-Cas9 allows for targeted mutagenesis, e.g., CRISPR-Cas9 can be a mutagenic agent, plants expressing a desired phenotype from the mutation, e.g., reduced susceptibility or resistance to a pathogen or plant disease, are therefore better identified because the CRISPR-Cas9 system and the nature of the mutation can be correlated, e.g., based on the CRISPR-Cas9, e.g., guide sequence thereof, that induced a favorable mutation, one can appreciate where there was binding, and based on other aspects of the particular CRISPR-Cas9 system, the favorable mutation arising from CRISPR-Cas9 as a mutagenic agent can provide where and how the Cas9 of the system acted; and hence where and how, e.g., the nature of the mutation, is divined by screening using CRISPR-Cas9. Likewise, one can target particular portions of a cell, e.g., plant cell, genome by selection of a CRISPR-Cas9 library directed to portions of that genome, whereby a population having targeted mutations arises, and from the phenotypes of the cells, the skilled person can readily correlate the mutations made to the phenotypes observed, such that when a favorable phenotype is observed, the nature of the CRISPR-Cas9 can provide information as to binding and the nature of the mutation that gave rise to the favorable phenotype, and this can be useful to ascertain whether certain mutations can indeed give rise to favorable phenotypes. CRISPR-Cas9 can be used for revealing and engineering gene functions, including as to all cells mentioned herein, including, for instance plants (including microalgae). Accordingly, CRISPR-Cas9 libraries are a tool, including in creating or screening plant populations, e.g., plant or crop genetics, breeding. Moreover, as there are the GeCKO libraries corresponding to the mouse and human genomes, from this disclosure all that it presents to the knowledge in the art, Applicants believe one skilled in the art can create libraries analogous to the mouse and human GeCKO libraries for any plant without any undue experimentation.

In one aspect, the invention provides kits containing any one or more of the elements disclosed in the above methods and compositions. In some embodiments, the kit comprises a vector system and instructions for using the kit. In some embodiments, the vector system comprises (a) a first regulatory element operably linked to a tracr mate sequence and one or more insertion sites for inserting a guide sequence upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridizable to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. Elements may be provided individually or in combinations, and may be provided in any suitable container, such as a vial, a bottle, or a tube. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples below, and the skilled person will be able to identify further PAM sequences for use with a given CRISPR enzyme.

The target polynucleotide of a CRISPR complex may include a number of disease-associated genes and polynucleotides as well as signaling biochemical pathway-associated genes and polynucleotides as listed in U.S. provisional patent applications 61/736,527 and 61/748,427 respectively, both entitled SYSTEMS METHODS AND COMPOSITIONS FOR SEQUENCE MANIPULATION filed on Dec. 12, 2012 and Jan. 2, 2013, respectively, the contents of all of which are herein incorporated by reference in their entirety. The target polynucleotide of a CRISPR complex can be a gene of previously unknown function wherein its presence or absence in a screen (integrated barcode of the sgRNA) reveals details about its function. The target polynucleotide of a CRISPR complex may also be a gene whose interaction with the screening agent (eg. drug or other selection agent) is discovered through its presence or absence in cells (barcode of the sgRNA) in the screen. Hence, in an aspect of the invention new drugs or pharmaceutical compositions may be tested for performance against all possible genetic KOs (or a subset of possible KOs; for example, genes associated with a particular enzymatic pathway) to understand how different organisms, e.g., humans (who carry different genetic KOs) might react to the drug and in which genetic background the drug might work better or worse.

Examples of genes and genomic loci that may be targeted by the CRISPR-Cas system guide RNA sequences described in Tables 1 and 10 (as provided in the compact discs created Apr. 11, 2014, as filed in connection with U.S. applications 61/960,777 and 61/995,636) may include but are not limited to sequences associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web.

Examples of disease-associated genes and polynucleotides are listed in Tables A and B. Disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web. Examples of signaling biochemical pathway-associated genes and polynucleotides are listed in Table C.

Mutations in these genes and pathways can result in production of improper proteins or proteins in improper amounts which affect function. Further examples of genes, diseases and proteins are hereby incorporated by reference from U.S. Provisional applications 61/736,527 and 61/748,427. Such genes, proteins and pathways may be the target polynucleotide of a CRISPR complex.

TABLE A

| DISEASE/DISORDERS | GENE(S) |
| --- | --- |
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Nestn); PEN-2 |
| Others | Nos1; Parp1; Nat1; Nat2 |
| Prion - related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |

TABLE A-continued

| DISEASE/DISORDERS | GENE(S) |
| --- | --- |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE B

| | |
| --- | --- |
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1 TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3); Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, |

TABLE B-continued

| | |
|---|---|
| | LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado- Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR (Alzheimer's), Atxn7, Atxn10). |
| Occular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE C

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; |

TABLE C-continued

| CELLULAR FUNCTION | GENES |
|---|---|
| | PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; E1F4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4, AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKC1; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |

TABLE C-continued

| CELLULAR FUNCTION | GENES |
|---|---|
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ: TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4: PDGFRB; TNF; |

TABLE C-continued

| CELLULAR FUNCTION | GENES |
|---|---|
| | INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5: PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2: ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2: MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |

TABLE C-continued

| CELLULAR FUNCTION | GENES |
|---|---|
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA, PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |

TABLE C-continued

| CELLULAR FUNCTION | GENES |
|---|---|
| VDR/RXR Activation | PRKCE; EP300; PRKCZ; RXRA; GADD45A; HES1; NCOR2; SP1; PRKC1; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1, MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/ Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |

TABLE C-continued

| CELLULAR FUNCTION | GENES |
|---|---|
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |

TABLE C-continued

| CELLULAR FUNCTION | GENES |
|---|---|
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 or Brn3a); Numb; Reln |

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011—Medical). Specific aspects of tandem repeat sequences have been found to be responsible for more than twenty human diseases (New insights into repeat instability: role of RNA•DNA hybrids. McIvor EI, Polak U, Napierala M. RNA Biol. 2010 September-October; 7(5):551-8). The CRISPR-Cas system may be harnessed to correct these defects of genomic instability.

A further aspect of the invention relates to utilizing the CRISPR-Cas system for correcting defects in the EMP2A and EMP2B genes that have been identified to be associated with Lafora disease. Lafora disease is an autosomal recessive condition which is characterized by progressive myoclonus epilepsy which may start as epileptic seizures in adolescence. A few cases of the disease may be caused by mutations in genes yet to be identified. The disease causes seizures, muscle spasms, difficulty walking, dementia, and eventually death. There is currently no therapy that has proven effective against disease progression. Other genetic abnormalities associated with epilepsy may also be targeted by the CRISPR-Cas system and the underlying genetics is further described in Genetics of Epilepsy and Genetic Epilepsies, edited by Giuliano Avanzini, Jeffrey L. Noebels, Mariani Foundation Paediatric Neurology:20; 2009).

In yet another aspect of the invention, the CRISPR-Cas system may be used to correct ocular defects that arise from several genetic mutations further described in Genetic Diseases of the Eye, Second Edition, edited by Elias I. Traboulsi, Oxford University Press, 2012.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

In some embodiments, the condition may be neoplasia. In some embodiments, where the condition is neoplasia, the genes to be targeted are any of those listed in Table A (in this case PTEN asn so forth). In some embodiments, the condition may be Age-related Macular Degeneration. In some embodiments, the condition may be a Schizophrenic Disorder. In some embodiments, the condition may be a Trinucleotide Repeat Disorder. In some embodiments, the condition may be Fragile X Syndrome. In some embodiments, the condition may be a Secretase Related Disorder. In some embodiments, the condition may be a Prion—related disorder. In some embodiments, the condition may be ALS. In some embodiments, the condition may be a drug addiction. In some embodiments, the condition may be Autism. In some embodiments, the condition may be Alzheimer's Disease. In some embodiments, the condition may be inflammation. In some embodiments, the condition may be Parkinson's Disease.

Examples of proteins associated with Parkinson's disease include but are not limited to α-synuclein, DJ-1, LRRK2, PINK1, Parkin, UCHL1, Synphilin-1, and NURR1. Examples of addiction-related proteins may include ABAT for example.

Examples of inflammation-related proteins may include the monocyte chemoattractant protein-1 (MCP1) encoded by the Ccr2 gene, the C—C chemokine receptor type 5 (CCR5) encoded by the Ccr5 gene, the IgG receptor IIB (FCGR2b, also termed CD32) encoded by the Fcgr2b gene, or the Fc epsilon R1g (FCER1g) protein encoded by the Fcer1g gene, for example.

Examples of cardiovascular diseases associated proteins may include IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), or CTSK (cathepsin K), for example.

Examples of Alzheimer's disease associated proteins may include the very low density lipoprotein receptor protein (VLDLR) encoded by the VLDLR gene, the ubiquitin-like modifier activating enzyme 1 (UBA1) encoded by the UBA1 gene, or the NEDD8-activating enzyme E1 catalytic subunit protein (UBE1C) encoded by the UBA3 gene, for example.

Examples of proteins associated Autism Spectrum Disorder may include the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, or the fragile X mental retardation autosomal homolog 2 protein (FXR2) encoded by the FXR2 gene, for example.

Examples of proteins associated Macular Degeneration may include the ATP-binding cassette, sub-family A (ABC1) member 4 protein (ABCA4) encoded by the ABCR gene, the apolipoprotein E protein (APOE) encoded by the APOE gene, or the chemokine (C—C motif) Ligand 2 protein (CCL2) encoded by the CCL2 gene, for example.

Examples of proteins associated Schizophrenia may include NRG1, ErbB4, CPLX1, TPH1, TPH2, NRXN1, GSK3A, BDNF, DISC1, GSK3B, and combinations thereof.

Examples of proteins involved in tumor suppression may include ATM (ataxia telangiectasia mutated), ATR (ataxia telangiectasia and Rad3 related), EGFR (epidermal growth factor receptor), ERBB2 (v-erb-b2 erythroblastic leukemia viral oncogene homolog 2), ERBB3 (v-erb-b2 erythroblastic leukemia viral oncogene homolog 3), ERBB4 (v-erb-b2 erythroblastic leukemia viral oncogene homolog 4), Notch 1, Notch 2, Notch 3, or Notch 4, for example.

Examples of proteins associated with a secretase disorder may include PSENEN (presenilin enhancer 2 homolog (*C. elegans*)), CTSB (cathepsin B), PSEN1 (presenilin 1), APP (amyloid beta (A4) precursor protein), APH1B (anterior pharynx defective 1 homolog B (*C. elegans*)), PSEN2 (presenilin 2 (Alzheimer disease 4)), or BACE1 (beta-site APP-cleaving enzyme 1), for example.

Examples of proteins associated with Amyotrophic Lateral Sclerosis may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins associated with prion diseases may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins related to neurodegenerative conditions in prion disorders may include A2M (Alpha-2-Macroglobulin), AATF (Apoptosis antagonizing transcription factor), ACPP (Acid phosphatase prostate), ACTA2 (Actin alpha 2 smooth muscle aorta), ADAM22 (ADAM metallopeptidase domain), ADORA3 (Adenosine A3 receptor), or ADRA1D (Alpha-1D adrenergic receptor for Alpha-1D adrenoreceptor), for example.

Examples of proteins associated with Immunodeficiency may include A2M [alpha-2-macroglobulin]; AANAT [arylalkylamine N-acetyltransferase]; ABCA1 [ATP-binding cassette, sub-family A (ABC1), member 1]; ABCA2 [ATP-binding cassette, sub-family A (ABC1), member 2]; or ABCA3 [ATP-binding cassette, sub-family A (ABC1), member 3]; for example.

Examples of proteins associated with Trinucleotide Repeat Disorders include AR (androgen receptor), FMR1 (fragile X mental retardation 1), HTT (huntingtin), or DMPK (dystrophia myotonica-protein kinase), FXN (frataxin), ATXN2 (ataxin 2), for example.

Examples of proteins associated with Neurotransmission Disorders include SST (somatostatin), NOS1 (nitric oxide synthase 1 (neuronal)), ADRA2A (adrenergic, alpha-2A-, receptor), ADRA2C (adrenergic, alpha-2C-, receptor), TACR1 (tachykinin receptor 1), or HTR2c (5-hydroxytryptamine (serotonin) receptor 2C), for example.

Examples of neurodevelopmental-associated sequences include A2BP1 [ataxin 2-binding protein 1], AADAT [aminoadipate aminotransferase], AANAT [arylalkylamine N-acetyltransferase], ABAT [4-aminobutyrate aminotransferase], ABCA1 [ATP-binding cassette, sub-family A (ABC1), member 1], or ABCA13 [ATP-binding cassette, sub-family A (ABC1), member 13], for example.

Further examples of preferred conditions treatable with the present system include may be selected from: Aicardi-Goutières Syndrome; Alexander Disease; Allan-Herndon-Dudley Syndrome; POLG-Related Disorders; Alpha-Mannosidosis (Type II and III); Alström Syndrome; Angelman; Syndrome; Ataxia-Telangiectasia; Neuronal Ceroid-Lipofuscinoses; Beta-Thalassemia; Bilateral Optic Atrophy and (Infantile) Optic Atrophy Type 1; Retinoblastoma (bilateral); Canavan Disease; Cerebrooculofacioskeletal Syndrome 1 [COFS1]; Cerebrotendinous Xanthomatosis; Cornelia de Lange Syndrome; MAPT-Related Disorders; Genetic Prion Diseases; Dravet Syndrome; Early-Onset Familial Alzheimer Disease; Friedreich Ataxia [FRDA]; Fryns Syndrome; Fucosidosis; Fukuyama Congenital Muscular Dystrophy; Galactosialidosis; Gaucher Disease; Organic Acidemias; Hemophagocytic Lymphohistiocytosis; Hutchinson-Gilford Progeria Syndrome; Mucolipidosis II; Infantile Free Sialic Acid Storage Disease; PLA2G6-Associated Neurodegeneration; Jervell and Lange-Nielsen Syndrome; Junctional Epidermolysis Bullosa; Huntington Disease; Krabbe Disease (Infantile); Mitochondrial DNA-Associated Leigh Syndrome and NARP; Lesch-Nyhan Syndrome; LISI-Associated Lissencephaly; Lowe Syndrome; Maple Syrup Urine Disease; MECP2 Duplication Syndrome; ATP7A-Related Copper Transport Disorders; LAMA2-Related Muscular Dystrophy; Arylsulfatase A Deficiency; Mucopolysaccharidosis Types I, II or III; Peroxisome Biogenesis Disorders, Zellweger Syndrome Spectrum; Neurodegeneration with Brain Iron Accumulation Disorders; Acid Sphingomyelinase Deficiency; Niemann-Pick Disease Type C; Glycine Encephalopathy; ARX-Related Disorders; Urea Cycle Disorders; COL1A1/2-Related Osteogenesis Imperfecta; Mitochondrial DNA Deletion Syndromes; PLP1-Related Disorders; Perry Syndrome; Phelan-McDermid Syndrome; Glycogen Storage Disease Type II (Pompe Disease) (Infantile); MAPT-Related Disorders; MECP2-Related Disorders; Rhizomelic Chondrodysplasia Punctata Type 1; Roberts Syndrome; Sandhoff Disease; Schindler Disease —Type 1; Adenosine Deaminase Deficiency; Smith-Lemli-Opitz Syndrome; Spinal Muscular Atrophy; Infantile-Onset Spinocerebellar Ataxia; Hexosaminidase A Deficiency; Thanatophoric Dysplasia Type 1; Collagen Type VI-Related Disorders; Usher Syndrome Type I; Congenital Muscular Dystrophy; Wolf-Hirschhorn Syndrome; Lysosomal Acid Lipase Deficiency; and Xeroderma Pigmentosum.

As will be apparent, it is envisaged that the present system can be used to target any polynucleotide sequence of interest. Some examples of conditions or diseases that might be usefully treated using the present system are included in the Tables above and examples of genes currently associated with those conditions are also provided there. However, the genes exemplified are not exhaustive.

EXAMPLES

Figure 2A:
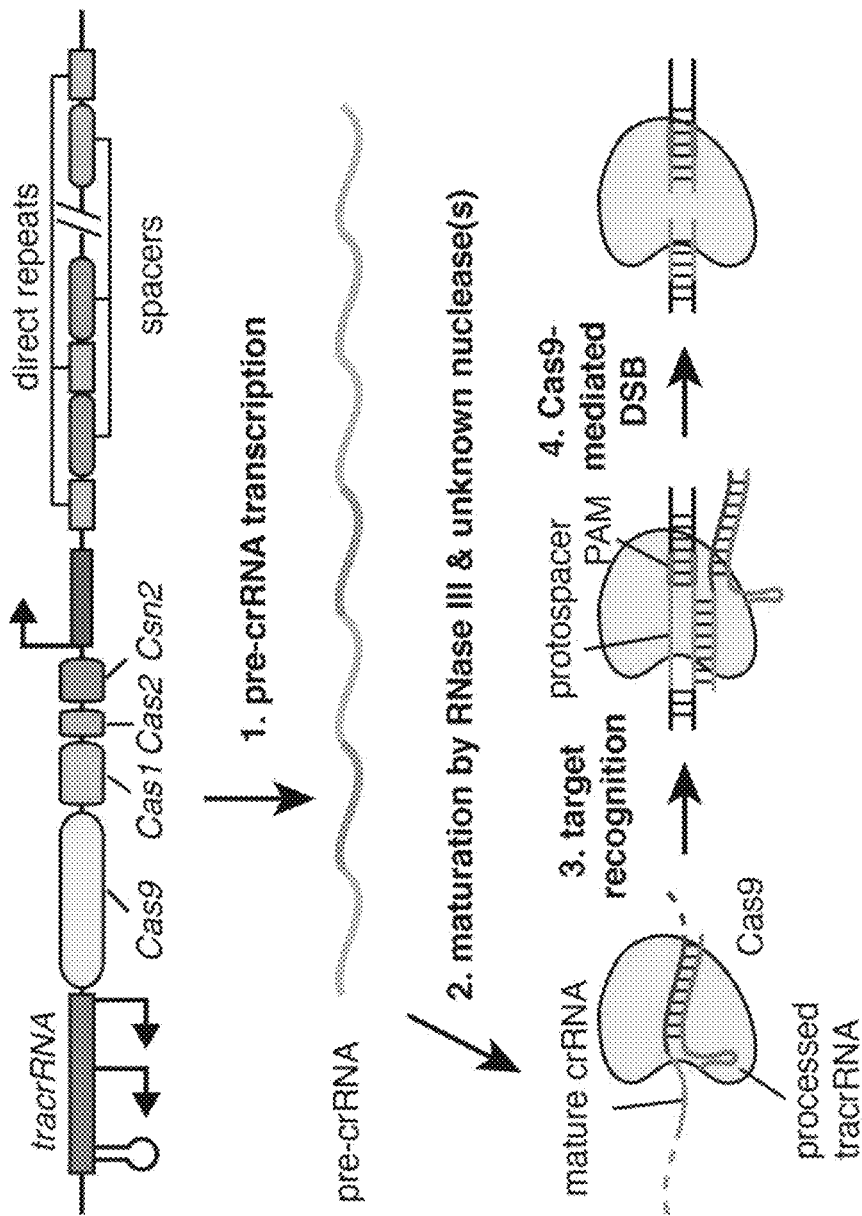
Figure 2B:
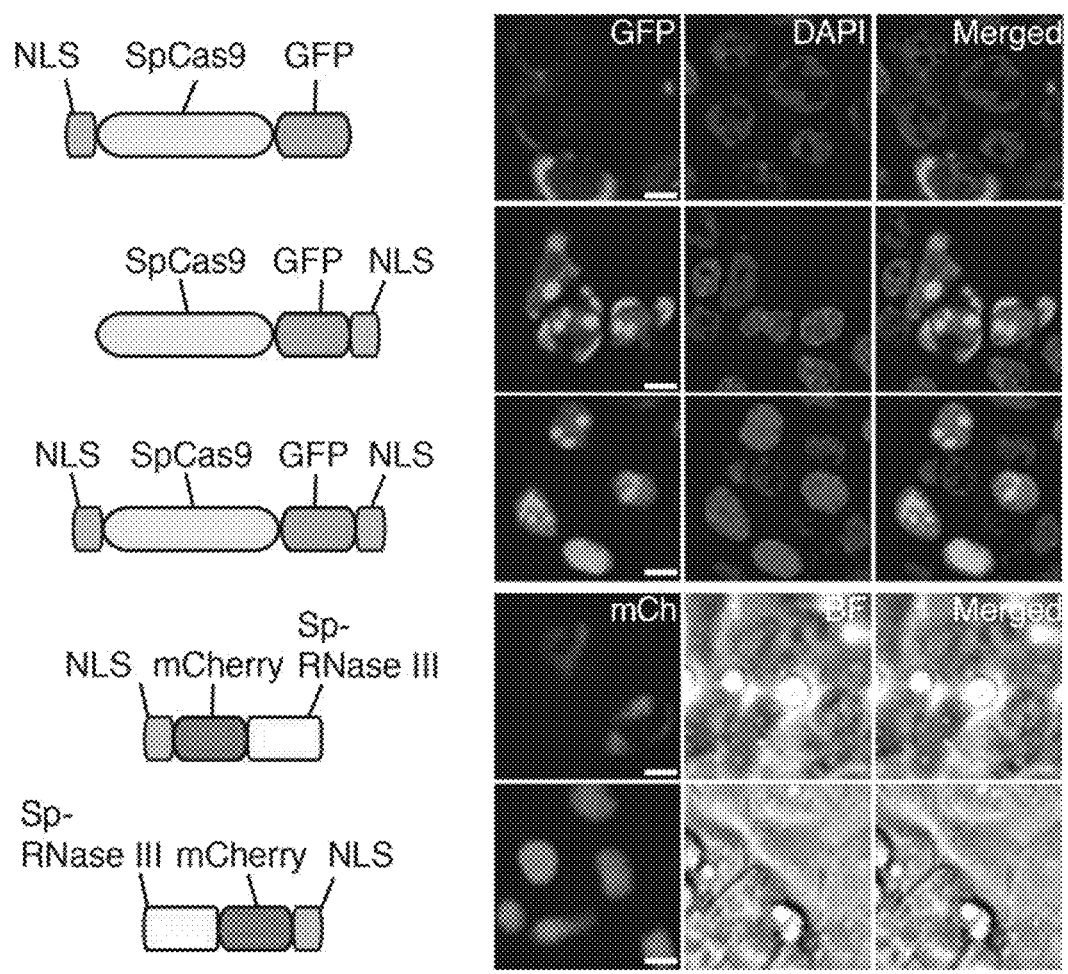

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are Example 1: CRISPR Complex Activity in the Nucleus of a Eukaryotic Cell An example type II CRISPR system is the type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps (FIG. 2A). First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer (FIG. 2A). This example describes an example process for adapting this RNA-programmable nuclease system to direct CRISPR complex activity in the nuclei of eukaryotic cells.

Cell Culture and Transfection

Human embryonic kidney (HEK) cell line HEK 293FT (Life Technologies) was maintained in Dulbecco's modified Eagle's Medium (DMEM) supplemented with 10% fetal bovine serum (HyClone), 2 mM GlutaMAX (Life Technologies), 100 U/mL penicillin, and 100 μg/mL streptomycin at 37° C. with 5% $CO_2$ incubation. Mouse neuro2A (N2A) cell line (ATCC) was maintained with DMEM supplemented with 5% fetal bovine serum (HyClone), 2 mM GlutaMAX (Life Technologies), 100 U/mL penicillin, and 100 μg/mL streptomycin at 37° C. with 5% $CO_2$.

HEK 293FT or N2A cells were seeded into 24-well plates (Corning) one day prior to transfection at a density of 200,000 cells per well. Cells were transfected using Lipofectamine 2000 (Life Technologies) following the manufacturer's recommended protocol. For each well of a 24-well plate a total of 800 ng of plasmids was used.

Surveyor Assay and Sequencing Analysis for Genome Modification

HEK 293FT or N2A cells were transfected with plasmid DNA as described above. After transfection, the cells were incubated at 37° C. for 72 hours before genomic DNA extraction. Genomic DNA was extracted using the Quick-Extract DNA extraction kit (Epicentre) following the manufacturer's protocol. Briefly, cells were resuspended in QuickExtract solution and incubated at 65° C. for 15 minutes and 98° C. for 10 minutes. Extracted genomic DNA was immediately processed or stored at −20° C.

Figure 7:
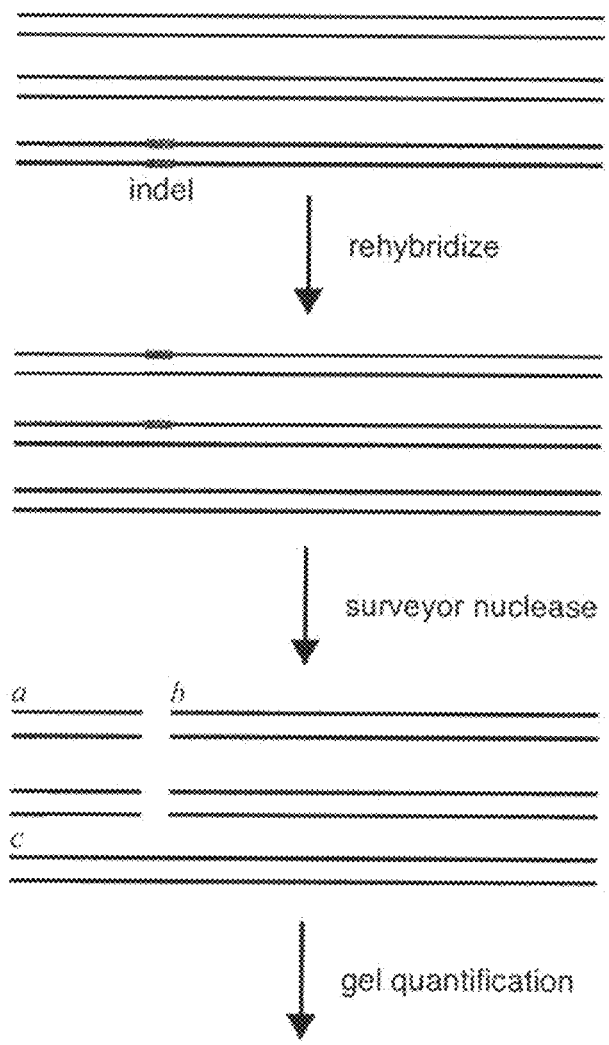
FIG. 7 shows a schematic of a surveyor nuclease assay for detection of double strand break-induced micro-insertions and micro-deletions.

The genomic region surrounding a CRISPR target site for each gene was PCR amplified, and products were purified using QiaQuick Spin Column (Qiagen) following manufacturer's protocol. A total of 400 ng of the purified PCR products were mixed with 2 μl 10× Taq polymerase PCR buffer (Enzymatics) and ultrapure water to a final volume of 20 μl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 minute. After re-annealing, products were treated with Surveyor nuclease and Surveyor enhancer S (Transgenomics) following the manufacturer's recommended protocol, and analyzed on 4-20% Novex TBE poly-acrylamide gels (Life Technologies). Gels were stained with SYBR Gold DNA stain (Life Technologies) for 30 minutes and imaged with a Gel Doc gel imaging system (Bio-rad). Quantification was based on relative band intensities, as a measure of the fraction of cleaved DNA. FIG. 7 provides a schematic illustration of this Surveyor assay.

Restriction Fragment Length Polymorphism Assay for Detection of Homologous Recombination.

HEK 293FT and N2A cells were transfected with plasmid DNA, and incubated at 37° C. for 72 hours before genomic DNA extraction as described above. The target genomic region was PCR amplified using primers outside the homology arms of the homologous recombination (HR) template. PCR products were separated on a 1% agarose gel and extracted with MinElute GelExtraction Kit (Qiagen). Purified products were digested with HindIII (Fermentas) and analyzed on a 6% Novex TBE poly-acrylamide gel (Life Technologies).

RNA Secondary Structure Prediction and Analysis

RNA secondary structure prediction was performed using the online webserver RNAfold developed at Institute for Theoretical Chemistry at the University of Vienna, using the centroid structure prediction algorithm (see e.g. A. R. Gruber et al., 2008, Cell 106(1): 23-24; and PA Carr and GM Church, 2009, Nature Biotechnology 27(12): 1151-62).

RNA Purification

HEK 293FT cells were maintained and transfected as stated above. Cells were harvested by trypsinization followed by washing in phosphate buffered saline (PBS). Total cell RNA was extracted with TRI reagent (Sigma) following manufacturer's protocol. Extracted total RNA was quantified using Naonodrop (Thermo Scientific) and normalized to same concentration.

Northern Blot Analysis of crRNA and tracrRNA Expression in Mammalian Cells

RNAs were mixed with equal volumes of 2× loading buffer (Ambion), heated to 95° C. for 5 min, chilled on ice for 1 min, and then loaded onto 8% denaturing polyacrylamide gels (SequaGel, National Diagnostics) after pre-running the gel for at least 30 minutes. The samples were electrophoresed for 1.5 hours at 40 W limit. Afterwards, the RNA was transferred to Hybond N+ membrane (GE Healthcare) at 300 mA in a semi-dry transfer apparatus (Bio-rad) at room temperature for 1.5 hours. The RNA was crosslinked to the membrane using autocrosslink button on Stratagene UV Crosslinker the Stratalinker (Stratagene). The membrane was pre-hybridized in ULTRAhyb-Oligo Hybridization Buffer (Ambion) for 30 min with rotation at 42° C., and probes were then added and hybridized overnight. Probes were ordered from IDT and labeled with [gamma-$^{32}$P] ATP (Perkin Elmer) with T4 polynucleotide kinase (New England Biolabs). The membrane was washed once with pre-warmed (42° C.) 2×SSC, 0.5% SDS for 1 min followed by two 30 minute washes at 42° C. The membrane was exposed to a phosphor screen for one hour or overnight at room temperature and then scanned with a phosphorimager (Typhoon).

Bacterial CRISPR System Construction and Evaluation

Figure 6A:
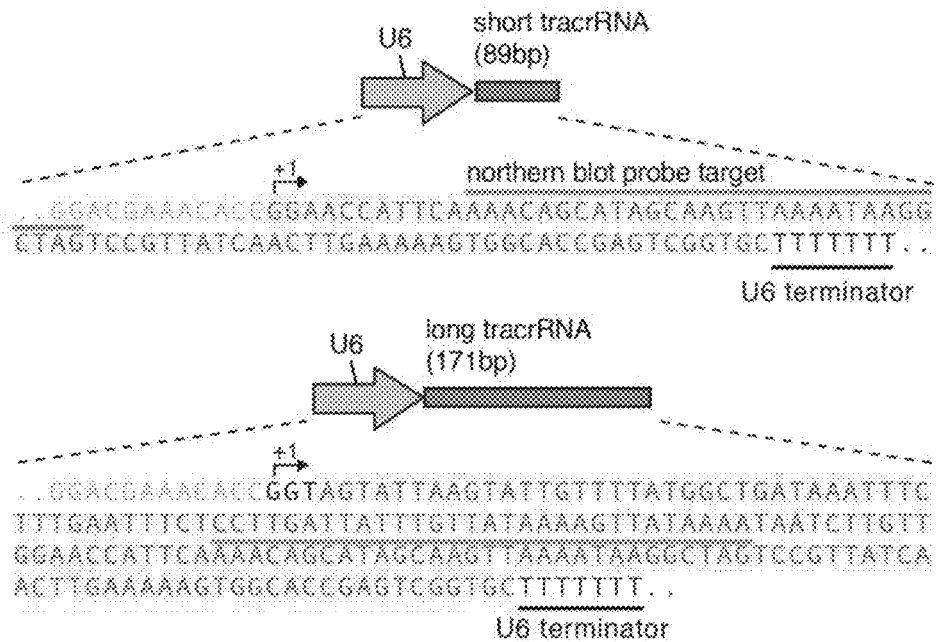
FIG. 6A-6C shows a comparison of different tracrRNA transcripts for Cas9-mediated gene targeting.
Figure 6B:
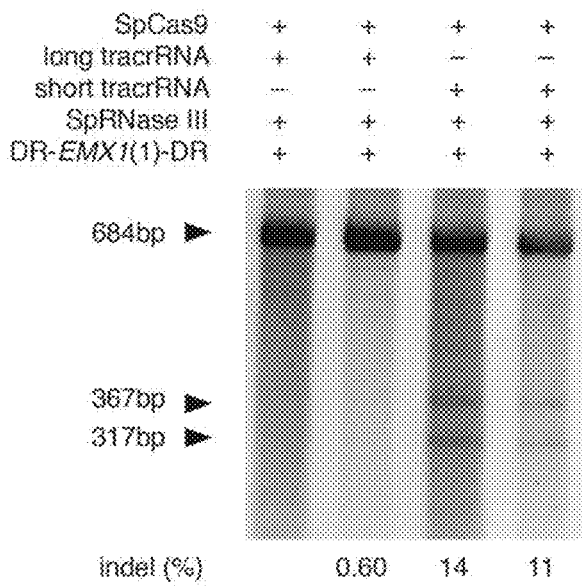
Figure 6C:
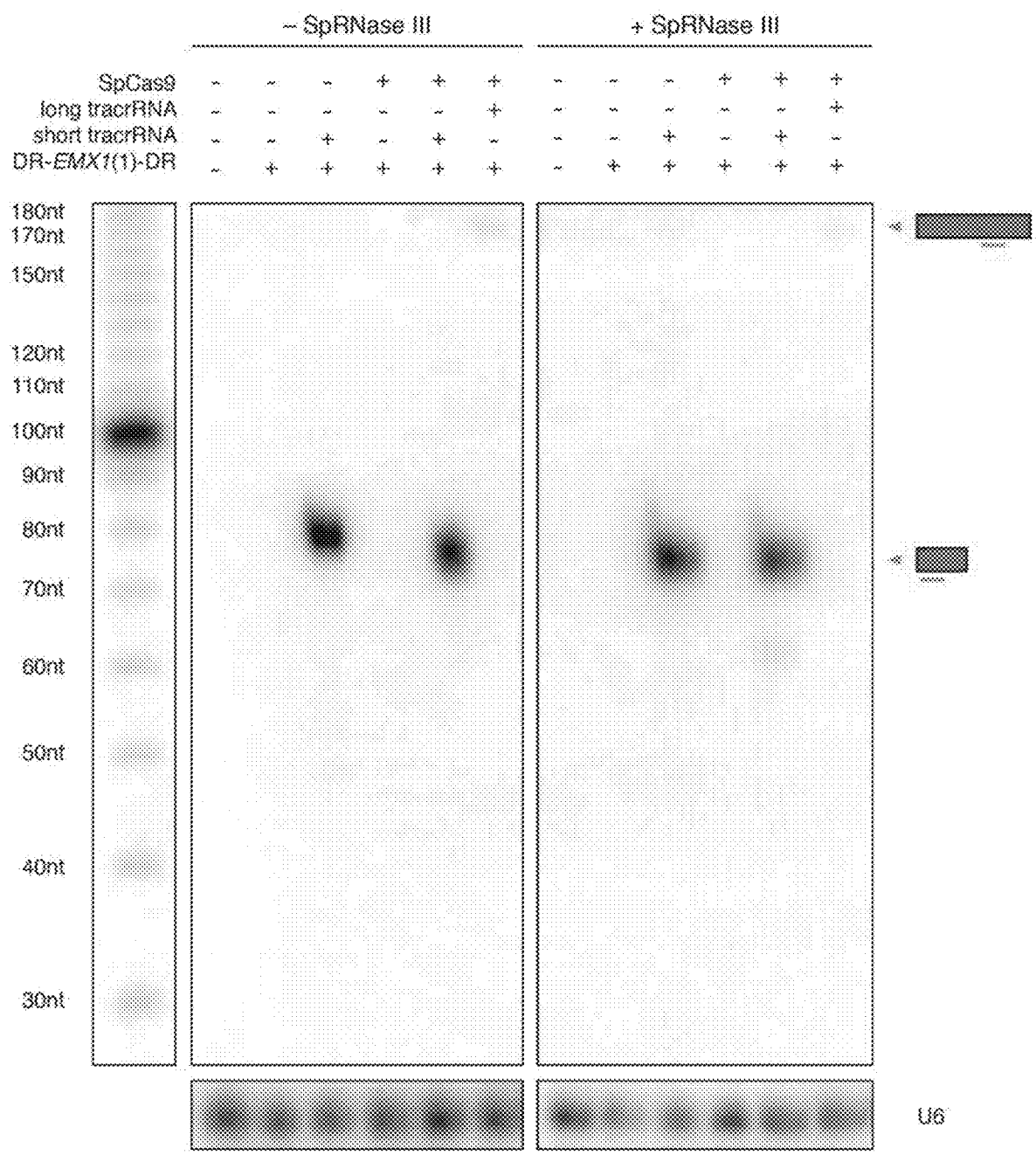

CRISPR locus elements, including tracrRNA, Cas9, and leader were PCR amplified from *Streptococcus pyogenes* SF370 genomic DNA with flanking homology arms for Gibson Assembly. Two BsaI type IIS sites were introduced in between two direct repeats to facilitate easy insertion of spacers (FIG. 8). PCR products were cloned into EcoRV-digested pACYC184 downstream of the tet promoter using Gibson Assembly Master Mix (NEB). Other endogenous CRISPR system elements were omitted, with the exception of the last 50 bp of Csn2. Oligos (Integrated DNA Technology) encoding spacers with complimentary overhangs were cloned into the BsaI-digested vector pDC000 (NEB) and then ligated with T7 ligase (Enzymatics) to generate pCRISPR plasmids. Challenge plasmids containing spacers with PAM expression in mammalian cells (expression constructs illustrated in FIG. 6A, with functionality as determined by results of the Surveyor assay shown in FIG. 6B). Transcription start sites are marked as +1, and transcription terminator and the sequence probed by northern blot are also indicated. Expression of processed tracrRNA was also confirmed by Northern blot. FIG. 6C shows results of a Northern blot analysis of total RNA extracted from 293FT cells transfected with U6 expression constructs carrying long or short tracrRNA, as well as SpCas9 and DR-EMX1(1)-DR. Left and right panels are from 293FT cells transfected without or with SpRNase III, respectively. U6 indicate loading control blotted with a probe targeting human U6 snRNA. Transfection of the short tracrRNA expression construct led to abundant levels of the processed form of tracrRNA (~75 bp). Very low amounts of long tracrRNA are detected on the Northern blot.

Figure 2C:
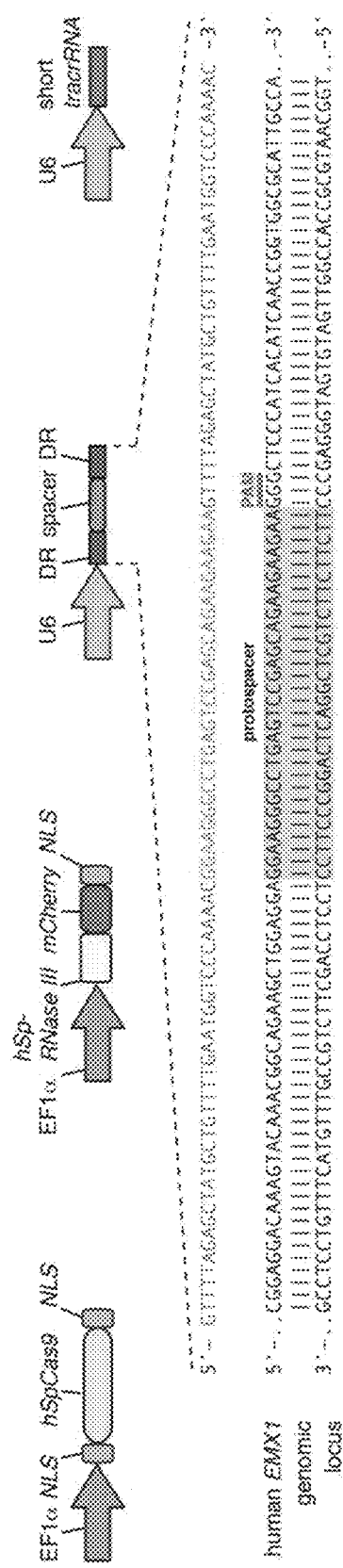

To promote precise transcriptional initiation, the RNA polymerase III-based U6 promoter was selected to drive the expression of tracrRNA (FIG. 2C). Similarly, a U6 promoter-based construct was developed to express a pre-crRNA array consisting of a single spacer flanked by two direct repeats (DRs, also encompassed by the term "tracr-mate sequences"; FIG. 2C). The initial spacer was designed to target a 33-base-pair (bp) target site (30-bp protospacer plus a 3-bp CRISPR motif (PAM) sequence satisfying the NGG recognition motif of Cas9) in the human EMX1 locus (FIG. 2C), a key gene in the development of the cerebral cortex.

Figure 2D:
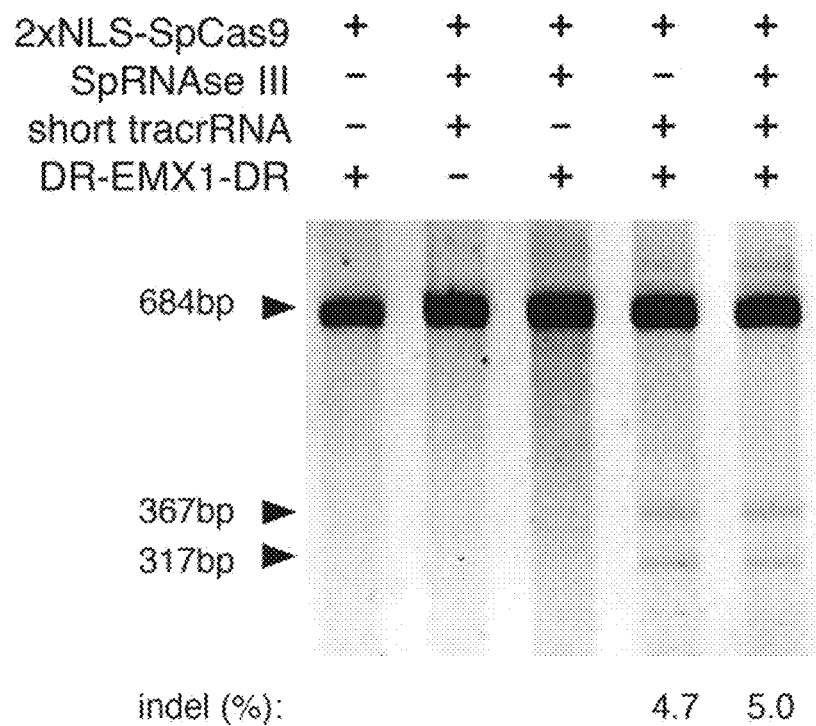

To test whether heterologous expression of the CRISPR system (SpCas9, SpRNase III, tracrRNA, and pre-crRNA) in mammalian cells can achieve targeted cleavage of mammalian chromosomes, HEK 293FT cells were transfected with combinations of CRISPR components. Since DSBs in mammalian nuclei are partially repaired by the non-homologous end joining (NHEJ) pathway, which leads to the formation of indels, the Surveyor assay was used to detect potential cleavage activity at the target EMX1 locus (FIG. 7) (see e.g. Guschin et al., 2010, Methods Mol Biol 649: 247). Co-transfection of all four CRISPR components was able to induce up to 5.0% cleavage in the protospacer (see FIG. 2D). Co-transfection of all CRISPR components minus SpRNase III also induced up to 4.7% indel in the protospacer, suggesting that there may be endogenous mammalian RNases that are capable of assisting with crRNA maturation, such as for example the related Dicer and Drosha enzymes. Removing any of the remaining three components abolished the genome cleavage activity of the CRISPR system (FIG. 2D). Sanger sequencing of amplicons containing the target locus verified the cleavage activity: in 43 sequenced clones, 5 mutated alleles (11.6%) were found. Similar experiments using a variety of guide sequences produced indel percentages as high as 29% (see FIGS. 3-6, 10, and 11). These results define a three-component system for efficient CRISPR-mediated genome modification in mammalian cells. To optimize the cleavage efficiency, Applicants also tested whether different isoforms of tracrRNA affected the cleavage efficiency and found that, in this example system, only the short (89-bp) transcript form was able to mediate cleavage of the human EMX1 genomic locus (FIG. 6B).

Figure 12A:
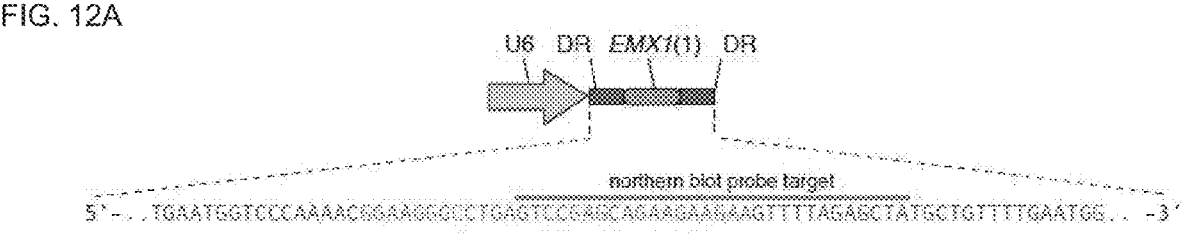
FIG. 12A-12B shows the results of a Northern blot analysis of crRNA processing in mammalian cells.
Figure 12B:
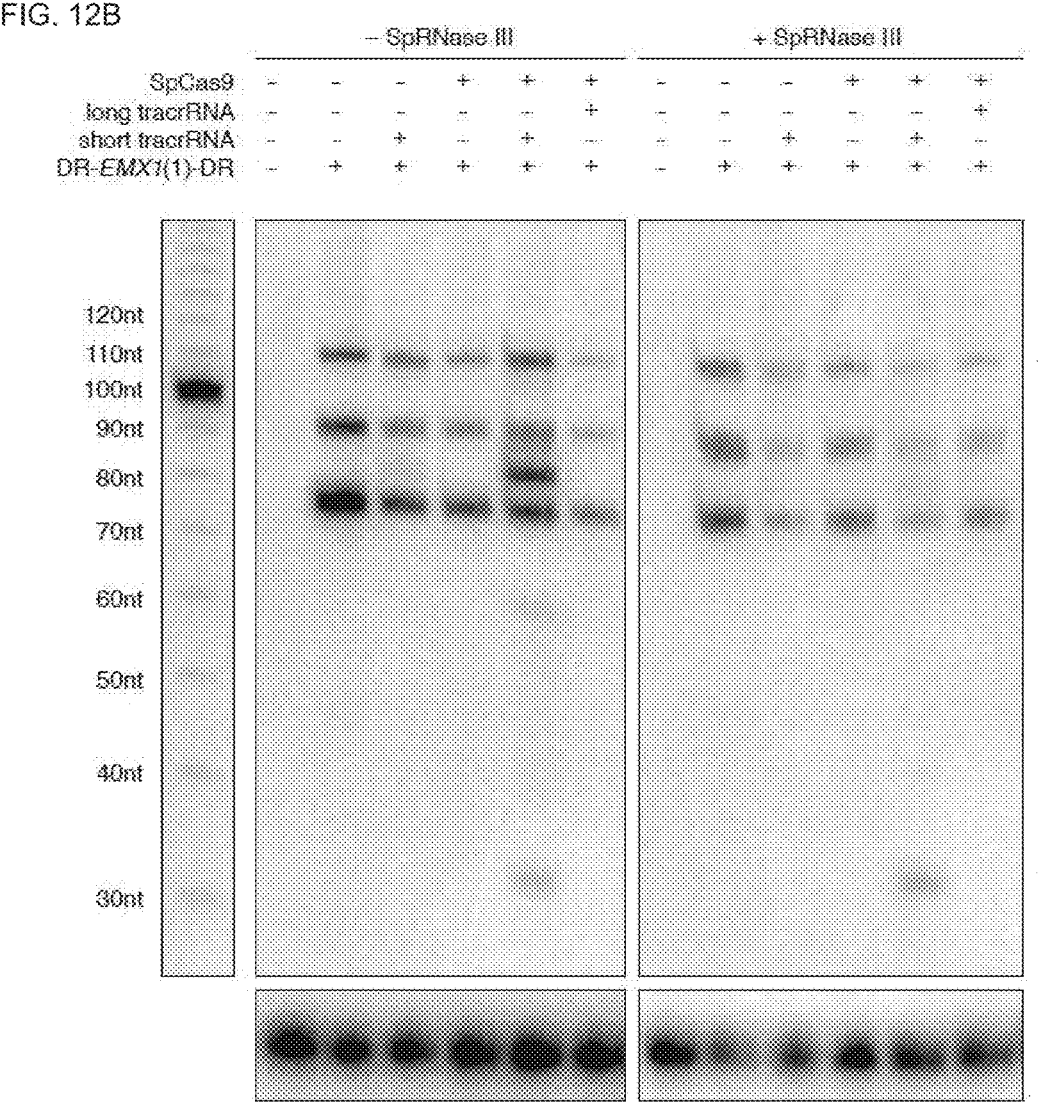

FIG. 12 provides an additional Northern blot analysis of crRNA processing in mammalian cells. FIG. 12A illustrates a schematic showing the expression vector for a single spacer flanked by two direct repeats (DR-EMX1(1)-DR). The 30 bp spacer targeting the human EMX1 locus protospacer 1 (see FIG. 6) and the direct repeat sequences are shown in the sequence beneath FIG. 12A. The line indicates the region whose reverse-complement sequence was used to generate Northern blot probes for EMX1(1) crRNA detection. FIG. 12B shows a Northern blot analysis of total RNA extracted from 293FT cells transfected with U6 expression constructs carrying DR-EMX1(1)-DR. Left and right panels are from 293FT cells transfected without or with SpRNase III respectively. DR-EMX1(1)-DR was processed into mature crRNAs only in the presence of SpCas9 and short tracrRNA and was not dependent on the presence of SpRNase III. The mature crRNA detected from transfected 293FT total RNA is ~33 bp and is shorter than the 39-42 bp mature crRNA from S. pyogenes. These results demonstrate that a CRISPR system can be transplanted into eukaryotic cells and reprogrammed to facilitate cleavage of endogenous mammalian target polynucleotides.

FIG. 2 illustrates the bacterial CRISPR system described in this example. FIG. 2A illustrates a schematic showing the CRISPR locus 1 from Streptococcus pyogenes SF370 and a proposed mechanism of CRISPR-mediated DNA cleavage by this system. Mature crRNA processed from the direct repeat-spacer array directs Cas9 to genomic targets consisting of complimentary protospacers and a protospacer-adjacent motif (PAM). Upon target-spacer base pairing, Cas9 mediates a double-strand break in the target DNA. FIG. 2B illustrates engineering of S. pyogenes Cas9 (SpCas9) and RNase III (SpRNase III) with nuclear localization signals (NLSs) to enable import into the mammalian nucleus. FIG. 2C illustrates mammalian expression of SpCas9 and SpRNase III driven by the constitutive EF1α promoter and tracrRNA and pre-crRNA array (DR-Spacer-DR) driven by the RNA Pol3 promoter U6 to promote precise transcription initiation and termination. A protospacer from the human EMX1 locus with a satisfactory PAM sequence is used as the spacer in the pre-crRNA array. FIG. 2D illustrates surveyor nuclease assay for SpCas9-mediated minor insertions and deletions. SpCas9 was expressed with and without SpRNase III, tracrRNA, and a pre-crRNA array carrying the EMX1-target spacer. FIG. 2E illustrates a schematic representation of base pairing between target locus and EMX1-targeting crRNA, as well as an example chromatogram showing a micro deletion adjacent to the SpCas9 cleavage site. FIG. 2F illustrates mutated alleles identified from sequencing analysis of 43 clonal amplicons showing a variety of micro insertions and deletions. Dashes indicate deleted bases, and non-aligned or mismatched bases indicate insertions or mutations. Scale bar=10 μm.

Figure 8A:
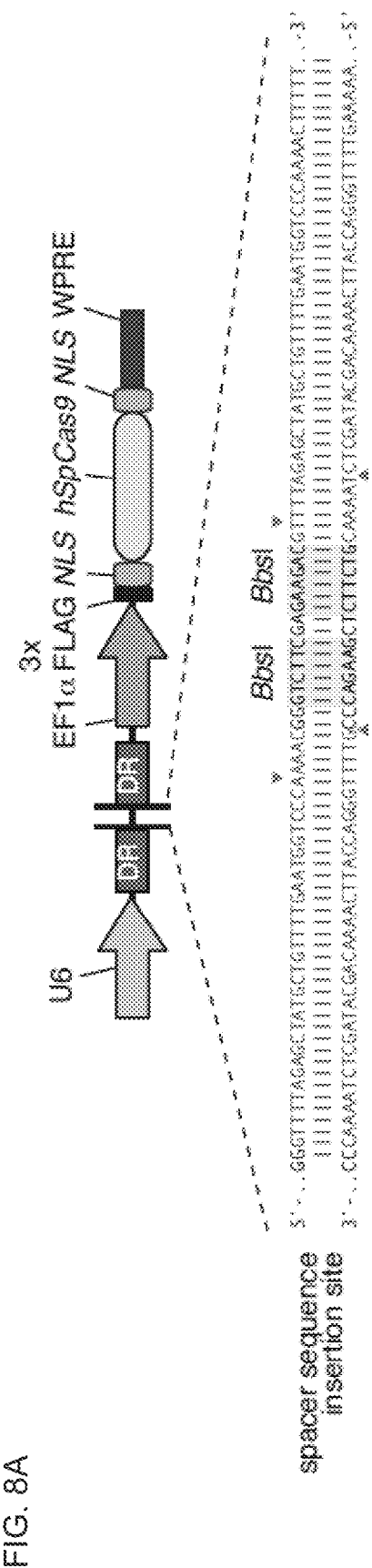
FIG. 8A-8B shows exemplary bicistronic expression vectors for expression of CRISPR system elements in eukaryotic cells.
Figure 8B:
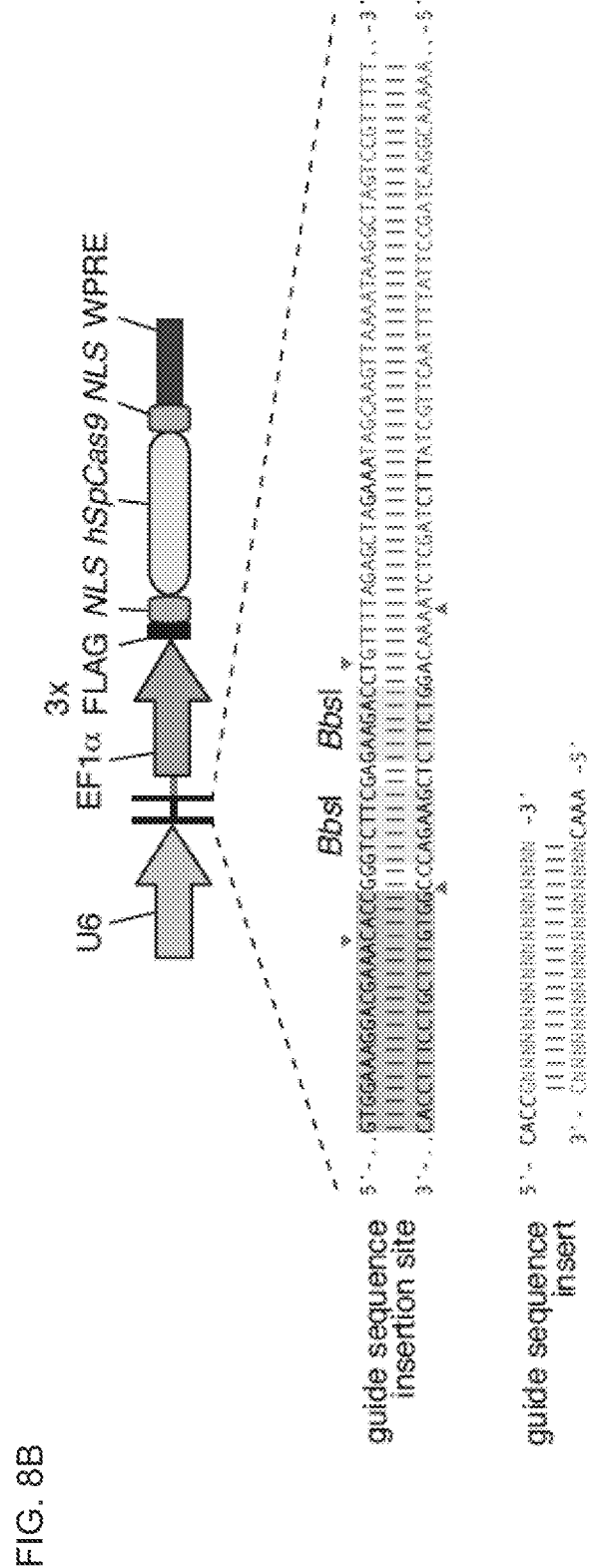

To further simplify the three-component system, a chimeric crRNA-tracrRNA hybrid design was adapted, where a mature crRNA (comprising a guide sequence) may be fused to a partial tracrRNA via a stem-loop to mimic the natural crRNA:tracrRNA duplex. To increase co-delivery efficiency, a bicistronic expression vector was created to drive co-expression of a chimeric RNA and SpCas9 in transfected cells. In parallel, the bicistronic vectors were used to express a pre-crRNA (DR-guide sequence-DR) with SpCas9, to induce processing into crRNA with a separately expressed tracrRNA (compare FIG. 11B top and bottom). FIG. 8 provides schematic illustrations of bicistronic expression vectors for pre-crRNA array (FIG. 8A) or chimeric crRNA (represented by the short line downstream of the guide sequence insertion site and upstream of the EF1α promoter in FIG. 8B) with hSpCas9, showing location of various elements and the point of guide sequence insertion. The expanded sequence around the location of the guide sequence insertion site in FIG. 8B also shows a partial DR sequence (GTTTTAGAGCTA) (SEQ ID NO: 11) and a partial tracrRNA sequence (TAGCAAGT-TAAAATAAGGCTAGTCCGTTTTT)(SEQ ID NO: 12). Guide sequences can be inserted between BbsI sites using annealed oligonucleotides. Sequence designs for the oligonucleotides are shown below the schematic illustrations in FIG. 8, with appropriate ligation adapters indicated. WPRE represents the Woodchuck hepatitis virus post-transcriptional regulatory element. The efficiency of chimeric RNA-mediated cleavage was tested by targeting the same EMX1 locus described above. Using both Surveyor assay and Sanger sequencing of amplicons, Applicants confirmed that the chimeric RNA design facilitates cleavage of human EMX1 locus with approximately a 4.7% modification rate (FIG. 3).

Figure 13A:
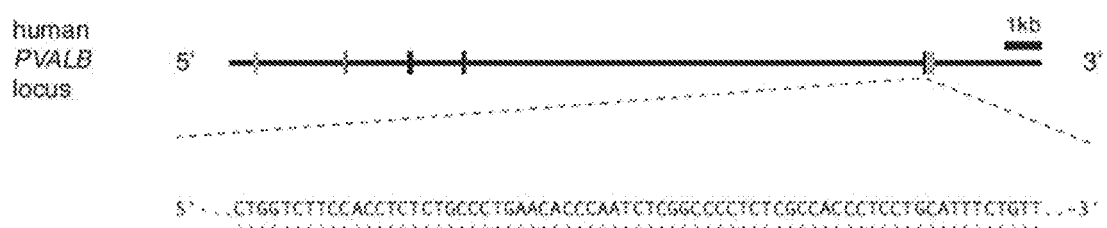
FIG. 13A-13B shows an exemplary selection of protospacers in the human PVALB (SEQ ID NO: 136) and mouse Th loci (SEQ ID NO: 137).
Figure 13B:
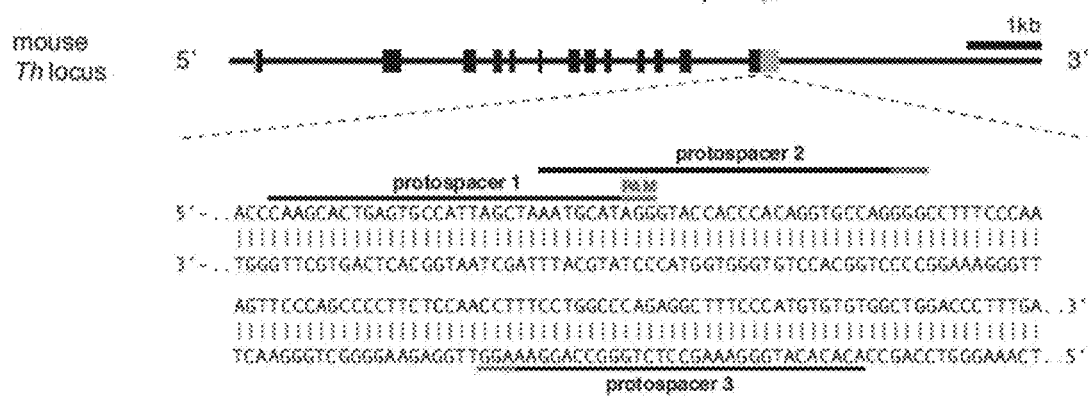

Generalizability of CRISPR-mediated cleavage in eukaryotic cells was tested by targeting additional genomic loci in both human and mouse cells by designing chimeric RNA targeting multiple sites in the human EMX1 and PVALB, as well as the mouse Th loci. FIG. 13 illustrates the selection of some additional targeted protospacers in human PVALB (FIG. 13A) and mouse Th (FIG. 13B) loci. Schematics of the gene loci and the location of three protospacers within the last exon of each are provided. The underlined sequences include 30 bp of protospacer sequence and 3 bp at the 3' end corresponding to the PAM sequences. Protospacers on the sense and anti-sense strands are indicated above and below the DNA sequences, respectively. A modification rate of 6.3% and 0.75% was achieved for the human PVALB and mouse Th loci respectively, demonstrating the broad applicability of the CRISPR system in modifying different loci across multiple organisms (FIG. 5). While cleavage was only detected with one out of three spacers for each locus using the chimeric constructs, all target sequences were cleaved with efficiency of indel production reaching 27% when using the co-expressed pre-crRNA arrangement (FIGS. 6 and 13).

Figure 11A:
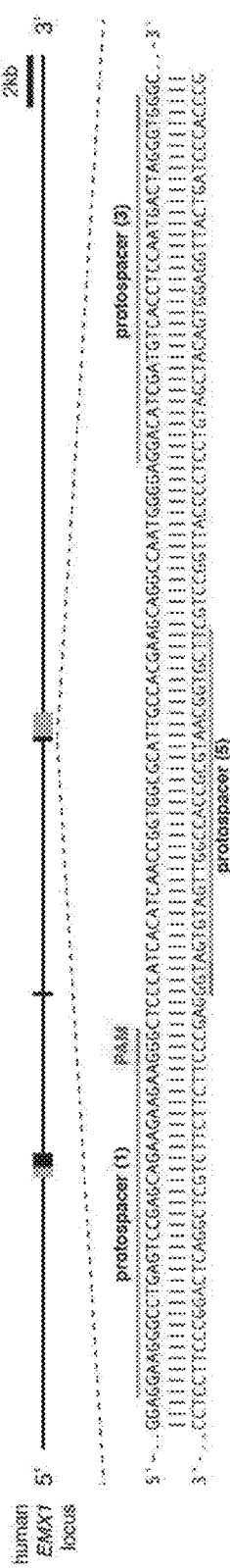
FIG. 11A-11C shows exemplary manipulations of a CRISPR system for targeting of genomic loci in mammalian cells.
Figure 11C:
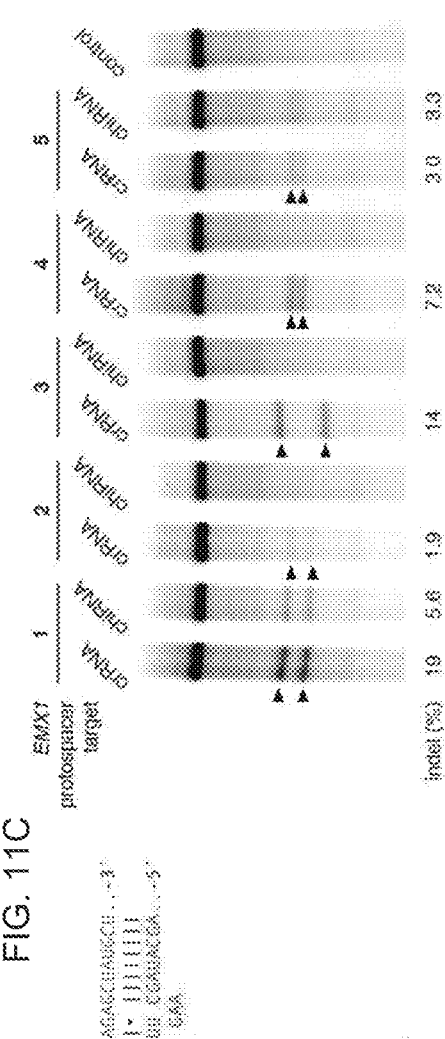
Figure 11B:
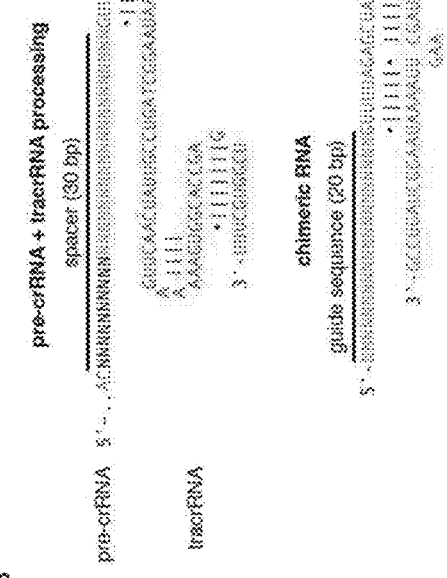

FIG. 11 provides a further illustration that SpCas9 can be reprogrammed to target multiple genomic loci in mammalian cells. FIG. 11A provides a schematic of the human EMX1 locus showing the location of five protospacers, indicated by the underlined sequences. FIG. 11B provides a schematic of the pre-crRNA/trcrRNA complex showing hybridization between the direct repeat region of the pre-crRNA and tracrRNA (top), and a schematic of a chimeric RNA design comprising a 20 bp guide sequence, and tracr mate and tracr sequences consisting of partial direct repeat and tracrRNA sequences hybridized in a hairpin structure (bottom). Results of a Surveyor assay comparing the efficacy of Cas9-mediated cleavage at five protospacers in the human EMX1 locus is illustrated in FIG. 11C. Each protospacer is targeted using either processed pre-crRNA/tracrRNA complex (crRNA) or chimeric RNA (chiRNA).

Since the secondary structure of RNA can be crucial for intermolecular interactions, a structure prediction algorithm based on minimum free energy and Boltzmann-weighted structure ensemble was used to compare the putative secondary structure of all guide sequences used in the genome targeting experiment (see e.g. Gruber et al., 2008, Nucleic Acids Research, 36: W70). Analysis revealed that in most cases, the effective guide sequences in the chimeric crRNA context were substantially free of secondary structure motifs, whereas the ineffective guide sequences were more likely to form internal secondary structures that could prevent base pairing with the target protospacer DNA. It is thus possible that variability in the spacer secondary structure might impact the efficiency of CRISPR-mediated interference when using a chimeric crRNA.

Figure 22A:
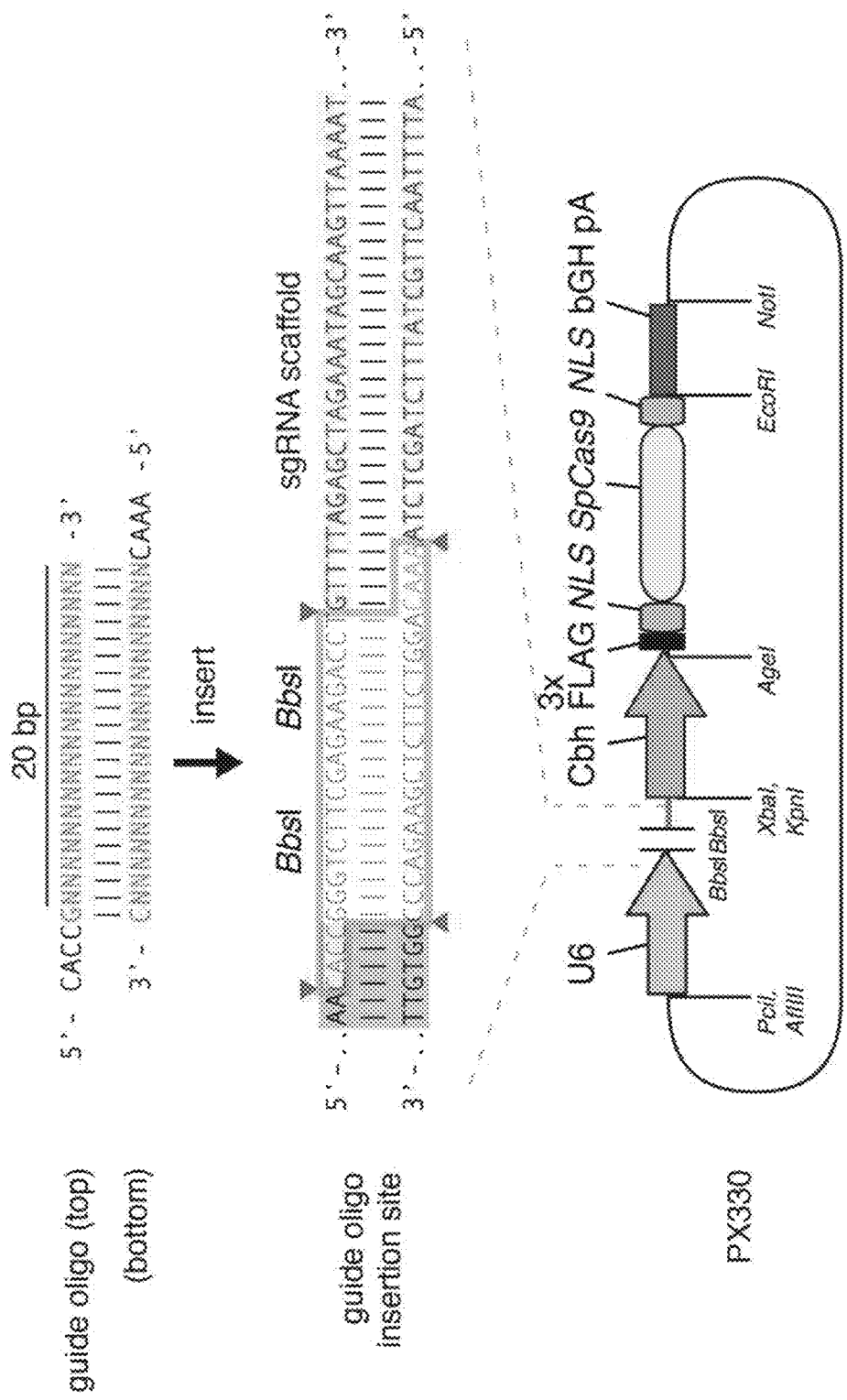
FIG. 22A-22B shows single vector designs for SpCas9.
Figure 22B:
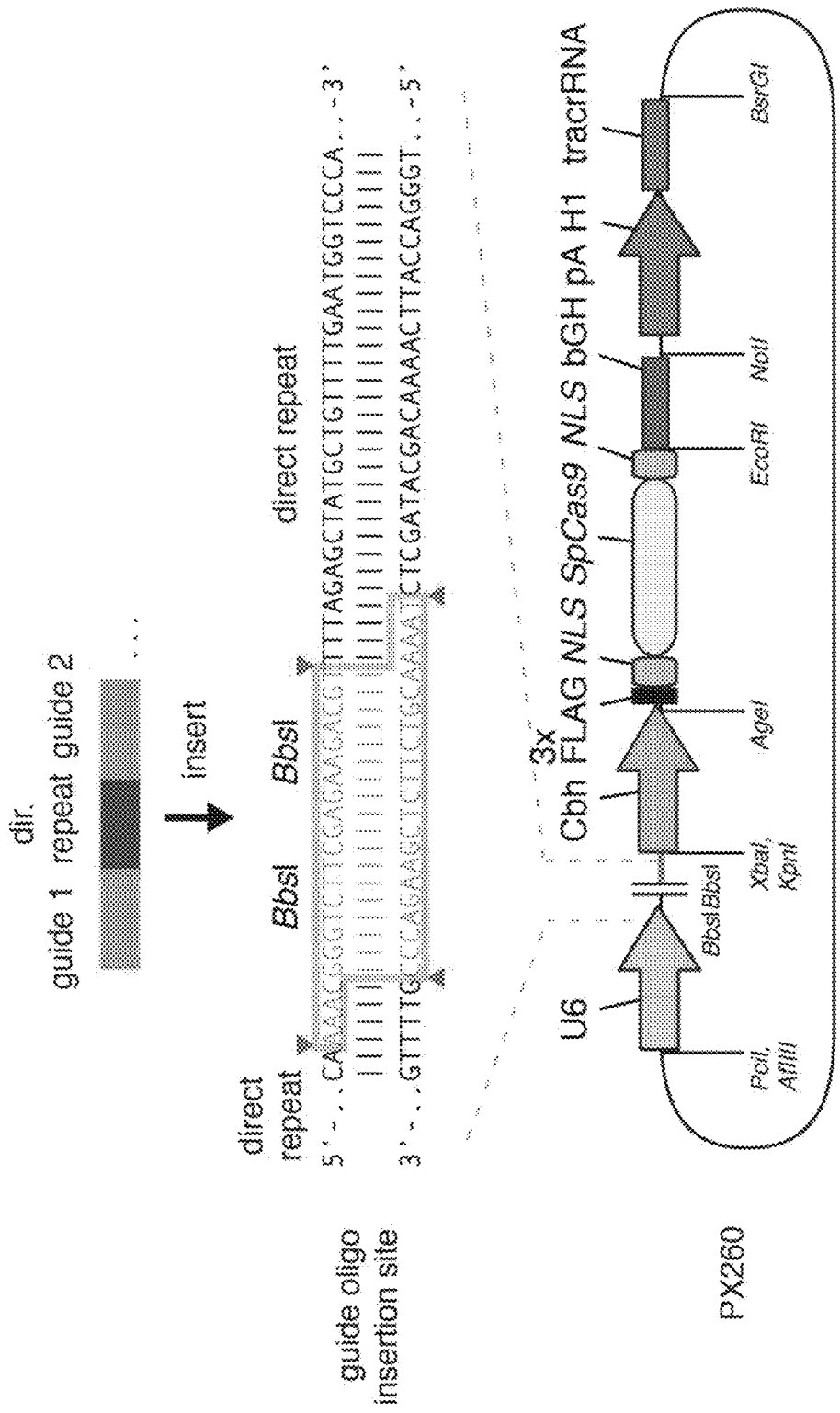
Figure 23C:
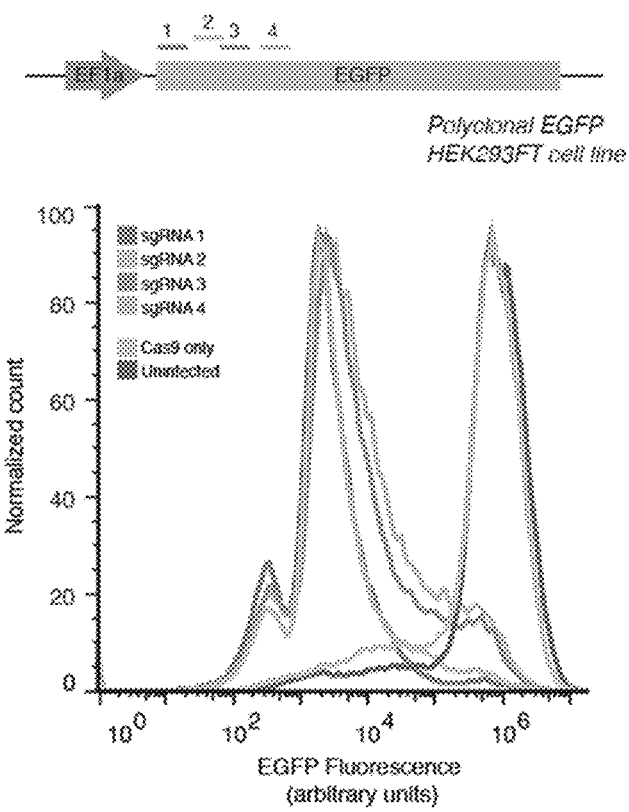
Figure 24A:
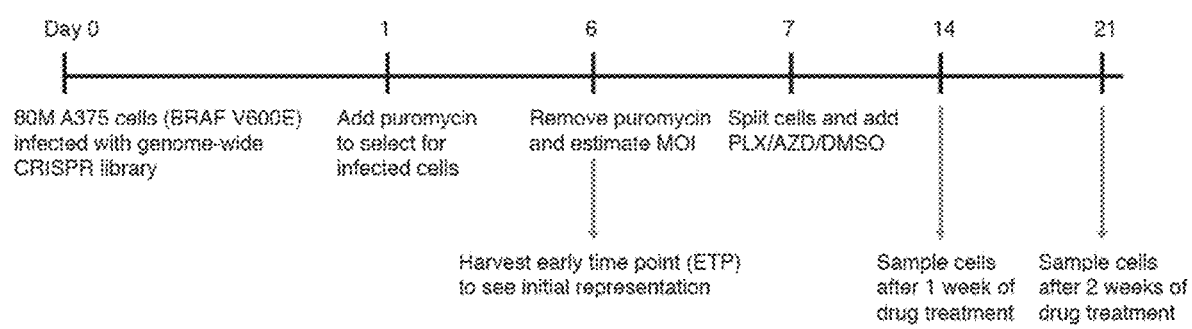
FIG. 24A-24F shows A) Timeline of Vemurafenib (PLX) resistance screen in A375 cells. B) Scatterplot of individual sgRNA abundances from biological replicates of DMSO treatment. C) Scatterplot of individual sgRNA abundances from biological replicates of PLX treatment. D) Boxplot showing the distribution of reads from different sgRNA. PLX has a statistically significant decrease in the average number of reads per sgRNA with an increase in the number in reads for the most abundant sgRNAs. E) Scatterplot of individual sgRNA abundances in PLX vs. DMSO treatment. F) Mapping of sgRNAs to genes and the calculating the median sgRNA enrichment value. By calculating an empirical distribution of p-values, a few gene knock outs display significant enrichment after PLX treatment, such as NF2, NF1, MED12, and MED15.
Figure 24B:
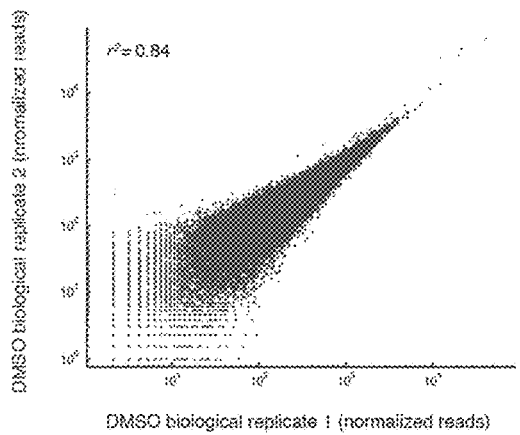
Figure 24C:
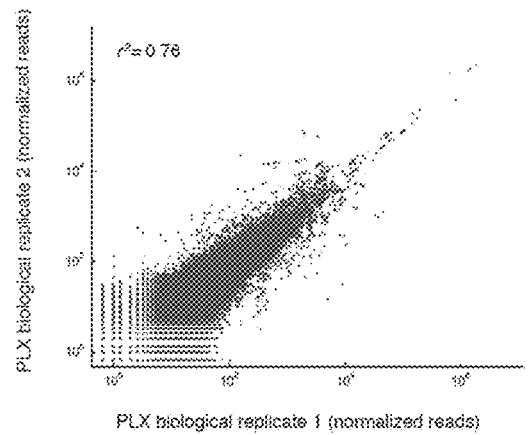
Figure 24D:
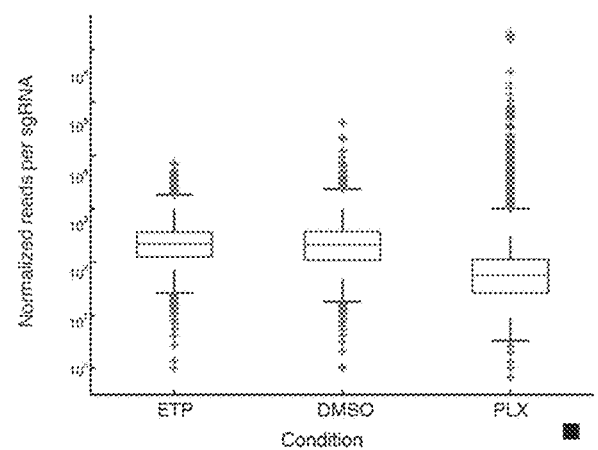
Figure 24E:
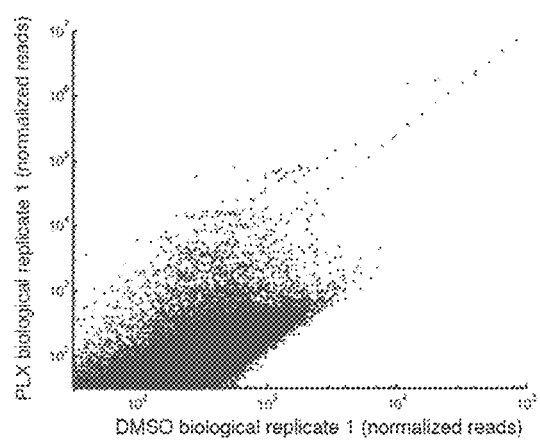
Figure 24F:
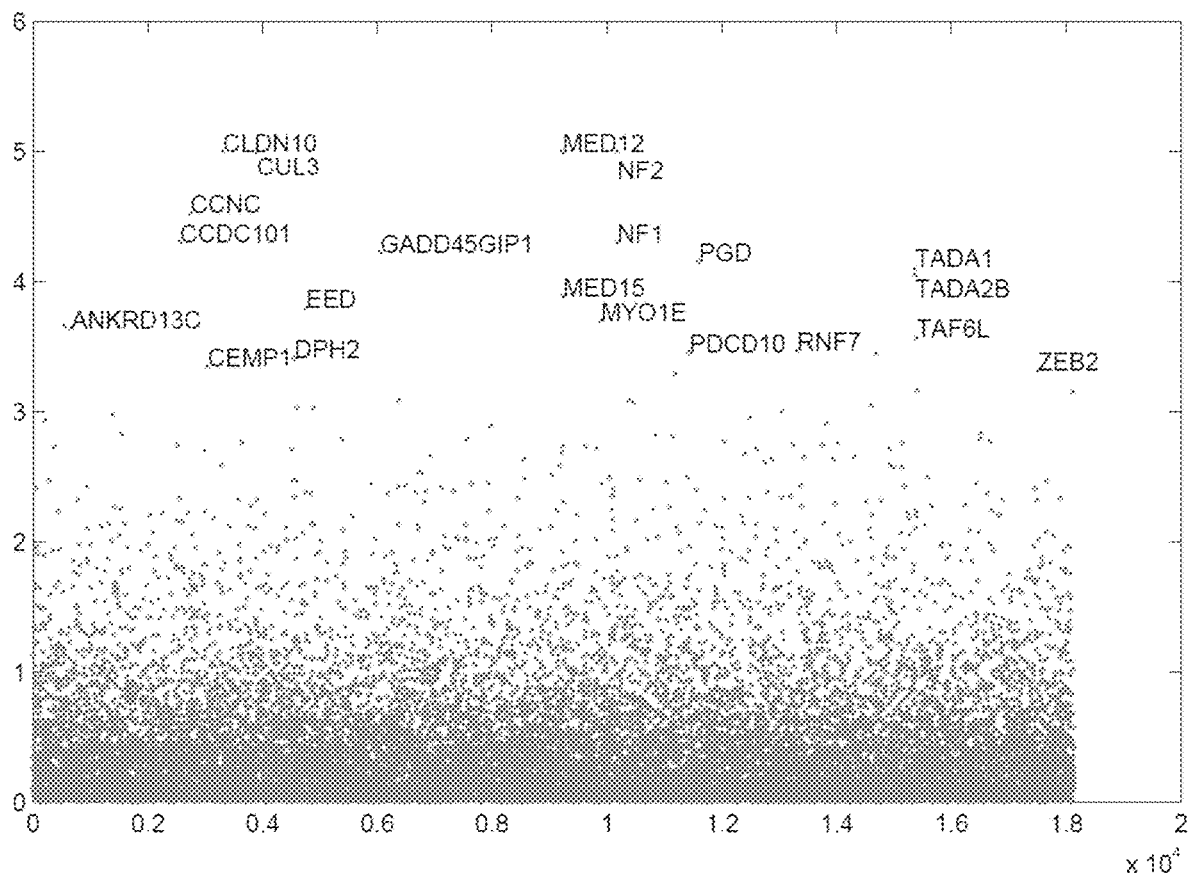

Further vector designs for SpCas9 are shown in FIG. 22, which illustrates single expression vectors incorporating a U6 promoter linked to an insertion site for a guide oligo, and a Cbh promoter linked to SpCas9 coding sequence. The vector shown in FIG. 22b includes a tracrRNA coding sequence linked to an H1 promoter.

In the bacterial assay, all spacers facilitated efficient CRISPR interference (FIG. 3C). These results suggest that there may be additional factors affecting the efficiency of CRISPR activity in mammalian cells.

Figure 3D:
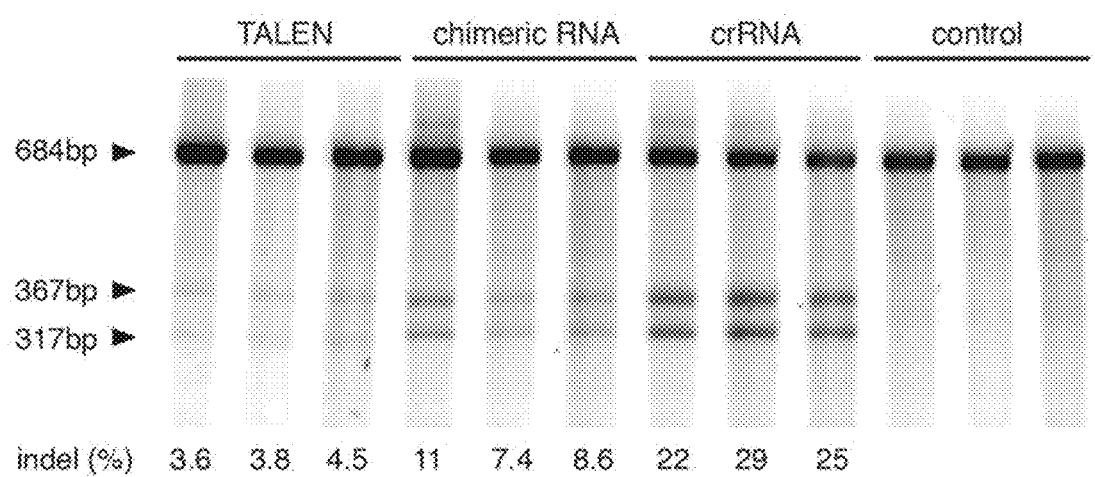

To investigate the specificity of CRISPR-mediated cleavage, the effect of single-nucleotide mutations in the guide sequence on protospacer cleavage in the mammalian genome was analyzed using a series of EMX1-targeting chimeric crRNAs with single point mutations (FIG. 3A). FIG. 3B illustrates results of a Surveyor nuclease assay comparing the cleavage efficiency of Cas9 when paired with different mutant chimeric RNAs. Single-base mismatch up to 12-bp 5' of the PAM substantially abrogated genomic cleavage by SpCas9, whereas spacers with mutations at farther upstream positions retained activity against the original protospacer target (FIG. 3B). In addition to the PAM, SpCas9 has single-base specificity within the last 12-bp of the spacer. Furthermore, CRISPR is able to mediate genomic cleavage as efficiently as a pair of TALE nucleases (TALEN) targeting the same EMX1 protospacer. FIG. 3C provides a schematic showing the design of TALENs targeting EMX1, and FIG. 3D shows a Surveyor gel comparing the efficiency of TALEN and Cas9 (n=3).

Figure 4A:
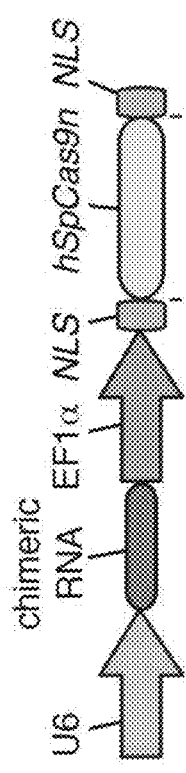
FIG. 4A-4G show an exemplary vector system and results for its use in directing homologous recombination in eukaryotic cells.
Figure 4B:
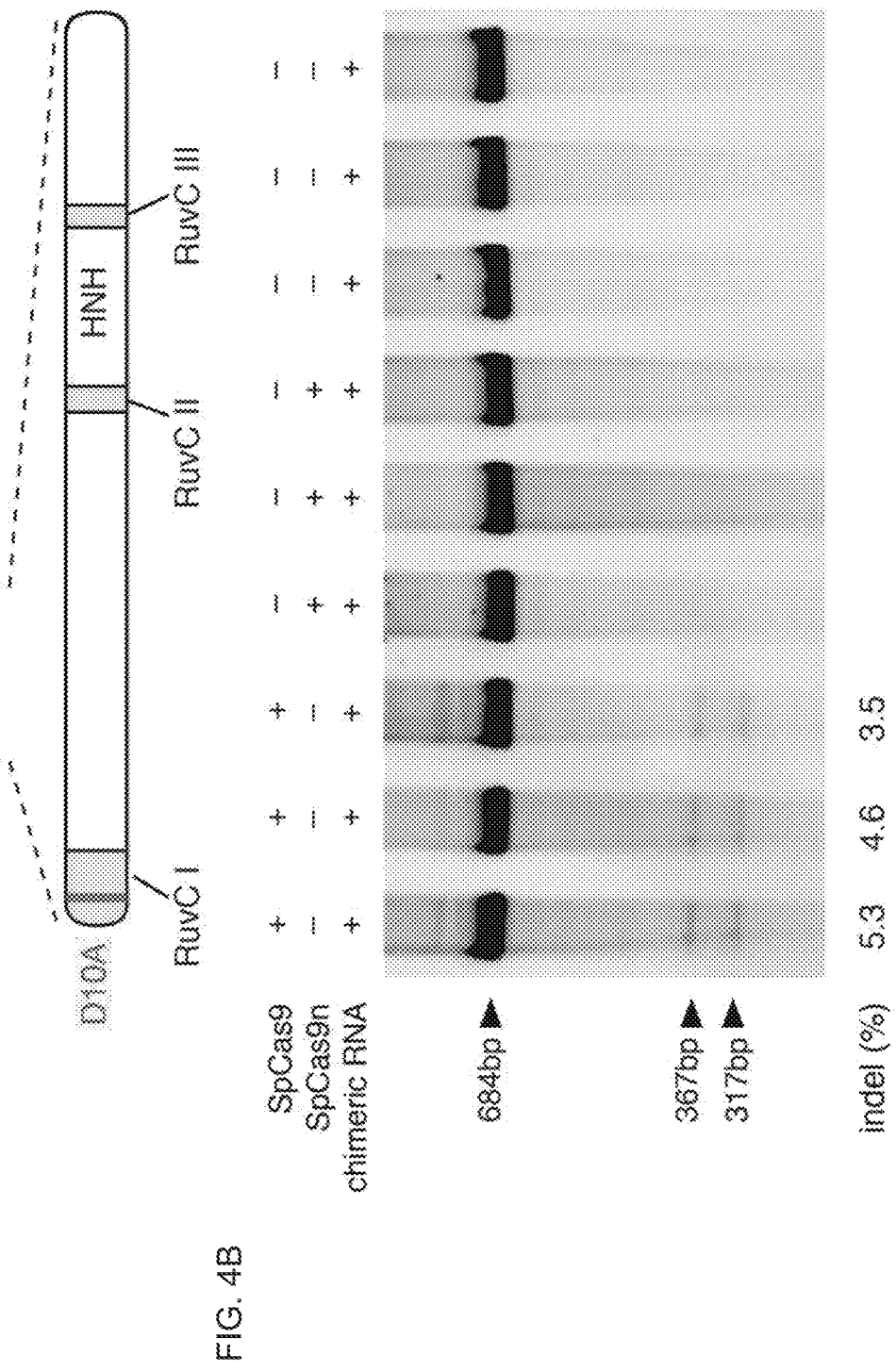
Figure 4C:
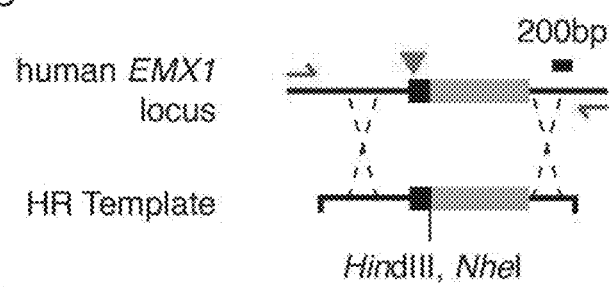
Figure 4D:
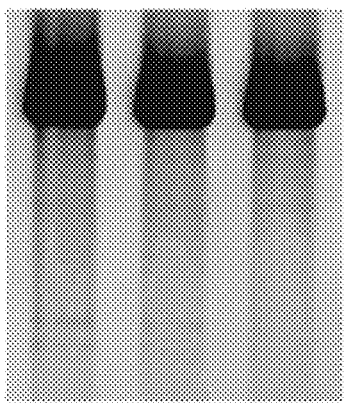
Figure 4E:
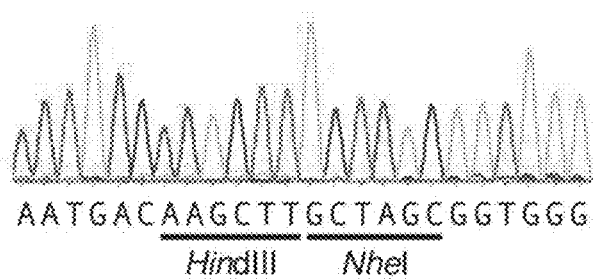

Having established a set of components for achieving CRISPR-mediated gene editing in mammalian cells through the error-prone NHEJ mechanism, the ability of CRISPR to stimulate homologous recombination (HR), a high fidelity gene repair pathway for making precise edits in the genome, was tested. The wild type SpCas9 is able to mediate site-specific DSBs, which can be repaired through both NHEJ and HR. In addition, an aspartate-to-alanine substitution (D10A) in the RuvC I catalytic domain of SpCas9 was engineered to convert the nuclease into a nickase (SpCas9n; illustrated in FIG. 4A) (see e.g. Sapranausaks et al., 2011, Nucleic Acids Research, 39: 9275; Gasiunas et al., 2012, Proc. Natl. Acad. Sci. USA, 109:E2579), such that nicked genomic DNA undergoes the high-fidelity homology-directed repair (HDR). Surveyor assay confirmed that SpCas9n does not generate indels at the EMX1 protospacer target. As illustrated in FIG. 4B, co-expression of EMX1-targeting chimeric crRNA with SpCas9 produced indels in the target site, whereas co-expression with SpCas9n did not (n=3). Moreover, sequencing of 327 amplicons did not detect any indels induced by SpCas9n. The same locus was selected to test CRISPR-mediated HR by co-transfecting HEK 293FT cells with the chimeric RNA targeting EMX1, hSpCas9 or hSpCas9n, as well as a HR template to introduce a pair of restriction sites (HindIII and NheI) near the protospacer. FIG. 4C provides a schematic illustration of the HR strategy, with relative locations of recombination points and primer annealing sequences (arrows). SpCas9 and SpCas9n indeed catalyzed integration of the HR template into the EMX1 locus. PCR amplification of the target region followed by restriction digest with HindIII revealed cleavage products corresponding to expected fragment sizes (arrows in restriction fragment length polymorphism gel analysis shown in FIG. 4D), with SpCas9 and SpCas9n mediating similar levels of HR efficiencies. Applicants further verified HR using Sanger sequencing of genomic amplicons (FIG. 4E). These results demonstrate the utility of CRISPR for facilitating targeted gene insertion in the mammalian genome. Given the 14-bp (12-bp from the spacer and 2-bp from the PAM) target specificity of the wild type SpCas9, the availability of a nickase can significantly reduce the likelihood of off-target modifications, since single strand breaks are not substrates for the error-prone NHEJ pathway.

Figure 4F:
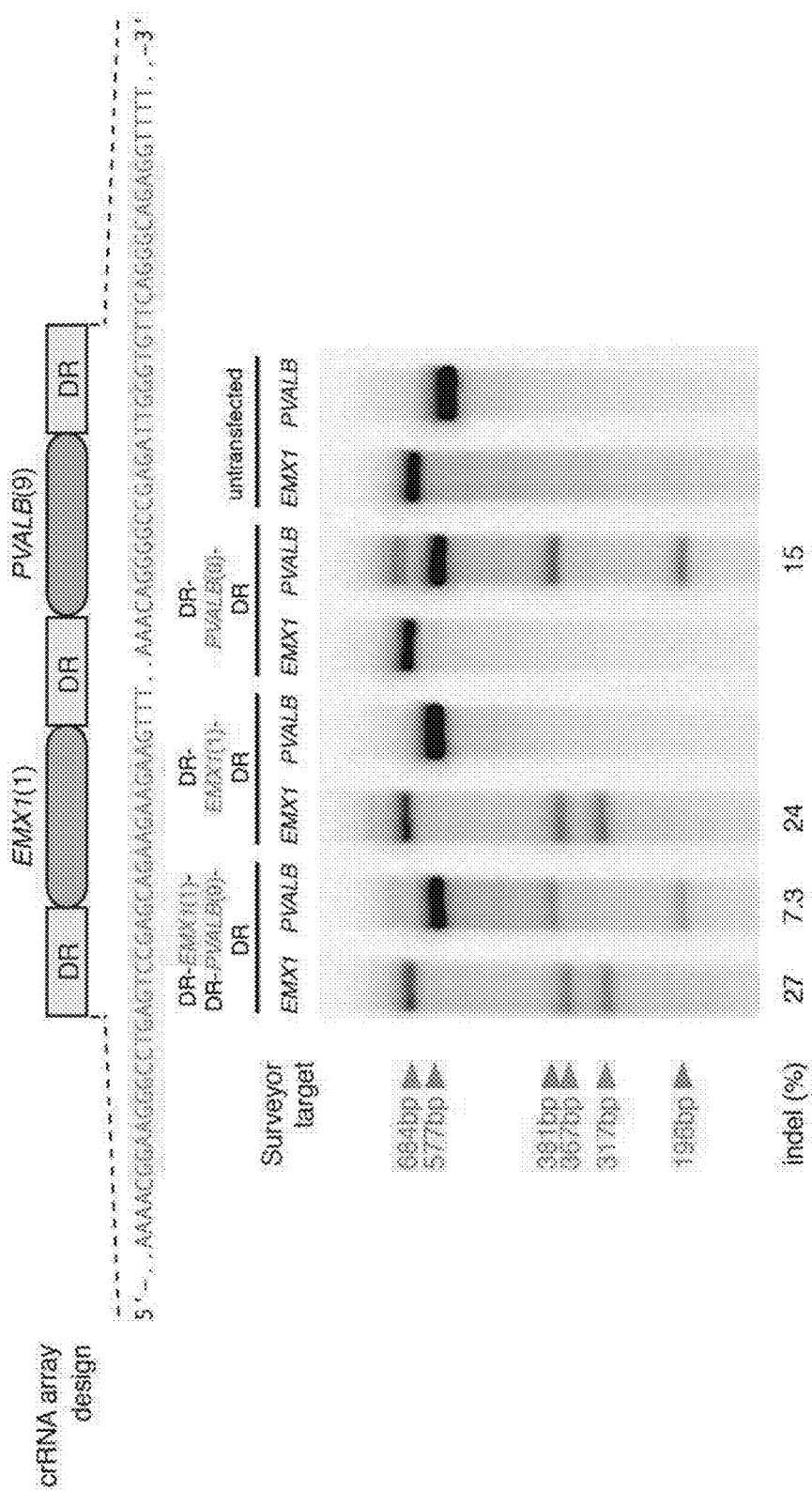
Figure 4G:
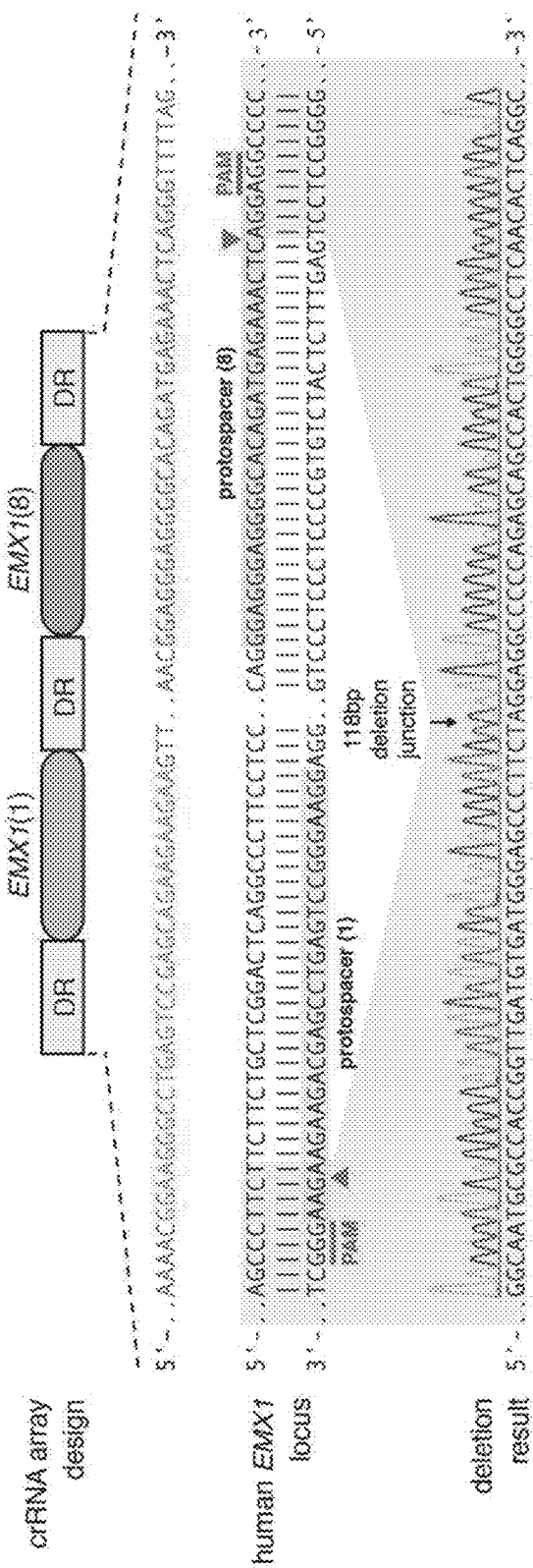

Expression constructs mimicking the natural architecture of CRISPR loci with arrayed spacers (FIG. 2A) were constructed to test the possibility of multiplexed sequence targeting. Using a single CRISPR array encoding a pair of EMX1- and PVALB-targeting spacers, efficient cleavage at both loci was detected (FIG. 4F, showing both a schematic design of the crRNA array and a Surveyor blot showing efficient mediation of cleavage). Targeted deletion of larger genomic regions through concurrent DSBs using spacers against two targets within EMX1 spaced by 119 bp was also tested, and a 1.6% deletion efficacy (3 out of 182 amplicons; FIG. 4G) was detected. This demonstrates that the CRISPR system can mediate multiplexed editing within a single genome.

Example 2: CRISPR System Modifications and Alternatives

Figure 10A:
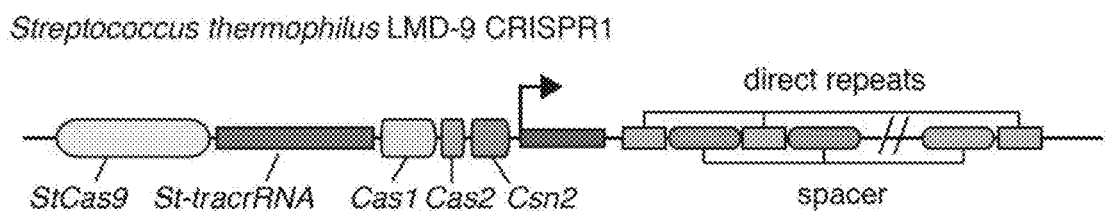
FIG. 10A-10D shows an exemplary CRISPR system, an example adaptation for expression in eukaryotic cells, and results of tests assessing CRISPR activity.
Figure 10B:
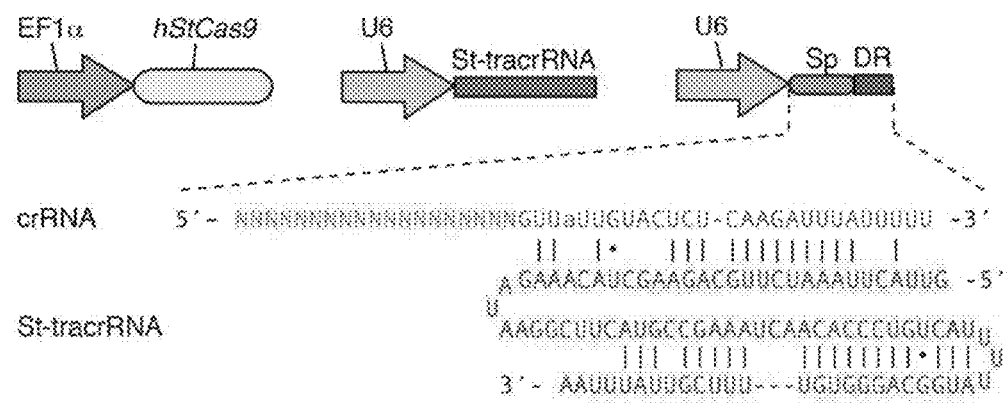
Figure 10C:
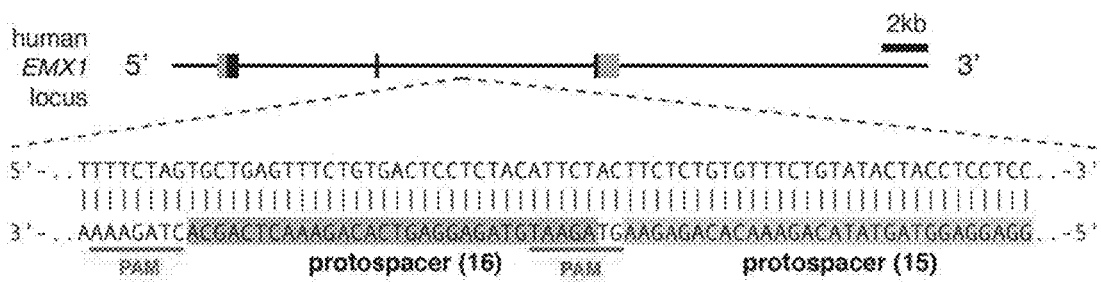
Figure 10D:
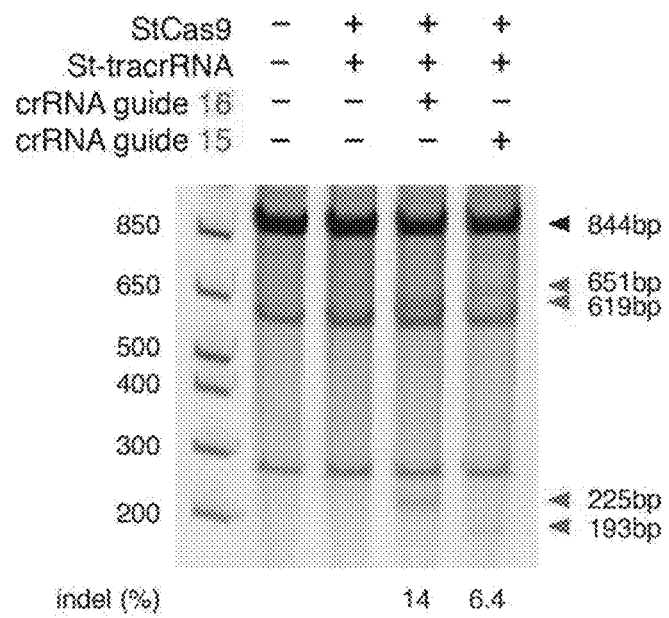
Figure 14:
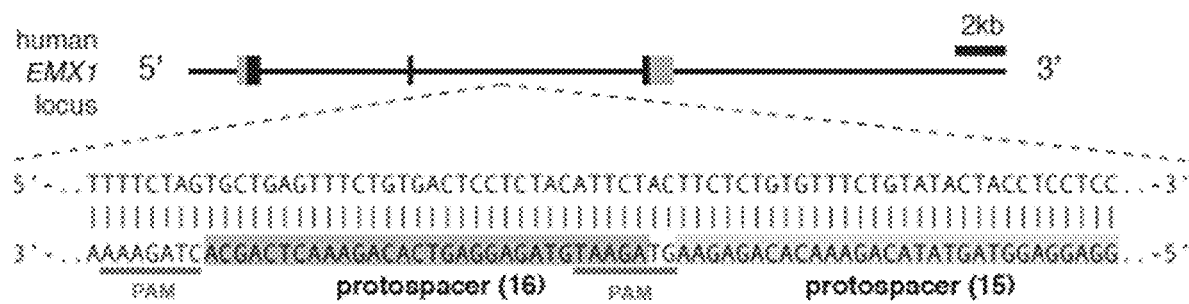
FIG. 14 shows example protospacer and corresponding PAM sequence targets of the S. thermophilus CRISPR system in the human EMX1 locus (SEQ ID NO: 130).

The ability to use RNA to program sequence-specific DNA cleavage defines a new class of genome engineering tools for a variety of research and industrial applications. Several aspects of the CRISPR system can be further improved to increase the efficiency and versatility of CRISPR targeting. Optimal Cas9 activity may depend on the availability of free $Mg^{2+}$ at levels higher than that present in the mammalian nucleus (see e.g. Jinek et al., 2012, Science, 337:816), and the preference for an NGG motif immediately downstream of the protospacer restricts the ability to target on average every 12-bp in the human genome (FIG. 9, evaluating both plus and minus strands of human chromosomal sequences). Some of these constraints can be overcome by exploring the diversity of CRISPR loci across the microbial metagenome (see e.g. Makarova et al., 2011, Nat Rev Microbiol, 9:467). Other CRISPR loci may be transplanted into the mammalian cellular milieu by a process similar to that described in Example 1. For example, FIG. 10 illustrates adaptation of the Type II CRISPR system from CRISPR 1 of *Streptococcus thermophilus* LMD-9 for heterologous expression in mammalian cells to achieve CRISPR-mediated genome editing. FIG. 10A provides a Schematic illustration of CRISPR 1 from *S. thermophilus* LMD-9. FIG. 10B illustrates the design of an expression system for the *S. thermophilus* CRISPR system. Human codon-optimized hStCas9 is expressed using a constitutive EF1α promoter. Mature versions of tracrRNA and crRNA are expressed using the U6 promoter to promote precise transcription initiation. Sequences from the mature crRNA and tracrRNA are illustrated. A single base indicated by the lower case "a" in the crRNA sequence is used to remove the polyU sequence, which serves as a RNA polIII transcriptional terminator. FIG. 10C provides a schematic showing guide sequences targeting the human EMX1 locus. FIG. 10D shows the results of hStCas9-mediated cleavage in the target locus using the Surveyor assay. RNA guide spacers 1 and 2 induced 14% and 6.4%, respectively. Statistical analysis of cleavage activity across biological replica at these two protospacer sites is also provided in FIG. 5. FIG. 14 provides a schematic of additional protospacer and corresponding PAM sequence targets of the *S. thermophilus* CRISPR system in the human EMX1 locus. Two protospacer sequences are highlighted and their corresponding PAM sequences satisfying NNAGAAW motif are indicated by underlining 3' with respect to the corresponding highlighted sequence. Both protospacers target the anti-sense strand.

Example 3: Sample Target Sequence Selection Algorithm

A software program is designed to identify candidate CRISPR target sequences on both strands of an input DNA sequence based on desired guide sequence length and a CRISPR motif sequence (PAM) for a specified CRISPR enzyme. For example, target sites for Cas9 from *S. pyogenes*, with PAM sequences NGG, may be identified by searching for 5'-$N_x$-NGG-3' both on the input sequence and on the reverse-complement of the input. Likewise, target sites for Cas9 of *S. thermophilus* CRISPR1, with PAM sequence NNAGAAW, may be identified by searching for 5'-$N_x$-NNAGAAW-3' (SEQ ID NO: 13) both on the input sequence and on the reverse-complement of the input. Likewise, target sites for Cas9 of *S. thermophilus* CRISPR3, with PAM sequence NGGNG, may be identified by searching for 5'-$N_x$-NGGNG-3' both on the input sequence and on the reverse-complement of the input. The value "x" in $N_x$ may be fixed by the program or specified by the user, such as 20.

Figure 18:
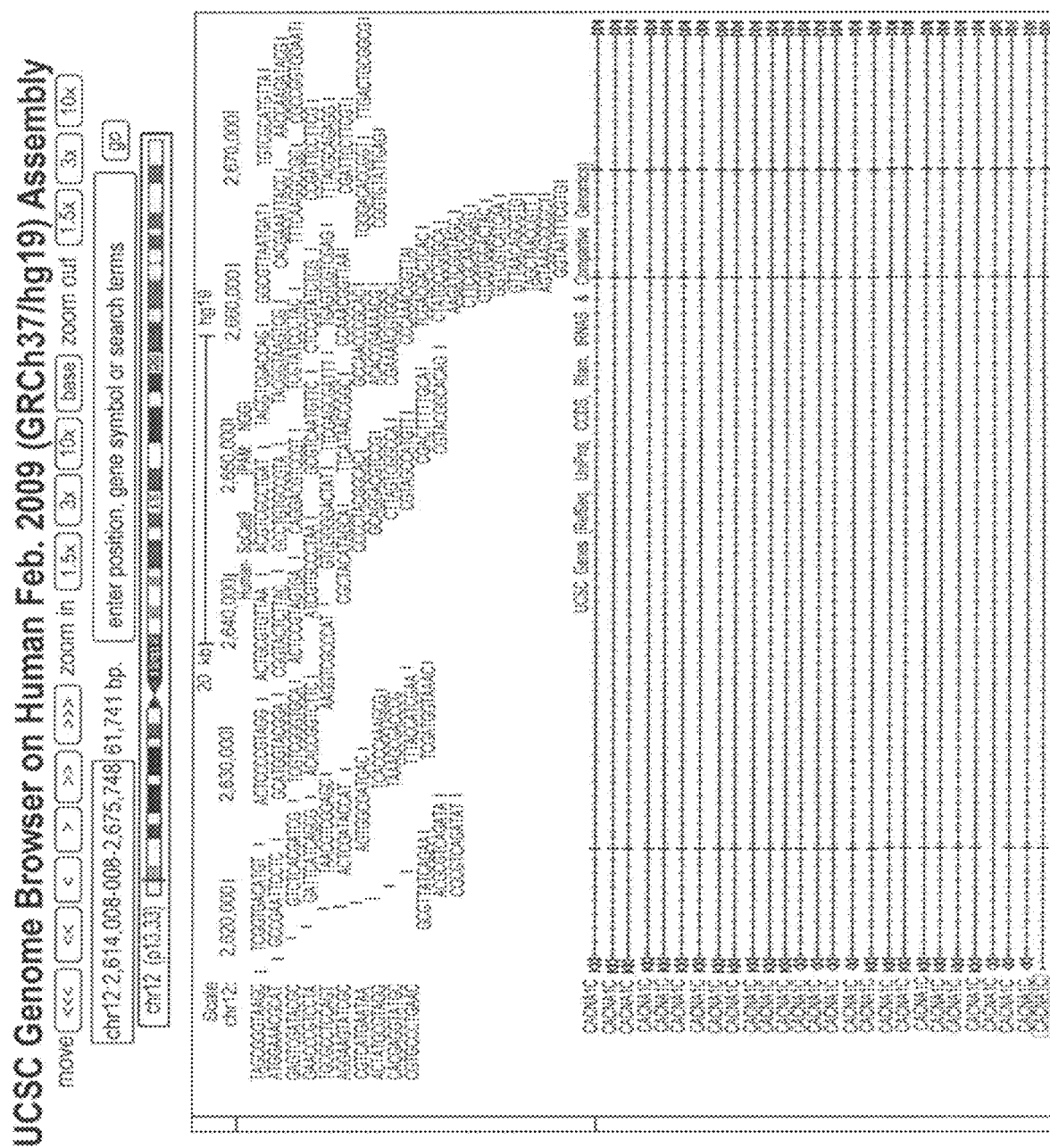
FIG. 18 shows an exemplary visualization of some *S. pyogenes* Cas9 target sites in the human genome using the UCSC genome browser.
Figure 19A:
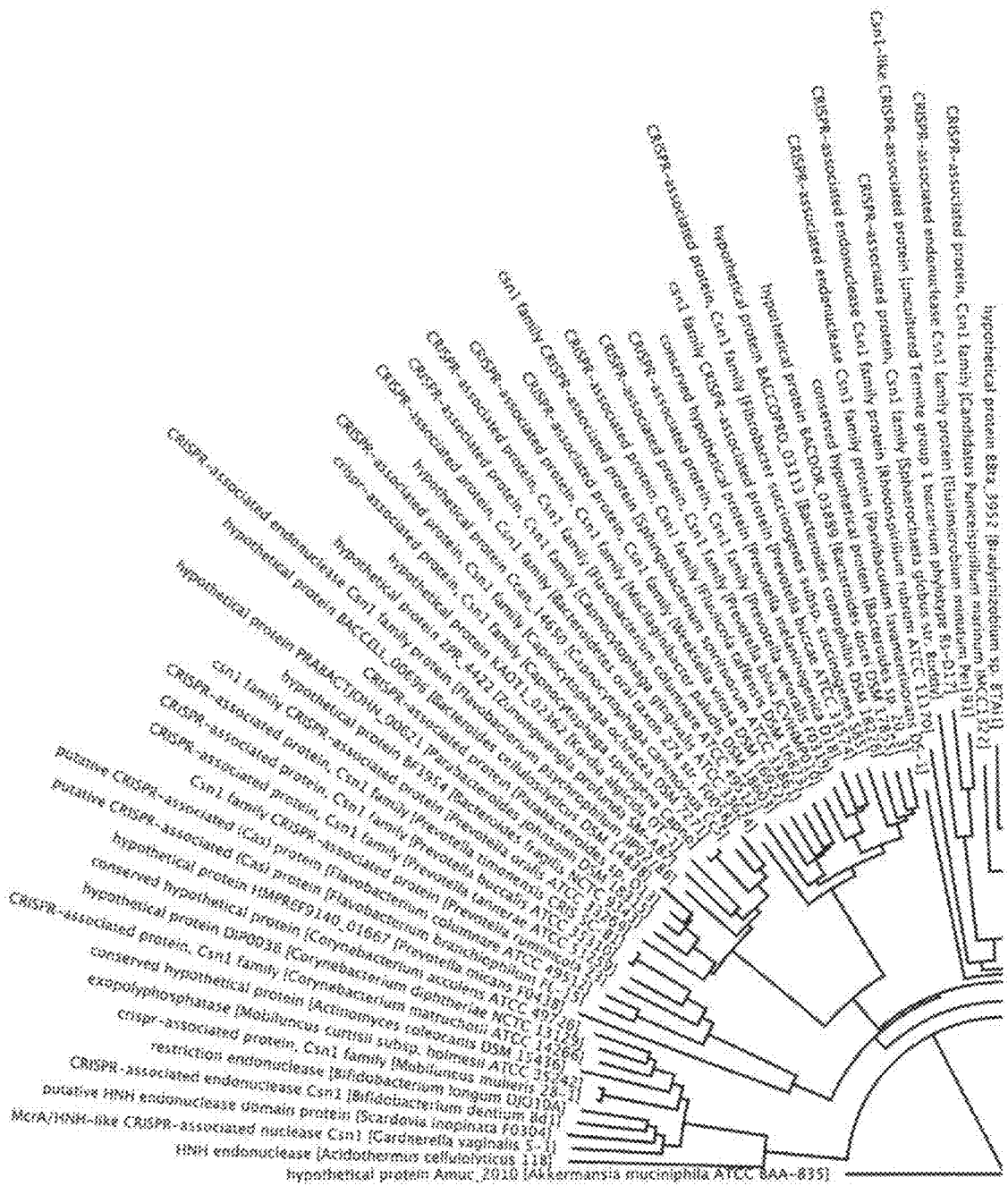
FIG. 19A-19D shows a circular depiction of the phylogenetic analysis revealing five families of Cas9s, including three groups of large Cas9s (~1400 amino acids) and two of small Cas9s (~1100 amino acids).
Figure 19B:
Figure 19C:
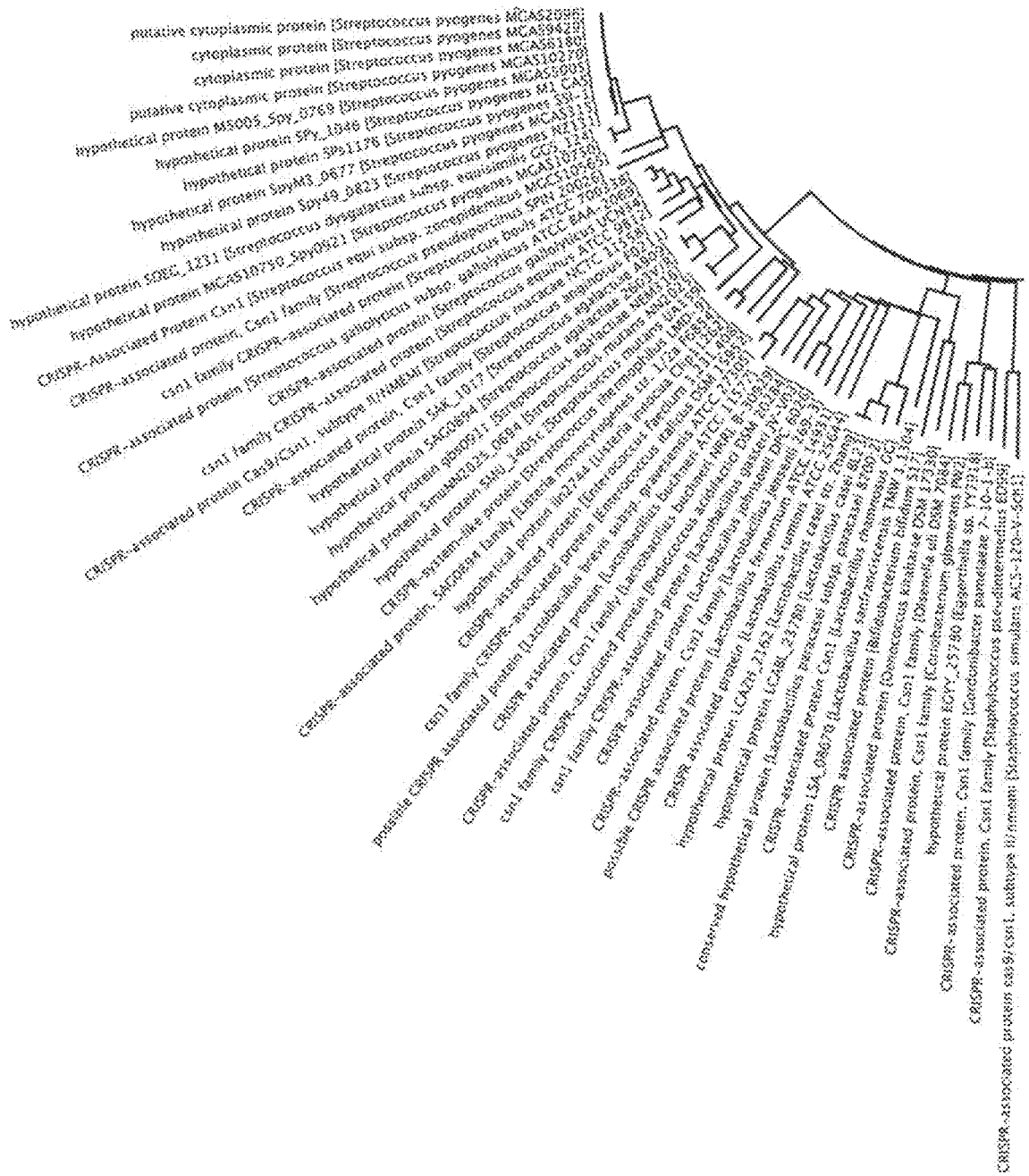
Figure 19D:
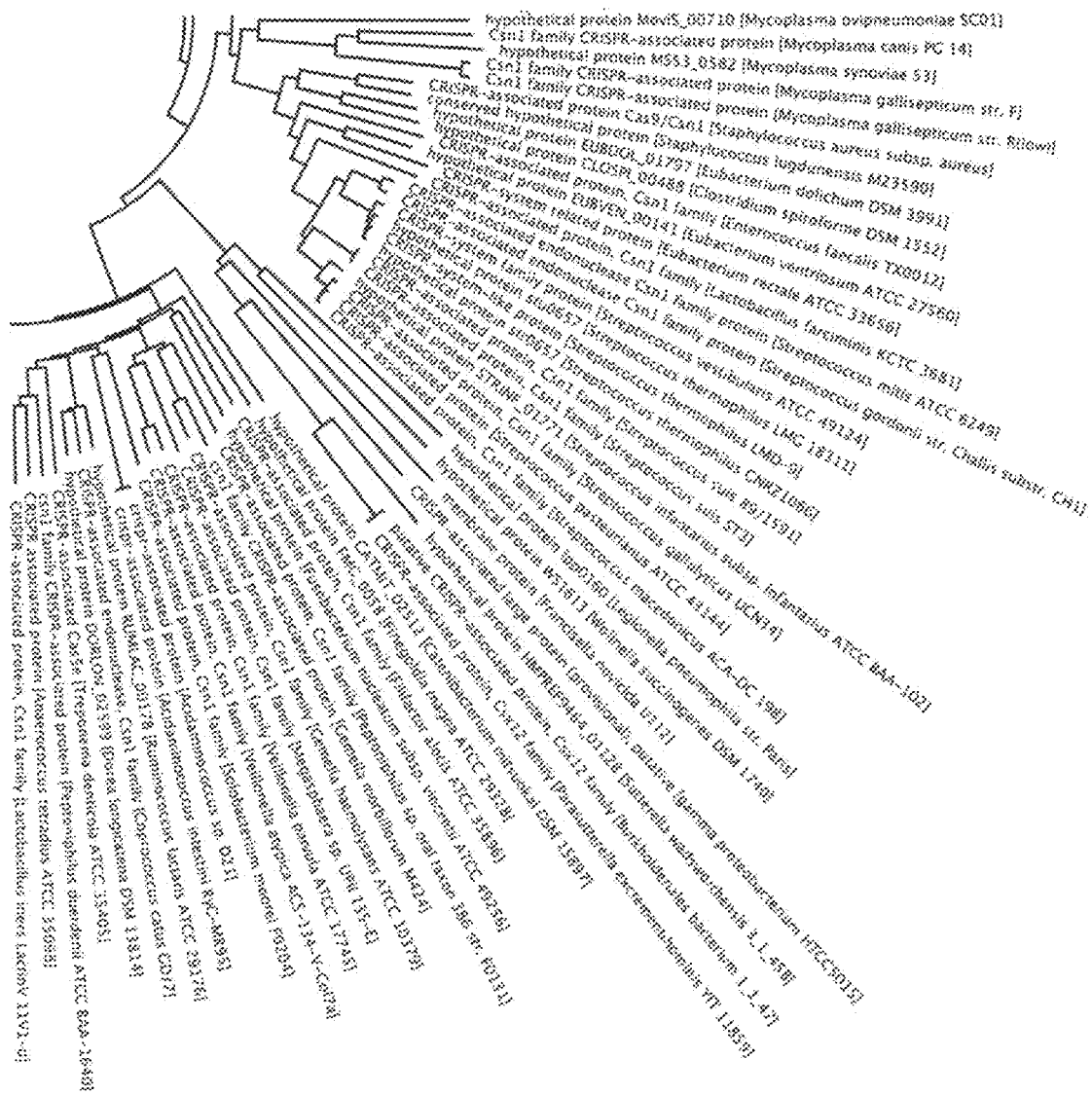
Figure 20A:
FIG. 20A-20F shows the linear depiction of the phylogenetic analysis revealing five families of Cas9s, including three groups of large Cas9s (~1400 amino acids) and two of small Cas9s (~1100 amino acids).
Figure 20B:
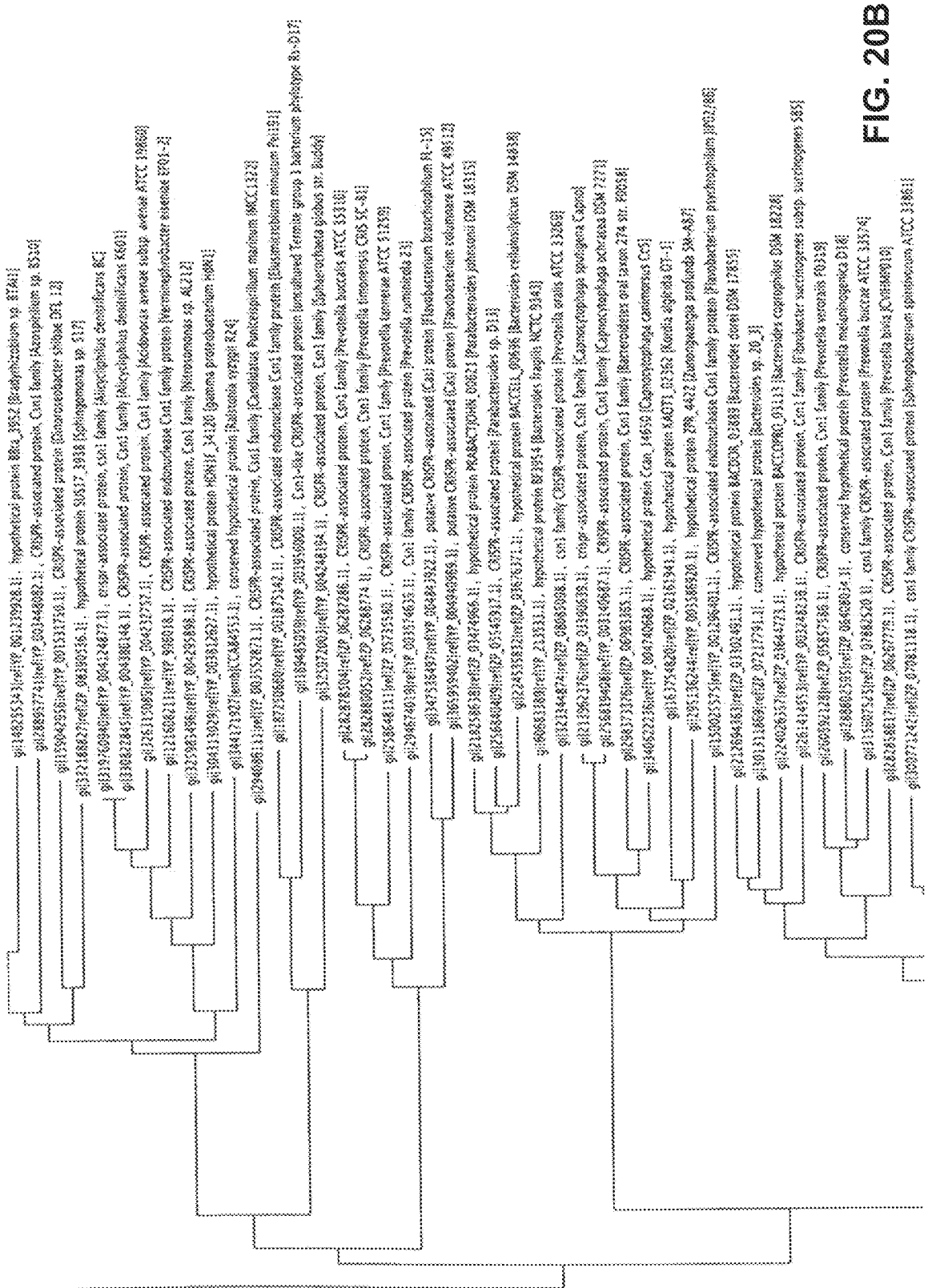
Figure 20C:
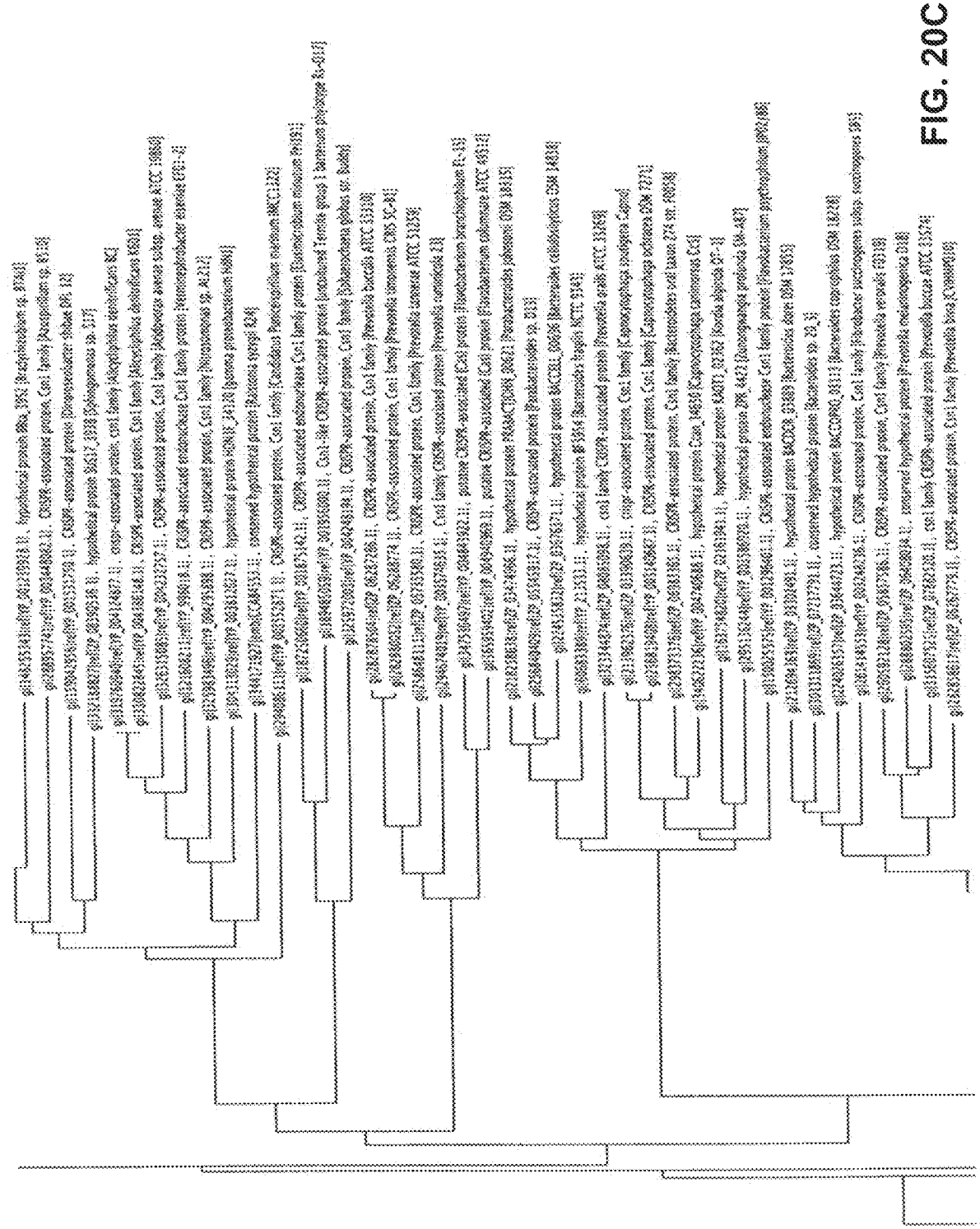
Figure 20D:
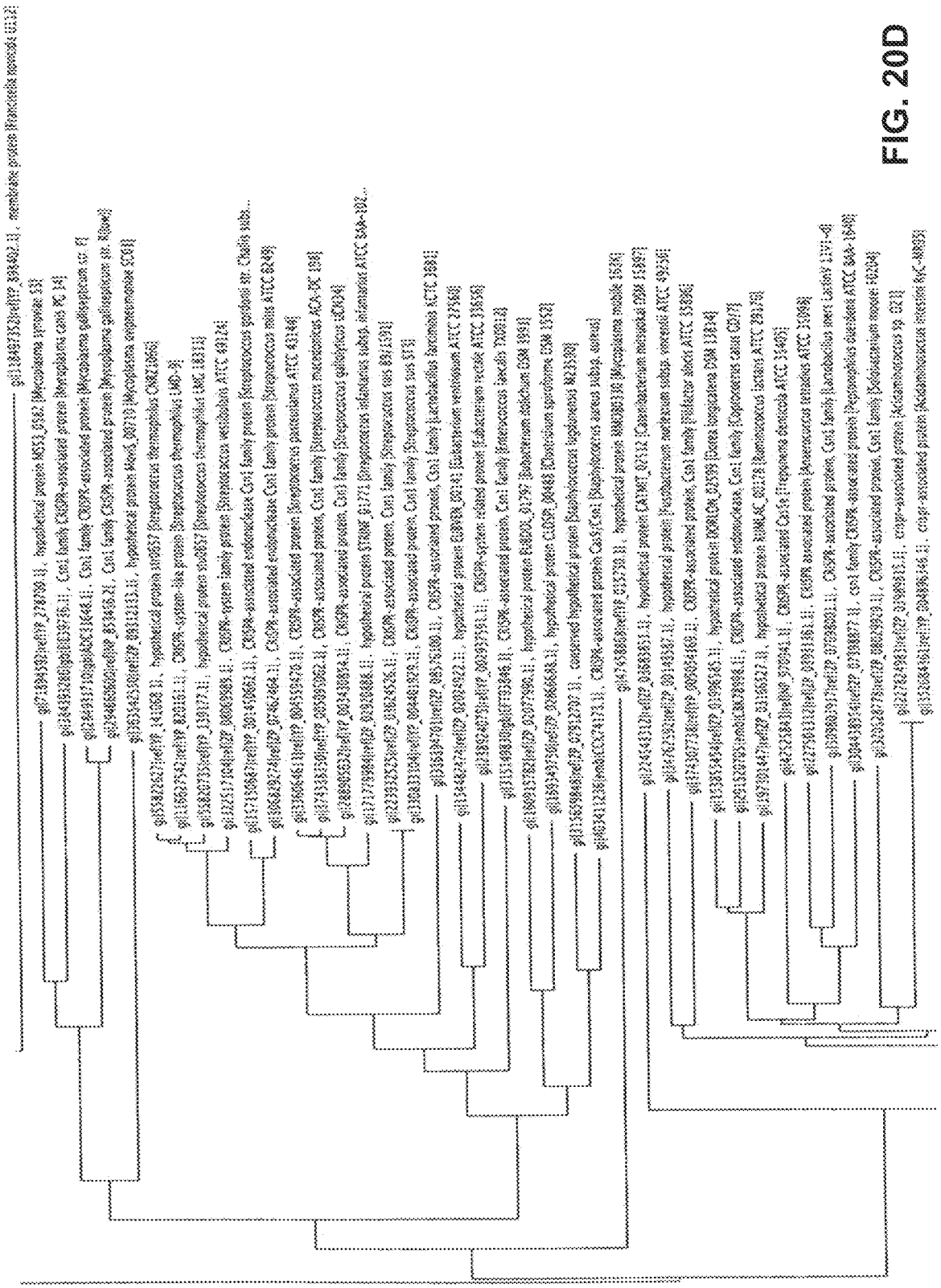
Figure 20E:
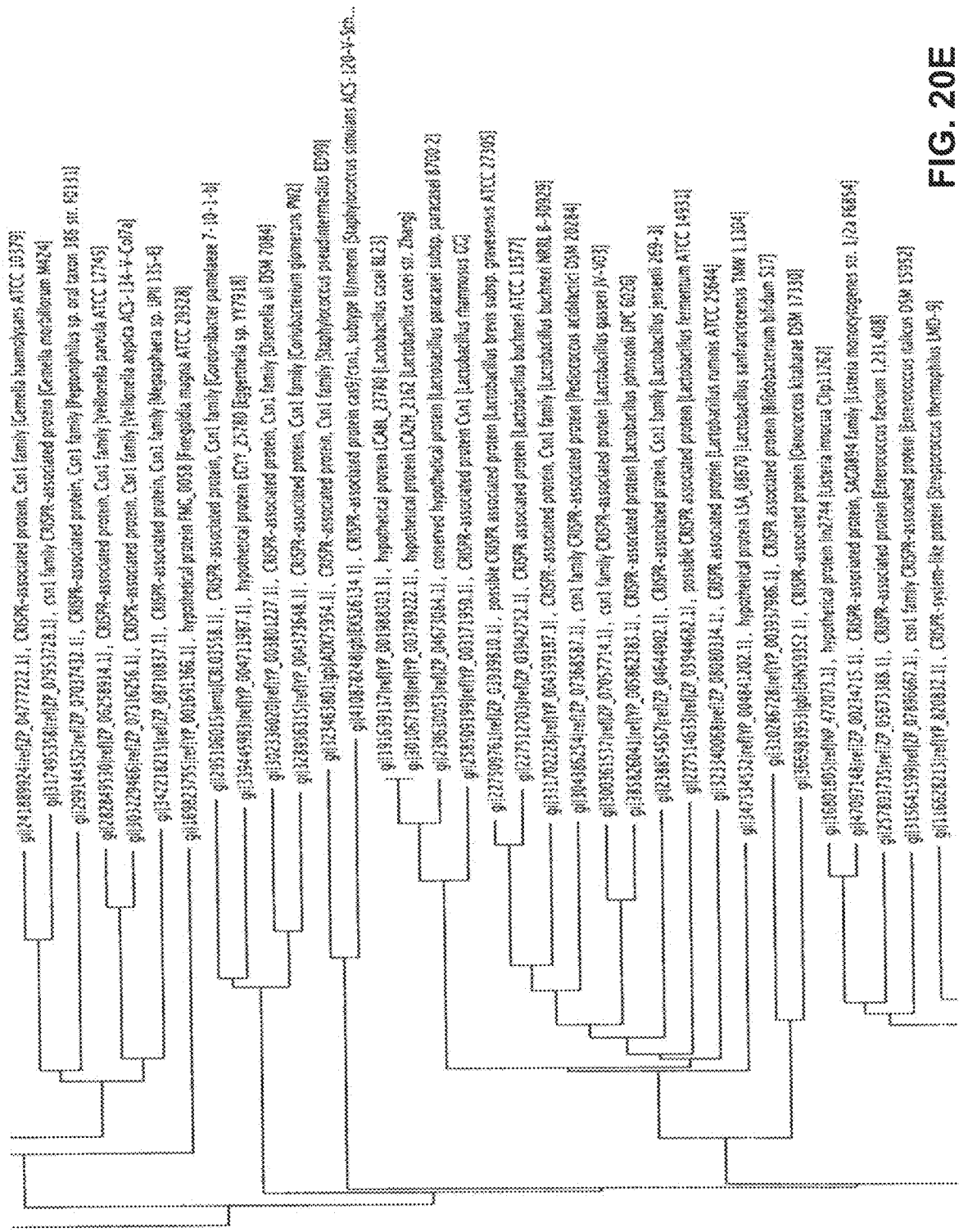
Figure 20F:
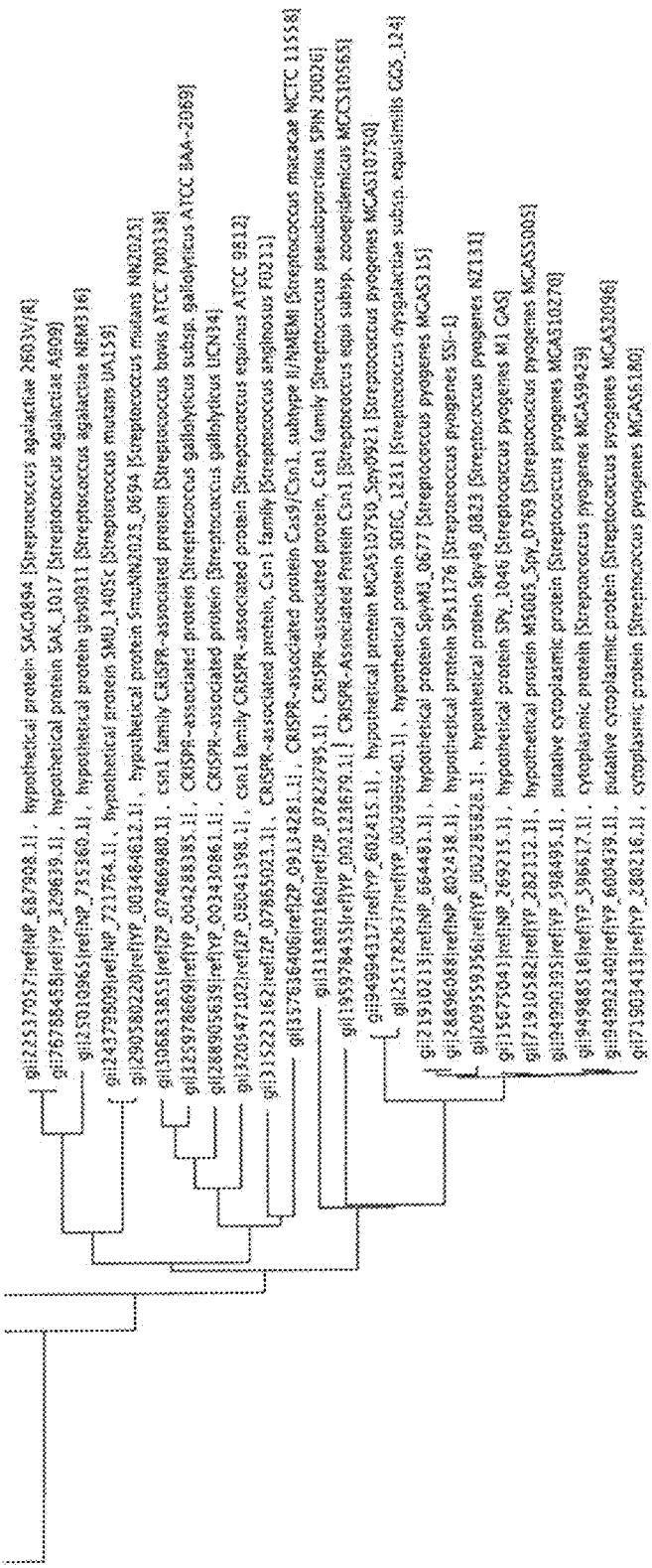
Figure 21A:
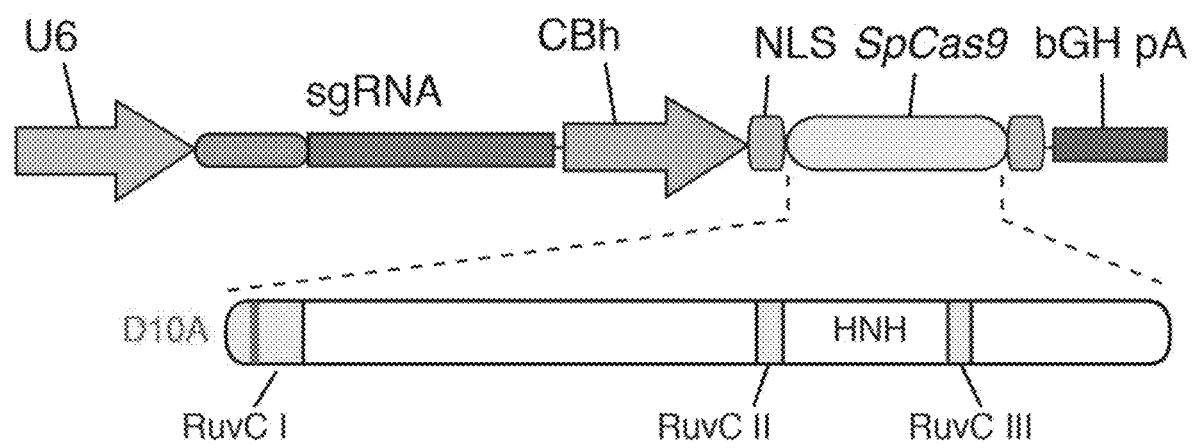
FIG. 21A-21D (a-d) shows genome editing via homologous recombination. (a) Schematic of SpCas9 nickase, with D10A mutation in the RuvC 1 catalytic domain. (b) Schematic representing homologous recombination (HR) at the human EMX1 locus using either sense or antisense single stranded oligonucleotides as repair templates. Red arrow above indicates sgRNA cleavage site; PCR primers for genotyping (Tables J and K) are indicated as arrows in right panel. (c) Sequence of region modified by HR.
Figure 21B:
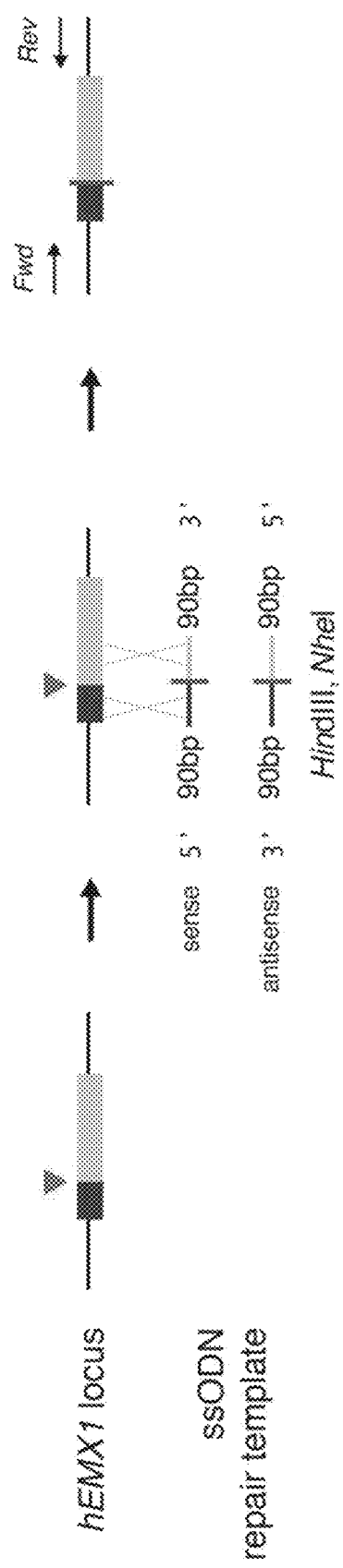
Figure 21C:
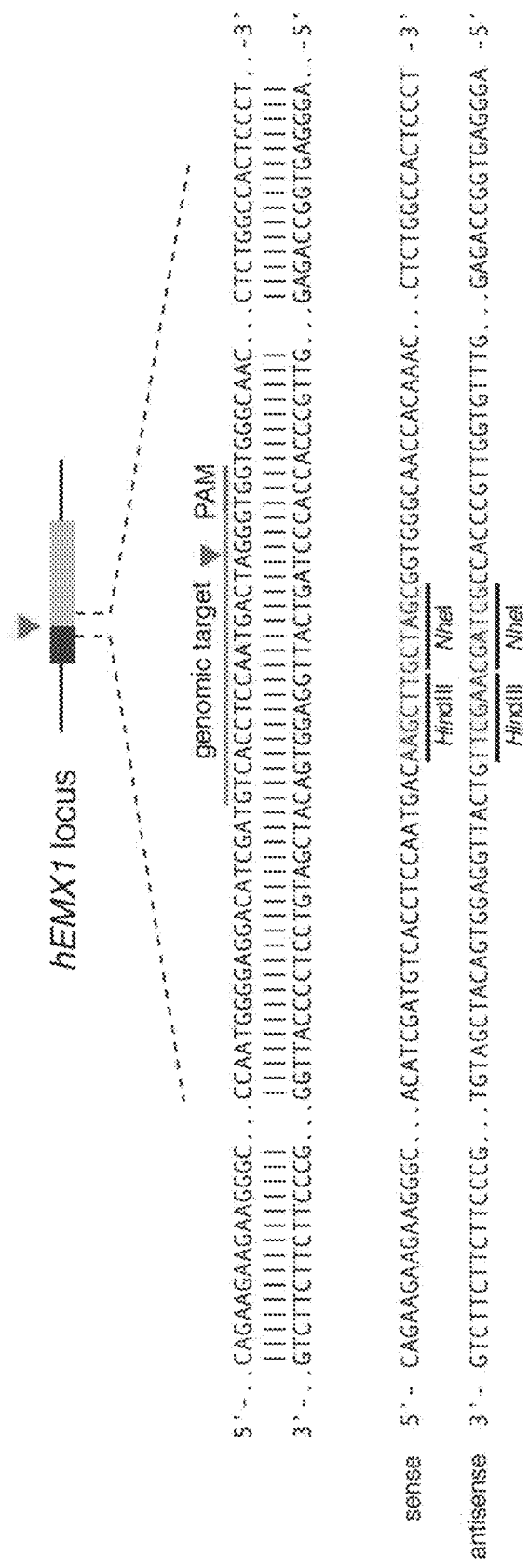
Figure 21D:
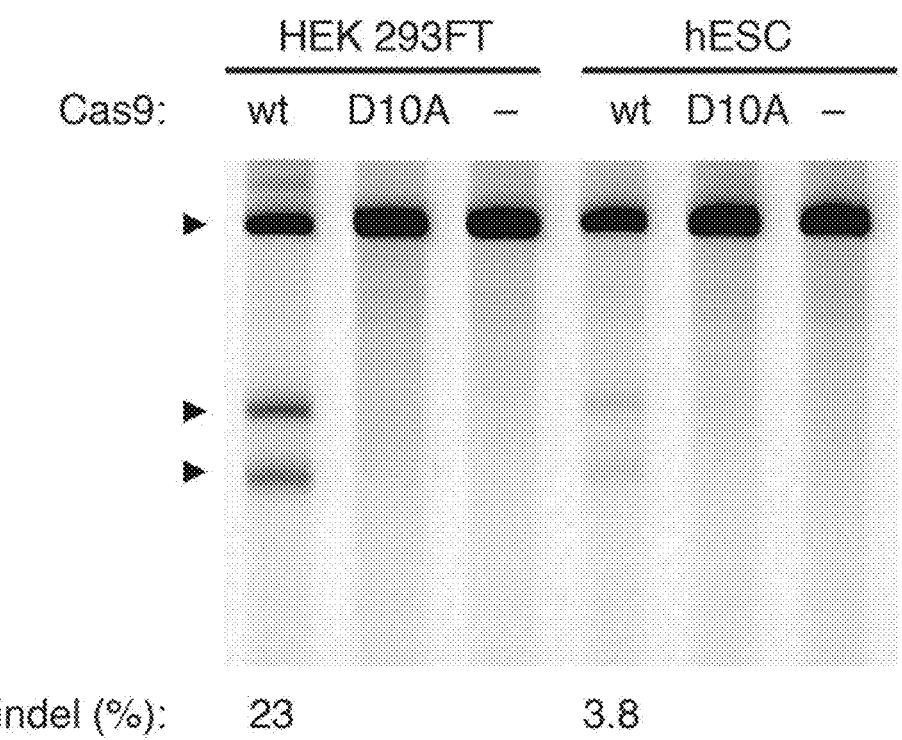

Since multiple occurrences in the genome of the DNA target site may lead to nonspecific genome editing, after identifying all potential sites, the program filters out sequences based on the number of times they appear in the relevant reference genome. For those CRISPR enzymes for which sequence specificity is determined by a 'seed' sequence, such as the 11-12 bp 5' from the PAM sequence, including the PAM sequence itself, the filtering step may be based on the seed sequence. Thus, to avoid editing at additional genomic loci, results are filtered based on the number of occurrences of the seed:PAM sequence in the relevant genome. The user may be allowed to choose the length of the seed sequence. The user may also be allowed to specify the number of occurrences of the seed:PAM sequence in a genome for purposes of passing the filter. The default is to screen for unique sequences. Filtration level is altered by changing both the length of the seed sequence and the number of occurrences of the sequence in the genome. The program may in addition or alternatively provide the sequence of a guide sequence complementary to the reported target sequence(s) by providing the reverse complement of the identified target sequence(s). An example visualization of some target sites in the human genome is provided in FIG. 18.

Further details of methods and algorithms to optimize sequence selection can be found in U.S. application Ser. No. 61/064,798; incorporated herein by reference.

Example 4: Evaluation of Multiple Chimeric crRNA-tracrRNA Hybrids

Figure 16A:
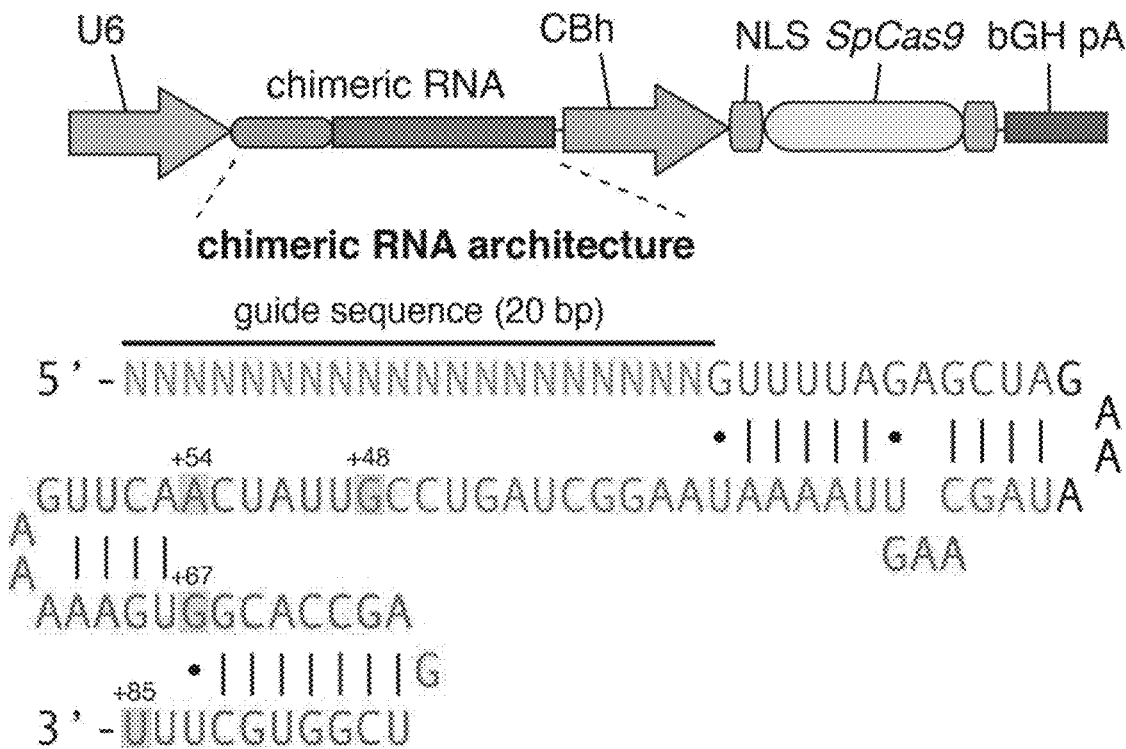
FIG. 16A-16C shows exemplary manipulation of a CRISPR system with chimeric RNAs and results of SURVEYOR assays for system activity in eukaryotic cells.

This example describes results obtained for chimeric RNAs (chiRNAs; comprising a guide sequence, a tracr mate sequence, and a tracr sequence in a single transcript) having tracr sequences that incorporate different lengths of wild-type tracrRNA sequence. FIG. 16a illustrates a schematic of a bicistronic expression vector for chimeric RNA and Cas9.

Figure 16B:
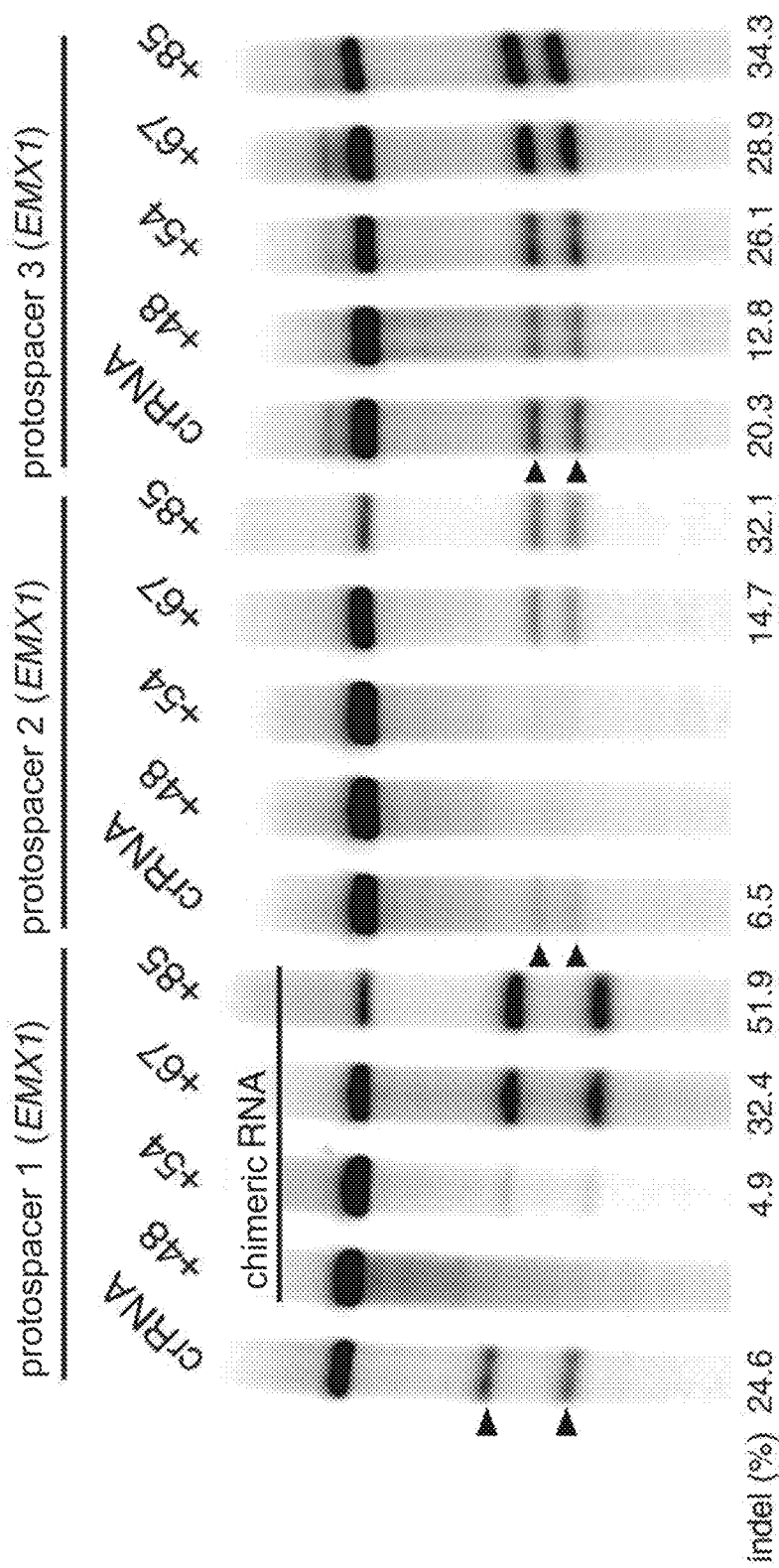
Figure 16C:
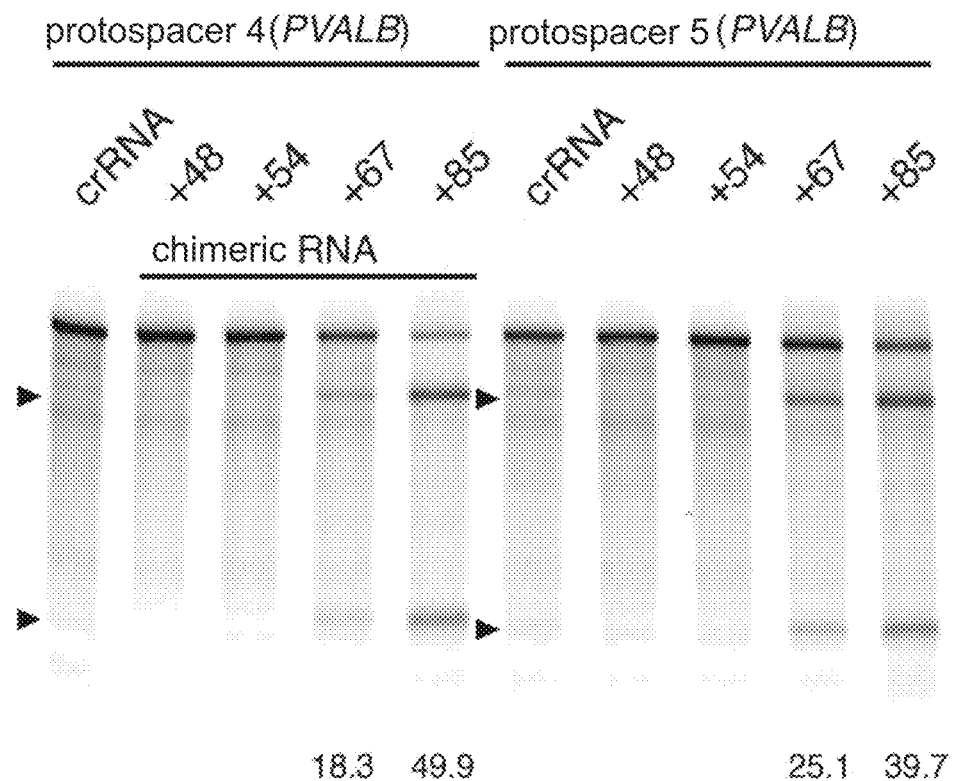

Cas9 is driven by the CBh promoter and the chimeric RNA is driven by a U6 promoter. The chimeric guide RNA consists of a 20 bp guide sequence (Ns) joined to the tracr sequence (running from the first "U" of the lower strand to the end of the transcript), which is truncated at various positions as indicated. The guide and tracr sequences are separated by the tracr-mate sequence GUUUUAGAGCUA (SEQ ID NO: 14) followed by the loop sequence GAAA. Results of SURVEYOR assays for Cas9-mediated indels at the human EMX1 and PVALB loci are illustrated in FIGS. 16b and 16c, respectively. Arrows indicate the expected SURVEYOR fragments. ChiRNAs are indicated by their "+n" designation, and crRNA refers to a hybrid RNA where guide and tracr sequences are expressed as separate transcripts. Quantification of these results, performed in triplicate, are illustrated by histogram in FIGS. 17a and 17b, corresponding to FIGS. 16b and 16c, respectively ("N.D." indicates no indels detected). Protospacer IDs and their corresponding genomic target, protospacer sequence, PAM sequence, and strand location are provided in Table D. Guide sequences were designed to be complementary to the entire protospacer sequence in the case of separate transcripts in the hybrid system, or only to the underlined portion in the case of chimeric RNAs.

increasing tracr sequence length was observed. Without wishing to be bound by any theory, the secondary structure formed by the 3' end of the tracrRNA may play a role in enhancing the rate of CRISPR complex formation.

Example 5: Cas9 Diversity

The CRISPR-Cas system is an adaptive immune mechanism against invading exogenous DNA employed by diverse species across bacteria and archaea. The type II CRISPR-Cas9 system consists of a set of genes encoding proteins responsible for the "acquisition" of foreign DNA into the CRISPR locus, as well as a set of genes encoding the "execution" of the DNA cleavage mechanism; these include the DNA nuclease (Cas9), a non-coding transactivating cr-RNA (tracrRNA), and an array of foreign DNA-derived spacers flanked by direct repeats (crRNAs). Upon maturation by Cas9, the tracRNA and crRNA duplex guide the Cas9 nuclease to a target DNA sequence specified by the spacer guide sequences, and mediates double-stranded breaks in the DNA near a short sequence motif in the target DNA that is required for cleavage and specific to each CRISPR-Cas system. The type II CRISPR-Cas systems are found throughout the bacterial kingdom and highly diverse

TABLE D (SEQ ID NOs: 15-19, respectively, in order of appearance)

| proto-spacer ID | genomic target | protospacer sequence (5' to 3') | PAM | strand |
|---|---|---|---|---|
| 1 | EMX1 | GGACATCGATGTCACCTCCAATGACTAGGG | TGG | + |
| 2 | EMX1 | CATTGGAGGTGACATCGATGTCCTCCCCAT | TGG | - |
| 3 | EMX1 | GGAAGGGCCTGAGTCCGAGCAGAAGAAGAA | GGG | + |
| 4 | PVALB | GGTGGCGAGAGGGGCCGAGATTGGGTGTTC | AGG | + |
| 5 | PVALB | ATGCAGGAGGGTGGCGAGAGGGGCCGAGAT | TGG | + |

Further details to optimize guide sequences can be found in U.S. application Ser. No. 61/836,127; incorporated herein by reference.

Figures 17A, 17B:
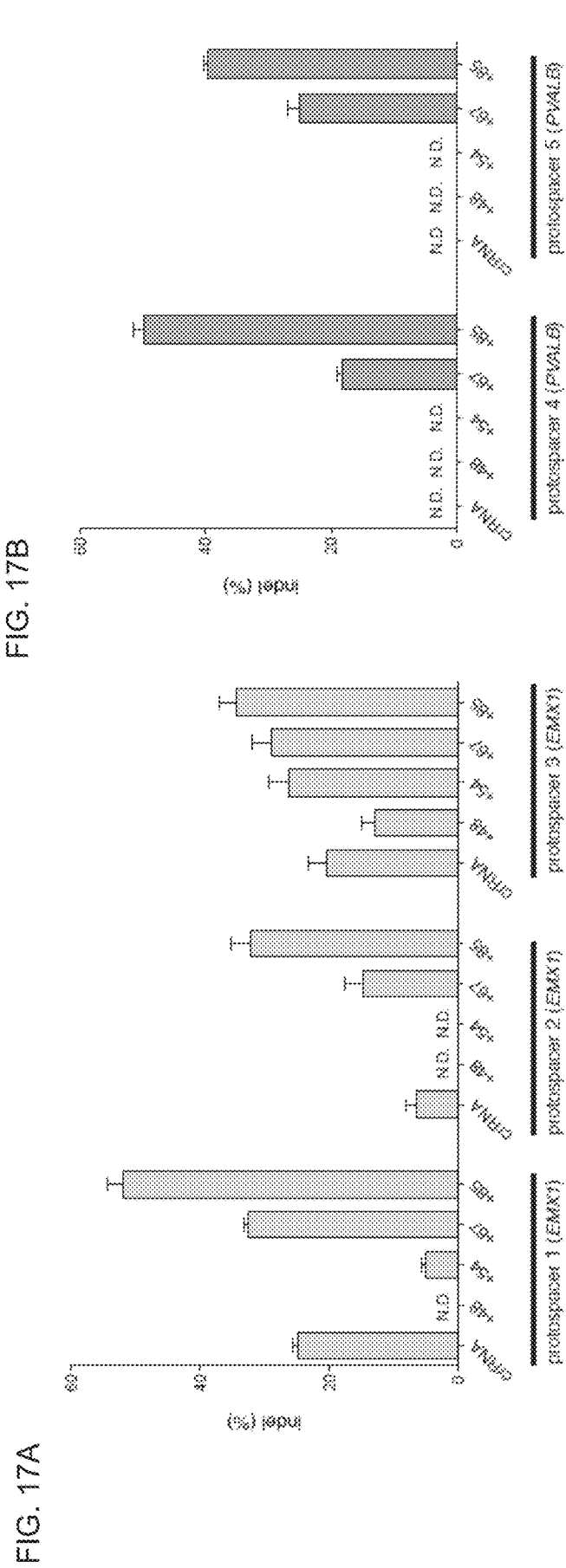
FIG. 17A-17B shows a graphical representation of the results of SURVEYOR assays for CRISPR system activity in eukaryotic cells.

Initially, three sites within the EMX1 locus in human HEK 293FT cells were targeted. Genome modification efficiency of each chiRNA was assessed using the SURVEYOR nuclease assay, which detects mutations resulting from DNA double-strand breaks (DSBs) and their subsequent repair by the non-homologous end joining (NHEJ) DNA damage repair pathway. Constructs designated chiRNA(+n) indicate that up to the +n nucleotide of wild-type tracrRNA is included in the chimeric RNA construct, with values of 48, 54, 67, and 85 used for n. Chimeric RNAs containing longer fragments of wild-type tracrRNA (chiRNA(+67) and chiRNA(+85)) mediated DNA cleavage at all three EMX1 target sites, with chiRNA(+85) in particular demonstrating significantly higher levels of DNA cleavage than the corresponding crRNA/tracrRNA hybrids that expressed guide and tracr sequences in separate transcripts (FIGS. 16b and 17a). Two sites in the PVALB locus that yielded no detectable cleavage using the hybrid system (guide sequence and tracr sequence expressed as separate transcripts) were also targeted using chiRNAs. chiRNA(+67) and chiRNA(+85) were able to mediate significant cleavage at the two PVALB protospacers (FIGS. 16c and 17b).

For all five targets in the EMX1 and PVALB loci, a consistent increase in genome modification efficiency with in in Cas9 protein sequence and size, tracrRNA and crRNA direct repeat sequence, genome organization of these elements, and the motif requirement for target cleavage. One species may have multiple distinct CRISPR-Cas systems.

Applicants evaluated 207 putative Cas9s from bacterial species identified based on sequence homology to known Cas9s and structures orthologous to known subdomains, including the HNH endonuclease domain and the RuvC endonuclease domains [information from the Eugene Koonin and Kira Makarova]. Phylogenetic analysis based on the protein sequence conservation of this set revealed five families of Cas9s, including three groups of large Cas9s (~1400 amino acids) and two of small Cas9s (~1100 amino acids) (see FIGS. 19 and 20A-F). Further details of Cas9s and mutations of the Cas9 enzyme to convert into a nickase or DNA binding protein and use of same with altered functionality can be found in U.S. application Serial Nos 61/836,101 and 61/835,936 incorporated herein by reference.

Example 6: Cas9 Orthologs

Applicants analyzed Cas9 orthologs to identify the relevant PAM sequences and the corresponding chimeric guide RNA. Having an expanded set of PAMs provides broader targeting across the genome and also significantly increases the number of unique target sites and provides potential for identifying novel Cas9s with increased levels of specificity in the genome.

The specificity of Cas9 orthologs can be evaluated by testing the ability of each Cas9 to tolerate mismatches between the guide RNA and its DNA target. For example, the specificity of SpCas9 has been characterized by testing the effect of mutations in the guide RNA on cleavage efficiency. Libraries of guide RNAs were made with single or multiple mismatches between the guide sequence and the target DNA. Based on these findings, target sites for SpCas9 can be selected based on the following guidelines:

To maximize SpCas9 specificity for editing a particular gene, one should choose a target site within the locus of interest such that potential 'off-target' genomic sequences abide by the following four constraints: First and foremost, they should not be followed by a PAM with either 5'-NGG or NAG sequences. Second, their global sequence similarity to the target sequence should be minimized. Third, a maximal number of mismatches should lie within the PAM-proximal region of the off-target site. Finally, a maximal number of mismatches should be consecutive or spaced less than four bases apart.

Similar methods can be used to evaluate the specificity of other Cas9 orthologs and to establish criteria for the selection of specific target sites within the genomes of target species. As mentioned previously phylogenetic analysis based on the protein sequence conservation of this set revealed five families of Cas9s, including three groups of large Cas9s (~1400 amino acids) and two of small Cas9s (~1100 amino acids) (see FIGS. 19 and 20A-F). Further details on Cas orthologs can be found in U.S. application Serial Nos 61/836,101 and 61/835,936 (respectively) incorporated herein by reference.

Example 7: Engineering of Plants (Micro-Algae) Using Cas9 to Target and Manipulate Plant Genes Methods of Delivering Cas9
Method 1: Applicants deliver Cas9 and guide RNA using a vector that expresses Cas9 under the control of a constitutive promoter such as Hsp70A-Rbc S2 or Beta2-tubulin.
Method 2: Applicants deliver Cas9 and T7 polymerase using vectors that expresses Cas9 and T7 polymerase under the control of a constitutive promoter such as Hsp70A-Rbc S2 or Beta2-tubulin. Guide RNA will be delivered using a vector containing T7 promoter driving the guide RNA.
Method 3: Applicants deliver Cas9 mRNA and in vitro transcribed guide RNA to algae cells. RNA can be in vitro transcribed. Cas9 mRNA will consist of the coding region for Cas9 as well as 3'UTR from Cop1 to ensure stabilization of the Cas9 mRNA.
For Homologous recombination, Applicants provide an additional homology directed repair template.

Sequence for a cassette driving the expression of Cas9 under the control of beta-2 tubulin promoter, followed by the 3' UTR of Cop1.

(SEQ ID NO: 20)
TCTTTCTTGCGCTATGACACTTCCAGCAAAAGGTAGGGCGGGCTGCGAGA

CGGCTTCCCGGCGCTGCATGCAACACCGATGATGCTTCGACCCCCCGAAG

CTCCTTCGGGGCTGCATGGGCGCTCCGATGCCGCTCCAGGGCGAGCGCTG

TTTAAATAGCCAGGCCCCCGATTGCAAAGACATTATAGCGAGCTACCAAA

-continued
GCCATATTCAAACACCTAGATCACTACCACTTCTACACAGGCCACTCGAG

CTTGTGATCGCACTCCGCTAAGGGGGCGCCTCTTCCTCTTCGTTTCAGTC

ACAACCCGCAAACATGTACCCATACGATGTTCCAGATTACGCTTCGCCGA

AGAAAAAGCGCAAGGTCGAAGCGTCCGACAAGAAGTACAGCATCGGCCTG

GACATCGGCACCAACTCTGTGGGCTGGGCCGTGATCACCGACGAGTACAA

GGTGCCCAGCAAGAAATTCAAGGTGCTGGGCAACACCGACCGGCACAGCA

TCAAGAAGAACCTGATCGGAGCCCTGCTGTTCGACAGCGGCGAAACAGCC

GAGGCCACCCGGCTGAAGAGAACCGCCAGAAGAAGATACACCAGACGGAA

GAACCGGATCTGCTATCTGCAAGAGATCTTCAGCAACGAGATGGCCAAGG

TGGACGACAGCTTCTTCCACAGACTGGAAGAGTCCTTCCTGGTGGAAGAG

GATAAGAAGCACGAGCGGCACCCCATCTTCGGCAACATCGTGGACGAGGT

GGCCTACCACGAGAAGTACCCCACCATCTACCACCTGAGAAAGAAACTGG

TGGACAGCACCGACAAGGCCGACCTGCGGCTGATCTATCTGGCCCTGGCC

CACATGATCAAGTTCCGGGGCCACTTCCTGATCGAGGGCGACCTGAACCC

CGACAACAGCGACGTGGACAAGCTGTTCATCCAGCTGGTGCAGACCTACA

ACCAGCTGTTCGAGGAAAACCCCATCAACGCCAGCGGCGTGGACGCCAAG

GCCATCCTGTCTGCCAGACTGAGCAAGAGCAGACGGCTGGAAAATCTGAT

CGCCCAGCTGCCCGGCGAGAAGAAGAATGGCCTGTTCGGCAACCTGATTG

CCCTGAGCCTGGGCCTGACCCCCAACTTCAAGAGCAACTTCGACCTGGCC

GAGGATGCCAAACTGCAGCTGAGCAAGGACACCTACGACGACGACCTGGA

CAACCTGCTGGCCCAGATCGGCGACCAGTACGCCGACCTGTTTCTGGCCG

CCAAGAACCTGTCCGACGCCATCCTGCTGAGCGACATCCTGAGAGTGAAC

ACCGAGATCACCAAGGCCCCCCTGAGCGCCTCTATGATCAAGAGATACGA

CGAGCACCACCAGGACCTGACCCTGCTGAAAGCTCTCGTGCGGCAGCAGC

TGCCTGAGAAGTACAAAGAGATTTTCTTCGACCAGAGCAAGAACGGCTAC

GCCGGCTACATTGACGGCGGAGCCAGCCAGGAAGAGTTCTACAAGTTCAT

CAAGCCCATCCTGGAAAAGATGGACGGCACCGAGGAACTGCTCGTGAAGC

TGAACAGAGAGGACCTGCTGCGGAAGCAGCGGACCTTCGACAACGGCAGC

ATCCCCCACCAGATCCACCTGGGAGAGCTGCACGCCATTCTGCGGCGGCA

GGAAGATTTTTACCCATTCCTGAAGGACAACGGGAAAAGATCGAGAAGA

TCCTGACCTTCCGCATCCCCTACTACGTGGGCCCTCTGGCCAGGGGAAAC

AGCAGATTCGCCTGGATGACCAGAAAGAGCGAGGAAACCATCACCCCCTG

GAACTTCGAGGAAGTGGTGGACAAGGGCGCTTCCGCCCAGAGCTTCATCG

AGCGGATGACCAACTTCGATAAGAACCTGCCCAACGAGAAGGTGCTGCCC

AAGCACAGCCTGCTGTACGAGTACTTCACCGTGTATAACGAGCTGACCAA

AGTGAAATACGTGACCGAGGGAATGAGAAAGCCCGCCTTCCTGAGCGGCG

AGCAGAAAAAGGCCATCGTGGACCTGCTGTTCAAGACCAACCGGAAAGTG

ACCGTGAAGCAGCTGAAAGAGGACTACTTCAAGAAAATCGAGTGCTTCGA

CTCCGTGGAAATCTCCGGCGTGGAAGATCGGTTCAACGCCTCCCTGGGCA

CATACCACGATCTGCTGAAAATTATCAAGGACAAGGACTTCCTGGACAAT

GAGGAAAACGAGGACATTCTGGAAGATATCGTGCTGACCCTGACACTGTT

```
TGAGGACAGAGAGATGATCGAGGAACGGCTGAAAACCTATGCCCACCTGT
TCGACGACAAAGTGATGAAGCAGCTGAAGCGGCGGAGATACACCGGCTGG
GGCAGGCTGAGCCGGAAGCTGATCAACGGCATCCGGGACAAGCAGTCCGG
CAAGACAATCCTGGATTTCCTGAAGTCCGACGGCTTCGCCAACAGAAACT
TCATGCAGCTGATCCACGACGACAGCCTGACCTTTAAAGAGGACATCCAG
AAAGCCCAGGTGTCCGCCAGGGCGATAGCCTGCACGAGCACATTGCCAA
TCTGGCCGGCAGCCCCGCCATTAAGAAGGGCATCCTGCAGACAGTGAAGG
TGGTGGACGAGCTCGTGAAAGTGATGGGCCGGCACAAGCCCGAGAACATC
GTGATCGAAATGGCCAGAGAGAACCAGACCACCCAGAAGGGACAGAAGAA
CAGCCGCGAGAATGAAGCGGATCGAAGAGGGCATCAAAGAGCTGGGCA
GCCAGATCCTGAAAGAACACCCCGTGGAAAACACCCAGCTGCAGAACGAG
AAGCTGTACCTGTACTACCTGCAGAATGGGCGGGATATGTACGTGGACCA
GGAACTGGACATCAACCGGCTGTCCGACTACGATGTGGACCATATCGTGC
CTCAGAGCTTTCTGAAGGACGACTCCATCGACAACAAGGTGCTGACCAGA
AGCGACAAGAACCGGGGCAAGAGCGACAACGTGCCCTCCGAAGAGGTCGT
GAAGAAGATGAAGAACTACTGGCGGCAGCTGCTGAACGCCAAGCTGATTA
CCCAGAGAAAGTTCGACAATCTGACCAAGGCCGAGAGAGGCGGCCTGAGC
GAACTGGATAAGGCCGGCTTCATCAAGAGACAGCTGGTGGAAACCCGGCA
GATCACAAAGCACGTGGCACAGATCCTGGACTCCCGGATGAACACTAAGT
ACGACGAGAATGACAAGCTGATCCGGGAAGTGAAAGTGATCACCCTGAAG
TCCAAGCTGGTGTCCGATTTCCGGAAGGATTTCCAGTTTTACAAAGTGCG
CGAGATCAACAACTACCACCACGCCCACGACGCCTACCTGAACGCCGTCG
TGGGAACCGCCCTGATCAAAAAGTACCCTAAGCTGGAAAGCGAGTTCGTG
TACGGCGACTACAAGGTGTACGACGTGCGGAAGATGATCGCCAAGAGCGA
GCAGGAAATCGGCAAGGCTACCGCCAAGTACTTCTTCTACAGCAACATCA
TGAACTTTTTCAAGACCGAGATTACCCTGGCCAACGGCGAGATCCGGAAG
CGGCCTCTGATCGAGACAAACGGCGAAACCGGGGAGATCGTGTGGGATAA
GGGCCGGGATTTTGCCACCGTGCGGAAAGTGCTGAGCATGCCCCAAGTGA
ATATCGTGAAAAAGACCGAGGTGCAGACAGGCGGCTTCAGCAAAGAGTCT
ATCCTGCCCAAGAGGAACAGCGATAAGCTGATCGCCAGAAAGAAGGACTG
GGACCCTAAGAAGTACGGCGGCTTCGACAGCCCCACCGTGGCCTATTCTG
TGCTGGTGGTGGCCAAAGTGGAAAAGGGCAAGTCCAAGAAACTGAAGAGT
GTGAAAGAGCTGCTGGGGATCACCATCATGGAAAGAAGCAGCTTCGAGAA
GAATCCCATCGACTTTCTGGAAGCCAAGGGCTACAAAGAAGTGAAAAAGG
ACCTGATCATCAAGCTGCCTAAGTACTCCCTGTTCGAGCTGGAAAACGGC
CGGAAGAGAATGCTGGCCTCTGCCGGCGAACTGCAGAAGGGAAACGAACT
GGCCCTGCCCTCCAAATATGTGAACTTCCTGTACCTGGCCAGCCACTATG
AGAAGCTGAAGGGCTCCCCCGAGGATAATGAGCAGAAACAGCTGTTTGTG
GAACAGCACAAGCACTACCTGGACGAGATCATCGAGCAGATCAGCGAGTT
CTCCAAGAGAGTGATCCTGGCCGACGCTAATCTGGACAAAGTGCTGTCCG
CCTACAACAAGCACCGGGATAAGCCCATCAGAGAGCAGGCCGAGAATATC
ATCCACCTGTTTACCCTGACCAATCTGGGAGCCCCTGCCGCCTTCAAGTA
CTTTGACACCACCATCGACCGGAAGAGGTACACCAGCACCAAAGAGGTGC
TGGACGCCACCCTGATCCACCAGAGCATCACCGGCCTGTACGAGACACGG
ATCGACCTGTCTCAGCTGGGAGGCGACAGCCCCAAGAAGAAGAGAAAGGT
GGAGGCCAGCTAAGGATCCGGCAAGACTGGCCCCGCTTGGCAACGCAACA
GTGAGCCCCTCCCTAGTGTGTTTGGGGATGTGACTATGTATTCGTGTGTT
GGCCAACGGGTCAACCCGAACAGATTGATACCCGCCTTGGCATTTCCTGT
CAGAATGTAACGTCAGTTGATGGTACT
```

Sequence for a cassette driving the expression of T7 polymerase under the control of beta-2 tubulin promoter, followed by the 3' UTR of Cop1:

(SEQ ID NO: 21)
```
TCTTTCTTGCGCTATGACACTTCCAGCAAAAGGTAGGGCGGGCTGCGAGA
CGGCTTCCCGGCGCTGCATGCAACACCGATGATGCTTCGACCCCCCGAAG
CTCCTTCGGGGCTGCATGGGCGCTCCGATGCCGCTCCAGGGCGAGCGCTG
TTTAAATAGCCAGGCCCCCGATTGCAAAGACATTATAGCGAGCTACCAAA
GCCATATTCAAACACCTAGATCACTACCACTTCTACACAGGCCACTCGAG
CTTGTGATCGCACTCCGCTAAGGGGCGCCTCTTCCTCTTCGTTTCAGTC
ACAACCCGCAAAcatgcctaagaagaagaggaaggttaacacgattaaca
tcgctaagaacgacttctctgacatcgaactggctgctatcccgttcaac
actctggctgaccattacggtgagcgtttagctcgcgaacagttggccct
tgagcatgagtcttacgagatgggtgaagcacgcttccgcaagatgtttg
agcgtcaacttaaagctggtgaggttgcggataacgctgccgccaagcct
ctcatcactaccctactccctaagatgattgcacgcatcaacgactggtt
tgaggaagtgaaagctaagcgcggcaagcgcccgacagccttccagttcc
tgcaagaaatcaagccggaagccgtagcgtacatcaccattaagaccact
ctggcttgcctaaccagtgctgacaatacaaccgttcaggctgtagcaag
cgcaatcggtcgggccattgaggacgaggctcgcttcggtcgtatccgtg
accttgaagctaagcacttcaagaaaaacgttgaggaacaactcaacaag
cgcgtagggcacgtctacaagaaagcatttatgcaagttgtcgaggctga
catgctctctaagggtctactcggtggcgaggcgtggtcttcgtggcata
aggaagactctattcatgtaggagtacgctgcatcgagatgctcattgag
tcaaccggaatggttagcttacaccgccaaaatgctggcgtagtaggtca
agactctgagactatcgaactcgcacctgaatacgctgaggctatcgcaa
cccgtgcaggtgcgctggctggcatctctccgatgttccaaccttgcgta
gttcctcctaagccgtggactggcattactggtggtggctattgggctaa
cggtcgtcgtcctctggcgctggtgcgtactcacagtaagaaagcactga
tgcgctacgaagacgtttacatgcctgaggtgtacaaagcgattaacatt
gcgcaaaacaccgcatggaaaatcaacaagaaagtcctagcggtcgccaa
cgtaatcaccaagtggaagcattgtccggtcgaggacatccctgcgattg
agcgtgaagaactcccgatgaaaccggaagacatcgacatgaatcctgag
```

```
gctctcaccgcgtggaaacgtgctgccgctgctgtgtaccgcaaggacaa ggctcgcaagtctcgccgtatcagccttgagttcatgcttgagcaagcca ataagtttgctaaccataaggccatctggttcccttacaacatggactgg cgcggtcgtgtttacgctgtgtcaatgttcaacccgcaaggtaacgatat gaccaaaggactgcttacgctggcgaaaggtaaaccaatcggtaaggaag gttactactggctgaaaatccacggtgcaaactgtgcgggtgtcgacaag gttccgttccctgagcgcatcaagttcattgaggaaaaccacgagaacat catggcttgcgctaagtctccactggagaacacttggtgggctgagcaag attctccgttctgcttccttgcgttctgctttgagtacgctggggtacag caccacggcctgagctataactgctcccttccgctggcgtttgacgggtc ttgctctggcatccagcacttctccgcgatgctccgagatgaggtaggtg gtcgcgcggttaacttgcttcctagtgaaaccgttcaggacatctacggg attgttgctaagaaagtcaacgagattctacaagcagacgcaatcaatgg gaccgataacgaagtagttaccgtgaccgatgagaacactggtgaaatct ctgagaaagtcaagctgggcactaaggcactggctggtcaatggctggct tacggtgttactcgcagtgtgactaagcgttcagtcatgacgctggctta cgggtccaaagagttcggcttccgtcaacaagtgctggaagataccattc agccagctattgattccggcaagggtctgatgttcactcagccgaatcag gctgctggatacatggctaagctgatttgggaatctgtgagcgtgacggt ggtagctgcggttgaagcaatgaactggcttaagtctgctgctaagctgc tggctgctgaggtcaaagataagaagactggagagattcttcgcaagcgt tgcgctgtgcattgggtaactcctgatggtttccctgtgtggcaggaata caagaagcctattcagacgcgcttgaacctgatgttcctcggtcagttcc gcttacagcctaccattaacaccaacaaagatagcgagattgatgcacac aaacaggagtctggtatcgctcctaactttgtacacagccaagacggtag ccaccttcgtaagactgtagtgtgggcacacgagaagtacggaatcgaat cttttgcactgattcacgactccttcggtacgattccggctgacgctgcg aacctgttcaaagcagtgcgcgaaactatggttgacacatatgagtcttg tgatgtactggctgatttctacgaccagttcgctgaccagttgcacgagt ctcaattggacaaaatgccagcacttccggctaaaggtaacttgaacctc cgtgacatcttagagtcggacttcgcgttcgcgtaaGGATCCGGCAAGAC

TGGCCCCGCTTGGCAACGCAACAGTGAGCCCCTCCCTAGTGTGTTTGGGG

ATGTGACTATGTATTCGTGTGTTGGCCAACGGGTCAACCCGAACAGATTG

ATACCCGCCTTGGCATTTCCTGTCAGAATGTAACGTCAGTTGATGGTACT
```

Sequence of guide RNA driven by the T7 promoter (T7 promoter, Ns represent targeting sequence):

```
                                        (SEQ ID NO: 22)
gaaatTAATACGACTCACTATANNNNNNNNNNNNNNNNNNNNgttttaga
gctaGAAAtagcaagttaaaataaggctagtccgttatcaacttgaaaaa
gtggcaccgagtcggtgctttttt
```

Gene Delivery:

Chlamydomonas reinhardtii strain CC-124 and CC-125 from the Chlamydomonas Resource Center will be used for electroporation. Electroporation protocol follows standard recommended protocol from the GeneArt Chlamydomonas Engineering kit.

Also, Applicants generate a line of Chlamydomonas reinhardtii that expresses Cas9 constitutively. This can be done by using pChlamyl (linearized using PvuI) and selecting for hygromycin resistant colonies. Sequence for pChlamyl containing Cas9 is below. In this way to achieve gene knockout one simply needs to deliver RNA for the guideRNA. For homologous recombination Applicants deliver guideRNA as well as a linearized homologous recombination template.

pChlamyl-Cas9:

```
                                        (SEQ ID NO: 23)
TGCGGTATTTCACACCGCATCAGGTGGCACTTTTCGGGGAAATGTGCGCG

GAACCCCTATTTGTTTATTTTTCTAAATACATTCAAATATGTATCCGCTC

ATGAGATTATCAAAAAGGATCTTCACCTAGATCCTTTTAAATTAAAAATG

AAGTTTTAAATCAATCTAAAGTATATATGAGTAAACTTGGTCTGACAGTT

ACCAATGCTTAATCAGTGAGGCACCTATCTCAGCGATCTGTCTATTTCGT

TCATCCATAGTTGCCTGACTCCCCGTCGTGTAGATAACTACGATACGGGA

GGGCTTACCATCTGGCCCCAGTGCTGCAATGATACCGCGAGACCCACGCT

CACCGGCTCCAGATTTATCAGCAATAAACCAGCCAGCCGGAAGGGCCGAG

CGCAGAAGTGGTCCTGCAACTTTATCCGCCTCCATCCAGTCTATTAATTG

TTGCCGGGAAGCTAGAGTAAGTAGTTCGCCAGTTAATAGTTTGCGCAACG

TTGTTGCCATTGCTACAGGCATCGTGGTGTCACGCTCGTCGTTTGGTATG

GCTTCATTCAGCTCCGGTTCCCAACGATCAAGGCGAGTTACATGATCCCC

CATGTTGTGCAAAAAAGCGGTTAGCTCCTTCGGTCCTCCGATCGTTGTCA

GAAGTAAGTTGGCCGCAGTGTTATCACTCATGGTTATGGCAGCACTGCAT

AATTCTCTTACTGTCATGCCATCCGTAAGATGCTTTTCTGTGACTGGTGA

GTACTCAACCAAGTCATTCTGAGAATAGTGTATGCGGCGACCGAGTTGCT

CTTGCCCGGCGTCAATACGGGATAATACCGCGCCACATAGCAGAACTTTA

AAAGTGCTCATCATTGGAAAACGTTCTTCGGGGCGAAAACTCTCAAGGAT

CTTACCGCTGTTGAGATCCAGTTCGATGTAACCCACTCGTGCACCCAACT

GATCTTCAGCATCTTTTACTTTCACCAGCGTTTCTGGGTGAGCAAAAACA

GGAAGGCAAATGCCGCAAAAAAGGGAATAAGGGCGACACGGAAATGTTG

AATACTCATACTCTTCCTTTTTCAATATTATTGAAGCATTTATCAGGGTT

ATTGTCTCATGACCAAAATCCCTTAACGTGAGTTTTCGTTCCACTGAGCG

TCAGACCCCGTAGAAAAGATCAAAGGATCTTCTTGAGATCCTTTTTTTCT

GCGCGTAATCTGCTGCTTGCAAACAAAAAAACCACCGCTACCAGCGGTGG

TTTGTTTGCCGGATCAAGAGCTACCAACTCTTTTTCCGAAGGTAACTGGC

TTCAGCAGAGCGCAGATACCAAATACTGTTCTTCTAGTGTAGCCGTAGTT

AGGCCACCACTTCAAGAACTCTGTAGCACCGCCTACATACCTCGCTCTGC

TAATCCTGTTACCAGTGGCTGTTGCCAGTGGCGATAAGTCGTGTCTTACC

GGGTTGGACTCAAGACGATAGTTACCGGATAAGGCGCAGCGGTCGGGCTG

AACGGGGGGTTCGTGCACACAGCCCAGCTTGGAGCGAACGACCTACACCG

AACTGAGATACCTACAGCGTGAGCTATGAGAAAGCGCCACGCTTCCCGAA
```

-continued

```
GGGAGAAAGGCGGACAGGTATCCGGTAAGCGGCAGGGTCGGAACAGGAGA
GCGCACGAGGGAGCTTCCAGGGGGAAACGCCTGGTATCTTTATAGTCCTG
TCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTT
CCTGGCCTTTTGCTGGCCTTTTGCTCACATGTTCTTTCCTGCGTTATCCC
CTGATTCTGTGGATAACCGTATTACCGCCTTTGAGTGAGCTGATACCGCT
CGCCGCAGCCGAACGACCGAGCGCAGCGAGTCAGTGAGCGAGGAAGCGGT
CGCTGAGGCTTGACATGATTGGTGCGTATGTTTGTATGAAGCTACAGGAC
TGATTTGGCGGGCTATGAGGGCGGGGGAAGCTCTGGAAGGGCCGCGATGG
GGCGCGCGGCGTCCAGAAGGCGCCATACGGCCCGCTGGCGGCACCCATCC
GGTATAAAAGCCCGCGACCCCGAACGGTGACCTCCACTTTCAGCGACAAA
CGAGCACTTATACATACGCGACTATTCTGCCGCTATACATAACCACTCAG
CTAGCTTAAGATCCCATCAAGCTTGCATGCCGGGCGCGCCAGAAGGAGCG
CAGCCAAACCAGGATGATGTTTGATGGGTATTTGAGCACTTGCAACCCT
TATCCGGAAGCCCCCTGGCCCACAAAGGCTAGGCGCCAATGCAAGCAGTT
CGCATGCAGCCCCTGGAGCGGTGCCCTCCTGATAAACCGGCCAGGGGCC
TATGTTCTTTACTTTTTTACAAGAGAAGTCACTCAACATCTTAAAATGGC
CAGGTGAGTCGACGAGCAAGCCCGGCGGATCAGGCAGCGTGCTTGCAGAT
TTGACTTGCAACGCCCGCATTGTGTCGACGAAGGCTTTTGGCTCCTCTGT
CGCTGTCTCAAGCAGCATCTAACCCTGCGTCGCCGTTTCCATTTGCAGGA
GATTCGAGGTACCATGTACCCATACGATGTTCCAGATTACGCTTCGCCGA
AGAAAAAGCGCAAGGTCGAAGCGTCCGACAAGAAGTACAGCATCGGCCTG
GACATCGGCACCAACTCTGTGGGCTGGGCCGTGATCACCGACGAGTACAA
GGTGCCCAGCAAGAAATTCAAGGTGCTGGGCAACACCGACCGGCACAGCA
TCAAGAAGAACCTGATCGGAGCCCTGCTGTTCGACAGCGGCGAAACAGCC
GAGGCCACCCGGCTGAAGAGAACCGCCAGAAGAAGATACACCAGACGGAA
GAACCGGATCTGCTATCTGCAAGAGATCTTCAGCAACGAGATGGCCAAGG
TGGACGACAGCTTCTTCCACAGACTGGAAGAGTCCTTCCTGGTGGAAGAG
GATAAGAAGCACGAGCGGCACCCCATCTTCGGCAACATCGTGGACGAGGT
GGCCTACCACGAGAAGTACCCCACCATCTACCACCTGAGAAAGAAACTGG
TGGACAGCACCGACAAGGCCGACCTGCGGCTGATCTATCTGGCCCTGGCC
CACATGATCAAGTTCCGGGGCCACTTCCTGATCGAGGGCGACCTGAACCC
CGACAACAGCGACGTGGACAAGCTGTTCATCCAGCTGGTGCAGACCTACA
ACCAGCTGTTCGAGGAAAACCCCATCAACGCCAGCGGCGTGGACGCCAAG
GCCATCCTGTCTGCCAGACTGAGCAAGAGCAGACGGCTGGAAAATCTGAT
CGCCCAGCTGCCCGGCGAGAAGAAGAATGGCCTGTTCGGCAACCTGATTG
CCCTGAGCCTGGGCCTGACCCCCAACTTCAAGAGCAACTTCGACCTGGCC
GAGGATGCCAAACTGCAGCTGAGCAAGGACACCTACGACGACGACCTGGA
CAACCTGCTGGCCCAGATCGGCGACCAGTACGCCGACCTGTTTCTGGCCG
CCAAGAACCTGTCCGACGCCATCCTGCTGAGCGACATCCTGAGAGTGAAC
ACCGAGATCACCAAGGCCCCCCTGAGCGCCTCTATGATCAAGAGATACGA
```

-continued

```
CGAGCACCACCAGGACCTGACCCTGCTGAAAGCTCTCGTGCGGCAGCAGC
TGCCTGAGAAGTACAAAGAGATTTTCTTCGACCAGAGCAAGAACGGCTAC
GCCGGCTACATTGACGGCGGAGCCAGCCAGGAAGAGTTCTACAAGTTCAT
CAAGCCCATCCTGGAAAAGATGGACGGCACCGAGGAACTGCTCGTGAAGC
TGAACAGAGAGGACCTGCTGCGGAAGCAGCGGACCTTCGACAACGGCAGC
ATCCCCCACCAGATCCACCTGGGAGAGCTGCACGCCATTCTGCGGCGGCA
GGAAGATTTTTACCCATTCCTGAAGGACAACCGGGAAAAGATCGAGAAGA
TCCTGACCTTCCGCATCCCCTACTACGTGGGCCCTCTGGCCAGGGGAAAC
AGCAGATTCGCCTGGATGACCAGAAAGAGCGAGGAAACCATCACCCCCTG
GAACTTCGAGGAAGTGGTGGACAAGGGCGCTTCCGCCCAGAGCTTCATCG
AGCGGATGACCAACTTCGATAAGAACCTGCCCAACGAGAAGGTGCTGCCC
AAGCACAGCCTGCTGTACGAGTACTTCACCGTGTATAACGAGCTGACCAA
AGTGAAATACGTGACCGAGGGAATGAGAAAGCCCGCCTTCCTGAGCGGCG
AGCAGAAAAAGGCCATCGTGGACCTGCTGTTCAAGACCAACCGGAAAGTG
ACCGTGAAGCAGCTGAAAGAGGACTACTTCAAGAAAATCGAGTGCTTCGA
CTCCGTGGAAATCTCCGGCGTGGAAGATCGGTTCAACGCCTCCCTGGGCA
CATACCACGATCTGCTGAAAATTATCAAGGACAAGGACTTCCTGGACAAT
GAGGAAAACGAGGACATTCTGGAAGATATCGTGCTGACCCTGACACTGTT
TGAGGACAGAGAGATGATCGAGGAACGGCTGAAAACCTATGCCCACCTGT
TCGACGACAAAGTGATGAAGCAGCTGAAGCGGCGGAGATACACCGGCTGG
GGCAGGCTGAGCCGGAAGCTGATCAACGGCATCCGGGACAAGCAGTCCGG
CAAGACAATCCTGGATTTCCTGAAGTCCGACGGCTTCGCCAACAGAAACT
TCATGCAGCTGATCCACGACGACAGCCTGACCTTTAAAGAGGACATCCAG
AAAGCCCAGGTGTCCGGCCAGGGCGATAGCCTGCACGAGCACATTGCCAA
TCTGGCCGGCAGCCCCGCCATTAAGAAGGGCATCCTGCAGACAGTGAAGG
TGGTGGACGAGCTCGTGAAAGTGATGGGCCGGCACAAGCCCGAGAACATC
GTGATCGAAATGGCCAGAGAGAACCAGACCACCCAGAAGGGACAGAAGAA
CAGCCGCGAGAGAATGAAGCGGATCGAAGAGGGCATCAAAGAGCTGGGCA
GCCAGATCCTGAAAGAACACCCCGTGGAAAACACCCAGCTGCAGAACGAG
AAGCTGTACCTGTACTACCTGCAGAATGGGCGGGATATGTACGTGGACCA
GGAACTGGACATCAACCGGCTGTCCGACTACGATGTGGACCATATCGTGC
CTCAGAGCTTTCTGAAGGACGACTCCATCGACAACAAGGTGCTGACCAGA
AGCGACAAGAACCGGGGCAAGAGCGACAACGTGCCCTCCGAAGAGGTCGT
GAAGAAGATGAAGAACTACTGGCGGCAGCTGCTGAACGCCAAGCTGATTA
CCCAGAGAAAGTTCGACAATCTGACCAAGGCCGAGAGAGGCGGCCTGAGC
GAACTGGATAAGGCCGGCTTCATCAAGAGACAGCTGGTGGAAACCCGGCA
GATCACAAAGCACGTGGCACAGATCCTGGACTCCCGGATGAACACTAAGT
ACGACGAGAATGACAAGCTGATCCGGGAAGTGAAAGTGATCACCCTGAAG
TCCAAGCTGGTGTCCGATTTCCGGAAGGATTTCCAGTTTTACAAAGTGCG
CGAGATCAACAACTACCACCACGCCCACGACGCCTACCTGAACGCCGTCG
TGGGAACCGCCCTGATCAAAAAGTACCCTAAGCTGGAAAGCGAGTTCGTG
```

-continued

```
TACGGCGACTACAAGGTGTACGACGTGCGGAAGATGATCGCCAAGAGCGA

GCAGGAAATCGGCAAGGCTACCGCCAAGTACTTCTTCTACAGCAACATCA

TGAACTTTTTCAAGACCGAGATTACCCTGGCCAACGGCGAGATCCGGAAG

CGGCCTCTGATCGAGACAAACGGCGAAACCGGGGAGATCGTGTGGGATAA

GGGCCGGGATTTTGCCACCGTGCGGAAAGTGCTGAGCATGCCCCAAGTGA

ATATCGTGAAAAAGACCGAGGTGCAGACAGGCGGCTTCAGCAAAGAGTCT

ATCCTGCCCAAGAGGAACAGCGATAAGCTGATCGCCAGAAAGAAGGACTG

GGACCCTAAGAAGTACGGCGGCTTCGACAGCCCCACCGTGGCCTATTCTG

TGCTGGTGGTGGCCAAAGTGGAAAAGGGCAAGTCCAAGAAACTGAAGAGT

GTGAAAGAGCTGCTGGGGATCACCATCATGGAAAGAAGCAGCTTCGAGAA

GAATCCCATCGACTTTCTGGAAGCCAAGGGCTACAAAGAAGTGAAAAAGG

ACCTGATCATCAAGCTGCCTAAGTACTCCCTGTTCGAGCTGGAAAACGGC

CGGAAGAGAATGCTGGCCTCTGCCGGCGAACTGCAGAAGGGAAACGAACT

GGCCCTGCCCTCCAAATATGTGAACTTCCTGTACCTGGCCAGCCACTATG

AGAAGCTGAAGGGCTCCCCCGAGGATAATGAGCAGAAACAGCTGTTTGTG

GAACAGCACAAGCACTACCTGGACGAGATCATCGAGCAGATCAGCGAGTT

CTCCAAGAGAGTGATCCTGGCCGACGCTAATCTGGACAAAGTGCTGTCCG

CCTACAACAAGCACCGGGATAAGCCCATCAGAGAGCAGGCCGAGAATATC

ATCCACCTGTTTACCCTGACCAATCTGGGAGCCCCTGCCGCCTTCAAGTA

CTTTGACACCACCATCGACCGGAAGAGGTACACCAGCACCAAAGAGGTGC

TGGACGCCACCCTGATCCACCAGAGCATCACCGGCCTGTACGAGACACGG

ATCGACCTGTCTCAGCTGGGAGGCGACAGCCCCAAGAAGAAGAGAAAGGT

GGAGGCCAGCTAACATATGATTCGAATGTCTTTCTTGCGCTATGACACTT

CCAGCAAAAGGTAGGGCGGGCTGCGAGACGGCTTCCCGGCGCTGCATGCA

ACACCGATGATGCTTCGACCCCCCGAAGCTCCTTCGGGGCTGCATGGGCG

CTCCGATGCCGCTCCAGGGCGAGCGCTGTTTAAATAGCCAGGCCCCCGAT

TGCAAAGACATTATAGCGAGCTACCAAAGCCATATTCAAACACCTAGATC

ACTACCACTTCTACACAGGCCACTCGAGCTTGTGATCGCACTCCGCTAAG

GGGGCGCCTCTTCCTCTTCGTTTCAGTCACAACCCGCAAACATGACACAA

GAATCCCTGTTACTTCTCGACCGTATTGATTCGGATGATTCCTACGCGAG

CCTGCGGAACGACCAGGAATTCTGGGAGGTGAGTCGACGAGCAAGCCCGG

CGGATCAGGCAGCGTGCTTGCAGATTTGACTTGCAACGCCCGCATTGTGT

CGACGAAGGCTTTTGGCTCCTCTGTCGCTGTCTCAAGCAGCATCTAACCC

TGCGTCGCCGTTTCCATTTGCAGCCGCTGGCCCGCCGAGCCCTGGAGGAG

CTCGGGCTGCCGGTGCCGCCGGTGCTGCGGGTGCCCGGCGAGAGCACCAA

CCCCGTACTGGTCGGCGAGCCCGGCCCGGTGATCAAGCTGTTCGGCGAGC

ACTGGTGCGGTCCGGAGAGCCTCGCGTCGGAGTCGGAGGCGTACGCGGTC

CTGGCGGACGCCCCGGTGCCGGTGCCCCGCCTCCTCGGCCGCGGCGAGCT

GCGGCCCGGCACCGGAGCCTGGCCGTGGCCCTACCTGGTGATGAGCCGGA

TGACCGGCACCACCTGGCGGTCCGCGATGGACGGCACGACCGACCGGAAC

GCGCTGCTCGCCCTGGCCCGCGAACTCGGCCGGGTGCTCGGCCGGCTGCA
```

```
CAGGGTGCCGCTGACCGGGAACACCGTGCTCACCCCCCATTCCGAGGTCT

TCCCGGAACTGCTGCGGGAACGCCGCGCGGCGACCGTCGAGGACCACCGC

GGGTGGGGCTACCTCTCGCCCCGGCTGCTGGACCGCCTGGAGGACTGGCT

GCCGGACGTGGACACGCTGCTGGCCGGCCGCGAACCCCGGTTCGTCCACG

GCGACCTGCACGGGACCAACATCTTCGTGGACCTGGCCGCGACCGAGGTC

ACCGGGATCGTCGACTTCACCGACGTCTATGCGGGAGACTCCCGCTACAG

CCTGGTGCAACTGCATCTCAACGCCTTCCGGGGCGACCGCGAGATCCTGG

CCGCGCTGCTCGACGGGGCGCAGTGGAAGCGGACCGAGGACTTCGCCCGC

GAACTGCTCGCCTTCACCTTCCTGCACGACTTCGAGGTGTTCGAGGAGAC

CCCGCTGGATCTCTCCGGCTTCACCGATCCGGAGGAACTGGCGCAGTTCC

TCTGGGGGCCGCCGGACACCGCCCCCGGCGCCTGATAAGGATCCGGCAAG

ACTGGCCCCGCTTGGCAACGCAACAGTGAGCCCCTCCCTAGTGTGTTTGG

GGATGTGACTATGTATTCGTGTGTTGGCCAACGGGTCAACCCGAACAGAT

TGATACCCGCCTTGGCATTTCCTGTCAGAATGTAACGTCAGTTGATGGTA

CT.
```

For all modified *Chlamydomonas reinhardtii* cells, Applicants use PCR, SURVEYOR nuclease assay, and DNA sequencing to verify successful modification.

Example 8: Selection of Guide RNA Sequences for Targeting a Given Gene Using a CRISPR-Cas System Applicants used HumanBody 2.0 expression data from Illumina to calculate for each exon the percent of "constitutiveness". The term "constitutiveness" as used herein relates to how many times the exon is not spliced out across different tissues. From this analysis, Applicants compiled a list of constitutive exons that are expressed across all measured tissues. Applicants then intersected this data with NCBI CCDS database (available at the website ncbi.nlm.nih.gov/CCDS/) and take CCDS exons which are 98% covered with a constitutive exon from as previously determined.

For each CCDS entry, Applicants took the two earliest constitutive exons. If there are not enough constitutive exons in this gene or no data Applicants added exon 2, 3 or both to get to 2 unique exons.

For each candidate exon Applicants found all the possible *S. pyogenes* sgRNA guide sequences (or guide sequence) of the form (N)20NGG. Applicants calculated an off target score for each guide sequence as follows:

(a) Applicants used a short-read aligner and mapped each 20mer guide sequence to the genome to find all the sequences that are similar to it allowing up to 3 mismatches.

(b) At this point if a guide has a match to a sequence in the genome with zero (perfect match) or one base mismatch it is discarded.

(c) For the other guide (closest off target is with two or more mismatches), Applicants calculated the following off target score:

$$OS = \sum_{\text{off targets}} (\text{sum mm location})(D(\text{mm})/D(\text{max}))$$

where:

sum mm location=sum of the mis-match locations from 3' to 5'.

The PAM (NGG) proximal base is 1 and the PAM distal base is 20.
D(mm)=distance in bp between mismatch locations.
D(max)=maximal possible distance between 2 or 3 mismatches.

Applicants then sort the guide sequences for each gene by off target score, take the two best for each gene up to a off target score of 400. Applicants then iteratively added guide sequences to genes choosing the next best guide sequence for each gene until the whole list of guide sequences contained 65017 guide sequences.

Example 9: Genome Scale CRISPR-Cas9 Knockout Screening in Human Cells

The simplicity of programming the CRISPR-associated nuclease Cas9 to modify specific genomic loci suggests a new way to interrogate gene function on the genome-wide scale. Applicants showed that lentiviral delivery of a genome-scale CRISPR-Cas9 knockout (GeCKO) library targeting 18,080 genes with 64,751 unique guide sequences enables both negative and positive selection screening in human cells. First, Applicants used the GeCKO library to identify genes essential for cell viability in cancer and pluripotent stem cells. Next, in a melanoma model, Applicants screened for candidate genes whose loss is involved in resistance to vemurafenib, a therapeutic that inhibits mutant protein kinase BRAF. Applicants' highest-ranking gene candidates include the previously-validated genes NF1 and MED12 as well as novel candidate genes (NF2, CUL3, TADA2B and TADA1). Notably, Applicants observed a high level of consistency between independent guide RNAs targeting the same gene and a high rate of validation, demonstrating the promise of genome-scale screening with Cas9.

A major goal since the completion of the Human Genome Project is the functional characterization of all annotated genetic elements in normal biological processes and disease. Genome-scale loss-of-function screens have provided a wealth of information in diverse model systems. In mammalian cells, RNA interference (RNAi) is the predominant method for genome-wide loss-of-function screening, but its utility is limited by the inherent incompleteness of protein depletion by RNAi and confounding off-target effects.

The RNA-guided CRISPR (clustered regularly interspaced short palindrome repeats)-associated nuclease Cas9 provides an effective means of introducing targeted loss-of function mutations at specific sites in the genome. Cas9 can be programmed to induce DNA double strand breaks (DSBs) at specific genomic loci through a synthetic single guide RNA (sgRNA), which when targeted to coding regions of genes can create frame shift indel mutations that result in a loss-of-function allele. Because the targeting specificity of Cas9 is conferred by short guide sequences, which can be easily generated at large scale by array-based oligonucleotide library synthesis, Applicants explored the potential of Cas9 for pooled genome-scale functional screening.

Figure 25A:
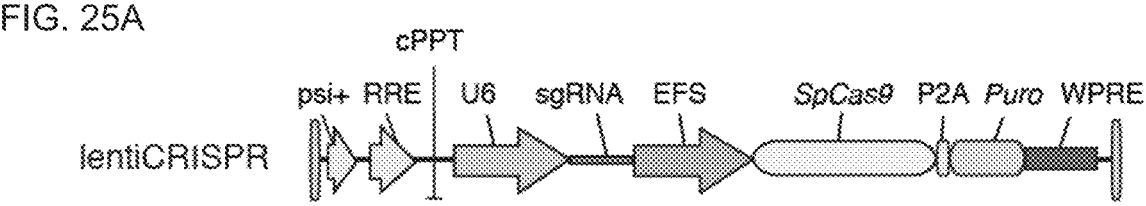
FIG. 25A-25C shows lentiviral delivery of Cas9 and sgRNA provides efficient depletion of target genes. (A) Lentiviral expression vector for Cas9 and sgRNA (lentiCRISPR). Puromycin selection marker (puro), psi packaging signal (psi+), rev response element (RRE), central polypurine tract (cPPT), and posttranscriptional regulatory element (WPRE). (B) Distribution of fluorescence from 293T-EGFP cells transduced by EGFP-targeting lentiCRISPR (sgRNAs 1-6, outlined peaks) and Cas9-only (green-shaded peak) vectors, and non-fluorescent 293T cells (grey shaded peak). (C) Distribution of fluorescence from 293T-EGFP cells transduced by EGFP-targeting shRNA (shRNAs 1-4, outlined peaks) and control shRNA (green-shaded peak) vectors, and non-fluorescent 293T cells (grey shaded peak).

Lentiviral vectors are commonly used for delivery of pooled short hairpin RNAs (shRNAs) in RNAi since they can be easily titrated to control transgene copy number, and are stably maintained as genomic integrants during subsequent cell replication. Therefore Applicants designed a single lentiviral vector to deliver Cas9, a puromycin selection marker, and a sgRNA into target cells (lentiCRISPR, FIGS. 25A and 46). The ability to simultaneously deliver Cas9 and sgRNA through a single vector enables application to any cell type of interest, without the need to first generate cell lines that express Cas9.

Figure 25B:
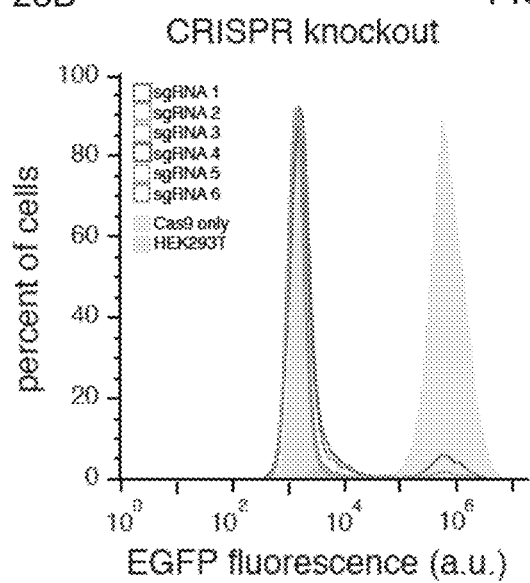
Figure 25C:
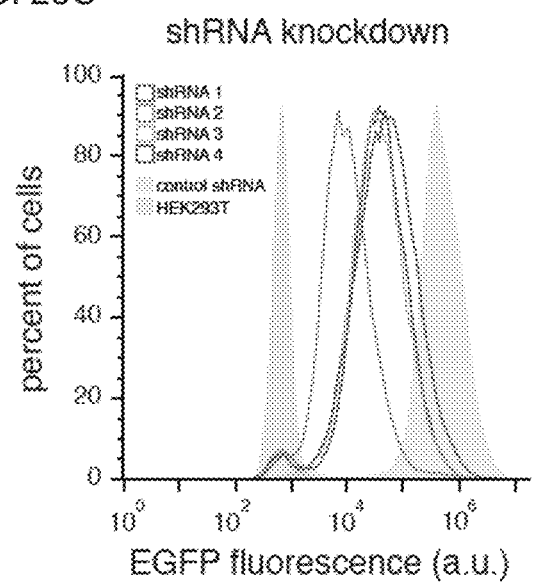
Figure 30A:
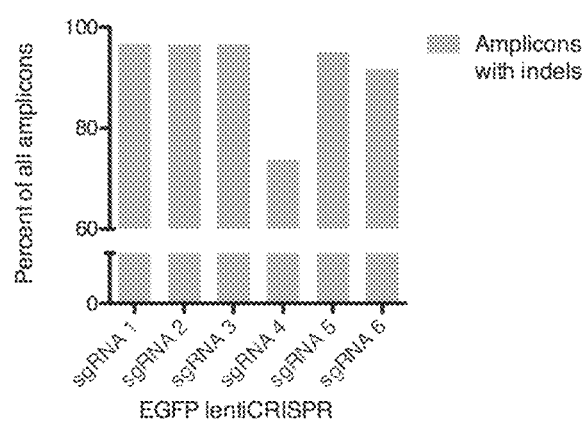
FIG. 30A-30B shows deep sequencing for indel analysis of EGFP locus after lentiCRISPR modification. (A) Deep-sequencing of genomic DNA from HEK293T-EGFP cells that were infected with EGFP-targeting lentiCRISPRs shows that most amplicons have insertion or deletion (indel) mutations. Genomic DNA was extracted from cells on day 11 post-infection. For each lentiCRISPR, $1-2 \times 10^4$ reads were used for the analysis. (B) Distribution of types of indel mutations. lentiCRISPR transduction leads to both frame-shift and in-frame indel mutations.
Figure 30B:
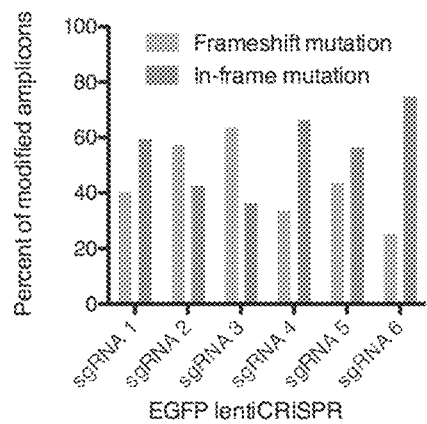

To determine the efficacy of gene knockout by lentiCRISPR transduction, Applicants tested six sgRNAs targeting enhanced green fluorescent protein (EGFP) in a HEK293T cell line containing a single-copy of EGFP (FIG. 29). After transduction at a low multiplicity of infection (MOI=0.3) followed by selection with puromycin, lentiCRISPRs abolished EGFP fluorescence in 93±8% (mean±s.d.) of cells after 11 days (FIG. 25B). Deep sequencing of the EGFP locus revealed a 92±9% indel frequency (n≥$10^4$ sequencing reads per condition; FIG. 30). In contrast, transduction of cells with lentiviral vectors expressing EGFP-targeting shRNA led to incomplete knockdown of EGFP fluorescence (FIG. 25C).

Given the high efficacy of gene knockout by lentiCRISPR, Applicants tested the feasibility of conducting genome-scale CRISPR knockout (GeCKO) screening with a pooled lentiCRISPR library. Applicants designed a library of sgRNAs targeting 5' constitutive exons (FIG. 26A) of 18,080 genes in the human genome with an average coverage of 3-4 sgRNAs per gene (Table 1); and each target site was selected to minimize off-target modification as described herein.

Figure 26A:
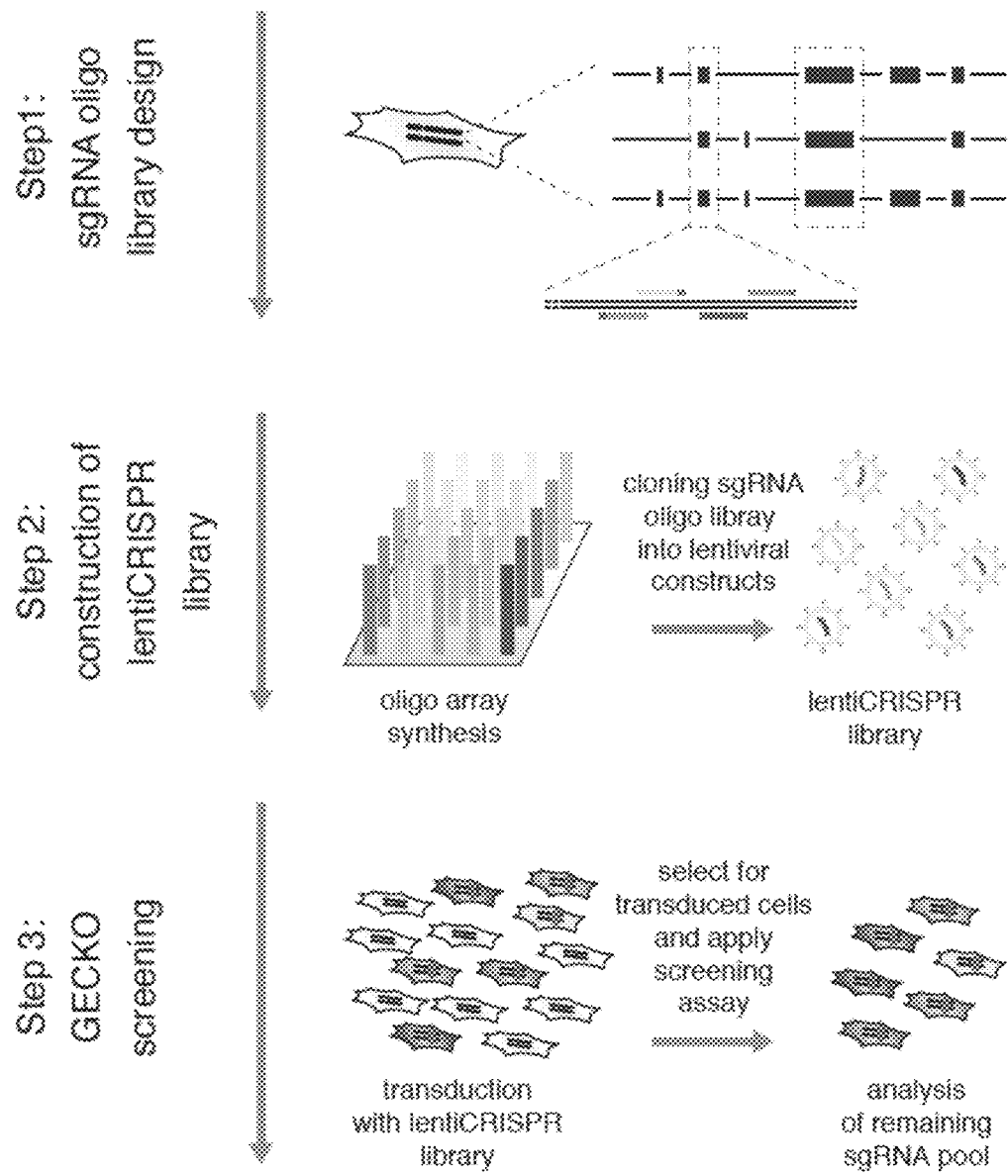
Figure 26B:
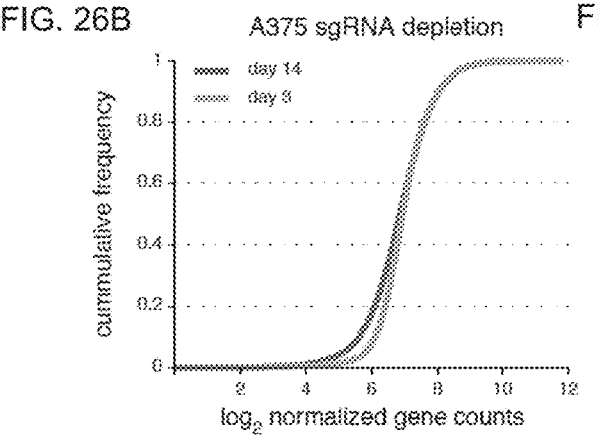
Figure 26C:
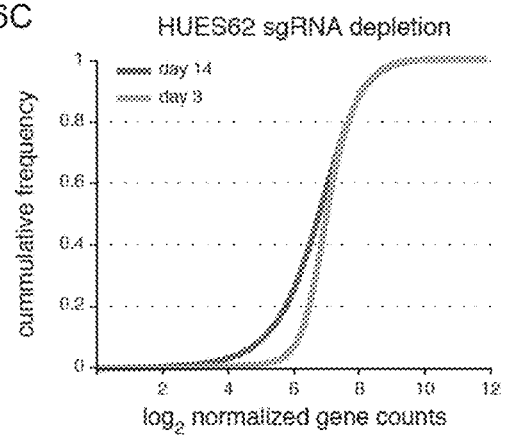
Figure 31:
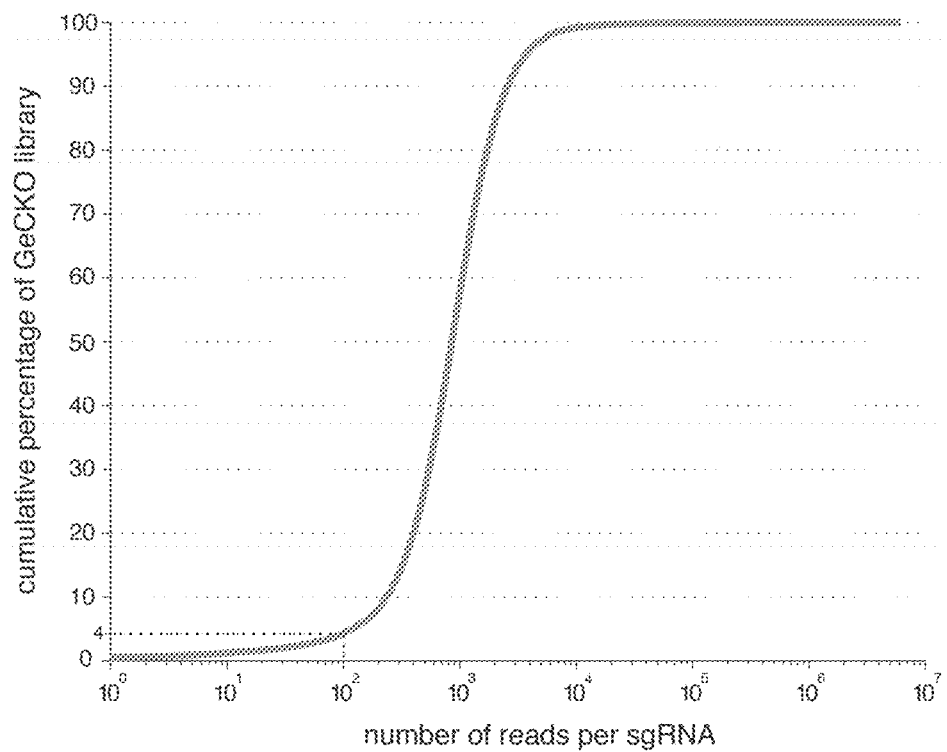
FIG. 31 shows Read coverage per sgRNA in a single experiment. Cumulative distribution of the number of reads per sgRNA in a single A375 experiment. The red line indicates that less than 4% of the sgRNAs are covered by less than 100 reads.
Figure 32:
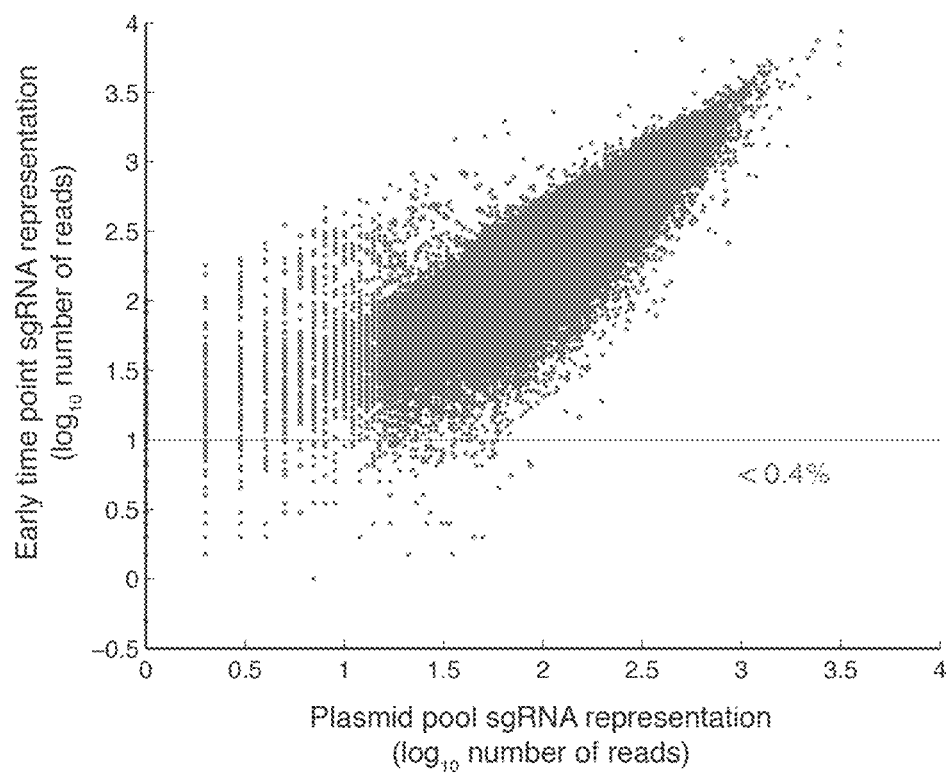
FIG. 32 shows Comparison of sgRNA representation between the plasmid pool to an early time point (day 7). Scatter plot of sgRNA representation ($\log_{10}$ number of reads) between the plasmid pool before virus production to a cell population 7 days post infection. Red line indicates that less than 0.4% of sgRNA have undetectable representation (less than 10 reads).
Figure 33A:
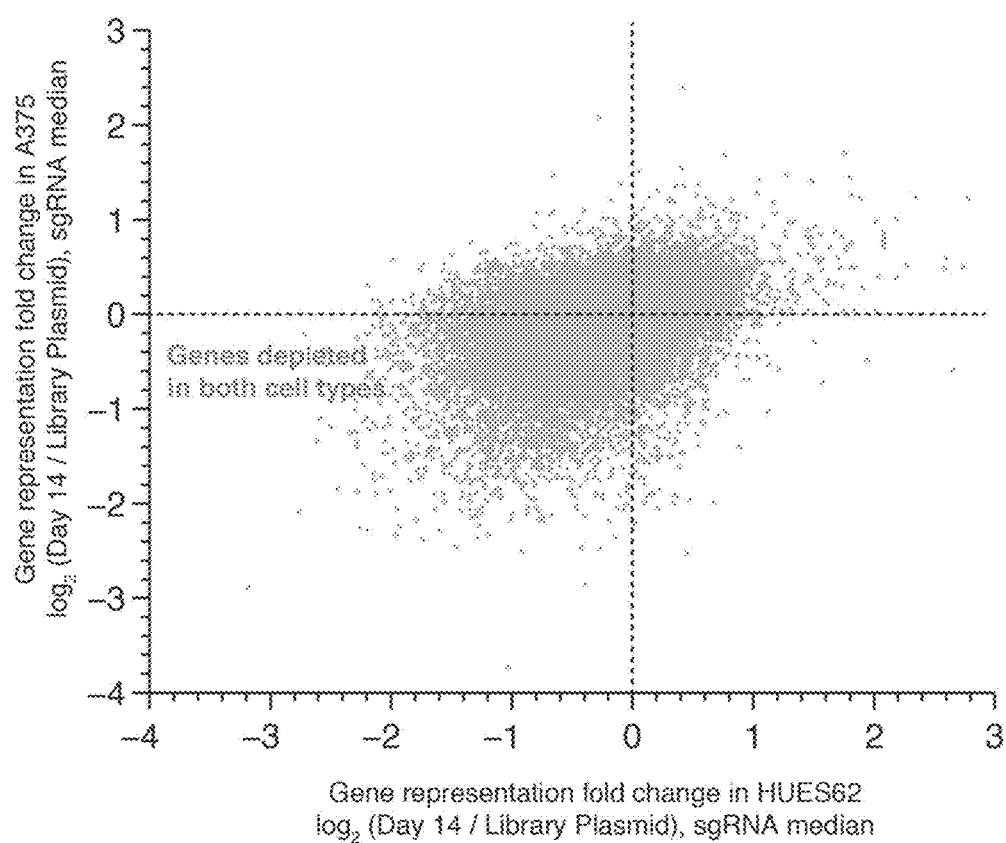
FIG. 33A-33C shows Comparison of gene and gene category depletion between A375 melanoma and HUES62 human ES cells. (A) Scatter plot of gene enrichment/depletion as $\log_2$ fold change of each gene between cells 14 days post-transduction and initial library plasmid in A375 melanoma cells and HUES62 hES cells. Gene enrichment/depletion was calculated using RIGER analysis of individual sgRNA depletion. Lower left quadrant contains genes depleted in both A375 and HUES62 cells. (B) Overlap between the top 1000 most depleted genes in each cell type. (C) Overlap between the top 100 most depleted Gene Ontology (GO) categories for each cell type as ranked by Gene Set Enrichment Analysis (GSEA) on the gene enrichment/depletion values.
Figure 33B:
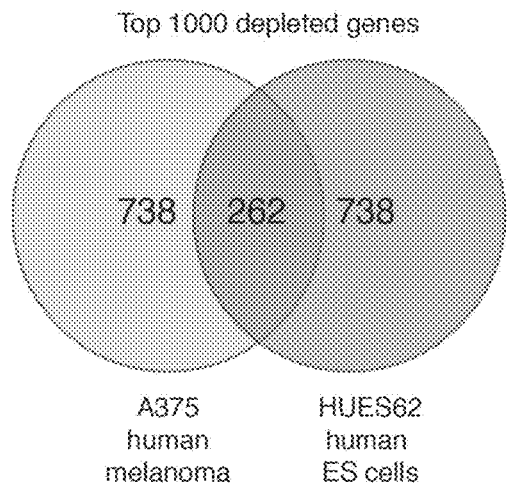
Figure 33C:
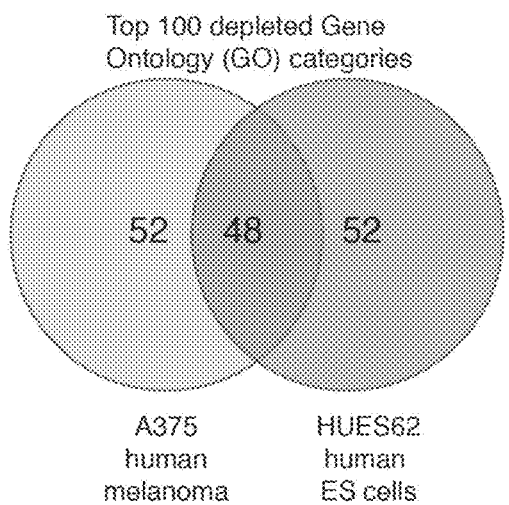

To test the efficacy of the full GeCKO library at achieving knockout of endogenous gene targets, Applicants conducted a negative selection screen by profiling the depletion of sgRNAs targeting essential survival genes (FIG. 26A). Applicants transduced the human melanoma cell line A375 and the human stem cell line HUES62 with the GeCKO library at a MOI of 0.3. As expected, deep sequencing (FIG. 31, 32) 14 days post-transduction revealed a significant reduction in the diversity of sgRNAs in the surviving A375 and HUES62 cells (FIG. 26B, C; Wilcoxon rank sum test, $p<10^{-10}$ for both cell types). Gene set enrichment analysis (GSEA) indicated that most of the depleted sgRNAs targeted essential genes such as ribosomal structural constituents (FIG. 26D, E, and Tables E, F). The overlap in highly depleted genes and functional gene categories between the two cell lines (FIG. 33) indicates that GeCKO can identify essential genes and that enrichment analysis of depleted sgRNAs can pinpoint gene targets in negative selection screens.

TABLE E

Gene Set Enrichment Analysis output for negative selection of essential genes in A375 cells after 14 additional days in culture. For the analysis, the ALL Gene Ontology set was used from the Molecular Signatures Database (MSigDB) with a minimum set size of 50 and max set size of 300.

| NAME | SIZE | ES | NES | NOMp | FDRq | FWERp | RANK AT MAX |
|---|---|---|---|---|---|---|---|
| RNA_PROCESSING | 165 | 0.39 | 5.78 | 0 | 0 | 0 | 2823 |
| STRUCTURAL_CONSTITUENT_OF_RIBOSOME | 71 | 0.58 | 5.68 | 0 | 0 | 0 | 2753 |

TABLE E-continued

Gene Set Enrichment Analysis output for negative selection of essential
genes in A375 cells after 14 additional days in culture. For the analysis, the ALL Gene Ontology
set was used from the Molecular Signatures Database (MSigDB) with a minimum set size of 50
and max set size of 300.

| NAME | SIZE | ES | NES | NOMp | FDRq | FWERp | RANK AT MAX |
|---|---|---|---|---|---|---|---|
| RIBONUCLEOPROTEIN_COMPLEX | 138 | 0.4 | 5.51 | 0 | 0 | 0 | 3865 |
| RNA_BINDING | 241 | 0.29 | 5.21 | 0 | 0 | 0 | 4664 |
| RIBONUCLEOPROTEIN_COMPLEX_BIOGENESIS_AND_ASSEMBLY | 81 | 0.45 | 4.67 | 0 | 0 | 0 | 2979 |
| NUCLEOPLASM | 271 | 0.24 | 4.62 | 0 | 0 | 0 | 4928 |
| RNA_SPLICING | 86 | 0.42 | 4.61 | 0 | 0 | 0 | 2768 |
| NUCLEOLUS | 120 | 0.36 | 4.56 | 0 | 0 | 0 | 5363 |
| NUCLEOPLASM_PART | 206 | 0.26 | 4.41 | 0 | 0 | 0 | 4047 |
| MRNA_METABOLIC_PROCESS | 79 | 0.42 | 4.25 | 0 | 0 | 0 | 4596 |
| MRNA_PROCESSING_GO_0006397 | 70 | 0.42 | 4.13 | 0 | 0 | 0 | 4596 |
| TRANSLATION | 166 | 0.27 | 4.09 | 0 | 0 | 0 | 1815 |
| DNA_METABOLIC_PROCESS | 250 | 0.21 | 3.86 | 0 | 0 | 0 | 6569 |
| BIOPOLYMER_CATABOLIC_PROCESS | 112 | 0.29 | 3.63 | 0 | 0 | 0 | 6456 |
| CHROMOSOMAL_PART | 93 | 0.32 | 3.61 | 0 | 0 | 0 | 4006 |
| PROTEIN_RNA_COMPLEX_ASSEMBLY | 62 | 0.38 | 3.6 | 0 | 0 | 0 | 2979 |
| DNA_DIRECTED_RNA_POLYMERASEII_HOLOENZYME | 65 | 0.38 | 3.6 | 0 | 0 | 0 | 3367 |
| MACROMOLECULE_CATABOLIC_PROCESS | 130 | 0.26 | 3.56 | 0 | 0 | 0 | 6456 |
| ORGANELLE_MEMBRANE | 287 | 0.18 | 3.56 | 0 | 0 | 0 | 7993 |
| CHROMOSOME | 119 | 0.28 | 3.54 | 0 | 0 | 0 | 3434 |
| DNA_REPLICATION | 99 | 0.3 | 3.53 | 0 | 0 | 0 | 3471 |
| MITOCHONDRIAL_PART | 138 | 0.26 | 3.52 | 0 | 0 | 0 | 5678 |
| ORGANELLE_ENVELOPE | 164 | 0.23 | 3.47 | 0 | 0 | 0 | 6682 |
| STRUCTURAL_MOLECULE_ACTIVITY | 218 | 0.2 | 3.43 | 0 | 0 | 0 | 4049 |
| ENVELOPE | 164 | 0.23 | 3.34 | 0 | 0 | 0 | 6682 |
| MACROMOLECULAR_COMPLEX_ASSEMBLY | 267 | 0.17 | 3.21 | 0 | 0 | 0 | 3419 |
| MITOSIS | 80 | 0.3 | 3.2 | 0 | 0 | 0 | 3551 |
| CELLULAR_COMPONENT_ASSEMBLY | 284 | 0.16 | 3.1 | 0 | 0 | 0 | 3419 |
| M_PHASE_OF_MITOTIC_CELL_CYCLE | 83 | 0.29 | 3.08 | 0 | 0 | 0 | 3551 |
| CELLULAR_MACROMOLECULE_CATABOLIC_PROCESS | 99 | 0.26 | 3.06 | 0 | 0 | 0 | 6249 |
| MICROTUBULE_CYTOSKELETON | 146 | 0.22 | 3.05 | 0 | 0 | 0 | 4125 |
| CELL_CYCLE_PROCESS | 190 | 0.19 | 3.01 | 0 | 0 | 0 | 4125 |
| RESPONSE_TO_ENDOGENOUS_STIMULUS | 192 | 0.18 | 2.93 | 0 | 0 | 0 | 7033 |
| RESPONSE_TO_DNA_DAMAGE_STIMULUS | 157 | 0.2 | 2.92 | 0 | 0 | 0 | 6569 |
| DNA_REPAIR | 121 | 0.23 | 2.92 | 0 | 0 | 0 | 6569 |
| MITOCHONDRIAL_ENVELOPE | 93 | 0.25 | 2.91 | 0 | 0 | 0 | 8216 |
| MITOCHONDRIAL_MEMBRANE | 82 | 0.27 | 2.91 | 0 | 0 | 0 | 8216 |
| CELL_CYCLE_PHASE | 168 | 0.19 | 2.88 | 0 | 2.82E−05 | 0.001 | 4070 |
| M_PHASE | 112 | 0.23 | 2.86 | 0 | 2.75E−05 | 0.001 | 3938 |
| PROTEIN_CATABOLIC_PROCESS | 67 | 0.3 | 2.86 | 0 | 2.68E−05 | 0.001 | 6456 |
| MICROTUBULE_ORGANIZING_CENTER | 65 | 0.3 | 2.85 | 0 | 2.61E−05 | 0.001 | 5445 |
| ORGANELLE_INNER_MEMBRANE | 72 | 0.28 | 2.78 | 0 | 7.79E−05 | 0.003 | 8154 |
| MITOCHONDRIAL_INNER_MEMBRANE | 64 | 0.3 | 2.77 | 0 | 7.61E−05 | 0.003 | 8154 |
| MITOTIC_CELL_CYCLE | 151 | 0.19 | 2.76 | 0 | 9.95E−05 | 0.004 | 2454 |
| DNA_DEPENDENT_DNA_REPLICATION | 53 | 0.31 | 2.73 | 0 | 1.22E−04 | 0.005 | 3170 |
| ATPASE_ACTIVITY | 110 | 0.22 | 2.68 | 0 | 1.88E−04 | 0.008 | 5581 |
| PROTEIN_FOLDING | 55 | 0.3 | 2.67 | 0 | 2.07E−04 | 0.009 | 7936 |
| CYTOSKELETAL_PART | 224 | 0.16 | 2.64 | 0 | 2.03E−04 | 0.009 | 4745 |
| CELLULAR_PROTEIN_CATABOLIC_PROCESS | 57 | 0.29 | 2.6 | 0 | 2.22E−04 | 0.01 | 6456 |
| NUCLEOSIDE_TRIPHOSPHATASE_ACTIVITY | 205 | 0.15 | 2.59 | 0 | 3.06E−04 | 0.014 | 6559 |
| ENDOMEMBRANE_SYSTEM | 211 | 0.15 | 2.57 | 0 | 3.62E−04 | 0.017 | 7971 |
| TRANSCRIPTION_FACTOR_COMPLEX | 89 | 0.23 | 2.57 | 0 | 3.55E−04 | 0.017 | 9975 |
| PYROPHOSPHATASE_ACTIVITY | 219 | 0.15 | 2.54 | 0 | 4.90E−04 | 0.024 | 6559 |
| HYDROLASE_ACTIVITY_ACTING_ON_ACID_ANHYDRIDES | 221 | 0.15 | 2.53 | 0 | 5.21E−04 | 0.026 | 6559 |
| REGULATION_OF_CELL_CYCLE | 175 | 0.16 | 2.53 | 0 | 5.12E−04 | 0.026 | 3551 |
| NUCLEAR_ENVELOPE | 72 | 0.25 | 2.51 | 0 | 6.23E−04 | 0.032 | 6682 |
| CENTROSOME | 56 | 0.29 | 2.51 | 0 | 6.12E−04 | 0.032 | 5445 |
| INTRACELLULAR_TRANSPORT | 271 | 0.15 | 2.48 | 0 | 7.09E−04 | 0.038 | 7734 |
| CATABOLIC_PROCESS | 218 | 0.14 | 2.45 | 0 | 9.14E−04 | 0.049 | 3576 |
| LIGASE_ACTIVITY | 94 | 0.22 | 2.44 | 0 | 9.17E−04 | 0.05 | 6249 |
| ATPASE_ACTIVITY_COUPLED | 91 | 0.22 | 2.39 | 0 | 0.00138 | 0.076 | 5581 |
| CELLULAR_CATABOLIC_PROCESS | 206 | 0.14 | 2.38 | 0 | 0.00141 | 0.079 | 3576 |
| MITOCHONDRIAL_MEMBRANE_PART | 50 | 0.27 | 2.32 | 0 | 0.00218 | 0.121 | 7993 |
| NUCLEASE_ACTIVITY | 55 | 0.26 | 2.31 | 0.002 | 0.00232 | 0.129 | 6720 |

TABLE E-continued

Gene Set Enrichment Analysis output for negative selection of essential
genes in A375 cells after 14 additional days in culture. For the analysis, the ALL Gene Ontology
set was used from the Molecular Signatures Database (MSigDB) with a minimum set size of 50
and max set size of 300.

| NAME | SIZE | ES | NES | NOMp | FDRq | FWERp | RANK AT MAX |
|---|---|---|---|---|---|---|---|
| CHROMOSOME_ORGANIZATION_AND_BIOGENESIS | 122 | 0.18 | 2.3 | 0 | 0.00246 | 0.14 | 4623 |
| MACROMOLECULE_LOCALIZATION | 230 | 0.13 | 2.21 | 0 | 0.00434 | 0.23 | 7886 |
| NUCLEAR_MEMBRANE | 50 | 0.25 | 2.04 | 0.002 | 0.01183 | 0.519 | 6682 |
| REGULATION_OF_PROTEIN_METABOLIC_PROCESS | 165 | 0.14 | 2.03 | 0 | 0.01208 | 0.531 | 8311 |
| LIGASE_ACTIVITY_FORMING_CARBON_NITROGEN_BONDS | 67 | 0.2 | 1.98 | 0.002 | 0.01638 | 0.65 | 6249 |
| KINASE_BINDING | 68 | 0.2 | 1.92 | 0.009 | 0.02197 | 0.739 | 9808 |
| PEPTIDYL_AMINO_ACID_MODIFICATION | 62 | 0.2 | 1.88 | 0.011 | 0.02821 | 0.827 | 12915 |
| ESTABLISHMENT_OF_PROTEIN_LOCALIZATION | 185 | 0.12 | 1.87 | 0.014 | 0.02952 | 0.851 | 8072 |
| ENZYME_BINDING | 174 | 0.12 | 1.86 | 0.008 | 0.02965 | 0.855 | 10013 |
| REGULATION_OF_TRANSCRIPTION_FROM_RNA_POLYMERASE_II_PROMOTER | 283 | 0.1 | 1.85 | 0.006 | 0.0316 | 0.875 | 4713 |
| COFACTOR_METABOLIC_PROCESS | 54 | 0.21 | 1.83 | 0.008 | 0.03423 | 0.894 | 10520 |
| REGULATION_OF_CELLULAR_PROTEIN_METABOLIC_PROCESS | 155 | 0.12 | 1.82 | 0.006 | 0.03515 | 0.902 | 8311 |
| RNA_POLYMERASE_II_TRANSCRIPTION_FACTOR_ACTIVITY | 179 | 0.12 | 1.8 | 0.012 | 0.03919 | 0.929 | 4869 |
| TRANSFERASE_ACTIVITY_TRANSFERRING_ACYL_GROUPS | 59 | 0.2 | 1.78 | 0.006 | 0.04205 | 0.94 | 5002 |
| PROTEIN_LOCALIZATION | 209 | 0.11 | 1.78 | 0.016 | 0.04372 | 0.948 | 7886 |
| SMALL_CONJUGATING_PROTEIN_LIGASE_ACTIVITY | 51 | 0.21 | 1.76 | 0.025 | 0.04791 | 0.962 | 12441 |
| CYTOSOL | 199 | 0.11 | 1.75 | 0.024 | 0.05038 | 0.97 | 4982 |
| REGULATION_OF_CELLULAR_COMPONENT_ORGANIZATION_AND_BIOGENESIS | 117 | 0.14 | 1.74 | 0.017 | 0.05232 | 0.977 | 4133 |
| POSITIVE_REGULATION_OF_CELLULAR_METABOLIC_PROCESS | 224 | 0.1 | 1.73 | 0.034 | 0.05359 | 0.981 | 4250 |
| ACID_AMINO_ACID_LIGASE_ACTIVITY | 57 | 0.2 | 1.73 | 0.021 | 0.05354 | 0.982 | 6249 |
| INTRACELLULAR_PROTEIN_TRANSPORT | 141 | 0.12 | 1.72 | 0.023 | 0.05523 | 0.984 | 6698 |
| PROTEIN_KINASE_BINDING | 60 | 0.19 | 1.72 | 0.022 | 0.05481 | 0.984 | 9808 |
| INTRINSIC_TO_ORGANELLE_MEMBRANE | 51 | 0.2 | 1.72 | 0.02 | 0.05486 | 0.985 | 7971 |
| POSITIVE_REGULATION_OF_RNA_METABOLIC_PROCESS | 119 | 0.13 | 1.71 | 0.024 | 0.0559 | 0.986 | 4250 |
| INTERPHASE | 68 | 0.17 | 1.7 | 0.026 | 0.05724 | 0.987 | 4070 |
| PROTEIN_TRANSPORT | 152 | 0.12 | 1.69 | 0.022 | 0.06056 | 0.988 | 8072 |
| ESTABLISHMENT_AND_OR_MAINTENANCE_OF_CHROMATIN_ARCHITECTURE | 76 | 0.17 | 1.69 | 0.03 | 0.06152 | 0.99 | 5256 |
| POSITIVE_REGULATION_OF_NUCLEOBASENUCLEOSIDENUCLEOTIDE_AND_NUCLEIC_ACID_METABOLIC_PROCESS | 153 | 0.12 | 1.68 | 0.031 | 0.06336 | 0.992 | 4250 |
| ENDOPLASMIC_RETICULUM | 278 | 0.09 | 1.68 | 0.026 | 0.06293 | 0.992 | 7817 |
| POSITIVE_REGULATION_OF_TRANSCRIPTIONDNA_DEPENDENT | 117 | 0.13 | 1.67 | 0.024 | 0.06531 | 0.993 | 4250 |
| POSITIVE_REGULATION_OF_METABOLIC_PROCESS | 230 | 0.09 | 1.65 | 0.028 | 0.06918 | 0.997 | 4250 |
| TRANSCRIPTION_ACTIVATOR_ACTIVITY | 170 | 0.11 | 1.65 | 0.039 | 0.07019 | 0.998 | 4537 |
| POSITIVE_REGULATION_OF_TRANSCRIPTION_FROM_RNA_POLYMERASE_II_PROMOTER | 64 | 0.17 | 1.63 | 0.025 | 0.07401 | 0.998 | 4250 |
| NUCLEOBASENUCLEOSIDE_AND_NUCLEOTIDE_METABOLIC_PROCESS | 51 | 0.19 | 1.63 | 0.037 | 0.07477 | 0.999 | 5750 |
| SMALL_PROTEIN_CONJUGATING_ENZYME_ACTIVITY | 52 | 0.19 | 1.62 | 0.027 | 0.07592 | 0.999 | 12441 |
| ENDOPLASMIC_RETICULUM_MEMBRANE | 81 | 0.15 | 1.61 | 0.041 | 0.08117 | 0.999 | 6591 |
| POSITIVE_REGULATION_OF_TRANSCRIPTION | 143 | 0.11 | 1.59 | 0.051 | 0.08681 | 0.999 | 4250 |
| NUCLEAR_ENVELOPE_ENDOPLASMIC_RETICULUM_NETWORK | 90 | 0.14 | 1.59 | 0.039 | 0.08705 | 0.999 | 6591 |
| NUCLEAR_TRANSPORT | 86 | 0.15 | 1.58 | 0.04 | 0.09042 | 1 | 7204 |
| ENDOPLASMIC_RETICULUM_PART | 92 | 0.14 | 1.57 | 0.042 | 0.09295 | 1 | 6669 |
| TRANSCRIPTION_COACTIVATOR_ACTIVITY | 120 | 0.12 | 1.57 | 0.044 | 0.09258 | 1 | 4536 |
| NUCLEOCYTOPLASMIC_TRANSPORT | 85 | 0.14 | 1.56 | 0.042 | 0.09541 | 1 | 7204 |

TABLE E-continued

Gene Set Enrichment Analysis output for negative selection of essential
genes in A375 cells after 14 additional days in culture. For the analysis, the ALL Gene Ontology
set was used from the Molecular Signatures Database (MSigDB) with a minimum set size of 50
and max set size of 300.

| NAME | SIZE | ES | NES | NOMp | FDRq | FWERp | RANK AT MAX |
|---|---|---|---|---|---|---|---|
| PROTEIN_C_TERMINUS_BINDING | 70 | 0.16 | 1.56 | 0.051 | 0.09668 | 1 | 12272 |
| NUCLEAR_CHROMOSOME | 51 | 0.18 | 1.54 | 0.062 | 0.10619 | 1 | 3434 |
| PROTEOLYSIS | 184 | 0.1 | 1.52 | 0.066 | 0.11481 | 1 | 6570 |
| CHROMATIN_MODIFICATION | 54 | 0.18 | 1.51 | 0.057 | 0.11578 | 1 | 3790 |
| INTERPHASE_OF_MITOTIC_CELL_CYCLE | 62 | 0.16 | 1.46 | 0.093 | 0.1459 | 1 | 4070 |
| HYDROLASE_ACTIVITY_ACTING_ON_ESTER_BONDS | 263 | 0.08 | 1.42 | 0.08 | 0.17096 | 1 | 10388 |
| GOLGI_APPARATUS_PART | 94 | 0.12 | 1.41 | 0.078 | 0.17588 | 1 | 10008 |
| TRANSCRIPTION_COFACTOR_ACTIVITY | 219 | 0.08 | 1.39 | 0.095 | 0.19304 | 1 | 4536 |
| PROTEIN_IMPORT | 62 | 0.15 | 1.39 | 0.121 | 0.19213 | 1 | 7185 |
| TRANSCRIPTION_FACTOR_BINDING | 298 | 0.07 | 1.37 | 0.111 | 0.20094 | 1 | 4802 |
| PROTEIN_HETERODIMERIZATION_ACTIVITY | 75 | 0.13 | 1.37 | 0.117 | 0.20087 | 1 | 7886 |
| MICROTUBULE_BASED_PROCESS | 76 | 0.13 | 1.34 | 0.146 | 0.22731 | 1 | 2409 |
| POSITIVE_REGULATION_OF_PROTEIN_METABOLIC_PROCESS | 72 | 0.13 | 1.32 | 0.144 | 0.24339 | 1 | 7879 |
| OXIDOREDUCTASE_ACTIVITY | 282 | 0.07 | 1.32 | 0.145 | 0.24362 | 1 | 9653 |
| PROTEIN_TARGETING | 108 | 0.11 | 1.31 | 0.158 | 0.24756 | 1 | 2572 |
| PHOSPHORIC_ESTER_HYDROLASE_ACTIVITY | 149 | 0.09 | 1.3 | 0.149 | 0.25681 | 1 | 10507 |
| GENERATION_OF_PRECURSOR_METABOLITES_AND_ENERGY | 122 | 0.1 | 1.29 | 0.175 | 0.263 | 1 | 10168 |
| GTPASE_ACTIVITY | 94 | 0.11 | 1.28 | 0.17 | 0.27137 | 1 | 6559 |
| REGULATION_OF_TRANSLATION | 89 | 0.12 | 1.28 | 0.182 | 0.26987 | 1 | 12650 |
| ANION_RANSMEMBRANE_TRANSPORTER_ACTIVITY | 59 | 0.14 | 1.27 | 0.155 | 0.27786 | 1 | 14818 |
| INORGANIC_CATION_TRANSMEMBRANE_TRANSPORTER_ACTIVITY | 56 | 0.14 | 1.25 | 0.203 | 0.29417 | 1 | 6084 |
| ALCOHOL_METABOLIC_PROCESS | 87 | 0.11 | 1.24 | 0.198 | 0.3057 | 1 | 5002 |
| SMALL_GTPASE_REGULATOR_ACTIVITY | 67 | 0.13 | 1.22 | 0.212 | 0.32345 | 1 | 9244 |
| CYTO_SKELETAL_PROTEIN_BINDING | 155 | 0.08 | 1.22 | 0.208 | 0.32316 | 1 | 3830 |
| PROTEIN_DOMAIN_SPECIFIC_BINDING | 70 | 0.13 | 1.22 | 0.214 | 0.32228 | 1 | 10281 |
| PROTEIN_DIMERIZATION_ACTIVITY | 177 | 0.08 | 1.21 | 0.231 | 0.32627 | 1 | 14919 |
| STRUCTURE_SPECIFIC_DNA_BINDING | 54 | 0.14 | 1.21 | 0.243 | 0.32383 | 1 | 7121 |
| GOLGI_APPARATUS | 216 | 0.07 | 1.21 | 0.22 | 0.32532 | 1 | 7875 |
| SEQUENCE_SPECIFIC_DNA_BINDING | 57 | 0.13 | 1.21 | 0.215 | 0.3236 | 1 | 11740 |
| POSITIVE_REGULATION_OF_CELLULAR_PROTEIN_METABOLIC_PROCESS | 70 | 0.12 | 1.19 | 0.247 | 0.34325 | 1 | 7879 |
| CARBOHYDRATE_METABOLIC_PROCESS | 177 | 0.08 | 1.19 | 0.217 | 0.34568 | 1 | 10067 |
| GTPASE_REGULATOR_ACTIVITY | 122 | 0.09 | 1.18 | 0.232 | 0.35845 | 1 | 9407 |
| SECRETION_BY_CELL | 112 | 0.09 | 1.17 | 0.243 | 0.36174 | 1 | 7757 |
| SECRETION | 174 | 0.08 | 1.16 | 0.269 | 0.37594 | 1 | 7820 |
| PHOSPHORIC_MONOESTER_HYDROLASE_ACTIVITY | 108 | 0.1 | 1.16 | 0.283 | 0.37476 | 1 | 9922 |
| CYTO_SKELETON_ORGANIZATION_AND_BIOGENESIS | 199 | 0.07 | 1.15 | 0.275 | 0.38345 | 1 | 8398 |
| PROTEIN_COMPLEX_BINDING | 53 | 0.13 | 1.13 | 0.298 | 0.39885 | 1 | 14915 |
| RESPONSE_TO_OTHER_ORGANISM | 78 | 0.11 | 1.12 | 0.301 | 0.41053 | 1 | 10042 |
| SECRETORY_PATHWAY | 80 | 0.11 | 1.11 | 0.285 | 0.41916 | 1 | 6638 |
| PROTEIN_COMPLEX_ASSEMBLY | 160 | 0.07 | 1.09 | 0.329 | 0.45045 | 1 | 2284 |
| NUCLEOTIDE_BINDING | 213 | 0.06 | 1.09 | 0.334 | 0.44914 | 1 | 5253 |
| GLYCOPROTEIN_BIOSYNTHETIC_PROCESS | 74 | 0.11 | 1.07 | 0.347 | 0.46709 | 1 | 9904 |
| RESPONSE_TO_BIOTIC_STIMULUS | 112 | 0.09 | 1.07 | 0.358 | 0.46716 | 1 | 11595 |
| DEPHOSPHORYLATION | 68 | 0.11 | 1.06 | 0.354 | 0.48637 | 1 | 3576 |
| NEGATIVE_REGULATION_OF_NUCLEOBASENUCLEOSIDENUCLEOTIDE_AND_NUCLEIC_ACID_METABOLIC_PROCESS | 208 | 0.06 | 1.04 | 0.398 | 0.51567 | 1 | 3307 |
| CARBOXYLIC_ACID_METABOLIC_PROCESS | 176 | 0.07 | 1.02 | 0.409 | 0.53327 | 1 | 13899 |
| RESPONSE_TO_ABIOTIC_STIMULUS | 81 | 0.1 | 1.01 | 0.437 | 0.55167 | 1 | 2485 |
| RAS_PROTEIN_SIGNAL_TRANSDUCTION | 64 | 0.11 | 0.99 | 0.459 | 0.56979 | 1 | 11509 |
| ACTIN_BINDING | 76 | 0.1 | 0.99 | 0.456 | 0.57185 | 1 | 11233 |
| PROTEIN_AMINO_ACID_DEPHOSPHORYLATION | 61 | 0.11 | 0.99 | 0.467 | 0.57088 | 1 | 3369 |
| APOPTOTIC_PROGRAM | 57 | 0.11 | 0.99 | 0.467 | 0.5697 | 1 | 12804 |

TABLE E-continued

Gene Set Enrichment Analysis output for negative selection of essential genes in A375 cells after 14 additional days in culture. For the analysis, the ALL Gene Ontology set was used from the Molecular Signatures Database (MSigDB) with a minimum set size of 50 and max set size of 300.

| NAME | SIZE | ES | NES | NOMp | FDRq | FWERp | RANK AT MAX |
|---|---|---|---|---|---|---|---|
| STRUCTURAL_CONSTITUENTS_OF_CYTOSKELETON | 54 | 0.11 | 0.98 | 0.464 | 0.57267 | 1 | 5005 |
| ENZYME_INHIBITOR_ACTIVITY | 118 | 0.08 | 0.97 | 0.484 | 0.59056 | 1 | 9572 |
| POSITIVE_REGULATION_OF_I_KAPPAB_KINASE_NF_KAPPAB_CASCADE | 84 | 0.09 | 0.96 | 0.475 | 0.59815 | 1 | 14222 |
| ORGANIC_ACID_METABOLIC_PROCESS | 178 | 0.06 | 0.96 | 0.487 | 0.59493 | 1 | 13899 |
| MONOCARBOXYLIC_ACID_METABOLIC_PROCESS | 87 | 0.09 | 0.96 | 0.516 | 0.59446 | 1 | 13681 |
| NEGATIVE_REGULATION_OF_CELLULAR_METABOLIC_PROCESS | 255 | 0.05 | 0.95 | 0.5 | 0.60411 | 1 | 3307 |
| GLYCOPROTEIN_METABOLIC_PROCESS | 90 | 0.09 | 0.95 | 0.507 | 0.60702 | 1 | 11014 |
| NEGATIVE_REGULATION_OF_METABOLIC_PROCESS | 257 | 0.05 | 0.94 | 0.502 | 0.61476 | 1 | 3307 |
| SMALL_GTPASE_MEDIATED_SIGNAL_TRANSDUCTION | 85 | 0.09 | 0.94 | 0.499 | 0.61255 | 1 | 11509 |
| PROTEIN_HOMODIMERIZATION_ACTIVITY | 118 | 0.07 | 0.94 | 0.515 | 0.6163 | 1 | 14919 |
| POSITIVE_REGULATION_OF_SIGNAL_TRANSDUCTION | 120 | 0.07 | 0.94 | 0.53 | 0.61278 | 1 | 15308 |
| RESPONSE_TO_RADIATION | 55 | 0.11 | 0.93 | 0.527 | 0.61353 | 1 | 2360 |
| CELLULAR_CARBOHYDRATE_METABOLIC_PROCESS | 124 | 0.07 | 0.91 | 0.552 | 0.64116 | 1 | 4663 |
| REGULATION_OF_I_KAPPAB_KINASE_NF_KAPPAB_CASCADE | 90 | 0.08 | 0.91 | 0.565 | 0.65121 | 1 | 15690 |
| LIPID_BIOSYNTHETIC_PROCESS | 96 | 0.08 | 0.88 | 0.581 | 0.69681 | 1 | 10784 |
| PURINE_NUCLEOTIDE_BINDING | 200 | 0.05 | 0.86 | 0.661 | 0.7253 | 1 | 15565 |
| PURINE_RIBONUCLEOTIDE_BINDING | 194 | 0.05 | 0.84 | 0.663 | 0.75173 | 1 | 5186 |
| AMINO_ACID_METABOLIC_PROCESS | 77 | 0.08 | 0.82 | 0.691 | 0.77186 | 1 | 12986 |
| PHOSPHOPROTEIN_PHOSPHATASE_ACTIVITY | 79 | 0.08 | 0.82 | 0.721 | 0.76882 | 1 | 3369 |
| ATP_BINDING | 149 | 0.05 | 0.8 | 0.729 | 0.79992 | 1 | 15510 |
| ADENYL_NUCLEOTIDE_BINDING | 162 | 0.05 | 0.78 | 0.752 | 0.81705 | 1 | 15539 |
| ELECTRON_TRANSPORT_GO_0006118 | 51 | 0.09 | 0.76 | 0.766 | 0.85094 | 1 | 9279 |
| MULTI_ORGANISM_PROCESS | 153 | 0.05 | 0.75 | 0.792 | 0.857 | 1 | 13249 |
| ADENYL_RIBONUCLEOTIDE_BINDING | 156 | 0.05 | 0.74 | 0.794 | 0.87127 | 1 | 15539 |
| REGULATION_OF_BINDING | 56 | 0.08 | 0.74 | 0.782 | 0.86663 | 1 | 5256 |
| IDENTICAL_PROTEIN_BINDING | 297 | 0.04 | 0.73 | 0.819 | 0.8703 | 1 | 14671 |
| REGULATION_OF_GROWTH | 54 | 0.08 | 0.71 | 0.824 | 0.89318 | 1 | 9818 |
| OXIDOREDUCTASE_ACTIVITY_ACTING_ON_CH_OH_GROUP_OF_DONORS | 61 | 0.08 | 0.71 | 0.83 | 0.89082 | 1 | 2727 |
| ELECTRON_CARRIER_ACTIVITY | 78 | 0.07 | 0.7 | 0.867 | 0.90169 | 1 | 13510 |
| GROWTH | 72 | 0.07 | 0.67 | 0.883 | 0.9323 | 1 | 2784 |
| CYSTEINE_TYPE_PEPTIDASE_ACTIVITY | 54 | 0.08 | 0.66 | 0.87 | 0.93021 | 1 | 7915 |
| HEMOPOIESIS | 71 | 0.07 | 0.65 | 0.905 | 0.94316 | 1 | 9936 |
| PROTEIN_AMINO_ACID_PHOSPHORYLATION | 268 | 0.03 | 0.64 | 0.89 | 0.94752 | 1 | 6898 |
| TRANSITION_METAL_ION_BINDING | 106 | 0.05 | 0.62 | 0.933 | 0.95526 | 1 | 4837 |
| ACTIN_CYTOSKELETON | 125 | 0.04 | 0.56 | 0.978 | 0.99424 | 1 | 10554 |
| AMINO_ACID_AND_DERIVATIVE_METABOLIC_PROCESS | 99 | 0.05 | 0.55 | 0.96 | 0.99288 | 1 | 13079 |
| NEGATIVE_REGULATION_OF_RNA_METABOLIC_PROCESS | 129 | 0.04 | 0.55 | 0.972 | 0.98941 | 1 | 7189 |
| REGULATION_OF_RESPONSE_TO_STIMULUS | 59 | 0.06 | 0.51 | 0.99 | 0.99725 | 1 | 7791 |
| ENZYME_ACTIVATOR_ACTIVITY | 120 | 0.04 | 0.49 | 0.996 | 0.9967 | 1 | 13202 |
| NITROGEN_COMPOUND_METABOLIC_PROCESS | 151 | 0.03 | 0.49 | 0.992 | 0.99283 | 1 | 16617 |

TABLE F

Gene Set Enrichment Analysis output for negative selection of essential
genes in HUES62 hES cells after 14 additional days in culture. For the analysis, the ALL Gene
Ontology set was used from from the Moleular Signatures Database (MSigDB) with a minimum
set size of 50 and max set size of 300.

| NAME | SIZE | ES | NES | NOMp | FDRq | FWERp | RANK AT MAX |
|---|---|---|---|---|---|---|---|
| RIBONUCLEOPROTEIN_COMPLEX_BIOGENESIS_AND_ASSEMBLY | 73 | 0.2 | 2.3 | 0 | 0.142 | 0.121 | 4298 |
| RNA_POLYMERASE_II_TRANSCRIPTION_FACTOR_ACTIVITY | 162 | 0.1 | 2.1 | 0 | 0.222 | 0.329 | 3199 |
| RNA_SPLICING | 76 | 0.2 | 2.1 | 0.006 | 0.204 | 0.416 | 6793 |
| RNA_PROCESSING | 144 | 0.1 | 2 | 0.004 | 0.219 | 0.534 | 5451 |
| PROTEIN_RNA_COMPLEX_ASSEMBLY | 57 | 0.2 | 2 | 0.006 | 0.189 | 0.563 | 4298 |
| MITOSIS | 71 | 0.2 | 1.9 | 0.008 | 0.244 | 0.716 | 5678 |
| M_PHASE_OF_MITOTIC_CELL_CYCLE | 74 | 0.2 | 1.9 | 0.01 | 0.255 | 0.788 | 5678 |
| REPRODUCTIVE_PROCESS | 137 | 0.1 | 1.8 | 0.019 | 0.414 | 0.947 | 6727 |
| MITOTIC_CELL_CYCLE | 137 | 0.1 | 1.8 | 0.019 | 0.403 | 0.958 | 8284 |
| REGULATION_OF_CELL_CYCLE | 157 | 0.1 | 1.7 | 0.039 | 0.647 | 0.995 | 9226 |
| RIBONUCLEOPROTEIN_COMPLEX | 115 | 0.1 | 1.6 | 0.043 | 0.717 | 0.998 | 6653 |
| MACROMOLECULAR_COMPLEX_ASSEMBLY | 242 | 0.1 | 1.6 | 0.03 | 0.691 | 1 | 4562 |
| TRANSLATION | 147 | 0.1 | 1.6 | 0.05 | 0.671 | 1 | 7108 |
| DNA_DIRECTED_RNA_POLYMERASEII_HOLOENZYME | 57 | 0.2 | 1.6 | 0.049 | 0.631 | 1 | 5123 |
| CHROMOSOMAL_PART | 77 | 0.1 | 1.6 | 0.063 | 0.701 | 1 | 8719 |
| CELLULAR_COMPONENT_ASSEMBLY | 257 | 0.1 | 1.5 | 0.062 | 0.688 | 1 | 4562 |
| RNA_BINDING | 216 | 0.1 | 1.5 | 0.056 | 0.696 | 1 | 5522 |
| M_PHASE | 101 | 0.1 | 1.5 | 0.08 | 0.687 | 1 | 8489 |
| MRNA_PROCES_SING_GO_0006397 | 63 | 0.2 | 1.5 | 0.068 | 0.663 | 1 | 4298 |
| REPRODUCTION | 226 | 0.1 | 1.5 | 0.053 | 0.632 | 1 | 6759 |
| MRNA_METABOLIC_PROCESS | 71 | 0.1 | 1.5 | 0.086 | 0.732 | 1 | 6950 |
| REGULATION_OF_KINASE_ACTIVITY | 133 | 0.1 | 1.5 | 0.083 | 0.733 | 1 | 7168 |
| ENZYME_BINDING | 154 | 0.1 | 1.4 | 0.087 | 0.735 | 1 | 10360 |
| REGULATION_OF_PROTEIN_KINASE_ACTIVITY | 131 | 0.1 | 1.4 | 0.1 | 0.773 | 1 | 7168 |
| NUCLEOLUS | 94 | 0.1 | 1.4 | 0.113 | 0.764 | 1 | 7137 |
| TRANSCRIPTION_FACTOR_COMPLEX | 81 | 0.1 | 1.4 | 0.113 | 0.742 | 1 | 8392 |
| CHROMOSOME | 102 | 0.1 | 1.4 | 0.091 | 0.721 | 1 | 2248 |
| STRUCTURAL_CONSTITUENT_OF_RIBOSOME | 60 | 0.2 | 1.4 | 0.098 | 0.709 | 1 | 10943 |
| CELL_ACTIVATION | 71 | 0.1 | 1.4 | 0.114 | 0.701 | 1 | 6829 |
| CELL_CYCLE_PHASE | 153 | 0.1 | 1.4 | 0.093 | 0.713 | 1 | 8333 |
| POSITIVE_REGULATION_OF_TRANSCRIPTION | 131 | 0.1 | 1.4 | 0.11 | 0.701 | 1 | 8116 |
| TRANSMISSION_OF_NERVE_IMPULSE | 170 | 0.1 | 1.4 | 0.12 | 0.699 | 1 | 11366 |
| APOPTOTIC_PROGRAM | 51 | 0.2 | 1.4 | 0.12 | 0.692 | 1 | 5013 |
| DNA_METABOLIC_PROCESS | 219 | 0.1 | 1.4 | 0.117 | 0.676 | 1 | 9608 |
| POSITIVE_REGULATION_OF_CELLULAR_METABOLIC_PROCESS | 204 | 0.1 | 1.3 | 0.146 | 0.745 | 1 | 8687 |
| MICROTUBULE_CYTOSKELETON | 132 | 0.1 | 1.3 | 0.142 | 0.739 | 1 | 1731 |
| KINASE_BINDING | 61 | 0.1 | 1.3 | 0.142 | 0.726 | 1 | 10359 |
| REGULATION_OF_ACTIVITY | 137 | 0.1 | 1.3 | 0.138 | 0.711 | 1 | 7168 |
| LYMPHOCYTE_ACTIVATION | 56 | 0.1 | 1.3 | 0.151 | 0.693 | 1 | 6829 |
| MACROMOLECULE_CATABOLIC_PROCESS | 116 | 0.1 | 1.3 | 0.145 | 0.68 | 1 | 13196 |
| LEUKOCYTE_ACTIVATION | 64 | 0.1 | 1.3 | 0.17 | 0.71 | 1 | 6829 |
| POSITIVE_REGULATION_OF_METABOLIC_PROCESS | 210 | 0.1 | 1.3 | 0.181 | 0.716 | 1 | 8687 |
| PROTEIN_KINASE_BINDING | 53 | 0.2 | 1.3 | 0.142 | 0.703 | 1 | 7909 |
| RESPONSE_TO_ENDOGENOUS_STIMULUS | 174 | 0.1 | 1.3 | 0.163 | 0.693 | 1 | 9799 |
| CELLULAR_MACROMOLECULE_CATABOLIC_PROCESS | 87 | 0.1 | 1.3 | 0.156 | 0.691 | 1 | 12929 |
| BIOPOLYMER_CATABOLIC_PROCESS | 103 | 0.1 | 1.3 | 0.185 | 0.697 | 1 | 6589 |
| POSITIVE_REGULATION_OF_NUCLEOBASE NUCLEOSIDENUCLEOTIDE_AND_NUCLEIC_ACID_METABOLIC_PROCESS | 141 | 0.1 | 1.3 | 0.18 | 0.692 | 1 | 8116 |
| ANION_TRANSMEMBRANE_TRANSPORTER_ACTIVITY | 56 | 0.1 | 1.3 | 0.177 | 0.702 | 1 | 6320 |
| CELL_PROJECTION | 94 | 0.1 | 1.3 | 0.2 | 0.691 | 1 | 7993 |
| SYNAPTIC_TRANSMISSION | 156 | 0.1 | 1.2 | 0.193 | 0.767 | 1 | 11366 |
| CARBOHYDRATE_BINDING | 61 | 0.1 | 1.2 | 0.192 | 0.757 | 1 | 2825 |
| CYTOKINE_PRODUCTION | 65 | 0.1 | 1.2 | 0.189 | 0.752 | 1 | 9817 |
| PROTEIN_CATABOLIC_PROCESS | 61 | 0.1 | 1.2 | 0.222 | 0.758 | 1 | 13196 |
| PHOSPHORIC_ESTER_HYDROLASE_ACTIVITY | 141 | 0.1 | 1.2 | 0.2 | 0.754 | 1 | 12864 |
| PROTEIN_TYROSINE_KINASE_ACTIVITY | 54 | 0.1 | 1.2 | 0.198 | 0.745 | 1 | 5783 |
| CALCIUM_ION_BINDING | 89 | 0.1 | 1.2 | 0.215 | 0.77 | 1 | 7829 |
| PHOSPHOTRANSFERASE_ACTIVITY_ALCOHOL_GROUP_AS_ACCEPTOR | 299 | 0.1 | 1.2 | 0.238 | 0.764 | 1 | 7371 |
| REGULATION_OF_CELL_PROLIFERATION | 273 | 0.1 | 1.2 | 0.235 | 0.774 | 1 | 8412 |
| CENTRAL_NERVOUS_SYSTEM_DEVELOPMENT | 112 | 0.1 | 1.2 | 0.256 | 0.821 | 1 | 7866 |
| REGULATION_OF_SIGNAL_TRANSDUCTION | 195 | 0.1 | 1.2 | 0.246 | 0.831 | 1 | 9366 |
| POSITIVE_REGULATION_OF_TRANSCRIPTIONDNA_DEPENDENT | 108 | 0.1 | 1.2 | 0.247 | 0.82 | 1 | 8055 |

TABLE F-continued

Gene Set Enrichment Analysis output for negative selection of essential genes in HUES62 hES cells after 14 additional days in culture. For the analysis, the ALL Gene Ontology set was used from from the Moleular Signatures Database (MSigDB) with a minimum set size of 50 and max set size of 300.

| NAME | SIZE | ES | NES | NOMp | FDRq | FWERp | RANK AT MAX |
|---|---|---|---|---|---|---|---|
| POSITIVE_REGULATION_OF_DEVELOPMENTAL_PROCESS | 195 | 0.1 | 1.2 | 0.259 | 0.834 | 1 | 12108 |
| POSITIVE_REGULATION_OF_RNA_METABOLIC_PROCESS | 110 | 0.1 | 1.2 | 0.279 | 0.829 | 1 | 8055 |
| PHOSPHORIC_MONOESTER_HYDROLASE_ACTIVITY | 103 | 0.1 | 1.1 | 0.275 | 0.826 | 1 | 12864 |
| NEGATIVE_REGULATION_OF_CELL_PROLIFERATION | 135 | 0.1 | 1.1 | 0.279 | 0.818 | 1 | 8723 |
| TRANSCRIPTION_ACTIVATOR_ACTIVITY_DNA_REPLICATION | 156 | 0.1 | 1.1 | 0.297 | 0.829 | 1 | 10875 |
| | 82 | 0.1 | 1.1 | 0.306 | 0.843 | 1 | 6359 |
| MONOCARBOXYLIC_ACID_METABOLIC_PROCESS | 77 | 0.1 | 1.1 | 0.3 | 0.839 | 1 | 13160 |
| NUCLEOPLASM_PART | 184 | 0.1 | 1.1 | 0.311 | 0.83 | 1 | 2383 |
| POSITIVE_REGULATION_OF_TRANSFERASE_ACTIVITY | 71 | 0.1 | 1.1 | 0.296 | 0.818 | 1 | 5202 |
| NEGATIVE_REGULATION_OF_METABOLIC_PROCESS | 232 | 0.1 | 1.1 | 0.311 | 0.831 | 1 | 5603 |
| MAPKKK_CASCADE_GO_0000165 | 87 | 0.1 | 1.1 | 0.339 | 0.835 | 1 | 5783 |
| MICROTUBULE_ORGANIZING_CENTER | 56 | 0.1 | 1.1 | 0.321 | 0.831 | 1 | 1731 |
| NEGATIVE_REGULATION_OF_CELLULAR_METABOLIC_PROCESS | 230 | 0.1 | 1.1 | 0.314 | 0.822 | 1 | 5603 |
| CELL_CYCLE_GO_0007049 | 273 | 0.1 | 1.1 | 0.322 | 0.815 | 1 | 8333 |
| PHOSPHORYLATION | 282 | 0.1 | 1.1 | 0.318 | 0.807 | 1 | 11887 |
| CELLULAR_PROTEIN_CATABOLIC_PROCESS | 51 | 0.1 | 1.1 | 0.341 | 0.821 | 1 | 12860 |
| MEMBRANE_ORGANIZATION_AND_BIOGENESIS | 124 | 0.1 | 1.1 | 0.329 | 0.818 | 1 | 3729 |
| PROTEINACEOUS_EXTRACELLULAR_MATRIX | 85 | 0.1 | 1.1 | 0.327 | 0.84 | 1 | 12100 |
| PROTEIN_DIMERIZATION_ACTIVITY | 160 | 0.1 | 1.1 | 0.351 | 0.837 | 1 | 9757 |
| G_PROTEIN_SIGNALING_COUPLED_TO_CAMP_NUCLEOTIDE_SECOND_MESSENGER | 58 | 0.1 | 1.1 | 0.365 | 0.831 | 1 | 4757 |
| ACID_AMINO_ACID_LIGASE_ACTIVITY | 53 | 0.1 | 1.1 | 0.364 | 0.83 | 1 | 5009 |
| EXTRACELLULAR_MATRIX | 85 | 0.1 | 1.1 | 0.335 | 0.828 | 1 | 12100 |
| NEGATIVE_REGULATION_OF_CELL_CYCLE | 67 | 0.1 | 1.1 | 0.385 | 0.837 | 1 | 13433 |
| DNA_REPAIR | 108 | 0.1 | 1.1 | 0.343 | 0.827 | 1 | 9370 |
| VESICLE_MEDIATED_TRANSPORT | 175 | 0.1 | 1.1 | 0.375 | 0.826 | 1 | 3962 |
| ORGANELLE_MEMBRANE | 262 | 0.1 | 1.1 | 0.335 | 0.823 | 1 | 11505 |
| PURINE_NUCLEOTIDE_BINDING | 183 | 0.1 | 1.1 | 0.349 | 0.824 | 1 | 5664 |
| CYTOSKELETAL_PART | 206 | 0.1 | 1 | 0.372 | 0.819 | 1 | 1731 |
| CYTOSOL | 183 | 0.1 | 1 | 0.369 | 0.828 | 1 | 12199 |
| PURINE_RIBONUCLEOTIDE_BINDING | 178 | 0.1 | 1 | 0.398 | 0.825 | 1 | 5664 |
| SEXUAL_REPRODUCTION | 117 | 0.1 | 1 | 0.396 | 0.842 | 1 | 12380 |
| ZINC_ION_BINDING | 76 | 0.1 | 1 | 0.395 | 0.836 | 1 | 2628 |
| CELL_CYCLE_PROCESS | 172 | 0.1 | 1 | 0.416 | 0.864 | 1 | 8333 |
| IDENTICAL_PROTEIN_BINDING | 265 | 0.1 | 1 | 0.421 | 0.861 | 1 | 2850 |
| LIGASE_ACTIVITY_FORMING_CARBON_NITROGEN_BONDS | 63 | 0.1 | 1 | 0.441 | 0.855 | 1 | 5120 |
| ANTI_APOPTOSIS | 105 | 0.1 | 1 | 0.444 | 0.852 | 1 | 4654 |
| SMALL_GTPASE_MEDIATED_SIGNAL_TRANSDUCTION | 78 | 0.1 | 1 | 0.453 | 0.854 | 1 | 10865 |
| CAMP_MEDIATED_SIGNALING | 59 | 0.1 | 1 | 0.418 | 0.857 | 1 | 4757 |
| REGULATION_OF_PROTEIN_METABOLIC_PROCESS | 154 | 0.1 | 1 | 0.467 | 0.855 | 1 | 3729 |
| TRANSCRIPTION_COACTIVATOR_ACTIVITY | 109 | 0.1 | 1 | 0.477 | 0.869 | 1 | 12523 |
| NUCLEAR_ENVELOPE | 62 | 0.1 | 1 | 0.464 | 0.871 | 1 | 2228 |
| OXIDOREDUCTASE_ACTIVITY | 257 | 0.1 | 1 | 0.458 | 0.871 | 1 | 6094 |
| ENZYME_REGULATOR_ACTIVITY | 279 | 0 | 1 | 0.478 | 0.884 | 1 | 12824 |
| EXTRACELLULAR_MATRIX_PART | 50 | 0.1 | 1 | 0.498 | 0.881 | 1 | 12058 |
| CATABOLIC_PROCESS | 200 | 0.1 | 1 | 0.49 | 0.894 | 1 | 13541 |
| NEUROGENESIS | 83 | 0.1 | 0.9 | 0.526 | 0.91 | 1 | 12169 |
| CYTOSKELETON_ORGANIZATION_AND_BIOGENESIS | 182 | 0.1 | 0.9 | 0.508 | 0.912 | 1 | 8813 |
| MACROMOLECULE_BIOSYNTHETIC_PROCESS | 276 | 0 | 0.9 | 0.511 | 0.912 | 1 | 12108 |
| CARBOHYDRATE_METABOLIC_PROCESS | 160 | 0.1 | 0.9 | 0.509 | 0.91 | 1 | 12203 |
| ACTIN_CYTOSKELETON_ORGANIZATION_AND_BIOGENESIS | 89 | 0.1 | 0.9 | 0.508 | 0.903 | 1 | 8813 |
| PROTEIN_DOMAIN_SPECIFIC_BINDING | 64 | 0.1 | 0.9 | 0.523 | 0.908 | 1 | 12290 |
| CATION_BINDING | 181 | 0.1 | 0.9 | 0.539 | 0.905 | 1 | 12366 |
| PROTEIN_C_TERMINUS_BINDING | 61 | 0.1 | 0.9 | 0.532 | 0.907 | 1 | 5785 |
| TRANSCRIPTION_FACTOR_BINDING | 271 | 0 | 0.9 | 0.543 | 0.9 | 1 | 11687 |
| RAS_PROTEIN_SIGNAL_TRANSDUCTION | 58 | 0.1 | 0.9 | 0.537 | 0.894 | 1 | 10865 |
| LYASE_ACTIVITY | 65 | 0.1 | 0.9 | 0.579 | 0.931 | 1 | 9672 |

TABLE F-continued

Gene Set Enrichment Analysis output for negative selection of essential
genes in HUES62 hES cells after 14 additional days in culture. For the analysis, the ALL Gene
Ontology set was used from from the Moleular Signatures Database (MSigDB) with a minimum
set size of 50 and max set size of 300.

| NAME | SIZE | ES | NES | NOMp | FDRq | FWERp | RANK AT MAX |
|---|---|---|---|---|---|---|---|
| NEGATIVE_REGULATION_OF_NUCLEOBASENUCLEOSIDENUCLEOTIDE_AND_NUCLEIC_ACID_METABOLIC_PROCESS | 186 | 0.1 | 0.9 | 0.57 | 0.926 | 1 | 3709 |
| PROTEIN_HOMODIMERIZATION_ACTIVITY | 108 | 0.1 | 0.9 | 0.578 | 0.922 | 1 | 11217 |
| ORGAN_MORPHOGENESIS | 128 | 0.1 | 0.9 | 0.582 | 0.928 | 1 | 12177 |
| SOLUBLE_FRACTION | 148 | 0.1 | 0.9 | 0.579 | 0.929 | 1 | 6965 |
| INTERPHASE_OF_MITOTIC_CELL_CYCLE | 57 | 0.1 | 0.9 | 0.601 | 0.924 | 1 | 8280 |
| REGULATION_OF_CATALYTIC_ACTIVITY | 240 | 0 | 0.9 | 0.617 | 0.921 | 1 | 5348 |
| CELLULAR_CATABOLIC_PROCESS | 188 | 0.1 | 0.9 | 0.616 | 0.919 | 1 | 12351 |
| POSITIVE_REGULATION_OF_CELLULAR_PROTEIN_METABOLIC_PROCESS | 65 | 0.1 | 0.9 | 0.598 | 0.916 | 1 | 8687 |
| STRUCTURAL_MOLECULE_ACTIVITY | 192 | 0.1 | 0.9 | 0.613 | 0.91 | 1 | 12175 |
| REGULATION_OF_MULTICELLULAR_ORGANISMAL_PROCESS | 136 | 0.1 | 0.9 | 0.603 | 0.912 | 1 | 12283 |
| TRANSCRIPTION_COFACTOR_ACTIVITY | 196 | 0.1 | 0.9 | 0.597 | 0.927 | 1 | 12429 |
| LIPID_BINDING | 79 | 0.1 | 0.9 | 0.63 | 0.923 | 1 | 12751 |
| REGULATION_OF_MAP_KINASE_ACTIVITY | 54 | 0.1 | 0.9 | 0.614 | 0.921 | 1 | 3169 |
| POSITIVE_REGULATION_OF_I_KAPPAB_KINASE_NF_KAPPAB_CASCADE | 76 | 0.1 | 0.9 | 0.603 | 0.919 | 1 | 9729 |
| POSITIVE_REGULATION_OF_PROTEIN_METABOLIC_PROCESS | 67 | 0.1 | 0.9 | 0.623 | 0.927 | 1 | 8687 |
| PROTEIN_AMINO_ACID_PHOSPHORYLATION | 251 | 0 | 0.9 | 0.635 | 0.925 | 1 | 11887 |
| HYDROLASE_ACTIVITY_ACTING_ON_ESTER_BONDS | 244 | 0 | 0.8 | 0.645 | 0.923 | 1 | 13028 |
| CYTOPLASMIC_VESICLE | 105 | 0.1 | 0.8 | 0.637 | 0.919 | 1 | 13797 |
| REGULATION_OF_I_KAPPAB_KINASE_NF_KAPPAB_CASCADE | 81 | 0.1 | 0.8 | 0.635 | 0.927 | 1 | 9729 |
| SKELETAL_DEVELOPMENT | 96 | 0.1 | 0.8 | 0.639 | 0.935 | 1 | 11294 |
| SMALL_GTPASE_REGULATOR_ACTIVITY | 62 | 0.1 | 0.8 | 0.673 | 0.945 | 1 | 12082 |
| REGULATION_OF_BINDING | 52 | 0.1 | 0.8 | 0.701 | 0.939 | 1 | 12761 |
| ENDOMEMBRANE_SYSTEM | 190 | 0.1 | 0.8 | 0.687 | 0.946 | 1 | 11505 |
| CYTOPLASMIC_MEMBRANE_BOUND_VESICLE | 102 | 0.1 | 0.8 | 0.709 | 0.949 | 1 | 13797 |
| TRANSITION_METAL_ION_BINDING | 94 | 0.1 | 0.8 | 0.708 | 0.946 | 1 | 2628 |
| MUSCLE_EVELOPMENT | 88 | 0.1 | 0.8 | 0.696 | 0.94 | 1 | 12772 |
| GAMETE_GENERATION | 96 | 0.1 | 0.8 | 0.695 | 0.94 | 1 | 12659 |
| RESPONSE_TO_DNA_DAMAGE_STIMULUS | 140 | 0.1 | 0.8 | 0.758 | 0.941 | 1 | 9799 |
| GTPASE_REGULATOR_ACTIVITY | 111 | 0.1 | 0.8 | 0.722 | 0.938 | 1 | 5348 |
| LIGASE_ACTIVITY | 86 | 0.1 | 0.8 | 0.739 | 0.947 | 1 | 5410 |
| NEGATIVE_REGULATION_OF_TRANSCRIPTION | 171 | 0.1 | 0.8 | 0.734 | 0.942 | 1 | 3709 |
| PROTEIN_KINASE_ACTIVITY | 256 | 0 | 0.8 | 0.765 | 0.944 | 1 | 7338 |
| STRUCTURAL_CONSTITUENT_OF_CYTOSKELETON | 50 | 0.1 | 0.8 | 0.743 | 0.944 | 1 | 2346 |
| VACUOLE | 62 | 0.1 | 0.8 | 0.727 | 0.945 | 1 | 6726 |
| NEGATIVE_REGULATION_OF_APOPTOSIS | 130 | 0.1 | 0.8 | 0.759 | 0.94 | 1 | 4654 |
| SECRETION | 158 | 0.1 | 0.8 | 0.756 | 0.936 | 1 | 11635 |
| REGULATION_OF_MOLECULAR_FUNCTION | 283 | 0 | 0.8 | 0.752 | 0.937 | 1 | 5603 |
| REGULATION_OF_TRANSPORT | 61 | 0.1 | 0.8 | 0.768 | 0.943 | 1 | 14839 |
| REGULATION_OF_TRANSLATION | 82 | 0.1 | 0.8 | 0.778 | 0.942 | 1 | 8502 |
| PROTEIN_IMPORT | 53 | 0.1 | 0.8 | 0.765 | 0.939 | 1 | 412 |
| ION_BINDING | 232 | 0 | 0.8 | 0.759 | 0.942 | 1 | 11557 |
| ORGANELLE_ENVELOPE | 147 | 0.1 | 0.8 | 0.782 | 0.937 | 1 | 3663 |
| GROWTH | 67 | 0.1 | 0.8 | 0.771 | 0.934 | 1 | 12240 |
| FATTY_ACID_METABOLIC_PROCESS | 56 | 0.1 | 0.8 | 0.787 | 0.934 | 1 | 12183 |
| NEGATIVE_REGULATION_OF_DEVELOPMENTAL_PROCESS | 173 | 0 | 0.7 | 0.794 | 0.94 | 1 | 4654 |
| I_KAPPAB_KINASE_NF_KAPPAB_CASCADE | 99 | 0.1 | 0.7 | 0.808 | 0.938 | 1 | 14020 |
| NEGATIVE_REGULATION_OF_PROGRAMMED_CELL_DEATH | 131 | 0.1 | 0.7 | 0.807 | 0.935 | 1 | 4654 |
| ENVELOPE | 147 | 0.1 | 0.7 | 0.788 | 0.929 | 1 | 3663 |
| PROTEIN_KINASE_CASCADE | 258 | 0 | 0.7 | 0.842 | 0.948 | 1 | 13666 |
| TRANSCRIPTION_COREPRESSOR_ACTIVITY | 78 | 0.1 | 0.7 | 0.826 | 0.945 | 1 | 3220 |
| REGULATION_OF_TRANSCRIPTION_FROM_RNA_POLYMERASED_II_PROMOTER | 255 | 0 | 0.7 | 0.806 | 0.949 | 1 | 3002 |
| MEMBRANE_BOUND_VESICLE | 104 | 0.1 | 0.7 | 0.85 | 0.95 | 1 | 11308 |
| ENZYME_ACTIVATOR_ACTIVITY | 111 | 0.1 | 0.7 | 0.852 | 0.948 | 1 | 12334 |
| TRANSFERASE_ACTIVITY_TRANSFERRING_HEXOSYL_GROUPS | 75 | 0.1 | 0.7 | 0.84 | 0.955 | 1 | 12906 |
| TRANSCRIPTION_REPRESSOR_ACTIVITY | 131 | 0.1 | 0.7 | 0.853 | 0.958 | 1 | 3240 |
| EXTRACELLULAR_REGION_PART | 294 | 0 | 0.7 | 0.868 | 0.956 | 1 | 12644 |
| RECEPTOR_COMPLEX | 51 | 0.1 | 0.7 | 0.868 | 0.976 | 1 | 2182 |
| NEGATIVE_REGULATION_OF_CATALYTIC_ACTIVITY | 64 | 0.1 | 0.7 | 0.903 | 0.977 | 1 | 4937 |

TABLE F-continued

Gene Set Enrichment Analysis output for negative selection of essential
genes in HUES62 hES cells after 14 additional days in culture. For the analysis, the ALL Gene
Ontology set was used from from the Moleular Signatures Database (MSigDB) with a minimum
set size of 50 and max set size of 300.

| NAME | SIZE | ES | NES | NOMp | FDRq | FWERp | RANK AT MAX |
|---|---|---|---|---|---|---|---|
| MITOCHONDRIAL_PART | 125 | 0 | 0.6 | 0.928 | 0.986 | 1 | 11489 |
| PROTEIN_COMPLEX_ASSEMBLY | 146 | 0 | 0.6 | 0.902 | 0.982 | 1 | 4562 |
| MICROTUBULE_BASED_PROCESS | 74 | 0.1 | 0.6 | 0.893 | 0.978 | 1 | 12093 |
| NUCLEAR_ENVELOPE_ENDOPLASMIC_RETICULUM_NETWORK | 82 | 0.1 | 0.6 | 0.91 | 0.994 | 1 | 3200 |
| ORGANELLE_INNER_MEMBRANE | 65 | 0.1 | 0.6 | 0.93 | 0.989 | 1 | 3663 |
| TRANSFERASE_ACTIVITY_TRANSFERRING_ACYL_GROUPS | 54 | 0.1 | 0.6 | 0.939 | 0.992 | 1 | 10232 |
| REGULATION_OF_GROWTH | 51 | 0.1 | 0.6 | 0.922 | 0.989 | 1 | 11803 |
| IMMUNE_SYSTEM_DEVELOPMENT | 75 | 0.1 | 0.6 | 0.957 | 0.984 | 1 | 14325 |
| ATPASE_ACTIVITY_COUPLED | 82 | 0.1 | 0.6 | 0.948 | 0.982 | 1 | 13690 |
| POSITIVE_REGULATION_OF_CATALYTIC_ACTIVITY | 142 | 0 | 0.6 | 0.935 | 0.978 | 1 | 5324 |
| ACTIN_FILAMENT_BASED_PROCESS | 99 | 0.1 | 0.6 | 0.959 | 0.984 | 1 | 8813 |
| POSITIVE_REGULATION_OF_TRANSCRIPTION_FROM_RNA_POLYMERASE_II_PROMOTER | 59 | 0.1 | 0.6 | 0.959 | 0.986 | 1 | 8009 |
| HEMOPOIETIC_OR_LYMPHOID_ORGAN_DEVELOPMENT | 71 | 0.1 | 0.6 | 0.968 | 0.982 | 1 | 14325 |
| HEMOPOIESIS | 69 | 0.1 | 0.6 | 0.976 | 0.987 | 1 | 6829 |
| INTERPHASE | 63 | 0.1 | 0.6 | 0.978 | 0.983 | 1 | 8280 |
| ACTIN_BINDING | 70 | 0.1 | 0.5 | 0.996 | 0.995 | 1 | 3563 |
| ENDOPLASMIC_RETICULUM | 253 | 0 | 0.5 | 0.986 | 0.992 | 1 | 15352 |

Figure 27A:
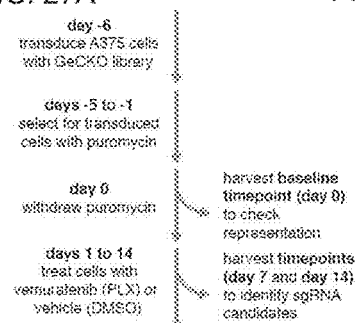
FIG. 27A-27F shows GeCKO screen in A375 melanoma cells reveals genes whose loss confers vemurafenib (PLX) resistance. (A) Timeline of PLX resistance screen in A375 melanoma cells. (B) Growth of A375 cells when treated with DMSO or PLX over 14 days. (C) Boxplot showing the distribution of sgRNA frequencies at different time points, with and without PLX treatment (vehicle=DMSO). The box extends from the first to the third quartile with the whiskers denoting 1.5 times the interquartile range. Enrichment of specific sgRNAs: 7 days of PLX treatment, 1 sgRNA greater than 10-fold enrichment; 14 days of PLX treatment, 379 and 49 sgRNAs greater than 10-fold and 100-fold enrichment respectively. (D) Rank correlation of normalized sgRNA read count between biological replicates and treatment conditions. (E) Scatterplot showing enrichment of specific sgRNAs after PLX treatment. (F) Identification of top candidate genes using the RNAi Gene Enrichment Ranking (RIGER) p value analysis.
Figure 27B:
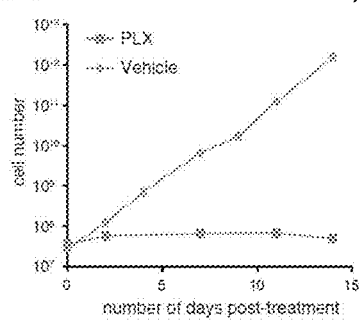
Figure 27C:
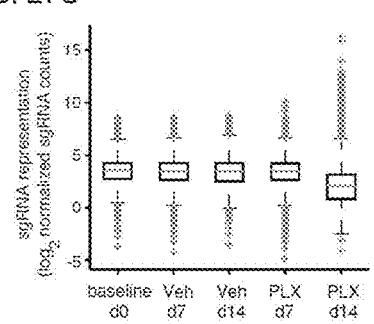
Figure 27D:
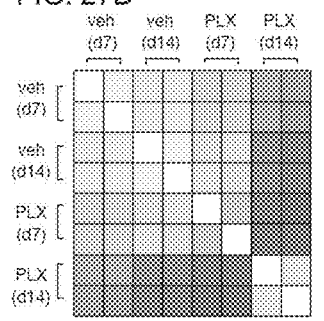
Figure 34:
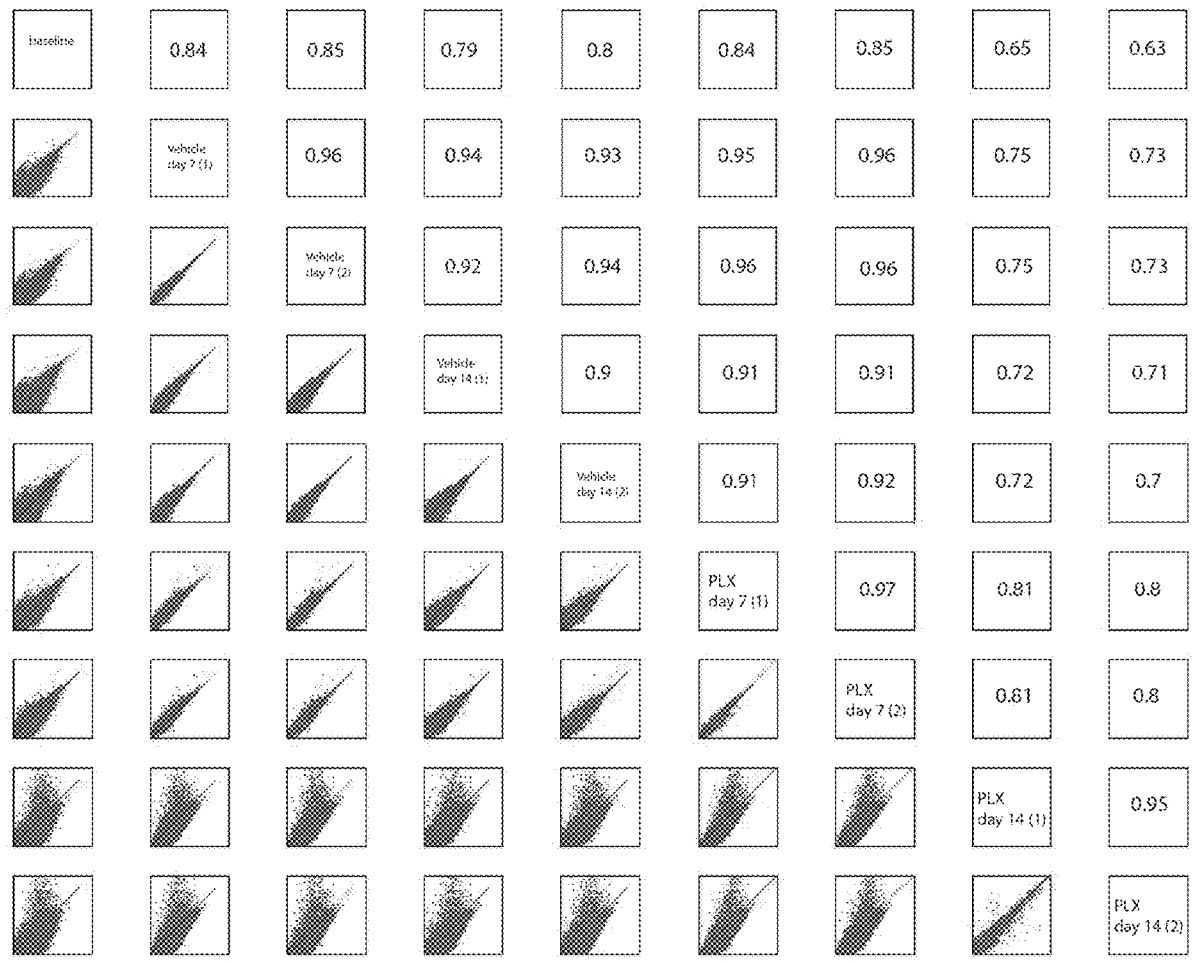
FIG. 34 shows Comparison of different treatment conditions and biological replicates in the first A375 PLX screen. Each square in the lower left half of the matrix compares the normalized sgRNA read count between two biological samples. Sample labels for each axis are indicated on the diagonal. For example, the box on the second row from the bottom and third column from the right compares PLX day 7 (2) on the x-axis with PLX day 14 (1) on the y-axis. The Pearson correlation coefficient for comparison (i,j) can be found in box (j,i); for the example described in the previous sentence, the correlation coefficient is 0.81.

To test the efficacy of GeCKO for positive selection, Applicants sought to identify gene knockouts that result in resistance to the BRAF protein kinase inhibitor vemurafenib (PLX) in melanoma (FIG. 27A). Exposure to PLX resulted in growth arrest of transduced A375 cells, which harbor the V600E gain-of-function BRAF mutation (FIG. 27B), therefore enabling the enrichment of a small group of cells that had been rendered drug-resistant by Cas9:sgRNA-mediated modification. After 14 days of PLX treatment, the sgRNA distribution was significantly different when compared with vehicle-treated cells (FIG. 27C; Wilcoxon rank-sum test, $p<10^{-10}$) and clustered separately from all other conditions (FIGS. 27D and 34).

Figure 27E:
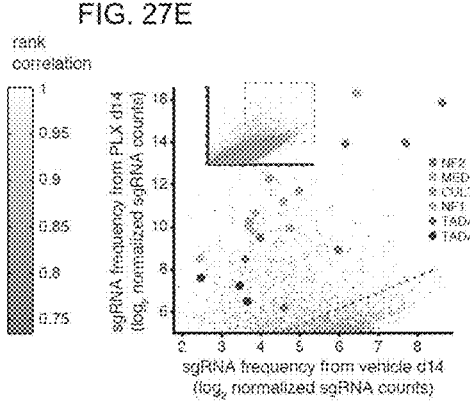
Figure 27F:
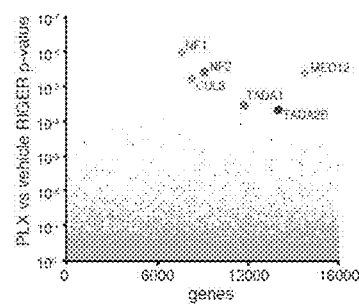
Figure 35A:
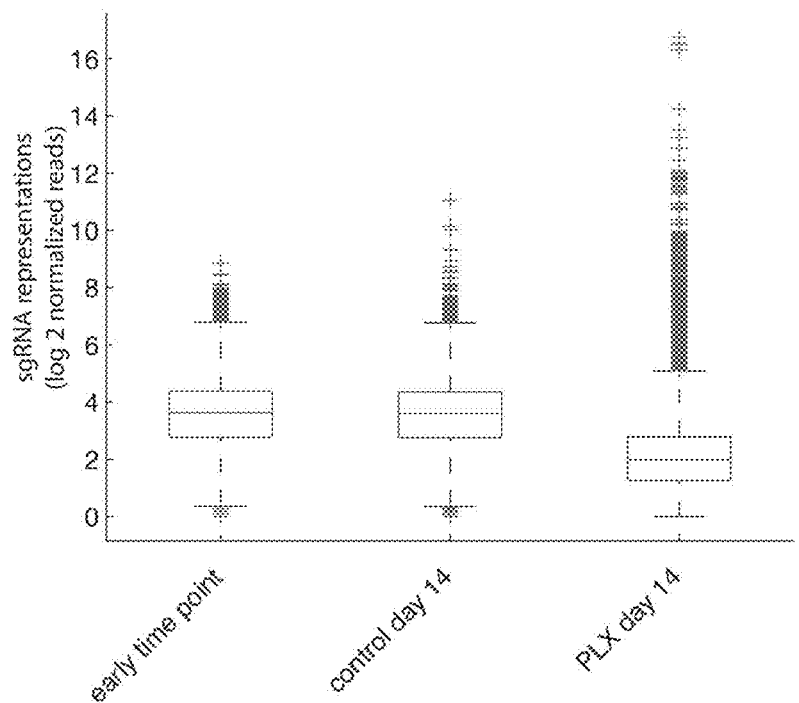
FIG. 35A-35B shows sgRNA and gene enrichment from the second A375 PLX screen. (A) Boxplot showing the distribution of reads from individual sgRNAs for the early timepoint, DMSO treated control, and PLX-4023 (PLX) treatment. The box extends from the first to the third quartile with the whiskers denoting 1.5 times the interquartile range. After 14 days of PLX treatment, while there is a decrease in the average number of reads per sgRNA, there is an increase in the number of reads for the most abundant sgRNAs. (B) Plot of the RIGER p value for genes enriched in PLX compared to vehicle control.
Figure 35B:
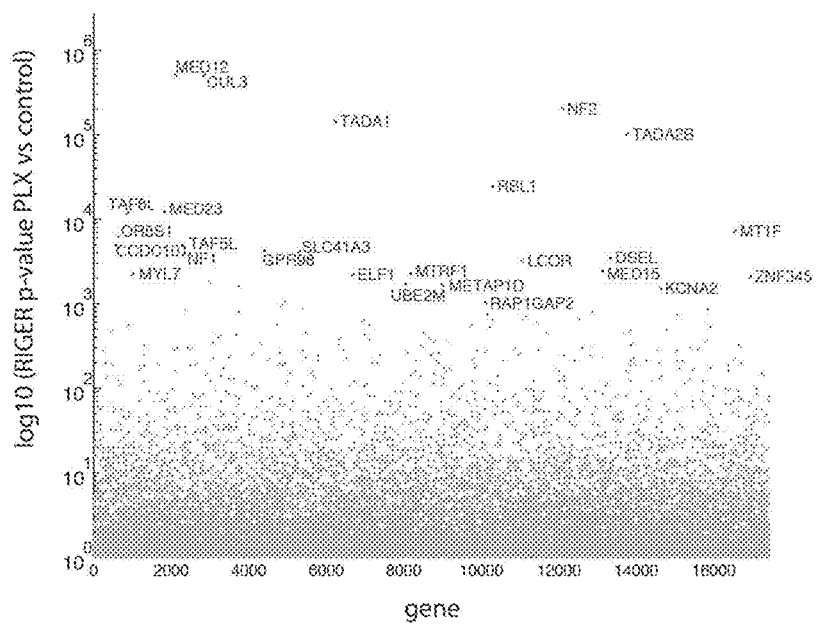
Figure 36:
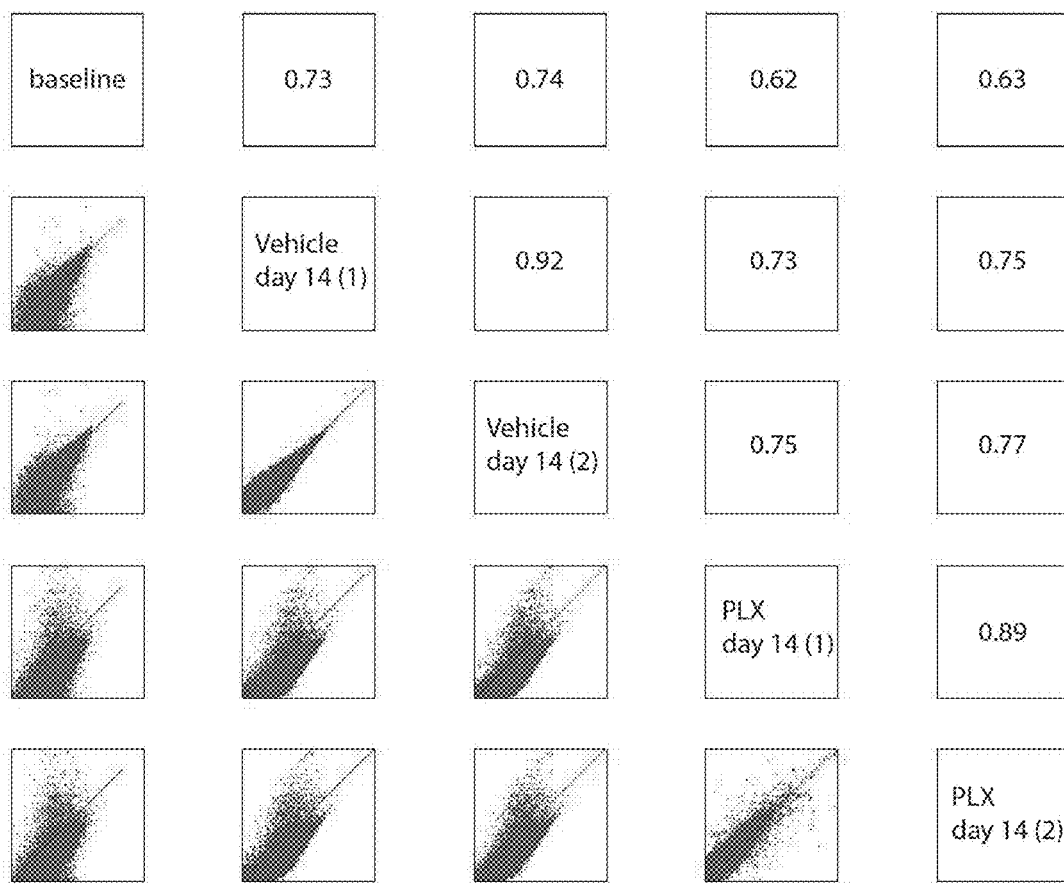
FIG. 36 shows Comparison of different treatment conditions and biological replicates in the infection replicate A375 screen. Each square in the lower left half of the matrix compares the normalized sgRNA read count between two biological samples. Sample labels for each axis are indicated on the diagonal. For example, the box on the second row from the bottom and third column from the right compares Vehicle day 14 (2) on the x-axis with PLX day 14 (1) on the y-axis. The Pearson correlation coefficient for comparison (i j) can be found in box (j,i); for the example described in the previous sentence, the correlation coefficient is 0.75.

For a set of genes, Applicants found enrichment of multiple sgRNAs that target each gene after 14 days of PLX treatment (FIG. 27E), suggesting that loss of these particular genes contributes to PLX resistance. Applicants used the RNAi Gene Enrichment Ranking (RIGER) algorithm to rank screening hits by the consistent enrichment among multiple sgRNAs targeting the same gene (FIGS. 27F, 45). Applicants' highest ranking genes contained previously reported candidates NF1 and MED12 and also several previously unknown genes, including neurofibromin 2 (NF2), Cullin 3 E3 ligase (CUL3), and members of the STAGA histone acetyltransferase complex (TADA1 and TADA2B). These candidates yielded new testable hypotheses regarding PLX resistance mechanisms. For example, NF1 and NF2, although unrelated in sequence, are each mutated in similar but distinct forms of neurofibromatosis. In addition, epigenetic dysregulation resulting from mutations in the mechanistically related STAGA and Mediator complexes may have a role in acquired drug resistance. All of these hits were also identified through a second independent transduction (FIGS. 35 and 36, and Tables G and H).

TABLE G

Output of the RIGER algorithm for the initial A375 PLX screen comparing
PLX (mean of the two replicates at day 14) to DMSO control (mean of the two
replicates at day 14). The weighted sum method was used to convert sgRNAs
to genes. Genes are sorted by RIGER rank.

| Gene | Hairpins | # Hairpins | Hairpin ranks | NES | Gene rank | p-value | p-value rank |
|---|---|---|---|---|---|---|---|
| NF2 | s_36796, s_36797, s_36798, s_36799 | 4 | 58, 415, 31, 22 | 8E-04 | 1 | 0.000004 | 2 |
| MED12 | s_33340, s_33341, s_33342, s_33343 | 4 | 53, 38, 45, 67 | 0.001 | 2 | 0.000004 | 3 |
| CUL3 | s_14311, s_14312, s_14313, s_14314, s_14315, s_14316 | 6 | 49523, 41, 17, 44, 6188, 18040 | 0.001 | 3 | 0.000006 | 5 |

TABLE G-continued

Output of the RIGER algorithm for the initial A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| CLDN10 | s_12138, s_12139, s_12140, s_12141 | 4 | 23, 24918, 69, 4914 | 0.002 | 4 | 0.000005 | 4 |
| NF1 | s_36794, s_36795 | 2 | 130, 1 | 0.002 | 5 | 0.000001 | 1 |
| TADA1 | s_55204, s_55205, s_55206, s_55207 | 4 | 137, 93, 5672, 927 | 0.003 | 6 | 0.000035 | 6 |
| TADA2B | s_55211, s_55212, s_55213 | 3 | 127, 249, 429 | 0.005 | 7 | 0.000046 | 7 |
| SPECC1 | s_53443, s_53444, s_53445, s_53446, s_53447, s_53448, s_53449, s_53450, s_53451 | 9 | 145, 26652, 43674, 56582, 58227, 59830, 20, 22519, 21861 | 0.005 | 8 | 0.000146 | 11 |
| CCDC101 | s_9430, s_9431, s_9432 | 3 | 333, 492, 198 | 0.007 | 9 | 0.000082 | 8 |
| ALG3 | s_2023, s_2024, s_2025, s_2026 | 4 | 2441, 297, 138, 22771 | 0.007 | 10 | 0.000118 | 9 |
| P4HB | s_39947, s_39948, s_39949 | 3 | 59088, 30, 576 | 0.01 | 11 | 0.000189 | 12 |
| EED | s_17448, s_17449, s_17450, s_17451 | 4 | 2886, 293, 443, 16470 | 0.011 | 12 | 0.000313 | 15 |
| TAF6L | s_55283, s_55284, s_55285 | 3 | 1977, 330, 532 | 0.011 | 13 | 0.000234 | 13 |
| MED15 | s_33355, s_33356, s_33357, s_33358 | 4 | 285, 504, 3489, 542 | 0.012 | 14 | 0.000382 | 17 |
| NPPC | s_37703, s_37704, s_37705, s_37706, s_37707, s_37708 | 6 | 204, 6109, 39836, 60416, 10125, 403 | 0.012 | 15 | 0.000575 | 24 |
| TAF5L | s_55276, s_55277 | 2 | 199, 831 | 0.012 | 16 | 0.000141 | 10 |
| PGD | s_41483, s_41484, s_41485 | 3 | 624, 484, 1163 | 0.013 | 17 | 0.000349 | 16 |
| LGALS4 | s_30886, s_30887, s_30888, s_30889 | 4 | 33, 678, 16507, 14753 | 0.014 | 18 | 0.00051 | 22 |
| TAOK1 | s_55349, s_55350, s_55351 | 3 | 696, 505, 5374 | 0.014 | 19 | 0.000429 | 19 |
| CD320 | s_10386, s_10387, s_10388, s_10389, s_10390, s_10391 | 6 | 17447, 182, 35806, 50696, 49163, 488 | 0.014 | 20 | 0.000824 | 30 |
| CCNC | s_10026, s_10027, s_10028, s_10029, s_10030 | 5 | 52916, 817, 518, 51901, 385 | 0.015 | 21 | 0.000735 | 25 |

TABLE G-continued

Output of the RIGER algorithm for the initial A375 PLX screen comparing
PLX (mean of the two replicates at day 14) to DMSO control (mean of the two
replicates at day 14). The weighted sum method was used to convert sgRNAs
to genes. Genes are sorted by RIGER rank.

| Gene | Hairpins | # Hairpins | Hairpin ranks | NES | Gene rank | p-value | p-value rank |
|---|---|---|---|---|---|---|---|
| SMARCB1 | s_52518, s_52519, s_52520 | 3 | 614, 733, 2280 | 0.016 | 22 | 0.000501 | 21 |
| ASIC1 | s_3947, s_3948, s_3949, s_3950, s_3951, s_3952 | 6 | 605, 53882, 17965, 48, 12823, 15216 | 0.016 | 23 | 0.001042 | 34 |
| MED19 | s_33371, s_33372, s_33373, s_33374 | 4 | 298, 3666, 7614, 748 | 0.017 | 24 | 0.000754 | 27 |
| GADD45GIP1 | s_22055, s_22056, s_22057, s_22058 | 4 | 832, 124, 9275, 1307 | 0.017 | 25 | 0.000795 | 29 |
| MED23 | s_33386, s_33387 | 2 | 430, 1171 | 0.018 | 26 | 0.000301 | 14 |
| ZDHHC15 | s_62858, s_62859, s_62860, s_62861 | 4 | 60, 48709, 953, 52940 | 0.019 | 27 | 0.000988 | 33 |
| TWF2 | s_59891, s_59892, s_59893, s_59894, s_59895, s_59896 | 6 | 25884, 211, 11866, 668, 55063, 18294 | 0.019 | 28 | 0.001489 | 41 |
| ADRA2B | s_1352, s_1353, s_1354 | 3 | 55393, 482, 1091 | 0.021 | 29 | 0.000873 | 31 |
| PDC | s_40830, s_40831, s_40832, s_40833, s_40834, s_40835 | 6 | 56956, 242, 720, 49078, 43057, 3523 | 0.021 | 30 | 0.001707 | 50 |
| KCTD10 | s_28876, s_28877, s_28878 | 3 | 1094, 3568, 534 | 0.021 | 31 | 0.000896 | 32 |
| MFSD9 | s_33784, s_33785 | 2 | 1176, 1027 | 0.021 | 32 | 0.000419 | 18 |
| TXNDC17 | s_59941, s_59942, s_59943, s_59944 | 4 | 25655, 509, 935, 6800 | 0.022 | 33 | 0.00128 | 38 |
| MED16 | s_33359, s_33360, s_33361, s_33362 | 4 | 912, 608, 20030, 4476 | 0.022 | 34 | 0.001299 | 40 |
| TADA3 | s_55214, s_55215 | 2 | 1504, 234 | 0.022 | 35 | 0.000455 | 20 |
| PDCD10 | s_40840, s_40841, s_40842, s_40843, s_40844 | 5 | 30804, 804, 1252, 20846, 561 | 0.023 | 36 | 0.001744 | 51 |
| TNFRSF17 | s_58081, s_58082, s_58083, s_58084 | 4 | 1184, 29, 50083, 12376 | 0.023 | 37 | 0.001491 | 42 |
| DARS | s_14981, s_14982, s_14983, s_14984, s_14985, s_14986 | 6 | 54968, 41173, 736, 52808, 20070, 493 | 0.023 | 38 | 0.002111 | 61 |
| ELMOD1 | s_18007, s_18008 | 2 | 221, 1617 | 0.024 | 39 | 0.000523 | 23 |

TABLE G-continued

Output of the RIGER algorithm for the initial A375 PLX screen comparing
PLX (mean of the two replicates at day 14) to DMSO control (mean of the two
replicates at day 14). The weighted sum method was used to convert sgRNAs
to genes. Genes are sorted by RIGER rank.

| Gene | Hairpins | # Hairpins | Hairpin ranks | NES | Gene rank | p-value | p-value rank |
|------|----------|------------|---------------|-----|-----------|---------|--------------|
| ARID1A | s_3477, s_3478, s_3479, s_3480 | 4 | 53744, 167, 1145, 4655 | 0.024 | 40 | 0.001505 | 43 |
| GNB2L1 | s_23260, s_23261, s_23262, s_23263 | 4 | 12534, 598, 1022, 8784 | 0.024 | 41 | 0.001556 | 44 |
| SCPEP1 | s_49407, s_49408, s_49409, s_49410 | 4 | 949, 61876, 883, 50303 | 0.024 | 42 | 0.001613 | 45 |
| KEAP1 | s_29029, s_29030, s_29031, s_29032 | 4 | 4069, 1053, 43892, 601 | 0.025 | 43 | 0.001632 | 47 |
| NCOR2 | s_36330, s_36331, s_36332, s_36333 | 4 | 991, 11014, 20939, 822 | 0.025 | 44 | 0.00166 | 48 |
| OR2T33 | s_39119, s_39120, s_39121 | 3 | 1342, 9376, 500 | 0.025 | 45 | 0.001231 | 37 |
| BCL2L12 | s_5187, s_5188, s_5189, s_5190 | 4 | 1605, 711, 5895, 1061 | 0.025 | 46 | 0.001761 | 53 |
| SPOPL | s_53635, s_53636, s_53637 | 3 | 1325, 664, 56183 | 0.026 | 47 | 0.001289 | 39 |
| FGGY | s_21004, s_21005, s_21006, s_21007, s_21008, s_21009 | 6 | 852, 9579, 32124, 29464, 27460, 388 | 0.026 | 48 | 0.002495 | 68 |
| CA7 | s_8596, s_8597, s_8598, s_8599, s_8600, s_8601 | 6 | 273, 62443, 30916, 21259, 7063, 905 | 0.026 | 49 | 0.002567 | 69 |
| JMJD4 | s_28292, s_28293, s_28294, s_28295, s_28296, s_28297 | 6 | 975, 19283, 81, 29765, 46303, 47416 | 0.026 | 50 | 0.002601 | 70 |
| MYO9B | s_35776, s_35777, s_35778, s_35779 | 4 | 1257, 326, 21804, 23954 | 0.027 | 51 | 0.001952 | 57 |
| FAM19A4 | s_19778, s_19779, s_19780, s_19781, s_19782, s_19783 | 6 | 62838, 909, 383, 23595, 32237, 42288 | 0.027 | 52 | 0.002769 | 76 |
| EBF4 | s_17294, s_17295, s_17296, s_17297 | 4 | 64198, 1219, 506, 15439 | 0.027 | 53 | 0.002002 | 59 |
| TTC4 | s_59623, s_59624, s_59625, s_59626, s_59627 | 5 | 1161, 52043, 51855, 23126, 218 | 0.028 | 54 | 0.002705 | 74 |

TABLE G-continued

Output of the RIGER algorithm for the initial A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| DPH2 | s_16717, s_16718, s_16719, s_16720, s_16721, s_16722 | 6 | 958, 363, 2412, 6120, 3930, 1644 | 0.028 | 55 | 0.00298 | 82 |
| DRAP1 | s_16840, s_16841, s_16842, s_16843 | 4 | 37730, 1221, 643, 31607 | 0.028 | 56 | 0.002136 | 62 |
| C1orf49 | s_7303, s_7304, s_7305, s_7306, s_7307, s_7308, s_7309 | 7 | 820, 63864, 34124, 47596, 60950, 413, 16428 | 0.028 | 57 | 0.003353 | 87 |
| ATXN2L | s_4596, s_4597 | 2 | 461, 1892 | 0.028 | 58 | 0.000746 | 26 |
| CCT8 | s_10201, s_10202 | 2 | 1836, 684 | 0.029 | 59 | 0.000757 | 28 |
| INA | s_27443, s_27444, s_27445, s_27446 | 4 | 2708, 1296, 502, 10303 | 0.029 | 60 | 0.00224 | 64 |
| SPRED1 | s_53662, s_53663, s_53664 | 3 | 1619, 50436, 448 | 0.029 | 61 | 0.001682 | 49 |
| FAM205A | s_19797, s_19798, s_19799 | 3 | 1158, 41145, 1417 | 0.03 | 62 | 0.001761 | 52 |
| ZNF679 | s_64444, s_64445, s_64446, s_64447 | 4 | 1393, 51433, 53714, 387 | 0.03 | 63 | 0.002404 | 66 |
| RARRES1 | s_46128, s_46129, s_46130, s_46131, s_46132 | 5 | 64493, 49693, 1031, 875, 32486 | 0.03 | 64 | 0.003121 | 86 |
| OXR1 | s_39853, s_39854, s_39855, s_39856, s_39857, s_39858, s_39859, s_39860, s_39861, s_39862, s_39863, s_39864 | 12 | 635, 13208, 3431, 40334, 44056, 34602, 40269, 15654, 27560, 14451, 43620, 75 | 0.031 | 65 | 0.004951 | 111 |
| ABCB5 | s_159, s_160, s_161, s_162, s_163, s_164, s_165, s_166, s_167 | 9 | 22148, 406, 716, 56705, 810, 24993, 32918, 2841, 8584 | 0.031 | 66 | 0.004499 | 103 |
| PCIF1 | s_40717, s_40718, s_40719 | 3 | 9090, 1441, 1264 | 0.031 | 67 | 0.00186 | 54 |
| TSPAN1 | s_59367, s_59368, s_59369, s_59370 | 4 | 2325, 13819, 864, 1297 | 0.031 | 68 | 0.002605 | 71 |
| GEN1 | s_22609, s_22610, s_22611, s_22612 | 4 | 11810, 887, 1299, 8422 | 0.031 | 69 | 0.002637 | 72 |

TABLE G-continued

Output of the RIGER algorithm for the initial A375 PLX screen comparing
PLX (mean of the two replicates at day 14) to DMSO control (mean of the two
replicates at day 14). The weighted sum method was used to convert sgRNAs
to genes. Genes are sorted by RIGER rank.

| Gene | Hairpins | # Hairpins | Hairpin ranks | NES | Gene rank | p-value | p-value rank |
|---|---|---|---|---|---|---|---|
| EIF3D | s_17807, s_17808, s_17809, s_17810 | 4 | 973, 21108, 1274, 24555 | 0.031 | 70 | 0.00265 | 73 |
| CD4 | s_10420, s_10421, s_10422, s_10423 | 4 | 1354, 17639, 21819, 786 | 0.032 | 71 | 0.002719 | 75 |
| RASGEF1C | s_46195, s_46196, s_46197 | 3 | 1741, 57044, 527 | 0.032 | 72 | 0.001958 | 58 |
| RFX4 | s_46955, s_46956, s_46957, s_46958, s_46959, s_46960, s_46961, s_46962 | 8 | 41956, 37657, 844, 23401, 35269, 57099, 19421, 368 | 0.032 | 73 | 0.004515 | 104 |
| EP300 | s_18347, s_18348, s_18349, s_18350 | 4 | 56572, 687, 1414, 17568 | 0.032 | 74 | 0.002802 | 77 |
| MMS19 | s_34268, s_34269, s_34270, s_34271 | 4 | 48047, 59609, 1127, 1271 | 0.032 | 75 | 0.002818 | 78 |
| HEBP1 | s_24995, s_24996, s_24997, s_24998 | 4 | 923, 46506, 1368, 10469 | 0.033 | 76 | 0.002925 | 80 |
| DOK2 | s_16643, s_16644, s_16645 | 3 | 35762, 1884, 306 | 0.033 | 77 | 0.00211 | 60 |
| BRD9 | s_5732, s_5733, s_5734, s_5735, s_5736, s_5737, s_5738 | 7 | 827, 22740, 6866, 12005, 15293, 4165, 858 | 0.033 | 78 | 0.004695 | 109 |
| MAP1LC3A | s_32578, s_32579, s_32580 | 3 | 1401, 28791, 1572 | 0.034 | 79 | 0.002217 | 63 |
| GPR123 | s_23666, s_23667 | 2 | 89, 2438 | 0.034 | 80 | 0.001072 | 35 |
| FH | s_21023, s_21024, s_21025, s_21026, s_21027, s_21028 | 6 | 49396, 14069, 866, 14355, 1035, 36483 | 0.035 | 81 | 0.004382 | 102 |
| NUGGC | s_38328, s_38329, s_38330 | 3 | 49325, 1969, 470 | 0.035 | 82 | 0.002409 | 67 |
| OR52E2 | s_39294, s_39295 | 2 | 1537, 2022 | 0.035 | 83 | 0.001141 | 36 |
| CRNN | s_13692, s_13693, s_13694, s_13695, s_13696, s_13697 | 6 | 21178, 62333, 62987, 230, 62464, 1287 | 0.036 | 84 | 0.004655 | 107 |
| HDAC6 | s_24909, s_24910, s_24911, s_24912 | 4 | 1432, 1157, 37523, 5836 | 0.036 | 85 | 0.003451 | 88 |
| AHCYL2 | s_1615, s_1616, s_1617, s_1618, | 6 | 1275, 536, 15539, 41104, 16156, | 0.038 | 86 | 0.005333 | 117 |

TABLE G-continued

Output of the RIGER algorithm for the initial A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| ZC3H18 | s_1619, s_1620 s_62742, s_62743, s_62744 | 3 | 7154 885, 2013, 4091 | 0.038 | 87 | 0.002841 | 79 |
| RGS2 | s_47074, s_47075, s_47076, s_47077, s_47078 | 5 | 1366, 43591, 49134, 34175, 951 | 0.038 | 88 | 0.005052 | 113 |
| TMED3 | s_57021, s_57022, s_57023 | 3 | 2154, 20038, 590 | 0.039 | 89 | 0.00293 | 81 |
| TXNIP | s_59960, s_59961, s_59962, s_59963, s_59964 | 5 | 62111, 1181, 48123, 1335, 37778 | 0.039 | 90 | 0.005299 | 116 |
| MLN | s_34131, s_34132, s_34133 | 3 | 1893, 4200, 1493 | 0.04 | 91 | 0.003008 | 83 |
| CLEC2B | s_12245, s_12246, s_12247 | 3 | 52935, 1491, 1898 | 0.04 | 92 | 0.003019 | 84 |
| CASQ2 | s_9253, s_9254, s_9255 | 3 | 2052, 1075, 53344 | 0.04 | 93 | 0.003063 | 85 |
| GMDS | s_23142, s_23143, s_23144, s_23145, s_23146, s_23147 | 6 | 27864, 18095, 53905, 1284, 13005, 944 | 0.042 | 94 | 0.006445 | 141 |
| UBE2M | s_60195, s_60196 | 2 | 1767, 2418 | 0.042 | 95 | 0.001626 | 46 |
| RNF7 | s_47784, s_47785, s_47786, s_47787, s_47788 | 5 | 1179, 21752, 1461, 1846, 56079 | 0.042 | 96 | 0.006005 | 129 |
| CRYGN | s_13791, s_13792, s_13793 | 3 | 818, 2294, 7260 | 0.042 | 97 | 0.003478 | 89 |
| NDUFA8 | s_36466, s_36467, s_36468 | 3 | 8398, 636, 2393 | 0.043 | 98 | 0.003571 | 90 |
| NCL | s_36291, s_36292, s_36293, s_36294, s_36295 | 5 | 13572, 1122, 9807, 8470, 1525 | 0.043 | 99 | 0.006281 | 133 |
| PLK4 | s_42605, s_42606, s_42607, s_42608, s_42609 | 5 | 11718, 1841, 10567, 191, 16298 | 0.043 | 100 | 0.006321 | 134 |

TABLE H

Output of the RIGER algorithm for the transduction replicate A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| MED12 | s_33340, s_33341, | 4 | 20, 18, 23, 36 | 0.00051 | 1 | 0.000002 | 1 |

TABLE H-continued

Output of the RIGER algorithm for the transduction replicate A375 PLX
screen comparing PLX (mean of the two replicates at day 14) to DMSO control (mean of the two
replicates at day 14). The weighted sum method was used to convert sgRNAs to genes. Genes
are sorted by RIGER rank.

| Gene | Hairpins | # Hairpins | Hairpin ranks | NES | Gene rank | p-value | p-value rank |
|---|---|---|---|---|---|---|---|
| CUL3 | s_33342, s_33343, s_14311, s_14312, s_14313, s_14314, s_14315, s_14316 | 6 | 59797, 26, 17, 29, 18391, 13751 | 0.0008262 | 2 | 0.000002 | 2 |
| NF2 | s_36796, s_36797, s_36798, s_36799 | 4 | 71, 295, 67, 42 | 0.001589 | 3 | 0.000005 | 3 |
| TADA1 | s_55204, s_55205, s_55206, s_55207 | 4 | 28, 85, 2999, 379 | 0.00185 | 4 | 0.000007 | 4 |
| TADA2B | s_55211, s_55212, s_55213 | 3 | 101, 107, 83 | 0.00213 | 5 | 0.00001 | 5 |
| RBL1 | s_46360, s_46361, s_46362 | 3 | 386, 94, 245 | 0.004575 | 6 | 0.000041 | 6 |
| TAF6L | s_55283, s_55284, s_55285 | 3 | 2738, 129, 361 | 0.006689 | 7 | 0.000085 | 8 |
| OR8S1 | s_39543, s_39544, s_39545, s_39546 | 4 | 255, 21226, 25406, 325 | 0.008042 | 8 | 0.000157 | 10 |
| MED23 | s_33386, s_33387 | 2 | 376, 535 | 0.009179 | 9 | 0.000081 | 7 |
| SLC41A3 | s_51930, s_51931, s_51932, s_51933 | 4 | 134, 50489, 441, 60192 | 0.009526 | 10 | 0.000244 | 14 |
| CCDC101 | s_9430, s_9431, s_9432 | 3 | 742, 511, 283 | 0.01002 | 11 | 0.000201 | 11 |
| LCOR | s_30684, s_30685, s_30686, s_30687 | 4 | 362, 44569, 4583, 418 | 0.01057 | 12 | 0.00031 | 17 |
| GPR98 | s_23900, s_23901, s_23902 | 3 | 392, 518, 48952 | 0.01074 | 13 | 0.000239 | 13 |
| KCNA2 | s_28512, s_28513, s_28514, s_28515, s_28516, s_28517, s_28518, s_28519 | 8 | 29441, 30891, 63671, 3716, 48582, 37548, 297, 194 | 0.01187 | 14 | 0.000666 | 27 |
| MED15 | s_33355, s_33356, s_33357, s_33358 | 4 | 227, 552, 711, 647 | 0.01231 | 15 | 0.000416 | 18 |
| MT1F | s_35127, s_35128 | 2 | 842, 183 | 0.01255 | 16 | 0.000141 | 9 |
| MYL7 | s_35662, s_35663, s_35664, s_35665 | 4 | 135, 46125, 598, 37747 | 0.01261 | 17 | 0.000445 | 20 |
| SLC7A11 | s_52194, s_52195, s_52196, s_52197, s_52198 | 5 | 16607, 313, 460, 5262, 27650 | 0.01288 | 18 | 0.000554 | 23 |
| MTRF1 | s_35317, s_35318, s_35319 | 3 | 17905, 41, 862 | 0.0145 | 19 | 0.000445 | 19 |

TABLE H-continued

Output of the RIGER algorithm for the transduction replicate A375 PLX
screen comparing PLX (mean of the two replicates at day 14) to DMSO control (mean of the two
replicates at day 14). The weighted sum method was used to convert sgRNAs to genes. Genes
are sorted by RIGER rank.

| Gene | Hairpins | # Hairpins | Hairpin ranks | NES | Gene rank | p-value | p-value rank |
|---|---|---|---|---|---|---|---|
| ELF1 | s_17940, s_17941, s_17942 | 3 | 35910, 873, 35 | 0.01465 | 20 | 0.000454 | 21 |
| METAP1D | s_33547, s_33548, s_33549, s_33550 | 4 | 411, 617, 35187, 34941 | 0.01479 | 21 | 0.000612 | 25 |
| FAM160A2 | s_19507, s_19508, s_19509, s_19510 | 4 | 48131, 49009, 459, 610 | 0.01497 | 22 | 0.000623 | 26 |
| TAF5L | s_55276, s_55277 | 2 | 57, 1089 | 0.0154 | 23 | 0.000207 | 12 |
| NF1 | s_36794, s_36795 | 2 | 1227, 12 | 0.01711 | 24 | 0.000261 | 15 |
| DSEL | s_16908, s_16909 | 2 | 642, 1068 | 0.01782 | 25 | 0.000287 | 16 |
| RAP1GAP2 | s_46063, s_46064, s_46065, s_46066 | 4 | 740, 58091, 49142, 709 | 0.01915 | 26 | 0.000992 | 29 |
| MPG | s_34467, s_34468, s_34469, s_34470, s_34471, s_34472 | 6 | 597, 474, 37985, 7657, 49238, 24732 | 0.0197 | 27 | 0.001548 | 41 |
| MED16 | s_33359, s_33360, s_33361, s_33362 | 4 | 619, 825, 25639, 27832 | 0.02023 | 28 | 0.001103 | 31 |
| XKR4 | s_62252, s_62253, s_62254, s_62255 | 4 | 29846, 897, 14605, 473 | 0.02069 | 29 | 0.001163 | 32 |
| ERP27 | s_18694, s_18695, s_18696, s_18697 | 4 | 57819, 843, 26738, 768 | 0.02156 | 30 | 0.001269 | 35 |
| MAB21L2 | s_32293, s_32294, s_32295 | 3 | 1088, 654, 49187 | 0.02162 | 31 | 0.000938 | 28 |
| ASIC5 | s_3967, s_3968, s_3969, s_3970, s_3971 | 5 | 84, 36168, 2836, 46662, 924 | 0.02172 | 32 | 0.001596 | 42 |
| MSMB | s_35048, s_35049, s_35050, s_35051, s_35052 | 5 | 63246, 51785, 916, 124, 60194 | 0.02184 | 33 | 0.001613 | 43 |
| ZNF182 | s_63394, s_63395, s_63396, s_63397 | 4 | 856, 814, 58286, 44944 | 0.02211 | 34 | 0.001328 | 37 |
| ZNF345 | s_63726, s_63727 | 2 | 1558, 196 | 0.02256 | 35 | 0.000479 | 22 |
| TNFSF18 | s_58159, s_58160, s_58161, s_58162 | 4 | 766, 19361, 905, 33444 | 0.02276 | 36 | 0.00141 | 39 |
| NDUFAF2 | s_36477, s_36478, s_36479 | 3 | 1232, 22725, 494 | 0.02312 | 37 | 0.001063 | 30 |
| PDCD10 | s_40840, s_40841, s_40842, s_40843, s_40844 | 5 | 43, 3962, 1002, 5014, 3313 | 0.02319 | 38 | 0.001844 | 49 |

TABLE H-continued

Output of the RIGER algorithm for the transduction replicate A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| CCNC | s_10026, s_10027, s_10028, s_10029, s_10030 | 5 | 48614, 1596, 868, 1864, 584 | 0.02425 | 39 | 0.002022 | 52 |
| SPRED1 | s_53662, s_53663, s_53664 | 3 | 950, 24805, 1164 | 0.02451 | 40 | 0.001188 | 33 |
| GDPD2 | s_22566, s_22567, s_22568, s_22569, s_22570, s_22571 | 6 | 367, 60779, 819, 52875, 24938, 6538 | 0.02456 | 41 | 0.002293 | 57 |
| DYRK3 | s_17200, s_17201, s_17202, s_17203 | 4 | 9900, 22246, 1101, 455 | 0.02457 | 42 | 0.001629 | 44 |
| MBP | s_33068, s_33069, s_33070, s_33071, s_33072, s_33073, s_33074, s_33075, s_33076 | 9 | 15442, 25428, 529, 29634, 16368, 8819, 36773, 478, 52354 | 0.02489 | 43 | 0.002965 | 71 |
| PARP3 | s_40316, s_40317, s_40318 | 3 | 506, 1352, 59418 | 0.02518 | 44 | 0.001243 | 34 |
| UBE2M | s_60195, s_60196 | 2 | 491, 1665 | 0.02542 | 45 | 0.000595 | 24 |
| HDGF | s_24936, s_24937, s_24938 | 3 | 756, 1285, 5163 | 0.02545 | 46 | 0.00127 | 36 |
| KCNC2 | s_28558, s_28559, s_28560, s_28561, s_28562, s_28563, s_28564 | 7 | 42492, 6191, 648, 54771, 50213, 652, 22159 | 0.02554 | 47 | 0.002731 | 66 |
| GALNS | s_22109, s_22110, s_22111, s_22112 | 4 | 999, 8504, 52589, 986 | 0.02604 | 48 | 0.00184 | 47 |
| METTL21B | s_33609, s_33610, s_33611, s_33612 | 4 | 46303, 472, 1171, 29308 | 0.02605 | 49 | 0.001842 | 48 |
| BTBD17 | s_5890, s_5891, s_5892 | 3 | 1185, 64382, 1200 | 0.02641 | 50 | 0.001371 | 38 |
| HSD11B1 | s_26144, s_26145, s_26146, s_26147, s_26148 | 5 | 1048, 391, 7446, 21804, 42773 | 0.02689 | 51 | 0.002482 | 61 |
| LGR5 | s_30925, s_30926, s_30927, s_30928 | 4 | 1394, 241, 38237, 49566 | 0.02892 | 52 | 0.002269 | 56 |
| BUB1B | s_5999, s_6000, s_6001, s_6002 | 4 | 30283, 1179, 47822, 935 | 0.02924 | 53 | 0.0023 | 58 |
| MRFAP1L1 | s_34603, s_34604, s_34605 | 3 | 18516, 421, 1627 | 0.02926 | 54 | 0.00168 | 45 |

TABLE H-continued

Output of the RIGER algorithm for the transduction replicate A375 PLX
screen comparing PLX (mean of the two replicates at day 14) to DMSO control (mean of the two
replicates at day 14). The weighted sum method was used to convert sgRNAs to genes. Genes
are sorted by RIGER rank.

| Gene | Hairpins | # Hairpins | Hairpin ranks | NES | Gene rank | p-value | p-value rank |
|---|---|---|---|---|---|---|---|
| CCDC83 | s_9835, s_9836, s_9837, s_9838 | 4 | 1148, 21192, 1041, 54459 | 0.02932 | 55 | 0.002316 | 59 |
| DRAP1 | s_16840, s_16841, s_16842, s_16843 | 4 | 33445, 508, 1328, 44015 | 0.02937 | 56 | 0.002321 | 60 |
| RELT | s_46777, s_46778, s_46779 | 3 | 187, 61852, 1740 | 0.02984 | 57 | 0.001756 | 46 |
| RANBP9 | s_46039, s_46040, s_46041 | 3 | 1837, 11418, 52 | 0.0307 | 58 | 0.001849 | 50 |
| HMMR | s_25651, s_25652, s_25653, s_25654 | 4 | 1502, 48474, 27570, 234 | 0.03099 | 59 | 0.002589 | 64 |
| MALSU1 | s_32462, s_32463, s_32464 | 3 | 1575, 5215, 920 | 0.03115 | 60 | 0.001886 | 51 |
| TACC1 | s_55171, s_55172, s_55173, s_55174, s_55175, s_55176 | 6 | 4921, 24086, 6177, 328, 10098, 1110 | 0.03181 | 61 | 0.003733 | 94 |
| HOXC13 | s_25901, s_25902, s_25903, s_25904 | 4 | 9058, 894, 1336, 22970 | 0.03205 | 62 | 0.00277 | 67 |
| EAPP | s_17273, s_17274, s_17275, s_17276 | 4 | 1388, 21167, 820, 26512 | 0.03259 | 63 | 0.002875 | 68 |
| C1QA | s_6997, s_6998, s_6999, s_7000, s_7001, s_7002 | 6 | 26254, 946, 914, 57738, 2934, 961 | 0.03263 | 64 | 0.003918 | 99 |
| SELRC1 | s_49728, s_49729, s_49730 | 3 | 1215, 6860, 1574 | 0.03276 | 65 | 0.00209 | 53 |
| B3GALNT2 | s_4738, s_4739, s_4740, s_4741, s_4742, s_4743 | 6 | 827, 29762, 38965, 31290, 23785, 981 | 0.03279 | 66 | 0.003962 | 101 |
| RBM15B | s_46395, s_46396, s_46397 | 3 | 893, 1695, 44505 | 0.03299 | 67 | 0.002127 | 54 |
| PDE12 | s_40901, s_40902, s_40903, s_40904, s_40905, s_40906 | 6 | 2381, 1262, 58589, 2108, 38, 10016 | 0.03326 | 68 | 0.004098 | 104 |
| PAFAH2 | s_40041, s_40042, s_40043, s_40044, s_40045, s_40046 | 6 | 5602, 61209, 1155, 63735, 375, 37029 | 0.03339 | 69 | 0.004132 | 106 |
| LAMA5 | s_30412, s_30413, s_30414, s_30415, s_30416, s_30417, | 8 | 9450, 1177, 17134, 27544, 874, 456, 38308, 45063 | 0.03369 | 70 | 0.005071 | 132 |

TABLE H-continued

Output of the RIGER algorithm for the transduction replicate A375 PLX
screen comparing PLX (mean of the two replicates at day 14) to DMSO control (mean of the two
replicates at day 14). The weighted sum method was used to convert sgRNAs to genes. Genes
are sorted by RIGER rank.

| Gene | Hairpins | # Hairpins | Hairpin ranks | NES | Gene rank | p-value | p-value rank |
|---|---|---|---|---|---|---|---|
| TDRD5 | s_30418, s_30419, s_55980, s_55981, s_55982, s_55983, s_55984, s_55985 | 6 | 1131, 41843, 44717, 513, 54260, 50377 | 0.03397 | 71 | 0.004252 | 108 |
| MBNL2 | s_33046, s_33047, s_33048, s_33049 | 4 | 60513, 1365, 1158, 40330 | 0.03435 | 72 | 0.003193 | 76 |
| ADI1 | s_1254, s_1255, s_1256, s_1257, s_1258, s_1259 | 6 | 1267, 209, 12112, 3449, 25692, 52308 | 0.03487 | 73 | 0.004464 | 111 |
| MED19 | s_33371, s_33372, s_33373, s_33374 | 4 | 306, 12467, 2378, 1694 | 0.03523 | 74 | 0.003361 | 81 |
| PRKRA | s_44162, s_44163, s_44164, s_44165, s_44166 | 5 | 47085, 863, 19810, 1257, 23209 | 0.03524 | 75 | 0.004253 | 109 |
| ATP1B4 | s_4304, s_4305, s_4306, s_4307 | 4 | 1486, 31149, 944, 43483 | 0.03532 | 76 | 0.003379 | 83 |
| PRR7 | s_44424, s_44425, s_44426, s_44427 | 4 | 904, 38806, 59763, 1506 | 0.03545 | 77 | 0.003414 | 84 |
| GBP2 | s_22365, s_22366, s_22367, s_22368, s_22369, s_22370 | 6 | 1003, 60810, 58109, 1029, 43443, 48442 | 0.03557 | 78 | 0.004654 | 116 |
| KCTD15 | s_28890, s_28891, s_28892, s_28893 | 4 | 23114, 8725, 1747, 290 | 0.03616 | 79 | 0.003546 | 87 |
| MAPKAPK3 | s_32778, s_32779, s_32780, s_32781 | 4 | 1795, 169, 21907, 29592 | 0.03631 | 80 | 0.003576 | 89 |
| MRPS12 | s_34814, s_34815, s_34816 | 3 | 1726, 1417, 15155 | 0.0364 | 81 | 0.002585 | 63 |
| TNR | s_58261, s_58262, s_58263, s_58264, s_58265, s_58266 | 6 | 1368, 52097, 29987, 60673, 37039, 106 | 0.03661 | 82 | 0.004941 | 127 |
| PET117 | s_41313, s_41314, s_41315 | 3 | 1789, 1416, 1742 | 0.03666 | 83 | 0.002611 | 65 |
| SRM | s_53860, s_53861, s_53862, s_53863, s_53864 | 5 | 1466, 5441, 2247, 3169, 430 | 0.03672 | 84 | 0.004589 | 114 |
| INO80E | s_27530, s_27531, s_27532, s_27533 | 4 | 46304, 1464, 1278, 16053 | 0.03707 | 85 | 0.003727 | 93 |

TABLE H-continued

Output of the RIGER algorithm for the transduction replicate A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| ZSWIM6 | s_64963, s_64964, s_64965, s_64966 | 4 | 25840, 1465, 19204, 1294 | 0.0372 | 86 | 0.003755 | 95 |
| SLC4A3 | s_52020, s_52021, s_52022, s_52023, s_52024, s_52025 | 6 | 29005, 52591, 64538, 39136, 1319, 334 | 0.03732 | 87 | 0.005147 | 134 |
| CDKL4 | s_10939, s_10940, s_10941, s_10942 | 4 | 63413, 1274, 36650, 1510 | 0.03795 | 88 | 0.003903 | 98 |
| EED | s_17448, s_17449, s_17450, s_17451 | 4 | 1999, 352, 1852, 22596 | 0.03863 | 89 | 0.004041 | 103 |
| MRPL17 | s_34661, s_34662, s_34663 | 3 | 2009, 1162, 1959 | 0.03885 | 90 | 0.002918 | 69 |
| ANGEL2 | s_2338, s_2339, s_2340, s_2341, s_2342 | 5 | 28245, 840, 1423, 56505, 62188 | 0.03886 | 91 | 0.005154 | 135 |
| PLK1 | s_42592, s_42593, s_42594, s_42595 | 4 | 18870, 1327, 15990, 1544 | 0.03896 | 92 | 0.00412 | 105 |
| CARS2 | s_9155, s_9156, s_9157 | 3 | 1198, 1989, 11196 | 0.03954 | 93 | 0.003005 | 72 |
| PODN | s_42919, s_42920, s_42921, s_42922, s_42923, s_42924 | 6 | 49093, 58125, 330, 36756, 41658, 1412 | 0.03971 | 94 | 0.005858 | 150 |
| AMPD2 | s_2260, s_2261, s_2262, s_2263, s_2264, s_2265 | 6 | 672, 1977, 27046, 41151, 34556, 1308 | 0.03997 | 95 | 0.005936 | 151 |
| TRIM67 | s_59007, s_59008 | 2 | 2416, 1455 | 0.04032 | 96 | 0.001521 | 40 |
| ACOX1 | s_673, s_674, s_675 | 3 | 618, 2238, 44076 | 0.04046 | 97 | 0.003153 | 74 |
| PRPF4B | s_44329, s_44330, s_44331 | 3 | 17853, 1143, 2063 | 0.04046 | 98 | 0.003153 | 75 |
| TCEB2 | s_55778, s_55779, s_55780, s_55781 | 4 | 3561, 1732, 1896, 1034 | 0.04073 | 99 | 0.004475 | 112 |
| VAX1 | s_61156, s_61157, s_61158, s_61159, s_61160 | 5 | 61659, 1770, 53, 22962, 60237 | 0.04079 | 100 | 0.005648 | 147 |

Figure 28A:
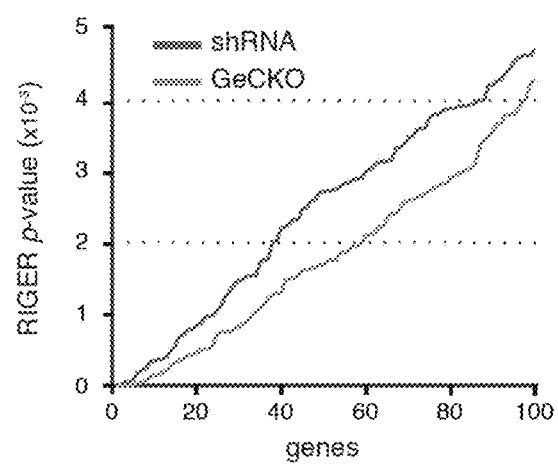
FIG. 28A-28E shows Comparison of GeCKO and shRNA screens and validation of neurofibromin 2 (NF2). (A) RIGER p values for the top 100 hits from GeCKO and shRNA screens for genes whose loss results in PLX resistance. Analysis using the Redundant siRNA Activity (RSA) algorithm shows a similar trend (fig. S9). (B) For the top 10 RIGER hits, the percent of unique sgRNAs (top) or shRNAs (bottom) targeting each gene that are in top 5% of all enriched sgRNAs or shRNAs. (C) Deep sequencing analysis of lentiCRISPR-mediated indel at the NF2 locus. (D) A375 cells transduced with NF2-targeting lentiCRISPR and shRNA vectors both show a decrease in NF2 protein levels. (E) Dose response curves for A375 cells transduced with individual NF2-targeting lentiCRISPR or shRNA vectors. Controls were EGFP-targeting lentiCRISPR or null hairpin shRNA vectors. Cells transduced with NF2-targeting lentiCRISPRs show a significant increase ($F_{1,8}$=30.3, p<0.001, n=4 replicates) in the half maximal effective concentration ($EC_{50}$) whereas cells transduced with NF2-targeting shRNA vectors do not ($F_{1,8}$=0.47, p=0.51, n=4 replicates).
Figure 28B:
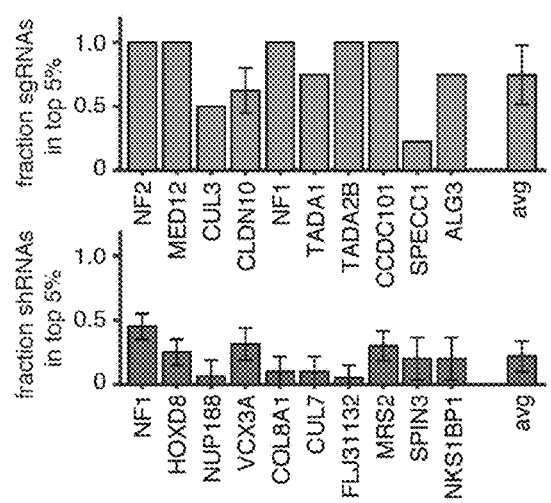
Figure 37:
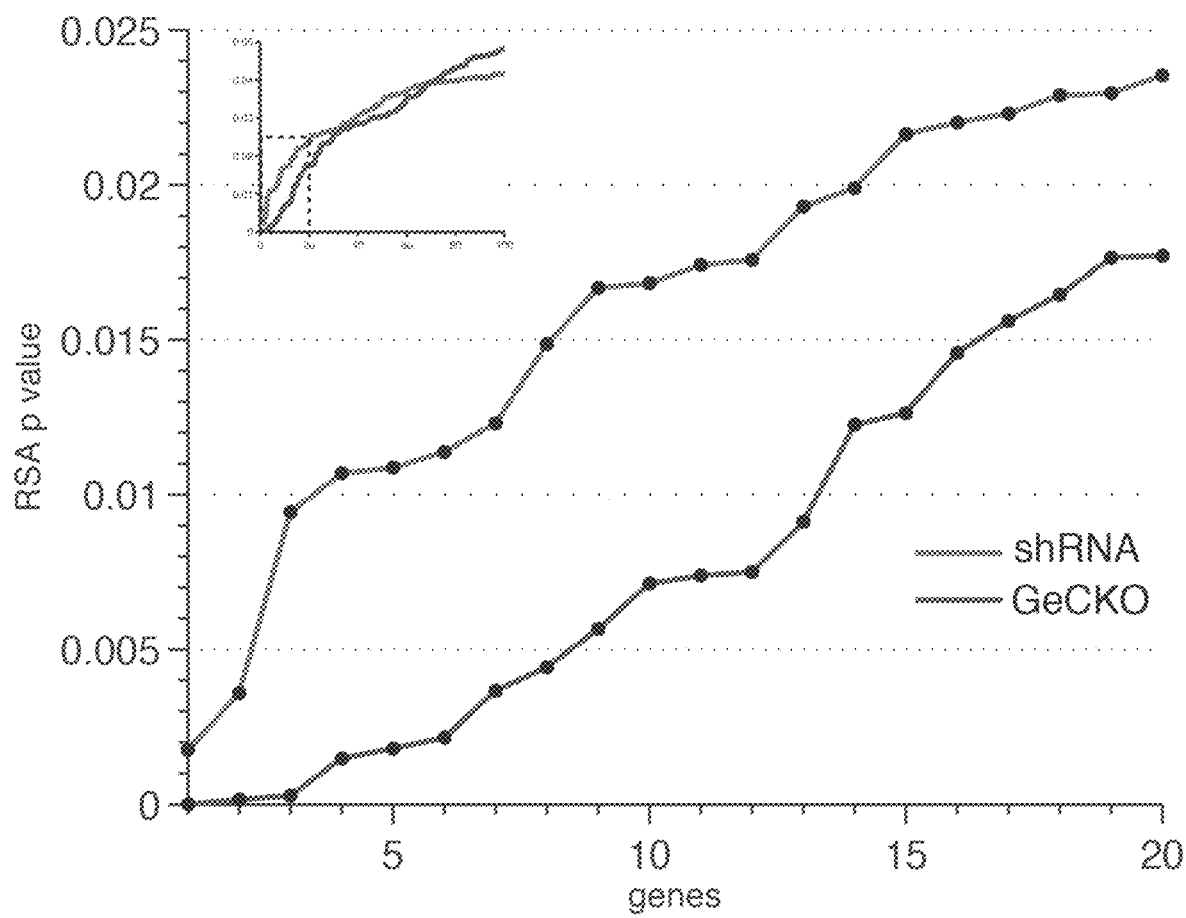
FIG. 37 shows Cumulative p value distribution for the top hits as determined by the Redundant siRNA Activity (RSA) algorithm. Lower p values signify a higher consistency of distinct reagents targeting the same genes. RSA calculates the significance of reagents concentrated near the top or bottom of an enrichment list through an iterative hypergeometric test
Figure 38A:
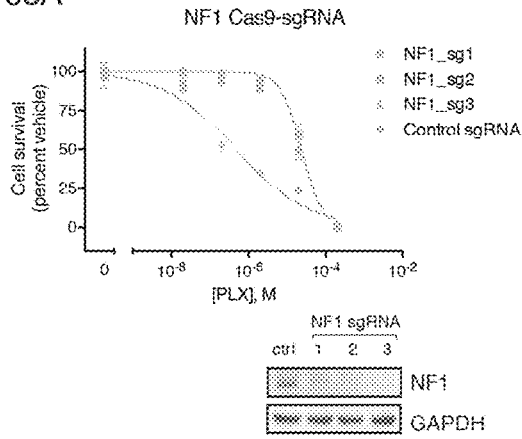
FIG. 38A-38F shows Array validation and comparison of the three highest-ranking genes using both CRISPR and shRNAs. Each panel shows cell survival data at different PLX doses as determined by CellTiter-Glo and protein quantification using western analysis. The gray line shows the mean of 2 control sgRNAs (targeting EGFP) or 2 control shRNAs (pLKO-nullT control vectors) and the colored line (blue for Cas9-sgRNAs, pink for shRNAs) shows the mean of all targeting reagents for the gene. n=4 replicates for dose response data. Shift in the dose response curve to the right of the control curve indicates greater resistance to PLX in the perturbed cell lines. (A), (B) Cas9-sgRNA and shRNA reagents respectively targeting NFL (C), (D) Cas9-sgRNA and shRNA reagents respectively targeting MED12. (E), (F) Cas9-sgRNA and shRNA reagents respectively targeting TADA2B gene.
Figure 38B:
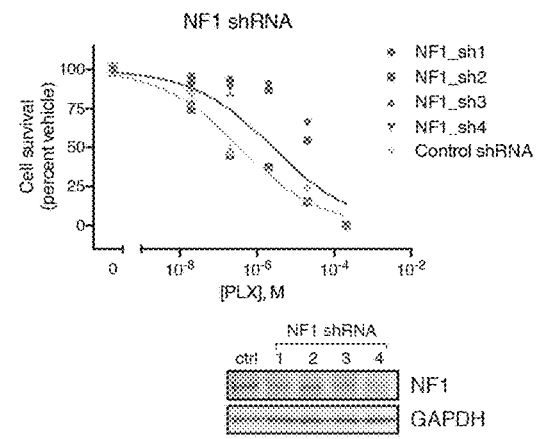
Figure 38C:
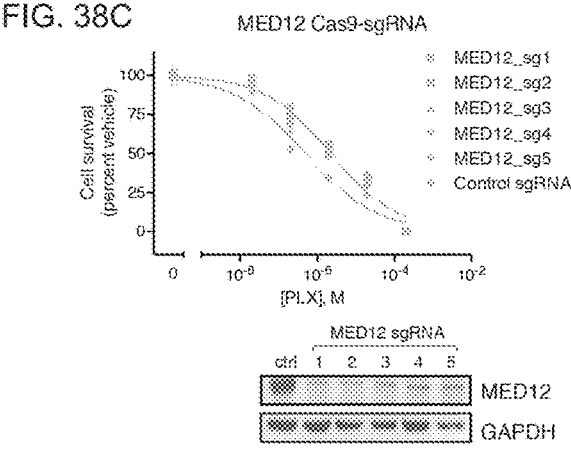
Figure 38D:
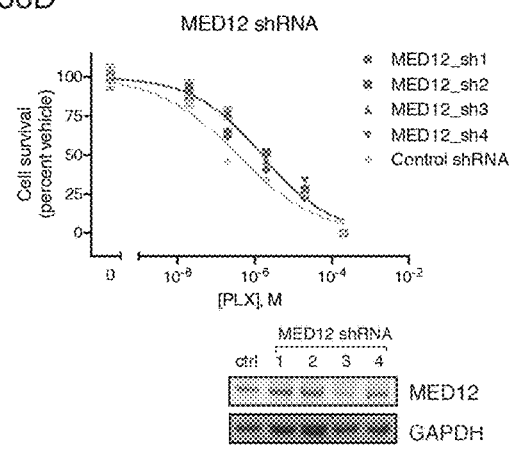
Figure 38E:
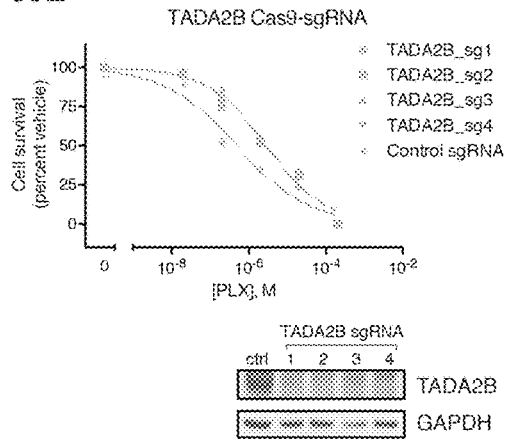
Figure 38F:
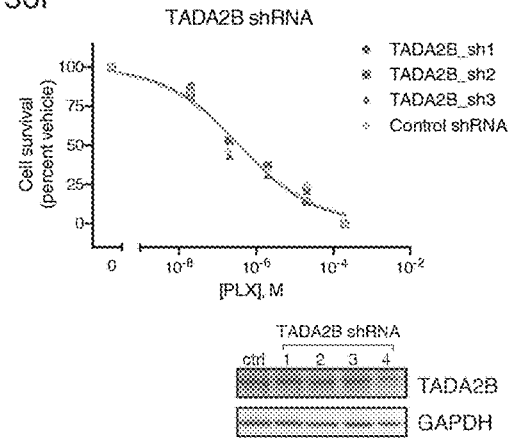

A similar screen to identify PLX drug resistance in A375 cells was previously conducted using a pooled library of 90,000 shRNAs. To compare the efficacy and reliability of genome-scale shRNA screen with GeCKO, Applicants used several methods to evaluate the degree of consistency among the multiple sgRNAs or shRNAs for the top candidate genes. First, Applicants calculated the aggregate p value distribution for the top 100 hits using either RIGER (FIG. 28A) or RSA (FIG. 37) scoring. Lower p values for the GeCKO versus shRNA screen indicate better scoring consistency among sgRNAs. Second, for the top 10 RIGER hits, 78±27% of the sgRNAs targeting each gene ranked among the top 5% of enriched sgRNAs, whereas 20±12% of shRNAs targeting each gene ranked among the top 5% of enriched shRNAs (FIG. 28B).

Figure 28C:
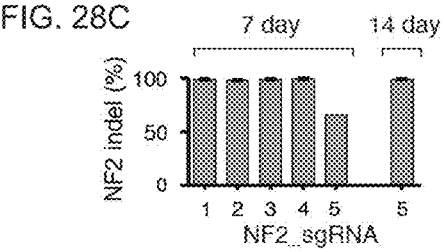
Figure 28D:
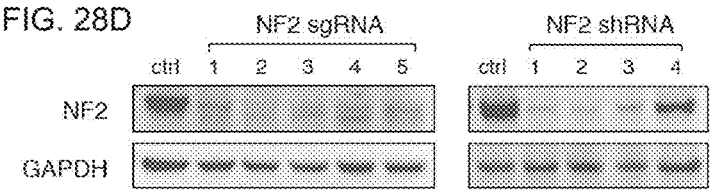
Figure 28E:
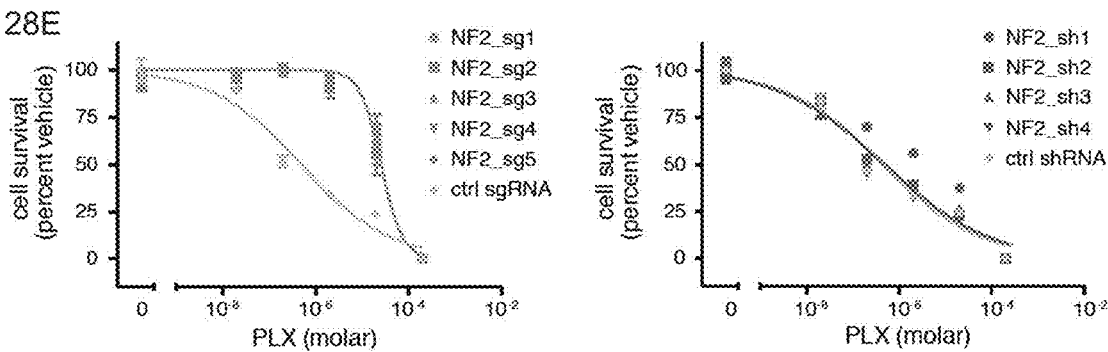
Figure 39A:
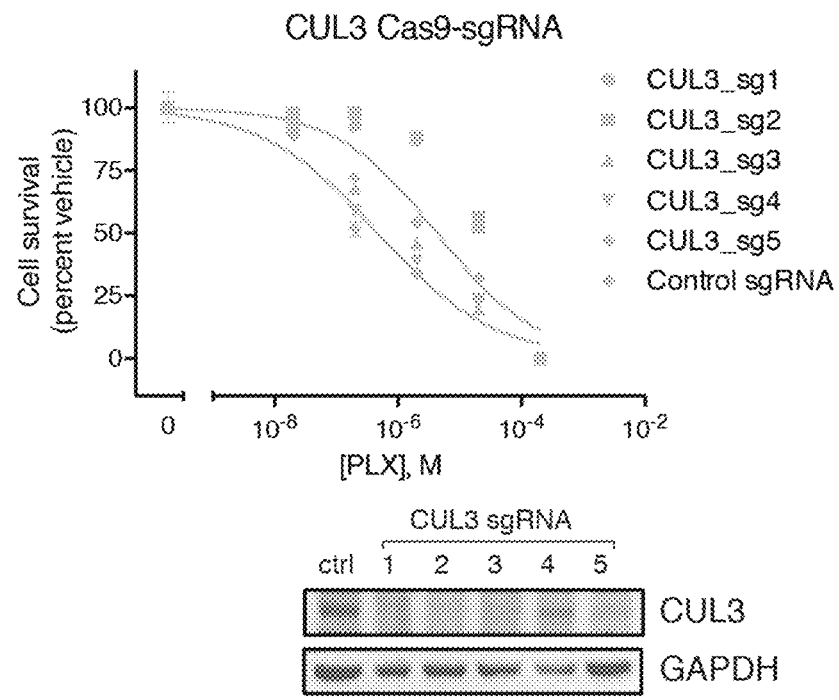
FIG. 39A-39B shows Array validation of the two additional high-ranking genes. Each panel shows cell survival data at different PLX doses as determined by CellTiter-Glo and protein quantification using western analysis. The gray line shows the mean of 2 control sgRNAs that target EGFP and the blue line shows the mean of Cas9-sgRNAs targeted to the gene. Shift in the dose response curve displays the reduced sensitivity to PLX in the perturbed cell lines. (A) Cas9-sgRNAs targeting CUL3. (B) Cas9-sgRNAs targeting TADA1. Western analysis was not performed for TADA1 since neither of the two antibodies attempted yielded a band of the correct molecular weight.
Figure 39B:
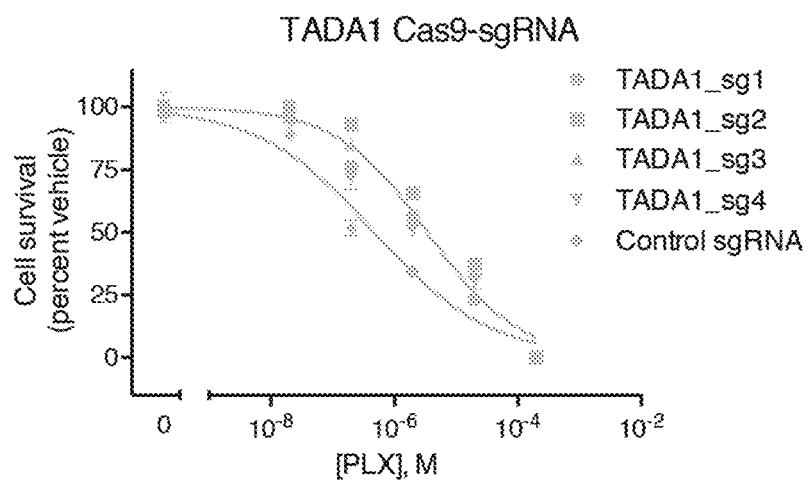
Figure 40:
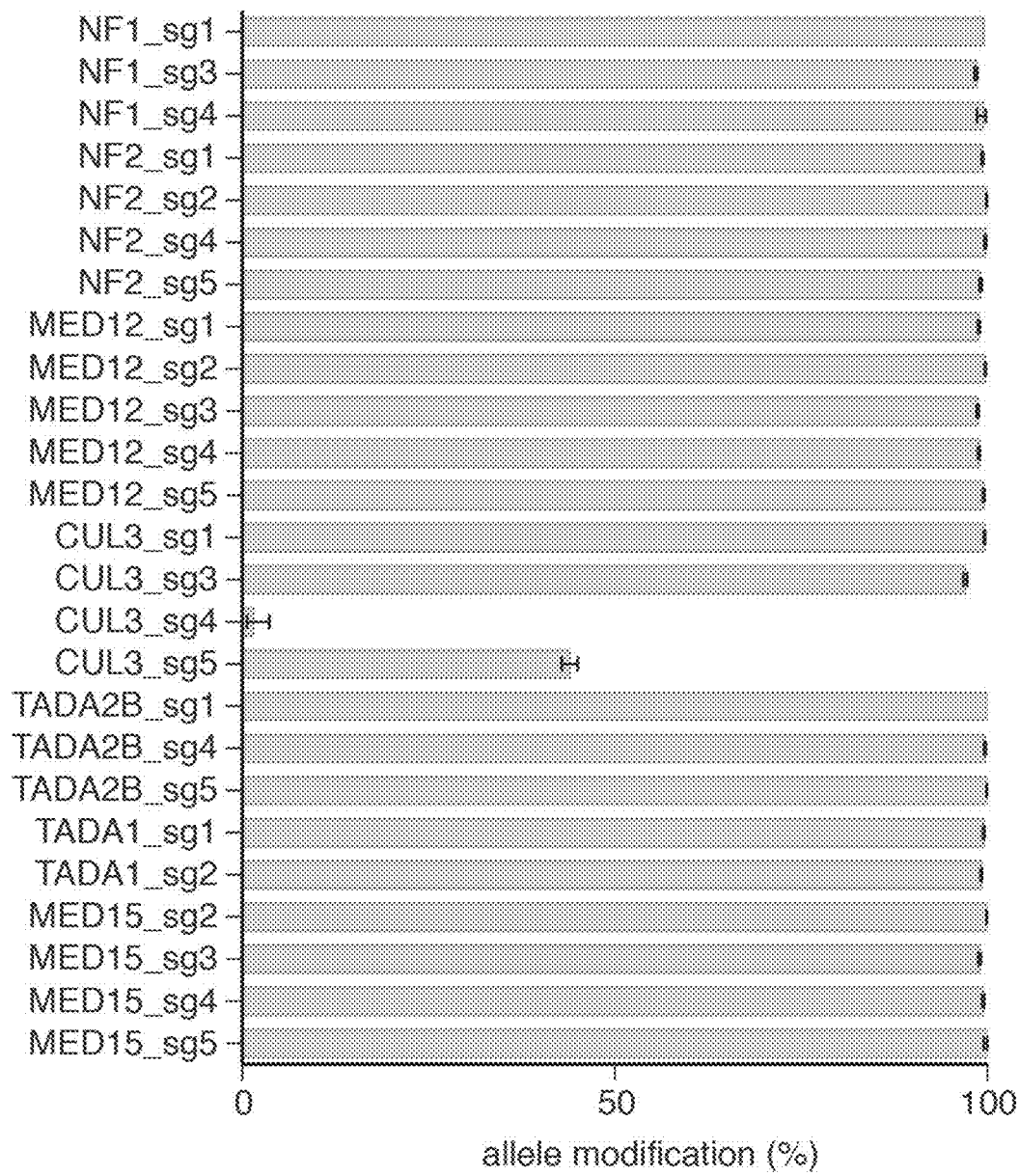
FIG. 40 shows Measurements of allele modification frequencies in 25 sgRNAs targeting the seven highest-ranking genes in the A375 GeCKO screen. Bar plot shows the percentage of modified alleles determined by PCR followed by deep sequencing. Error bars representing Wilson intervals.
Figure 41:
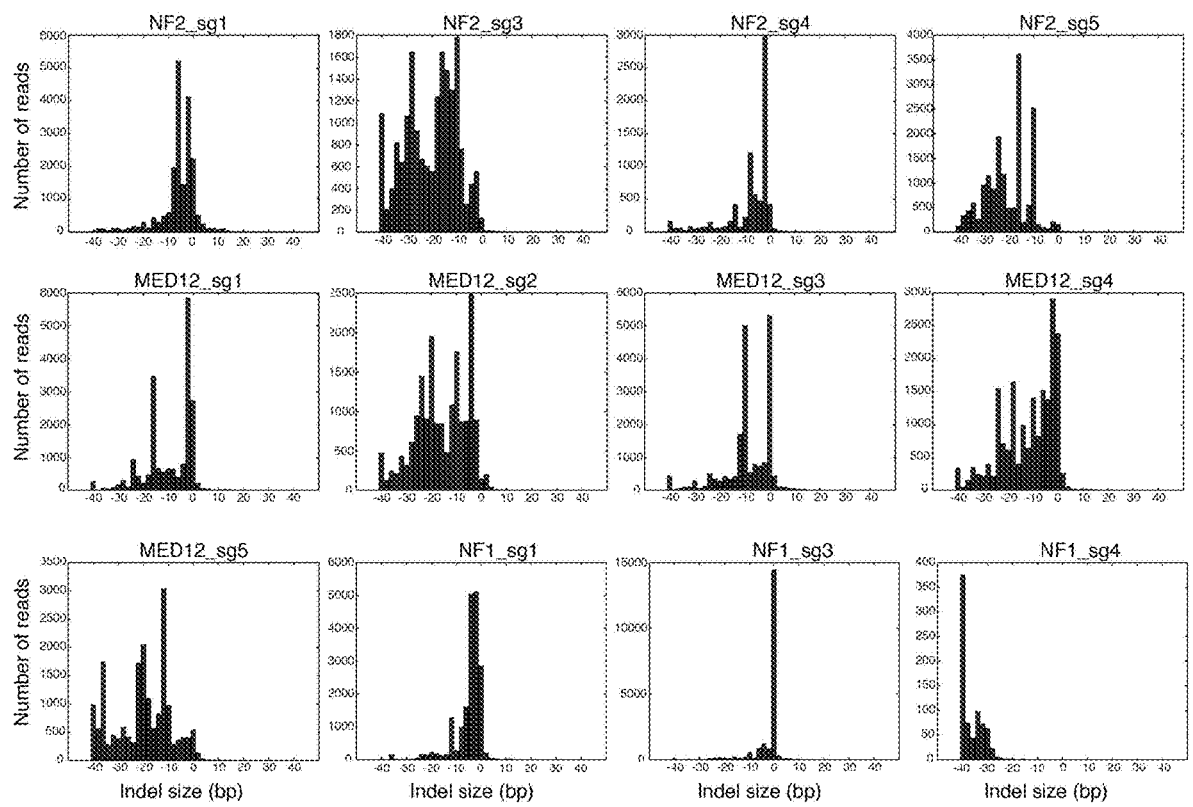
FIG. 41 shows Histograms of on-target indel sizes for NF2, MED12, and NF1. Each subpanel shows the distribution of indel sizes for a single sgRNA at its intended genomic target locus. Each locus is PCR amplified and deep sequenced. Negative values indicate deletions and positive values indicate insertions.
Figure 42:
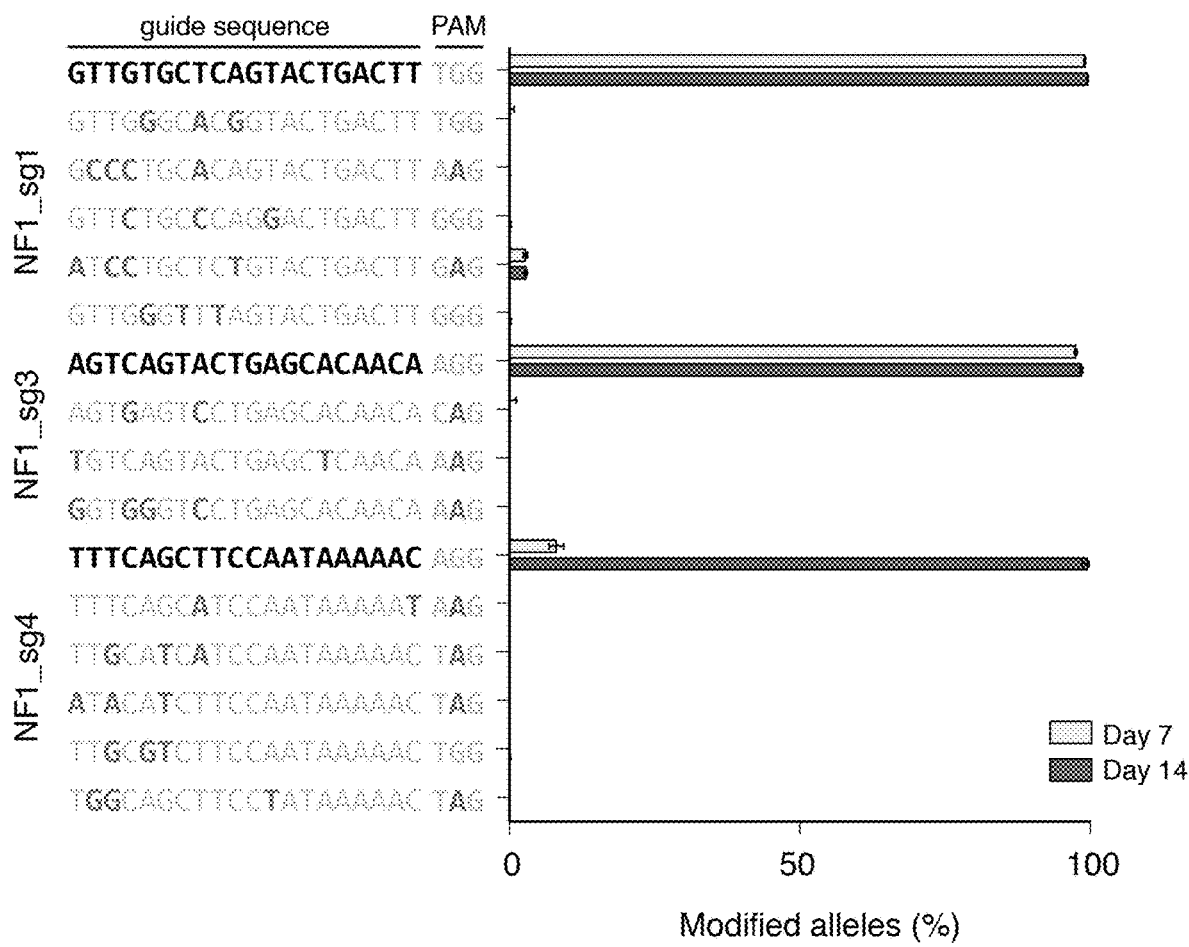
FIG. 42 shows Measurements of on and off target allele modification frequencies for three sgRNAs targeting NF1 Each row represents a genomic locus consisting of a 20 bp sgRNA site (in black or gray letters) followed by a 3 bp PAM sequence (in light blue letters). Sequences in bold black letters indicate the genomic sequences that the GeCKO library sgRNAs were designed to target. Below each bold line are 3 to 5 predicted potential off target genomic sequences identified using the CRISPR design tool (available at the website tools.genome-engineering.org). Red nucleotides highlight the differences in these off target sequences from the on target site. Each locus (on and off target) was PCR amplified and then deep sequenced. Bars show the percentage of modified alleles 7 and 14 days post transduction with error bars representing Wilson intervals.
Figure 43:
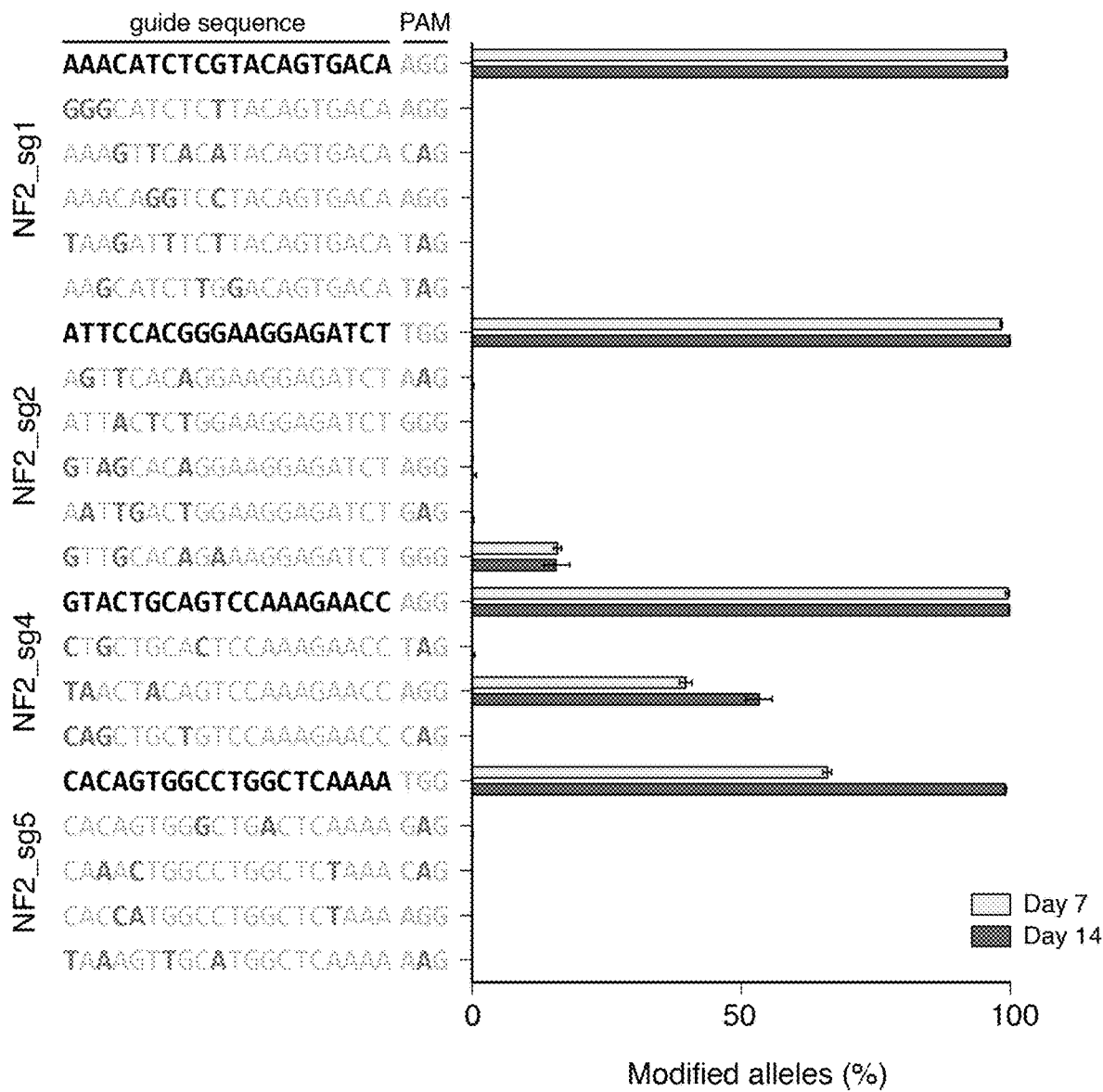
FIG. 43 shows Measurements of on and off target allele modification frequencies for three sgRNAs targeting NF2. Each row represents a genomic locus consisting of a 20 bp sgRNA site (in black or gray letters) followed by a 3 bp PAM sequence (in light blue letters). Sequences in bold black letters indicate the genomic sequences that the GeCKO library sgRNAs were designed to target. Below each bold line are 3 to 5 predicted potential off target genomic sequences identified using the CRISPR design tool (available at the website tools.genome-engineering.org). Red nucleotides highlight the differences in these off target sequences from the on target site. Each locus (on and off target) was PCR amplified and then deep sequenced. Bars show the percentage of modified alleles 7 and 14 days post transduction with error bars representing Wilson intervals.
Figure 44:
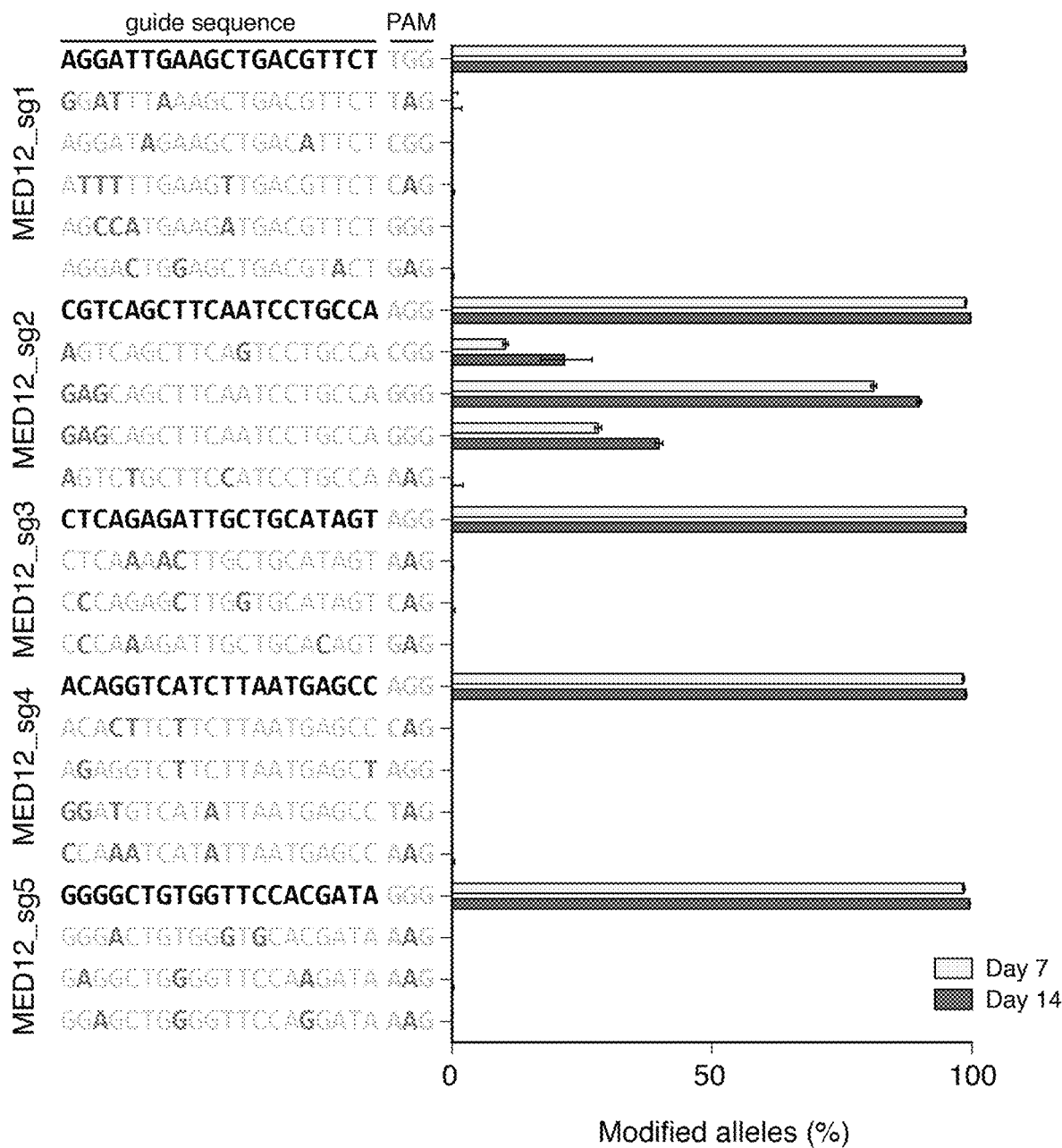
FIG. 44 shows Measurements of on and off target allele modification frequencies for three sgRNAs targeting MED12. Each row represents a genomic locus consisting of a 20 bp sgRNA site (in black or gray letters) followed by a 3 bp PAM sequence (in light blue letters). Sequences in bold black letters indicate the genomic sequences that the GeCKO library sgRNAs were designed to target. Below each bold line are 3 to 5 predicted potential off target genomic sequences identified using the CRISPR design tool (available at the website tools.genome-engineering.org). Red nucleotides highlight the differences in these off target sequences from the on target site. Each locus (on and off target) was PCR amplified and then deep sequenced. Bars show the percentage of modified alleles 7 and 14 days post transduction with error bars representing Wilson intervals.

Applicants validated top ranking genes from the GeCKO screen individually using 3-5 sgRNAs (FIGS. 28C-E, 38, 39). For NF2, Applicants found that 4/5 sgRNAs resulted in >98% allele modification 7 days post-transduction, and all 5 sgRNAs showed >99% allele modification 14 days post-transduction (FIG. 28C). Applicants compared sgRNA and shRNA-mediated protein depletion and PLX resistance using Western blot (FIG. 28D) and cell growth assays (FIG. 28E). Interestingly, while all five sgRNAs conferred resistance to PLX, only the best shRNA achieved sufficient knockdown to increase PLX resistance (FIG. 28E), suggesting that even low levels of NF2 are sufficient to retain sensitivity to PLX. Additionally, sgRNAs targeting NF1, MED12, CUL3, TADA1, and TADA2B led to a decrease in protein expression and increased resistance to PLX (FIGS. 38, 39). Deep sequencing confirmed a high rate of mutagenesis at targeted loci (FIGS. 40, 41), with a small subset of off-target sites exhibiting indels (FIGS. 42-44), which may be alleviated using an offset nicking approach that was shown to reduce off-target modifications.

GeCKO screening provides a complementary method to RNAi for systematic perturbation of gene function through generation of loss of function alleles. This can be useful in cases where incomplete knockdown retains gene function. The ability to achieve targeted genome modifications on a large scale using custom Cas9:sgRNA libraries presents unique opportunities to probe a broad range of coding and non-coding genomic elements.

GeCKO screening is carried out in three steps: Step 1—Library Design. Constitutive exons near the 5' end of transcripts are identified using Illumina Human BodyMap 2.0 and NCBI CCDS datasets. sgRNAs were ranked by an off-target score using a metric that includes the number of off-targets in the genome and the type of mutations (distance from protospacer-adjacent motif and clustering of mismatches) and those with lowest off-target scores were selected. This resulted in a library in which most genes have an average of 3 or 4 sgRNAs. Step 2—Viral vector generation. The sgRNA library was synthesized using array synthesis and cloned as a pool into the lentiCRISPR transfer plasmid for virus production. Viral vectors were produced in HEK293T cells and concentrated to increase viral titer. Cells of interest were infected at a low MOI (0.3) to ensure that most cells receive only 1 viral construct with high probability. Step 3—Readout. 24 hours after transduction, cells were selected with puromycin so that only cells transduced with a lentiCRISPR construct are preserved. At this point the cells can be used to carry out either positive or negative selection screens.

Screening timeline considerations: After infection, cells are selected with puromycin. For most cell types, 0.5-2 ug/ml puromycin works well, although the minimum dose that kills all cells without any viral transduction should be determined in advance and the minimum concentration should be used for selection. Usually, only 2-3 days of puromycin selection is needed to select for cells with viral integration and expression but a longer period of selection has the added benefit of allowing for enough time for genome modification by Cas9. As shown in the deep sequencing of the individual target (array) validations from the PLX resistance screen gene hits, genome modification increases over time. For most targets, genome modification was nearly complete after only 7 days. Some lentiCRISPRs had lower modification that increased by 14 days post-transduction (for example, NF1_sg4 in FIG. 42, NF2_sg5 in FIG. 43). As expected, for some sgRNAs, off-target modification also increases with time, albeit by a smaller amount (for example, NF2_sg4 in FIG. 42, MED12_sg2 in FIG. 43). In general, it is advisable to keep puromycin selection (and Cas9 expression since they are co-expressed) for at least 7 days post-transduction and possibly longer depending on the needs of the particular experiment.

Identification of gene candidates: Before any experiment, it is important to determine the distribution of sgRNAs before any selection pressure has been applied. This baseline sgRNA distribution will be used to infer either depletion or enrichment of specific sgRNA species. For both positive and negative selection screens, hits are identified by comparing the distribution of sgRNAs after selection with the baseline sgRNA distribution. Candidate genes are identified by searching for sgRNAs whose frequency has either significantly reduced or increased after selection for negative and positive screens respectively.

Using multiple sgRNAs to target the same gene, and transduction replicates are the main experimental features that enable discrimination between true and false positive hits. The reason is that each screen will have some background rate, meaning that with some probability an sgRNA can be enriched (or depleted) despite having no effect on the studied phenotype. The required number of unique sgRNAs for the same genes should be determined by the background rate of the screen and the overall efficacy of sgRNAs. As increasing sgRNA numbers per gene comes with a cost of increasing library complexity, additional infection replicates can compensate for it as long as there is a minimal number of sgRNAs that can effectively mediate gene targeting. Finally, ranking of the top hits requires the conversion of sgRNA scores into gene rankings. A simple method is to rank gene hits according to the mean or median of all sgRNAs for each respective gene. Applicants recommend combining this simple method with other analysis such as RIGER and RSA.

GeCKO versus shRNA screening: GeCKO screening operates through a fundamentally different mechanism than shRNA based screening. Whereas shRNAs reduce protein expression by targeting the mRNA, GeCKO achieves protein knockdown via frameshift mutations introduced into the genomic coding region. GeCKO-mediated frameshift mutations are achieved through targeted DNA double strand breaks (DSB) and subsequent mutagenic repair via the non-homologous end joining (NHEJ) pathway, which produces indels at the site of DSB. The indel being introduced into the DSB is random (FIG. 44), with some indels leading to frameshift mutations that cause premature termination of the transgene. Other indels with lengths that are multiples of three will not result in the frameshift of the candidate genes. In this scenario, the gene product might still be functional. In contrast, shRNA knockdown can generate a spectrum of expression levels of the target genes. Therefore GeCKO screening can provide potential advantages over shRNA, where the population of cells that has been homozygously knocked out can provide more screening sensitivity especially when probing gene products that can function normally even at significantly reduced concentrations.

Vemurafenib (PLX) resistance mechanisms: The protein kinase BRAF, a key regulator of the MAPK signaling cascade, is mutated in more than half of malignant melanomas and in several other types of cancer, such as thyroid, colorectal, lung, and hairy cell leukemia. The V600E mutant form of BRAF is a common gain of function mutation that allows BRAF to remain in a constitutively active state and phosphorylate MEK without forming a phosphorylated BRAF dimer. Vemurafenib (PLX) is a FDA-approved, ATP-competitive RAF inhibitor that displays higher binding affinity for V600E mutant BRAF over other RAF isoforms, including wild-type BRAF. Over 50% of melanoma patients with mutated BRAF treated with PLX display tumor reduction, but the effect is short-lived and resistance develops in a majority of cases. By applying the GeCKO library to A375 cells (which are homozygous for the BRAF V600E mutation), Applicants identified several genes whose loss resulted in resistance to PLX.

In the PLX screen, Applicants identified and validated NF2, NF1, MED12, CUL3, TADA1, and TADA2B as genes whose loss results in PLX resistance. Loss of NF1 and MED12 were previously identified resistance mechanisms from two separate, large-scale RNAi screens. MED12, a member of the Mediator transcription complex, is a negative regulator of TGF-βR and its loss results in activation of TGF-βR signaling and MEK/ERK. NF1 is a negative regulator of NRAS activity and its loss phenocopies activating NRAS mutations, an established PLX resistance mechanism.

Although they have similar names, NF1 and NF2 are tumor suppressors that function via distinct pathways. NF2 (or Merlin, Moesin-Ezrin-Radixin-Like Protein) is a tumor suppressor gene that encodes a cytoskeletal protein. Loss of NF2 leads to constitutive mTOR activation and cell proliferation by a MEK/ERK-independent mechanism and involves the Hippo signaling pathway. Mutation and copy number variation of the E3 ligase CUL3 has been described in lung squamous cell carcinomas and renal cell carcinomas. Quantitative proteomics in T24T bladder cancer cells found that silencing of CUL3 restored the expression of cytoskeleton proteins that are underexpressed in T24T, such as moesin and erzin. This suggests a possible interaction between CUL3 and NF2/merlin, a similar cytoskeletal protein to those ubiquitinated by CUL3.

TADA1 and TADA2B are chromatin-modifying enzymes involved in transcription and are members of the multiprotein STAGA (SPT3-TAF9-GCN5-acetylase) complex. The STAGA complex recruits Mediator complex proteins (such as MED12) to the oncoprotein c-Myc to activate proliferation. Applicants noted that CCDC101 had a high RIGER rank in both infection replicates (see Table I) and is also a subunit of the STAGA complex and thus may lead to PLX resistance through a similar mechanism as TADA1 and TADA2B. Since many of the gene hits from the PLX screen interact with each other and are involved in established cell proliferation pathways, therapeutics targeted to these pathways could be combined with BRAF inhibition to achieve better clinical outcomes in melanoma and other cancers.

Other applications of GeCKO screening: In addition to facilitating loss-of-function gene screening, GeCKO and similar Cas9-sgRNA libraries can be customized to carry out a variety of genome-scale perturbations to study the effect of non-coding elements, transcriptional changes, and epigenetic modulations. In this library, Applicants target the constitutive exons near the 5' end of genes for loss-of-function but sgRNAs can also be targeted to promoters, enhancers, intronic, and intergenic regions. Screens targeting non-coding regions or a mix of coding and non-coding regions can elucidate how these different elements contribute to gene expression and biological function. As Applicants have recently shown, Cas9 with mutated catalytic residues can be fused to a transcriptional activation domain such as VP16 or repressor domain such as SID4× or KRAB to create a Cas9 transcriptional modulator without any nuclease activity. By replacing the Cas9 in the lentiCRISPR plasmid with a null-nuclease version (eg. with D10A and H840A mutations), libraries of sgRNAs for activation can be used to investigate how activation of different transcripts or different splice variants contribute to a screen phenotype. A null-nuclease Cas9 could also be fused with different effector domains capable of modifying the epigenetic state at a particular locus. Previous work from Applicants and others has demonstrated transcriptional changes using zinc-finger proteins and transcriptional activator like effectors (TALEs) fused to histone (de)acetylases, histone (de)methylases, DNA (de)methylases and other epigenetic modifiers. The easy programmability of Cas9 DNA binding using sgRNAs that can be array synthesized en masse opens up many new possibilities for genome-scale screens.

TABLE I

Comparison of the top 20 hits between the two A375 PLX infection replicate screens by RIGER rank. RNAi gene enrichment ranking (RIGER) uses a two-sample weighted likelihood ratio test to measure the support for a gene using the enrichment of the sgRNAs (or shRNAs) for each gene.

| 1st infection | | | 2nd infection | | |
|---|---|---|---|---|---|
| Gene symbol | RIGER rank | RIGER p-value | Gene symbol | RIGER rank | RIGER p-value |
| NF2 | 1 | 0.000004 | MED12 | 1 | 0.000002 |
| MED12 | 2 | 0.000004 | CUL3 | 2 | 0.000002 |
| CUL3 | 3 | 0.000006 | NF2 | 3 | 0.000005 |
| CLDN10 | 4 | 0.000005 | TADA1 | 4 | 0.000007 |
| NF1 | 5 | 0.000001 | TADA2B | 5 | 0.00001 |
| TADA1 | 6 | 0.000035 | RBL1 | 6 | 0.000041 |
| TADA2B | 7 | 0.000046 | TAF6L | 7 | 0.000085 |
| SPECC1 | 8 | 0.000146 | OR8S1 | 8 | 0.000157 |
| CCDC101 | 9 | 0.000082 | MED23 | 9 | 0.000081 |
| ALG3 | 10 | 0.000118 | SLC41A3 | 10 | 0.000244 |
| P4HB | 11 | 0.000189 | CCDC101 | 11 | 0.000201 |
| EED | 12 | 0.000313 | LCOR | 12 | 0.00031 |
| TAF6L | 13 | 0.000234 | GPR98 | 13 | 0.000239 |
| MED15 | 14 | 0.000382 | KCNA2 | 14 | 0.000666 |
| NPPC | 15 | 0.000575 | MED15 | 15 | 0.000416 |
| TAF5L | 16 | 0.000141 | MT1F | 16 | 0.000141 |
| PGD | 17 | 0.000349 | MYL7 | 17 | 0.000445 |
| LGALS4 | 18 | 0.00051 | SLC7A11 | 18 | 0.000554 |
| TAOK1 | 19 | 0.000429 | MTRF1 | 19 | 0.000445 |
| CD320 | 20 | 0.000824 | ELF1 | 20 | 0.000454 | appear in the top 20 of the other replicate infection
appears in the top 100 of the other replicate infection (in bold)

TABLE J

Comparison of the top 20 hits between the two A375 PLX infection replicate screens by RSA rank. Redundant siRNA activity (RSA) uses an enrichment cutoff and hypergeometric test to measure the support for a gene using the enrichment of the sgRNAs (or shRNAs) for each gene.

| 1st infection | | | 2nd infection | | |
|---|---|---|---|---|---|
| Gene symbol | RSA rank | RSA log p value | Gene symbol | RSA rank | RSA log p value |
| MED12 | 1 | −12.467 | MED12 | 1 | −11.954 |
| NF2 | 2 | −9.147 | NF2 | 2 | −8.766 |
| CUL3 | 3 | −8.578 | CUL3 | 3 | −8.174 |
| MED15 | 4 | −7.684 | TADA2B | 4 | −6.512 |
| TADA2B | 5 | −7.418 | CCDC101 | 5 | −6.319 |
| RBL1 | 6 | −6.316 | DPH2 | 6 | −6.141 |
| TADA1 | 7 | −5.815 | MED15 | 7 | −5.609 |
| CCNC | 8 | −5.483 | NF1 | 8 | −5.418 |
| CCDC101 | 9 | −5.313 | CLDN10 | 9 | −5.174 |

TABLE J-continued

Comparison of the top 20 hits between the two A375 PLX infection replicate screens by RSA rank. Redundant siRNA activity (RSA) uses an enrichment cutoff and hypergeometric test to measure the support for a gene using the enrichment of the sgRNAs (or shRNAs) for each gene.

| 1st infection | | | 2nd infection | | |
|---|---|---|---|---|---|
| Gene symbol | RSA rank | RSA log p value | Gene symbol | RSA rank | RSA log p value |
| PDCD10 | 10 | −5.278 | PGD | 10 | −4.944 |
| NOTCH2NL | 11 | −4.988 | TADA1 | 11 | −4.909 |
| PCLO | 12 | −4.971 | ZEB2 | 12 | −4.892 |
| PPP1R8 | 13 | −4.947 | CCNC | 13 | −4.697 |
| C1QA | 14 | −4.667 | TAF6L | 14 | −4.402 |
| DR1 | 15 | −4.311 | SMARCB1 | 15 | −4.371 |
| KCTD10 | 16 | −4.284 | BCL2L12 | 16 | −4.228 |
| PDE12 | 17 | −4.236 | PDCD10 | 17 | −4.16 |
| SLC25A17 | 18 | −4.209 | GADD45GIP1 | 18 | −4.107 |
| BRD9 | 19 | −4.206 | ZNF592 | 19 | −4.037 |
| PET117 | 20 | −4.168 | ACTA2 | 20 | −4.033 |

<u>appear</u> <u>in</u> <u>the</u> <u>20</u> <u>top</u> <u>of</u> <u>other</u> <u>replicate</u> <u>infection</u>
appears in the 100 top of other replicate infection (in bold)

TABLE K

Cas9-sgRNA array screening constructs used. Names and targeting sequence for all Cas9-sgRNA constructs used for validation in A375 screen. Cas9-sgRNAs (SEQ ID NOs: 24-51, respectively, in order of appearance) with names in italics are contained in the GeCKO library.

| Name | sgRNA 20 bp sequence |
|---|---|
| *NF2_sg1* | AAACATCTCGTACAGTGACA |
| *NF2_sg2* | ATTCCACGGGAAGGAGATCT |
| *NF2_sg3* | CCTGGCTTCTTACGCCGTCC |
| *NF2_sg4* | GTACTGCAGTCCAAAGAACC |
| NF2_sg5 | CACAGTGGCCTGGCTCAAAA |
| *MED12_sg1* | AGGATTGAAGCTGACGTTCT |
| *MED12_sg2* | CGTCAGCTTCAATCCTGCCA |
| *MED12_sg3* | CTCAGAGATTGCTGCATAGT |
| *MED12_sg4* | ACAGGTCATCTTAATGAGCC |
| MED12_sg5 | GGGGCTGTGGTTCCACGATA |
| *NF1_sg1* | GTTGTGCTCAGTACTGACTT |
| *NF1_sg2* | ACACTGGAAAAATGTCTTGC |
| NF1_sg3 | AGTCAGTACTGAGCACAACA |
| *CUL3_sg1* | CTTACCTGGATATAGTCAAC |
| *CUL3_sg2* | GAATCCTGTTGACTATATCC |
| *CUL3_sg3* | GACCTAAAATCATTAACATC |
| *CUL3_sg4* | TGCCAGATGTTAATGATTTT |
| CUL3_sg5 | TTATTTAGTCGTGTGCCAAA |
| *TADA1_sg1* | ACTGGGCTAACCTAAAGCTG |
| *TADA1_sg2* | TCTGCTTGAACCACAGCTTT |
| *TADA1_sg3* | GGAGGAAATCATTGTGAGAA |
| TADA1_sg4 | TCTTTAGTGCAATCAGAATC |
| *TADA2B_sg1* | ACGGCGGGCGCTTCACGCTC |
| *TADA2B_sg2* | GCCATCGAGCAGTTCGGCTT |
| *TADA2B_sg3* | GCACCTTCTCGCGATCTGAC |
| TADA2B_sg4 | GCTCCTGTCAGATCGCGAGA |
| Control_sg1 (EGFP_sg5) | GAAGTTCGAGGGCGACACCC |
| Control_sg2 (EGFP_sg6) | GGTGAACCGCATCGAGCTGA |

TABLE L shRNA array screening constructs (SEQ ID NOs: 52-66, respectively, in order of appearance) used. Names and The RNAi Consortium (TRC) identification numbers for all shRNA constructs used for validation in A375 screen.

| Name | TRC ID | Targeting Sequence |
|---|---|---|
| NF2_sh1 | TRCN0000010397 | GAAGCAACCCAAGACGTTCAC |
| NF2_sh2 | TRCN0000018338 | TAGTTCTCTGACCTGAGTCTT |
| NF2_sh3 | TRCN0000039974 | GCTCTGGATATTCTGCACAAT |
| NF2_sh4 | TRCN0000039975 | GCTTCGTGTTAATAAGCTGAT |
| MED12_sh1 | TRCN0000018574 | GCAGCATTATTGCAGAGAAAT |
| MED12_sh2 | TRCN0000018575 | GCTGTTCTCAAGGCTGTGTTT |
| MED12_sh3 | TRCN0000018576 | CGGGTACTTCATACTTTGGAA |
| MED12_sh4 | TRCN0000018578 | GCAGAGAAATTACGTTGTAAT |
| NF1_sh1 | TRCN0000039714 | GCCAACCTTAACCTTTCTAAT |
| NF1_sh2 | TRCN0000039715 | CCTCACAACAACCAACACTTT |
| NF1_sh3 | TRCN0000039716 | CCTGACACTTACAACAGTCAA |
| NF1_sh4 | TRCN0000039717 | GCTGGCAGTTTCAAACGTAAT |
| TADA2B_sh1 | TRCN0000237951 | CGTGACTGTGAAGACTATTAT |
| TADA2B_sh2 | TRCN0000237949 | ATGATTACGAGATCGAGTATG |
| TADA2B_sh3 | TRCN0000237950 | ACATCGCCCGTGACTACAATC |
| NullT_1 | TRCN0000208001 | n/a |
| NullT_2 | TRCN0000231782 | n/a |

GeCKO library design: A genome-scale sgRNA library was constructed as follows: First, early constitutive exons were identified for all coding genes. Then, sgRNAs to target these early constitutive exons were selected by choosing sgRNAs that were predicted to have minimal off-target activity.

To identify constitutive exons, RNA sequencing data from the Illumina Human Body Map 2.0 (GEO accession number: GSE30611) was mapped to the reference human genome (hg19) using TopHat v1.0.14 and transcripts were reconstructed with Cufflinks v1.0.2, as previously described in Merkin J. et al. Science 338, 1593 (Dec. 21, 2012). Exons expressed across all tissues in the Illumina dataset were chosen as constitutive exons for sgRNA targeting. In addition, for each gene, the first and last exons were excluded along with any exon that contained an alternative splicing site.

For the constitutive exons, genomic sequences were retrieved from the NCBI Consensus CoDing Sequence database (available at the website of ncbi.nlm.nih.gov/CCDS/). For each CCDS entry, the two earliest constitutive exons were chosen as candidate exons for library design. For genes without RNA sequencing data or where no exons qualified as constitutive, exons 2 and 3 were included as candidate exons for library design.

Next, for each candidate exon, all possible S. pyogenes Cas9 sgRNA sequences of the form $(N)_{20}NGG$ were listed as candidate targets. Each 20mer candidate sgRNA was mapped to a precompiled index containing all 20mer sequences in the human genome followed by either NGG or NAG. This mapping was done using Bowtie short read aligner, allowing up to 3 base mismatches.

The following heuristic was used to rank sgRNAs for each exon based on the characterized sequence specificity of Cas9 nuclease. First, any sgRNAs with other targets in the genome that match exactly or differ by only 1 base are discarded. For the remaining sgRNAs, Applicants calculated the following off target score:

$$OS = \sum_{off\ targets} (\text{sum mm location})(D(mm)/D(max))$$

sum mm location=sum of the mismatch locations from 3' to 5'. The PAM (NGG) proximal base is 1 and the PAM distal base is 20.
D(mm)=distance in bp between mismatch locations.
D(max)=maximal possible distance between 2 or 3 mismatches.

When mismatches are clustered more closely together, the cutting efficiency of Cas9 is significantly lower. Therefore, in the OS, the location of mismatches is weighted by their distances from each other. For each gene, the best (lowest OS) sgRNAs were chosen with the constraint that no sgRNAs have a OS>400. This resulted in a library of 64,751 unique sgRNAs targeting 18,080 coding genes with an average of 3-4 sgRNAs per gene. For all sgRNAs, an extra 5' G was added to improve U6 transcription.

Array oligo synthesis and pooled library cloning: DNA oligonucleotide library synthesis was performed on a programmable microarray using a B3 Synthesizer (CustomArray) and SAFC Proligo reagents (Sigma), as recommended by the manufacturer. The synthesis products were cleaved from the microarray and deprotected by overnight incubation in 28-30% ammonium hydroxide at 65° C., dried, resuspended in TE buffer and then purified using a QIAquick spin column (Qiagen). Full-length oligonucleotides (74 nt) were amplified by PCR using Phusion HS Flex (NEB) and size-selected using a 2% agarose E-Gel EX (Life Technologies, Qiagen).

ArrayF
(SEQ ID NO: 67)
TAACTTGAAAGTATTTCGATTTCTTGGCTTTATATATCTTGTGGAAAG
GAC GAAACACCG ArrayR
(SEQ ID NO: 68)
ACTTTTTCAAGTTGATAACGGACTAGCCTTATTTTAACTTGCTATTTC
T AGCTCTAAAAC The lentiCRISPR vector was digested with BsmBI (Fermentas) and treated with alkaline phosphatase (Fermentas) at 37° C. for 2 hours and gel-purified on a 1% E-Gel EX (Life Technologies, Qiagen). A 20 ul Gibson ligation reaction (NEB) was performed using 10 ng of the gel-purified inserts and 25 ng of the vector. From the ligation, 0.5 ul of the reaction was transformed into 25 ul of electrocompetent cells (Lucigen) according to the manufacturer's protocol using a GenePulser (BioRad). To ensure no loss of representation, 36 parallel transformations were performed using the same ligation reaction and plated onto 245 mm×245 mm plates (Corning) with carbenicillin selection (50 ug/ml), which yielded 166× library coverage. Colonies were scraped off plates and combined before plasmid DNA extraction using Endotoxin-Free Plasmid Maxiprep (Qiagen).

Lentivirus production and purification: To produce lentivirus, twelve T-225 flasks of HEK293T cells (Broad RNAi Platform) were seeded at ~40% confluence the day before transfection in D10 media (DMEM supplemented with 10% fetal bovine serum). One hour prior to transfection, media was removed and 13 mL of pre-warmed reduced serum OptiMEM media (Life Technologies) was added to each flask. Transfection was performed using Lipofectamine 2000 and Plus reagent (Life Technologies). For each flask, 200 ul of Plus reagent was diluted in 4 ml OptiMEM (Life Technologies) with 20 ug of lentiCRISPR plasmid library, 10 ug of pVSVg, and 15 ug of psPAX2 (Addgene). 100 ul of Lipofectamine 2000 was diluted in 4 ml OptiMEM and, after 5 min, it was added to the mixture of DNA and Plus reagent. The complete mixture was incubated for 20 min before being added to cells. After 6 h, the media was changed to 30 ml D10 supplemented with 1% BSA (Sigma).

After 60 h, the media was removed and centrifuged at 3,000 rpm at 4° C. for 10 min to pellet cell debris. The supernatant was filtered through a 0.45 um low protein binding membrane (Millipore Steriflip HV/PVDF). To achieve 300× concentration of the GeCKO pooled library, the virus was ultracentrifuged (Sorvall) at 24,000 rpm for 2 h at 4° C. and then resuspended overnight at 4° C. in D10 supplemented with 1% BSA. Aliquots were stored at −80° C.

Cell transduction using the GeCKO library: Cells were transduced with the GeCKO library via spinfection. To find optimal virus volumes for achieving an MOI of 0.3-0.5, each new cell type and new virus lots were tested by spinfecting 3×10⁶ cells with several different volumes of virus. Briefly, 3×10⁶ cells per well were plated into a 12 well plate in the appropriate standard media for the cell type (see below) supplemented with 8 ug/ml polybrene (Sigma). For A375 cells (ATCC), standard media was R10: RPMI 1640 supplemented with 10% FBS. For HUES62 (Harvard Stem Cell Institute iPS Core Facility), standard media consists of mTeSR1 (STEMCELL Technologies) supplemented with 1× Normocin (InvivoGen). Each well received a different titrated virus amount (usually between 5 and 50 ul) along with a no-transduction control. The 12-well plate was centrifuged at 2,000 rpm for 2 h at 37° C. After the spin, media was aspirated and fresh media (without polybrene) was added.

Cells were incubated overnight and then enzymatically detached using trypsin (Corning) for A375 and Accutase (STEMCELL) for HUES62. Cells were counted and each well was split into duplicate wells. One replicate received 0.5 ug/mL puromycin (Sigma) for HUES62 cells or 1 ug/ml puromycin for A375 cells. After 3 days (or as soon as no surviving cells remained in the no-transduction control under puromycin selection), cells were counted to calculate a percent transduction. Percent transduction is calculated as cell count from the replicate with puromycin divided by cell count from the replicate without puromycin multiplied by 100. The virus volume yielding a MOI closest to 0.4 was chosen for large-scale screening.

Large-scale spinfection of $5 \times 10^7$ to $1 \times 10^8$ A375 or HUES62 cells was carried out in the same way as described above using 12-well plates with $3 \times 10^6$ cells per well. Wells were pooled together into larger flasks on the day after spinfection.

HUES62 depletion screen: $6 \times 10^7$ HUES62 human embryonic stem (hES) cells were transduced as described above. 30 uL of the concentrated GECKO library was applied to each well containing $3 \times 10^6$ cells, resulting in an transduction efficiency of 30% (approximately 270 cells per lentiCRISPR construct). Puromycin (0.5 ug/mL) was added to the cells 24 hours post transduction and maintained for 7 days. On day 7, cells were split into replicate flasks with a minimum of $2 \times 10^7$ cells per replicate and cultured for an additional 14 days before genomic DNA extraction and analysis. During the screen, hES cells were fed daily with mTeSR1.

A375 PLX-4032 resistance screen: $8 \times 10^7$ A375 cells were transduced as described above with $2 \times 10^6$ cells plated per transduction well. 10 uL of the concentrated GECKO library was applied to each well containing $2 \times 10^6$ cells, attaining a transduction efficiency of 30% (approximately 370 cells per lentiCRISPR construct or in aspects of the invention, this may be approximately 400 cells per lentiCRISPR construct). Puromycin (1 ug/mL) was added to the cells 24 hours post transduction and maintained for 7 days. On day 7, cells were split into drug conditions in duplicate with a minimum of $2.6 \times 10^7$ cells per replicate and an additional $3 \times 10^7$ cells were frozen down for genomic DNA analysis. Two replicates were cultured in R10 supplemented with 2 uM PLX4032 (Selleckchem) and two replicates were cultured in R10 supplemented with an equal volume DMSO (Sigma Aldrich). Replicates were either passaged or fresh media was added every 2-3 days. Cell pellets with a minimum of $3 \times 10^7$ cells were taken at 7 days after drug addition and 14 days after drug addition at which point the screen was terminated.

Genomic DNA sequencing: Frozen cell pellets were thawed and genomic DNA was extracted with a Blood & Cell Culture Midi kit (Qiagen). PCR was performed in two steps: For the first PCR, the amount of input genomic DNA (gDNA) for each sample was calculated in order to achieve 300× coverage over the GECKO library, which resulted in 130 ug DNA per sample (assuming 6.6 ug of gDNA for $10^6$ cells). For each sample, Applicants performed 13 separate 100 ul reactions with 10 ug genomic DNA in each reaction using Herculase II Fusion DNA Polymerase (Agilent) and then combined the resulting amplicons. Primers sequences (SEQ ID NOs: 69 and 70, respectively, in order of appearance) to amplify lentiCRISPR sgRNAs for the first PCR are:

```
F1
   AATGGACTATCATATGCTTACCGTAACTTGAAAGTATTTCG

R1
   CTTTAGTTTGTATGTCTGTTGCTATTATGTCTACTATTCTTTCC
```

A second PCR was performed to attach Illumina adaptors and to barcode samples. The second PCR was done in a 100 ul reaction volume using 5 ul of the product (preferably the pooled product) from the first PCR. Primers for the second PCR include both a variable length sequence to increase library complexity and an 8 bp barcode for multiplexing of different biological samples:

```
F2
                                     (SEQ ID NO: 71)
AATGATACGGCGACCACCGAGATCTACACTCTTTCCCTACACGACGCTCT
TCCGATCT(1-9 bp variable length sequence)
(8 bp barcode) tcttgtggaaaggacgaaacaccg R2
                                     (SEQ ID NO: 72)
CAAGCAGAAGACGGCATACGAGATGTGACTGGAGTTCAGACGTGTGCTCT
TCCGATCT tctactattctttcccctgcactgt
```

Resulting amplicons from the second PCR were gel extracted, quantified, mixed and sequenced using a HiSeq 2500 (Illumina). Amplification was carried out with 18 cycles for the first PCR and 24 cycles for the second PCR.

Data processing and initial analysis: Raw FASTQ files were demultiplexed using the FASTX-Toolkit (available at the website of hannonlab.cshl.edu/fastx_toolkit/) and processed to contain only the unique sgRNA sequence. To align the processed reads to the library, the designed sgRNA sequences from the library were assembled into a Burrows-Wheeler index using the Bowtie build-index function. Reads were then aligned to the index using the Bowtie aligner. After alignment, the number of uniquely aligned reads for each library sequence was calculated.

The numbers of reads for each unique sgRNA for a given sample were normalized as follows:

$$\text{normalized reads per } sgRNA = \frac{\text{reads per } sgRNA}{\text{total reads for all } sgRNAs \text{ in sample}} \times 10^5$$

Array lentiCRISPR array screen: Individual lentiCRISPRs from the GECKO pool were produced as above except that viral supernatants were not concentrated by ultracentrifugation. For each lentiCRISPR, $5 \times 10^5$ A375 cells were infected via spinfection at 2,000 rpm for 2 h at 37° C. in R10 supplemented with 8 ug/ml polybrene. After 14 days of puromycin selection, infections were plated into separate dishes for Western blotting and the cell viability assay.

Western blotting: A375 cells were lysed in Cell Lysis Buffer (Cell Signaling 9803) with protease inhibitors (Sigma P8340). Lysates were homogenized using a Bioruptor sonicator (Diagenode) for 5 minutes (30s on-30s off cycle, high power) and then centrifuged at 15,000 rpm for 20 min at 4° C. Supernatants were quantified using the BCA assay (Thermo/Pierce). 20 ug of protein was denatured at 70C for 10 minutes before gel electrophoresis on a 4-12% Bis-Tris gel (Life Technologies). Proteins were transferred to nitrocellulose membranes at 60V overnight at 4° C. Antibodies used: Anti-NF2 (1:1000, Abcam ab109244), Anti-NF1 (1:1000, Abcam ab17963), Anti-MED12 (1:1000, Cell Signaling 4529S), Anti-CUL3 (1:1000, Cell Signaling 2759S), Anti-TADA2B (1:1000, Sigma HPA035770), Anti-GAPDH (1:5000, Cell Signaling 3683S). Membranes were developed by SuperSignal West Femto ECL (Thermo/Pierce) and imaged using BioRad ChemiDoc MP imaging system.

Cell viability assay: lentiCRISPR-infected A375 cells were plated in quadruplicate into 96-well plates at a density of 5×10³ cells per well. Either PLX or vehicle (DMSO) was added 1 day after plating. PLX was added at the following concentrations: 20 nM, 200 nM, 2 uM, 20 uM, and 200 uM. Drug/vehicle was renewed every 2-3 days using a Janus liquid handler (PerkinElmer).

After 5 days of drug/vehicle treatment, cell viability was measured using CellTiter Glo (Promega). After allowing cells to reach room temperature, media was aspirated from the cells and CellTiter Glo (diluted 1:4 in phosphate-buffered saline) was added. Plates were placed on an orbital shaker for 2 min followed by a 10 min room temperature incubation. Luminescence was read out on an EnVision plate imager (PerkinElmer).

Flow cytometry analysis of GFP knockout or knockdown: lentiCRISPR with sgRNAs targeting EGFP (SEQ ID NOs: 73-76 and 50-51, respectively, in order of appearance) were cloned using the following sequences (annotated in FIG. 28):

```
EGFP sgRNA 1
GGGCGAGGAGCTGTTCACCG

EGFP sgRNA 2
GAGCTGGACGGCGACGTAAA

EGFP sgRNA 3
GGCCACAAGTTCAGCGTGTC

EGFP sgRNA 4
GGAGCGCACCATCTTCTTCA

EGFP sgRNA 5
GAAGTTCGAGGGCGACACCC

EGFP sgRNA 6
GGTGAACCGCATCGAGCTGA
```

Four shRNAs targeting EGFP in a pLKO (puromycin-selectable) vector were used (Broad RNAi Platform):

| EGFP shRNA 1 | TRCN0000072194 |
| EGFP shRNA 2 | TRCN0000072181 |
| EGFP shRNA 3 | TRCN0000072201 |
| EGFP shRNA 4 | TRCN0000072198 |

Control lentiCRISPR contained no spacer sequence and control shRNA was null hairpin TRCN0000208001.

For both lentiCRISPRs and shRNAs, virus was produced using a similar protocol as presented above but without ultracentrifuge purification. HEK293T cells with a single copy of EGFP (Broad RNAi Platform) were infected on Day 0 and then analyzed by flow cytometry on Day 5 and Day 11 post-infection. Flow cytometry was performed on a BD Accuri C6 cytometer in 96-well plates. Analysis was done in FlowJo (Treestar) by first gating for viable cells using forward and side scatter and then gating the fluorescence histogram.

Sequencing data analysis and indel detection: Off target loci in the human genome were identified for individual spacers using the CRISPR design tool (available at the website tools.genome-engineering.org). On-target and off-target loci were PCR amplified using Herculase II Fusion polymerase (Agilent), normalized, and pooled in equimolar proportions. Pooled libraries were denatured, diluted to a 14 pM concentration and sequenced using the MiSeq Personal Sequencer (Illumina). Sequencing data was demultiplexed using paired barcodes, aligned to reference amplicons, and analyzed for indels as described previously. Indel length analysis was performed by mapping the distance between multiple short reference sequences in individual reads.

Aspects of the invention also encompass a two vector, genome-wide KO system. Details are as follows:

1) Applicants utilize A375 (BRAF V600E mutation-containing) cells having Cas9 alone integrated into the genome. This may be done with lentivirus but may also be done with other methods of integration (integrase, recombinase, transposase, etc.) Typically the integration cassette will include Cas9 and a selectable marker to make sure that only cells with Cas9 active are kept. For e.g., the vector is EF1a-Cas9-2A-Blasticidin.

2) The A375 cells comprising Cas9 are exposed to a library of viruses. Each virus has U6 driving one sgRNA ("spacer" or "guide"). Thus in this case, the library delivers only the guide instead of Cas9 plus guide. The rationale for this approach is that it may be easier to produce a high titer virus with only having to deliver the guide. In aspects of the invention it may be practical for large scale screening and virus production to have only the variable part (the guide, which is one of 65,000 different guides) in the library virus and keep the constant part (Cas9) out of the library.

3) The rest of the screen proceeds from this point identically to the single vector system as described in this example which may include the following steps: Adding PLX (drug targeted to BRAF with V600E mutation); Killing most of the cells; Letting the cells that survive grow out; Extracting genomic DNA and Performing next generation (next gen) sequencing to find out which guides conferred the ability to survive PLX selection. Applicants have utilized the two vector system to knock out EGFP and hence this two vector system may be applied to a full-scale screen.

Example 10: Improved Lentiviral Vectors and Genome-Wide Libraries for CRISPR Screening in Human and Mouse Cells Initial genome-wide, targeted loss-of-function screens using the CRISPR (clustered regularly interspaced short palindrome repeats)-associated nuclease Cas9 in human and mouse cells have revealed new mechanisms of resistance to cancer therapeutics (including vemurafenib, etoposide, and 6-TG) and identified genes essential for cell survival. When compared to screens using genome-wide libraries of RNAi reagents, screens with Genome-scale CRISPR Knock-Out (GeCKO) libraries demonstrate higher consistency amongst unique reagents targeting the same gene and have a higher target validation rate among top screen candidates[1].

Figure 47A:
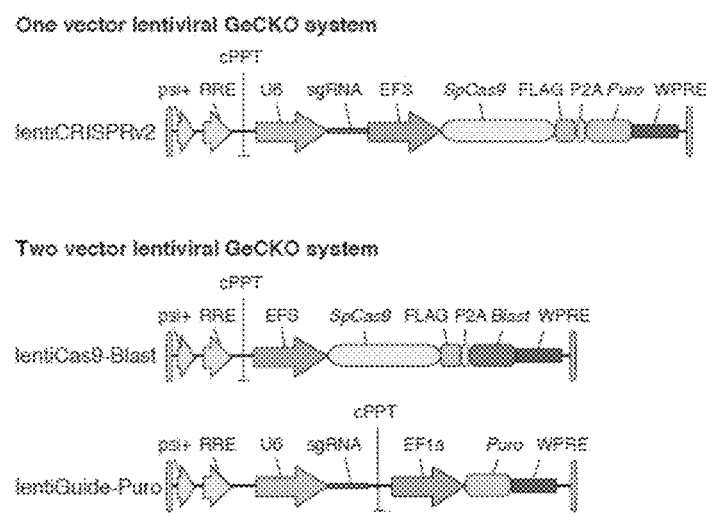
FIG. 47A-47B shows New lentiviral CRISPR designs produce viruses with higher functional titer. (A) Lentiviral expression vector for *Streptococcus pyogenes* Cas9 and sgRNA in the improved one vector system (lentiCRISPR v2) and the two vector system (lentiCas9-Blast, lentiGuide-Puro). Psi packaging signal (psi+), rev response element (RRE), central polypurine tract (cPPT), elongation factor-1a short promoter (EFS), FLAG octapeptide tag (FLAG), 2A self-cleaving peptide (P2A), puromycin selection marker (puro), posttranscriptional regulatory element (WPRE), blasticidin selection marker (blast), and elongation factor-1α promoter (EF1a). (B) Relative functional viral titer of viruses made from lentiCRISPR v1, lentiCRISPR v2, and lentiGuide-Puro vector with a EGFP-targeting sgRNA (n=3 transductions). HEK293FT cells were transduced with serial dilutions of virus and, after 24 hours, selected using puromycin (1 ug/ml). Puromycin-resistant cells were measured after 4 days from the start of selection using the CellTiter-Glo (Promega) luciferase assay. Relative titers were calculated using viral volumes that yielded less than 20% puromycin-resistant cells in order to minimize the number of cells with multiple infections. Numbers above each bar indicate the size of the packaged virus for each construct.
Figure 47B:
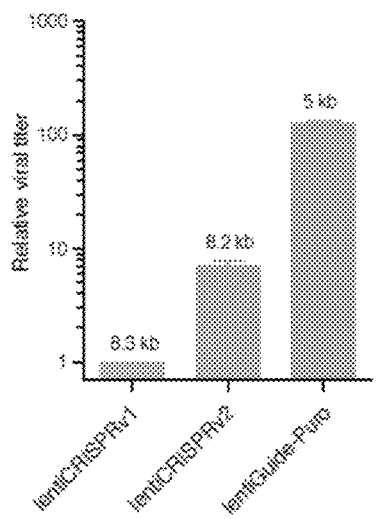

Applicants sought to improve both the lentiviral packaging and pooled library design of Applicant's original CRISPR screening system as described in Example 9. In the system described in Example 9, a pooled library of synthesized oligonucleotides was cloned into a lentiviral backbone containing both the Cas9 nuclease and the target-specific synthetic short guide RNA (sgRNA). This lentiviral vector (lentiCRISPR v1) had a low titer and required concentration of the virus using an ultracentrifuge or ultrafiltration membrane before performing a screen. To create a new vector capable of producing higher-titer virus, Applicants removed one of the nuclear localization signals (NLS), codon-optimized the remaining NLS and P2A bicistronic linker sequence, and changed the placement of the U6-driven sgRNA cassette (FIG. 47A). This optimized vector (lentiCRISPR v2) has a 7.1-fold increase in functional viral titer over lentiCRISPRv1 (FIG. 47B).

Figure 48A:
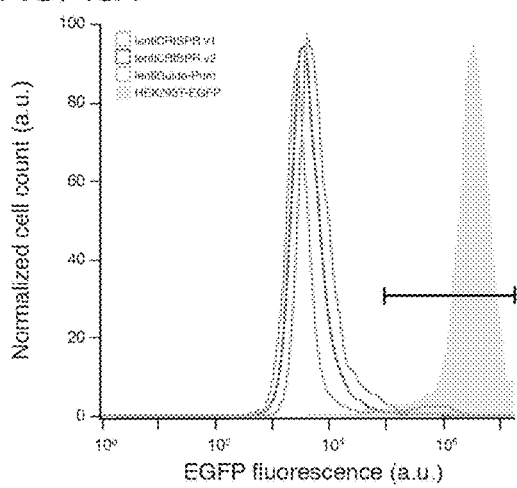
FIG. 48A-48B shows Flow cytometry of HEK293T-EGFP 7 days after lentiCRISPR transduction. (A) Representative histograms of EGFP fluorescence from single transductions of HEK293T-EGFP cells with lentiCRISPR v1, lentiCRISPR v2, lentiGuide-Puro or no virus. For lentiGuide-Puro, HEK293T-EGFP cells had previously been transduced with lentiCas9-Blast. Twenty-four hours after transduction, cells were selected in puromycin and then analyzed by flow cytometry at 7 days after infection. (B) Percentage of EGFP positive cells (as given by gate drawn in panel A) per viral construct (error bars indicate s.e.m, n=3 biological replicate transductions).
Figure 48B:
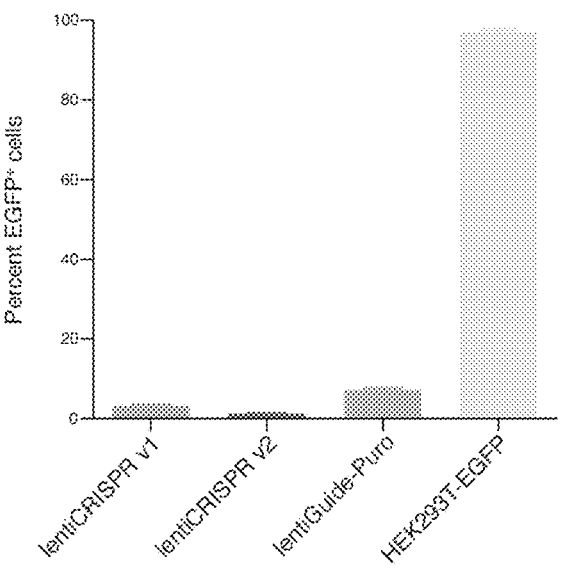

To further increase viral titer, Applicants also cloned a two vector system, in which the Cas9 nuclease and the sgRNA library are delivered in separate lentiviruses with separate antibiotic selection markers (FIG. 47A). The new lenti-Guide-Puro virus has a 127-fold increase in functional viral titer over the original lentiCRISPR v1 (FIG. 47B). The increased viral titers of lentiCRISPR v2 and lentiGuide-Puro will greatly reduce reagent costs for GeCKO screens and enable infection without the need for concentration of viral supernatant. Cas9-mediated gene knock-out of a genomically-integrated copy of EGFP is efficient with both new lentiCRISPR systems (FIG. 48).

In addition to the vector improvements, Applicants designed and synthesized new human and mouse genome GeCKO libraries (See Tables 2A, 2B, 3, 4, 5, 6, 7, 8 and 9). These new libraries have a uniform coverage of 6 sgRNAs for each gene with higher gene and exon coverage (Table M).

with the combined library (122,417 sgRNAs) with 6 sgRNAs per gene or with either sub-library. This flexibility allows use of a smaller sub-library in situations where cell numbers are limiting (eg. primary cells, in vivo screens) or both sub-libraries together for better coverage. Similar to the human genome-wide library, Applicants also designed a GeCKOv2 mouse library with 2 sub-libraries containing 3 sgRNAs for each gene. The human and mouse libraries have been cloned into lentiCRISPR v2 and lentiGuide-Puro and deep sequenced.

Lentiviral cloning and production: For determination of lentiCRISPR v1, lentiCRISPR v2, and lentiGuide-Puro viral titers, the following sgRNA targeting EGFP (with no known targets in the human genome) was cloned into all 3 lentiviral transfer vectors:

TABLE M

Comparison of new GeCKO v2 human and mouse sgRNA libraries with existing CRISPR libraries.

|  | Wang et al. (2014) library | Shalem et al. (2014) GeCKO v1 library | Yusa et al. (2014) library | GeCKO v2 human library | GeCKO v2 mouse library |
| --- | --- | --- | --- | --- | --- |
| Species | human | human | mouse | human | mouse |
| Number of genes targeted | 7,114 | 18,080 | 19,150 | 19,052 | 20,661 |
| Targeting constructs per gene | 10 per gene | variable (typically 3 to 4 per gene) | variable (typically 4 to 5 per gene) | 6 per gene (3 in Library A, 3 in Library B) | 6 per gene (3 in Library A, 3 in Library B) |
| Number of miRNA targeted | none | none | none | 1864 | 1175 |
| Targeting constructs per miRNA | n/a | n/a | n/a | 4 per miRNA | 4 per miRNA |
| Control (non-targeting) sgRNAs | 100 | none | none | 1000 | 1000 |
| Total sgRNA constructs | 73,151 | 64,751 | 87,897 | 122,417 (65,386 in Library A, 58,031 in Library B) | 130,209 (67,405 in Library A, 62,804 in Library B) |
| Viral plasmid vector | Dual vector: sgRNA only | Single vector: Cas9 and sgRNA (lentiCRISPR v1) | Dual vector: sgRNA only | Single and dual vector: lentiCRISPR v2 and lentiGuide-Puro | Single and dual vector: lentiCRISPR v2 and lentiGuide-Puro |

New GeCKO libraries target an increased number of genes with uniform coverage (6 sgRNAs per gene divided into sub-libraries with 3 sgRNAs per gene—see Tables 3, 4, 7 and 8). The GeCKO v2 libraries also contain sgRNAs that target microRNAs (Tables 5 and 9) and control sgRNAs (Tables 2A, 2B and 6) that do not target in the genome. The libraries have been cloned into lentiCRISPR v2 (which includes Cas9 in the same vector) and lentiGuide-Puro (sgRNA-only vector) and are available in either format.

Applicants also improved the calculation of off-target scores based on recent empirical data and added sgRNAs to target micro RNAs (miRNAs) by directing mutations to the mature hairpin structure. The GeCKOv2 human library described in the Example now covers 19,052 genes, which is almost 1,000 genes more than the original GeCKO library described in Example 9. The library is divided into 2 sub-libraries (A and B). Each sub-library contains 3 sgRNAs for all genes and 1000 control sgRNAs that do not target any sequence in the genome. Library A also contains 7288 sgRNAs to target 1864 miRNAs. Screens can be performed EGFP sgRNA
(SEQ ID NO: 73)
GGGCGAGGAGCTGTTCACCG To clone the sgRNA guide sequence, plasmids were cut and dephosporylated with FastDigest BsmBI and FastAP (Fermentas) at 37° C. for 2 hours. Oligonucleotides for the EGFP sgRNA guide sequence (Integrated DNA Technologies) were phosphorylated using polynucleotide kinase (Fermentas) at 37° C. for 30 minutes and then annealed by heating to 95° C. for 5 minutes and cooling to 25° C. at 1.5° C./minute. Using T7 ligase (Enzymatics), annealed oligos were ligated into gel purified vectors (Qiagen) at 25° C. for 5 minutes. Cloned transfer plasmids were amplified using a endotoxin-free midi-prep kit (Qiagen).

To make lentivirus, the transfer plasmids were co-transfected with packaging plasmids pMD2.G and psPAX2 (Addgene plasmids 12259 and 12260), as described previously in Shalem, O. et al. Genome-scale CRISPR-Cas9 knockout screening in human cells. Science 343, 84-87 (2014). Briefly, for each virus, a T-75 flask of 80% confluent HEK293T cells was transfected in OptiMEM (Life Technologies) using 10 ug of the transfer plasmid, 5 ug pMD2.G, 7.5 ug psPAX2, 100 ul of Plus Reagent (Life Technologies), and 50 ul of Lipofectamine 2000 (Life Technologies). After 6 hours, media was changed to D10 media, DMEM (Life Technologies) with 10% fetal bovine serum (Hyclone), with 1% bovine serum albumin (Sigma) added to improve virus stability. After 60 hours, viral supernatants were harvested and centrifuged at 3,000 rpm at 4° C. for 10 min to pellet cell debris. The supernatant was filtered through a 0.45 urn low protein binding membrane (Millipore) and used immediately.

Lentiviral functional titration: Lentiviruses were titered in a functional assay by measuring puromycin resistance after transduction. For each viral construct, $2.5 \times 10^4$ HEK293T-EGFP cells were transduced in suspension (i.e. during plating) with 10, 100, or 1000 ul of viral supernatant in wells of a 24-well plate. For lentiGuide-Puro transduction the HEK293T-EGFP cells also had a genomically-integrated copy of Cas9 from previous transduction with lentiCas9-Blast. Each transduction condition (construct and virus volume) was performed in triplicate. In each well, D10 culture media was added to make the final volume 1.5 ml. Cell without any virus added were also plated in six wells (3 wells for puromycin treatment, 3 wells as control).

At 24 hours post-transduction, media was changed to D10 with 1 ug/ml puromycin (Sigma) for all wells except the uninfected controls without puromycin. At 3 days post-transduction, cells in all wells were split 1:5 to prevent any well from reaching confluence. Except for the uninfected controls without puromycin, new D10 media was supplemented with 1 ug/ul puromycin. At 5 days post-transduction, all cells in the uninfected control wells treated with puromycin were floating/dead, which was verified using Trypan Blue exclusion (Sigma).

For the remaining wells, adherent cells were present and cell viability was measured using CellTiter Glo (Promega) following the manufacturer's protocol. After allowing cells to reach room temperature, media was aspirated from the cells and CellTiter Glo (diluted 1:1 in phosphate-buffered saline) was added. Plates were covered with foil, placed on an orbital shaker for 2 min, and then incubated for 10 minutes at room temperature. Luminescence was read out on an Synergy H4 plate imager (Biotek) using a 1 second integration time and auto-gain to utilize the full dynamic range of the detector. Positive controls (untranduced cells without puromycin) and negative controls (empty wells) were included in the assay.

Fold differences in titer between viral constructs were calculated using luminescence values. Specifically, comparisons were made between pairs of viruses for the same volume of supernatant. Only viral volumes for which cell survival was greater than 1% and less than 20% of control (untransduced) cells were directly compared. Assuming Poisson statistics, 20% cell survival imples that approximately 90% of cells surviving puromycin selection were infected by only a single virus.

Flow cytometry data was collected from the same set of infections using a BD Accuri C6 flow cytometer. Using FlowJo (TreeStar), cells were distinguished from debris and doublets by gating in forward vs. side scatter area plots. EGFP fluorescence was measured in the gated population from transduced and uninfected HEK293T-EGFP cells.

Design of new GeCKO libraries: Genome wide sgRNA libraries for the human and mouse genomes were designed using the following steps:

(1) Identification of conserved exons: For the human library, RNA sequencing data from the Illumina Human Body Map 2.0 (GEO accession number: GSE30611) was mapped to the reference human genome (hg19) using TopHat v1.0.14 and transcripts were reconstructed with Cufflinks v1.0.2. Exons expressed across all tissues in the Illumina dataset were chosen as constitutive exons for sgRNA targeting. In addition, for each gene, the first and last exons were excluded along with any exon that contained an alternative splicing site. For the mouse library, Applicants chose constitutive exons as exons that are shared by all RefGene (available at the website refgene.com/) transcripts for the same gene. Applicants then chose for each gene, 4 constitutive exons for targeting, in cases where there are not enough constitutive exons Applicants added exons starting from the second coding constitutive exon towards the end of the gene. In both mouse and human coding exons where identified using the CCDS database (available at the website ncbi.nlm.nih.gov/CCDS/CcdsBrowse.cgi).

(2) Choice of sgRNA sequences: For each candidate exon, all possible S. pyogenes Cas9 sgRNA sequences of the form $(N)_{20}$NGG were listed as candidate targets. Each 20mer candidate sgRNA was mapped to a precompiled index containing all 20mer sequences in the human genome followed by either NGG or NAG. This mapping was done using Bowtie short read aligner, allowing up to 3 base mismatches.

Off target score was calculated as follows, as described in Hsu, P. D. et al. DNA targeting specificity of RNA-guided Cas9 nucleases. Nat Biotechnol 31, 827-832 (2013): For a single off-target position:

$$\prod_{n \in M} (1 - W[e]) \times \frac{1}{\left(\frac{(19-d)}{19} \times 4 + 1\right)} \times \frac{1}{n_{mm}^2}$$

Then these are aggregated as follows:

$$S_{guide} = \frac{100}{100 + \sum_{i=1}^{n_{mm}} S_{hit}(h_i)}$$

W: weight of the location of base mismatch (from Hsu, P. D. et al. DNA targeting specificity of RNA-guided Cas9 nucleases. Nat Biotechnol 31, 827-832 (2013)).
d: mean pairwise distance between mismatches.
$n_{mm}$: number of mutations
$s_{hit}(h_i)$: the score for a single off-target
Applicants then chose for each gene 6 sgRNAs such that there were no more than 2 sgRNAs per exon.

(3) Targeting of mature miRNAs: For the design of miRNA targeting guides Applicants took the hairpin miRNA sequence coordinates from the mirBASE database (available at the website mirbase.org). Applicants then listed all the possible $(N)_{20}$NGG sequences and chose 4 sgRNAs per miRNA preferentially choosing sgRNAs that target the stem region in the stem loop.

GeCKO library pooled synthesis and cloning: DNA oligonucleotide library synthesis was completed on a programmable microarray using a B3 Synthesizer (CustomArray) and SAFC Proligo reagents (Sigma), as recommended by the manufacturer. The synthesis products were cleaved from the microarray and deprotected by overnight incubation in 28-30% ammonium hydroxide at 65° C., dried, resuspended in 30 ul TE buffer and then purified using a QIAquick spin column (Qiagen). Full-length oligonucleotides (74 nt) were amplified by PCR using Phusion HS Flex (NEB). For the PCR reaction, the manufacturer's protocol was followed using 0.1 ul of synthesized oligonucleotide template, primers Array F and ArrayR (see below), an annealing temperature of 63° C., an extension time of 15 s, and 20 cycles. After PCR, the 140 bp amplicon was size-selected using a 2% agarose E-Gel EX (Life Technologies, Qiagen).

ArrayF
(SEQ ID NO: 77)
TAACTTGAAAGTATTTCGATTTCTTGGCTTTATATATCTTGTGGAAAGG
AC GAAACACCG ArrayR
(SEQ ID NO: 78)
ACTTTTTCAAGTTGATAACGGACTAGCCTTATTTTAACTTGCTATTTCT
AGCTCTAAAAC The vector backbone (lentiCRISPR v2 or lentiGuide-Puro) was digested with BsmBI (Fermentas) and treated with FastAP (Fermentas) at 37° C. for 2 hours and gel-purified on a 1% E-Gel EX (Life Technologies, Qiagen). A 20 ul Gibson ligation reaction (NEB) was performed using 10 ng of the gel-purified inserts and 25 ng of the vector (for lentiCRISPR v2) and using 5 ng of the gel-purified inserts and 25 ng of the vector (for lentiGuide-Puro). From the ligation, 0.5 ul of the reaction was transformed into 25 ul of electrocompetent cells (Lucigen) according to the manufacturer's protocol using a GenePulser (BioRad). To ensure no loss of representation, sufficient parallel transformations were performed using the same ligation reaction and plated onto 245 mm×245 mm plates (Corning) with carbenicillin selection (50 ug/ml), which yielded 30-200× library coverage. Colonies were scraped off plates and combined before plasmid DNA extraction using Endotoxin-Free Plasmid Maxiprep (Qiagen).

Library sequencing and validation: To check library representation, synthesis fidelity, and bias, libraries were amplified and then deep sequenced. First, libraries were PCR amplified for 16 cycles using Phusion Flash High-Fidelity (Thermo) with primers to add adaptors for Illumina sequencing. For all libraries, PCR reactions were performed in duplicate and barcoded to allow quantification of bias introduced by PCR. Samples were sequenced on a MiSeq following the manufacturer's protocol using a v3 150 cycle kit with 10% PhiX (Illumina).

PCR replicates were demultiplexed using FASTX-Toolkit (Hannon Lab, CSHL) and adaptors were trimmed using cutadapt to leave only the sgRNA guide sequence. Alignment of the guide sequence to the appropriate GeCKO library index was done using Bowtie with parameters to tolerate up to a single nucleotide mismatch. The Bowtie alignment was then read into Matlab for further analysis (Mathworks). For all libraries, greater than 90% of sgRNAs were represented with at least one sequencing read and the difference in representation between the 90$^{th}$ and 10$^{th}$ percentile sgRNAs was always less than 10-fold.

Vector maps and reagent distribution: All lentiCRISPR plasmids (FIGS. 49, 50 and 51) and GeCKO libraries are available on Addgene and vector maps are available at the website genome-engineering.org/gecko/.

Design specification on changes between lentiCRISPRv1 and lentiCRISPRv2 are indicated below. The lentiCRISPRv2 encompasses the following aspects:

Novel hybrid LKO/FUGW design
  5' lenti elements and backbone are from FUGW,
  3' lenti elements are from LKO (Applicants took this approach because the 3' lenti elements in LKO have less wasted space after WPRE)
Human codon-optimized FLAG tag was moved to C term of Cas9
Removed N-terminal NLS
Removed 2 residue linker between Cas9 and 2A
  A convenient restriction site (BamHI) is now integrated at beginning of 2A sequence
Unique human codon-optimized NLS
Unique human codon-optimized P2A
Moved U6 Pol3 cassette to after cPPT. Now directly upstream of EFS Pol2 cassette.
Enzyme sites for easy modular removal of Pol3 cassette, Pol2 promoter, Cas9 CDS LTR-LTR distance is now 8.2 kb: This is >100 bp shorter than the lentiCRISPRv1 vector.

Applicants have shown that these improved lentiCRISPR vectors and human and mouse libraries will make it easier to perform GeCKO screens with enhanced lentiviral delivery options and greater choice over library size for different screening applications.

Example 11: Generation of Gene Knockout Cell Library

This example demonstrates how to generate a library of cells where each cell has a single gene knocked out:

Applicants make a library of ES cells where each cell has a single gene knocked out, and the entire library of ES cells will have every single gene knocked out. This library is useful for the screening of gene function in cellular processes as well as diseases.

To make this cell library, Applicants integrate Cas9 driven by an inducible promoter (e.g. doxycycline inducible promoter) into the ES cell. In addition, Applicants integrate a single guide RNA targeting a specific gene in the ES cell. To make the ES cell library, Applicants simply mix ES cells with a library of genes encoding guide RNAs targeting each gene in the human genome. Applicants first introduce a single BxB1 attB site into the AAVS1 locus of the human ES cell. Then Applicants use the BxB1 integrase to facilitate the integration of individual guide RNA genes into the BxB1 attB site in AAVS1 locus. To facilitate integration, each guide RNA gene is contained on a plasmid that carries of a single attP site. This way BxB1 will recombine the attB site in the genome with the attP site on the guide RNA containing plasmid.

To generate the cell library, Applicants take the library of cells that have single guide RNAs integrated and induce Cas9 expression. After induction, Cas9 mediates double strand break at sites specified by the guide RNA. To verify the diversity of this cell library, Applicants carry out whole exome sequencing to ensure that Applicants are able to observe mutations in every single targeted gene. This cell library can be used for a variety of applications, including who library-based screens, or can be sorted into individual cell clones to facilitate rapid generation of clonal cell lines with individual human genes knocked out.

Example 12: Plasmid Genome-Wide Libraries Comprising a Plurality of Unique Guide Sequences The following plasmid libraries were deposited with ATCC on Jun. 10, 2014:

GeCKO1—library of sgRNA plasmids each encoding selected guide sequences and cloned into vector (lentiCRISPRv2)—ATCC Deposit No. PTA121339;

GeCKO2—half library A (human) sgRNA plasmids each encoding selected guide sequences and cloned into vector—ATCC Deposit No. PTA121340;

GeCKO2—half library B (human) of sgRNA plasmids each encoding selected guide sequences and cloned into vector—ATCC Deposit No. PTA121341;

GeCKO2—half library A (mouse) sgRNA plasmids each encoding selected guide sequences and cloned into vector—ATCC Deposit No. PTA121342; and GeCKO2—half library A (mouse) sgRNA plasmids each encoding selected guide sequences and cloned into vector—ATCC Deposit No. PTA121343.

The deposited libraries comprise pool of vectors each comprising sequence encoding a individual guide sequence of library useful according to the present invention, namely that may be used in the libraries, methods and/or kits of the present invention. The guide sequences are capable of targeting a plurality of target sequences in genomic loci, wherein the targeting results in a KO of gene function.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES (CONTENTS OF WHICH ARE INCORPORATED HEREIN IN THEIR ENTIRETY)

1. Urnov, F. D., Rebar, E. J., Holmes, M. C., Zhang, H. S. & Gregory, P. D. Genome editing with engineered zinc finger nucleases. *Nat. Rev. Genet.* 11, 636-646 (2010).
2. Bogdanove, A. J. & Voytas, D. F. TAL effectors: customizable proteins for DNA targeting. *Science* 333, 1843-1846 (2011).
3. Stoddard, B. L. Homing endonuclease structure and function. *Q. Rev. Biophys.* 38, 49-95 (2005).
4. Bae, T. & Schneewind, O. Allelic replacement in *Staphylococcus aureus* with inducible counter-selection. *Plasmid* 55, 58-63 (2006).
5. Sung, C. K., Li, H., Claverys, J. P. & Morrison, D. A. An rpsL cassette, janus, for gene replacement through negative selection in *Streptococcus pneumoniae*. *Appl. Environ. Microbiol.* 67, 5190-5196 (2001).
6. Sharan, S. K., Thomason, L. C., Kuznetsov, S. G. & Court, D. L. Recombineering: a homologous recombination-based method of genetic engineering. *Nat. Protoc.* 4, 206-223 (2009).
7. Jinek, M. et al. A programmable dual-RNA-guided DNA endonuclease in adaptive bacterial immunity. *Science* 337, 816-821 (2012).
8. Deveau, H., Garneau, J. E. & Moineau, S. CRISPR/Cas system and its role in phage-bacteria interactions. *Annu. Rev. Microbiol.* 64, 475-493 (2010).
9. Horvath, P. & Barrangou, R. CRISPR/Cas, the immune system of bacteria and archaea. *Science* 327, 167-170 (2010).
10. Terns, M. P. & Terns, R. M. CRISPR-based adaptive immune systems. *Curr. Opin. Microbiol* 4, 321-327 (2011).
11. van der Oost, J., Jore, M. M., Westra, E. R., Lundgren, M. & Brouns, S. J. CRISPR-based adaptive and heritable immunity in prokaryotes. *Trends. Biochem. Sci.* 34, 401-407 (2009).
12. Brouns, S. J. et al. Small CRISPR RNAs guide antiviral defense in prokaryotes. *Science* 321, 960-964 (2008).
13. Carte, J., Wang, R., Li, H., Terns, R. M. & Terns, M. P. Cas6 is an endoribonuclease that generates guide RNAs for invader defense in prokaryotes. *Genes Dev.* 22, 3489-3496 (2008).
14. Deltcheva, E. et al. CRISPR RNA maturation by trans-encoded small RNA and host factor RNase III. *Nature* 471, 602-607 (2011).
15. Hatoum-Aslan, A., Maniv, I. & Marraffini, L. A. Mature clustered, regularly interspaced, short palindromic repeats RNA (crRNA) length is measured by a ruler mechanism anchored at the precursor processing site. *Proc. Natl. Acad. Sci. U.S.A.* 108, 21218-21222 (2011).
16. Haurwitz, R. E., Jinek, M., Wiedenheft, B., Zhou, K. & Doudna, J. A. Sequence- and structure-specific RNA processing by a CRISPR endonuclease. *Science* 329, 1355-1358 (2010).
17. Deveau, H. et al. Phage response to CRISPR-encoded resistance in *Streptococcus thermophilus*. *J. Bacteria* 190, 1390-1400 (2008).
18. Gasiunas, G., Barrangou, R., Horvath, P. & Siksnys, V. Cas9-crRNA ribonucleoprotein complex mediates specific DNA cleavage for adaptive immunity in bacteria. *Proc. Natl. Acad. Sci. U.S.A.* (2012).
19. Makarova, K. S., Aravind, L., Wolf, Y. I. & Koonin, E. V. Unification of Cas protein families and a simple scenario for the origin and evolution of CRISPR-Cas systems. *Biol. Direct.* 6, 38 (2011).
20. Barrangou, R. RNA-mediated programmable DNA cleavage. *Nat. Biotechnol.* 30, 836-838 (2012).
21. Brouns, S. J. Molecular biology. A Swiss army knife of immunity. *Science* 337, 808-809 (2012).
22. Carroll, D. A CRISPR Approach to Gene Targeting. *Mol. Ther.* 20, 1658-1660 (2012).
23. Bikard, D., Hatoum-Aslan, A., Mucida, D. & Marraffini, L. A. CRISPR interference can prevent natural transformation and virulence acquisition during in vivo bacterial infection. *Cell Host Microbe* 12, 177-186 (2012).
24. Sapranauskas, R. et al. The *Streptococcus thermophilus* CRISPR/Cas system provides immunity in *Escherichia coli*. *Nucleic Acids Res*. (2011).
25. Semenova, E. et al. Interference by clustered regularly interspaced short palindromic repeat (CRISPR) RNA is governed by a seed sequence. *Proc. Natl. Acad. Sci. U.S.A.* (2011).
26. Wiedenheft, B. et al. RNA-guided complex from a bacterial immune system enhances target recognition through seed sequence interactions. *Proc. Natl. Acad. Sci. U.S.A.* (2011).
27. Zahner, D. & Hakenbeck, R. The *Streptococcus pneumoniae* beta-galactosidase is a surface protein. *J. Bacteriol.* 182, 5919-5921 (2000).
28. Marraffini, L. A., Dedent, A. C. & Schneewind, O. Sortases and the art of anchoring proteins to the envelopes of gram-positive bacteria. *Microbiol. Mol. Biol. Rev.* 70, 192-221 (2006).
29. Motamedi, M. R., Szigety, S. K. & Rosenberg, S. M. Double-strand-break repair recombination in *Escherichia*

29. *coli*: physical evidence for a DNA replication mechanism in vivo. *Genes Dev.* 13, 2889-2903 (1999).
30. Hosaka, T. et al. The novel mutation K87E in ribosomal protein S12 enhances protein synthesis activity during the late growth phase in *Escherichia coli*. *Mol. Genet. Genomics* 271, 317-324 (2004).
31. Costantino, N. & Court, D. L. Enhanced levels of lambda Red-mediated recombinants in mismatch repair mutants. *Proc. Natl. Acad. Sci. U.S.A.* 100, 15748-15753 (2003).
32. Edgar, R. & Qimron, U. The *Escherichia coli* CRISPR system protects from lambda lysogenization, lysogens, and prophage induction. *J. Bacteria* 192, 6291-6294 (2010).
33. Marraffini, L. A. & Sontheimer, E. J. Self versus non-self discrimination during CRISPR RNA-directed immunity. *Nature* 463, 568-571 (2010).
34. Fischer, S. et al. An archaeal immune system can detect multiple Protospacer Adjacent Motifs (PAMs) to target invader DNA. *J. Biol. Chem.* 287, 33351-33363 (2012).
35. Gudbergsdottir, S. et al. Dynamic properties of the *Sulfolobus* CRISPR/Cas and CRISPR/Cmr systems when challenged with vector-borne viral and plasmid genes and protospacers. *Mol. Microbiol.* 79, 35-49 (2011).
36. Wang, H. H. et al. Genome-scale promoter engineering by coselection MAGE. *Nat Methods* 9, 591-593 (2012).
37. Cong, L. et al. Multiplex Genome Engineering Using CRISPR/Cas Systems. *Science* 339, 819 (Feb. 15, 2013).
38. Mali, P. et al. RNA-Guided Human Genome Engineering via Cas9. *Science* 339, 823 (Feb. 15, 2013).
39. Hoskins, J. et al. Genome of the bacterium *Streptococcus pneumoniae* strain R6. *J. Bacteriol.* 183, 5709-5717 (2001).
40. Havarstein, L. S., Coomaraswamy, G. & Morrison, D. A. An unmodified heptadecapeptide pheromone induces competence for genetic transformation in *Streptococcus pneumoniae*. *Proc. Natl. Acad. Sci. U.S.A.* 92, 11140-11144 (1995).
41. Horinouchi, S. & Weisblum, B. Nucleotide sequence and functional map of pC194, a plasmid that specifies inducible chloramphenicol resistance. *J. Bacteriol.* 150, 815-825 (1982).
42. Horton, R. M. In Vitro Recombination and Mutagenesis of DNA: SOEing Together Tailor-Made Genes. *Methods Mol. Biol.* 15, 251-261 (1993).
43. Podbielski, A., Spellerberg, B., Woischnik, M., Pohl, B. & Lutticken, R. Novel series of plasmid vectors for gene inactivation and expression analysis in group A streptococci (GAS). *Gene* 177, 137-147 (1996).
44. Husmann, L. K., Scott, J. R., Lindahl, G. & Stenberg, L. Expression of the Arp protein, a member of the M protein family, is not sufficient to inhibit phagocytosis of *Streptococcus pyogenes*. *Infection and immunity* 63, 345-348 (1995).
45. Gibson, D. G. et al. Enzymatic assembly of DNA molecules up to several hundred kilobases. *Nat Methods* 6, 343-345 (2009).
46. Garneau J. E. et al. The CRISPR/Cas bacterial immune system cleaves bacteriophage and plasmid DNA. *Nature* 468, 67-71 (4 Nov. 2010)
47. Barrangou R. et al. CRISPR provides acquired resistance against viruses in prokaryotes. Science. 2007 Mar. 23; 315(5819):1709-12.
48. Ishino Y. et al. Nucleotide sequence of the iap gene, responsible for alkaline phosphatase isozyme conversion in *Escherichia coli*, and identification of the gene product. J Bacteriol. 1987 December; 169(12):5429-33.
49. Mojica F. J. M et al. Biological significance of a family of regularly spaced repeats in the genomes of Archaea, Bacteria and mitochondria. Molecular Microbiology (2000) 36(1), 244-246.
50. Jansen R. et al. Identification of genes that are associated with DNA repeats in prokaryotes. Molecular Microbiology (2002) 43(6), 1565-1575.
51. Luo B et al., Highly parallel identification of essential genes in cancer cells. Proc Natl Acad Sci USA. 2008 Dec. 23; 105(51):20380-5
52. Paddison P J et al., A resource for large-scale RNA-interference-based screens in mammals. Nature. 2004 Mar. 25; 428(6981):427-31
53. Berns K et al., A large-scale RNAi screen in human cells identifies new components of the p53 pathway, Nature. 2004 Mar. 25; 428(6981):431-7
54. Moffat J et al., A lentiviral RNAi library for human and mouse genes applied to an arrayed viral high-content screen. Cell. 2006 Mar. 24; 124(6):1283-98.
55. Zeng Y et al., Both natural and designed micro RNAs can inhibit the expression of cognate mRNAs when expressed in human cells. Mol Cell. 2002 June; 9(6): 1327-33.
56. Hemann et al., An epi-allelic series of p53 hypomorphs created by stable RNAi produces distinct tumor phenotypes in vivo. Nat Genet. 2003 March; 33(3):396-400. Epub 2003 Feb. 3.
57. Stewart S A et al., Lentivirus-delivered stable gene silencing by RNAi in primary cells. RNA. 2003 April; 9(4):493-501.
58. Brummelkamp T R et al., A system for stable expression of short interfering RNAs in mammalian cells. Science. 2002 Apr. 19; 296(5567):550-3. Epub 2002 Mar. 21.
59. E. S. Lander, Initial impact of the sequencing of the human genome. Nature 470, 187 (Feb. 10, 2011).
60. V. N. Ngo et al., A loss-of-function RNA interference screen for molecular targets in cancer. Nature 441, 106 (Apr. 29, 2006).
61. M. Boutros et al., Genome-wide RNAi analysis of growth and viability in *Drosophila* cells. Science 303, 832 (Feb. 6, 2004).
62. R. Rad et al., PiggyBac transposon mutagenesis: a tool for cancer gene discovery in mice. Science 330, 1104 (Nov. 19, 2010).
63. A. H. Tong et al., Global mapping of the yeast genetic interaction network. Science 303, 808 (Feb. 6, 2004).
64. J. E. Carette et al., Haploid genetic screens in human cells identify host factors used by pathogens. Science 326, 1231 (Nov. 27, 2009).
65. A. L. Jackson et al., Widespread siRNA "off-target" transcript silencing mediated by seed region sequence complementarity. Rna 12, 1179 (July, 2006).
66. W. G. Kaelin, Use and Abuse of RNAi to Study Mammalian Gene Function. Science 337, 421 (Jul. 26, 2012).
67. C. J. Echeverri et al., Minimizing the risk of reporting false positives in large-scale RNAi screens. Nature methods 3, 777 (October, 2006).
68. S. Konermann et al., Optical control of mammalian endogenous transcription and epigenetic states. Nature 500, 472 (Aug. 22, 2013).
69. L. A. Gilbert et al., CRISPR-Mediated Modular RNA-Guided Regulation of Transcription in Eukaryotes. Cell, (July, 2013).
70. P. Perez-Pinera et al., RNA-guided gene activation by CRISPR-Cas9—based transcription factors. Nature methods, (Jul. 25, 2013).

71. M. L. Maeder et al., CRISPR RNA—guided activation of endogenous human genes. Nature methods, (Jul. 25, 2013).
72. A. P. Blanchard, L. Hood, Sequence to array: probing the genome's secrets. Nat Biotechnol 14, 1649 (December, 1996).
73. P. D. Hsu et al., DNA targeting specificity of RNA-guided Cas9 nucleases. Nat Biotechnol 31, 827 (September, 2013).
74. A. Subramanian et al., Gene set enrichment analysis: a knowledge-based approach for interpreting genome-wide expression profiles. Proc Natl Acad Sci USA 102, 15545 (Oct. 25, 2005).
75. C. M. Johannessen et al., COT drives resistance to RAF inhibition through MAP kinase pathway reactivation. Nature 468, 968 (Dec. 16, 2010).
76. K. T. Flaherty et al., Inhibition of mutated, activated BRAF in metastatic melanoma. The New England journal of medicine 363, 809 (Aug. 26, 2010).
77. H. Davies et al., Mutations of the BRAF gene in human cancer. Nature 417, 949 (Jun. 27, 2002).
78. S. Huang et al., MED12 Controls the Response to Multiple Cancer Drugs through Regulation of TGF-β; Receptor Signaling. Cell 151, 937 (Nov. 21, 2012).
79. S. R. Whittaker et al., A Genome-Scale RNA Interference Screen Implicates NF1 Loss in Resistance to RAF Inhibition. Cancer Discovery 3, 350 (Apr. 7, 2013).
80. A. L. Lin, D. H. Gutmann, Advances in the treatment of neurofibromatosis-associated tumours. Nature reviews. Clinical oncology, (Aug. 13, 2013).
81. Y. Fu et al., High-frequency off-target mutagenesis induced by CRISPR-Cas nucleases in human cells. Nature Biotechnology, 1 (Jul. 23, 2013).
82. F. A. Ran et al., Double Nicking by RNA-Guided CRISPR Cas9 for Enhanced Genome Editing Specificity. Cell, 1 (Aug. 28, 2013).
83. C. Trapnell, L. Pachter, S. L. Salzberg, TopHat: discovering splice junctions with RNA-Seq. Bioinformatics 25, 1105 (May 1, 2009).
84. C. Trapnell et al., Differential gene and transcript expression analysis of RNA-seq experiments with TopHat and Cufflinks. Nature protocols 7, 562 (March, 2012).
85. J. Merkin, C. Russell, P. Chen, C. B. Burge, Evolutionary dynamics of gene and isoform regulation in Mammalian tissues. Science 338, 1593 (Dec. 21, 2012).
86. B. Langmead, C. Trapnell, M. Pop, S. L. Salzberg, Ultrafast and memory-efficient alignment of short DNA sequences to the human genome. Genome biology 10, R25 (2009).
87. P. Mali et al., CAS9 transcriptional activators for target specificity screening and paired nickases for cooperative genome engineering. Nat Biotechnol 31, 833 (September, 2013).
88. G. Giaever et al., Functional profiling of the *Saccharomyces cerevisiae* genome. Nature 418, 387 (2002).
89. M. Costanzo et al., The genetic landscape of a cell. Science 327, 425 (Jan. 22, 2010).
90. A. Fire et al., Potent and specific genetic interference by double-stranded RNA in *Caenorhabditis elegans*. Nature. 1998 Feb. 19; 391(6669):806-11.
91. H. W. Cheung et al., Systematic investigation of genetic vulnerabilities across cancer cell lines reveals lineage-specific dependencies in ovarian cancer. Proceedings of the National Academy of Sciences 108, 12372 (Jul. 26, 2011).
92. M. Booker et al., False negative rates in *Drosophila* cell-based RNAi screens: a case study, BMC Genomics 12, 50 (2011).
93. G. Guo, W. Wang, A. Bradley, Mismatch repair genes identified using genetic screens in Blm-deficient embryonic stem cells. Nature 429, 891 (2004).
94. K. Chylinski, A. Le Rhun, E. Charpentier, The tracrRNA and Cas9 families of type II CRISPR-Cas immunity systems. RNA Biology 10, 726 (2013).
95. W. Y. Hwang et al., Efficient genome editing in zebrafish using a CRISPR-Cas system. Nat Biotech 31, 227 (2013).
96. H. Wang et al., One-step generation of mice carrying mutations in multiple genes by CRISPR/Cas-mediated genome engineering. Cell 153, 910 (2013).
97. T. Horii, D. Tamura, S. Morita, M. Kimura, I. Hatada, Generation of an ICF Syndrome Model by Efficient Genome Editing of Human Induced Pluripotent Stem Cells Using the CRISPR System. International Journal of Molecular Sciences 14, 19774 (2013).
98. T. Yan, S. E. Berry, A. B. Desai, T. J. Kinsella, DNA mismatch repair (MMR) mediates 6-thioguanine genotoxicity by introducing single-strand breaks to signal a G2-M arrest in MMR-proficient RKO cells. Clinical Cancer Research 9, 2327 (Jun. 1, 2003, 2003).
99. R. D. Kolodner, G. T. Marsischky, Eukaryotic DNA mismatch repair. Current Opinion in Genetics & Development 9, 89 (1999).
100. D. J. Burgess et al., Topoisomerase levels determine chemotherapy response in vitro and in vivo. Proceedings of the National Academy of Sciences 105, 9053 (Jul. 1, 2008).
101. B. Scappini et al., Changes associated with the development of resistance to imatinib (STI571) in two leukemia cell lines expressing p210 Bcr/Abl protein. Cancer 100, 1459 (2004).
102. S. Xue, M. Barna, Specialized ribosomes: a new frontier in gene regulation and organismal biology. Nat Rev Mol Cell Biol 13, 355 (2012).
103. C. M. Johnston et al., Large-scale population study of human cell lines indicates that dosage compensation is virtually complete. PLoS Genet 4, e9 (2008).
104. Luke A. Gilbert et al., CRISPR-mediated modular RNA-guided regulation of transcription in eukaryotes. Cell 154, 442 (2013).
105. Lei S. Qi et al., Repurposing CRISPR as an RNA-guided platform for sequence-specific control of gene expression. Cell 152, 1173 (2013).
106. T. J. Cradick, E. J. Fine, C. J. Antico, G. Bao, CRISPR/Cas9 systems targeting β-globin and CCR5 genes have substantial off-target activity. Nucleic Acids Research, (Aug. 11, 2013).
107. J. M. Engreitz et al., The Xist lncRNA exploits three-dimensional genome architecture to spread across the X chromosome. Science. 2013 Aug. 16; 341(6147).
108. K. Yoshimoto et al., Complex DNA repair pathways as possible therapeutic targets to overcome temozolomide resistance in glioblastoma. Front Oncol. 2012 Dec. 5; 2:186.
109. X. Liu, M. Vorontchikhina, Y. L. Wang, F. Faiola, E. Martinez, STAGA recruits Mediator to the MYC oncoprotein to stimulate transcription and cell proliferation. Molecular and cellular biology 28, 108 (January, 2008).
110. B. Langmead, S. L. Salzberg, Fast gapped-read alignment with Bowtie 2. Nat Meth 9, 357-359 (2012).

111. S. S. Liu et al., Identification and characterization of a novel gene, clorf109, encoding a CK2 substrate that is involved in cancer cell proliferation. Journal of Biomedical Science 19, 49 (2012).
112. R. Renella et al., Codanin-1 mutations in congenital dyserythropoietic anemia type 1 affect HP1α localization in erythroblasts. Blood 117, 6928-6938 (2011).
113. S. H. Chen et al., A Knockout Mouse Approach Reveals that TCTP Functions as an Essential Factor for Cell Proliferation and Survival in a Tissue—or Cell Type—specific Manner. Molecular Biology of the Cell 18, 2525-2532 (2007).
114. C. Cayrol et al., The THAP-zinc finger protein THAP1 regulates endothelial cell proliferation through modulation of pRB/E2F cell-cycle target genes. Blood 109, 584-594 (2007).
115. B. Sonnichsen et al., Full-genome RNAi profiling of early embryogenesis in *Caenorhabditis elegans*. Nature 434, 462-469 (2005).
116. J. F. Rual et al., Toward Improving *Caenorhabditis elegans* Phenome Mapping With an ORFeome-Based RNAi Library. Genome Research 14, 2162-2168 (2004).
117. J L. Mummery-Widmer et al., Genome-wide analysis of Notch signalling in *Drosophila* by transgenic RNAi. Nature 458, 987-992 (2009).
118. A. C. Spradling et al., The Berkeley *Drosophila* Genome Project Gene Disruption Project: Single P-Element Insertions Mutating 25% of Vital *Drosophila* Genes. Genetics 153, 135-177 (1999).
119. A. Amsterdam et al. Identification of 315 genes essential for early zebrafish development. Proc Natl Acad Sci USA. 2004 Aug. 31; 101(35):12792-7.
120. Shalem, O. et al. Genome-scale CRISPR-Cas9 knockout screening in human cells. Science 343, 84-87 (2014).
121. Martin, M. Cutadapt removes adapter sequences from high-throughput sequencing reads. EMBnet.journal 17, 10-12 (2011).
122. Wang, T., Wei, J. J., Sabatini, D. M. & Lander, E. S. Genetic screens in human cells using the CRISPR-Cas9 system. Science 343, 80-84 (2014).
123. Koike-Yusa, H., Li, Y., Tan, E.-P., Velasco-Herrera, M. D. C. & Yusa, K. Genome-wide recessive genetic screening in mammalian cells with a lentiviral CRISPR-guide RNA library. Nat Biotechnol (2013). doi:10.1038/nbt.2800

What is claimed is:

1. A genome-wide screening method comprising knocking out in parallel a plurality of genes in a genome by a method which comprises:
introducing into a population of cells comprised in a single composition:
I. a plurality of CRISPR-Cas system guide polynucleotide sequences, each comprising a guide sequence that targets a DNA molecule encoding a gene product, and
II. a CRISPR-Cas protein or a polynucleotide sequence encoding the CRISPR-Cas protein,
wherein each guide sequence directs sequence-specific binding of a CRISPR complex to a target sequence in a genomic locus of the DNA molecule encoding the gene product,
wherein the CRISPR complex comprises a CRISPR-Cas protein complexed with a guide sequence that is hybridized to the target sequence,
wherein the CRISPR-Cas protein cleaves the genomic locus,
whereby each cell in the population of cells has a unique gene knocked out in parallel, and wherein each cell in the population of cells has a single CRISPR-Cas system guide polynucleotide sequence introduced therein,
wherein the CRISPR-Cas protein is a Cas9 protein, and
wherein the method further comprises selecting the population of cells for a phenotype by treating a population of cancer cells with a chemotherapy and obtaining cancer cells having resistance to the chemotherapy, performing sequencing to profile the depletion or enrichment of the CRISPR-Cas system guide polynucleotide sequences in selected cancer cells, and identifying one or more gene products associated with the resistance to the chemotherapy.

2. The method of claim 1, wherein the cell is a eukaryotic cell.

3. The method of claim 2, wherein the eukaryotic cell is an animal or a plant cell.

4. The method of claim 2, wherein the eukaryotic cell is a human cell.

5. The method of claim 1, wherein the CRISPR-Cas system guide polynucleotide sequence and the CRISPR-Cas protein are comprised in one or more vectors.

6. The method of claim 5, wherein the CRISPR-Cas system guide polynucleotide sequence and the CRISPR-Cas protein are comprised in one vector.

7. The method of claim 6, wherein the vector is a lentivirus, a adenovirus, or a AAV.

8. The method of claim 5, wherein the one or more vectors is a lentivirus, an adenovirus, or an adeno-associated virus (AAV).

9. The method of claim 1, wherein the targeting is of about 100 or more sequences.

10. The method of claim 1, wherein the Cas9 protein is *Streptococcus pyogenes* Cas9.

11. The method of claim 1, wherein the Cas9 is *Staphylococcus aureus* Cas9.

12. The method of claim 1, wherein the targeting is of about 1,000 or more sequences.

13. The method of claim 1, wherein the targeting is of about 20,000 or more sequences.

14. The method of claim 1, wherein the targeting is of about the entire genome.

15. The method of claim 1, wherein the method comprises performing sequencing to profile the depletion or enrichment of the CRISPR-Cas system guide polynucleotide sequences in the selected cells and using the depletion or enrichment of the CRISPR-Cas system guide polynucleotide sequences to identify one or more gene products associated with the phenotype.

* * * * *

SEQUENCE LISTING

```
<160> NUMBER OF SEQ ID NOS: 310

<210> SEQ ID NO 1
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 1
nnnnnnnnnn nnnnnnnnnn nnagaaw                                           27

<210> SEQ ID NO 2
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 2
nnnnnnnnnn nnnnagaaw                                                    19

<210> SEQ ID NO 3
<211> LENGTH: 27
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 3
nnnnnnnnnn nnnnnnnnnn nnagaaw                                         27

<210> SEQ ID NO 4
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other

<400> SEQUENCE: 4
nnnnnnnnnn nnnagaaw                                                   18

<210> SEQ ID NO 5
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 5
nnnnnnnnnn nnnnnnnnnn gttttgtac tctcaagatt tagaaataaa tcttgcagaa       60
gctacaaaga taaggcttca tgccgaaatc aacaccctgt cattttatgg cagggtgttt      120
tcgttattta attttt                                                     137

<210> SEQ ID NO 6
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 6
nnnnnnnnnn nnnnnnnnnn gttttgtac tctcagaaat gcagaagcta caaagataag       60
```

```
gcttcatgcc gaaatcaaca ccctgtcatt ttatggcagg gtgttttcgt tatttaattt    120
ttt                                                                  123

<210> SEQ ID NO 7
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 7
nnnnnnnnnn nnnnnnnnnn gttttgtac tctcagaaat gcagaagcta caaagataag      60
gcttcatgcc gaaatcaaca ccctgtcatt ttatggcagg gtgttttttt               110

<210> SEQ ID NO 8
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 8
nnnnnnnnnn nnnnnnnnnn gttttagagc tagaaatagc aagttaaaat aaggctagtc     60
cgttatcaac ttgaaaaagt ggcaccgagt cggtgctttt tt                       102

<210> SEQ ID NO 9
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 9
nnnnnnnnnn nnnnnnnnnn gttttagagc tagaaatagc aagttaaaat aaggctagtc     60
cgttatcaac ttgaaaaagt gttttttt                                        88

<210> SEQ ID NO 10
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 10
```

```
nnnnnnnnnn nnnnnnnnnn gttttagagc tagaaatagc aagttaaaat aaggctagtc    60
cgttatcatt tttttt                                                    76

<210> SEQ ID NO 11
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
gttttagagc ta                                                        12

<210> SEQ ID NO 12
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
tagcaagtta aaataaggct agtccgtttt t                                   31

<210> SEQ ID NO 13
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(22)
<223> OTHER INFORMATION: a, c, t, g, unknown or other

<400> SEQUENCE: 13
nnnnnnnnnn nnnnnnnnnn nnagaaw                                        27

<210> SEQ ID NO 14
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
guuuuagagc ua                                                        12

<210> SEQ ID NO 15
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
ggacatcgat gtcacctcca atgactaggg tgg                                 33
```

<210> SEQ ID NO 16
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
cattggaggt gacatcgatg tcctccccat tgg                                33

<210> SEQ ID NO 17
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
ggaagggcct gagtccgagc agaagaagaa ggg                                33

<210> SEQ ID NO 18
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
ggtggcgaga ggggccgaga ttgggtgttc agg                                33

<210> SEQ ID NO 19
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
atgcaggagg gtggcgagag gggccgagat tgg                                33

<210> SEQ ID NO 20
<211> LENGTH: 4677
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
tctttcttgc gctatgacac ttccagcaaa aggtagggcg ggctgcgaga cggcttcccg     60
gcgctgcatg caacaccgat gatgcttcga cccccgaag ctccttcggg gctgcatggg    120
cgctccgatg ccgctccagg gcgagcgctg tttaaatagc caggccccg attgcaaaga    180 cattatagcg agctaccaaa gccatattca aacacctaga tcactaccac ttctacacag    240
gccactcgag cttgtgatcg cactccgcta aggggcgcc tcttcctctt cgtttcagtc    300
acaacccgca aacatgtacc catacgatgt tccagattac gcttcgccga agaaaaagcg    360

```
caaggtcgaa gcgtccgaca agaagtacag catcggcctg acatcggca ccaactctgt      420 gggctgggcc gtgatcaccg acgagtacaa ggtgcccagc aagaaattca aggtgctggg      480
caacaccgac cggcacagca tcaagaagaa cctgatcgga gccctgctgt cgacagcgg      540 cgaaacagcc gaggccaccc ggctgaagag aaccgccaga agaagataca ccagacggaa      600
gaaccggatc tgctatctgc aagagatctt cagcaacgag atggccaagg tggacgacag      660
cttcttccac agactggaag agtccttcct ggtggaagag ataagaagc acgagcggca      720 ccccatcttc ggcaacatcg tggacgaggt ggcctaccac agaagtacc ccaccatcta      780 ccacctgaga aagaaactgg tggacagcac cgacaaggcc gacctgcggc tgatctatct      840
ggccctggcc cacatgatca agttccgggg ccacttcctg atcgagggcg acctgaaccc      900
cgacaacagc gacgtggaca gctgttcat ccagctggtg cagacctaca ccagctgtt      960 cgaggaaaac cccatcaacg ccagcggcgt ggacgccaag gccatcctgt ctgccagact     1020
gagcaagagc agacggctgg aaaatctgat cgcccagctg cccggcgaga agaagaatgg     1080
cctgttcggc aacctgattg ccctgagcct gggcctgacc cccaacttca gagcaactt     1140 cgacctggcc gaggatgcca aactgcagct gagcaaggac acctacgacg acgacctgga     1200
caacctgctg gcccagatcg gcgaccagta cgccgacctg tttctggccg ccaagaacct     1260
gtccgacgcc atcctgctga gcgacatcct gagagtgaac accgagatca ccaaggcccc     1320
cctgagcgcc tctatgatca agatacga cgagcaccac caggacctga ccctgctgaa     1380
agctctcgtg cggcagcagc tgcctgagaa gtacaaagag atttcttcg accagagcaa     1440 gaacggctac gccggctaca ttgacggcgg agccagccag gaagagttct acaagttcat     1500
caagcccatc ctggaaaaga tggacggcac cgaggaactg ctcgtgaagc tgaacagaga     1560
ggacctgctg cggaagcagc ggaccttcga caacggcagc atccccacc agatccacct     1620 gggagagctg cacgccattc tgcggcggca ggaagatttt tacccattcc tgaaggacaa     1680
ccgggaaaag atcgagaaga tcctgacctt ccgcatcccc tactacgtgg gccctctggc     1740
caggggaaac agcagattcg cctggatgac cagaaagagc gaggaaaacca tcaccccctg     1800 gaacttcgag gaagtggtgg acaagggcgc ttccgcccag agcttcatcg agcggatgac     1860
caacttcgat aagaacctgc caacgagaa ggtgctgccc aagcacagcc tgctgtacga     1920
gtacttcacc gtgtataacg agctgaccaa agtgaaatac gtgaccgagg aatgagaaa     1980 gcccgccttc ctgagcggcg agcagaaaaa ggccatcgtg gacctgctgt tcaagaccaa     2040
ccggaaagtg accgtgaagc agctgaaaga ggactacttc aagaaaatcg agtgcttcga     2100
ctccgtggaa atctccggcg tggaagatcg gttcaacgcc tccctgggca taccacga     2160 tctgctgaaa attatcaagg acaaggactt cctggacaat gaggaaaacg aggacattct     2220
ggaagatatc gtgctgaccc tgacactgtt tgaggacaga gagatgatcg aggaacggct     2280
gaaaacctat gcccacctgt tcgacgacaa agtgatgaag cagctgaagc ggcggagata     2340
caccggctgg ggcaggctga gccggaagct gatcaacggc atccgggaca gcagtccgg     2400 caagacaatc ctggatttcc tgaagtccga cggcttcgcc aacagaaact tcatgcagct     2460
gatccacgac gacagcctga cctttaaaga ggacatccag aaagcccagg tgtccggcca     2520
gggcgatagc ctgcacgagc acattgccaa tctggccggc agcccgccca ttaagaaggg     2580
catcctgcag acagtgaagg tggtggacga gctcgtgaaa gtgatgggcc ggcacaagcc     2640
cgagaacatc gtgatcgaaa tggccagaga gaaccagacc acccagaagg gacagaagaa     2700
```
cagccgcgag agaatgaagc ggatcgaaga gggcatcaaa gagctgggca gccagatcct    2760
gaaagaacac cccgtggaaa acacccagct gcagaacgag aagctgtacc tgtactacct    2820
gcagaatggg cgggatatgt acgtggacca ggaactggac atcaaccggc tgtccgacta    2880
cgatgtggac catatcgtgc ctcagagctt tctgaaggac gactccatcg acaacaaggt    2940
gctgaccaga agcgacaaga accggggcaa gagcgacaac gtgccctccg aagaggtcgt    3000
gaagaagatg aagaactact ggcggcagct gctgaacgcc aagctgatta cccagagaaa    3060
gttcgacaat ctgaccaagg ccgagagagg cggcctgagc gaactggata aggccggctt    3120
catcaagaga cagctggtgg aaacccggca gatcacaaag cacgtggcac agatcctgga    3180
ctcccggatg aacactaagt acgacgagaa tgacaagctg atccgggaag tgaaagtgat    3240
caccctgaag tccaagctgg tgtccgattt ccggaaggat ttccagtttt acaaagtgcg    3300
cgagatcaac aactaccacc acgcccacga cgcctacctg aacgccgtcg tgggaaccgc    3360
cctgatcaaa aagtaccctaagctggaaag cgagttcgtg tacggcgact acaaggtgta    3420
cgacgtgcgg aagatgatcg ccaagagcga gcaggaaatc ggcaaggcta ccgccaagta    3480
cttcttctac agcaacatca tgaacttttt caagaccgag attaccctgg ccaacggcga    3540
gatccggaag cggcctctga tcgagacaaa cggcgaaacc ggggagatcg tgtgggataa    3600
gggccgggat tttgccaccg tgcggaaagt gctgagcatg ccccaagtga atatcgtgaa    3660
aaagaccgag gtgcagacag gcggcttcag caaagagtct atcctgccca gaggaacag    3720
cgataagctg atcgccagaa agaaggactg ggaccctaag aagtacggcg gcttcgacag    3780
ccccaccgtg gcctattctg tgctggtggt ggccaaagtg gaaaagggca gtccaagaa    3840
actgaagagt gtgaaagagc tgctggggat caccatcatg gaaagaagca gcttcgagaa    3900
gaatcccatc gactttctgg aagccaaggg ctacaaagaa gtgaaaaagg acctgatcat    3960
caagctgcct aagtactccc tgttcgagct ggaaaacggc cggaagagaa tgctggcctc    4020
tgccggcgaa ctgcagaagg gaaacgaact ggccctgccc tccaaatatg tgaacttcct    4080
gtacctggcc agccactatg agaagctgaa gggctccccc gaggataatg agcagaaaca    4140
gctgtttgtg aacagcaca agcactacct ggacgagatc atcgagcaga tcagcgagtt    4200
ctccaagaga gtgatcctgg ccgacgctaa tctggacaaa gtgctgtccg cctacaacaa    4260
gcaccgggat aagcccatca gagagcaggc cgagaatatc atccacctgt ttaccctgac    4320
caatctggga gcccctgccg ccttcaagta cttgacacc accatcgacc ggaagaggta    4380
caccagcacc aaagaggtgc tggacgccac cctgatccac cagagcatca ccggcctgta    4440
cgagacacgg atcgacctgt ctcagctggg aggcgacagc cccaagaaga gagaaaggt    4500
ggaggccagc taaggatccg gcaagactgg ccccgcttgg caacgcaaca gtgagcccct    4560
ccctagtgtg tttggggatg tgactatgta ttcgtgtgtt ggccaacggg tcaaccggaa    4620
cagattgata cccgccttgg catttcctgt cagaatgtaa cgtcagttga tggtact    4677

<210> SEQ ID NO 21
<211> LENGTH: 3150
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21
tctttcttgc gctatgacac ttccagcaaa aggtagggcg ggctgcgaga cggcttcccg    60

```
gcgctgcatg caacaccgat gatgcttcga ccccccgaag ctccttcggg gctgcatggg     120
cgctccgatg ccgctccagg gcgagcgctg tttaaatagc caggccccg attgcaaaga     180
cattatagcg agctaccaaa gccatattca aacacctaga tcactaccac ttctacacag    240
gccactcgag cttgtgatcg cactccgcta aggggcgcc tcttcctctt cgtttcagtc     300
acaacccgca aacatgccta agaagaagag gaaggttaac acgattaaca tcgctaagaa    360
cgacttctct gacatcgaac tggctgctat cccgttcaac actctggctg accattacgg    420
tgagcgttta gctcgcgaac agttggccct tgagcatgag tcttacgaga tgggtgaagc    480
acgcttccgc aagatgtttg agcgtcaact taaagctggt gaggttgcgg ataacgctgc    540
cgccaagcct ctcatcacta ccctactccc taagatgatt gcacgcatca acgactggtt    600
tgaggaagtg aaagctaagc gcggcaagcg cccgacagcc ttccagttcc tgcaagaaat    660
caagccggaa gccgtagcgt acatcaccat taagaccact ctggcttgcc taaccagtgc    720
tgacaataca accgttcagg ctgtagcaag cgcaatcggt cgggccattg aggacgaggc    780
tcgcttcggt cgtatccgtg accttgaagc taagcacttc aagaaaaacg ttgaggaaca    840
actcaacaag cgcgtagggc acgtctacaa gaaagcattt atgcaagttg tcgaggctga    900
catgctctct aagggtctac tcggtggcga ggcgtggtct tcgtggcata aggaagactc    960
tattcatgta ggagtacgct gcatcgagat gctcattgag tcaaccggaa tggttagctt   1020
acaccgccaa aatgctggcg tagtaggtca agactctgag actatcgaac tcgcacctga   1080
atacgctgag gctatcgcaa cccgtgcagg tgcgctggct ggcatctctc cgatgttcca   1140
accttgcgta gttcctccta agccgtggac tggcattact ggtggtggct attgggctaa   1200
cggtcgtcgt cctctggcgc tggtgcgtac tcacagtaag aaagcactga tgcgctacga   1260
agacgtttac atgcctgagg tgtacaaagc gattaacatt gcgcaaaaca ccgcatggaa   1320
aatcaacaag aaagtcctag cggtcgccaa cgtaatcacc aagtggaagc attgtccggt   1380
cgaggacatc cctgcgattg agcgtgaaga actcccgatg aaaccggaag acatcgacat   1440
gaatcctgag gctctcaccg cgtggaaacg tgctgccgct gctgtgtacc gcaaggacaa   1500
ggctcgcaag tctcgccgta tcagccttga gttcatgctt gagcaagcca ataagtttgc   1560
taaccataag gccatctggt tcccttacaa catggactgg cgcggtcgtg tttacgctgt   1620
gtcaatgttc aacccgcaag gtaacgatat gaccaaagga ctgcttacgc tggcgaaagg   1680
taaaccaatc ggtaaggaag gttactactg gctgaaaatc cacggtgcaa actgtgcggg   1740
tgtcgacaag gttccgttcc ctgagcgcat caagttcatt gaggaaaacc acgagaacat   1800
catggcttgc gctaagtctc cactggagaa cacttggtgg gctgagcaag attctccgtt   1860
ctgcttcctt gcgttctgct ttgagtacgc tggggtacag caccacgcc tgagctataa   1920
ctgctccctt ccgctggcgt ttgacgggtc ttgctctggc atccagcact tctccgcgat   1980
gctccgagat gaggtaggtg tcgcgcggt taacttgctt cctagtgaaa ccgttcagga   2040
catctacggg attgttgcta agaaagtcaa cgagattcta caagcagacg caatcaatgg   2100
gaccgataac gaagtagtta ccgtgaccga tgagaacact ggtgaaatct ctgagaaagt   2160
caagctgggc actaaggcac tggctggtca atggctggct tacggtgtta ctcgcagtgt   2220
gactaagcgt tcagtcatga cgctggctta cgggtccaaa gagttcggct tccgtcaaca   2280
agtgctggaa gataccattc agccagctat tgattccggc aagggtctga tgttcactca   2340
gccgaatcag gctgctggat acatggctaa gctgatttgg gaatctgtga gcgtgacggt   2400
```

| | |
|---|---|
| ggtagctgcg gttgaagcaa tgaactggct taagtctgct gctaagctgc tggctgctga | 2460 |
| ggtcaaagat aagaagactg gagagattct tcgcaagcgt tgcgctgtgc attgggtaac | 2520 |
| tcctgatggt ttccctgtgt ggcaggaata caagaagcct attcagacgc gcttgaacct | 2580 |
| gatgttcctc ggtcagttcc gcttacagcc taccattaac accaacaaag atagcgagat | 2640 |
| tgatgcacac aaacaggagt ctggtatcgc tcctaacttt gtacacagcc aagacggtag | 2700 |
| ccaccttcgt aagactgtag tgtgggcaca cgagaagtac ggaatcgaat cttttgcact | 2760 |
| gattcacgac tccttcggta cgattccggc tgacgctgcg aacctgttca agcagtgcg | 2820 |
| cgaaactatg gttgacacat atgagtcttg tgatgtactg gctgatttct acgaccagtt | 2880 |
| cgctgaccag ttgcacgagt ctcaattgga caaaatgcca gcacttccgg ctaaaggtaa | 2940 |
| cttgaacctc cgtgacatct tagagtcgga cttcgcgttc gcgtaaggat ccggcaagac | 3000 |
| tggcccccgct tggcaacgca acagtgagcc cctccctagt gtgtttgggg atgtgactat | 3060 |
| gtattcgtgt gttggccaac gggtcaaccc gaacagattg atacccgcct tggcatttcc | 3120 |
| tgtcagaatg taacgtcagt tgatggtact | 3150 |

<210> SEQ ID NO 22
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (23)..(42)
<223> OTHER INFORMATION: a, c, t, g, unknown or other

<400> SEQUENCE: 22

| | |
|---|---|
| gaaattaata cgactcacta tannnnnnnn nnnnnnnnnn nngttttaga gctagaaata | 60 |
| gcaagttaaa ataaggctag tccgttatca acttgaaaaa gtggcaccga gtcggtgctt | 120 |
| ttttt | 125 |

<210> SEQ ID NO 23
<211> LENGTH: 8452
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

| | |
|---|---|
| tgcggtattt cacaccgcat caggtggcac ttttcgggga atgtgcgcg gaacccctat | 60 |
| ttgtttattt ttctaaatac attcaaatat gtatccgctc atgagattat caaaaaggat | 120 |
| cttcacctag atccttttaa attaaaaatg aagttttaaa tcaatctaaa gtatatatga | 180 |
| gtaaacttgg tctgacagtt accaatgctt aatcagtgag gcacctatct cagcgatctg | 240 |
| tctatttcgt tcatccatag ttgcctgact ccccgtcgtg tagataacta cgatacggga | 300 |
| gggcttacca tctggcccca gtgctgcaat gataccgcga gacccacgct caccggctcc | 360 |
| agatttatca gcaataaacc agccagccgg aagggccgag cgcagaagtg gtcctgcaac | 420 |
| tttatccgcc tccatccagt ctattaattg ttgccgggaa gctagagtaa gtagttcgcc | 480 |
| agttaatagt ttgcgcaacg ttgttgccat tgctacaggc atcgtggtgt cacgctcgtc | 540 |
| gtttggtatg gcttcattca gctccggttc ccaacgatca aggcgagtta catgatcccc | 600 |

```
catgttgtgc aaaaaagcgg ttagctcctt cggtcctccg atcgttgtca gaagtaagtt      660
ggccgcagtg ttatcactca tggttatggc agcactgcat aattctctta ctgtcatgcc      720
atccgtaaga tgcttttctg tgactggtga gtactcaacc aagtcattct gagaatagtg      780
tatgcggcga ccgagttgct cttgcccggc gtcaataegg gataataccg cgccacatag      840
cagaacttta aaagtgctca tcattggaaa acgttcttcg gggcgaaaac tctcaaggat      900
cttaccgctg ttgagatcca gttcgatgta acccactcgt gcacccaact gatcttcagc      960
atcttttact ttcaccagcg tttctgggtg agcaaaaaca ggaaggcaaa atgccgcaaa     1020
aaagggaata agggcgacac ggaaatgttg aatactcata ctcttccttt ttcaatatta     1080
ttgaagcatt tatcagggtt attgtctcat gaccaaaatc ccttaacgtg agttttcgtt     1140
ccactgagcg tcagaccccg tagaaaagat caaaggatct tcttgagatc cttttttttct     1200 gcgcgtaatc tgctgcttgc aaacaaaaaa accaccgcta ccagcggtgg tttgtttgcc     1260
ggatcaagag ctaccaactc tttttccgaa ggtaactggc ttcagcagag cgcagatacc     1320
aaatactgtt cttctagtgt agccgtagtt aggccaccac ttcaagaact ctgtagcacc     1380
gcctacatac ctcgctctgc taatcctgtt accagtggct gttgccagtg gcgataagtc     1440
gtgtcttacc gggttggact caagacgata gttaccggat aaggcgcagc ggtcgggctg     1500
aacggggggt tcgtgcacac agcccagctt ggagcgaacg acctacaccg aactgagata     1560
cctacagcgt gagctatgag aaagcgccac gcttcccgaa gggagaaagg cggacaggta     1620
tccggtaagc ggcagggtcg gaacaggaga gcgcacgagg gagcttccag ggggaaacgc     1680
ctggtatctt tatagtcctg tcgggtttcg ccacctctga cttgagcgtc gatttttgtg     1740
atgctcgtca gggggggcgga gcctatggaa aaacgccagc aacgcggcct ttttacggtt     1800
cctggccttt tgctggcctt tgctcacat gttctttcct gcgttatccc ctgattctgt     1860
ggataaccgt attaccgcct ttgagtgagc tgataccgct cgccgcagcc gaacgaccga     1920
gcgcagcgag tcagtgagcg aggaagcggt cgctgaggct tgacatgatt ggtgcgtatg     1980
tttgtatgaa gctacaggac tgatttggcg gctatgagg gcggggaag ctctggaagg     2040 gccgcgatgg ggcgcgcggc gtccagaagg cgccatacgg cccgctggcg gcacccatcc     2100
ggtataaaag cccgcgaccc cgaacggtga cctccacttt cagcgacaaa cgagcactta     2160
tacatacgcg actattctgc cgctatacat aaccactcag ctagcttaag atcccatcaa     2220
gcttgcatgc cgggcgcgcc agaaggagcg cagccaaacc aggatgatgt tgatggggt     2280 atttgagcac ttgcaaccct tatccggaag ccccctggcc cacaaaggct aggcgccaat     2340
gcaagcagtt cgcatgcagc ccctggagcg gtgccctcct gataaaccgg ccagggggcc     2400
tatgttcttt acttttttac aagagaagtc actcaacatc ttaaaatggc caggtgagtc     2460
gacgagcaag cccggcggat caggcagcgt gcttgcagat ttgacttgca acgcccgcat     2520
tgtgtcgacg aaggcttttg gctcctctgt cgctgtctca gcagcatct aaccctgcgt     2580 cgccgtttcc atttgcagga gattcgaggt accatgtacc catacgatgt tccagattac     2640
gcttcgccga agaaaagcg caaggtcgaa gcgtccgaca agaagtacag catcggcctg     2700
gacatcggca ccaactctgt gggctgggcc gtgatcaccg acgagtacaa ggtgcccagc     2760
aagaaattca aggtgctggg caacaccgac cggcacagca tcaagaagaa cctgatcgga     2820
gccctgctgt tcgacagcgg cgaaacagcc gaggccaccc ggctgaagag aaccgccaga     2880
agaagataca ccagacggaa gaaccggatc tgctatctgc aagagatctt cagcaacgag     2940
```

```
atggccaagg tggacgacag cttcttccac agactggaag agtccttcct ggtggaagag    3000
gataagaagc acgagcggca ccccatcttc ggcaacatcg tggacgaggt ggcctaccac    3060
gagaagtacc ccaccatcta ccacctgaga aagaaactgg tggacagcac cgacaaggcc    3120
gacctgcggt tgatctatct ggccctggcc cacatgatca agttccgggg ccacttcctg    3180
atcgagggcg acctgaaccc cgacaacagc gacgtggaca agctgttcat ccagctggtg    3240
cagacctaca accagctgtt cgaggaaaac cccatcaacg ccagcggcgt ggacgccaag    3300
gccatcctgt ctgccagact gagcaagagc agacggctgg aaaatctgat cgcccagctg    3360
cccggcgaga gaagaatgg cctgttcggc aacctgattg ccctgagcct gggcctgacc    3420
cccaacttca gagcaacttc gacctggcc gaggatgcca actgcagct gagcaaggac    3480 acctacgacg acgacctgga caacctgctg gcccagatcg cgaccagta cgccgacctg    3540 tttctggccg ccaagaacct gtccgacgcc atcctgctga gcgacatcct gagagtgaac    3600
accgagatca ccaaggcccc cctgagcgcc tctatgatca agagatacga cgagcaccac    3660
caggacctga ccctgctgaa agctctcgtg cggcagcagc tgcctgagaa gtacaaagag    3720
attttcttcg accagagcaa gaacggctac gccggctaca ttgacggcgg agccagccag    3780
gaagagttct acaagttcat caagcccatc ctggaaaaga tggacggcac cgaggaactg    3840
ctcgtgaagc tgaacagaga ggacctgctg cggaagcagc ggaccttcga caacggcagc    3900
atcccccacc agatccacct gggagagctg cacgccattc tgcggcggca ggaagatttt    3960
tacccattcc tgaaggacaa ccgggaaaag atcgagaaga tcctgacctt ccgcatcccc    4020
tactacgtgg gccctctggc caggggaaac agcagattcg cctggatgac cagaaagagc    4080
gaggaaacca tcacccctg gaacttcgag gaagtggtgg acaagggcgc ttccgcccag    4140
agcttcatcg agcggatgac caacttcgat aagaacctgc ccaacgagaa ggtgctgccc    4200
aagcacagcc tgctgtacga gtacttcacc gtgtataacg agctgaccaa agtgaaatac    4260
gtgaccgagg gaatgagaaa gcccgccttc ctgagcggcg agcagaaaaa ggccatcgtg    4320
gacctgctgt tcaagaccaa ccggaaagtg accgtgaagc agctgaaaga ggactacttc    4380
aagaaaatcg agtgcttcga ctccgtggaa atctccggcg tggaagatcg gttcaacgcc    4440
tccctgggca cataccacga tctgctgaaa attatcaagg acaaggactt cctggacaat    4500
gaggaaaacg aggacattct ggaagatatc gtgctgaccc tgacactgtt tgaggacaga    4560
gagatgatcg aggaacggct gaaaacctat gcccacctgt tcgacgacaa agtgatgaag    4620
cagctgaagc ggcggagata caccggctgg ggcaggctga gccggaagct gatcaacggc    4680
atccgggaca gcagtccgg caagacaatc ctggatttcc tgaagtccga cggcttcgcc    4740
aacagaaact tcatgcagct gatccacgac gacagcctga cctttaaaga ggacatccag    4800
aaagcccagg tgtccggcca gggcgatagc ctgcacgagc acattgccaa tctggccggc    4860
agccccgcca ttaagaaggg catcctgcag acagtgaagg tggtggacga gctcgtgaaa    4920
gtgatgggcc ggcacaagcc cgagaacatc gtgatcgaaa tggccagaga gaaccagacc    4980
acccagaagg acagaagaa cagccgcgag agaatgaagc ggatcgaaga gggcatcaaa    5040
gagctgggca gccagatcct gaaagaacac cccgtggaaa acacccagct gcagaacgag    5100
aagctgtacc tgtactacct gcagaatggg cgggatatgt acgtggacca ggaactggac    5160
atcaaccggc tgtccgacta cgatgtggac catatcgtgc ctcagagctt tctgaaggac    5220
gactccatcg acaacaaggt gctgaccaga agcgacaaga accggggcaa gagcgacaac    5280
gtgccctccg aagaggtcgt gaagaagatg aagaactact ggcggcagct gctgaacgcc    5340
```

```
aagctgatta cccagagaaa gttcgacaat ctgaccaagg ccgagagagg cggcctgagc    5400
gaactggata aggccggctt catcaagaga cagctggtgg aaacccggca gatcacaaag    5460
cacgtggcac agatcctgga ctcccggatg aacactaagt acgacgagaa tgacaagctg    5520
atccgggaag tgaaagtgat caccctgaag tccaagctgg tgtccgattt ccggaaggat    5580
ttccagtttt acaaagtgcg cgagatcaac aactaccacc acgcccacga cgcctacctg    5640
aacgccgtcg tgggaaccgc cctgatcaaa agtaccccta agctggaaag cgagttcgtg    5700
tacggcgact acaaggtgta cgacgtgcgg aagatgatcg ccaagagcga gcaggaaatc    5760
ggcaaggcta ccgccaagta cttcttctac agcaacatca tgaactttt caagaccgag    5820 attaccctgg ccaacggcga gatccggaag cggcctctga tcgagacaaa cggcgaaacc    5880
ggggagatcg tgtgggataa gggccgggat tttgccaccg tgcggaaagt gctgagcatg    5940
ccccaagtga atatcgtgaa aaagaccgag gtgcagacag cggcttcag caaagagtct    6000 atcctgccca agaggaacag cgataagctg atcgccagaa agaaggactg ggaccctaag    6060
aagtacggcg gcttcgacag ccccaccgtg gcctattctg tgctggtggt ggccaaagtg    6120
gaaaagggca gtccaagaa actgaagagt gtgaaagagc tgctggggat caccatcatg    6180
gaaagaagca gcttcgagaa gaatcccatc gactttctgg aagccaaggg ctacaaagaa    6240
gtgaaaaagg acctgatcat caagctgcct aagtactccc tgttcgagct ggaaaacggc    6300
cggaagagaa tgctggcctc tgccggcgaa ctgcagaagg gaaacgaact ggccctgccc    6360
tccaaatatg tgaacttcct gtacctggcc agccactatg agaagctgaa gggctccccc    6420
gaggataatg agcagaaaca gctgtttgtg gaacagcaca gcactacct ggacgagatc    6480 atcgagcaga tcagcgagtt ctccaagaga gtgatcctgg ccgacgctaa tctggacaaa    6540
gtgctgtccg cctacaacaa gcaccgggat aagcccatca gagagcaggc cgagaatatc    6600
atccacctgt ttaccctgac caatctggga gcccctgccg ccttcaagta ctttgacacc    6660
accatcgacc ggaagaggta caccagcacc aaagaggtgc tggacgccac cctgatccac    6720
cagagcatca ccggcctgta cgagacacgg atcgacctgt ctcagctggg aggcgacagc    6780
cccaagaaga gagaaaggt ggaggccagc taacatatga ttcgaatgtc tttcttgcgc    6840
tatgacactt ccagcaaaag gtagggcggg ctgcgagacg gcttcccggc gctgcatgca    6900
acaccgatga tgcttcgacc ccccgaagct ccttcggggc tgcatgggcg ctccgatgcc    6960
gctccagggc gagcgctgtt taaatagcca ggccccgat tgcaaagaca ttatagcgag    7020
ctaccaaagc catattcaaa cacctagatc actaccactt ctacacaggc cactcgagct    7080
tgtgatcgca ctccgctaag ggggcgcctc ttcctcttcg tttcagtcac aacccgcaaa    7140
catgacacaa gaatccctgt tacttctcga ccgtattgat tcggatgatt cctacgcgag    7200
cctgcggaac gaccaggaat tctgggaggt gagtcgacga gcaagcccgg cggatcaggc    7260
agcgtgcttg cagatttgac ttgcaacgcc gcattgtgt cgacgaaggc ttttggctcc    7320
tctgtcgctg tctcaagcag catctaaccc tgcgtcgccg tttccatttg cagccgctgg    7380
cccgccgagc cctggaggag ctcgggctgc cggtgccgcc ggtgctgcgg gtgcccggcg    7440
agagcaccaa ccccgtactg gtcggcgagc ccggcccggt gatcaagctg ttcggcgagc    7500
actggtgcgg tccggagagc ctcgcgtcgg agtcggaggc gtacgcggtc ctggcggacg    7560
ccccggtgcc ggtgccccgc ctcctcggcc gcggcgagct gcggcccggc accgagcct    7620 ggccgtggcc ctacctggtg atgagccgga tgaccggcac cacctggcgg tccgcgatgg    7680
```

-continued

| | |
|---|---|
| acggcacgac cgaccggaac gcgctgctcg ccctggcccg cgaactcggc cgggtgctcg | 7740 |
| gccggctgca cagggtgccg ctgaccggga acaccgtgct cacccccat tccgaggtct | 7800 |
| tcccggaact gctgcgggaa cgccgcgcgg cgaccgtcga ggaccaccgc gggtggggct | 7860 |
| acctctcgcc ccggctgctg gaccgcctgg aggactggct gccggacgtg gacacgctgc | 7920 |
| tggccggccg cgaaccccgg ttcgtccacg gcgacctgca cgggaccaac atcttcgtgg | 7980 |
| acctggccgc gaccgaggtc accgggatcg tcgacttcac cgacgtctat gcgggagact | 8040 |
| cccgctacag cctggtgcaa ctgcatctca acgccttccg gggcgaccgc gagatcctgg | 8100 |
| ccgcgctgct cgacggggcg cagtggaagc ggaccgagga cttcgcccgc gaactgctcg | 8160 |
| ccttcacctt cctgcacgac ttcgaggtgt tcgaggagac cccgctggat ctctccggct | 8220 |
| tcaccgatcc ggaggaactg gcgcagttcc tctgggggcc gccggacacc gcccccggcg | 8280 |
| cctgataagg atccggcaag actggccccg cttggcaacg caacagtgag cccctcccta | 8340 |
| gtgtgtttgg ggatgtgact atgtattcgt gtgttggcca acgggtcaac ccgaacagat | 8400 |
| tgatacccgc cttggcattt cctgtcagaa tgtaacgtca gttgatggta ct | 8452 |

<210> SEQ ID NO 24
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 24
aaacatctcg tacagtgaca                                              20

<210> SEQ ID NO 25
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 25
attccacggg aaggagatct                                              20

<210> SEQ ID NO 26
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 26
cctggcttct tacgccgtcc                                              20

<210> SEQ ID NO 27
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 27

```
gtactgcagt ccaaagaacc                                              20

<210> SEQ ID NO 28
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
cacagtggcc tggctcaaaa                                              20

<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
aggattgaag ctgacgttct                                              20

<210> SEQ ID NO 30
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
cgtcagcttc aatcctgcca                                              20

<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
ctcagagatt gctgcatagt                                              20

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
acaggtcatc ttaatgagcc                                              20

<210> SEQ ID NO 33
<211> LENGTH: 20
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 33
ggggctgtgg ttccacgata                                              20

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
gttgtgctca gtactgactt                                              20

<210> SEQ ID NO 35
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
acactggaaa aatgtcttgc                                              20

<210> SEQ ID NO 36
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
agtcagtact gagcacaaca                                              20

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
cttacctgga tatagtcaac                                              20

<210> SEQ ID NO 38
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
gaatcctgtt gactatatcc                                              20
```

```
<210> SEQ ID NO 39
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
gacctaaaat cattaacatc                                                 20

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
tgccagatgt taatgatttt                                                 20

<210> SEQ ID NO 41
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
ttatttagtc gtgtgccaaa                                                 20

<210> SEQ ID NO 42
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
actgggctaa cctaaagctg                                                 20

<210> SEQ ID NO 43
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
tctgcttgaa ccacagcttt                                                 20

<210> SEQ ID NO 44
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 44
ggaggaaatc attgtgagaa                                               20

<210> SEQ ID NO 45
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
tctttagtgc aatcagaatc                                               20

<210> SEQ ID NO 46
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
acggcgggcg cttcacgctc                                               20

<210> SEQ ID NO 47
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
gccatcgagc agttcggctt                                               20

<210> SEQ ID NO 48
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
gcaccttctc gcgatctgac                                               20

<210> SEQ ID NO 49
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
gctcctgtca gatcgcgaga                                               20

<210> SEQ ID NO 50
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 50
gaagttcgag ggcgacaccc                                                    20

<210> SEQ ID NO 51
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
ggtgaaccgc atcgagctga                                                    20

<210> SEQ ID NO 52
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
gaagcaaccc aagacgttca c                                                  21

<210> SEQ ID NO 53
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
tagttctctg acctgagtct t                                                  21

<210> SEQ ID NO 54
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
gctctggata ttctgcacaa t                                                  21

<210> SEQ ID NO 55
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
gcttcgtgtt aataagctga t                                                  21
```

```
<210> SEQ ID NO 56
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
gcagcattat tgcagagaaa t                                              21

<210> SEQ ID NO 57
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
gctgttctca aggctgtgtt t                                              21

<210> SEQ ID NO 58
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
cgggtacttc atactttgga a                                              21

<210> SEQ ID NO 59
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
gcagagaaat tacgttgtaa t                                              21

<210> SEQ ID NO 60
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
gccaacctta acctttctaa t                                              21

<210> SEQ ID NO 61
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 61
cctcacaaca accaacactt t                                          21

<210> SEQ ID NO 62
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
cctgacactt acaacagtca a                                          21

<210> SEQ ID NO 63
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
gctggcagtt tcaaacgtaa t                                          21

<210> SEQ ID NO 64
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
cgtgactgtg aagactatta t                                          21

<210> SEQ ID NO 65
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
atgattacga gatcgagtat g                                          21

<210> SEQ ID NO 66
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
acatcgcccg tgactacaat c                                          21

<210> SEQ ID NO 67
<211> LENGTH: 60
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
taacttgaaa gtatttcgat ttcttggctt tatatatctt gtggaaagga cgaaacaccg    60

<210> SEQ ID NO 68
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68 acttttcaa gttgataacg gactagcctt attttaactt gctatttcta gctctaaaac    60

<210> SEQ ID NO 69
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
aatggactat catatgctta ccgtaacttg aaagtatttc g                        41

<210> SEQ ID NO 70
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
ctttagtttg tatgtctgtt gctattatgt ctactattct ttcc                     44

<210> SEQ ID NO 71
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (59)..(75)
<223> OTHER INFORMATION: a, c, t, g, unknown or other
<220> FEATURE:
<221> NAME/KEY: variation
<222> LOCATION: (60)..(67)
<223> OTHER INFORMATION: /replace=" "
<220> FEATURE:
<221> NAME/KEY: misc_feature
<222> LOCATION: (1)..(99)
<223> OTHER INFORMATION: /note="Variation nucleotides given in the
      sequence have no preference with respect to those in the
      annotations for the variation positions"

<400> SEQUENCE: 71
aatgatacgg cgaccaccga gatctacact ctttccctac acgacgctct tccgatctnn    60
```

```
nnnnnnnnnn nnnntcttg tggaaaggac gaaacaccg              99
```

<210> SEQ ID NO 72
<211> LENGTH: 83
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72

```
caagcagaag acggcatacg agatgtgact ggagttcaga cgtgtgctct tccgatcttc   60
tactattctt tcccctgcac tgt                                          83
```

<210> SEQ ID NO 73
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73

```
gggcgaggag ctgttcaccg                                              20
```

<210> SEQ ID NO 74
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74

```
gagctggacg gcgacgtaaa                                              20
```

<210> SEQ ID NO 75
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75

```
ggccacaagt tcagcgtgtc                                              20
```

<210> SEQ ID NO 76
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76

```
ggagcgcacc atcttcttca                                              20
```

<210> SEQ ID NO 77
<211> LENGTH: 60
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77
taacttgaaa gtatttcgat ttcttggctt tatatatctt gtggaaagga cgaaacaccg    60

<210> SEQ ID NO 78
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78 acttttcaa gttgataacg gactagcctt attttaactt gctatttcta gctctaaaac     60

<210> SEQ ID NO 79
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 79
gttttagagc tatgctgttt tgaatggtcc caaaacggaa gggcctgagt ccgagcagaa    60
gaagaagttt tagagctatg ctgttttgaa tggtcccaaa ac                      102

<210> SEQ ID NO 80
<211> LENGTH: 100
<212> TYPE: DNA
<213> ORGANISM: Homo sapiens

<400> SEQUENCE: 80
cggaggacaa agtacaaacg gcagaagctg gaggaggaag ggcctgagtc cgagcagaag    60
aagaagggct cccatcacat caaccggtgg cgcattgcca                        100

<210> SEQ ID NO 81
<211> LENGTH: 50
<212> TYPE: DNA
<213> ORGANISM: Homo sapiens

<400> SEQUENCE: 81
agctggagga ggaagggcct gagtccgagc agaagaagaa gggctcccac              50

<210> SEQ ID NO 82
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
gaguccgagc agaagaagaa guuuuagagc                                    30

<210> SEQ ID NO 83
<211> LENGTH: 49
```

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
agctggagga ggaagggcct gagtccgagc agaagagaag ggctcccat         49

<210> SEQ ID NO 84
<211> LENGTH: 53
<212> TYPE: DNA
<213> ORGANISM: Homo sapiens

<400> SEQUENCE: 84
ctggaggagg aagggcctga gtccgagcag aagaagaagg gctcccatca cat    53

<210> SEQ ID NO 85
<211> LENGTH: 52
<212> TYPE: DNA
<213> ORGANISM: Homo sapiens

<400> SEQUENCE: 85
ctggaggagg aagggcctga gtccgagcag aagagaaggg ctcccatcac at     52

<210> SEQ ID NO 86
<211> LENGTH: 54
<212> TYPE: DNA
<213> ORGANISM: Homo sapiens

<400> SEQUENCE: 86
ctggaggagg aagggcctga gtccgagcag aagaaagaag gctcccatc acat    54

<210> SEQ ID NO 87
<211> LENGTH: 50
<212> TYPE: DNA
<213> ORGANISM: Homo sapiens

<400> SEQUENCE: 87
ctggaggagg aagggcctga gtccgagcag aagaagggct cccatcacat        50

<210> SEQ ID NO 88
<211> LENGTH: 47
<212> TYPE: DNA
<213> ORGANISM: Homo sapiens

<400> SEQUENCE: 88
ctggaggagg aagggcctga gcccgagcag aagggctccc atcacat           47

<210> SEQ ID NO 89
<211> LENGTH: 48
<212> TYPE: DNA
<213> ORGANISM: Homo sapiens

<400> SEQUENCE: 89
ctggaggagg aagggcctga gtccgagcag aagaagaagg gctcccat          48

<210> SEQ ID NO 90
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:

```
                        Synthetic oligonucleotide"

<400> SEQUENCE: 90
gaguccgagc agaagaagau                                               20

<210> SEQ ID NO 91
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
gaguccgagc agaagaagua                                               20

<210> SEQ ID NO 92
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
gaguccgagc agaagaacaa                                               20

<210> SEQ ID NO 93
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
gaguccgagc agaagaugaa                                               20

<210> SEQ ID NO 94
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
gaguccgagc agaaguagaa                                               20

<210> SEQ ID NO 95
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
gaguccgagc agaugaagaa                                               20

<210> SEQ ID NO 96
<211> LENGTH: 20
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
gaguccgagc acaagaagaa                                                     20

<210> SEQ ID NO 97
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
gaguccgagg agaagaagaa                                                     20

<210> SEQ ID NO 98
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
gaguccgugc agaagaagaa                                                     20

<210> SEQ ID NO 99
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
gagucggagc agaagaagaa                                                     20

<210> SEQ ID NO 100
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
gagaccgagc agaagaagaa                                                     20

<210> SEQ ID NO 101
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
```
aatgacaagc ttgctagcgg tggg                                              24

<210> SEQ ID NO 102
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
aaaacggaag ggcctgagtc cgagcagaag aagaagttt                              39

<210> SEQ ID NO 103
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
aaacaggggc cgagattggg tgttcagggc agaggtttt                              39

<210> SEQ ID NO 104
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
aaaacggaag ggcctgagtc cgagcagaag aagaagtt                               38

<210> SEQ ID NO 105
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
aacggaggga ggggcacaga tgagaaactc agggttttag                             40

<210> SEQ ID NO 106
<211> LENGTH: 38
<212> TYPE: DNA
<213> ORGANISM: Homo sapiens

<400> SEQUENCE: 106
agcccttctt cttctgctcg gactcaggcc cttcctcc                               38

<210> SEQ ID NO 107
<211> LENGTH: 40
<212> TYPE: DNA
<213> ORGANISM: Homo sapiens

<400> SEQUENCE: 107
cagggaggga ggggcacaga tgagaaactc aggaggcccc                             40

-continued

```
<210> SEQ ID NO 108
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
ggcaatgcgc caccggttga tgtgatggga gcccttctag gaggccccca gagcagccac    60
tggggcctca acactcaggc                                                80

<210> SEQ ID NO 109
<211> LENGTH: 33
<212> TYPE: DNA
<213> ORGANISM: Homo sapiens

<400> SEQUENCE: 109
catcgatgtc ctccccattg gcctgcttcg tgg                                 33

<210> SEQ ID NO 110
<211> LENGTH: 33
<212> TYPE: DNA
<213> ORGANISM: Homo sapiens

<400> SEQUENCE: 110
ttcgtggcaa tgcgccaccg gttgatgtga tgg                                 33

<210> SEQ ID NO 111
<211> LENGTH: 33
<212> TYPE: DNA
<213> ORGANISM: Homo sapiens

<400> SEQUENCE: 111
tcgtggcaat gcgccaccgg ttgatgtgat ggg                                 33

<210> SEQ ID NO 112
<211> LENGTH: 33
<212> TYPE: DNA
<213> ORGANISM: Homo sapiens

<400> SEQUENCE: 112
tccagcttct gccgtttgta ctttgtcctc cgg                                 33

<210> SEQ ID NO 113
<211> LENGTH: 33
<212> TYPE: DNA
<213> ORGANISM: Homo sapiens

<400> SEQUENCE: 113
ggagggaggg gcacagatga gaaactcagg agg                                 33

<210> SEQ ID NO 114
<211> LENGTH: 33
<212> TYPE: DNA
<213> ORGANISM: Homo sapiens

<400> SEQUENCE: 114
aggggccgag attgggtgtt cagggcagag agg                                 33

<210> SEQ ID NO 115
<211> LENGTH: 33
<212> TYPE: DNA
```

```
<213> ORGANISM: Mus musculus

<400> SEQUENCE: 115
caagcactga gtgccattag ctaaatgcat agg                                  33

<210> SEQ ID NO 116
<211> LENGTH: 33
<212> TYPE: DNA
<213> ORGANISM: Mus musculus

<400> SEQUENCE: 116
aatgcatagg gtaccaccca caggtgccag ggg                                  33

<210> SEQ ID NO 117
<211> LENGTH: 33
<212> TYPE: DNA
<213> ORGANISM: Mus musculus

<400> SEQUENCE: 117
acacacatgg gaaagcctct gggccaggaa agg                                  33

<210> SEQ ID NO 118
<211> LENGTH: 37
<212> TYPE: DNA
<213> ORGANISM: Homo sapiens

<400> SEQUENCE: 118
ggaggaggta gtatacagaa acacagagaa gtagaat                              37

<210> SEQ ID NO 119
<211> LENGTH: 37
<212> TYPE: DNA
<213> ORGANISM: Homo sapiens

<400> SEQUENCE: 119
agaatgtaga ggagtcacag aaactcagca ctagaaa                              37

<210> SEQ ID NO 120
<211> LENGTH: 98
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
ggacgaaaca ccggaaccat tcaaaacagc atagcaagtt aaaataaggc tagtccgtta     60
tcaacttgaa aaagtggcac cgagtcggtg cttttttt                             98

<210> SEQ ID NO 121
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 121
ggacgaaaca ccggtagtat taagtattgt tttatggctg ataaatttct ttgaatttct     60
ccttgattat ttgttataaa agttataaaa taatcttgtt ggaaccattc aaaacagcat    120
agcaagttaa aataaggcta gtccgttatc aacttgaaaa agtggcaccg agtcggtgct    180
``` tttttt                                                                        186

<210> SEQ ID NO 122
<211> LENGTH: 95
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
gggttttaga gctatgctgt tttgaatggt cccaaaacgg gtcttcgaga agacgtttta      60
gagctatgct gttttgaatg gtcccaaaac ttttt                                 95

<210> SEQ ID NO 123
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (5)..(34)
<223> OTHER INFORMATION: a, c, t, g, unknown or other

<400> SEQUENCE: 123
aaacnnnnnn nnnnnnnnnn nnnnnnnnnn nnnngt                                36

<210> SEQ ID NO 124
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(36)
<223> OTHER INFORMATION: a, c, t, g, unknown or other

<400> SEQUENCE: 124
taaaacnnnn nnnnnnnnnn nnnnnnnnnn nnnnnn                                36

<210> SEQ ID NO 125
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
gtggaaagga cgaaacaccg ggtcttcgag aagacctgtt ttagagctag aaatagcaag      60
ttaaaataag gctagtccgt tttt                                             84

<210> SEQ ID NO 126
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:

```
    Synthetic oligonucleotide"
<220> FEATURE:
<221> NAME/KEY: modified_base
<222> LOCATION: (6)..(24)
<223> OTHER INFORMATION: a, c, t, g, unknown or other

<400> SEQUENCE: 126
caccgnnnnn nnnnnnnnnn nnnn                                              24

<210> SEQ ID NO 127
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (5)..(23)
<223> OTHER INFORMATION: a, c, t, g, unknown or other

<400> SEQUENCE: 127
aaacnnnnnn nnnnnnnnnn nnnc                                              24

<210> SEQ ID NO 128
<211> LENGTH: 46
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(19)
<223> OTHER INFORMATION: a, c, u, g, unknown or other

<400> SEQUENCE: 128
nnnnnnnnnn nnnnnnnnng uuauuguacu cucaagauuu auuuuu                      46

<210> SEQ ID NO 129
<211> LENGTH: 91
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
guuacuuaaa ucuugcagaa gcuacaaaga uaaggcuuca ugccgaaauc aacacccugu       60
cauuuuaugg cagguguuu ucguuauuua a                                       91

<210> SEQ ID NO 130
<211> LENGTH: 70
<212> TYPE: DNA
<213> ORGANISM: Homo sapiens

<400> SEQUENCE: 130
ttttctagtg ctgagtttct gtgactcctc tacattctac ttctctgtgt ttctgtatac      60
tacctcctcc                                                             70

<210> SEQ ID NO 131
<211> LENGTH: 122
<212> TYPE: DNA
<213> ORGANISM: Homo sapiens
```

<400> SEQUENCE: 131
ggaggaaggg cctgagtccg agcagaagaa gaagggctcc catcacatca accggtggcg    60
cattgccacg aagcaggcca atggggagga catcgatgtc acctccaatg actagggtgg   120
gc                                                                  122

<210> SEQ ID NO 132
<211> LENGTH: 48
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(32)
<223> OTHER INFORMATION: a, c, u, g, unknown or other

<400> SEQUENCE: 132
acnnnnnnnn nnnnnnnnnn nnnnnnnnnn nnguuuuaga gcuaugcu                 48

<210> SEQ ID NO 133
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 133
agcauagcaa guuaaaauaa ggcuaguccg uuaucaacuu gaaaaagugg caccgagucg    60
gugcuuu                                                              67

<210> SEQ ID NO 134
<211> LENGTH: 62
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 134
nnnnnnnnnn nnnnnnnnnn guuuuagagc uagaaauagc aaguuaaaau aaggcuaguc    60
cg                                                                   62

<210> SEQ ID NO 135
<211> LENGTH: 73
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135

```
tgaatggtcc caaaacggaa gggcctgagt ccgagcagaa gaagaagttt tagagctatg    60
ctgttttgaa tgg                                                      73

<210> SEQ ID NO 136
<211> LENGTH: 69
<212> TYPE: DNA
<213> ORGANISM: Homo sapiens

<400> SEQUENCE: 136
ctggtcttcc acctctctgc cctgaacacc caatctcggc ccctctcgcc accctcctgc    60
atttctgtt                                                           69

<210> SEQ ID NO 137
<211> LENGTH: 138
<212> TYPE: DNA
<213> ORGANISM: Mus musculus

<400> SEQUENCE: 137
acccaagcac tgagtgccat tagctaaatg catagggtac cacccacagg tgccaggggc    60
ctttcccaaa gttcccagcc ccttctccaa cctttcctgg cccagaggct ttcccatgtg   120
tgtggctgga ccctttga                                                138

<210> SEQ ID NO 138
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 138
aaaaccaccc ttctctctgg c                                             21

<210> SEQ ID NO 139
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 139
ggagattgga gacacggaga g                                             21

<210> SEQ ID NO 140
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 140
ctggaaagcc aatgcctgac                                               20

<210> SEQ ID NO 141
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic primer"

<400> SEQUENCE: 141
ggcagcaaac tccttgtcct                                                    20

<210> SEQ ID NO 142
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 142
gtgctttgca gaggcctacc                                                    20

<210> SEQ ID NO 143
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 143
cctggagcgc atgcagtagt                                                    20

<210> SEQ ID NO 144
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 144
accttctgtg tttccaccat tc                                                 22

<210> SEQ ID NO 145
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 145
ttggggagtg cacagacttc                                                    20

<210> SEQ ID NO 146
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 146
ggctccctgg gttcaaagta                                                    20

<210> SEQ ID NO 147
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 147 agagggtct ggatgtcgta a                                            21

<210> SEQ ID NO 148
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 148
tagctctaaa acttcttctt ctgctcggac                                  30

<210> SEQ ID NO 149
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 149
ctagccttat tttaacttgc tatgctgttt                                  30

<210> SEQ ID NO 150
<211> LENGTH: 99
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 150
nnnnnnnnnn nnnnnnnnnn guuuuagagc uagaaauagc aaguuaaaau aaggcuaguc    60
cguuaucaac uugaaaaagu ggcaccgagu cggugcuuu                           99

<210> SEQ ID NO 151
<211> LENGTH: 12
<212> TYPE: DNA
<213> ORGANISM: Homo sapiens

<400> SEQUENCE: 151
tagcgggtaa gc                                                      12

<210> SEQ ID NO 152
<211> LENGTH: 12
<212> TYPE: DNA
<213> ORGANISM: Homo sapiens

<400> SEQUENCE: 152
tcggtgacat gt                                                      12
```

<210> SEQ ID NO 153
<211> LENGTH: 12
<212> TYPE: DNA
<213> ORGANISM: Homo sapiens

<400> SEQUENCE: 153
actccccgta gg                                                          12

<210> SEQ ID NO 154
<211> LENGTH: 12
<212> TYPE: DNA
<213> ORGANISM: Homo sapiens

<400> SEQUENCE: 154
actgcgtgtt aa                                                          12

<210> SEQ ID NO 155
<211> LENGTH: 12
<212> TYPE: DNA
<213> ORGANISM: Homo sapiens

<400> SEQUENCE: 155
acgtcgcctg at                                                          12

<210> SEQ ID NO 156
<211> LENGTH: 12
<212> TYPE: DNA
<213> ORGANISM: Homo sapiens

<400> SEQUENCE: 156
taggtcgacc ag                                                          12

<210> SEQ ID NO 157
<211> LENGTH: 12
<212> TYPE: DNA
<213> ORGANISM: Homo sapiens

<400> SEQUENCE: 157
ggcgttaatg at                                                          12

<210> SEQ ID NO 158
<211> LENGTH: 12
<212> TYPE: DNA
<213> ORGANISM: Homo sapiens

<400> SEQUENCE: 158
tgtcgcatgt ta                                                          12

<210> SEQ ID NO 159
<211> LENGTH: 12
<212> TYPE: DNA
<213> ORGANISM: Homo sapiens

<400> SEQUENCE: 159
atggaaacgc at                                                          12

<210> SEQ ID NO 160
<211> LENGTH: 12
<212> TYPE: DNA
<213> ORGANISM: Homo sapiens

<400> SEQUENCE: 160

```
gccgaattcc tc                                                    12

<210> SEQ ID NO 161
<211> LENGTH: 12
<212> TYPE: DNA
<213> ORGANISM: Homo sapiens

<400> SEQUENCE: 161
gcatggtacg ga                                                    12

<210> SEQ ID NO 162
<211> LENGTH: 12
<212> TYPE: DNA
<213> ORGANISM: Homo sapiens

<400> SEQUENCE: 162
cggtactctt ac                                                    12

<210> SEQ ID NO 163
<211> LENGTH: 12
<212> TYPE: DNA
<213> ORGANISM: Homo sapiens

<400> SEQUENCE: 163
gcctgtgccg ta                                                    12

<210> SEQ ID NO 164
<211> LENGTH: 12
<212> TYPE: DNA
<213> ORGANISM: Homo sapiens

<400> SEQUENCE: 164
tacggtaagt cg                                                    12

<210> SEQ ID NO 165
<211> LENGTH: 12
<212> TYPE: DNA
<213> ORGANISM: Homo sapiens

<400> SEQUENCE: 165
cacgaaatta cc                                                    12

<210> SEQ ID NO 166
<211> LENGTH: 12
<212> TYPE: DNA
<213> ORGANISM: Homo sapiens

<400> SEQUENCE: 166
aaccaagata cg                                                    12

<210> SEQ ID NO 167
<211> LENGTH: 12
<212> TYPE: DNA
<213> ORGANISM: Homo sapiens

<400> SEQUENCE: 167
gagtcgatac gc                                                    12

<210> SEQ ID NO 168
<211> LENGTH: 12
<212> TYPE: DNA
<213> ORGANISM: Homo sapiens

<400> SEQUENCE: 168
```

```
gtctcacgat cg                                                       12

<210> SEQ ID NO 169
<211> LENGTH: 12
<212> TYPE: DNA
<213> ORGANISM: Homo sapiens

<400> SEQUENCE: 169
tcgtcgggtg ca                                                       12

<210> SEQ ID NO 170
<211> LENGTH: 12
<212> TYPE: DNA
<213> ORGANISM: Homo sapiens

<400> SEQUENCE: 170
actccgtagt ga                                                       12

<210> SEQ ID NO 171
<211> LENGTH: 12
<212> TYPE: DNA
<213> ORGANISM: Homo sapiens

<400> SEQUENCE: 171
caggacgtcc gt                                                       12

<210> SEQ ID NO 172
<211> LENGTH: 12
<212> TYPE: DNA
<213> ORGANISM: Homo sapiens

<400> SEQUENCE: 172
tcgtatccct ac                                                       12

<210> SEQ ID NO 173
<211> LENGTH: 12
<212> TYPE: DNA
<213> ORGANISM: Homo sapiens

<400> SEQUENCE: 173
tttcaaggcc gg                                                       12

<210> SEQ ID NO 174
<211> LENGTH: 12
<212> TYPE: DNA
<213> ORGANISM: Homo sapiens

<400> SEQUENCE: 174
cgccggtgga at                                                       12

<210> SEQ ID NO 175
<211> LENGTH: 12
<212> TYPE: DNA
<213> ORGANISM: Homo sapiens

<400> SEQUENCE: 175
gaacccgtcc ta                                                       12

<210> SEQ ID NO 176
<211> LENGTH: 12
<212> TYPE: DNA
<213> ORGANISM: Homo sapiens
```

```
<400> SEQUENCE: 176
gattcatcag cg                                                          12

<210> SEQ ID NO 177
<211> LENGTH: 12
<212> TYPE: DNA
<213> ORGANISM: Homo sapiens

<400> SEQUENCE: 177
acaccggtct tc                                                          12

<210> SEQ ID NO 178
<211> LENGTH: 12
<212> TYPE: DNA
<213> ORGANISM: Homo sapiens

<400> SEQUENCE: 178
atcgtgccct aa                                                          12

<210> SEQ ID NO 179
<211> LENGTH: 12
<212> TYPE: DNA
<213> ORGANISM: Homo sapiens

<400> SEQUENCE: 179
gcgtcaatgt tc                                                          12

<210> SEQ ID NO 180
<211> LENGTH: 12
<212> TYPE: DNA
<213> ORGANISM: Homo sapiens

<400> SEQUENCE: 180
ctccgtatct cg                                                          12

<210> SEQ ID NO 181
<211> LENGTH: 12
<212> TYPE: DNA
<213> ORGANISM: Homo sapiens

<400> SEQUENCE: 181
ccgattcctt cg                                                          12

<210> SEQ ID NO 182
<211> LENGTH: 12
<212> TYPE: DNA
<213> ORGANISM: Homo sapiens

<400> SEQUENCE: 182
tgcgcctcca gt                                                          12

<210> SEQ ID NO 183
<211> LENGTH: 12
<212> TYPE: DNA
<213> ORGANISM: Homo sapiens

<400> SEQUENCE: 183
taacgtcgga gc                                                          12

<210> SEQ ID NO 184
<211> LENGTH: 12
<212> TYPE: DNA
<213> ORGANISM: Homo sapiens
```

```
<400> SEQUENCE: 184
aaggtcgccc at                                                              12

<210> SEQ ID NO 185
<211> LENGTH: 12
<212> TYPE: DNA
<213> ORGANISM: Homo sapiens

<400> SEQUENCE: 185
gtcggggact at                                                              12

<210> SEQ ID NO 186
<211> LENGTH: 12
<212> TYPE: DNA
<213> ORGANISM: Homo sapiens

<400> SEQUENCE: 186
ttcgagcgat tt                                                              12

<210> SEQ ID NO 187
<211> LENGTH: 12
<212> TYPE: DNA
<213> ORGANISM: Homo sapiens

<400> SEQUENCE: 187
tgagtcgtcg ag                                                              12

<210> SEQ ID NO 188
<211> LENGTH: 12
<212> TYPE: DNA
<213> ORGANISM: Homo sapiens

<400> SEQUENCE: 188
tttacgcaga gg                                                              12

<210> SEQ ID NO 189
<211> LENGTH: 12
<212> TYPE: DNA
<213> ORGANISM: Homo sapiens

<400> SEQUENCE: 189
aggaagtatc gc                                                              12

<210> SEQ ID NO 190
<211> LENGTH: 12
<212> TYPE: DNA
<213> ORGANISM: Homo sapiens

<400> SEQUENCE: 190
actcgatacc at                                                              12

<210> SEQ ID NO 191
<211> LENGTH: 12
<212> TYPE: DNA
<213> ORGANISM: Homo sapiens

<400> SEQUENCE: 191
cgctacatag ca                                                              12

<210> SEQ ID NO 192
<211> LENGTH: 12
<212> TYPE: DNA
```

```
<213> ORGANISM: Homo sapiens

<400> SEQUENCE: 192
ttcataaccg gc                                                          12

<210> SEQ ID NO 193
<211> LENGTH: 12
<212> TYPE: DNA
<213> ORGANISM: Homo sapiens

<400> SEQUENCE: 193
ccaaacggtt aa                                                          12

<210> SEQ ID NO 194
<211> LENGTH: 12
<212> TYPE: DNA
<213> ORGANISM: Homo sapiens

<400> SEQUENCE: 194
cgattccttc gt                                                          12

<210> SEQ ID NO 195
<211> LENGTH: 12
<212> TYPE: DNA
<213> ORGANISM: Homo sapiens

<400> SEQUENCE: 195
cgtcatgaat aa                                                          12

<210> SEQ ID NO 196
<211> LENGTH: 12
<212> TYPE: DNA
<213> ORGANISM: Homo sapiens

<400> SEQUENCE: 196
agtggcgatg ac                                                          12

<210> SEQ ID NO 197
<211> LENGTH: 12
<212> TYPE: DNA
<213> ORGANISM: Homo sapiens

<400> SEQUENCE: 197
cccctacggc ac                                                          12

<210> SEQ ID NO 198
<211> LENGTH: 12
<212> TYPE: DNA
<213> ORGANISM: Homo sapiens

<400> SEQUENCE: 198
gccaacccgc ac                                                          12

<210> SEQ ID NO 199
<211> LENGTH: 12
<212> TYPE: DNA
<213> ORGANISM: Homo sapiens

<400> SEQUENCE: 199
tgggacaccg gt                                                          12

<210> SEQ ID NO 200
<211> LENGTH: 12
```

<212> TYPE: DNA
<213> ORGANISM: Homo sapiens

<400> SEQUENCE: 200
ttgactgcgg cg                                                      12

<210> SEQ ID NO 201
<211> LENGTH: 12
<212> TYPE: DNA
<213> ORGANISM: Homo sapiens

<400> SEQUENCE: 201
actatgcgta gg                                                      12

<210> SEQ ID NO 202
<211> LENGTH: 12
<212> TYPE: DNA
<213> ORGANISM: Homo sapiens

<400> SEQUENCE: 202
tcacccaaag cg                                                      12

<210> SEQ ID NO 203
<211> LENGTH: 12
<212> TYPE: DNA
<213> ORGANISM: Homo sapiens

<400> SEQUENCE: 203
gcaggacgtc cg                                                      12

<210> SEQ ID NO 204
<211> LENGTH: 12
<212> TYPE: DNA
<213> ORGANISM: Homo sapiens

<400> SEQUENCE: 204
acaccgaaaa cg                                                      12

<210> SEQ ID NO 205
<211> LENGTH: 12
<212> TYPE: DNA
<213> ORGANISM: Homo sapiens

<400> SEQUENCE: 205
cggtgtattg ag                                                      12

<210> SEQ ID NO 206
<211> LENGTH: 12
<212> TYPE: DNA
<213> ORGANISM: Homo sapiens

<400> SEQUENCE: 206
cacgaggtat gc                                                      12

<210> SEQ ID NO 207
<211> LENGTH: 12
<212> TYPE: DNA
<213> ORGANISM: Homo sapiens

<400> SEQUENCE: 207
taaagcgacc cg                                                      12

<210> SEQ ID NO 208

```
<211> LENGTH: 12
<212> TYPE: DNA
<213> ORGANISM: Homo sapiens

<400> SEQUENCE: 208
cttagtcggc ca                                                          12

<210> SEQ ID NO 209
<211> LENGTH: 12
<212> TYPE: DNA
<213> ORGANISM: Homo sapiens

<400> SEQUENCE: 209
cgaaaacgtg gc                                                          12

<210> SEQ ID NO 210
<211> LENGTH: 12
<212> TYPE: DNA
<213> ORGANISM: Homo sapiens

<400> SEQUENCE: 210
cgtgccctga ac                                                          12

<210> SEQ ID NO 211
<211> LENGTH: 12
<212> TYPE: DNA
<213> ORGANISM: Homo sapiens

<400> SEQUENCE: 211
tttaccatcg aa                                                          12

<210> SEQ ID NO 212
<211> LENGTH: 12
<212> TYPE: DNA
<213> ORGANISM: Homo sapiens

<400> SEQUENCE: 212
cgtagccatg tt                                                          12

<210> SEQ ID NO 213
<211> LENGTH: 12
<212> TYPE: DNA
<213> ORGANISM: Homo sapiens

<400> SEQUENCE: 213
cccaaacggt ta                                                          12

<210> SEQ ID NO 214
<211> LENGTH: 12
<212> TYPE: DNA
<213> ORGANISM: Homo sapiens

<400> SEQUENCE: 214
gcgttatcag aa                                                          12

<210> SEQ ID NO 215
<211> LENGTH: 12
<212> TYPE: DNA
<213> ORGANISM: Homo sapiens

<400> SEQUENCE: 215
tcgatggtaa ac                                                          12
```

```
<210> SEQ ID NO 216
<211> LENGTH: 12
<212> TYPE: DNA
<213> ORGANISM: Homo sapiens

<400> SEQUENCE: 216
cgactttttg ca                                                         12

<210> SEQ ID NO 217
<211> LENGTH: 12
<212> TYPE: DNA
<213> ORGANISM: Homo sapiens

<400> SEQUENCE: 217
tcgacgactc ac                                                         12

<210> SEQ ID NO 218
<211> LENGTH: 12
<212> TYPE: DNA
<213> ORGANISM: Homo sapiens

<400> SEQUENCE: 218
acgcgtcaga ta                                                         12

<210> SEQ ID NO 219
<211> LENGTH: 12
<212> TYPE: DNA
<213> ORGANISM: Homo sapiens

<400> SEQUENCE: 219
cgtacggcac ag                                                         12

<210> SEQ ID NO 220
<211> LENGTH: 12
<212> TYPE: DNA
<213> ORGANISM: Homo sapiens

<400> SEQUENCE: 220
ctatgccgtg ca                                                         12

<210> SEQ ID NO 221
<211> LENGTH: 12
<212> TYPE: DNA
<213> ORGANISM: Homo sapiens

<400> SEQUENCE: 221
cgcgtcagat at                                                         12

<210> SEQ ID NO 222
<211> LENGTH: 12
<212> TYPE: DNA
<213> ORGANISM: Homo sapiens

<400> SEQUENCE: 222
aagatcggta gc                                                         12

<210> SEQ ID NO 223
<211> LENGTH: 12
<212> TYPE: DNA
<213> ORGANISM: Homo sapiens

<400> SEQUENCE: 223
cttcgcaagg ag                                                         12
```

<210> SEQ ID NO 224
<211> LENGTH: 12
<212> TYPE: DNA
<213> ORGANISM: Homo sapiens

<400> SEQUENCE: 224
gtcgtggact ac                                                         12

<210> SEQ ID NO 225
<211> LENGTH: 12
<212> TYPE: DNA
<213> ORGANISM: Homo sapiens

<400> SEQUENCE: 225
ggtcgtcatc aa                                                         12

<210> SEQ ID NO 226
<211> LENGTH: 12
<212> TYPE: DNA
<213> ORGANISM: Homo sapiens

<400> SEQUENCE: 226
gttaacagcg tg                                                         12

<210> SEQ ID NO 227
<211> LENGTH: 12
<212> TYPE: DNA
<213> ORGANISM: Homo sapiens

<400> SEQUENCE: 227
tagctaaccg tt                                                         12

<210> SEQ ID NO 228
<211> LENGTH: 12
<212> TYPE: DNA
<213> ORGANISM: Homo sapiens

<400> SEQUENCE: 228
agtaaaggcg ct                                                         12

<210> SEQ ID NO 229
<211> LENGTH: 12
<212> TYPE: DNA
<213> ORGANISM: Homo sapiens

<400> SEQUENCE: 229
ggtaatttcg tg                                                         12

<210> SEQ ID NO 230
<211> LENGTH: 15
<212> TYPE: DNA
<213> ORGANISM: Homo sapiens

<400> SEQUENCE: 230
cagaagaaga agggc                                                      15

<210> SEQ ID NO 231
<211> LENGTH: 51
<212> TYPE: DNA
<213> ORGANISM: Homo sapiens

<400> SEQUENCE: 231
ccaatgggga ggacatcgat gtcacctcca atgactaggg tggtgggcaa c              51

<210> SEQ ID NO 232
<211> LENGTH: 15
<212> TYPE: DNA
<213> ORGANISM: Homo sapiens

<400> SEQUENCE: 232
ctctggccac tccct                                              15

<210> SEQ ID NO 233
<211> LENGTH: 52
<212> TYPE: DNA
<213> ORGANISM: Homo sapiens

<400> SEQUENCE: 233
acatcgatgt cacctccaat gacaagcttg ctagcggtgg gcaaccacaa ac      52

<210> SEQ ID NO 234
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(25)
<223> OTHER INFORMATION: a, c, t, g, unknown or other

<400> SEQUENCE: 234
caccgnnnnn nnnnnnnnnn nnnnn                                   25

<210> SEQ ID NO 235
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (5)..(24)
<223> OTHER INFORMATION: a, c, t, g, unknown or other

<400> SEQUENCE: 235
aaacnnnnnn nnnnnnnnnn nnnnc                                   25

<210> SEQ ID NO 236
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
aacaccgggt cttcgagaag acctgtttta gagctagaaa tagcaagtta aaat    54

<210> SEQ ID NO 237
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 237
caaaacgggt cttcgagaag acgttttaga gctatgctgt tttgaatggt ccca         54

<210> SEQ ID NO 238
<211> LENGTH: 720
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 238
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagtaa   720

<210> SEQ ID NO 239
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
gttgtgctca gtactgactt tgg                                            23

<210> SEQ ID NO 240
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
gttgggcacg gtactgactt tgg                                            23

<210> SEQ ID NO 241
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
gccctgcaca gtactgactt aag          23

<210> SEQ ID NO 242
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
gttctgccca ggactgactt ggg          23

<210> SEQ ID NO 243
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
atcctgctct gtactgactt gag          23

<210> SEQ ID NO 244
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
gttgggttta gtactgactt ggg          23

<210> SEQ ID NO 245
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
agtcagtact gagcacaaca agg          23

<210> SEQ ID NO 246
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
agtgagtcct gagcacaaca cag          23

<210> SEQ ID NO 247
<211> LENGTH: 23
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
tgtcagtact gagctcaaca aag                                             23

<210> SEQ ID NO 248
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
ggtgggtcct gagcacaaca aag                                             23

<210> SEQ ID NO 249
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
tttcagcttc caataaaaac agg                                             23

<210> SEQ ID NO 250
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
tttcagcatc caataaaaat aag                                             23

<210> SEQ ID NO 251
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
ttgcatcatc caataaaaac tag                                             23

<210> SEQ ID NO 252
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
atacatcttc caataaaaac tag                                             23
```

```
<210> SEQ ID NO 253
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
ttgcgtcttc caataaaaac tgg                                                23

<210> SEQ ID NO 254
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
tggcagcttc ctataaaaac tag                                                23

<210> SEQ ID NO 255
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
aaacatctcg tacagtgaca agg                                                23

<210> SEQ ID NO 256
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
gggcatctct tacagtgaca agg                                                23

<210> SEQ ID NO 257
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
aaagttcaca tacagtgaca cag                                                23

<210> SEQ ID NO 258
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 258
aaacaggtcc tacagtgaca agg         23

<210> SEQ ID NO 259
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
taagatttct tacagtgaca tag         23

<210> SEQ ID NO 260
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
aagcatcttg gacagtgaca tag         23

<210> SEQ ID NO 261
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
attccacggg aaggagatct tgg         23

<210> SEQ ID NO 262
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
agttcacagg aaggagatct aag         23

<210> SEQ ID NO 263
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
attactctgg aaggagatct ggg         23

<210> SEQ ID NO 264
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
gtagcacagg aaggagatct agg                                             23

<210> SEQ ID NO 265
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
aattgactgg aaggagatct gag                                             23

<210> SEQ ID NO 266
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
gttgcacaga aaggagatct ggg                                             23

<210> SEQ ID NO 267
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
gtactgcagt ccaaagaacc agg                                             23

<210> SEQ ID NO 268
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
ctgctgcact ccaaagaacc tag                                             23

<210> SEQ ID NO 269
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
```
taactacagt ccaaagaacc agg                                                23

<210> SEQ ID NO 270
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
cagctgctgt ccaaagaacc cag                                                23

<210> SEQ ID NO 271
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
cacagtggcc tggctcaaaa tgg                                                23

<210> SEQ ID NO 272
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
cacagtgggc tgactcaaaa gag                                                23

<210> SEQ ID NO 273
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
caaactggcc tggctctaaa cag                                                23

<210> SEQ ID NO 274
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
caccatggcc tggctctaaa agg                                                23

<210> SEQ ID NO 275
<211> LENGTH: 23
<212> TYPE: DNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 275
taaagttgca tggctcaaaa aag                                           23

<210> SEQ ID NO 276
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
aggattgaag ctgacgttct tgg                                           23

<210> SEQ ID NO 277
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
ggatttaaag ctgacgttct tag                                           23

<210> SEQ ID NO 278
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
aggatagaag ctgacattct cgg                                           23

<210> SEQ ID NO 279
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
atttttgaag ttgacgttct cag                                           23

<210> SEQ ID NO 280
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
agccatgaag atgacgttct ggg                                           23

<210> SEQ ID NO 281
```

```
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
aggactggag ctgacgtact gag                                          23

<210> SEQ ID NO 282
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
cgtcagcttc aatcctgcca agg                                          23

<210> SEQ ID NO 283
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
agtcagcttc agtcctgcca cgg                                          23

<210> SEQ ID NO 284
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
gagcagcttc aatcctgcca ggg                                          23

<210> SEQ ID NO 285
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
agtctgcttc catcctgcca aag                                          23

<210> SEQ ID NO 286
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
```

```
ctcagagatt gctgcatagt agg                                                     23

<210> SEQ ID NO 287
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
ctcaaaactt gctgcatagt aag                                                     23

<210> SEQ ID NO 288
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
cccagagctt ggtgcatagt cag                                                     23

<210> SEQ ID NO 289
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
cccaaagatt gctgcacagt gag                                                     23

<210> SEQ ID NO 290
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
acaggtcatc ttaatgagcc agg                                                     23

<210> SEQ ID NO 291
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
acacttcttc ttaatgagcc cag                                                     23

<210> SEQ ID NO 292
<211> LENGTH: 23
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 292
agaggtcttc ttaatgagct agg                                            23

<210> SEQ ID NO 293
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
ggatgtcata ttaatgagcc tag                                            23

<210> SEQ ID NO 294
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
ccaaatcata ttaatgagcc aag                                            23

<210> SEQ ID NO 295
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
ggggctgtgg ttccacgata ggg                                            23

<210> SEQ ID NO 296
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
gggactgtgg gtgcacgata aag                                            23

<210> SEQ ID NO 297
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
gaggctgggg ttccaagata aag                                            23
```

<210> SEQ ID NO 298
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 298
ggagctgggg ttccaggata aag                                         23

<210> SEQ ID NO 299
<211> LENGTH: 12743
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 299
ttaatgtagt cttatgcaat actcttgtag tcttgcaaca tggtaacgat gagttagcaa      60
catgccttac aaggagagaa aaagcaccgt gcatgccgat tggtggaagt aaggtggtac     120
gatcgtgcct tattaggaag gcaacagacg ggtctgacat ggattggacg aaccactgaa     180
ttgccgcatt gcagagatat tgtatttaag tgcctagctc gatacataaa cgggtctctc     240
tggttagacc agatctgagc ctgggagctc tctggctaac tagggaaccc actgcttaag     300
cctcaataaa gcttgccttg agtgcttcaa gtagtgtgtg cccgtctgtt gtgtgactct     360
ggtaactaga gatccctcag acccttttag tcagtgtgga aaatctctag cagtggcgcc     420
cgaacaggga cttgaaagcg aaagggaaac cagaggagct ctctcgacgc aggactcggc     480
ttgctgaagc gcgcacggca agaggcgagg ggcggcgact ggtgagtacg ccaaaaattt     540
tgactagcgg aggctagaag gagagagatg ggtgcgagag cgtcagtatt aagcggggga     600
gaattagatc gcgatgggaa aaaattcggt taaggccagg gggaaagaaa aaatataaat     660
taaaacatat agtatgggca agcagggagc tagaacgatt cgcagttaat cctggcctgt     720
tagaaacatc agaaggctgt agacaaatac tgggacagct acaaccatcc cttcagacag     780
gatcagaaga acttagatca ttatataata cagtagcaac cctctattgt gtgcatcaaa     840
ggatagagat aaaagacacc aaggaagctt tagacaagat agaggaagag caaaacaaaa     900
gtaagaccac cgcacagcaa gcggccgctg atcttcagac ctggaggagg agatatgagg     960
gacaattgga gaagtgaatt atataaatat aaagtagtaa aaattgaacc attaggagta    1020
gcacccacca aggcaaagag aagagtggtg cagagagaaa aaagagcagt gggaatagga    1080
gctttgttcc ttgggttctt gggagcagca ggaagcacta tgggcgcagc gtcaatgacg    1140
ctgacggtac aggccagaca attattgtct ggtatagtgc agcagcagaa caatttgctg    1200
agggctattg aggcgcaaca gcatctgttg caactcacag tctggggcat caagcagctc    1260
caggcaagaa tcctggctgt ggaaagatac ctaaaggatc aacagctcct ggggatttgg    1320
ggttgctctg gaaaactcat ttgcaccact gctgtgcctt ggaatgctag ttggagtaat    1380
aaatctctgg aacagatttg gaatcacacg acctggatgg agtgggacag agaaattaac    1440
aattacacaa gcttaataca ctccttaatt gaagaatcgc aaaaccagca agaaaagaat    1500
gaacaagaat tattggaatt agataaatgg gcaagtttgt ggaattggtt taacataaca    1560
aattggctgt ggtatataaa attattcata atgatagtag gaggcttggt aggtttaaga    1620

```
atagtttttg ctgtactttc tatagtgaat agagttaggc agggatattc accattatcg    1680
tttcagaccc acctcccaac cccgagggga cccagagagg gcctatttcc catgattcct    1740
tcatatttgc atatacgata caaggctgtt agagagataa ttagaattaa tttgactgta    1800
aacacaaaga tattagtaca aaatacgtga cgtagaaagt aataatttct tgggtagttt    1860
gcagttttaa aattatgttt taaaatggac tatcatatgc ttaccgtaac ttgaaagtat    1920
ttcgatttct tggctttata tatcttgtgg aaaggacgaa acaccggaga cggttgtaaa    1980
tgagcacaca aaatacacat gctaaaatat tatattctat gacctttata aaatcaacca    2040
aaatcttctt tttaataact ttagtatcaa taattagaat ttttatgttc cttttttgcaa   2100
acttttaata aaaatgagca aaataaaaaa acgctagttt tagtaactcg cgttgttttc    2160
ttcacccttta ataatagcta ctccaccact tgttcctaag cggtcagctc ctgcttcaat   2220
cattttttga gcatcttcaa atgttctaac tccaccagct gctttaacta aagcattgtc    2280
tttaacaact gacttcatta gtttaacatc ttcaaatgtt gcacctgatt ttgaaaatcc    2340
tgttgatgtt ttaacaaatt ctaatccagc ttcaacagct atttcacaag ctttcatgat    2400
ttcttctttt gttaataaac aattttccat aatacattta acaacatgtg atccagctgc    2460
tttttttaca gctttcatgt cttctaaaac taattcataa ttttttgtctt ttaatgcacc   2520
aatatttaat accatatcaa tttctgttgc accatcttta attgcttcag aaacttcgaa    2580
tgcttttgta gctgttgtgc atgcacctag aggaaaacct acaacatttg ttattcctac    2640
atttgtgcct tttaataatt cttacaata gcttgttcaa tatgaattaa cacaaactgt     2700
tgcaaaatca aattcaattg cttcatcaca taattgttta atttcagctt tcgtagcatc    2760
ttgttttaat aatgtgtgat ctatatattt gtttagtttc attttttctc ctatatattc    2820
attttttaatt ttaattcttt aataatttcg tctactttaa ctttagcgtt ttgaacagat   2880
tcaccaacac ctataaaata aattttttagt ttaggttcag ttccacttgg gcgaacagca   2940
aatcatgact tatcttctaa ataaaatttt agtaagtctt gtcctggcat attatacatt    3000
ccatcgatgt agtcttcaac attaacaact ttaagtccag caatttgagt taagggtgtt    3060
gctctcaatg atttcattaa tggttcaatt ttttaatttct tttcttctgg tttaaaattc   3120
aagtttaaag tgaaagtgta atatgcaccc atttctttaa ataaatcttc taaatagtct    3180
actaatgttt tattttgttt tttataaaat caagcagcct ctgctattaa tatagaagct    3240
tgtattccat ctttatctct agctgagtca tcaattacat atccataact ttcttcataa    3300
gcaaaaacaa aatttaatcc gttatcttct tctttagcaa tttctctacc cattcattta    3360
aatccagtta aagttttttac aatattaact ccatattttt catgagcgat tctatcaccc   3420
aaatcacttg ttacaaaact tgaatataga gccggatttt ttggaatgct atttaagcgt    3480
tttagatttg ataattttca atcaattaaa attggtcctg tttgatttcc atctaatctt    3540
acaaaatgac catcatgttt tattgccatt ccaaatctgt cagcatctgg gtcattcata    3600
ataataatat ctgcatcatg tttaatacca tattcaagcg gtattttca tgcaggatca     3660
aattctggat ttggatttac aacatttta atgtttcat cttcaaatgc atgctcttca      3720
acctcaataa cgttatatcc tgattcacgt aatatttttg gggtaaattt agttcctgtt    3780
ccattaactg cgctaaaaat aattttttaaa tcttttttag cttcttgctc ttttttgtac   3840
gtctctgttt tagagctaga aatagcaagt taaaataagg ctagtccgtt atcaacttga    3900
aaagtggca ccgagtcggt gctttttttga attctgatc ttgagacaaa tggcagtatt     3960
catccacaat tttaaaagaa aagggggggat tgggggtac agtgcagggg aagaatagt     4020
```

```
agacataata gcaacagaca tacaaactaa agaattacaa aaacaaatta caaaaattca   4080
aaattttcgg gtttattaca gggacagcag agatccactt tggcgccggc tcgagtggct   4140
ccggtgcccg tcagtgggca gagcgcacat cgcccacagt ccccgagaag ttgggggag    4200 gggtcggcaa ttgaaccggt gcctagaaaa ggtggcgcgg ggtaaactgg gaaagtgatg   4260
tcgtgtactg gctccgcctt tttcccgagg gtggggagaa accgtatata agtgcagtag   4320
tcgccgtgaa cgttcttttt cgcaacgggt ttgccgccag aacacaggtg tcgtgacgcg   4380
ggatccgcca ccatggatta caaagacgat gacgataaga tggccccaaa gaagaagcgg   4440
aaggtcggta tccacggagt cccagcagcc gacaagaagt acagcatcgg cctggacatc   4500
ggcaccaact ctgtgggctg gccgtgatc accgacgagt acaaggtgcc cagcaagaaa    4560
ttcaaggtgc tgggcaacac cgaccggcac agcatcaaga gaacctgat cggagccctg    4620 ctgttcgaca gcggcgaaac agccgaggcc acccggctga agagaaccgc cagaagaaga   4680
tacaccagac ggaagaaccg gatctgctat ctgcaagaga tcttcagcaa cgagatggcc   4740
aaggtggacg acagcttctt ccacagactg gaagagtcct tcctggtgga agaggataag   4800
aagcacgagc ggcaccccat cttcggcaac atcgtggacg aggtggccta ccacgagaag   4860
taccccacca tctaccacct gagaaagaaa ctggtggaca gcaccgacaa ggccgacctg   4920
cggctgatct atctggccct ggcccacatg atcaagttcc ggggccactt cctgatcgag   4980
ggcgacctga accccgacaa cagcgacgtg gacaagctgt tcatccagct ggtgcagacc   5040
tacaaccagc tgttcgagga aaaccccatc aacgccagcg gcgtggacgc caaggccatc   5100
ctgtctgcca gactgagcaa gagcagacgg ctggaaaatc tgatcgccca gctgcccggc   5160
gagaagaaga atggcctgtt cggcaacctg attgccctga gcctgggcct gacccccaac   5220
ttcaagagca acttcgacct ggccgaggat gccaaactgc agctgagcaa ggacacctac   5280
gacgacgacc tggacaacct gctggcccag atcggcgacc agtacgccga cctgtttctg   5340
gccgccaaga acctgtccga cgccatcctg ctgagcgaca tcctgagagt gaacaccgag   5400
atcaccaagg ccccctgag cgcctctatg atcaagagat acgacgagca ccaccaggac   5460
ctgaccctgc tgaaagctct cgtgcggcag cagctgcctg agaagtacaa agagattttc   5520
ttcgaccaga gcaagaacgg ctacgccggc tacattgacg gcggagccag ccaggaagag   5580
ttctacaagt tcatcaagcc catcctggaa aagatggacg gcaccgagga actgctcgtg   5640
aagctgaaca gagaggacct gctgcggaag cagcggacct tcgacaacgg cagcatcccc   5700
caccagatcc acctgggaga gctgcacgcc attctgcgc ggcaggaaga tttttacccca   5760 ttcctgaagg acaaccggga aaagatcgag aagatcctga ccttccgcat cccctactac   5820
gtgggccctc tggccagggg aaacagcaga ttcgcctgga tgaccagaaa gagcgaggaa   5880
accatcaccc cctggaactt cgaggaagtg gtggacaagg gcgcttccgc ccagagcttc   5940
atcgagcgga tgaccaactt cgataagaac ctgcccaacg agaaggtgct gcccaagcac   6000
agcctgctgt acgagtactt caccgtgtat aacgagctga ccaaagtgaa atacgtgacc   6060
gagggaatga gaaagcccgc cttcctgagc ggcgagcaga aaaaggccat cgtggacctg   6120
ctgttcaaga ccaaccggaa agtgaccgtg aagcagctga aggaggacta cttcaagaaa   6180
atcgagtgct tcgactccgt ggaaatctcc ggcgtggaag atcggttcaa cgcctccctg   6240
ggcacatacc acgatctgct gaaaattatc aaggacaagg acttcctgga caatgaggaa   6300
aacgaggaca ttctggaaga tatcgtgctg accctgacac tgtttgagga cagagagatg   6360
```

```
atcgaggaac ggctgaaaac ctatgcccac ctgttcgacg acaaagtgat gaagcagctg   6420
aagcggcgga gatacaccgg ctggggcagg ctgagccgga agctgatcaa cggcatccgg   6480
gacaagcagt ccggcaagac aatcctggat ttcctgaagt ccgacggctt cgccaacaga   6540
aacttcatgc agctgatcca cgacgacagc ctgaccttta agaggacat ccagaaagcc   6600 caggtgtccg gccagggcga tagcctgcac gagcacattg ccaatctggc cggcagcccc   6660
gccattaaga agggcatcct gcagacagtg aaggtggtgg acgagctcgt gaaagtgatg   6720
ggccggcaca agcccgagaa catcgtgatc gaaatggcca gagagaacca gaccacccag   6780
aagggacaga agaacagccg cgagagaatg aagcggatcg aagagggcat caaagagctg   6840
ggcagccaga tcctgaaaga acaccccgtg gaaaacaccc agctgcagaa cgagaagctg   6900
tacctgtact acctgcagaa tgggcgggat atgtacgtgg accaggaact ggacatcaac   6960
cggctgtccg actacgatgt ggaccatatc gtgcctcaga gctttctgaa ggacgactcc   7020
atcgacaaca aggtgctgac cagaagcgac aagaaccggg gcaagagcga caacgtgccc   7080
tccgaagagg tcgtgaagaa gatgaagaac tactggcggc agctgctgaa cgccaagctg   7140
attacccaga gaaagttcga caatctgacc aaggccgaga gaggcggcct gagcgaactg   7200
gataaggccg gcttcatcaa gagacagctg gtggaaaccc ggcagatcac aaagcacgtg   7260
gcacagatcc tggactcccg gatgaacact aagtacgacg agaatgacaa gctgatccgg   7320
gaagtgaaag tgatcaccct gaagtccaag ctggtgtccg atttccggaa ggatttccag   7380
ttttacaaag tgcgcgagat caacaactac caccacgccc acgacgccta cctgaacgcc   7440
gtcgtgggaa ccgccctgat caaaaagtac cctaagctgg aaagcgagtt cgtgtacggc   7500
gactacaagg tgtacgacgt gcggaagatg atcgccaaga gcgagcagga aatcggcaag   7560
gctaccgcca agtacttctt ctacagcaac atcatgaact tttcaagac cgagattacc   7620 ctggccaacg gcgagatccg gaagcggcct ctgatcgaga caaacggcga aaccggggag   7680
atcgtgtggg ataaggcccg ggattttgcc accgtgcgga aagtgctgag catgccccaa   7740
gtgaatatcg tgaaaaagac cgaggtgcag acaggcggct tcagcaaaga gtctatcctg   7800
cccaagagga cagcgataa gctgatcgcc agaaagaagg actgggaccc taagaagtac   7860
ggcggcttcg acagccccac cgtggcctat tctgtgctgg tggtggccaa agtggaaaag   7920
ggcaagtcca gaaactgaa gagtgtgaaa gagctgctgg ggatcaccat catggaaaga   7980
agcagcttcg agaagaatcc catcgacttt ctggaagcca agggctacaa agaagtgaaa   8040
aaggacctga tcatcaagct gcctaagtac tcccctgttcg agctgaaaaa cggccggaag   8100
agaatgctgg cctctgccgg cgaactgcag aagggaaacg aactggccct gccctccaaa   8160
tatgtgaact tcctgtacct ggccagccac tatgagaagc tgaagggctc ccccgaggat   8220
aatgagcaga aacagctgtt tgtggaacag cacaagcact acctggacga gatcatcgag   8280
cagatcagcg agttctccaa gagagtgatc ctggccgacg ctaatctgga caaagtgctg   8340
tccgcctaca acaagcaccg ggataagccc atcagagagc aggccgagaa tatcatccac   8400
ctgtttaccc tgaccaatct gggagcccct gccgccttca gtactttga caccaccatc   8460 gaccggaaga ggtacaccag caccaaagag gtgctggacg ccaccctgat ccaccagagc   8520
atcaccggcc tgtacgagac acggatcgac ctgtctcagc tgggaggcga caagcgtcct   8580
gctgctacta agaaagctgg tcaagctaag aaaaagaaag ctagcggcag cggcgccacc   8640
aacttcagcc tgctgaagca ggccggcgac gtggaggaga ccccggcccc catgaccgag   8700
tacaagccca cggtgcgcct cgccacccgc gacgacgtcc ccagggccgt acgcaccctc   8760
```

```
gccgccgcgt tcgccgacta ccccgccacg cgccacaccg tcgatccgga ccgccacatc   8820
gagcgggtca ccgagctgca agaactcttc ctcacgcgcg tcgggctcga catcggcaag   8880
gtgtgggtcg cggacgacgg cgcggccgtg gcggtctgga ccacgccgga gagcgtcgaa   8940 gcggggggcgg tgttcgccga gatcggcccg cgcatggccg agttgagcgg ttcccggctg   9000
gccgcgcagc aacagatgga aggcctcctg gcgccgcacc ggcccaagga gcccgcgtgg   9060
ttcctggcca ccgtcggagt ctcgcccgac caccagggca agggtctggg cagcgccgtc   9120
gtgctccccg gagtggaggc ggccgagcgc gccggggtgc ccgccttcct ggagacctcc   9180
gcgccccgca acctccccct ctacgagcgg ctcggcttca ccgtcaccgc cgacgtcgag   9240
gtgcccgaag accgcgcac ctggtgcatg acccgcaagc ccggtgcctg aacgcgttaa   9300
gtcgacaatc aacctctgga ttacaaaatt tgtgaaagat tgactggtat tcttaactat   9360
gttgctcctt ttacgctatg tggatacgct gctttaatgc cttttgtatca tgctattgct   9420 tcccgtatgg ctttcatttt ctcctccttg tataaatcct ggttgctgtc tctttatgag   9480
gagttgtggc ccgttgtcag gcaacgtggc gtggtgtgca ctgtgtttgc tgacgcaacc   9540
cccactggtt ggggcattgc caccacctgt cagctccttt ccgggacttt cgctttcccc   9600
ctccctattg ccacggcgga actcatcgcc gcctgccttg cccgctgctg gacaggggct   9660
cggctgttgg gcactgacaa ttccgtggtg ttgtcgggga aatcatcgtc ctttccttgg   9720
ctgctcgcct gtgttgccac ctggattctg cgcgggacgt ccttctgcta cgtcccttcg   9780
gccctcaatc cagcggacct tccttcccgc ggcctgctgc cggctctgcg gcctcttccg   9840
cgtcttcgcc ttcgccctca gacgagtcgg atctcccttt gggccgcctc ccgcgtcga   9900 ctttaagacc aatgacttac aaggcagctg tagatcttag ccactttta aaagaaaagg   9960 ggggactgga agggctaatt cactcccaac gaagacaaga tctgcttttt gcttgtactg  10020
ggtctctctg gttagaccag atctgagcct gggagctctc tggctaacta gggaacccac  10080
tgcttaagcc tcaataaagc ttgccttgag tgcttcaagt agtgtgtgcc cgtctgttgt  10140
gtgactctgg taactagaga tccctcagac ccttttagtc agtgtggaaa atctctagca  10200
gtacgtatag tagttcatgt catcttatta ttcagtattt ataacttgca aagaaatgaa  10260
tatcagagag tgagaggaac ttgtttattg cagcttataa tggttacaaa taaagcaata  10320
gcatcacaaa tttcacaaat aaagcatttt tttcactgca ttctagttgt ggtttgtcca  10380
aactcatcaa tgtatcttat catgtctggc tctagctatc ccgcccctaa ctccgcccat  10440 cccgcccta actccgccca gttccgccca ttctccgccc catggctgac taattttttt  10500
tatttatgca gaggccgagg ccgcctcggc ctctgagcta ttccagaagt agtgaggagg  10560
cttttttgga ggcctaggga cgtacccaat tcgccctata gtgagtcgta ttacgcgcgc  10620
tcactggccg tcgttttaca acgtcgtgac tgggaaaacc ctggcgttac ccaacttaat  10680
cgccttgcag cacatccccc tttcgccagc tggcgtaata gcgaagaggc ccgcaccgat  10740
cgcccttccc aacagttgcg cagcctgaat ggcgaatggg acgcgccctg tagcggcgca  10800
ttaagcgcgg cgggtgtggt ggttacgcgc agcgtgaccg ctacacttgc cagcgcccta  10860
gcgcccgctc ctttcgcttt cttcccttcc tttctcgcca cgttcgccgg ctttccccgt  10920
caagctctaa atcgggggct ccctttaggg ttccgattta gtgctttacg gcacctcgac  10980
cccaaaaaac ttgattaggg tgatggttca cgtagtgggc catcgccctg atagacggtt  11040
tttcgccctt tgacgttgga gtccacgttc tttaatagtg gactcttgtt ccaaactgga  11100
```

```
acaacactca accctatctc ggtctattct tttgatttat aagggatttt gccgatttcg    11160
gcctattggt taaaaaatga gctgatttaa caaaaattta acgcgaattt taacaaaata    11220
ttaacgctta caatttaggt ggcacttttc ggggaaatgt gcgcggaacc cctatttgtt    11280 tattttcta aatacattca aatatgtatc cgctcatgag acaataaccc tgataaatgc     11340
ttcaataata ttgaaaaagg aagagtatga gtattcaaca tttccgtgtc gcccttattc    11400 cctttttgc ggcattttgc cttcctgttt ttgctcaccc agaaacgctg gtgaaagtaa     11460
aagatgctga agatcagttg ggtgcacgag tgggttacat cgaactggat ctcaacagcg    11520
gtaagatcct tgagagtttt cgccccgaag aacgttttcc aatgatgagc acttttaaag    11580
ttctgctatg tggcgcggta ttatcccgta ttgacgccgg gcaagagcaa ctcggtcgcc    11640
gcatacacta ttctcagaat gacttggttg agtactcacc agtcacagaa aagcatctta    11700
cggatggcat gacagtaaga gaattatgca gtgctgccat aaccatgagt gataacactg    11760
cggccaactt acttctgaca acgatcggag gaccgaagga gctaaccgct tttttgcaca    11820
acatggggga tcatgtaact cgccttgatc gttgggaacc ggagctgaat gaagccatac    11880
caaacgacga gcgtgacacc acgatgcctg tagcaatggc aacaacgttg cgcaaactat    11940
taactggcga actacttact ctagcttccc ggcaacaatt aatagactgg atggaggcgg    12000
ataaagttgc aggaccactt ctgcgctcgg cccttccggc tggctggttt attgctgata    12060
aatctggagc cggtgagcgt gggtctcgcg gtatcattgc agcactgggg ccagatggta    12120
agccctcccg tatcgtagtt atctacacga cggggagtca ggcaactatg gatgaacgaa    12180
atagacagat cgctgagata ggtgcctcac tgattaagca ttggtaactg tcagaccaag    12240
tttactcata tatactttag attgatttaa aacttcattt ttaatttaaa aggatctagg    12300
tgaagatcct ttttgataat ctcatgacca aaatccctta acgtgagttt tcgttccact    12360
gagcgtcaga ccccgtagaa aagatcaaag gatcttcttg agatcctttt tttctgcgcg    12420
taatctgctg cttgcaaaca aaaaaaccac cgctaccagc ggtggtttgt ttgccggatc    12480
aagagctacc aactcttttt ccgaaggtaa ctggcttcag cagagcgcag ataccaaata    12540
ctgttcttct agtgtagccg tagttaggcc accacttcaa gaactctgta gcaccgccta    12600
catacctcgc tctgctaatc ctgttaccag tggctgctgc cagtggcgat aagtcgtgtc    12660
ttaccgggtt ggactcaaga cgatagttac cggataaggc gcagcggtcg ggctgaacgg    12720
ggggttcgtg cacacagccc agc                                           12743
```

<210> SEQ ID NO 300
<211> LENGTH: 14873
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 300

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360
```

```
acccccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg cccsctattg acgtcaatga cggtaaatgg cccgcctggc     540
```
(corrected) 
```
acccccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc    1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga gaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctgggatt    1920 tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aaggggggat    2460
tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta aggtaccgag ggcctatttc ccatgattcc ttcatatttg    2640
catatacgat acaaggctgt tagagagata attagaatta atttgactgt aaacacaaag    2700
```

-continued

```
atattagtac aaaatacgtg acgtagaaag taataaattc ttgggtagtt tgcagtttta    2760
aaattatgtt ttaaaatgga ctatcatatg cttaccgtaa cttgaaagta tttcgatttc    2820
ttggctttat atatcttgtg gaaaggacga acaccggag acggttgtaa atgagcacac     2880
aaaatacaca tgctaaaata ttatattcta tgacctttat aaaatcaacc aaaatcttct    2940
ttttaataac tttagtatca ataattagaa tttttatgtt cctttttgca aacttttaat    3000
aaaaatgagc aaaataaaaa aacgctagtt ttagtaactc gcgttgtttt cttcacctt     3060
aataatagct actccaccac ttgttcctaa gcggtcagct cctgcttcaa tcattttttg    3120
agcatcttca aatgttctaa ctccaccagc tgctttaact aaagcattgt ctttaacaac    3180
tgacttcatt agtttaacat cttcaaatgt tgcacctgat tttgaaaatc ctgttgatgt    3240
tttaacaaat tctaatccag cttcaacagc tatttcacaa gctttcatga tttcttcttt    3300
tgttaataaa caattttcca taatacattt aacaacatgt gatccagctg cttttttta    3360
agctttcatg tcttctaaaa ctaattcata attttttgtct tttaatgcac caatatttaa   3420
taccatatca atttctgttg caccatcttt aattgcttca gaaacttcga atgcttttgt    3480
agctgttgtg catgcaccta gaggaaaacc tacaacattt gttattccta catttgtgcc    3540
ttttaataat tctttacaat agcttgttca atatgaatta acacaaactg ttgcaaaatc    3600
aaattcaatt gcttcatcac ataattgttt aatttcagct ttcgtagcat cttgttttaa    3660
taatgtgtga tctatatatt tgtttagttt cattttttct cctatatat catttttaat    3720
tttaattctt taataatttc gtctacttta actttagcgt tttgaacaga ttcaccaaca   3780
cctataaaat aaattttttag tttaggttca gttccacttg ggcgaacagc aaatcatgac   3840
ttatcttcta aataaaattt tagtaagtct tgtcctggca tattatacat tccatcgatg    3900
tagtcttcaa cattaacaac tttaagtcca gcaatttgag ttaagggtgt tgctctcaat    3960
gatttcatta atggttcaat ttttaatttc ttttcttctg gtttaaaatt caagtttaaa    4020
gtgaaagtgt aatatgcacc catttcttta aataaatctt ctaaatagtc tactaatgtt    4080
ttattttgtt ttttataaaa tcaagcagcc tctgctatta atatagaagc ttgtattcca    4140
tctttatctc tagctgagtc atcaattaca tatccataac tttcttcata agcaaaaaca    4200
aaatttaatc cgttatcttc ttctttagca atttctctac ccattcattt aaatccagtt    4260
aaagttttta caatattaac tccatatttt tcatgagcga ttctatcacc caaatcactt    4320
gttacaaaac ttgaatatag agccggattt tttggaatgc tatttaagcg ttttagattt    4380
gataattttc aatcaattaa aattggtcct gtttgatttc catctaatct tacaaaatga    4440
ccatcatgtt ttattgccat tccaaatctg tcagcatctg ggtcattcat aataataata    4500
tctgcatcat gttaatacc atattcaagc ggtatttttc atgcaggatc aaattctgga   4560
tttggattta caacattttt aaatgtttca tcttcaaatg catgctcttc aacctcaata    4620
acgttatatc ctgattcacg taatattttt ggggtaaatt tagttcctgt tccattaact    4680
gcgctaaaaa taatttttaa atcttttta gcttcttgct ctttttgta cgtctctgtt      4740
ttagagctag aaatagcaag ttaaaataag gctagtccgt tatcaacttg aaaaagtggc    4800
accgagtcgg tgctttttg aattcgctag ctaggtcttg aaaggagtgg gaattggctc     4860
cggtgcccgt cagtgggcag agcgcacatc gcccacagtc cccgagaagt tggggggagg    4920
ggtcggcaat tgatccggtg cctagagaag gtggcgcggg gtaaactggg aaagtgatgt    4980
cgtgtactgg ctccgccttt ttcccgaggg tgggggagaa ccgtatataa gtgcagtagt    5040
cgccgtgaac gttcttttc gcaacgggtt tgccgccaga acacaggacc ggttctagag    5100
```

```
cgctgccacc atggacaaga agtacagcat cggcctggac atcggcacca actctgtggg    5160
ctgggccgtg atcaccgacg agtacaaggt gcccagcaag aaattcaagg tgctgggcaa    5220
caccgaccgg cacagcatca agaagaacct gatcggagcc ctgctgttcg acagcggcga    5280
aacagccgag gccacccggc tgaagagaac cgccagaaga agatacacca gacggaagaa    5340
ccggatctgc tatctgcaag agatcttcag caacgagatg gccaaggtgg acgacagctt    5400
cttccacaga ctggaagagt ccttcctggt ggaagaggat aagaagcacg agcggcaccc    5460
catcttcggc aacatcgtgg acgaggtggc ctaccacgag aagtacccca ccatctacca    5520
cctgagaaag aaactggtgg acagcaccga caaggccgac ctgcggctga tctatctggc    5580
cctggcccac atgatcaagt tccggggcca cttcctgatc gagggcgacc tgaaccccga    5640
caacagcgac gtggacaagc tgttcatcca gctggtgcag acctacaacc agctgttcga    5700
ggaaaacccc atcaacgcca gcggcgtgga cgccaaggcc atcctgtctg ccagactgag    5760
caagagcaga cggctggaaa atctgatcgc ccagctgccc ggcgagaaga gaatggcct    5820
gttcggaaac ctgattgccc tgagcctggg cctgaccccc aacttcaaga gcaacttcga    5880
cctgccgag gatgccaaac tgcagctgag caaggacacc tacgacacg acctggacaa    5940
cctgctggcc cagatcggcg accagtacgc cgacctgttt ctggccgcca gaacctgtc    6000
cgacgccatc ctgctgagcg acatcctgag agtgaacacc gagatcacca aggcccccct    6060
gagcgcctct atgatcaaga gatacgacga gcaccaccag gacctgaccc tgctgaaagc    6120
tctcgtgcgg cagcagctgc ctgagaagta caaagagatt ttcttcgacc agagcaagaa    6180
cggctacgcc ggctacattg acggcggagc cagccaggaa gagttctaca gttcatcaa    6240
gcccatcctg gaaaagatgg acggcaccga ggaactgctc gtgaagctga cagagagga    6300
cctgctgcgg aagcagcgga ccttcgacaa cggcagcatc ccccaccaga tccacctggg    6360
agagctgcac gccattctgc ggcggcagga agattttac ccattcctga aggacaaccg    6420
ggaaaagatc gagaagatcc tgaccttccg catccctac tacgtgggcc ctctggccag    6480
gggaaacagc agattcgcct ggatgaccag aaagagcgag gaaaccatca cccctggaa    6540
cttcgaggaa gtggtggaca agggcgcttc cgcccagagc ttcatcgagc ggatgaccaa    6600
cttcgataag aacctgccca cgagaaggt gctgcccaag cacagcctgc tgtacgagta    6660
cttcaccgtg tataacgagc tgaccaaagt gaaatacgtg accgagggaa tgagaaagcc    6720
cgccttcctg agcggcgagc agaaaaaggc catcgtggac ctgctgttca gaccaaccg    6780
gaaagtgacc gtgaagcagc tgaaagagga ctacttcaag aaaatcgagt gcttcgactc    6840
cgtggaaatc tccggcgtgg aagatcggtt caacgcctcc ctgggcacat accacgatct    6900
gctgaaaatt atcaaggaca aggacttcct ggacaatgag gaaacgagg acattctgga    6960
agatatcgtg ctgaccctga cactgtttga ggacagagag atgatcgagg aacggctgaa    7020
aacctatgcc cacctgttcg acgacaaagt gatgaagcag ctgaagcggc ggagatacac    7080
cggctgggc aggctgagcc ggaagctgat caacggcatc cgggacaagc agtccggcaa    7140
gacaatcctg gatttcctga agtccgacgg cttcgccaac agaaacttca tgcagctgat    7200
ccacgacgac agcctgacct ttaaagagga catccagaaa gccaggtgt ccggccaggg    7260
cgatagcctg cacgagcaca ttgccaatct ggccggcagc cccgccatta agaagggcat    7320
cctgcagaca gtgaaggtgg tggacgagct cgtgaaagtg atgggccggc acaagcccga    7380
gaacatcgtg atcgaaatgg ccagagagaa ccagaccacc cagaagggac agaagaacag    7440
```

-continued

```
ccgcgagaga atgaagcgga tcgaagaggg catcaaagag ctgggcagcc agatcctgaa      7500
agaacacccc gtggaaaaca cccagctgca gaacgagaag ctgtacctgt actacctgca      7560
gaatgggcgg gatatgtacg tggaccagga actggacatc aaccggctgt ccgactacga      7620
tgtggaccat atcgtgcctc agagctttct gaaggacgac tccatcgaca acaaggtgct      7680
gaccagaagc gacaagaacc ggggcaagag cgacaacgtg ccctccgaag aggtcgtgaa      7740
gaagatgaag aactactggc ggcagctgct gaacgccaag ctgattaccc agagaaagtt      7800
cgacaatctg accaaggccg agagaggcgg cctgagcgaa ctggataagg ccggcttcat      7860
caagagacag ctggtggaaa cccggcagat cacaaagcac gtggcacaga tcctggactc      7920
ccggatgaac actaagtacg acgagaatga caagctgatc cgggaagtga agtgatcac      7980 cctgaagtcc aagctggtgt ccgatttccg gaaggatttc cagttttaca agtgcgcga      8040 gatcaacaac taccaccacg cccacgacgc ctacctgaac gccgtcgtgg aaccgccct      8100 gatcaaaaag taccctaagc tggaaagcga gttcgtgtac ggcgactaca aggtgtacga      8160
cgtgcggaag atgatcgcca agagcgagca ggaaatcggc aaggctaccg ccaagtactt      8220
cttctacagc aacatcatga acttttttcaa gaccgagatt accctggcca acggcgagat      8280
ccggaagcgg cctctgatcg agacaaacgg cgaaaccggg gagatcgtgt gggataaggg      8340
ccgggatttt gccaccgtgc ggaaagtgct gagcatgccc caagtgaata tcgtgaaaaa      8400
gaccgaggtg cagacaggcg gcttcagcaa agagtctatc ctgcccaaga ggaacagcga      8460
taagctgatc gccagaaaga aggactggga ccctaagaag tacggcggct cgacagccc      8520 caccgtggcc tattctgtgc tggtggtggc caaagtggaa aagggcaagt ccaagaaact      8580
gaagagtgtg aaagagctgc tggggatcac catcatggaa agaagcagct cgagaagaa      8640 tcccatcgac tttctggaag ccaagggcta caaagaagtg aaaaaggacc tgatcatcaa      8700
gctgcctaag tactccctgt tcgagctgga aaacggccgg aagagaatgc tggcctctgc      8760
cggcgaactg cagaagggaa acgaactggc cctgcccctcc aaatatgtga acttcctgta      8820
cctggccagc cactatgaga agctgaaggg ctcccccgag gataatgagc agaaacagct      8880
gtttgtggaa cagcacaagc actacctgga cgagatcatc gagcagatca gcgagttctc      8940
caagagagtg atcctggccg acgctaatct ggacaaagtg ctgtccgcct acaacaagca      9000
ccgggataag cccatcagag agcaggccga gaatatcatc cacctgttta ccctgaccaa      9060
tctgggagcc cctgccgcct tcaagtactt tgacaccacc atcgaccgga gaggtacac      9120 cagcaccaaa gaggtgctgg acgccaccct gatccaccag agcatcaccg gcctgtacga      9180
gacacggatc gacctgtctc agctgggagg cgacaagcga cctgccgcca caagaaggc      9240 tggacaggct aagaagaaga aagattacaa agacgatgac gataagggat ccggcgcaac      9300
aaacttctct ctgctgaaac aagccggaga tgtcgaagag aatcctggac cgaccgagta      9360
caagcccacg gtgcgcctcg ccacccgcga cgacgtcccc agggccgtac gcaccctcgc      9420
cgccgcgttc gccgactacc ccgccacgcg ccacaccgtc gatccggacc gccacatcga      9480
gcgggtcacc gagctgcaag aactcttcct cacgcgcgtc gggctcgaca tcggcaaggt      9540
gtgggtcgcg gacgacggcg ccgccgtggc ggtctggacc acgccggaga gcgtcgaagc      9600
gggggcggtg ttcgccgaga tcggcccgcg catggccgag ttgagcggtt ccggctggc      9660 cgcgcagcaa cagatggaag gcctcctggc gccgcaccgg cccaaggagc cgcgtggtt      9720 cctgccccacc gtcggagtct cgcccgacca ccagggcaag gtctgggca gcgccgtcgt      9780 gctccccgga gtggaggcgg ccgagcgcgc cggggtgccc gccttcctgg agacctccgc      9840
```

```
gccccgcaac ctcccttct acgagcggct cggcttcacc gtcaccgccg acgtcgaggt   9900
gcccgaagga ccgcgcacct ggtgcatgac ccgcaagccc ggtgcctgaa cgcgttaagt   9960
cgacaatcaa cctctggatt acaaaatttg tgaaagattg actggtattc ttaactatgt  10020
tgctcctttt acgctatgtg gatacgctgc tttaatgcct ttgtatcatg ctattgcttc  10080
ccgtatggct ttcattttct cctccttgta taaatcctgg ttgctgtctc tttatgagga  10140
gttgtgcccc gttgtcaggc aacgtggcgt ggtgtgcact gtgtttgctg acgcaacccc  10200
cactggttgg ggcattgcca ccacctgtca gctccttttcc gggactttcg ctttccccct  10260
ccctattgcc acggcggaac tcatcgccgc ctgccttgcc cgctgctgga caggggctcg  10320
gctgttgggc actgacaatt ccgtggtgtt gtcggggaaa tcatcgtcct tccttggct   10380
gctcgcctgt gttgccacct ggattctgcg cgggacgtcc ttctgctacg tcccttcggc  10440
cctcaatcca gcggaccttc cttcccgcgg cctgctgccg gctctgcggc ctcttccgcg  10500
tcttcgcctt cgccctcaga cgagtcggat ctccctttgg gccgcctccc cgcgtcgact  10560
ttaagaccaa tgacttacaa ggcagctgta gatcttagcc actttttaaa agaaaagggg  10620
ggactggaag ggctaattca ctcccaacga agacaagatc tgcttttgc ttgtactggg  10680
tctctctggt tagaccagat ctgagcctgg gagctctctg gctaactagg gaacccactg  10740
cttaagcctc aataaagctt gccttgagtg cttcaagtag tgtgtgcccg tctgttgtgt  10800
gactctggta actagagatc cctcagaccc ttttagtcag tgtggaaaat ctctagcagg  10860
gcccgtttaa acccgctgat cagcctcgac tgtgccttct agttgccagc catctgttgt  10920
ttgcccctcc cccgtgcctt ccttgaccct ggaaggtgcc actcccactg tccttttccta 10980
ataaaatgag gaaattgcat cgcattgtct gagtaggtgt cattctattc tgggggtgg  11040
ggtggggcag gacagcaagg gggaggattg ggaagacaat agcaggcatg ctggggatgc  11100
ggtgggctct atggcttctg aggcggaaag aaccagctgg ggctctaggg ggtatcccca  11160
cgcgccctgt agcggcgcat taagcgcggc gggtgtggtg gttacgcgca gcgtgaccgc  11220
tacacttgcc agcgccctag cgcccgctcc tttcgctttc ttcccttcct ttctcgccac  11280
gttcgccggc tttccccgtc aagctctaaa tcggggctc cctttagggt tccgatttag  11340
tgctttacgg cacctcgacc ccaaaaaact tgattagggt gatggttcac gtagtgggcc  11400
atcgccctga tagacggttt ttcgcccttt gacgttggag tccacgttct ttaatagtgg  11460
actcttgttc caaactggaa caacactcaa ccctatctcg gtctattctt ttgatttata  11520
agggattttg ccgatttcgg cctattggtt aaaaaatgag ctgatttaac aaaaatttaa  11580
cgcgaattaa ttctgtggaa tgtgtgtcag ttagggtgtg gaaagtcccc aggctcccca  11640
gcaggcagaa gtatgcaaag catgcatctc aattagtcag caaccaggtg tggaaagtcc  11700
ccaggctccc cagcaggcag aagtatgcaa agcatgcatc tcaattagtc agcaaccata  11760
gtcccgcccc taactccgcc catcccgccc ctaactccgc ccagttccgc ccattctccg  11820
ccccatggct gactaatttt ttttatttat gcagaggccg aggccgcctc tgcctctgag  11880
ctattccaga agtagtgagg aggcttttttt ggaggcctag gcttttgcaa aaagctcccg  11940
ggagcttgta tatccatttt cggatctgat cagcacgtgt tgacaattaa tcatcggcat  12000
agtatatcgg catagtataa tacgacaagg tgaggaacta aaccatggcc aagttgacca  12060
gtgccgttcc ggtgctcacc gcgcgcgacg tcgccgagc ggtcgagttc tggaccgacc  12120
ggctcgggtt ctcccgggac ttcgtggagg acgacttcgc cggtgtggtc cgggacgacg  12180
```

```
tgaccctgtt catcagcgcg gtccaggacc aggtggtgcc ggacaacacc ctggcctggg    12240
tgtgggtgcg cggcctggac gagctgtacg ccgagtggtc ggaggtcgtg tccacgaact    12300
tccgggacgc ctccgggccg gccatgaccg agatcggcga gcagccgtgg gggcgggagt    12360
tcgccctgcg cgacccggcc ggcaactgcg tgcacttcgt ggccgaggag caggactgac    12420
acgtgctacg agatttcgat tccaccgccg ccttctatga aaggttgggc ttcggaatcg    12480
ttttccggga cgccggctgg atgatcctcc agcgcgggga tctcatgctg gagttcttcg    12540
cccaccccaa cttgtttatt gcagcttata atggttacaa ataaagcaat agcatcacaa    12600
atttcacaaa taaagcattt ttttcactgc attctagttg tggtttgtcc aaactcatca    12660
atgtatctta tcatgtctgt ataccgtcga cctctagcta gagcttggcg taatcatggt    12720
catagctgtt tcctgtgtga aattgttatc cgctcacaat tccacacaac atacgagccg    12780
gaagcataaa gtgtaaagcc tggggtgcct aatgagtgag ctaactcaca ttaattgcgt    12840
tgcgctcact gcccgctttc cagtcgggaa acctgtcgtg ccagctgcat taatgaatcg    12900
gccaacgcgc ggggagaggc ggtttgcgta ttgggcgctc ttccgcttcc tcgctcactg    12960
actcgctgcg ctcggtcgtt cggctgcggc gagcggtatc agctcactca aaggcggtaa    13020
tacggttatc cacagaatca ggggataacg caggaaagaa catgtgagca aaaggccagc    13080
aaaaggccag gaaccgtaaa aaggccgcgt tgctggcgtt tttccatagg ctccgccccc    13140
ctgacgagca tcacaaaaat cgacgctcaa gtcagaggtg gcgaaacccg acaggactat    13200
aaagatacca ggcgtttccc cctggaagct ccctcgtgcg ctctcctgtt ccgaccctgc    13260
cgcttaccgg atacctgtcc gcctttctcc cttcgggaag cgtggcgctt tctcatagct    13320
cacgctgtag gtatctcagt tcggtgtagg tcgttcgctc caagctgggc tgtgtgcacg    13380
aaccccccgt tcagcccgac cgctgcgcct tatccggtaa ctatcgtctt gagtccaacc    13440
cggtaagaca cgacttatcg ccactggcag cagccactgg taacaggatt agcagagcga    13500
ggtatgtagg cggtgctaca gagttcttga agtggtggcc taactacggc tacactagaa    13560
gaacagtatt tggtatctgc gctctgctga agccagttac cttcggaaaa agagttggta    13620
gctcttgatc cggcaaacaa accaccgctg gtagcggtgg tttttttgtt tgcaagcagc    13680
agattacgcg cagaaaaaaa ggatctcaag aagatccttt gatcttttct acggggtctg    13740
acgctcagtg gaacgaaaac tcacgttaag ggattttggt catgagatta tcaaaaagga    13800
tcttcaccta gatcctttta aattaaaaat gaagttttaa atcaatctaa agtatatatg    13860
agtaaacttg gtctgacagt taccaatgct taatcagtga ggcacctatc tcagcgatct    13920
gtctatttcg ttcatccata gttgcctgac tccccgtcgt gtagataact acgatacggg    13980
agggcttacc atctggcccc agtgctgcaa tgataccgcg agacccacgc tcaccggctc    14040
cagatttatc agcaataaac cagccagccg gaagggccga gcgcagaagt ggtcctgcaa    14100
ctttatccgc ctccatccag tctattaatt gttgccggga agctagagta agtagttcgc    14160
cagttaatag tttgcgcaac gttgttgcca ttgctacagg catcgtggtg tcacgctcgt    14220
cgtttggtat ggcttcattc agctccggtt cccaacgatc aaggcgagtt acatgatccc    14280
ccatgttgtg caaaaaagcg gttagctcct tcggtcctcc gatcgttgtc agaagtaagt    14340
tggccgcagt gttatcactc atggttatgg cagcactgca taattctctt actgtcatgc    14400
catccgtaag atgcttttct gtgactggtg agtactcaac caagtcattc tgagaatagt    14460
gtatgcggcg accgagttgc tcttgcccgg cgtcaatacg ggataatacc gcgccacata    14520
gcagaacttt aaaagtgctc atcattggaa aacgttcttc ggggcgaaaa ctctcaagga    14580
```

```
tcttaccgct gttgagatcc agttcgatgt aacccactcg tgcacccaac tgatcttcag    14640
catcttttac tttcaccagc gtttctgggt gagcaaaaac aggaaggcaa aatgccgcaa    14700
aaaagggaat aagggcgaca cggaaatgtt gaatactcat actcttcctt tttcaatatt    14760
attgaagcat ttatcagggt tattgtctca tgagcggata catatttgaa tgtatttaga    14820
aaaataaaca aatagggggtt ccgcgcacat ttccccgaaa agtgccacct gac           14873
```

<210> SEQ ID NO 301
<211> LENGTH: 12860
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 301

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt cgcgctgctt cgcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc    1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
```

```
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctggggatt    1920
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagacagag acagatcc attcgattag tgaacggatc ggcactgcgt    2400
gcgccaattc tgcagacaaa tggcagtatt catccacaat tttaaaagaa aaggggggat    2460
tgggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta agctagctag gtcttgaaag gagtgggaat tggctccggt    2640
gcccgtcagt gggcagagcg cacatcgccc acagtccccg agaagttggg gggaggggtc    2700
ggcaattgat ccggtgccta gagaaggtgg cgcggggtaa actgggaaag tgatgtcgtg    2760
tactggctcc gccttttttcc cgagggtggg ggagaaccgt atataagtgc agtagtcgcc    2820
gtgaacgttc ttttcgcaa cgggtttgcc gccagaacac aggaccggtt ctagagcgct    2880
gccaccatgg acaagaagta cagcatcggc ctggacatcg gcaccaactc tgtgggctgg    2940
gccgtgatca ccgacgagta caaggtgccc agcaagaaat tcaaggtgct gggcaacacc    3000
gaccggcaca gcatcaagaa gaacctgatc ggagccctgc tgttcgacag cggcgaaaca    3060
gccgaggcca cccggctgaa gagaaccgcc agaagaagat acaccagacg gaagaaccgg    3120
atctgctatc tgcaagagat cttcagcaac gagatggcca aggtggacga cagcttcttc    3180
cacagactgg aagagtcctt cctggtggaa gaggataaga gcacgagcg caccccatc    3240
ttcggcaaca tcgtggacga ggtggcctac acgagaagt accccaccat ctaccacctg    3300
agaaagaaac tggtggacag caccgacaag gccgacctgc ggctgatcta tctggcctg    3360
gcccacatga tcaagttccg gggccacttc ctgatcgagg cgacctgaa ccccgacaac    3420
agcgacgtgg acaagctgtt catccagctg gtgcagacct acaaccagct gttcgaggaa    3480
aaccccatca cgccagcgg cgtggacgcc aaggccatcc tgtctgccag actgagcaag    3540
agcagacggc tggaaaatct gatcgcccag ctgcccggcg agaagaagaa tggcctgttc    3600
ggaaacctga ttgccctgag cctgggcctg acccccaact tcaagagcaa cttcgacctg    3660
gccgaggatg ccaaactgca gctgagcaag gacacctacg acgacgacct ggacaacctg    3720
ctggcccaga tcggcgacca gtacgccgac ctgtttctgg ccgccaagaa cctgtccgac    3780
gccatcctgc tgagcgacat cctgagagtg aacaccgaga tcaccaaggc ccccctgagc    3840
gcctctatga tcaagagata cgacgagcac caccaggacc tgaccctgct gaaagctctc    3900
gtgcggcagc agctgcctga aagtacaaa gagattttct tcgaccagag caagaacggc    3960
tacgccggct acattgacgg cggagccagc caggaagagt tctacaagtt catcaagccc    4020
atcctggaaa agatggacgg caccgaggaa ctgctcgtga agctgaacag agaggacctg    4080
```

```
ctgcggaagc agcggacctt cgacaacggc agcatccccc accagatcca cctgggagag    4140
ctgcacgcca ttctgcggcg gcaggaagat ttttacccat tcctgaagga caaccgggaa    4200
aagatcgaga agatcctgac cttccgcatc ccctactacg tgggccctct ggccagggga    4260
aacagcagat tcgcctggat gaccagaaag agcgaggaaa ccatcacccc ctggaacttc    4320
gaggaagtgg tggacaaggg cgcttccgcc cagagcttca tcgagcggat gaccaacttc    4380
gataagaacc tgcccaacga gaaggtgctg cccaagcaca gcctgctgta cgagtacttc    4440
accgtgtata acgagctgac caaagtgaaa tacgtgaccg agggaatgag aaagcccgcc    4500
ttcctgagcg gcgagcagaa aaaggccatc gtggacctgc tgttcaagac caaccggaaa    4560
gtgaccgtga agcagctgaa agaggactac ttcaagaaaa tcgagtgctt cgactccgtg    4620
gaaatctccg gcgtggaaga tcggttcaac gcctccctgg gcacatacca cgatctgctg    4680
aaaattatca aggacaagga cttcctggac aatgaggaaa acgaggacat tctggaagat    4740
atcgtgctga ccctgacact gtttgaggac agagagatga tcgaggaacg gctgaaaacc    4800
tatgcccacc tgttcgacga caaagtgatg aagcagctga gcggcggag atacaccggc    4860
tggggcaggc tgagccggaa gctgatcaac ggcatccggg acaagcagtc cggcaagaca    4920
atcctggatt tcctgaagtc cgacggcttc gccaacagaa acttcatgca gctgatccac    4980
gacgacagcc tgacctttaa agaggacatc cagaaagccc aggtgtccgg ccagggcgat    5040
agcctgcacg agcacattgc caatctggcc ggcagccccg ccattaagaa gggcatcctg    5100
cagacagtga aggtggtgga cgagctcgtg aaagtgatgg gccggcacaa gcccgagaac    5160
atcgtgatcg aaatggccag agagaaccag accacccaga agggacagaa gaacagccgc    5220
gagagaatga agcggatcga agagggcatc aaagagctgg gcagccagat cctgaaagaa    5280
caccccgtgg aaaacaccca gctgcagaac gagaagctgt acctgtacta cctgcagaat    5340
gggcgggata tgtacgtgga ccaggaactg gacatcaacc ggctgtccga ctacgatgtg    5400
gaccatatcg tgcctcagag ctttctgaag gacgactcca tcgacaacaa ggtgctgacc    5460
agaagcgaca agaaccgggg caagagcgac aacgtgccct ccgaagaggt cgtgaagaag    5520
atgaagaact actggcggca gctgctgaac gccaagctga ttacccagag aaagttcgac    5580
aatctgacca aggccgagag aggcggcctg agcgaactgg ataaggccgg cttcatcaag    5640
agacagctgg tggaaacccg gcagatcaca aagcacgtgg cacagatcct ggactcccgg    5700
atgaacacta gtacgacga gaatgacaag ctgatccggg aagtgaaagt gatcaccctg    5760
aagtccaagc tggtgtccga tttccggaag gatttccagt tttacaaagt gcgcgagatc    5820
aacaactacc accacgccca cgacgcctac ctgaacgccg tcgtgggaac cgccctgatc    5880
aaaaagtacc ctaagctgga aagcgagttc gtgtacggcg actacaaggt gtacgacgtg    5940
cggaagatga tcgccaagag cgagcaggaa atcggcaagg ctaccgccaa gtacttcttc    6000
tacagcaaca tcatgaactt tttcaagacc gagattaccc tggccaacgg cgagatccgg    6060
aagcggcctc tgatcgagac aaacggcgaa accggggaga tcgtgtggga taagggccgg    6120
gattttgcca ccgtgcggaa agtgctgagc atgccccaag tgaatatcgt gaaaaagacc    6180
gaggtgcaga caggcggctt cagcaaagag tctatcctgc ccaagaggaa cagcgataag    6240
ctgatcgcca gaaagaagga ctgggaccct aagaagtacg gcggcttcga cagccccacc    6300
gtggcctatt ctgtgctggt ggtggccaaa gtggaaaagg gcaagtccaa gaaactgaag    6360
agtgtgaaag agctgctggg gatcaccatc atggaaagaa gcagcttcga gaagaatccc    6420
```

```
atcgactttc tggaagccaa gggctacaaa gaagtgaaaa aggacctgat catcaagctg    6480
cctaagtact ccctgttcga gctggaaaac ggccggaaga gaatgctggc ctctgccggc    6540
gaactgcaga agggaaacga actggccctg ccctccaaat atgtgaactt cctgtacctg    6600
gccagccact atgagaagct gaagggctcc cccgaggata tgagcagaa  acagctgttt    6660
gtggaacagc acaagcacta cctggacgag atcatcgagc agatcagcga gttctccaag    6720
agagtgatcc tggccgacgc taatctggac aaagtgctgt ccgcctacaa caagcaccgg    6780
gataagccca tcagagagca ggccgagaat atcatccacc tgtttaccct gaccaatctg    6840
ggagcccctg ccgccttcaa gtactttgac accaccatcg accggaagag gtacaccagc    6900
accaaagagg tgctggacgc caccctgatc caccagagca tcaccggcct gtacgagaca    6960
cggatcgacc tgtctcagct ggaggcgac aagcgacctg ccgccacaaa gaaggctgga    7020
caggctaaga agaagaaaga ttacaaagac gatgacgata agggatccgg cgcaacaaac    7080
ttctctctgc tgaaacaagc cggagatgtc gaagagaatc ctggaccgat ggccaagcct    7140
ttgtctcaag aagaatccac cctcattgaa agagcaacgg ctacaatcaa cagcatcccc    7200
atctctgaag actacagcgt cgccagcgca gctctctcta gcgacggccg catcttcact    7260
ggtgtcaatg tatatcattt tactgggggga ccttgtgcag aactcgtggt gctgggcact    7320
gctgctgctg cggcagctgg caacctgact tgtatcgtcg cgatcggaaa tgagaacagg    7380
ggcatcttga gccgtgcgg acggtgccga caggtgcttc tcgatctgca tcctgggatc    7440
aaagccatag tgaaggacag tgatggacag ccgacggcag ttgggattcg tgaattgctg    7500
ccctctggtt atgtgtggga gggctaagaa ttcgatatca agcttatcga taatcaacct    7560
ctggattaca aaatttgtga aagattgact ggtattctta actatgttgc tccttttacg    7620
ctatgtggat acgctgcttt aatgcctttg tatcatgcta ttgcttcccg tatggctttc    7680
attttctcct ccttgtataa atcctggttg ctgtctcttt atgaggagtt gtggcccgtt    7740
gtcaggcaac gtggcgtggt gtgcactgtg tttgctgacg caaccccac tggttggggc    7800
attgccacca cctgtcagct cctttccggg actttcgctt tccccctccc tattgccacg    7860
gcggaactca tcgccgcctg ccttgcccgc tgctggacag gggctcggct gttgggcact    7920
gacaattccg tggtgttgtc ggggaaatca tcgtcctttc cttggctgct cgcctgtgtt    7980
gccacctgga ttctgcgcgg gacgtccttc tgctacgtcc cttcggccct caatccagcg    8040
gaccttcctt cccgcggcct gctgccggct ctgcggcctc ttccgcgtct tcgccttcgc    8100
cctcagacga gtcggatctc cctttgggcc gcctccccgc atcgataccg tcgacctcga    8160
gacctagaaa aacatggagc aatcacaagt agcaatacag cagctaccaa tgctgattgt    8220
gcctggctag aagcacaaga ggaggaggag gtgggttttc cagtcacacc tcaggtacct    8280
ttaagaccaa tgacttacaa ggcagctgta gatcttagcc acttttta aa agaaaagggg    8340
ggactggaag ggctaattca ctcccaacga agacaagata tccttgatct gtggatctac    8400
cacacacaag gctacttccc tgattggcag aactacacac cagggccagg gatcagatat    8460
ccactgacct ttggatggtg ctacaagcta gtaccagttg agcaagagaa ggtagaagaa    8520
gccaatgaag agagaacac  ccgcttgtta caccctgtga gcctgcatgg gatggatgac    8580
ccggagagag aagtattaga gtggaggttt gacagccgcc tagcatttca tcacatggcc    8640
cgagagctgc atccggactg tactgggtct ctctggttag accagatctg agcctgggag    8700
ctctctggct aactagggaa cccactgctt aagcctcaat aaagcttgcc ttgagtgctt    8760
caagtagtgt gtgcccgtct gttgtgtgac tctggtaact agagatccct cagacccttt    8820
```

```
tagtcagtgt ggaaaatctc tagcagggcc cgtttaaacc cgctgatcag cctcgactgt   8880
gccttctagt tgccagccat ctgttgtttg cccctccccc gtgccttcct tgaccctgga   8940
aggtgccact cccactgtcc tttcctaata aaatgaggaa attgcatcgc attgtctgag   9000
taggtgtcat tctattctgg ggggtggggt ggggcaggac agcaagggg  aggattggga   9060 agacaatagc aggcatgctg gggatgcggt gggctctatg gcttctgagg cggaaagaac   9120
cagctggggc tctaggggggt atccccacgc gccctgtagc ggcgcattaa gcgcggcggg   9180
tgtggtggtt acgcgcagcg tgaccgctac acttgccagc gccctagcgc ccgctccttt   9240
cgctttcttc ccttccttc tcgccacgtt cgccggcttt ccccgtcaag ctctaaatcg   9300
ggggctccct ttagggttcc gatttagtgc tttacggcac ctcgacccca aaaaacttga   9360
ttagggtgat ggttcacgta gtgggccatc gccctgatag acggttttc  gcctttgac   9420 gttggagtcc acgttcttta atagtggact cttgttccaa actggaacaa cactcaaccc   9480
tatctcggtc tattcttttg atttataagg gattttgccg atttcggcct attggttaaa   9540
aaatgagctg atttaacaaa aatttaacgc gaattaattc tgtggaatgt gtgtcagtta   9600
gggtgtggaa agtccccagg ctccccagca ggcagaagta tgcaaagcat gcatctcaat   9660
tagtcagcaa ccaggtgtgg aaagtcccca ggctccccag caggcagaag tatgcaaagc   9720
atgcatctca attagtcagc aaccatagtc ccgcccctaa ctccgcccat cccgccccta   9780
actccgccca gttccgccca ttctccgccc catggctgac tattttttt  tatttatgca   9840 gaggccgagg ccgcctctgc ctctgagcta ttccagaagt agtgaggagg ctttttttgga   9900 ggcctaggct tttgcaaaaa gctcccggga gcttgtatat ccattttcgg atctgatcag   9960
cacgtgttga caattaatca tcggcatagt atatcggcat agtataatac gacaaggtga  10020
ggaactaaac catggccaag ttgaccagtg ccgttccggt gctcaccgcg cgcgacgtcg  10080
ccggagcggt cgagttctgg accgaccggc tcgggttctc ccgggacttc gtggaggacg  10140
acttcgccgg tgtggtccgg gacgacgtga ccctgttcat cagcgcggtc caggaccagg  10200
tggtgccgga caacccctg  gcctgggtgt gggtgcgcgg cctggacgag ctgtacgccg  10260
agtggtcgga ggtcgtgtcc acgaacttcc gggacgcctc cgggcgggcc atgaccgaga  10320
tcggcgagca gccgtggggg cgggagttcg ccctgcgcga cccggccggc aactgcgtgc  10380
acttcgtggc cgaggagcag gactgacacg tgctacgaga tttcgattcc accgccgcct  10440
tctatgaaag gttgggcttc ggaatcgttt tccggacgc  cggctggatg atcctccagc  10500
gcggggatct catgctggag ttcttcgccc accccaactt gtttattgca gcttataatg  10560
gttacaaata aagcaatagc atcacaaatt tcacaaataa agcatttttt tcactgcatt  10620
ctagttgtgt tttgtccaaa ctcatcaatg tatcttatca tgtctgtata ccgtcgacct  10680
ctagctagag cttggcgtaa tcatggtcat agctgttttcc tgtgtgaaat tgttatccgc  10740
tcacaattcc acacaacata cgagccggaa gcataaagtg taaagcctgg ggtgcctaat  10800
gagtgagcta actcacatta attgcgttgc gctcactgcc cgctttccag tcgggaaacc  10860
tgtcgtgcca gctgcattaa tgaatcggcc aacgcgcggg gagaggcggt ttgcgtattg  10920
ggcgctcttc cgcttcctcg ctcactgact cgctgcgctc ggtcgttcgg ctgcggcgag  10980
cggtatcagc tcactcaaag gcggtaatac ggttatccac agaatcaggg gataacgcag  11040
gaaagaacat gtgagcaaaa ggccagcaaa aggccaggaa ccgtaaaaag gccgcgttgc  11100
tggcgttttt ccataggctc cgcccccctg acgagcatca caaaaatcga cgctcaagtc  11160
```

```
agaggtggcg aaacccgaca ggactataaa gataccaggc gtttccccct ggaagctccc    11220
tcgtgcgctc tcctgttccg accctgccgc ttaccggata cctgtccgcc tttctccctt    11280
cgggaagcgt ggcgctttct catagctcac gctgtaggta tctcagttcg gtgtaggtcg    11340
ttcgctccaa gctgggctgt gtgcacgaac cccccgttca gcccgaccgc tgcgccttat    11400
ccggtaacta tcgtcttgag tccaacccgg taagacacga cttatcgcca ctggcagcag    11460
ccactggtaa caggattagc agagcgaggt atgtaggcgg tgctacagag ttcttgaagt    11520
ggtggcctaa ctacggctac actagaagaa cagtatttgg tatctgcgct ctgctgaagc    11580
cagttacctt cggaaaaaga gttggtagct cttgatccgg caaacaaacc accgctggta    11640
gcggtggttt ttttgtttgc aagcagcaga ttacgcgcag aaaaaaagga tctcaagaag    11700
atcctttgat cttttctacg gggtctgacg ctcagtggaa cgaaaactca cgttaaggga    11760
ttttggtcat gagattatca aaaaggatct tcacctagat ccttttaaat taaaaatgaa    11820
gttttaaatc aatctaaagt atatatgagt aaacttggtc tgacagttac caatgcttaa    11880
tcagtgaggc acctatctca gcgatctgtc tatttcgttc atccatagtt gcctgactcc    11940
ccgtcgtgta gataactacg atacgggagg gcttaccatc tggccccagt gctgcaatga    12000
taccgcgaga cccacgctca ccggctccag atttatcagc aataaaccag ccagccggaa    12060
gggccgagcg cagaagtggt cctgcaactt tatccgcctc catccagtct attaattgtt    12120
gccgggaagc tagagtaagt agttcgccag ttaatagttt gcgcaacgtt gttgccattg    12180
ctacaggcat cgtggtgtca cgctcgtcgt ttggtatggc ttcattcagc tccggttccc    12240
aacgatcaag gcgagttaca tgatccccca tgttgtgcaa aaaagcggtt agctccttcg    12300
gtcctccgat cgttgtcaga agtaagttgg ccgcagtgtt atcactcatg gttatggcag    12360
cactgcataa ttctcttact gtcatgccat ccgtaagatg cttttctgtg actggtgagt    12420
actcaaccaa gtcattctga gaatagtgta tgcggcgacc gagttgctct tgcccggcgt    12480
caatacggga taataccgcg ccacatagca gaactttaaa agtgctcatc attggaaaac    12540
gttcttcggg gcgaaaactc tcaaggatct taccgctgtt gagatccagt tcgatgtaac    12600
ccactcgtgc acccaactga tcttcagcat cttttacttt caccagcgtt tctgggtgag    12660
caaaaacagg aaggcaaaat gccgcaaaaa agggaataag ggcgacacgg aaatgttgaa    12720
tactcatact cttcctttt caatattatt gaagcattta tcagggttat tgtctcatga    12780
gcggatacat atttgaatgt atttagaaaa ataaacaaat aggggttccg cgcacatttc    12840
cccgaaaagt gccacctgac                                                12860
```

<210> SEQ ID NO 302
<211> LENGTH: 10182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 302

```
cccgggtgca aagatggata aagttttaaa cagagaggaa tctttgcagc taatggacct      60
tctaggtctt gaaaggagtg ggaattggct ccggtgcccg tcagtgggca gagcgcacat     120
cgcccacagt ccccgagaag ttgggggag gggtcggcaa ttgatccggt gcctagagaa     180
ggtggcgcgg ggtaaactgg gaaagtgatg tcgtgtactg gctccgcctt tttcccgagg    240
gtgggggaga accgtatata agtgcagtag tcgccgtgaa cgttcttttt cgcaacgggt    300
```

```
ttgccgccag aacacaggta agtgccgtgt gtggttcccg cgggcctggc ctctttacgg    360
gttatggccc ttgcgtgcct tgaattactt ccactggctg cagtacgtga ttcttgatcc    420
cgagcttcgg gttggaagtg ggtgggagag ttcgaggcct tgcgcttaag gagccccttc    480
gcctcgtgct tgagttgagg cctggcctgg gcgctgggc cgccgcgtgc gaatctggtg     540
gcaccttcgc gcctgtctcg ctgctttcga taagtctcta gccatttaaa attttttgatg   600
acctgctgcg acgcttttttt tctggcaaga tagtcttgta aatgcgggcc aagatctgca   660
cactggtatt tcggttttttg gggccgcggg cggcgacggg gcccgtgcgt cccagcgcac   720
atgttcggcg aggcggggcc tgcgagcgcg gccaccgaga tcggacgggg gtagtctca    780
agctggccgg cctgctctgg tgcctggcct cgcgccgccg tgtatcgccc cgccctgggc   840
ggcaaggctg gcccggtcgg caccagttgc gtgagcggaa agatggccgc ttcccggccc   900
tgctgcaggg agctcaaaat ggaggacgcg cgctcggga gagcgggcgg gtgagtcacc    960
cacacaaagg aaaagggcct ttccgtcctc agccgtcgct tcatgtgact ccacggagta   1020
ccgggcgccg tccaggcacc tcgattagtt ctcgagcttt tggagtacgt cgtctttagg   1080
ttgggggggag gggttttatg cgatggagtt tccccacact gagtgggtgg agactgaagt  1140
taggccagct tggcacttga tgtaattctc cttggaattt gccctttttg agtttggatc   1200
ttggttcatt ctcaagcctc agacagtggt tcaaagtttt tttcttccat ttcaggtgtc   1260
gtgacgtacg gccaccatga ccgagtacaa gcccacggtg cgcctcgcca cccgcgacga   1320
cgtcccagg gccgtacgca ccctcgccgc cgcgttcgcc gactaccccg ccacgcgcca   1380
caccgtcgat ccggaccgcc acatcgagcg ggtcaccgag ctgcaagaac tcttcctcac   1440
gcgcgtcggg ctcgacatcg gcaaggtgtg ggtcgcggac gacggcgccg ccgtggcggt   1500
ctggaccacg ccggagagcg tcgaagcggg ggcggtgttc gccgagatcg gcccgcgcat   1560
ggccgagttg agcggttccc ggctggccgc gcagcaacag atggaaggcc tcctggcgcc   1620
gcaccggccc aaggagcccg cgtggttcct ggccaccgtc ggagtctcgc ccgaccacca   1680
gggcaagggt ctgggcagcg ccgtcgtgct ccccggagtg gaggcggccg agcgcgccgg   1740
ggtgcccgcc ttcctggaga cctccgcgcc ccgcaacctc cccttctacg agcggctcgg   1800
cttcaccgtc accgccgacg tcgaggtgcc cgaaggaccg cgcacctggt gcatgacccg   1860
caagcccggt gcctgaacgc gttaagtcga caatcaacct ctggattaca aaatttgtga   1920
aagattgact ggtattctta actatgttgc tccttttacg ctatgtggat acgctgcttt   1980
aatgcctttg tatcatgcta ttgcttcccg tatggctttc attttctcct ccttgtataa   2040
atcctggttg ctgtctcttt atgaggagtt gtggcccgtt gtcaggcaac gtggcgtggt   2100
gtgcactgtg tttgctgacg caaccccac tggttgggc attgccacca cctgtcagct   2160
cctttccggg actttcgctt tccccctccc tattgccacg gcggaactca tcgccgcctg   2220
ccttgcccgc tgctggacag gggctcggct gttgggcact gacaattccg tggtgttgtc   2280
ggggaaatca tcgtcctttc cttggctgct cgcctgtgtt gccacctgga ttctgcgcgg   2340
gacgtccttc tgctacgtcc cttcggccct caatccagcg gaccttcctt cccgcggcct   2400
gctgccggct ctgcggcctc ttccgcgtct tcgccttcgc cctcagacga gtcggatctc   2460
cctttgggcc gcctccccgc gtcgacttta agaccaatga cttacaaggc agctgtagat   2520
cttagccact ttttaaaaga aagggggga ctggaagggc taattcactc ccaacgaaga   2580
caagatctgc ttttttgcttg tactgggtct ctctggttag accagatctg agcctgggag   2640
```

```
ctctctggct aactagggaa cccactgctt aagcctcaat aaagcttgcc ttgagtgctt    2700
caagtagtgt gtgcccgtct gttgtgtgac tctggtaact agagatccct cagacccttt    2760
tagtcagtgt ggaaaatctc tagcagtacg tatagtagtt catgtcatct tattattcag    2820
tatttataac ttgcaaagaa atgaatatca gagagtgaga ggaacttgtt tattgcagct    2880
tataatggtt acaaataaag caatagcatc acaaatttca caaataaagc attttttca     2940
ctgcattcta gttgtggttt gtccaaactc atcaatgtat cttatcatgt ctggctctag    3000
ctatcccgcc cctaactccg cccatcccgc cctaactcc gcccagttcc gcccattctc     3060
cgccccatgg ctgactaatt ttttttattt atgcagaggc cgaggccgcc tcggcctctg    3120
agctattcca gaagtagtga ggaggctttt ttggaggcct agggacgtac ccaattcgcc    3180
ctatagtgag tcgtattacg cgcgctcact ggccgtcgtt ttacaacgtc gtgactggga    3240
aaaccctggc gttacccaac ttaatcgcct tgcagcacat ccccctttcg ccagctggcg    3300
taatagcgaa gaggcccgca ccgatcgccc ttcccaacag ttgcgcagcc tgaatggcga    3360
atgggacgcg ccctgtagcg cgcattaag cgcggcgggt gtggtggtta cgcgcagcgt     3420
gaccgctaca cttgccagcg ccctagcgcc cgctcctttc gctttcttcc cttcctttct    3480
cgccacgttc gccggctttc cccgtcaagc tctaaatcgg gggctccctt tagggttccg    3540
atttagtgct ttacggcacc tcgaccccaa aaaacttgat tagggtgatg gttcacgtag    3600
tgggccatcg ccctgataga cggtttttcg ccctttgacg ttggagtcca cgttctttaa    3660
tagtggactc ttgttccaaa ctggaacaac actcaaccct atctcggtct attcttttga    3720
tttataaggg attttgccga tttcggccta ttggttaaaa aatgagctga tttaacaaaa    3780
atttaacgcg aattttaaca aatattaac gcttacaatt taggtggcac ttttcgggga    3840
aatgtgcgcg gaacccctat ttgtttattt ttctaaatac attcaaatat gtatccgctc    3900
atgagacaat aaccctgata aatgcttcaa taatattgaa aaaggaagag tatgagtatt    3960
caacatttcc gtgtcgccct tattcccttt tttgcggcat tttgccttcc tgttttgct     4020
cacccagaaa cgctggtgaa agtaaaagat gctgaagatc agttgggtgc acgagtgggt    4080
tacatcgaac tggatctcaa cagcggtaag atccttgaga gttttcgccc cgaagaacgt    4140
tttccaatga tgagcacttt taaagttctg ctatgtggcg cggtattatc ccgtattgac    4200
gccgggcaag agcaactcgg tcgccgcata cactattctc agaatgactt ggttgagtac    4260
tcaccagtca cagaaaagca tcttacggat ggcatgacag taagagaatt atgcagtgct    4320
gccataacca tgagtgataa cactgcggcc aacttacttc tgacaacgat cggaggaccg    4380
aaggagctaa ccgcttttt gcacaacatg ggggatcatg taactcgcct tgatcgttgg     4440
gaaccggagc tgaatgaagc cataccaaac gacgagcgtg acaccacgat gcctgtagca    4500
atggcaacaa cgttgcgcaa actattaact ggcgaactac ttactctagc ttcccggcaa    4560
caattaatag actggatgga ggcggataaa gttgcaggac cacttctgcg ctcggccctt    4620
ccggctggct ggtttattgc tgataaatct ggagccggtg agcgtgggtc tcgcggtatc    4680
attgcagcac tggggccaga tggtaagccc tcccgtatcg tagttatcta cacgacgggg    4740
agtcaggcaa ctatggatga acgaaataga cagatcgctg agataggtgc ctcactgatt    4800
aagcattggt aactgtcaga ccaagtttac tcatatatac tttagattga tttaaaactt    4860
catttttaat ttaaaaggat ctaggtgaag atccttttg ataatctcat gaccaaaatc     4920
ccttaacgtg agttttcgtt ccactgagcg tcagaccccg tagaaaagat caaaggatct    4980
tcttgagatc cttttttct gcgcgtaatc tgctgcttgc aaacaaaaaa accaccgcta     5040
```

```
ccagcggtgg tttgtttgcc ggatcaagag ctaccaactc tttttccgaa ggtaactggc    5100
ttcagcagag cgcagatacc aaatactgtt cttctagtgt agccgtagtt aggccaccac    5160
ttcaagaact ctgtagcacc gcctacatac ctcgctctgc taatcctgtt accagtggct    5220
gctgccagtg gcgataagtc gtgtcttacc gggttggact caagacgata gttaccggat    5280
aaggcgcagc ggtcgggctg aacggggggt tcgtgcacac agcccagctt ggagcgaacg    5340
acctacaccg aactgagata cctacagcgt gagctatgag aaagcgccac gcttcccgaa    5400
gggagaaagg cggacaggta tccggtaagc ggcagggtcg aacaggaga gcgcacgagg     5460
gagcttccag ggggaaacgc ctggtatctt tatagtcctg tcgggtttcg ccacctctga    5520
cttgagcgtc gatttttgtg atgctcgtca ggggggcgga gcctatggaa aaacgccagc    5580
aacgcggcct ttttacggtt cctggccttt tgctggcctt tgctcacat gttctttcct     5640
gcgttatccc ctgattctgt ggataaccgt attaccgcct ttgagtgagc tgataccgct    5700
cgccgcagcc gaacgaccga gcgcagcgag tcagtgagcg aggaagcgga agagcgccca    5760
atacgcaaac cgcctctccc cgcgcgttgg ccgattcatt aatgcagctg gcacgacagg    5820
tttcccgact ggaaagcggg cagtgagcgc aacgcaatta atgtgagtta gctcactcat    5880
taggcacccc aggctttaca ctttatgctt ccggctcgta tgttgtgtgg aattgtgagc    5940
ggataacaat ttcacacagg aaacagctat gaccatgatt acgccaagcg cgcaattaac    6000
cctcactaaa gggaacaaaa gctggagctg caagcttaat gtagtcttat gcaatactct    6060
tgtagtcttg caacatggta acgatgagtt agcaacatgc cttacaagga gagaaaagc     6120
accgtgcatg ccgattggtg gaagtaaggt ggtacgatcg tgccttatta ggaaggcaac    6180
agacgggtct gacatggatt ggacgaacca ctgaattgcc gcattgcaga gatattgtat    6240
ttaagtgcct agctcgatac ataaacgggt ctctctggtt agaccagatc tgagcctggg    6300
agctctctgg ctaactaggg aacccactgc ttaagcctca ataaagcttg ccttgagtgc    6360
ttcaagtagt gtgtgcccgt ctgttgtgtg actctggtaa ctagagatcc ctcagaccct    6420
tttagtcagt gtggaaaatc tctagcagtg gcgcccgaac agggacttga aagcgaaagg    6480
gaaaccagag gagctctctc gacgcaggac tcggcttgct gaagcgcgca cggcaagagg    6540
cgaggggcgg cgactggtga gtacgccaaa aattttgact agcggaggct agaaggagag    6600
agatgggtgc gagagcgtca gtattaagcg ggggagaatt agatcgcgat gggaaaaaat    6660
tcggttaagg ccaggggggaa agaaaaaata taaattaaaa catatagtat gggcaagcag    6720
ggagctagaa cgattcgcag ttaatcctgg cctgttagaa acatcagaag ctgtagaca     6780
aatactggga cagctacaac catcccttca gacaggatca gaagaactta gatcattata    6840
taatacagta gcaaccctct attgtgtgca tcaaaggata gagataaaag acaccaagga    6900
agctttagac aagatagagg aagagcaaaa caaaagtaag accaccgcac agcaagcggc    6960
cgctgatctt cagacctgga ggaggagata tgagggacaa ttggagaagt gaattatata    7020
aatataaagt agtaaaaatt gaaccattag gagtagcacc caccaaggca agagaagag     7080
tggtgcagag agaaaaaaga gcagtgggaa taggagcttt gttccttggg ttcttgggag    7140
cagcaggaag cactatgggc gcagcgtcaa tgacgctgac ggtacaggcc agacaattat    7200
tgtctggtat agtgcagcag cagaacaatt tgctgagggc tattgaggcg caacagcatc    7260
tgttgcaact cacagtctgg ggcatcaagc agctccaggc aagaatcctg gctgtggaaa    7320
gatacctaaa ggatcaacag ctcctgggga tttggggttg ctctggaaaa ctcatttgca    7380
```

```
ccactgctgt gccttggaat gctagttgga gtaataaatc tctggaacag atttggaatc    7440
acacgacctg gatggagtgg gacagagaaa ttaacaatta cacaagctta atacactcct    7500
taattgaaga atcgcaaaac cagcaagaaa agaatgaaca agaattattg gaattagata    7560
aatgggcaag tttgtggaat tggtttaaca taacaaattg gctgtggtat ataaaattat    7620
tcataatgat agtaggaggc ttggtaggtt taagaatagt ttttgctgta ctttctatag    7680
tgaatagagt taggcaggga tattcaccat tatcgtttca gacccacctc ccaaccccga    7740
ggggacccag agagggccta tttcccatga ttccttcata tttgcatata cgatacaagg    7800
ctgttagaga gataattaga attaatttga ctgtaaacac aaagatatta gtacaaaata    7860
cgtgacgtag aaagtaataa tttcttgggt agtttgcagt tttaaaatta tgttttaaaa    7920
tggactatca tatgcttacc gtaacttgaa agtatttcga tttcttggct ttatatatct    7980
tgtggaaagg acgaaacacc ggagacggtt gtaaatgagc acacaaaata cacatgctaa    8040
aatattatat tctatgacct ttataaaatc aaccaaaatc ttcttttttaa taactttagt    8100
atcaataatt agaattttta tgttcctttt tgcaaacttt taataaaaat gagcaaaata    8160
aaaaaacgct agttttagta actcgcgttg ttttcttcac ctttaataat agctactcca    8220
ccacttgttc ctaagcggtc agctcctgct tcaatcattt tttgagcatc ttcaaatgtt    8280
ctaactccac cagctgcttt aactaaagca ttgtctttaa caactgactt cattagttta    8340
acatcttcaa atgttgcacc tgattttgaa aatcctgttg atgttttaac aaattctaat    8400
ccagcttcaa cagctatttc acaagctttc atgatttctt cttttgttaa taaacaattt    8460
tccataatac atttaacaac atgtgatcca gctgcttttt ttacagcttt catgtcttct    8520
aaaactaatt cataattttt gtcttttaat gcaccaatat ttaataccat atcaatttct    8580
gttgcaccat ctttaattgc ttcagaaact tcgaatgctt ttgtagctgt tgtgcatgca    8640
cctagaggaa aacctacaac atttgttatt cctacatttg tgccttttaa taattcttta    8700
caatagcttg ttcaatatga attaacacaa actgttgcaa aatcaaattc aattgcttca    8760
tcacataatt gtttaatttc agctttcgta gcatcttgtt ttaataatgt gtgatctata    8820
tatttgttta gtttcatttt ttctcctata tattcatttt taattttaat tcttaataa    8880
tttcgtctac tttaacttta gcgttttgaa cagattcacc aacacctata aaataaattt    8940
ttagtttagg ttcagttcca cttgggcgaa cagcaaatca tgacttatct tctaaataaa    9000
attttagtaa gtcttgtcct ggcatattat acattccatc gatgtagtct tcaacattaa    9060
caactttaag tccagcaatt tgagttaagg gtgttgctct caatgatttc attaatggtt    9120
caatttttaa tttctttttct tctggtttaa aattcaagtt taaagtgaaa gtgtaatatg    9180
cacccatttc tttaaataaa tcttctaaat agtctactaa tgttttattt tgtttttat    9240
aaaatcaagc agcctctgct attaatatag aagcttgtat tccatcttta tctctagctg    9300
agtcatcaat tacatatcca taactttctt cataagcaaa aacaaaattt aatccgttat    9360
cttcttcttt agcaatttct ctacccattc atttaaatcc agttaaagtt ttacaatat    9420
taactccata ttttcatga gcgattctat cacccaaatc acttgttaca aaacttgaat    9480
atagagccgg attttttgga atgctattta agcgttttag atttgataat tttcaatcaa    9540
ttaaaattgg tcctgtttga tttccatcta atcttacaaa atgaccatca tgttttattg    9600
ccattccaaa tctgtcagca tctgggtcat tcataataat aatatctgca tcatgtttaa    9660
taccatattc aagcggtatt tttcatgcag gatcaaattc tggatttgga tttacaacat    9720
ttttaaatgt ttcatcttca aatgcatgct cttcaaccct aataacgtta tatcctgatt    9780
```

-continued

```
cacgtaatat ttttggggta aatttagttc ctgttccatt aactgcgcta aaaataattt      9840 ttaaatctttt tttagcttct tgctcttttt tgtacgtctc tgttttagag ctagaaatag      9900
caagttaaaa taaggctagt ccgttatcaa cttgaaaaag tggcaccgag tcggtgcttt      9960
tttaagcttg gcgtaactag atcttgagac aaatggcagt attcatccac aattttaaaa     10020
gaaaaggggg gattgggggg tacagtgcag gggaaagaat agtagacata atagcaacag     10080
acatacaaac taaagaatta caaaaacaaa ttacaaaaat tcaaaatttt cgggtttatt     10140
acagggacag cagagatcca ctttggcgcc ggctcgaggg gg                        10182
```

<210> SEQ ID NO 303
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 303
nnnnnnnnnn nnnnnnnnnn ngg                                                 23

<210> SEQ ID NO 304
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other

<400> SEQUENCE: 304
nnnnnnnnnn nnngg                                                          15

<210> SEQ ID NO 305
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 305
nnnnnnnnnn nnnnnnnnnn ngg                                                 23

-continued

```
<210> SEQ ID NO 306
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other

<400> SEQUENCE: 306
nnnnnnnnnn nngg                                                          14

<210> SEQ ID NO 307
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 307
nnnnnnnnnn nnnnnnnnnn nggng                                              25

<210> SEQ ID NO 308
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 308
nnnnnnnnnn nnnggng                                                       17

<210> SEQ ID NO 309
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 309
nnnnnnnnnn nnnnnnnnnn nggng                                             25

<210> SEQ ID NO 310
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 310 nnnnnnnnnnn nnggng                                                      16
```